United States Patent
Zhang et al.

(10) Patent No.: US 12,139,499 B2
(45) Date of Patent: Nov. 12, 2024

(54) HETEROARYL COMPOUNDS FOR TREATING HUNTINGTON'S DISEASE

(71) Applicant: PTC THERAPEUTICS, INC., Warren, NJ (US)

(72) Inventors: Nanjing Zhang, Princeton, NJ (US); Suresh Babu, Pennington, NJ (US); Scott J. Barraza, Piscataway, NJ (US); Anuradha Bhattacharyya, Edison, NJ (US); Guangming Chen, Bridgewater, NJ (US); Gary Mitchell Karp, Princeton Junction, NJ (US); Andrew J. Kassick, Wexford, PA (US); Anthony R. Mazzotti, Rahway, NJ (US); Young-Choon Moon, Belle Mead, NJ (US); Jana Narasimhan, Scotch Plains, NJ (US); Nadiya Sydorenko, Princeton, NJ (US); Anthony Turpoff, Hillsborough, NJ (US); Matthew G. Woll, Dunellen, NJ (US); Wuming Yan, Wayne, NJ (US)

(73) Assignee: PTC THERAPEUTICS, INC., Warren, NJ (US)

( * ) Notice: Subject to any disclaimer, the term of this patent is extended or adjusted under 35 U.S.C. 154(b) by 172 days.

(21) Appl. No.: 17/254,828

(22) PCT Filed: Jun. 25, 2019

(86) PCT No.: PCT/US2019/038895
§ 371 (c)(1),
(2) Date: Dec. 21, 2020

(87) PCT Pub. No.: WO2020/005877
PCT Pub. Date: Jan. 2, 2020

(65) Prior Publication Data
US 2021/0284660 A1    Sep. 16, 2021

Related U.S. Application Data

(60) Provisional application No. 62/690,540, filed on Jun. 27, 2018.

(51) Int. Cl.
| | |
|---|---|
| *C07D 519/00* | (2006.01) |
| *C07D 417/14* | (2006.01) |
| *C07D 471/04* | (2006.01) |
| *C07D 487/04* | (2006.01) |
| *C07D 513/04* | (2006.01) |

(52) U.S. Cl.
CPC ......... *C07D 519/00* (2013.01); *C07D 417/14* (2013.01); *C07D 471/04* (2013.01); *C07D 487/04* (2013.01); *C07D 513/04* (2013.01)

(58) Field of Classification Search
CPC ................ C07D 519/00; C07D 417/14; C07D 471/04; C07D 487/04; C07D 513/04

USPC ..................................................... 514/210.16
See application file for complete search history.

(56) References Cited

U.S. PATENT DOCUMENTS

| | | | |
|---|---|---|---|
| 3,558,618 | A | 1/1971 | Trepanier |
| 4,122,274 | A | 10/1978 | Juby |
| 4,342,870 | A | 8/1982 | Kennis et al. |
| 4,613,603 | A | 9/1986 | Sanofi |
| 5,089,633 | A | 2/1992 | Powers et al. |
| 5,599,816 | A | 2/1997 | Chu et al. |
| 5,627,274 | A | 5/1997 | Kole et al. |
| 5,665,593 | A | 9/1997 | Kole et al. |
| 5,916,808 | A | 6/1999 | Kole et al. |
| 5,916,916 | A | 6/1999 | Hauser et al. |
| 5,976,879 | A | 11/1999 | Kole et al. |
| 6,172,216 | B1 | 1/2001 | Bennett et al. |

(Continued)

FOREIGN PATENT DOCUMENTS

| | | |
|---|---|---|
| CN | 101360738 A | 2/2009 |
| CN | 102971311 A | 3/2013 |

(Continued)

OTHER PUBLICATIONS

Potkin et al., "New directions in therapeutics for Huntington disease", Future Neurology, vol. 13(2):101-121, May 2018.
Wermuth, "The Practice of Medicinal Chemistry", 2nd ed., 2003, Chapters 9-10.
H. Kubinyi, "3D QSAR in Drug Design—Theory Methods and Applications", pp. vii-ix and pp. 243-244, 1998.
MacDonald et al., "Quantification Assays for Total and Polyglutamine-Expanded Huntingtin Proteins", PLOS One, 2014, vol. 9(5), dated May 2014, e96854, pp. 1-17.

(Continued)

*Primary Examiner* — Kahsay Habte
(74) *Attorney, Agent, or Firm* — Hoffmann & Baron, LLP

(57) ABSTRACT

The present description relates to compounds, forms, and pharmaceutical compositions thereof and methods of using such compounds, forms, or compositions thereof for treating or ameliorating Huntington's disease.

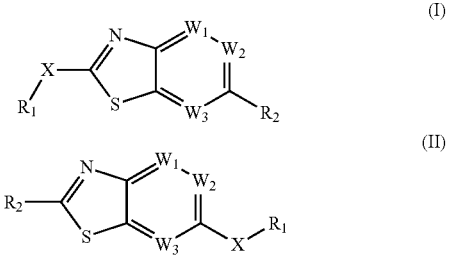

In particular, the present description relates to substituted benzothiazole compounds of Formula (I), forms and pharmaceutical compositions thereof and methods of using such compounds, forms, or compositions thereof for treating or ameliorating Huntington's disease.

9 Claims, No Drawings

(56) References Cited

U.S. PATENT DOCUMENTS

| | | |
|---|---|---|
| 6,210,892 B1 | 4/2001 | Bennett et al. |
| 6,214,986 B1 | 4/2001 | Bennett et al. |
| 6,468,607 B1 | 10/2002 | Takehara et al. |
| 6,630,488 B1 | 10/2003 | Lamothe et al. |
| 6,977,255 B2 | 12/2005 | Robertson et al. |
| 7,326,711 B2 | 2/2008 | Wang et al. |
| 7,399,767 B2 | 7/2008 | Zhang et al. |
| 7,473,784 B2 * | 1/2009 | Liu .................. A61P 29/00 548/161 |
| 7,569,337 B2 | 8/2009 | Auberson |
| 7,576,110 B2 | 8/2009 | Cowart et al. |
| 7,655,657 B2 | 2/2010 | Stoner et al. |
| 7,897,792 B2 | 3/2011 | Iikuea et al. |
| 7,910,578 B2 | 3/2011 | Peters et al. |
| 8,143,274 B2 | 3/2012 | Hattori et al. |
| 8,314,119 B2 | 11/2012 | Schrimpf et al. |
| 8,337,941 B2 | 12/2012 | Gubernator et al. |
| 8,563,550 B2 | 10/2013 | Pevarello et al. |
| 8,633,019 B2 | 1/2014 | Paushkin et al. |
| 8,765,747 B2 | 7/2014 | Choi et al. |
| 8,846,661 B2 | 9/2014 | Schrimpf et al. |
| 8,921,361 B2 | 12/2014 | Cmiljanovic et al. |
| 8,940,716 B2 | 1/2015 | Ye et al. |
| 9,340,537 B2 | 5/2016 | Furet et al. |
| 9,371,336 B2 | 6/2016 | Lee et al. |
| 9,399,649 B2 | 7/2016 | Chen et al. |
| 9,617,268 B2 | 4/2017 | Woll et al. |
| 9,969,754 B2 | 5/2018 | Ratni et al. |
| 2002/0099208 A1 | 7/2002 | Yu et al. |
| 2003/0004164 A1 | 1/2003 | Bebbington et al. |
| 2003/0199526 A1 | 10/2003 | Choquette et al. |
| 2004/0224952 A1 | 11/2004 | Cowart et al. |
| 2005/0054836 A1 | 3/2005 | Krainer et al. |
| 2005/0074801 A1 | 4/2005 | Monia et al. |
| 2005/0159597 A1 | 7/2005 | Ji et al. |
| 2006/0172962 A1 | 8/2006 | Vickers et al. |
| 2006/0205741 A1 | 9/2006 | Zhang et al. |
| 2007/0078144 A1 | 4/2007 | Stockwell et al. |
| 2007/0105807 A1 | 5/2007 | Sazani et al. |
| 2007/0191374 A1 | 8/2007 | Hodgetts |
| 2008/0171792 A1 | 7/2008 | Jobdevairakkam et al. |
| 2008/0255162 A1 | 10/2008 | Bruendl et al. |
| 2009/0163464 A1 | 6/2009 | Black et al. |
| 2009/0163515 A1 | 6/2009 | Birault et al. |
| 2009/0170793 A1 | 7/2009 | Gaur |
| 2009/0264433 A1 | 10/2009 | Russell et al. |
| 2010/0004233 A1 | 1/2010 | Iikura et al. |
| 2010/0035279 A1 | 2/2010 | Gubernator et al. |
| 2010/0267721 A1 | 10/2010 | Hohlweg et al. |
| 2011/0086833 A1 | 4/2011 | Paushkin et al. |
| 2011/0118289 A1 | 5/2011 | Giordani et al. |
| 2012/0083495 A1 | 4/2012 | Heemskerk et al. |
| 2013/0046093 A1 | 2/2013 | Lee et al. |
| 2014/0051672 A1 | 2/2014 | Cheung et al. |
| 2014/0121197 A1 | 5/2014 | Burli et al. |
| 2014/0206661 A1 | 7/2014 | Axford et al. |
| 2014/0329825 A1 | 11/2014 | Heback et al. |
| 2015/0005289 A1 | 1/2015 | Qi et al. |
| 2015/0018301 A1 | 1/2015 | Lee et al. |
| 2015/0057218 A1 | 2/2015 | Zhong et al. |
| 2015/0080383 A1 | 3/2015 | Yang et al. |
| 2015/0119380 A1 | 4/2015 | Woll et al. |
| 2016/0244762 A1 | 8/2016 | Vorechovsky et al. |
| 2017/0000794 A1 | 1/2017 | Naryshkin |
| 2017/0001995 A1 | 1/2017 | Metzger et al. |
| 2017/0002016 A1 | 1/2017 | Shishido et al. |
| 2017/0096411 A1 | 4/2017 | Vechorkin et al. |
| 2017/0121197 A1 | 5/2017 | Tale |
| 2017/0151225 A1 | 6/2017 | Dahl |
| 2017/0355989 A1 | 12/2017 | Konstantinova et al. |
| 2018/0118748 A1 | 5/2018 | Slaugenhaupt et al. |
| 2018/0161456 A1 | 6/2018 | Naryshkin et al. |
| 2018/0282347 A1 | 10/2018 | Arlt et al. |
| 2019/0264267 A1 | 8/2019 | Yang et al. |
| 2020/0056173 A1 | 2/2020 | Vargeese et al. |
| 2020/0080083 A1 | 3/2020 | Vargeese et al. |

FOREIGN PATENT DOCUMENTS

| | | | |
|---|---|---|---|
| CN | 103533835 A | 1/2014 | |
| CN | 101426772 A | 5/2014 | |
| CN | 104768960 B | 3/2017 | |
| DE | 2345064 A1 | 4/1974 | |
| EP | 1227084 A1 | 7/2002 | |
| EP | 2560008 A2 | 2/2013 | |
| EP | 2841428 B1 | 8/2018 | |
| FR | 2914188 A1 | 10/2008 | |
| GB | 1047935 | 11/1966 | |
| GB | 1383409 | 2/1975 | |
| JP | 1981-150091 A | 3/1983 | |
| JP | S61-36282 | 2/1986 | |
| JP | 2006219453 A | 8/2006 | |
| JP | 2009-508957 A | 3/2009 | |
| JP | 2009-545540 | 12/2009 | |
| JP | 2012-530071 A | 11/2012 | |
| JP | 2013-40945 | 2/2013 | |
| JP | 2017-512834 | 5/2017 | |
| JP | 2017-533237 A | 11/2017 | |
| WO | 1993/023398 A1 | 11/1993 | |
| WO | 1994/026887 A1 | 11/1994 | |
| WO | 1996/039407 A1 | 12/1996 | |
| WO | 1998/025930 A1 | 6/1998 | |
| WO | 2001/053266 A1 | 7/2001 | |
| WO | 2002/062290 A2 | 8/2002 | |
| WO | 2002/087589 A1 | 11/2002 | |
| WO | 2004/009558 A1 | 1/2004 | |
| WO | 2004/019002 A2 | 3/2004 | |
| WO | 2004/029053 A1 | 4/2004 | |
| WO | 2004/043458 A1 | 5/2004 | |
| WO | 2004/113335 A2 | 12/2004 | |
| WO | 2005/012288 A1 | 2/2005 | |
| WO | 2005/019215 A1 | 3/2005 | |
| WO | 2005/061513 A1 | 7/2005 | |
| WO | 2005/066166 A2 | 7/2005 | |
| WO | 2005/072720 A1 | 8/2005 | |
| WO | 2005/105801 A1 | 11/2005 | |
| WO | 2006/131835 A2 | 12/2006 | |
| WO | 2006/138418 A2 | 12/2006 | |
| WO | 2007/003604 A2 | 1/2007 | |
| WO | 2007/018738 A1 | 2/2007 | |
| WO | WO-2007016392 A2 * | 2/2007 | ........... C07D 417/04 |
| WO | 2007/047913 A2 | 4/2007 | |
| WO | 2007/056580 A2 | 5/2007 | |
| WO | 2007/065892 A1 | 6/2007 | |
| WO | 2007/071055 A1 | 6/2007 | |
| WO | 2007/089584 A2 | 8/2007 | |
| WO | 2007/089611 A2 | 8/2007 | |
| WO | 2007/090073 A2 | 8/2007 | |
| WO | 2007/109211 A2 | 9/2007 | |
| WO | WO-2007110364 A1 * | 10/2007 | ........... C07D 263/58 |
| WO | 2007/130383 A2 | 11/2007 | |
| WO | 2007/133561 A2 | 11/2007 | |
| WO | 2007/133756 A2 | 11/2007 | |
| WO | 2007/135121 A1 | 11/2007 | |
| WO | 2008/011109 A2 | 1/2008 | |
| WO | 2008/014822 A1 | 2/2008 | |
| WO | 2008/020302 A2 | 2/2008 | |
| WO | 2008/049864 A1 | 5/2008 | |
| WO | 2008/077188 A1 | 7/2008 | |
| WO | 2009/042907 A1 | 4/2009 | |
| WO | 2009/085945 A1 | 7/2009 | |
| WO | 2009/114874 A2 | 9/2009 | |
| WO | 2009/126635 A1 | 10/2009 | |
| WO | 2009/151546 A2 | 12/2009 | |
| WO | 2009/156861 A2 | 12/2009 | |
| WO | 2010/000032 A1 | 1/2010 | |
| WO | 2010/019236 A1 | 2/2010 | |
| WO | 2010/024903 A1 | 3/2010 | |
| WO | 2010/045303 A2 | 4/2010 | |
| WO | 2010/071819 A1 | 6/2010 | |
| WO | 2010/093425 A1 | 8/2010 | |
| WO | 2010/130934 A2 | 11/2010 | |

(56) References Cited

FOREIGN PATENT DOCUMENTS

| | | |
|---|---|---|
| WO | 2010/145208 A1 | 12/2010 |
| WO | 2011/032045 A1 | 3/2011 |
| WO | 2011/050245 A1 | 4/2011 |
| WO | 2011/057204 A2 | 5/2011 |
| WO | 2011/062853 A1 | 5/2011 |
| WO | 2011/085990 A1 | 7/2011 |
| WO | 2011/097641 A1 | 8/2011 |
| WO | 2011/097643 A1 | 8/2011 |
| WO | 2011/097644 A2 | 8/2011 |
| WO | 2012/012467 A2 | 1/2012 |
| WO | 2012/019106 A2 | 2/2012 |
| WO | 2012/075393 A2 | 6/2012 |
| WO | 2012/103806 A1 | 8/2012 |
| WO | 2012/104823 A2 | 8/2012 |
| WO | 2012/109395 A1 | 8/2012 |
| WO | 2012/116965 A1 | 9/2012 |
| WO | 2013/019938 A1 | 2/2013 |
| WO | 2013/020993 A1 | 2/2013 |
| WO | 2013/022990 A1 | 2/2013 |
| WO | 2013/033223 A1 | 3/2013 |
| WO | 2013/059606 A1 | 4/2013 |
| WO | 2013/068769 A1 | 5/2013 |
| WO | 2013/101974 A1 | 7/2013 |
| WO | 2013/112788 A1 | 8/2013 |
| WO | 2013/119916 A1 | 8/2013 |
| WO | 2013/130689 A1 | 9/2013 |
| WO | 2013/142236 A1 | 9/2013 |
| WO | 2013/151877 A1 | 10/2013 |
| WO | 2013/163190 A1 | 10/2013 |
| WO | 2014/012050 A2 | 1/2014 |
| WO | 2014/028459 A1 | 2/2014 |
| WO | 2014/059341 A2 | 4/2014 |
| WO | 2014/059356 A2 | 4/2014 |
| WO | 2014/066836 A1 | 5/2014 |
| WO | 2014/069675 A1 | 5/2014 |
| WO | 2014/116845 A1 | 7/2014 |
| WO | 2014/121287 A2 | 8/2014 |
| WO | 2014/135244 A1 | 9/2014 |
| WO | 2014/184163 A1 | 11/2014 |
| WO | 2014/209841 A2 | 12/2014 |
| WO | 2015/024876 A2 | 12/2014 |
| WO | 2015/017589 A1 | 2/2015 |
| WO | 2015/095446 A1 | 6/2015 |
| WO | 2015/095449 A1 | 6/2015 |
| WO | 2015/105657 A1 | 7/2015 |
| WO | 2015/107425 A2 | 7/2015 |
| WO | 2015/107494 A1 | 7/2015 |
| WO | 2015/110446 A1 | 7/2015 |
| WO | 2017/080967 A1 | 7/2015 |
| WO | 2015/143185 A1 | 9/2015 |
| WO | 2015/173181 A1 | 11/2015 |
| WO | 2015/197503 A1 | 12/2015 |
| WO | 2016/071283 A1 | 5/2016 |
| WO | 2016/087417 A1 | 6/2016 |
| WO | 2016/128343 A1 | 8/2016 |
| WO | 2016/131776 A2 | 8/2016 |
| WO | 2016/144351 A1 | 9/2016 |
| WO | 2016/170163 A1 | 10/2016 |
| WO | 2016/184832 A1 | 11/2016 |
| WO | 2017/023987 A1 | 2/2017 |
| WO | 2017/081111 A1 | 5/2017 |
| WO | 2017/097728 A1 | 6/2017 |
| WO | 2017/100726 A1 | 6/2017 |
| WO | 2017/153601 A1 | 9/2017 |
| WO | 2017/175068 A1 | 10/2017 |
| WO | 2017/189829 A1 | 11/2017 |
| WO | 2017/210134 A1 | 12/2017 |
| WO | 2018/013770 A1 | 1/2018 |
| WO | 2018/081091 A1 | 5/2018 |
| WO | 2018/187209 A1 | 10/2018 |
| WO | 2018/218133 A1 | 11/2018 |
| WO | 2018/226622 A1 | 12/2018 |
| WO | 2019/005980 A1 | 1/2019 |
| WO | 2019/005993 A1 | 1/2019 |
| WO | 2019/028440 A1 | 2/2019 |
| WO | 2019/165073 A1 | 8/2019 |
| WO | 2019/183364 A1 | 9/2019 |
| WO | 2019/183367 A1 | 9/2019 |
| WO | 2019/191092 A1 | 10/2019 |
| WO | 2019/191229 A1 | 10/2019 |
| WO | 2020/005873 A1 | 1/2020 |
| WO | 2020/005877 A1 | 1/2020 |
| WO | 2020/005882 A1 | 1/2020 |
| WO | 2020/190793 A1 | 9/2020 |
| WO | 2020/231977 A1 | 11/2020 |
| WO | 2021/007378 A1 | 1/2021 |
| WO | 2021/084495 A1 | 5/2021 |
| WO | 2021/207453 A1 | 10/2021 |
| WO | 2022/103980 A1 | 5/2022 |
| WO | 2023/009816 A1 | 2/2023 |

OTHER PUBLICATIONS

Palacino et al., "SMN2 splice modulators enhance U1-pre-mRNA association and rescue SM0A mice", Nature: Chemical Biology, pp. 511-517 and 5 Supplemental pp. S1-S20, vol. 11, Jun. 1, 2015.

Pryor et al., "Huntingtin promotes mTORC1 signaling in the pathogenesis of Huntington's disease", Sci. Signal, dated Oct. 28, 2014, vol. 7, Issue 349, ra103, pp. 1-12.

Brunhilde Wirth et al., "Moving towards treatments for spinal muscular atrophy: hopes and limits", Expert Opinion on Emerging drugs, 20(3):353-356, Apr. 28, 2015.

Chiara Zanetta et al., "Molecular Therapeutic Strategies for Spinal Muscular Atrophies: Current and Future Clinical Trials", Clinical Therapeutics, 36(1):128-140, Dec. 17, 2013.

Coady et al., 2010, "Trans-splicing-mediated improvement in a severe mouse model of spinal muscular atrophy", J. Neurosci., vol. 30(1), pp. 126-130, 2010.

Combring et al., "Respiratory syncytial virus fusion inhibitors. Part 6: An examination of the effect of structural variation for the benzimidazol-2-one heterocycle moiety", Bioorganic & Medicinal Chemistry Letters, 17(17):4784-4790, Aug. 4, 2007.

European Patent Office, Communication pursuant to Article 94(3) EPC, European Application No. 14877918.4, dated Mar. 23, 2018.

Greene, Protective Groups in Organic Syntehsis, 1991, Wiley, New York, pp. v-xxi and 1-17.

Higuchi and W. Stella, "Pro-drugs as novel delivery systems", vol. 14 of the A.C.S., Symposium Series and in Bioreversible Carriers in Drug Design, ed., Edward B. Roche, American Pharmaceutical Association and Pergamon Press (1975).

Hua et al., "Peripheral SMN restoration is essential or long-term rescue of a severe SMA mouse model", Nature, vol. 478(7367), pp. 123-126, 2012.

Jarecki et al., "Diverse small-molecule modulators of SMN expression found by high-throughput compound screening: early leads towards a therapeutic for spinal muscular atrophy", Human molecular genetics, 14(14):2003-2018, 2005.

Knight et al., "Isoform-specific phosphoinositide 3-kinase inhibitors from an arylmorpholine scaffold", Bioorganic & Medicinal Chemistry, vol. 12(17):4749-4759, 2004.

Kocar, Transformations of 3-aminopyridazines. Synthesis of 4-oxo-4H-pyrimido [1,2-b]pyridazine and 1-(substituted pyridazin-3-yl)-1H-1,2,3-triazole derivatives, Arkivoc, vol. 8, 2002, 143-156.

Le et al., "SMND7, the major product of the centromeric survival motor neuron (SMN2) gene, extends survival in mice with spinal muscular atrophy and associates with full-length SMN", Human Molecular Genetics, vol. 14(5), pp. 845-857, 2005.

Liu et al., "A novel nuclear structure containing the survival of motor neurons protein", EMBO J. vol. 15(14), pp. 3555-3565 (1996).

Makhortova et al., "A screen for regulators of survival of motor neuron proteins levels", Nature chemical biology, vol. 7 (8):544-552, 2011.

Markus Riessland et al., "The benzamide M344, a novel histone deacetylase inhibitor, significantly increases SMN2 RNA/protein levels in spinal muscular atrophy cells", Hum Genet 120:101-110, May 26, 2006.

(56) References Cited

OTHER PUBLICATIONS

Naryshkin et al., "SMN2 splicing modifiers improve motor function and longevity in mice with spinal muscular atrophy", Science, vol. 345(6197):688-693, 2014 (including supplementary materials).

Passini et al., "Antisense Oligonucleotides delivered to the mouse CNS ameliorate symptoms of severe spinal muscular atrophy", Sci Transl. Med., vol. 3(72), 2001.

Peng, Lijie et al., "Identification of pyrido[1,2-alpha]pyrimidine-4-ones as new molecules improving the transcriptional functions of estrogen-related receptor alpha", Journal of medicinal chemistry, vol. 54(21):7729-7733, 2011.

PubChem/NCBI Database accession No. CID 377422 [online], 2005, retrieved on Jul. 4, 2016, URL http://pubchem.nci.nlm.nih.gov/compound/377422.

Seisuke Mimori et al., "Protective Effects of 4-phenylbutyrate derivatives on the neuronal cell death and endoplasmic reticulum stress," Biological & Pharmaceutical Bulletin of Japan, 35(1):84-90, Jan. 1, 2012.

Shao, Ning et al., "Synthesis and structure-activity relationship (SAR) study of 4-azabenzoxazole analogues as H3 antagonists", Bioorganic & Medicinal chemistry letters, vol. 22(5):2075-2078, 2012.

Sin et al., "Respiratory syncytial virus fusion inhibitors. Part 7: Structure-activity relationships associated with a series of isatin oximes that demonstrate antiviral activity in vivo", Bioorganic & Medicinal Chemistry Letters, 19(16):4857-4862, Aug. 15, 2009.

Yuo et al., 2008, "5-(N-ethyl-N-isopropyl)-amiloride enhances SMN2 exon 7 inclusion and protein expression in spinal muscular atrophy cells", Annals of neurology, vol. 63(1):26-34, 2008.

Lazarev et al., "Factors Affecting Aggregate Formation in Cell Models of Huntington's Disease and Amyotrophic Lateral Sclerosis", Acta Naturae, vol. 5(2):81-89, Apr. 2013.

International Search Report for PCT/US2018/035954, dated Oct. 1, 2018.

Written Opinion of the International Searching Authority for PCT/US2018/035954, dated Oct. 1, 2018.

International Search Report for PCT/US2018/039775, dated Oct. 29, 2018.

Written Opinion of the International Searching Authority for PCT/US2018/039775, dated Oct. 29, 2018.

International Search Report in PCT/US2016/066042, dated Mar. 16, 2017.

Written Opinion of the International Searching Authority for PCT/US2016/066042, dated Mar. 16, 2017.

International Search Report for PCT/US2019/024068, dated Jul. 10, 2019.

Written Opinion of the International Searching Authority for PCT/US2019/024068, dated Jul. 10, 2019.

International Search Report for PCT/US2019/024278, dated May 28, 2019.

Written Opinion of the International Searching Authority for PCT/US2019/024278, dated May 28, 2019.

International Search Report for PCT/EP2012/065499, dated Sep. 28, 2012.

Written Opinion of the International Searching Authority for PCT/EP2012/065499, dated Sep. 28, 2012.

International Search Report for PCT/EP2014/059699, dated Aug. 25, 2014.

Written Opinion of the International Searching Authority for PCT/EP2014/059699, dated Aug. 25, 2014.

International Search Report for PCT/EP2015/051066, dated Feb. 19, 2015.

Written Opinion of the International Searching Authority for PCT/EP2015/051066, dated Feb. 19, 2015.

International Search Report for PCT/EP2015/060343, dated Jul. 13, 2015.

Written Opinion of the International Searching Authority for PCT/EP2015/060343, dated Jul. 13, 2015.

International Search Report for PCT/EP2016/060952, dated Jun. 29, 2016.

Written Opinion of the International Searching Authority for PCT/EP2016/060952, dated Jun. 29, 2016.

International Search Report for PCT/EP2016/063894, dated Jan. 19, 2017.

Written Opinion of the International Searching Authority for PCT/EP2016/063894, dated Jan. 19, 2017.

Chloé Copin et al, "SnAr versus Buchwald-Hartwig Amination/Amidation in the Imidazo[2,1-b][1,3,4]thiadiazole Series", European Journal of Organic Chemistry, vol. 2015(31), Sep. 29, 2015, p. 6932-6942.

Database Registry, Chemical Abstracts Service, Feb. 22, 2018, Database Accession No. 2178867-25-7.

Database Registry, Chemical Abstracts Service, Sep. 18, 2017, Database Accession No. 2128311-64-6.

Database Registry, Chemical Abstracts Service, Sep. 24, 2017, Database Accession No. 2130300-22-8.

Database Registry, Chemical Abstracts Service, Sep. 25, 2017, Database Accession No. 2130694-60-7.

Fascio Mirta L et al, "Synthesis and antiviral activity of some imidazo[1,2-b][1,3,4]thiadiazole carbohydrate derivatives", Carbohydrate Research,vol. 480, May 21, 2019 , p. 61-66.

Ingo Knepper et al., "3-Acylindoles as versatile starting materials for pyridine ring annulation: synthesis of 1-deazapurine isosteres", Tetrahedron,vol. 67(29):5293-5303, May 14, 2011.

K.K. Abdul Khader et al., "Regioselective synthesis of C-2 substituted imidazo[4,5-b]pyridines utilizing palladium catalysed C—N bond forming reactions with enolizable heterocy", Tetrahedron Letters, vol. 55(10):1778-1783, Feb. 1, 2014.

Mariusz Mojzych et al., "Synthesis of pyrazolo[4,3-e][1,2,4]triazine sulfonamides, novel Sildenafil analogs with tyrosinase inhibitory activity", Bioorganic & Medicinal Chemistry, vol. 22, pp. 6616-6624, Oct. 18, 2014.

Mazzone G et al, "Sintesi e valutazione biologica preliminare di imidazo[2,1-b]-1,3-4-tiadiazoli-2,6-diarilsostituti", Farmaco, Edizione Scientifica, Societa Chimica Italiana, Pavia, IT,vol. 39(7), Jan. 1, 1984, p. 585-598. English Abstract Only.

Patel Harun M et al, "2,5,6-Trisubstituted imidazo[2,1-b][1,3,4]thiadiazoles: Search for antihyperlipidemnic agents", European Journal of Medicinal Chemistry, Editions Scientifique Elsevier, Paris, FR, vol. 65, Apr. 18, 2013, p. 119-133.

ISR in PCT/US2019/038889, dated Aug. 8, 2019.
WO in PCT/US2019/038889, mailed Aug. 8, 2019.
ISR in PCT/US2019/038895, dated Aug. 14, 2019.
WO in PCT/US2019/038895, mailed Aug. 14, 2019.
ISR in PCT/US19/38900, dated Aug. 20, 2019.
WO in PCT/US19/38900, mailed Aug. 20, 2019.

J. S. Nair et al: "Synthesis and Fluorescence Properties of 3-Benzoxa- and Thiazol-2-ylquinoline-5 or 7-maleimides.", Cheminform, vol. 36, No. 2, Sep. 1, 2004 (Sep. 1, 2004), pp. 1944-1949.

Naik et al: "Studies in the Vilsmeier-Haack reaction: Part XVI., Synthesis of 7-amino-3-hetrarylquinoline fluorophore and derivatives", Indian Journal of Chemistry, Council of Scientific and Industrial Research (CS I R), DE, vol. 15B, No. 6, Jan. 1, 1977 (Jan. 1, 1977), pp. 506-508.

USPTO, Office Action dated Feb. 4, 2021 in U.S. Appl. No. 16/617,450. See whole document in general and compounds on pp. 10-14 and 15-18 in particular.

International Search Report for PCT/EP2016/076905, dated Feb. 9, 2017.

Written Opinion of the International Searching Authority for PCT/EP2016/076905, dated Feb. 9, 2017.

International Search Report for PCT/EP2016/077190, dated Mar. 1, 2017.

Written Opinion of the International Searching Authority for PCT/EP2016/077190, dated Mar. 1, 2017.

International Search Report for PCT/EP2016/079816, dated Jan. 19, 2016.

Written Opinion of the International Searching Authority for PCT/EP2016/079816, dated Jan. 19, 2016.

International Search Report for PCT/US2013/025292, dated Aug. 30, 2013.

Written Opinion of the International Searching Authority for PCT/US2013/025292, dated Aug. 30, 2013.

(56) References Cited

OTHER PUBLICATIONS

International Search Report in PCT/US2018/039794, dated Oct. 25, 2018.
Written Opinion of the International Searching Authority in PCT/US2018/039794, dated Oct. 25, 2018.
International Search Report from PCT/US2020/041300, dated Oct. 16, 2020.
Written Opinion from PCT/US2020/041300, dated Oct. 16, 2020.
Pubchem, Substance Record for SID 249779947, Mar. 31, 2015, "4H-Quinolizin-4-one1; Hydrobromide".
Andreassi, C. et al. 2001. Human Molecular Genetics 10, 2841-2849. "Aclarubicin treatment restores SMN levels to cells derived from type I spinal muscular atrophy patients."
Artursson P., et al. 1991. Biochem Biophys Res Comm 175, 880-5. "Correlation between oral drug absorption in humans and apparent drug permeability coefficients in human intestinal epithelial (Caco-2) cells."
Baldo, B. et al. 2012. J. Biol. Chem. 287, 1406-1414. "A screen for enhancers of clearance identifies huntingtin as a heat shock protein 90 (Hsp90) client protein."
Barbaro, B.A. et al. 2015. Human Molecular Genetics 24, 913-925 (published online Oct. 9, 2014). "Comparative study of naturally occurring huntingtin fragments in *Drosophila* points to exon 1 as the most pathogenic species in Huntington's disease."
Bates, G.P. et al. 2015. Nature Reviews, Disease Primers 1, 15005 (published online Apr. 23, 2015). "Huntington disease."
Bengart, P. et al. 2004. Nucleic Acids Res. 32, W154-W159. "Riboswitch finder—a tool for indentification of riboswitch RNAs."
Bhattacharyya, A. et al. 2007 Drug Discovery Today 12, 553-560. "Mining the GEMS—a novel platform technology targeting post-transcriptional control mechanisms."
Bibillo, A and Eickbush, T.H. 2002. J. Biol. Chem. 277, 34836-34845. "High Processivity of the Reverse Transcriptase from a Non-long Terminal Repeat Retrotransposon."
Carroll, J.B. et al. 2015. Lancet Neurol 14, 1135-1142 (No. 11—Nov. 2015). "Treating the whole body in Huntington's disease."
Cartegni, L. et al. 2003. Nucleic Acids Res. 31, 3568-3571. "ESEfinder: a web resource to identify exonic splicing enhancers."
Crooks, G. E., et al. 2004. Genome Research 14, 1188-1190. "WebLogo: a sequence logo generator."
Daguenet et al. 2015. EMBO reports 16, 1640-1655 (published online Nov. 13, 2015). "The pathogenicity of splicing defects: mechanistic insights into pre-mRNA processing inform novel therapeutic approaches."
DiFiglia, et al 1997. Science 277, 1990-1993. "Aggregation of Huntingtin in Neuronal Intranuclear Inclusions and Dystrophic Neurites in Brain".
Dobin, A. et al. 2013. Bioinformatics 29, 15-21. "STAR: ultrafast universal RNA-seq aligner."
Evers, M.M. et al. 2015. Molecular Neurodegeneration 10, Article No. 21 (published online Apr. 28, 2015). "Making (anti-) sense out of huntingtin levels in Huntington disease."
Fardaei, M. et al. 2002. Human Molecular Genetics 11, 805-814. "Three proteins, MBNL, MBLL and MBXL, co-localize in vivo with nuclear foci of expanded-repeat transcripts in DM1 and DM2 cells."
Fernandez-Nogales, M. et al. 2014. Nature Medicine 20, 881-885. "Huntington's disease is a four-repeat tauopathy with tau nuclear rods."
Gipson, T. A. et al. 2013. RNA Biology 10, 1647-1652. "Aberrantly spliced HTT, a new player in Huntington's disease pathogenesis."
Gray, M. et al. 2008. J. Neurosci. 28, 6182-6195. "Full-length human mutant huntingtin with a stable polyglutamine repeat can elicit progressive and selective neuropathogenesis in BACHD mice."
Griffiths-Jones, S. et al. 2005. Nucleic Acids Res. 33, D121-D124. "Rfam: annotating non-coding RNAs in complete genomes."
Griffiths-Jones, S. et al. 2006. Nucleic Acids Res. 34, D140-D144. "miRBase: microRNA sequences, targets and gene nomenclature."
Grillo, G. et al. 2003. Nucleic Acids Res. 31, 3608-3612. "PatSearch: a program for the detection of patterns and structural motifs in nucleotide sequences."
Grimson, A. et al. 2007. Molecular Cell 27, 91-105. "MicroRNA Targeting Specificity in Mammals: Determinants beyond Seed Pairing."
Heemskerk, J. et al. 2002. Nature Neuroscience Supplement 5, 1027-1029. "From chemical to drug: neurodegeneration drug screening and the ethics of clinical trials."
Heemskerk, J, et al. 2002. Trends Neurosci. 25, 494-496. "Teaching old drugs new tricks."
Heemskerk, J. et al. 2005. Chapter 16—"Therapeutics Development for Hereditary Disorders" in ed. Waxman, S. From Neuroscience to Neurology: Neuroscience, Molecular Medicine, and the Therapeutic Transformation of Neurology, pp. 285-291.
Hernandez-Imas, E. et al. 2015. PLoS One 10, e141735 (published online Oct. 28, 2015). "Functional Analysis of Mutations in Exon 9 of NF1 Revales the Presence of Several Elements Regulating Splicing."
Hodges, A. et al. 2006. Human Molecular Genetics 15, 965-977. "Regional and cellular gene expression changes in human Huntington's disease brain."
Hua et al. 2007. PLoS Biol 5, e73. Enhancement of SMN2 Exon 7 "Inclusion by Antisense Oligonucleotides Targeting the Exon."
Hua et al. 2008. American J. of Human Genetics 82, 834-848. "Antisense Masking of an hnRNP A1/A2 Intronic Splicing Silencer Corrects SMN2 Splicing in Transgenic Mice."
Hughes, A.C. et al. 2014. J. Mol. Biol. 426, 1428-1438. "Identification of Novel Alternative Splicing Events in the Huntingtin Gene and Assessment of the Functional Consequences Using Structural Protein Homology Modelling."
The Huntington's Disease Collaborative Research Group, 1993, Cell, 72, pp. 971-983 (1993). "A novel gene containing a trinucleotide repeat that is expanded and unstable on Huntington's Disease chromosomes."
Janas, A. M. 2015. "A Stem Cell Model of the Motor Circuit Reveals Distinct Requirements for SMN in Motor Neuron Survival and Function."
Jacobs, G.H. et al. 2006. Nucleic Acids Res. 34, suppl_1, D37-D40. "Transterm—extended search facilities and improved integration with other databases."
Kanadia, R.N. et al. 2003. Science 302, 1978-1980. "A Muscleblind Knockout Model for Myotonic Dystrophy."
Kaplan, A. et al. 2012. Prog. Neurobiol. 99(3), 262-280. "Therapeutic approaches to preventing cell death in Huntington disease."
Kim, D. et al. 2013. Genome Biology 14, Article No. R36. "TopHat2: accurate alignment of transcriptomes in the presence of insertions, deletions and gene fusions."
Kordasiewicz, H.B. et al. 2012. Neuron, 74, 1031-1044. "Sustained Therapeutic Reversal of Huntington's Disease by Transient Repression of Huntingtin Synthesis".
Kuhn, A. et al. 2007. Human Molecular Genetics 16, 1845-1861. "Mutant huntingtin's effects on striatal gene expression in mice recapitulate changes observed in human Huntington's disease brain and do not differ with mutant huntingtin length or wild-type huntingtin dosage."
Labadorf, A.T. et al. 2015. Plos One 10(10): e0141298 (published online Oct. 23, 2015). "Evidence of Extensive Alternative Splicing in Post Mortem Human Brain HTT Transcription by mRNA Sequencing." (including supplemental information).
Labadorf, A. et al. 2015. PLoS One 10(12): e0143563 (published online Dec. 4, 2015). "RNA Sequence Analysis of Human Huntington Disease Brain Reveals an Extensive Increase in Inflammatory and Developmental Gene Expression."
Labbadia, J. et al. 2013. Trends Biochem. Sci. 38, 378-385. "Huntington's disease: underlying molecular mechanisms and emerging concepts."
Landles, C. et al. 2010. J. Bio. Chem. 285, 8808-8823. "Protoelysis of Mutant Huntington Produces an Exon 1 Fragment That Accumulates as an Aggregated Protein in Neuronal Nuclei in Huntington Disease."

(56) References Cited

OTHER PUBLICATIONS

Lei, et al. 2005. Nucleic Acids Res 33, 3897-3909. "Exonization of AluYa5 in the human ACE gene requires mutations in both 3' and 5' splice sites and is facilitated by a conserved splicing enhancer."
Liang, Y. et al. 2009. Brain Res. 2009 1286, 221-229. "ATF3 plays a protective role against toxicity by N-terminal fragment of mutant huntingtin in stable PC12 cell line."
Love, M. I. et al. 2014. Genome Biology 15, 550. "Moderated estimation of fold change and dispersion for RNA-seq data with DESeq2."
Lunkes, A. et al. 2002. Molecular Cell 10, 259-269. "Proteases Acting on Mutant Huntingtin Generate Cleaved Products that Differentially Build Up Cytoplasmic and Nuclear Inclusions."
Macke, T.J. 2001. Nucleic Acids Res. 29, 4724-4735. "RNAMotif, an RNA secondary structure definition and search algorithm."
Mahmood, I. et al. 1996. Xenobiotica 26, 887-895. "Interspecies scaling: predicting clearance of drugs in humans. Three different approaches."
Mahmood, I. 2006. Pharm. Sci. 95, 1810-1821. "Prediction of human drug clearance from animal data: Application of the rule of exponents and 'fu corrected intercept method' (FCIM)."
Mahmoudi, S et al. 2010. PLoS Biology 8(11), e10000521. "WRAP53 is Essential for Cajal Body and for Targeting the Survival of Motor Neuron Complex to Cajal Bodies."
Mangiarini, L. 1996. Cell 87, 493-506. "Exon 1 of the HD Gene with an Expanded CAG Repeat Is Sufficient to Cause a Progressive Neurological Phenotype in Transgenic Mice."
Mantione, K.J. et al. 2014. Med. Sci. Monit. Basic Res. 20, 138-141. "Comparing Bioinformation Gene Expression Profiling Methods: Microarray and RNA-Seq."
Mendoza, L.G. et al. 1999. BioTechniques 27, 778-788. "Hight-Throughput Microarray-Based Enzyme-Linked Immunosorbent Assay (ELISA)."
Mielcarek, M. et al. 2014. PLOS Genetics 10: 8 e1004550. "Dysfunction of the CNS-Heart Axis in Mouse Models of Huntington's Disease."
Mignone, F. et al. 2005. Nucleic Acids Res. 33, D141-D146. "UTRdb and UTRsite: a collection of sequences and regulatory motifs of the untranslated regions of eukaryotic mRNAs."
Mort, M. et al. 2015. J. of Huntington's Disease 4(2 of 4), 161-171. "Huntingtin Exists as Multiple Splice Forms in Human Brain."
Neuder, A. et al. 2014. BMC Medical Genomics 7:60. "A common gene expression signature in Huntington's disease patient brain regions."
Paganetti, P. et al. 2009. ChemBioChem 10, 1678-1688. "Development of Method for the High-Throughput Quantification of Cellular Proteins."
Pouladi, M. et al. 2013. Nature Review Neuroscience 14, 709-721. "Choosing an animal model for the study of Huntington's disease."
Ratovitski, T. et al. 2012. Cell Cycle 11, 2006-2021. "Huntingtin protein interactions altered by polyglutamine expansion as determined by quantitative proteomic analysis."
Reiner, A. et al. 2011. International Review of Neurobiology 98, 325-372. "Genetics and neuropathology of Huntington's disease."
Ruzo, A. et al. 2015. PLoS One 10, e0127678 (published online May 26, 2015). "Discovery of Novel Isoforms of Huntingtin Reveals a New Hominid-Specific Exon."
Sadeghian, H. et al. 2011. Arch. Neurol. 68, 650-652. "Huntington Chorea Presenting with Motor Neuron Disease."
Sathasivam, K. et al. 2013. Proc. Natl. Acad. Sci. 110, 2366-2370. "Aberrant splicing of HTT generates the pathogenic exon 1 protein in Huntington disease."
Schilling, G. et al. 2007. J Neuropathol. Exp. Neurol. 66, 313-320. "Characterization of Huntingtin Pathologic Fragments in Human Huntington Disease, Transgenic Mice, and Cell Models."
Schwab, C. et al. 2008. J. Neuropathol Exp Neurol 67, 1159-1165. "Colocalization of Transactivation-Responsive DNA-Binding Protein 43 and Huntingtin in Inclusions of Huntington Disease."
Shlyakhtenko, L.S. et al. 2007. Nanomedicine: Nanotech., Bio., and Med. 3, 192-197. "Single-molecule selection and recovery of structure-specific antibodies using atomic force microscopy."
Southwell, A.L. et al. 2013. Hum. Mol. Genet. 22, 18-34. "A fully humanized transgenic mouse model of Huntington disease."
Stanek, L.M. et al. 2014. Human Gene Therapy 25, 461-474. "Silencing Mutant Huntingtin by Adeno-Associated Virus-Mediated RNA Interference Ameliorates Disease Manifestations in the YAC128 Mouse Model of Huntington's Disease."
Stoilov, P. et al. 2008. Proc. Natl. Acad. Sci. 105, 11218-11223. "A high-throughput screening strategy identifies cardiotonic steroids as alternative splicing modulators."
Taylor et al. 1999. Nat. Biotechnol. 17, 1097-1100 "Induction of endogenous Bcl-xS through the control of Bcl-x pre-mRNA splicing by antisense oligonucleotides."
Van der Burg, J.M.M. et al. 2009. The Lancet (Neurology) 8, 765-774. "Beyond the brain: widespread pathology in Huntington's disease."
Varma, H. et al. 2008. Comb Chem High Throughput Screen 11, 238-248. "High Throughput Screening for Neurodegeneration and Complex Disease Phenotypes."
Vickers et al., 2006. J. Immunol. 176, 3652-3661 "Modification of MyD88 mRNA splicing and inhibition of IL-1beta signaling in cell culture and in mice with a 2'-O-methoxyethyl-modified oligonucleotide."
Wachter, A. 2014. Trends in Genetics 30, 172-181. "Gene regulation by structured mRNA elements."
Weiland, M. et al. 2012. Methods 56, 351-357. "Engineering of ribozyme-based riboswitches for mammalian cells."
Wild, E.J. et al. 2014. Movement Disorders 29, 1434-1445. "Targets for Future Clinical Trials in Huntington's Disease: What's in the Pipeline?"
Wilton et al. 1999. Neuromuscul. Disord. 9, 330-338. "Specific removal of the nonsense mutation from the mdx dystrophin mRNA using antisense oligonucleotides."
Xiong, H.Y. et al. 2015. Science 347, 1254806 (published online Dec. 18, 2014.) "The human splicing code reveals new insights into the genetic determinants of disease."
Yen, L. et al. 2004. Nature 431, 471-6. "Exogenous control of mammalian gene expression through modulation of RNA self-cleavage."
Yeo, G. et al. 2004. J. Comput. Biol. 11, 377-394. "Maximum entropy modeling of short sequence motifs with applications to RNA splicing signals."
Younis et al. 2010. Molecular and Cellular Biology 30, 1718-1728. "Rapid-Response Splicing Reporter Screens Identify Differential Regulators of Constitutive and Alternative Splicing."
Yu, S. et al. 2014. Trends in Pharmacological Sci. 35, 53-62. "Drugging unconventional targets: insights from Huntington's disease."
Zona, S. et al. 2014. Biochimica et Biophysica Acta 1839, 1316-1322. "FOXM1: An emerging master regulator of DNA damage response and genotoxic agent resistance."
Nair, A.B. et al. 2016. J. Basic and Clinical Pharmacy 7, 27-31. "A simple and practical guide for dose conversion between animals and human."
Neuder, A. et al. 2017. Scientific Reports 7, 1307 (published online May 2, 2017). "The pathogenic exon 1 HTT protein is produced by incomplete splicing in Huntington's disease patients."
Nopoulos, P. C. 2016. Dialogues Clin Neurosci 18, 91-98. "Huntington disease: a single-gene degenerative disorder of the striatum."
Ratni, H. et al. 2016. J. Med. Chem. 59, 6086-6100. "Specific Correction of Alternative Survival Motor Neuron 2 Splicing by Small Molecules: Discovery of a Potential Novel Medicine To Treat Spinal Muscular Atrophy."
Rüb, U. et al. 2016. Brain Pathol. 26, 726-740. "Huntington's disease (HD): the neuropathology of a multisystem neurodegenerative disorder of the human brain."
Saudou, F. et al. 2016. Neuron 89, 910-926. "The Biology of Huntingtin."
Wang, G. et al. 2016. Proc. Natl. Acad. Sci. 113, 3359-3364. "Ablation of huntingtin in adult neurons is nondeleterious but its depletion in young mice causes acute pancreatitis."

(56) References Cited

OTHER PUBLICATIONS

Woll, M.G. et al. 2016. J. Med. Chem. 59, 6070-6085. "Discovery and Optimization of Small Molecule Splicing Modifiers of Survival Motor Neuron 2 as a Treatment for Spinal Muscular Atrophy."
International Search Report for PCT/US20/32446, dated Jul. 7, 2020.
Written Opinion of the International Searching Authority in PCT/US20/32446, dated Jul. 7, 2020.
Chemical Abstracts Registry No. 2107242-04-04, indexed in the Registry file on STN CAS Online Aug. 2, 2017. (Year: 2017).
Daldin et al., "Polyglutamine expansion affects huntingtin conformation in multiple Huntington's disease models", Scientific Reports, vol. 7, 15 pages, 2017.
Gleave et al., "Synthesis and evaluation of 3-amino-6-aryl-pyridazines as selective CB2 agonists for the treatment of inflammatory pain", Bioorganic & Medicinal Chemistry Letters, vol. 20, pp. 465-468, 2010.
Kaida et al., "U1 snRNP protects pre-mRNAs from premature cleavage and polyadenylation"; Nature, vol. 468, pp. 664-669; Dec. 2, 2010.
Ross & Tabrizi, "Huntington's disease: from molecular pathogenesis to clinical treatment"; The Lancet Neurology, vol. 10, pp. 83-98, Jan. 2011.
Wang et al., "Mechanism of alternative splicing and its regulation (Review)", Biomedical Reports, vol. 3, pp. 152-158, 2015.
Berg, J.M., Tymoczko, J.L., & Stryer, L., *Biochemistry* ($5^{th}$ ed.), p. 798, 2002.
Opposition in European Patent No. 3,386,511, Feb. 25, 2022, 29 pages.
Bhattacharyya et al., Small molecule splicing modifiers with systemic HTT-lowering activity Nature Communications 12(7299), 2021.
Boudreau et al., 2009. "Nonallele-Specific Silencing of Mutant and Wild-Type Huntingtin Demonstrates Therapeutic Efficacy in Huntington"s Disease Mice. Molecular Therapy: The Journal of the American Society of Gene Therapy 17 (6): 1053-63.
Campagne et al., 2019. "Structural Basis of a Small Molecule Targeting RNA for a Specific Splicing Correction." Nature Chemical Biology 15 (12): 1191-98, 2019.
Connelly et al., 2016. "The Emerging Role of RNA as a Therapeutic Target for Small Molecules." Cell Chemical Biology 23 (9): 1077-90.
Effenberger et al., 2016. "Modulating Splicing with Small Molecular Inhibitors of the Spliceosome." Wiley Interdisciplinary Reviews. RNA 8 (2). https://doi.org/10.1002/wrna.1381.
Holste et al., 2008. "Strategies for Identifying RNA Splicing Regulatory Motifs and Predicting Alternative Splicing Events." PLoS Computational Biology 4 (1): e21.
Marxreiter et al., 2020. "Huntington Lowering Strategies." International Journal of Molecular Sciences 21 (6).
Mount et al., A catalogue of splice junction sequences Nucleic Acids Research 10(2):459-472 (Jan. 22, 1982).
Nishigaki et al., Syntheses of 9-Deazatheophyllines and 6-Deoxy-9-deazatheophyllines Chemical and Pharmaceutical Bulletin 28(5):1636-1641 (1980).
Ratni et al., Discovery of Risdiplam, a Selective Survival of Motor Neuron-2 (SMN2) Gene Splicing Modifier . . . , Journal of Medicinal Chemistry, 61(15), 6501-6517 (2018).
Ritz et al., Dose-Response Analysis Using R PLos ONE 10(12) (Dec. 30, 2015).
Romo et al., 2018. "A Fresh Look at Huntington mRNA Processing in Huntington" s Disease. "Journal of Huntington" s Disease 7 (2): 101-8.
Schilling Judith, Meike Broemer, Ilian Atanassov, Yvonne Duernberger, Ina Vorberg, Christoph Dieterich, Alina Dagane, et al. 2019. "Deregulated Splicing Is a Major Mechanism of RNA-Induced Toxicity in Huntington" s Disease. Journal of Molecular Biology 431 (9): 1869-77.
Sibley et al., 2016. "Lessons from Non-Canonical Splicing." Nature Reviews. Genetics 17 (7): 407-21.

Sivaramakrishnan et al., Binding to SMN2 pre-mRNA-protein complex elicits specificity for small molecule splicing modifiers Nature Communications 8(1) (Nov. 2017).
Southwell et al. 2018. "Huntingtin Suppression Restores Cognitive Function in a Mouse Model of Huntington" s Disease. Science Translational Medicine (10) 1-12.
Southwell et al. 2017. "A Novel Humanized Mouse Model of Huntington Disease for Preclinical Development of Therapeutics Targeting Mutant Huntingtin Alleles." Human Molecular Genetics 26 (6): 1115-32.
Tabrizi et al., Huntington Lowering Strategies for Disease Modification in Huntington's Disease J. Neuron 101(5):801-819 (Mar. 6, 2019).
Wild et al., 2017. "Therapies Targeting DNA and RNA in Huntington" s Disease. Lancet Neurology 16 (10): 837-47.
International Search Report in PCT/US2021/059010, dated Apr. 26, 2022.
Written Opinion of the International Searching Authority in PCT/US2021/059010, dated Apr. 26, 2022.
Reply to Opposition in European Patent No. 3,386,511, Jul. 7, 2022, 427 pages.
EPO Board Communication in Opposition in European Patent No. 3,386,511, Oct. 18, 2022, 12 pages.
International Search Report in PCT/US2021/026316, dated Aug. 5, 2021.
Written Opinion of the International Searching Authority in PCT/US2021/026316, dated Aug. 5, 2021.
Burli et al., "Design, Synthesis, and Biological Evaluation of Potent and Selective Class IIa Histone Deacetylase (HDAC) Inhibitors as a Potential Therapy for Huntington's Disease", Journal of Medicinal Chemistry, vol. 56, pp. 9934-9954, 2013.
Chemical Abstracts Registry No. 1381103-87-2, indexed in the Registry file on STN CAS Online Jul. 4, 2012. (Year: 2012).
Chemical Abstracts Registry No. 1381109-95-0, indexed in the Registry file on STN CAS Online Jul. 4, 2012. (Year: 2012).
Chemical Abstracts Registry No. 1381103-06-5, indexed in the Registry file on STN CAS Online Jul. 4, 2012. (Year: 2012).
Chemical Abstracts Registry No. 1381085-12-6, indexed in the Registry file on STN CAS Online Jul. 4, 2012. (Year: 2012).
Chemical Abstracts Registry No. 1381084-38-3, indexed in the Registry file on STN CAS Online Jul. 4, 2012. (Year: 2012).
Chemical Abstracts Registry No. 1381084-19-0, indexed in the Registry file on STN CAS Online Jul. 4, 2012. (Year: 2012).
Chemical Abstracts Registry No. 1381069-02-8, indexed in the Registry file on STN CAS Online Jul. 4, 2012. (Year: 2012).
Chemical Abstracts Registry No. 1381060-23-6, indexed in the Registry file on STN CAS Online Jul. 4, 2012. (Year: 2012).
Chemical Abstracts Registry No. 1381036-73-2, indexed in the Registry file on STN CAS Online Jul. 4, 2012. (Year: 2012).
Chemical Abstracts Registry No. 1381033-11-9, indexed in the Registry file on STN CAS Online Jul. 4, 2012. (Year: 2012).
Chemical Abstracts Registry No. 1381016-89-2, indexed in the Registry file on STN CAS Online Jul. 4, 2012. (Year: 2012).
Chemical Abstracts Registry No. 1381016-41-6, indexed in the Registry file on STN CAS Online Jul. 4, 2012. (Year: 2012).
Chemical Abstracts Registry No. 1381013-97-3, indexed in the Registry file on STN CAS Online Jul. 4, 2012. (Year: 2012).
Chemical Abstracts Registry No. 1380991-96-7, indexed in the Registry file on STN CAS Online Jul. 4, 2012. (Year: 2012).
Chemical Abstracts Registry No. 1380991-09-2, indexed in the Registry file on STN CAS Online Jul. 4, 2012. (Year: 2012).
Chemical Abstracts Registry No. 1380955-66-7, indexed in the Registry file on STN CAS Online Jul. 4, 2012. (Year: 2012).
Chemical Abstracts Registry No. 1380889-28-0, indexed in the Registry file on STN CAS Online Jul. 3, 2012. (Year: 2012).
Chemical Abstracts Registry No. 1380857-75-9, indexed in the Registry file on STN CAS Online Jul. 3, 2012. (Year: 2012).
Chemical Abstracts Registry No. 1350420-68-6, indexed in the Registry file on STN CAS Online Dec. 7, 2011. (Year: 2011).
Chemical Abstracts Registry No. 1350191-80-8, indexed in the Registry file on STN CAS Online Dec. 7, 2011. (Year: 2011).
Chemical Abstracts Registry No. 919610-78-9, indexed in the Registry file on STN CAS Online Feb. 6, 2007. (Year: 2007).

(56) References Cited

OTHER PUBLICATIONS

Chemical Abstracts Registry No. 919610-77-8, indexed in the Registry file on STN CAS Online Feb. 6, 2007. (Year: 2007).
Chemical Abstracts Registry No. 919610-71-2, indexed in the Registry file on STN CAS Online Feb. 6, 2007. (Year: 2007).
Chemical Abstracts Registry No. 919610-70-1, indexed in the Registry file on STN CAS Online Feb. 6, 2007. (Year: 2007).
Chemical Abstracts Registry No. 919610-69-8, indexed in the Registry file on STN CAS Online Feb. 6, 2007. (Year: 2007).
Chemical Abstracts Registry No. 919494-40-9, indexed in the Registry file on STN CAS Online Feb. 6, 2007. (Year: 2007).
Chemical Abstracts Registry No. 919494-38-5, indexed in the Registry file on STN CAS Online Feb. 6, 2007. (Year: 2007).
Chemical Abstracts Registry No. 919494-22-7, indexed in the Registry file on STN CAS Online Feb. 6, 2007. (Year: 2007).
Chemical Abstracts Registry No. 1348577-48-9, indexed in the Registry file on STN CAS Online Dec. 4, 2011. (Year: 2011).
Chemical Abstracts Registry No. 1380990-95-3, indexed in the Registry file on STN CAS Online Jul. 4, 2012. (Year: 2012).
Chemical Abstracts Registry No. 1380944-26-2, indexed in the Registry file on STN CAS Online Jul. 4, 2012. (Year: 2012).
Chemical Abstracts Registry No. 1380879-49-1, indexed in the Registry file on STN CAS Online Jul. 3, 2012. (Year: 2012).
Chemical Abstracts Registry No. 1380858-18-3, indexed in the Registry file on STN CAS Online Jul. 3, 2012. (Year: 2012).
Chemical Abstracts Registry No. 1381109-36-9, indexed in the Registry file on STN CAS Online Jul. 4, 2012. (Year: 2012).
Chemical Abstracts Registry No. 1381106-70-2, indexed in the Registry file on STN CAS Online Jul. 4, 2012. (Year: 2012).
Chemical Abstracts Registry No. 1380864-49-2, indexed in the Registry file on STN CAS Online Jul. 3, 2012. (Year: 2012).
Chemical Abstracts Registry No. 1380859-62-0, indexed in the Registry file on STN CAS Online Jul. 3, 2012. (Year: 2012).
Chemical Abstracts Registry No. 1381035-24-0, indexed in the Registry file on STN CAS Online Jul. 4, 2012. (Year: 2012).
Chemical Abstracts Registry No. 2059673-20-8, indexed in the Registry file on STN CAS Online Jan. 26, 2017. (Year: 2017).
Chemical Abstracts Registry No. 2224380-48-5, indexed in the Registry file on STN CAS Online May 20, 2018.
Chemical Abstracts Registry No. 2055492-51-6, indexed in the Registry file on STN CAS Online Jan. 5, 2017.
Chemical Abstracts Registry No. 1608159-30-3, indexed in the Registry file on STN CAS Online May 22, 2014.
Chemical Abstracts Registry No. 1349790-59-5, indexed in the Registry file on STN CAS Online Dec. 6, 2011.
Chemical Abstracts Registry No. 1349075-20-2, indexed in the Registry file on STN CAS Online Dec. 5, 2011.
Chemical Abstracts Registry No. 1348522-09-7, indexed in the Registry file on STN CAS Online Dec. 4, 2011.
Chemical Abstracts Registry No. 1348048-78-1, indexed in the Registry file on STN CAS Online Dec. 4, 2011.
Chemical Abstracts Registry No. 1347905-79-6, indexed in the Registry file on STN CAS Online Dec. 4, 2011.
Chemical Abstracts Registry No. 1347641-28-4, indexed in the Registry file on STN CAS Online Dec. 2, 2011.
Chemical Abstracts Registry No. 1347614-67-8, indexed in the Registry file on STN CAS Online Dec. 2, 2011.
Chemical Abstracts Registry No. 1347467-65-5, indexed in the Registry file on STN CAS Online Dec. 2, 2011.
Chemical Abstracts Registry No. 2213453-82-6, indexed in the Registry file on STN CAS Online Apr. 16, 2018.
Chemical Abstracts Registry No. 2170880-44-9, indexed in the Registry file on STN CAS Online Jan. 24, 2018.
Chemical Abstracts Registry No. 2170880-30-3, indexed in the Registry file on STN CAS Online Jan. 24, 2018.
Chemical Abstracts Registry No. 2170880-29-0, indexed in the Registry file on STN CAS Online Jan. 24, 2018.
Chemical Abstracts Registry No. 2170876-00-1, indexed in the Registry file on STN CAS Online Jan. 24, 2018.
Chemical Abstracts Registry No. 2170875-99-5, indexed in the Registry file on STN CAS Online Jan. 24, 2018.
Chemical Abstracts Registry No. 2138484-61-2, indexed in the Registry file on STN CAS Online Nov. 3, 2017.
Chemical Abstracts Registry No. 2117679-02-2, indexed in the Registry file on STN CAS Online Aug. 21, 2017.
Chemical Abstracts Registry No. 2098833-57-7, indexed in the Registry file on STN CAS Online Jun. 21, 2017.
Chemical Abstracts Registry No. 2096985-34-9, indexed in the Registry file on STN CAS Online May 23, 2017.
Chemical Abstracts Registry No. 1957192-78-7, indexed in the Registry file on STN CAS Online Jul. 21, 2016.
Chemical Abstracts Registry No. 1579964-39-8, indexed in the Registry file on STN CAS Online Apr. 3, 2014.
Chemical Abstracts Registry No. 1381102-22-2, indexed in the Registry file on STN CAS Online Jul. 4, 2012.
Chemical Abstracts Registry No. 1381055-52-2, indexed in the Registry file on STN CAS Online Jul. 4, 2012.
Chemical Abstracts Registry No. 1380859-69-7, indexed in the Registry file on STN CAS Online Jul. 4, 2012.
Chemical Abstracts Registry No. 1283718-58-0, indexed in the Registry file on STN CAS Online Apr. 21, 2011.
Chemical Abstracts Registry No. 919610-72-3, indexed in the Registry file on STN CAS Online Feb. 6, 2007.
Chemical Abstracts Registry No. 919496-89-2, indexed in the Registry file on STN CAS Online Feb. 6, 2007.
Chemical Abstracts Registry No. 919494-45-4, indexed in the Registry file on STN CAS Online Feb. 6, 2007.
Chemical Abstracts Registry No. 919494-44-3, indexed in the Registry file on STN CAS Online Feb. 6, 2007.
Chemical Abstracts Registry No. 919494-39-6, indexed in the Registry file on STN CAS Online Feb. 6, 2007.
Chemical Abstracts Registry No. 919494-26-1, indexed in the Registry file on STN CAS Online Feb. 6, 2007.
Chemical Abstracts Registry No. 919494-23-8, indexed in the Registry file on STN CAS Online Feb. 6, 2007.
Chemical Abstracts Registry No. 919494-19-2, indexed in the Registry file on STN CAS Online Feb. 6, 2007.
Chemical Abstracts Registry No. 919493-72-4, indexed in the Registry file on STN CAS Online Feb. 6, 2007.
Chemical Abstracts Registry No. 919493-71-3, indexed in the Registry file on STN CAS Online Feb. 6, 2007.
Chemical Abstracts Registry No. 848953-00-4, indexed in the Registry file on STN CAS Online Apr. 21, 2005.
Chemical Abstracts Registry No. 848952-99-8, indexed in the Registry file on STN CAS Online Apr. 21, 2005.
Chemical Abstracts Registry No. 120821-79-6, indexed in the Registry file on STN CAS Online May 26, 1989.
Chemical Abstracts Registry No. 1369171-97-0, indexed in the Registry file on STN CAS Online Apr. 16, 2012.
Chemical Abstracts Registry No. 1330263-81-4, indexed in the Registry file on STN CAS Online Sep. 9, 2011.
Alessandro Stella et al., A short and straightforward approach towards 6-amino and 6-aminoalkyl thiazolo[4,5-c]pyridazines, Tetrahedron Letters, 54(8) (2013) pp. 830-833.
Thuraya Al-Harthy et al., "Design, synthesis and antimicrobial evaluation of novel 2-arylbenzothiazole analogs bearing fluorine and piperazine moieties," Monatshefte fur Chemie (2018) 149(3) pp. 645-651.
Hye Ri Park et al., "Oxazolopyridines and thiazolopyridines as monoamine oxidase B inhibitors for the treatment of Parkinson's disease." Bioorganic & Medicinal Chemistry, 21(17) (2013) pp. 5480-5487.
Chemical Abstracts Registry No. 1368225-46-0, indexed in the Registry file on STN CAS Online Apr. 15, 2012.
Chemical Abstracts Registry No. 1330013-08-5, indexed in the Registry file on STN CAS Online Sep. 8, 2011.
Chemical Abstracts Registry No. 1329755-78-3, indexed in the Registry file on STN CAS Online Sep. 8, 2011.
Chemical Abstracts Registry No. 1329572-44-2, indexed in the Registry file on STN CAS Online Sep. 7, 2011.
Chemical Abstracts Registry No. 1329511-91-2, indexed in the Registry file on STN CAS Online Sep. 7, 2011.

(56) References Cited

OTHER PUBLICATIONS

Chemical Abstracts Registry No. 1327110-38-2, indexed in the Registry file on STN CAS Online Sep. 2, 2011.
Chemical Abstracts Registry No. 1310217-40-3, indexed in the Registry file on STN CAS Online Jun. 23, 2011.
Chemical Abstracts Registry No. 1310089-22-5, indexed in the Registry file on STN CAS Online Jun. 23, 2011.
Chemical Abstracts Registry No. 1267789-60-5, indexed in the Registry file on STN CAS Online Mar. 10, 2011.
Chemical Abstracts Registry No. 1267620-08-5, indexed in the Registry file on STN CAS Online Mar. 9, 2011.
Chemical Abstracts Registry No. 1267544-92-2, indexed in the Registry file on STN CAS Online Mar. 9, 2011.
Chemical Abstracts Registry No. 1267173-86-3, indexed in the Registry file on STN CAS Online Mar. 9, 2011.
Chemical Abstracts Registry No. 1267173-76-1, indexed in the Registry file on STN CAS Online Mar. 9, 2011.
Chemical Abstracts Registry No. 1266786-33-7, indexed in the Registry file on STN CAS Online Mar. 8, 2011.
"Chemical Encyclopedia", scientific publishing house "Great Russian Encyclopedia," Moskva, vol. 4, pp. 499-501, 1995.
V.V. Boltromeyuk, "General Chemistry", Minsk, Graduate School, Grodno State Medical University, Department of General and Bioorganic Chemistry, p. 65, 2012 (textbook).
Chemical Abstracts Registry No. 1202076-20-7, indexed in the Registry file on STN CAS Online Jan. 13, 2010.
Chemical Abstracts Registry No. 1202076-21-8, indexed in the Registry file on STN CAS Online Jan. 13, 2010.
Chemical Abstracts Registry No. 1202076-22-9, indexed in the Registry file on STN CAS Online Jan. 13, 2010.
Chemical Abstracts Registry No. 889062-91-3, indexed in the Registry file on STN CAS Online Jun. 23, 2006.
Chemical Abstracts Registry No. 667457-86-5, indexed in the Registry file on STN CAS Online Mar. 25, 2004.
Chemical Abstracts Registry No. 1691540-69-8, indexed in the Registry file on STN CAS Online Apr. 26, 2015.
Chemical Abstracts Registry No. 1691540-67-6, indexed in the Registry file on STN CAS Online Apr. 26, 2015.
Chemical Abstracts Registry No. 1691538-20-1, indexed in the Registry file on STN CAS Online Apr. 26, 2015.
Chemical Abstracts Registry No. 1691538-17-6, indexed in the Registry file on STN CAS Online Apr. 26, 2015.
International Search Report in PCT/US2022/038870, dated Nov. 9, 2022.
Written Opinion of the International Searching Authority in PCT/US2022/038870, dated Nov. 9, 2022.
Glenn Noronha, et al. Discovery of [7-(2,6-Dichlorophenyl)-5-methylbenzo[1,2,4]triazin-3-yl]-[4-(2-pyrrolidin-1-ylethoxy)phenyl]amine—A Potent, Orally Active Src Kinase Inhibitor with Antitumor Activity in Preclinical Assays. Bioorg. Med. Chem. Lett., vol. 17, No. 3, pp. 602-608, 2007.
Cheung et al., "Discovery of Small Molecule Splicing Modulators of Survival Motor Neuron-2 (SMN2) for the Treatment of Spinal Muscular Atrophy (SMA)", J. Med. Chem, vol. 61(24):11021-11036, Aug. 15, 2018 (received), Nov. 8, 2018 (published), pp. A-P.
Sara D. Reis et al., "Modulation of Molecular Chaperones in Huntington's Disease and Other Polyglutamine Disorders," Molecular Neurobiology, vol. 54, pp. 5829-5854, (2016) (Sep. 22, 2016).
Hideshi Nakamura et al., Synthesis and Chemiluminescence of 5-[(2-Pyridyl)-, (2-Pyrazinyl)-, and (Substituted 2-pyrazinyl)amino]-1,2,4-trioxanes, The Chemical Society of Japan, vol. 61, No. 10, (1988) pp. 3776-3778.
Written Opinion of the International Searching Authority in PCT/US2021/059139, mailed Mar. 14, 2022.
International Search Report for PCT/US2021/059139, mailed Mar. 14, 2022.
Stephen M. Berge, et al., "Pharmaceutical Salts," Journal of Pharmaceutical Sciences, vol. 66, No. 1, pp. 1-19 (1977).
Chemical Abstracts Registry No. 1207531-45-0, indexed in the Registry file on STN CAS Online Mar. 1, 2010.
"Drug Structure—Activity Relationship", edited by Li Renli, China Medical Science and Technology Press, 1st edition, Jan. 2004, 1st printing, pp. 182-183).

\* cited by examiner

HETEROARYL COMPOUNDS FOR TREATING HUNTINGTON'S DISEASE

CROSS-REFERENCE TO RELATED APPLICATIONS

This application is a U.S. National Stage filing under 35 U.S.C. § 371 of International Application No. PCT/US2019/038895, filed Jun. 25, 2019, which in turn claims priority to U.S. Provisional Application No. 62/690,540, filed Jun. 27, 2018, the entire contents of which are incorporated by reference herein.

An aspect of the present description relates to compounds, forms, and pharmaceutical compositions thereof and methods of using such compounds, forms, or compositions thereof useful for treating or ameliorating Huntington's disease. In particular, another aspect of the present description relates to substituted benzothiazole compounds, forms and pharmaceutical compositions thereof and methods of using such compounds, forms, or compositions thereof for treating or ameliorating Huntington's disease.

BACKGROUND

Huntington's disease (HD) is a progressive, autosomal dominant neurodegenerative disorder of the brain, having symptoms characterized by involuntary movements, cognitive impairment, and mental deterioration. Death, typically caused by pneumonia or coronary artery disease, usually occurs 13 to 15 years after the onset of symptoms. The prevalence of HD is between three and seven individuals per 100,000 in populations of western European descent. In North America, an estimated 30,000 people have HD, while an additional 200,000 people are at risk of inheriting the disease from an affected parent. The disease is caused by an expansion of uninterrupted trinucleotide CAG repeats in the "mutant" huntingtin (Htt) gene, leading to production of HTT (Htt protein) with an expanded poly-glutamine (polyQ) stretch, also known as a "CAG repeat" sequence. There are no current small molecule therapies targeting the underlying cause of the disease, leaving a high unmet need for medications that can be used for treating or ameliorating HD. Consequently, there remains a need to identify and provide small molecule compounds for treating or ameliorating HD.

All other documents referred to herein are incorporated by reference into the present application as though fully set forth herein.

SUMMARY

An aspect of the present description includes compounds comprising, a compound of Formula (I) or Formula (II):

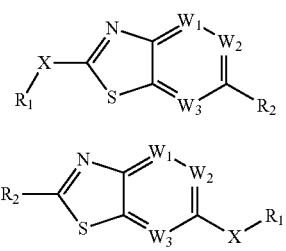

or a form thereof, wherein $R_1$, $R_2$, X, $W_1$, $W_2$, and $W_3$ are as defined herein.

An aspect of the present description includes a method for treating or ameliorating HD in a subject in need thereof comprising, administering to the subject an effective amount of a compound of Formula (I) or Formula (II) or a form thereof.

An aspect of the present description includes a method for use of a compound of Formula (I) or Formula (II) or a form or composition thereof for treating or ameliorating HD in a subject in need thereof comprising, administering to the subject an effective amount of the compound of Formula (I) or Formula (II) or a form or composition thereof.

An aspect of the present description includes a use for a compound of Formula (I) or a form thereof for treating or ameliorating HD in a subject in need thereof comprising, administering to the subject an effective amount of the compound of Formula (I) or a form thereof.

An aspect of the present description includes a use for a compound of Formula (I) or a form thereof in the manufacture of a medicament for treating or ameliorating HD in a subject in need thereof comprising, administering to the subject an effective amount of the medicament.

An aspect of the present description includes a use for a compound of Formula (I) or a form thereof in a combination product with one or more therapeutic agents for treating or ameliorating HD in a subject in need thereof comprising, administering to the subject an effective amount of the compound of Formula (I) or a form thereof in combination with an effective amount of the one or more agents.

DETAILED DESCRIPTION

An aspect of the present description relates to compounds comprising, a compound of Formula (I) or Formula (II):

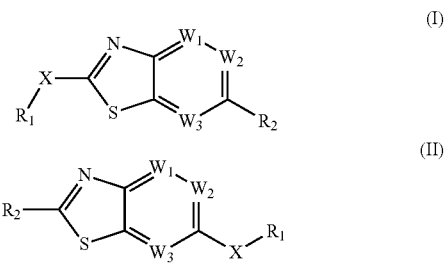

or a form thereof, wherein:

$W_1$, $W_2$ and $W_3$ are independently C—$R_a$ or N;

$R_a$ is, in each instance, independently selected from hydrogen, cyano, halogen, hydroxy, $C_{1-6}$alkyl, halo-$C_{1-6}$alkyl, $C_{1-6}$alkyl-carbonyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, ($C_{1-6}$alkyl)$_2$-amino, amino-$C_{1-6}$alkyl, and hydroxy-$C_{1-6}$alkyl;

X is selected from N—$R_b$, O, or a bond;

$R_b$ is selected from hydrogen and $C_{1-6}$alkyl;

$R_1$ is selected from $C_{3-10}$cycloalkyl and heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and wherein, each instance of $C_{3-10}$cycloalkyl and heterocyclyl is optionally substituted with one, two three, or four $R_3$ substituents and optionally, with one additional $R_4$ substituent, or,

3 wherein, alternatively, each instance of $C_{3-10}$cycloalkyl and heterocyclyl is optionally substituted with one, two, three, four, or five $R_3$ substituents;

$R_3$ is, in each instance, independently selected from cyano, halogen, hydroxy, $C_{1-6}$alkyl, halo-$C_{1-6}$alkyl, $C_{1-6}$alkyl-carbonyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, $(C_{1-6}$alkyl$)_2$-amino, amino-$C_{1-6}$alkyl, and hydroxy-$C_{1-6}$alkyl;

$R_4$ is selected from $C_{3-10}$cycloalkyl, phenyl, heterocyclyl, and heteroaryl;

wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, wherein heteroaryl is a 3-7 membered monocyclic or 6-10 membered bicyclic ring system having 1, 2, 3, or 4 heteroatom ring members independently selected from N, O, or S, and wherein, each instance of $C_{3-10}$cycloalkyl, phenyl, heterocyclyl, and heteroaryl is optionally substituted with one, two or three $R_7$ substituents;

$R_2$ is selected from phenyl and heteroaryl, wherein heteroaryl is a 3-7 membered monocyclic or 6-10 membered bicyclic ring system having 1, 2, 3, or 4 heteroatom ring members independently selected from N, O, or S, wherein, each instance of phenyl and heteroaryl is optionally substituted with one, two or three $R_5$ substituents and optionally, with one additional $R_6$ substituent, or, wherein, alternatively, each instance of phenyl and heteroaryl is optionally substituted with one, two, three or four $R_5$ substituents;

$R_5$ is, in each instance, independently selected from cyano, halogen, hydroxy, $C_{1-6}$alkyl, halo-$C_{1-6}$alkyl, $C_{1-6}$alkyl-carbonyl, $C_{1-6}$alkoxy, halo-$C_{1-6}$alkoxy, $C_{1-6}$alkoxy-$C_{1-6}$alkyl, $C_{1-6}$alkoxy-carbonyl, $C_{1-6}$alkoxy-carbonyl-$C_{1-6}$alkyl, carboxyl, $C_{1-6}$alkyl-carboxyl, amino, $C_{1-6}$alkyl-amino, $(C_{1-6}$alkyl$)_2$-amino, amino-$C_{1-6}$alkyl, amino-carbonyl, and hydroxy-$C_{1-6}$alkyl;

$R_6$ is selected from $C_{3-10}$cycloalkyl, phenyl, phenyl-$C_{1-6}$alkoxy, phenyl-oxy, heterocyclyl, and heteroaryl;

wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, wherein heteroaryl is a 3-7 membered monocyclic or 6-10 membered bicyclic ring system having 1, 2, 3, or 4 heteroatom ring members independently selected from N, O, or S, and wherein, each instance of $C_{3-10}$cycloalkyl, phenyl, heterocyclyl, and heteroaryl is optionally substituted with one, two or three $R_7$ substituents; and $R_7$ is, in each instance, independently selected from cyano, halogen, hydroxy, $C_{1-6}$alkyl, halo-$C_{1-6}$alkyl, $C_{1-6}$alkyl-carbonyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, $(C_{1-6}$alkyl$)_2$-amino, amino-$C_{1-6}$alkyl, and hydroxy-$C_{1-6}$alkyl;

wherein a form of the compound is selected from the group consisting of a salt, hydrate, solvate, racemate, enantiomer, diastereomer, stereoisomer, and tautomer form thereof.

4

ASPECTS OF THE DESCRIPTION

Another aspect of the present description includes a compound of Formula (I) or Formula

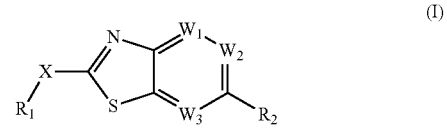

(I)

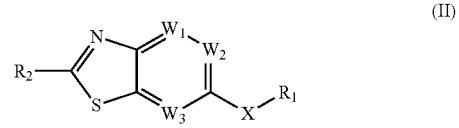

(II)

or a form thereof, wherein:

$W_1$, $W_2$ and $W_3$ are independently C—$R_a$ or N;

$R_a$ is, in each instance, independently selected from hydrogen, cyano, halogen, hydroxy, $C_{1-6}$alkyl, halo-$C_{1-6}$alkyl, $C_{1-6}$alkyl-carbonyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, $(C_{1-6}$alkyl$)_2$-amino, amino-$C_{1-6}$alkyl, and hydroxy-$C_{1-6}$alkyl;

X is selected from N—$R_b$, O, or a bond;

$R_b$ is selected from hydrogen and $C_{1-6}$alkyl;

$R_1$ is selected from $C_{3-10}$cycloalkyl and heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and wherein, each instance of $C_{3-10}$cycloalkyl and heterocyclyl is optionally substituted with one, two three, or four $R_3$ substituents and optionally, with one additional $R_4$ substituent, or, wherein, alternatively, each instance of $C_{3-10}$cycloalkyl and heterocyclyl is optionally substituted with one, two, three, four, or five $R_3$ substituents;

$R_3$ is, in each instance, independently selected from cyano, halogen, hydroxy, $C_{1-6}$alkyl, halo-$C_{1-6}$alkyl, $C_{1-6}$alkyl-carbonyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, $(C_{1-6}$alkyl$)_2$-amino, amino-$C_{1-6}$alkyl, and hydroxy-$C_{1-6}$alkyl;

$R_4$ is selected from $C_{3-10}$cycloalkyl, phenyl, heterocyclyl, and heteroaryl;

wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, wherein heteroaryl is a 3-7 membered monocyclic or 6-10 membered bicyclic ring system having 1, 2, 3, or 4 heteroatom ring members independently selected from N, O, or S, and wherein, each instance of $C_{3-10}$cycloalkyl, phenyl, heterocyclyl, and heteroaryl is optionally substituted with one, two or three $R_7$ substituents;

$R_2$ is selected from phenyl and heteroaryl, wherein heteroaryl is a 3-7 membered monocyclic or 6-10 membered bicyclic ring system having 1, 2, 3, or 4 heteroatom ring members independently selected from N, O, or S, wherein, each instance of phenyl and heteroaryl is optionally substituted with one, two or three $R_5$ substituents and optionally, with one additional $R_6$ substituent, or, wherein, alternatively, each instance of phenyl and heteroaryl is optionally substituted with one, two, three or four $R_5$ substituents;

$R_5$ is, in each instance, independently selected from cyano, halogen, hydroxy, $C_{1-6}$alkyl, halo-$C_{1-6}$alkyl, $C_{1-6}$alkyl-carbonyl, $C_{1-6}$alkoxy, halo-$C_{1-6}$alkoxy, $C_{1-6}$alkoxy-$C_{1-6}$alkyl, $C_{1-6}$alkoxy-carbonyl, $C_{1-6}$alkoxy-carbonyl-$C_{1-6}$alkyl, carboxyl, $C_{1-6}$alkyl-carboxyl, amino, $C_{1-6}$alkyl-amino, ($C_{1-6}$alkyl)$_2$-amino, amino-$C_{1-6}$alkyl, amino-carbonyl, and hydroxy-$C_{1-6}$alkyl;

$R_6$ is selected from $C_{3-10}$cycloalkyl, phenyl, phenyl-$C_{1-6}$alkoxy, phenyl-oxy, heterocyclyl, and heteroaryl;

wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, wherein heteroaryl is a 3-7 membered monocyclic or 6-10 membered bicyclic ring system having 1, 2, 3, or 4 heteroatom ring members independently selected from N, O, or S, and wherein, each instance of $C_{3-10}$cycloalkyl, phenyl, heterocyclyl, and heteroaryl is optionally substituted with one, two or three $R_7$ substituents; and $R_7$ is, in each instance, independently selected from cyano, halogen, hydroxy, $C_{1-6}$alkyl, halo-$C_{1-6}$alkyl, $C_{1-6}$alkyl-carbonyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, ($C_{1-6}$alkyl)$_2$-amino, amino-$C_{1-6}$alkyl, and hydroxy-$C_{1-6}$alkyl.

One aspect includes a compound of Formula (I) or Formula (II), wherein $W_1$, $W_2$ and $W_3$ are C—$R_a$.

One aspect includes a compound of Formula (I) or Formula (II), wherein $W_1$ is N.

Another aspect includes a compound of Formula (I) or Formula (II), wherein $W_1$ is N, and $W_2$ and $W_3$ are C—$R_a$.

One aspect includes a compound of Formula (I) or Formula (II), wherein $W_2$ is N.

Another aspect includes a compound of Formula (I) or Formula (II), wherein $W_2$ is N, and $W_1$ and $W_3$ are C—$R_a$.

One aspect includes a compound of Formula (I) or Formula (II), wherein $W_3$ is N.

Another aspect includes a compound of Formula (I) or Formula (II), wherein $W_3$ is N, and $W_1$ and $W_2$ are C—$R_a$.

One aspect includes a compound of Formula (I) or Formula (II), wherein $W_1$ and $W_2$ are N.

Another aspect includes a compound of Formula (I) or Formula (II), wherein $W_1$ and $W_2$ are N and $W_3$ is C—$R_a$.

One aspect includes a compound of Formula (I) or Formula (II), wherein $W_1$ and $W_3$ are N.

Another aspect includes a compound of Formula (I) or Formula (II), wherein $W_1$ and $W_3$ are N and $W_2$ is C—$R_a$.

One aspect includes a compound of Formula (I) or Formula (II), wherein $W_2$ and $W_3$ are N.

Another aspect includes a compound of Formula (I) or Formula (II), wherein $W_2$ and $W_3$ are N and $W_2$ is C—$R_a$.

One aspect includes a compound of Formula (I) or Formula (II), wherein $W_1$, $W_2$ and $W_3$ are N.

One aspect includes a compound of Formula (I) or Formula (II), wherein $R_a$ is, in each instance, independently selected from hydrogen, cyano, halogen, hydroxy, $C_{1-6}$alkyl, halo-$C_{1-6}$alkyl, $C_{1-6}$alkyl-carbonyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, ($C_{1-6}$alkyl)$_2$-amino, amino-$C_{1-6}$alkyl, and hydroxy-$C_{1-6}$alkyl.

Another aspect includes a compound of Formula (I) or Formula (II), wherein $R_a$ is, in each instance, independently selected from hydrogen, cyano, halogen, hydroxy, and $C_{1-6}$alkoxy.

Another aspect includes a compound of Formula (I) or Formula (II), wherein $R_a$ is, in each instance, hydrogen.

Another aspect includes a compound of Formula (I) or Formula (II), wherein $R_a$ is, in each instance, cyano.

Another aspect includes a compound of Formula (I) or Formula (II), wherein $R_a$ is, in each instance, halogen selected from bromo, chloro, fluoro, and iodo.

Another aspect includes a compound of Formula (I) or Formula (II), wherein $R_a$ is, in each instance, halogen selected from chloro and fluoro.

Another aspect includes a compound of Formula (I) or Formula (II), wherein $R_a$ is, in each instance, hydroxy.

Another aspect includes a compound of Formula (I) or Formula (II), wherein $R_a$ is, in each instance, $C_{1-6}$alkoxy selected from methoxy, ethoxy, propoxy, isopropoxy, and tert-butoxy.

Another aspect includes a compound of Formula (I) or Formula (II), wherein $R_a$ is, in each instance, methoxy.

One aspect includes a compound of Formula (I) or Formula (II), wherein X is selected from N—$R_b$, O, or a bond.

Another aspect includes a compound of Formula (I) or Formula (II), wherein X is N—$R_b$.

Another aspect includes a compound of Formula (I) or Formula (II), wherein X is O.

Another aspect includes a compound of Formula (I) or Formula (II), wherein X is a bond.

One aspect includes a compound of Formula (I) or Formula (II), wherein $R_b$ is selected from hydrogen and $C_{1-6}$alkyl.

Another aspect includes a compound of Formula (I) or Formula (II), wherein $R_b$ is hydrogen.

Another aspect includes a compound of Formula (I) or Formula (II), wherein $R_b$ is $C_{1-6}$alkyl selected from methyl, ethyl, propyl, isopropyl, and tert-butyl.

Another aspect includes a compound of Formula (I) or Formula (II), wherein $R_b$ is $C_{1-6}$alkyl selected from methyl and ethyl.

One aspect includes a compound of Formula (I) or Formula (II), wherein $R_1$ is selected from $C_{3-10}$cycloalkyl and heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and wherein, each instance of $C_{3-10}$cycloalkyl and heterocyclyl is optionally substituted with one, two three, or four $R_3$ substituents and optionally, with one additional $R_4$ substituent, or, wherein, alternatively, each instance of $C_{3-10}$cycloalkyl and heterocyclyl is optionally substituted with one, two, three, four, or five $R_3$ substituents.

Another aspect includes a compound of Formula (I) or Formula (II), wherein $R_1$ is $C_{3-10}$cycloalkyl selected from cyclopropyl, cylcobutyl, cyclopentyl, cyclohexyl, cycloheptyl, cyclooctyl, bicyclo[2.2.1]hexanyl, and adamantyl, optionally substituted with one, two three, or four $R_3$ substituents and optionally, with one additional $R_4$ substituent, or, alternatively, optionally substituted with one, two, three, four, or five $R_3$ substituents.

Another aspect includes a compound of Formula (I) or Formula (II), wherein $R_1$ is $C_{3-10}$cycloalkyl selected from cylcobutyl and cyclohexyl, optionally substituted with one, two three, or four $R_3$ substituents and optionally, with one additional $R_4$ substituent, or, alternatively, optionally substituted with one, two, three, four, or five $R_3$ substituents.

Another aspect includes a compound of Formula (I) or Formula (II), wherein $R_1$ is heterocyclyl selected from azetidinyl, tetrahydrofuranyl, pyrrolidinyl, piperidinyl, piperazinyl, 1H-azepinyl, 2,3,6,7-tetrahydro-1H-azepinyl, azepanyl, 1,4-diazepanyl, 1,2,5,6-tetrahydropyridinyl, 1,2,3,6-tetrahydropyridinyl, octahydroindolizinyl, octahydro-1H-pyrrolo[3,2-c]pyridinyl, (3aS,7aR)-octahydro-1H-pyrrolo[3,2-c]pyridinyl, 1-azabicyclo[2.2.2]octyl, 3-azabicyclo[3.1.0]hexyl, (1R,5S)-3-azabicyclo[3.1.0]hexyl, 3-azabicyclo[3.2.1]octyl, 8-azabicyclo[3.2.1]octyl, (1R,5S)-8-azabicyclo[3.2.1]octyl, 8-azabicyclo[3.2.1]oct-2-en-yl, (1R,5S)-8-azabicyclo[3.2.1]oct-2-en-yl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 1,4-diazabicyclo[3.1.1]heptyl, 3,6-diazabicyclo[3.2.0]heptyl, 2,5-diazabicyclo[2.2.2]octyl, 1,4-diazabicyclo[3.2.1]octyl, 3,8-diazabicyclo[3.2.1]octyl, (1R,5S)-3,8-diazabicyclo[3.2.1]octyl, 1,4-diazabicyclo[3.2.2]nonyl, 3,8-diazabicyclo[4.2.0]octyl, (1S,6R)-3,8-diazabicyclo[4.2.0]octyl, (1R,6S)-3,8-diazabicyclo[4.2.0]octyl, 2-azaspiro[3.3]heptyl, 4,7-diazaspiro[2.5]octyl, 2,6-diazaspiro[3.3]heptyl, 2,6-diazaspiro[3.4]octyl, 1,6-diazaspiro[3.5]nonyl, 1,7-diazaspiro[3.5]nonyl, 2,6-diazaspiro[3.5]nonyl, 5,8-diazaspiro[3.5]nonyl, 1,7-diazaspiro[4.4]nonyl, 2,7-diazaspiro[4.4]nonyl, 2,7-diazaspiro[4.5]decyl, and 6,9-diazaspiro[4.5]decyl, optionally substituted with one, two three, or four $R_3$ substituents and optionally with one additional $R_4$ substituent, or, alternatively, optionally substituted with one, two, three, four, or five $R_3$ substituents.

Another aspect includes a compound of Formula (I) or Formula (II), wherein $R_1$ is heterocyclyl selected from azetidinyl, pyrrolidinyl, piperidinyl, piperazinyl, 2,3,6,7-tetrahydro-1H-azepinyl, azepanyl, 1,4-diazepanyl, 1,2,3,6-tetrahydropyridinyl, octahydroindolizinyl, octahydro-1H-pyrrolo[3,2-c]pyridinyl, (3aS,7aR)-octahydro-1H-pyrrolo[3,2-c]pyridinyl, 1-azabicyclo[2.2.2]octyl, 8-azabicyclo[3.2.1]octyl, (1R,5S)-8-azabicyclo[3.2.1]octyl, 9-azabicyclo[3.3.1]nonyl, 3,8-diazabicyclo[4.2.0]octyl, (1S,6R)-3,8-diazabicyclo[4.2.0]octyl, (1R,6S)-3,8-diazabicyclo[4.2.0]octyl, 2-azaspiro[3.3]heptyl, 2,6-diazaspiro[3.3]heptyl, 1,6-diazaspiro[3.5]nonyl, 1,7-diazaspiro[3.5]nonyl, 2,6-diazaspiro[3.5]nonyl, 2,7-diazaspiro[3.5]nonyl, and 2,7-diazaspiro[4.4]nonyl, optionally substituted with one two three, or four $R_3$ substituents and optionally, with one additional $R_4$ substituent, or, alternatively, optionally substituted with one, two, three, four, or five $R_3$ substituents.

Another aspect includes a compound of Formula (I) or Formula (II), wherein $R_1$ is heterocyclyl selected from azetidin-2-yl, azetidin-3-yl, tetrahydrofuran-3-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1H-azepin-2-yl, 1H-azepin-3-yl, 1H-azepin-4-yl, 2,3,6,7-tetrahydro-1H-azepin-4-yl, azepan-2-yl, azepan-3-yl, azepan-4-yl, 1,4-diazepan-1-yl, 1,4-diazepan-2-yl, 1,4-diazepan-3-yl, 1,2,5,6-tetrahydropyridin-5-yl, 1,2,3,6-tetrahydropyridin-4-yl, octahydroindolizin-7-yl, octahydro-1H-pyrrolo[3,2-c]pyridin-1-yl, (3aS,7aR)-octahydro-1H-pyrrolo[3,2-c]pyridin-1-yl, 1-azabicyclo[2.2.2]oct-4-yl, 3-azabicyclo[3.1.0]hexan-3-yl, 3-azabicyclo[3.2.1]octan-8-yl, 8-azabicyclo[3.2.1]oct-3-yl, (1R,5S)-8-azabicyclo[3.2.1]octan-3-yl, 8-azabicyclo[3.2.1]oct-2-en-3-yl, (1R,5S)-8-azabicyclo[3.2.1]oct-2-en-3-yl, 9-azabicyclo[3.3.1]non-3-yl, (1R,5S)-9-azabicyclo[3.3.1]nonan-3-yl, 2,5-diazabicyclo[2.2.1]heptan-2-yl, (1S,4S)-2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, (1R,5S)-3,8-diazabicyclo[3.2.1]octan-3-yl, 1,4-diazabicyclo[3.2.2]nonan-4-yl, 3,8-diazabicyclo[4.2.0]oct-8-yl, (1S,6R)-3,8-diazabicyclo[4.2.0]oct-8-yl, (1R,6S)-3,8-diazabicyclo[4.2.0]oct-8-yl, 2-azaspiro[3.3]hept-2-yl, 2-azaspiro[3.3]hept-6-yl, 4,7-diazaspiro[2.5]oct-4-yl, 4,7-diazaspiro[2.5]oct-7-yl, 2,6-diazaspiro[3.3]hept-2-yl, 2,6-diazaspiro[3.4]oct-2-yl, 2,6-diazaspiro[3.4]oct-6-yl, 1,6-diazaspiro[3.5]non-1-yl, 1,7-diazaspiro[3.5]non-1-yl, 1,7,-diazaspiro[4.4]non-1-yl, 1,7-diazaspiro[4.4]non-7-yl, 2,6-diazaspiro[3.5]non-2-yl, 2,6-diazaspiro[3.5]non-6-yl, 2,7-diazaspiro[3.5]non-7-yl, 5,8-diazaspiro[3.5]non-8-yl, 2,7-diazaspiro[4.4]non-2-yl, 2,7-diazaspiro[4.5]deca-2-yl, 2,7-diazaspiro[4.5]dec-7-yl, and 6,9-diazaspiro[4.5]dec-9-yl, optionally substituted with one, two three, or four $R_3$ substituents and optionally, with one additional $R_4$ substituent, or, alternatively, optionally substituted with one, two, three, four, or five $R_3$ substituents.

Another aspect includes a compound of Formula (I) or Formula (II), wherein $R_1$ is heterocyclyl selected from azetidin-3-yl, pyrrolidin-3-yl, piperidin-1-yl, piperidin-3-yl, piperidin-4-yl, piperazin-1-yl, 2,3,6,7-tetrahydro-1H-azepin-4-yl, azepan-4-yl, 1,4-diazepan-1-yl, 1,2,3,6-tetrahydropyridin-4-yl, octahydroindolizin-7-yl, octahydro-1H-pyrrolo[3,2-c]pyridin-1-yl, (3aS,7aR)-octahydro-1H-pyrrolo[3,2-c]pyridin-1-yl, 1-azabicyclo[2.2.2]oct-4-yl, 3-azabicyclo[3.2.1]octan-8-yl, 8-azabicyclo[3.2.1]oct-3-yl, 9-azabicyclo[3.3.1]non-3-yl, 3,8-diazabicyclo[4.2.0]oct-8-yl, (1S,6R)-3,8-diazabicyclo[4.2.0]oct-8-yl, (1R,6S)-3,8-diazabicyclo[4.2.0]oct-8-yl, 2-azaspiro[3.3]hept-6-yl, 2,6-diazaspiro[3.3]hept-2-yl, 1,6-diazaspiro[3.5]non-1-yl, 1,7-diazaspiro[3.5]non-1-yl, 2,6-diazaspiro[3.5]non-2-yl, 2,7-diazaspiro[3.5]non-7-yl, and 2,7-diazaspiro[4.4]non-2-yl, optionally substituted with one, two three, or four $R_3$ substituents and optionally, with one additional $R_4$ substituent, or, alternatively, each instance of heterocyclyl 1 is optionally substituted with one, two, three, four, or five $R_3$ substituents.

One aspect includes a compound of Formula (I) or Formula (II), wherein $R_3$ is, in each instance, independently selected from cyano, halogen, hydroxy, $C_{1-6}$alkyl, halo-$C_{1-6}$alkyl, $C_{1-6}$alkoxy, $C_{1-6}$alkyl-carbonyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, $(C_{1-6}$alkyl$)_2$-amino, amino-$C_{1-6}$alkyl, and hydroxy-$C_{1-6}$alkyl.

Another aspect includes a compound of Formula (I) or Formula (II), wherein $R_3$ is, in each instance, independently selected from halogen, hydroxy, $C_{1-6}$alkyl, halo-$C_{1-6}$alkyl, amino, $C_{1-6}$alkyl-amino, $(C_{1-6}$alkyl$)_2$-amino, and hydroxy-$C_{1-6}$alkyl.

Another aspect includes a compound of Formula (I) or Formula (II), wherein $R_3$ is, in each instance, halogen selected from bromo, chloro, fluoro, and iodo.

Another aspect includes a compound of Formula (I) or Formula (II), wherein $R_3$ is, in each instance, fluoro.

Another aspect includes a compound of Formula (I) or Formula (II), wherein $R_3$ is, in each instance, hydroxy.

Another aspect includes a compound of Formula (I) or Formula (II), wherein $R_3$ is, in each instance, $C_{1-6}$alkyl selected from methyl, ethyl, propyl, isopropyl, and tert-butyl.

Another aspect includes a compound of Formula (I) or Formula (II), wherein $R_3$ is, in each instance, $C_{1-6}$alkyl selected from methyl and ethyl.

Another aspect includes a compound of Formula (I) or Formula (II), wherein $R_3$ is, in each instance, halo-$C_{1-6}$alkyl, wherein $C_{1-6}$alkyl is selected from methyl, ethyl, propyl, isopropyl, butyl, isobutyl, sec-butyl, and tert-butyl partially or completely substituted with one or more halogens selected from bromo, chloro, fluoro, and iodo where allowed by available valences.

Another aspect includes a compound of Formula (I), wherein $R_3$ is, in each instance, halo-$C_{1-6}$alkyl selected from fluoroethyl.

Another aspect includes a compound of Formula (I) or Formula (II), wherein $R_3$ is, in each instance, amino.

Another aspect includes a compound of Formula (I) or Formula (II), wherein $R_3$ is, in each instance, $C_{1-6}$alkylamino wherein $C_{1-6}$alkyl is selected from methyl, ethyl, propyl, isopropyl, butyl, isobutyl, sec-butyl, and tert-butyl.

Another aspect includes a compound of Formula (I), wherein $R_3$ is, in each instance, methylamino.

Another aspect includes a compound of Formula (I), wherein $R_3$ is, in each instance, $(C_{1-6}alkyl)_2$-amino wherein $C_{1-6}$alkyl is independently selected from methyl, ethyl, propyl, isopropyl, butyl, isobutyl, sec-butyl, and tert-butyl.

Another aspect includes a compound of Formula (I), wherein $R_3$ is, in each instance, dimethylamino.

Another aspect includes a compound of Formula (I) or Formula (II), wherein $R_3$ is, in each instance, hydroxy-$C_{1-6}$alkyl, wherein $C_{1-6}$alkyl is selected from methyl, ethyl, propyl, isopropyl, butyl, isobutyl, sec-butyl, and tert-butyl partially or completely substituted with one or more hydroxy groups where allowed by available valences.

Another aspect includes a compound of Formula (I), wherein $R_3$ is, in each instance, hydroxy-$C_{1-6}$alkyl selected from hydroxymethyl and hydroxyethyl.

One aspect includes a compound of Formula (I) or Formula (II), wherein $R_4$ is selected from $C_{3-10}$cycloalkyl, phenyl, heterocyclyl, and heteroaryl;
  wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S,
  wherein heteroaryl is a 3-7 membered monocyclic or 6-10 membered bicyclic ring system having 1, 2, 3, or 4 heteroatom ring members independently selected from N, O, or S, and
  wherein, each instance of $C_{3-10}$cycloalkyl, phenyl, heterocyclyl, and heteroaryl is optionally substituted with one, two or three $R_7$ substituents.

One aspect includes a compound of Formula (I) or Formula (II), wherein $R_4$ is $C_{3-10}$cycloalkyl selected from cyclopropyl, cylcobutyl, cyclopentyl, cyclohexyl, cycloheptyl, cyclooctyl, bicyclo[2.2.1]hexanyl, and adamantyl, optionally substituted with one, two or three $R_7$ substituents.

Another aspect includes a compound of Formula (I) or Formula (II), wherein $R_4$ is cyclopropyl, optionally substituted with one, two or three $R_7$ substituents.

One aspect includes a compound of Formula (I) or Formula (II), wherein $R_2$ is selected from phenyl and heteroaryl,
  wherein heteroaryl is a 3-7 membered monocyclic or 6-10 membered bicyclic ring system having 1, 2, 3, or 4 heteroatom ring members independently selected from N, O, or S,
  wherein, each instance of phenyl and heteroaryl is optionally substituted with one, two or three $R_5$ substituents and optionally, with one additional $R_6$ substituent, or,
  wherein, alternatively, each instance of phenyl and heteroaryl is optionally substituted with one, two, three or four $R_5$ substituents.

Another aspect includes a compound of Formula (I) or Formula (II), wherein $R_2$ is phenyl, optionally substituted with one, two or three $R_5$ substituents and optionally, with one additional $R_6$ substituent, or, alternatively, optionally substituted with one, two, three or four $R_5$ substituents.

Another aspect includes a compound of Formula (I) or Formula (II), wherein $R_2$ is heteroaryl selected from furanyl, 1H-pyrazolyl, 1H-imidazolyl, 1H-1,2,3-triazolyl, 4H-1,2,4-triazolyl, 1,2,4-oxadiazolyl, 1,3,4-oxadiazolyl, pyridinyl, pyridazinyl, pyrimidinyl, pyrazinyl, 1H-indolyl, 2H-indolyl, 1H-indazolyl, 2H-indazolyl, indolizinyl, benzofuranyl, 1H-benzimidazolyl, 1,3-benzoxazolyl, furo[2,3-b]pyridinyl, furo[2,3-c]pyridinyl, furo[3,2-b]pyridinyl, furo[3,2-c]pyridinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, 1H-pyrazolo[4,3-b]pyridinyl, 2H-pyrazolo[4,3-b]pyridinyl, 2H-pyrazolo[4,3-c]pyridinyl, pyrazolo[1,5-a]pyrazinyl, pyrazolo[1,5-a]pyrimidinyl, imidazo[1,2-a]pyridinyl, imidazo[1,2-a]pyrimidinyl, imidazo[1,2-a]pyrazinyl, imidazo[1,2-b]pyridazinyl, imidazo[1,2-c]pyrimidinyl, imidazo[1,5-a]pyridinyl, imidazo[2,1-b][1,3]thiazolyl, imidazo[2,1-b][1,3,4]thiadiazolyl, [1,3]oxazolo[4,5-b]pyridinyl, [1,2,4]triazolo[1,5-a]pyridnyl, [1,2,4]triazolo[1,5-b]pyridazinyl, and quinolinyl, optionally substituted with one, two or three $R_5$ substituents and optionally, with one additional $R_6$ substituent, or, alternatively, optionally substituted with one, two, three or four $R_5$ substituents.

Another aspect includes a compound of Formula (I) or Formula (II), wherein $R_2$ is heteroaryl selected from 1H-indazolyl, 2H-indazolyl, 1H-benzimidazolyl, 1,3-benzoxazolyl, furo[3,2-b]pyridinyl, pyrrolo[1,2-a]pyrazinyl, 1H-pyrazolo[4,3-b]pyridinyl, 2H-pyrazolo[4,3-b]pyridinyl, pyrazolo[1,5-a]pyrimidinyl, imidazo[1,2-a]pyridinyl, imidazo[1,2-a]pyrimidinyl, imidazo[1,2-a]pyrazinyl, imidazo[1,2-b]pyridazinyl, imidazo[2,1-b][1,3]thiazolyl, imidazo[2,1-b][1,3,4]thiadiazolyl, [1,2,4]triazolo[1,5-a]pyridnyl, and [1,2,4]triazolo[1,5-b]pyridazinyl, optionally substituted with one, two or three $R_5$ substituents and optionally, with one additional $R_6$ substituent, or, alternatively, optionally substituted with one, two, three or four $R_5$ substituents.

Another aspect includes a compound of Formula (I) or Formula (II), wherein $R_2$ is heteroaryl selected from furan-2-yl, furan-3-yl, 1H-pyrazol-3-yl, 1H-pyrazol-4-yl, 1H-pyrazol-5-yl, 1H-imidazol-1-yl, 1H-imidazol-4-yl, 1H-1,2,3-triazol-1-yl, 4H-1,2,4-triazol-4-yl, 1,2,4-oxadiazol-3-yl, 1,3,4-oxadiazol-2-yl, pyridin-2-yl, pyridin-3-yl, pyridin-4-yl, pyridazin-3-yl, pyridazin-4-yl, pyridazin-5-yl, pyrimidin-4-yl, pyrazin-1-yl, 1H-indol-3-yl, 1H-indol-4-yl, 1H-indol-5-yl, 1H-indol-6-yl, 1H-indazol-5-yl, 1H-indazol-6-yl, 2H-indazol-5-yl, 2H-indazol-6-yl, indolizin-2-yl, benzofuran-2-yl, benzofuran-5-yl, 1H-benzimidazol-2-yl, 1H-benzimidazol-5-yl, 1H-benzimidazol-6-yl, 1,3-benzoxazol-2-yl, 1,3-benzoxazol-5-yl, 1,3-benzoxazol-6-yl, furo[2,3-b]pyridine-6-yl, furo[2,3-c]pyridin-2-yl, furo[3,2-b]pyridin-2-yl, furo[3,2-c]pyridin-2-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyridin-5-yl, 1H-pyrazolo[4,3-b]pyridin-5-yl, 2H-pyrazolo[4,3-b]pyridin-5-yl, 2H-pyrazolo[4,3-c]pyridin-5-yl, pyrazolo[1,5-a]pyrazin-2-yl, pyrazolo[1,5-a]pyrimidin-5-yl, imidazo[1,2-a]pyridin-2-yl, imidazo[1,2-a]pyridin-6-yl, imidazo[1,2-a]pyrimidin-2-yl, imidazo[1,2-a]pyrimidin-6- yl, imidazo[1,2-a]pyrazin-2-yl, imidazo[1,2-a]pyrazin-3-yl, imidazo[1,2-a]pyrazin-6-yl, imidazo[1,2-b]pyridazin-2-yl, imidazo[1,2-b]pyridazin-6-yl, imidazo[1,2-c]pyrimidin-2-yl, imidazo[1,5-a]pyridin-6-yl, imidazo[1,5-a]pyridin-7-yl, imidazo[2,1-b][1,3]thiazol-6-yl, imidazo[2,1-b][1,3,4]thiadiazol-6-yl, [1,3]oxazolo[4,5-b]pyridin-2-yl, [1,2,4]triazolo[1,5-a]pyridin-5-yl, [1,2,4]triazolo[1,5-a]pyridin-6-yl, [1,2,4]triazolo[1,5-b]pyridn-6-yl, [1,2,4]triazolo[1,5-b]pyridazin-5-yl, [1,2,4]triazolo[1,5-b]pyridazin-6-yl, quinolin-6-yl, quinolin-7-yl, and quinolin-8-yl, optionally substituted with one, two or three $R_5$ substituents and optionally, with one additional $R_6$ substituent, or, alternatively, optionally substituted with one, two, three or four $R_5$ substituents.

Another aspect includes a compound of Formula (I) or Formula (II), wherein $R_2$ is heteroaryl selected from 1H-indazol-5-yl, 2H-indazol-5-yl, 1H-benzimidazol-6-yl, 1,3-benzoxazol-6-yl, furo[2,3-b]pyridine-6-yl, pyrrolo[1,2-a]pyrazin-7-yl, 1H-pyrazolo[4,3-b]pyridin-5-yl, 2H-pyrazolo[4,3-b]pyridin-5-yl, pyrazolo[1,5-a]pyrimidin-5-yl, imidazo[1,2-a]pyridin-6-yl, imidazo[1,2-a]pyrimidin-6-yl, imidazo[1,2-a]pyrazin-2-yl, imidazo[1,2-a]pyrazin-6-yl, imidazo[1,2-b]pyridazin-6-yl, imidazo[2,1-b][1,3]thiazol-6-yl, imidazo[2,1-b][1,3,4]thiadiazol-6-yl, [1,2,4]triazolo[1,5-a]pyridin-6-yl, and [1,2,4]triazolo[1,5-b]pyridazin-6-yl, optionally substituted with one, two or three $R_5$ substituents and optionally, with one additional $R_6$ substituent, or, alternatively, optionally substituted with one, two, three or four $R_5$ substituents.

One aspect includes a compound of Formula (I) or Formula (II), wherein $R_5$ is, in each instance, independently selected from cyano, halogen, hydroxy, $C_{1-6}$alkyl, halo-$C_{1-6}$alkyl, $C_{1-6}$alkyl-carbonyl, $C_{1-6}$alkoxy, halo-$C_{1-6}$alkoxy, $C_{1-6}$alkoxy-$C_{1-6}$alkyl, $C_{1-6}$alkoxy-carbonyl, $C_{1-6}$alkoxy-carbonyl-$C_{1-6}$alkyl, carboxyl, $C_{1-6}$alkyl-carboxyl, amino, $C_{1-6}$alkyl-amino, ($C_{1-6}$alkyl)$_2$-amino, amino-$C_{1-6}$alkyl, amino-carbonyl, and hydroxy-$C_{1-6}$alkyl.

Another aspect includes a compound of Formula (I) or Formula (II), wherein $R_5$ is, in each instance, independently selected from cyano, halogen, hydroxy, $C_{1-6}$alkyl, halo-$C_{1-6}$alkyl, $C_{1-6}$alkoxy$C_{1-6}$alkoxy-carbonyl-$C_{1-6}$alkyl, carboxyl, $C_{1-6}$alkyl-carboxyl, amino, $C_{1-6}$alkyl-amino, ($C_{1-6}$alkyl)$_2$-amino, amino-$C_{1-6}$alkyl, and amino-carbonyl.

Another aspect includes a compound of Formula (I) or Formula (II), wherein $R_5$ is, in each instance, cyano.

Another aspect includes a compound of Formula (I) or Formula (II), wherein $R_5$ is, in each instance, halogen selected from bromo, chloro, fluoro, and iodo.

Another aspect includes a compound of Formula (I) or Formula (II), wherein $R_5$ is, in each instance, fluoro.

Another aspect includes a compound of Formula (I) or Formula (II), wherein $R_5$ is, in each instance, hydroxy.

Another aspect includes a compound of Formula (I) or Formula (II), wherein $R_5$ is, in each instance, $C_{1-6}$alkyl selected from methyl, ethyl, propyl, isopropyl, and tert-butyl.

Another aspect includes a compound of Formula (I) or Formula (II), wherein $R_5$ is, in each instance, $C_{1-6}$alkyl selected from methyl and ethyl.

Another aspect includes a compound of Formula (I) or Formula (II), wherein $R_5$ is, in each instance, halo-$C_{1-6}$alkyl, wherein $C_{1-6}$alkyl is selected from methyl, ethyl, propyl, isopropyl, butyl, isobutyl, sec-butyl, and tert-butyl partially or completely substituted with one or more halogens selected from bromo, chloro, fluoro, and iodo where allowed by available valences.

Another aspect includes a compound of Formula (I), wherein $R_5$ is, in each instance, halo-$C_{1-6}$alkyl selected from trifluoromethyl.

Another aspect includes a compound of Formula (I) or Formula (II), wherein $R_5$ is, in each instance, $C_{1-6}$alkoxy selected from methoxy, ethoxy, propoxy, isopropoxy, and tert-butoxy.

Another aspect includes a compound of Formula (I) or Formula (II), wherein $R_a$ is, in each instance, methoxy.

Another aspect includes a compound of Formula (I) or Formula (II), wherein $R_5$ is, in each instance, $C_{1-6}$alkoxy-carbonyl-$C_{1-6}$alkyl, wherein $C_{1-6}$alkoxy is selected from methoxy, ethoxy, propoxy, isopropoxy, and tert-butoxy, and wherein $C_{1-6}$alkyl is selected from methyl, ethyl, propyl, isopropyl, and tert-butyl.

Another aspect includes a compound of Formula (I) or Formula (II), wherein $R_5$ is, in each instance, —CH$_2$CO$_2$CH$_3$.

Another aspect includes a compound of Formula (I) or Formula (II), wherein $R_5$ is, in each instance, carboxyl.

Another aspect includes a compound of Formula (I) or Formula (II), wherein $R_5$ is, in each instance, $C_{1-6}$alkyl-carboxyl, wherein $C_{1-6}$alkyl is selected from methyl, ethyl, propyl, isopropyl, and tert-butyl.

Another aspect includes a compound of Formula (I) or Formula (II), wherein $R_5$ is, in each instance, —CH$_2$CO$_2$H.

Another aspect includes a compound of Formula (I) or Formula (II), wherein $R_5$ is, in each instance, amino.

Another aspect includes a compound of Formula (I) or Formula (II), wherein $R_5$ is, in each instance, $C_{1-6}$alkyl-amino wherein $C_{1-6}$alkyl is selected from methyl, ethyl, propyl, isopropyl, butyl, isobutyl, sec-butyl, and tert-butyl.

Another aspect includes a compound of Formula (I), wherein $R_5$ is, in each instance, methylamino.

Another aspect includes a compound of Formula (I), wherein $R_5$ is, in each instance, ($C_{1-6}$alkyl)$_2$-amino wherein $C_{1-6}$alkyl is independently selected from methyl, ethyl, propyl, isopropyl, butyl, isobutyl, sec-butyl, and tert-butyl.

Another aspect includes a compound of Formula (I), wherein $R_5$ is, in each instance, dimethylamino.

Another aspect includes a compound of Formula (I), wherein $R_5$ is, in each instance, amino-$C_{1-6}$alkyl wherein $C_{1-6}$alkyl is independently selected from methyl, ethyl, propyl, isopropyl, butyl, isobutyl, sec-butyl, and tert-butyl.

Another aspect includes a compound of Formula (I), wherein $R_5$ is, in each instance, methanamine.

Another aspect includes a compound of Formula (I), wherein $R_5$ is, in each instance, amino-carbonyl.

Another aspect includes a compound of Formula (I) or Formula (II), wherein $R_6$ is selected from $C_{3-10}$cycloalkyl, phenyl, phenyl-$C_{1-6}$alkoxy, phenyl-oxy, heterocyclyl, and heteroaryl;
  wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S,
  wherein heteroaryl is a 3-7 membered monocyclic or 6-10 membered bicyclic ring system having 1, 2, 3, or 4 heteroatom ring members independently selected from N, O, or S, and wherein, each instance of $C_{3-10}$cycloalkyl, phenyl, heterocyclyl, and heteroaryl is optionally substituted with one, two or three $R_7$ substituents.

Another aspect includes a compound of Formula (I) or Formula (II), wherein $R_6$ is $C_{3-10}$cycloalkyl selected from cyclopropyl, cylcobutyl, cyclopentyl, cyclohexyl, cycloheptyl, cyclooctyl, bicyclo[2.2.1]hexanyl, and adamantyl, optionally substituted with one, two or three $R_7$ substituents.

Another aspect includes a compound of Formula (I) or Formula (II), wherein $R_6$ is cyclopropyl, optionally substituted with one, two or three $R_7$ substituents.

Another aspect includes a compound of Formula (I) or Formula (II), wherein $R_6$ is phenyl-$C_{1-6}$alkoxy, wherein $C_{1-6}$alkoxy is selected from methoxy, ethoxy, propoxy, isopropoxy, and tert-butoxy, and wherein $C_{1-6}$alkyl is selected from methyl, ethyl, propyl, isopropyl, and tert-butyl, and wherein, phenyl is optionally substituted with one, two or three $R_7$ substituents.

Another aspect includes a compound of Formula (I) or Formula (II), wherein $R_6$ is benzyloxy.

Another aspect includes a compound of Formula (I) or Formula (II), wherein $R_6$ is phenyl-oxy, wherein, phenyl is optionally substituted with one, two or three $R_7$ substituents.

Another aspect includes a compound of Formula (I) or Formula (II), wherein $R_6$ is benzyloxy.

Another aspect includes a compound of Formula (I) or Formula (II), wherein $R_6$ is heteroaryl selected from furanyl, 1H-pyrazolyl, 1H-imidazolyl, 1H-1,2,3-triazolyl, 4H-1,2,4-triazolyl, 1,2,4-oxadiazolyl, 1,3,4-oxadiazolyl, pyridinyl, pyridazinyl, pyrimidinyl, and pyrazinyl, optionally substituted with one, two or three $R_7$ substituents.

Another aspect includes a compound of Formula (I) or Formula (II), wherein $R_6$ is heteroaryl selected from 1H-pyrazolyl and 1H-imidazolyl, optionally substituted with one, two or three $R_7$ substituents.

Another aspect includes a compound of Formula (I) or Formula (II), wherein $R_6$ is heteroaryl selected from furan-2-yl, furan-3-yl, 1H-pyrazol-3-yl, 1H-pyrazol-4-yl, 1H-pyrazol-5-yl, 1H-imidazol-1-yl, 1H-imidazol-4-yl, 1H-1,2,3-triazol-1-yl, 4H-1,2,4-triazol-4-yl, 1,2,4-oxadiazol-3-yl, 1,3,4-oxadiazol-2-yl, pyridin-2-yl, pyridin-3-yl, pyridin-4-yl, pyridazin-3-yl, pyridazin-4-yl, pyridazin-5-yl, pyrimidin-4-yl, pyrazin-1-yl, optionally substituted with one, two or three $R_7$ substituents.

Another aspect includes a compound of Formula (I) or Formula (II), wherein $R_6$ is heteroaryl selected from 1H-pyrazol-4-yl and 1H-imidazol-1-yl, optionally substituted with one, two or three $R_7$ substituents.

One aspect includes a compound of Formula (I) or Formula (II), wherein $R_7$ is, in each instance, independently selected from cyano, halogen, hydroxy, $C_{1-6}$alkyl, halo-$C_{1-6}$alkyl, $C_{1-6}$alkyl-carbonyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, $(C_{1-6}$alkyl$)_2$-amino, amino-$C_{1-6}$alkyl, and hydroxy-$C_{1-6}$alkyl.

Another aspect includes a compound of Formula (I) or Formula (II), wherein $R_7$ is, in each instance, halogen, hydroxy, $C_{1-6}$alkyl, halo-$C_{1-6}$alkyl, $C_{1-6}$alkyl-carbonyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, $(C_{1-6}$alkyl$)_2$-amino, amino-$C_{1-6}$alkyl, and hydroxy-$C_{1-6}$alkyl.

Another aspect includes a compound of Formula (I) or Formula (II), wherein $R_7$ is, in each instance, halogen selected from bromo, chloro, fluoro, and iodo.

Another aspect includes a compound of Formula (I) or Formula (II), wherein $R_7$ is, in each instance, fluoro.

One aspect of the compound of Formula (I) includes a compound selected from Formula (Ia), Formula (Ib), Formula (Ic), Formula (Id), Formula (Ie), Formula (If), Formula (Ig), or Formula (Ih):

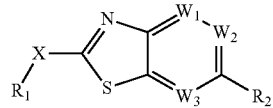

(Ia)

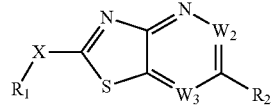

(Ib)

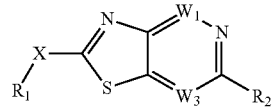

(Ic)

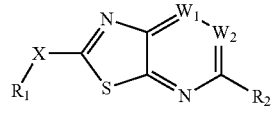

(Id)

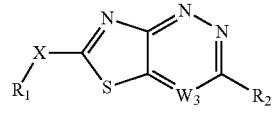

(Ie)

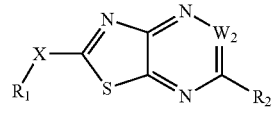

(If)

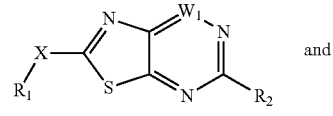

(Ig)

and

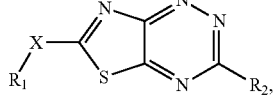

(Ih)

or a form thereof.

Another aspect of the compound of Formula (I) includes a compound selected from Formula (Ia), Formula (Ib), Formula (Ic), Formula (Id), Formula (Ie), Formula (If), or Formula (Ig):

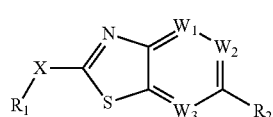

(Ia)

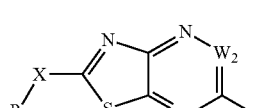

(Ib)

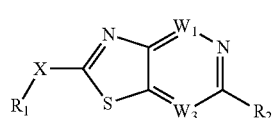

(Ic)

-continued

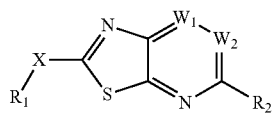 (Id)

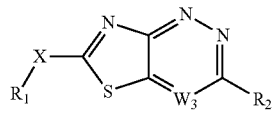 (Ie)

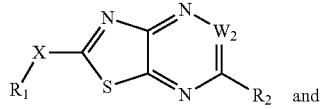 (If)

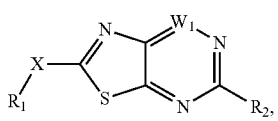 (Ig)

or a form thereof.

One aspect of the compound of Formula (II) includes a compound selected from Formula (IIa), Formula (IIb), Formula (IIc), Formula (IId), Formula (IIe), Formula (IIf), Formula (IIg) or Formula (IIh):

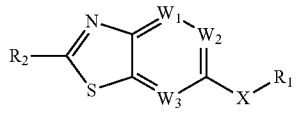 (IIa)

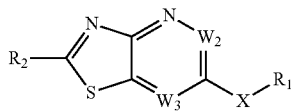 (IIb)

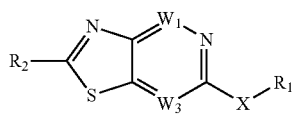 (IIc)

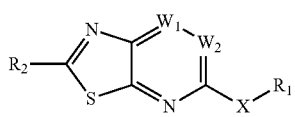 (IId)

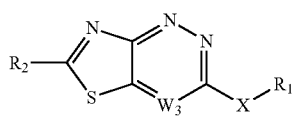 (IIe)

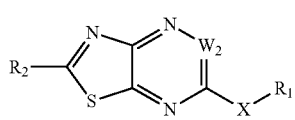 (IIf)

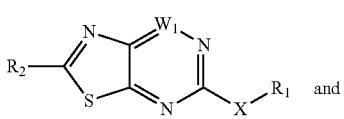 (IIg)

-continued

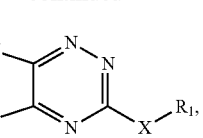 (IIh)

or a form thereof.

Another aspect of the compound of Formula (II) includes a compound selected from Formula (IIa) or Formula (IIb):

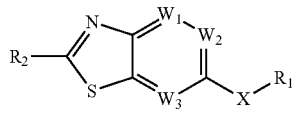 (IIa)

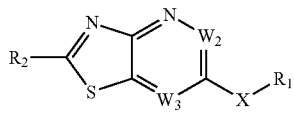 (IIb)

or a form thereof.

One aspect of the compound of Formula (Ia), Formula (Ib), Formula (Ic), Formula (Id), Formula (Ie), Formula (If), Formula (Ig) or Formula (Ih) includes a compound selected from Formula (Ia1), Formula (Ib1), Formula (Ic1), Formula (Id1), Formula (Ie1), Formula (If1), Formula (Ig1), or Formula (Ih1):

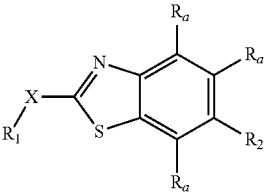 (Ia1)

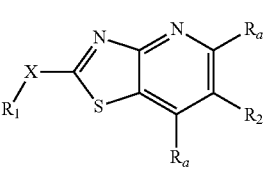 (Ib1)

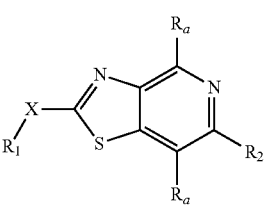 (Ic1)

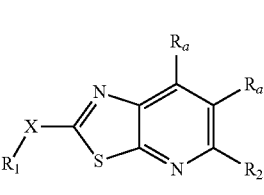 (Id1)

(Ie1)

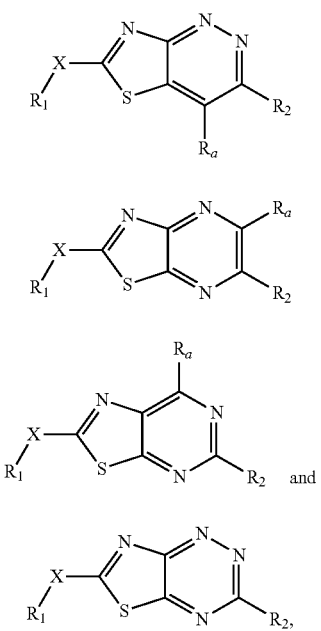

(If1)

(Ig1)

(Ih1)

or a form thereof.

Another aspect of the compound of Formula (Ia), Formula (Ib), Formula (Ic), Formula (Id), Formula (Ie), Formula (If) or Formula (Ig) includes a compound selected from Formula (Ia1), Formula (Ib1), Formula (Ic1), Formula (Id1), Formula (Ie1), Formula (If1), or Formula (Ig1):

(Ia1)

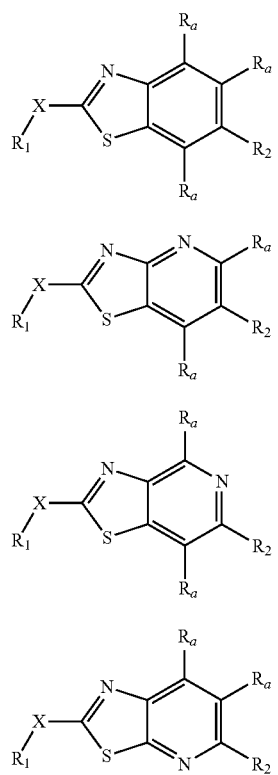

(Ib1)

(Ic1)

(Id1)

(Ie1)

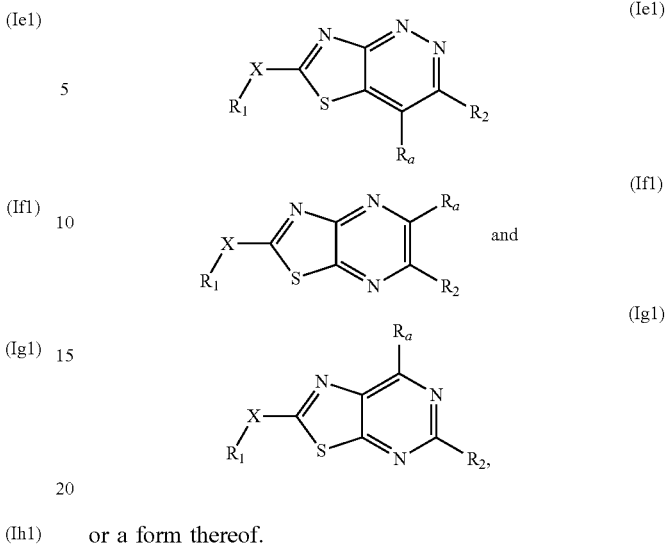

(If1)

(Ig1)

or a form thereof.

One aspect of the compound of Formula (IIa), Formula (IIb), Formula (IIc), Formula (IId), Formula (IIe), Formula (IIf), Formula (IIg) or Formula (IIh) includes a compound selected from Formula (IIa1), Formula (IIb1), Formula (Ic1), Formula (IId1), Formula (IIe1), Formula (IIf1), Formula (IIg1) or Formula (IIh1):

(IIa1)

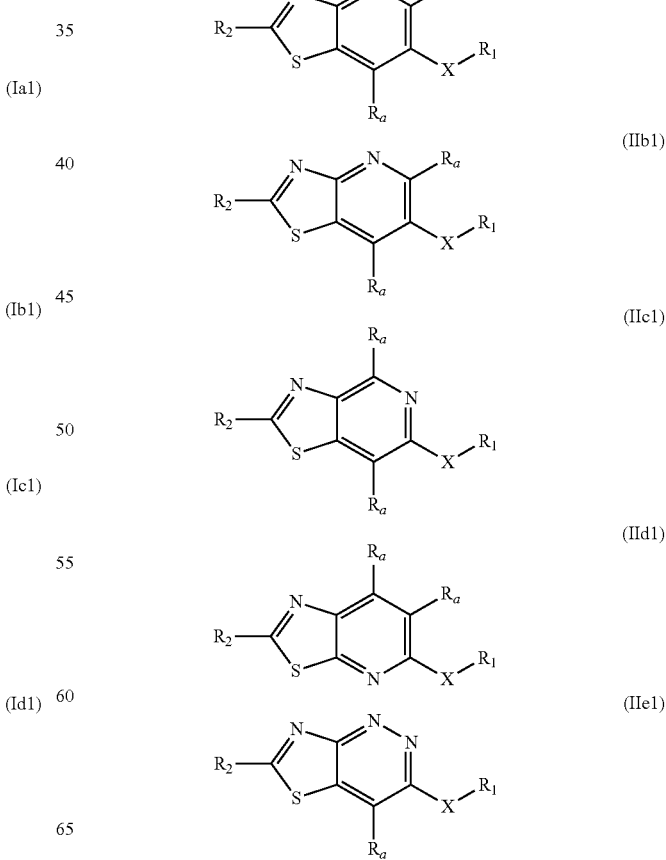

(IIb1)

(IIc1)

(IId1)

(IIe1)

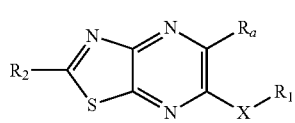
(IIf1)

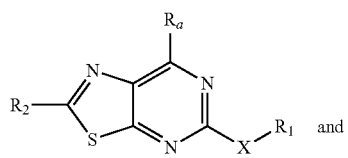
(IIg1)

and

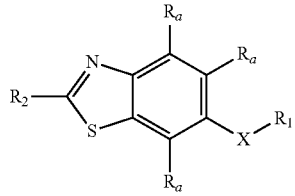
(IIh1)

or a form thereof.

Another aspect of the compound of Formula (IIa) or Formula (IIb) includes a compound selected from Formula (IIa1) or Formula (IIb1):

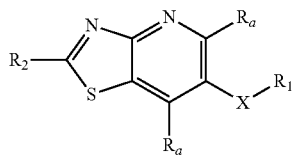
(IIa1)

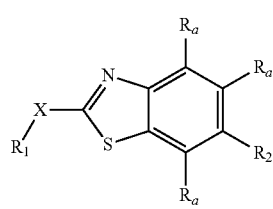
(IIb1)

or a form thereof.

Another aspect of the compound of Formula (I) includes the compound of Formula (Ia1):

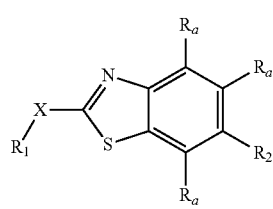
(Ia1)

or a form thereof.

Another aspect of the compound of Formula (I) includes the compound of Formula (Ib1):

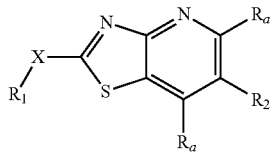
(Ib1)

or a form thereof.

Another aspect of the compound of Formula (I) includes the compound of Formula (Ic1):

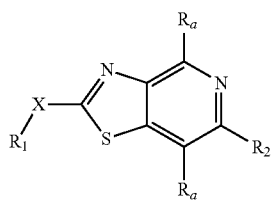
(Ic1)

or a form thereof.

Another aspect of the compound of Formula (I) includes the compound of Formula (Id1):

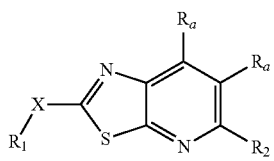
(Id1)

or a form thereof.

Another aspect of the compound of Formula (I) includes the compound of Formula (Ie1):

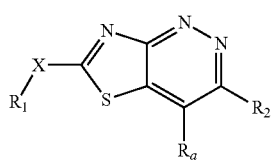
(Ie1)

or a form thereof.

Another aspect of the compound of Formula (I) includes the compound of Formula (If1):

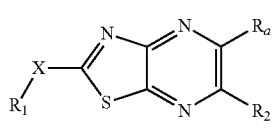
(If1)

or a form thereof.

Another aspect of the compound of Formula (I) includes the compound of Formula (Ig1):

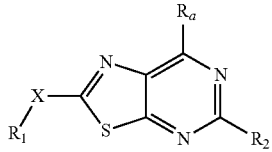

(Ig1)

or a form thereof.

Another aspect of the compound of Formula (II) includes the compound of Formula (IIa1):

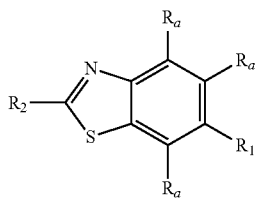

(IIa1)

or a form thereof.

Another aspect of the compound of Formula (II) includes the compound of Formula (IIb1):

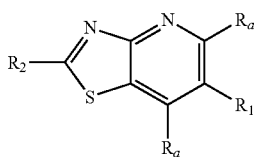

(IIb1)

or a form thereof.

An aspect of the compound of Formula (I) or Formula (II) or a form thereof includes a compound selected from the group consisting of:

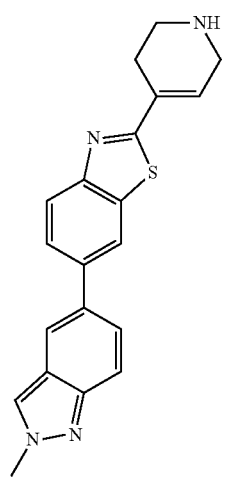

1

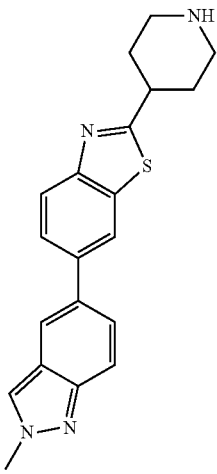

2

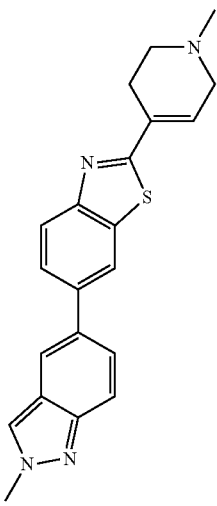

3

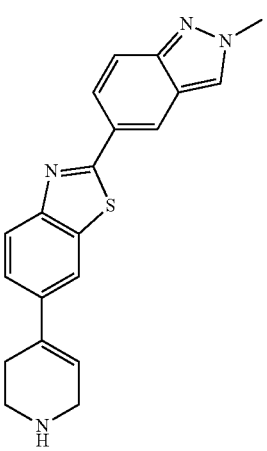

4

-continued
5
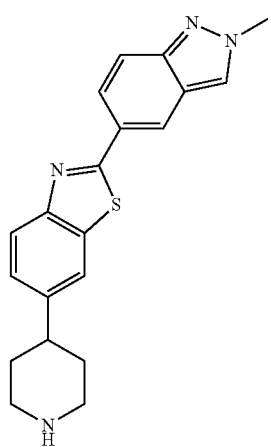
6
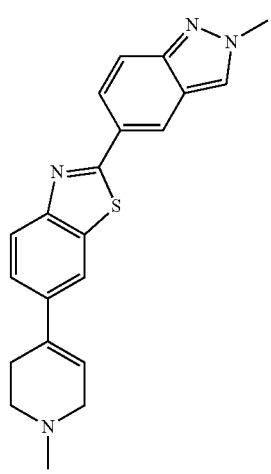
7
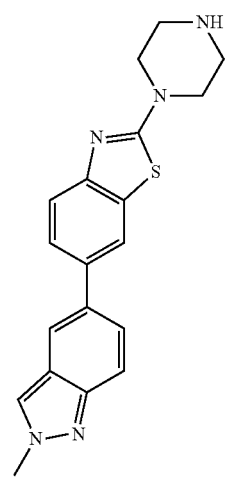
-continued
8
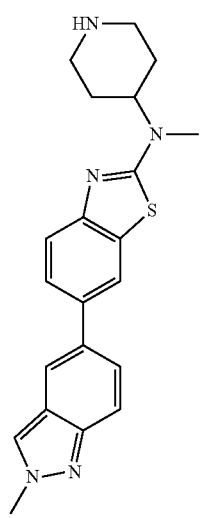
9
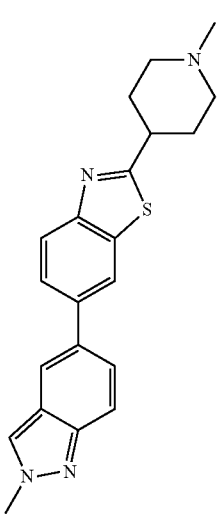
10
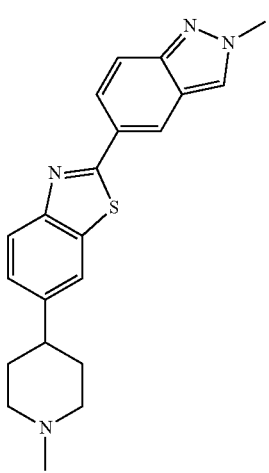

11
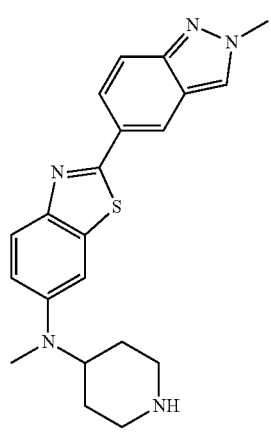
12
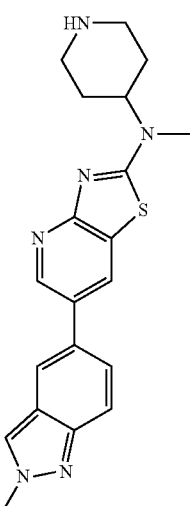
13
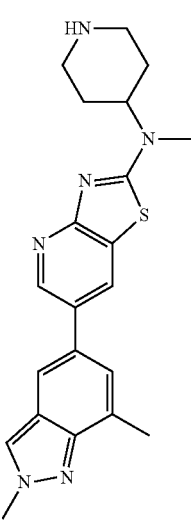
14
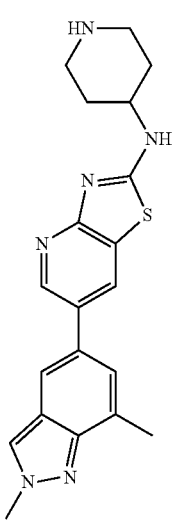
15
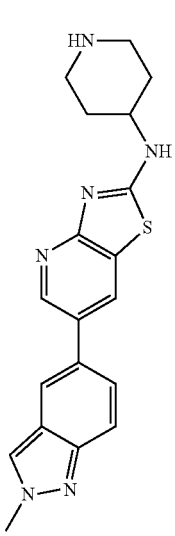
16
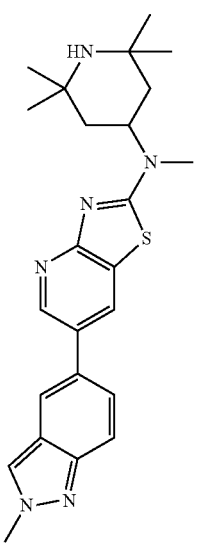

-continued
17
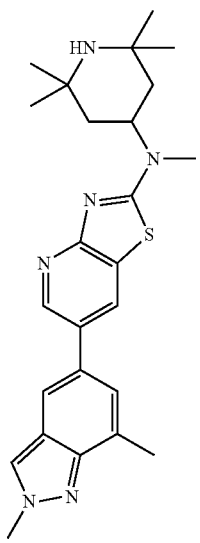
18
19
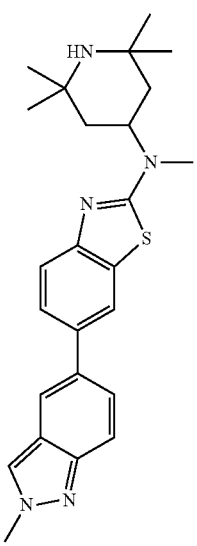
-continued
20
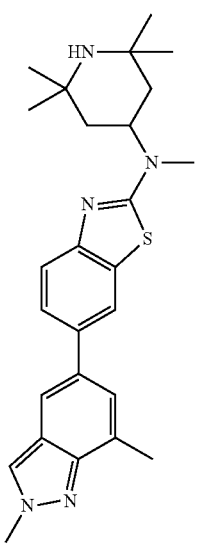
21
22
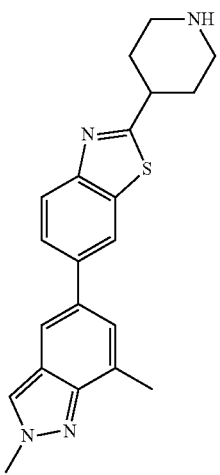

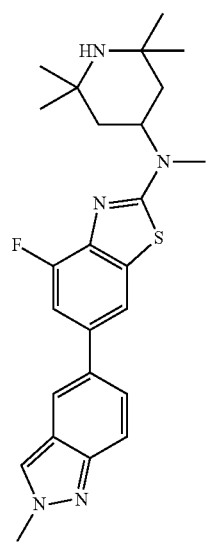
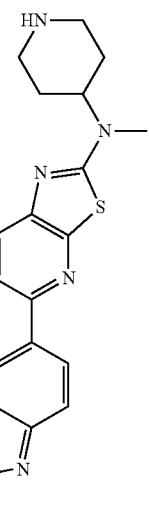
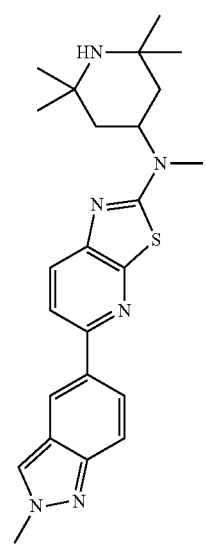
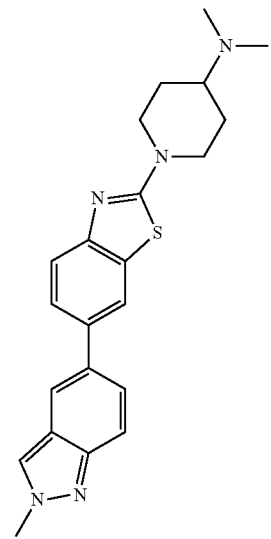

31 -continued
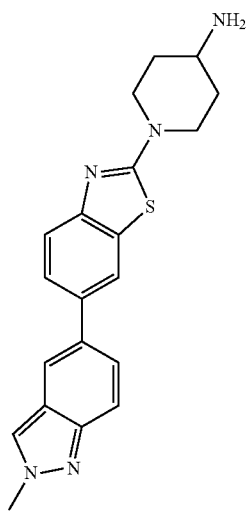
29
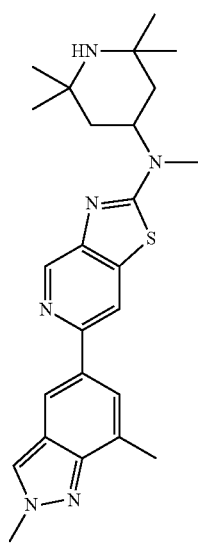
31
32 -continued
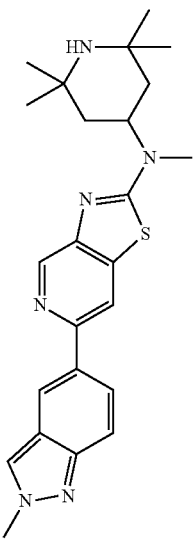
32
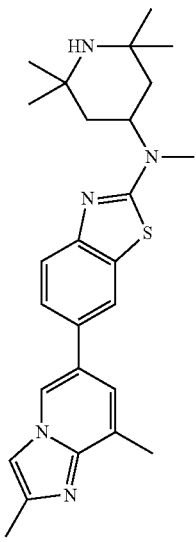
33
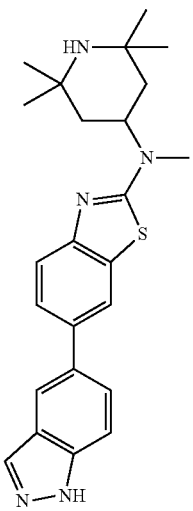
34

-continued
35
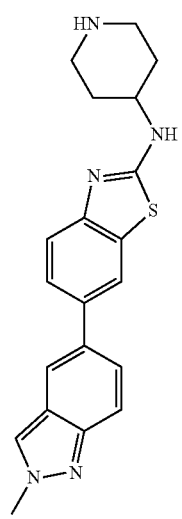
36
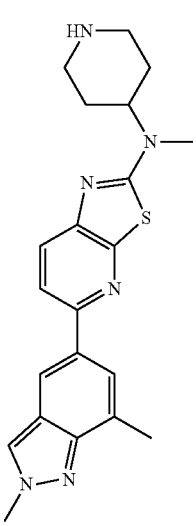
37
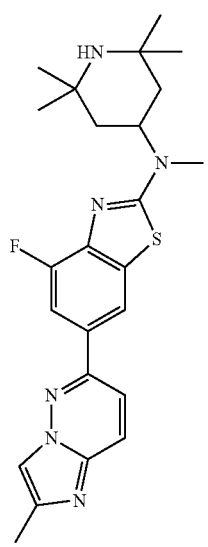
-continued
38
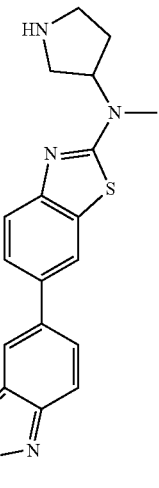
39
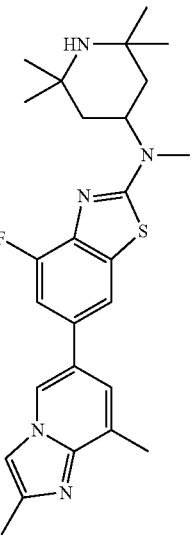
40
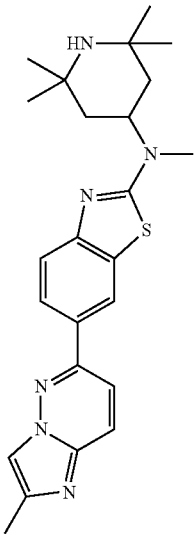

35
-continued
41
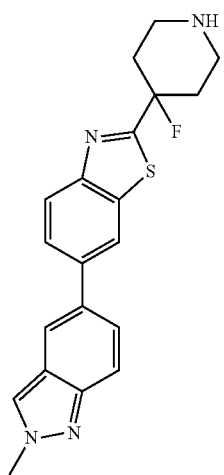
42
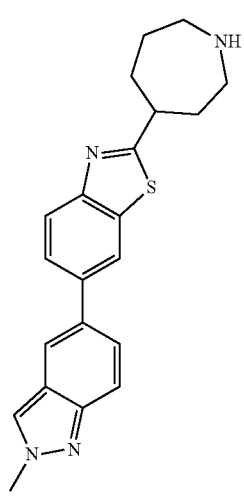
43
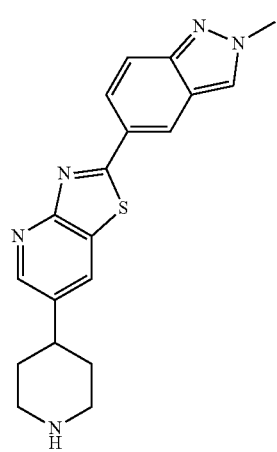
36
-continued
44
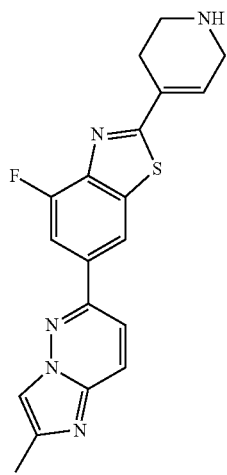
45
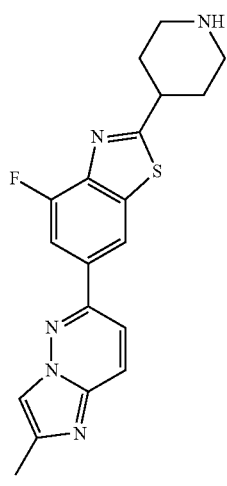
46
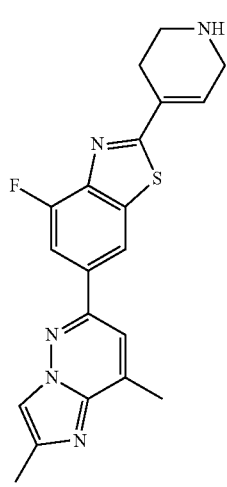

47
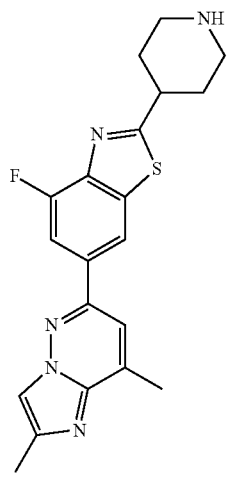
48
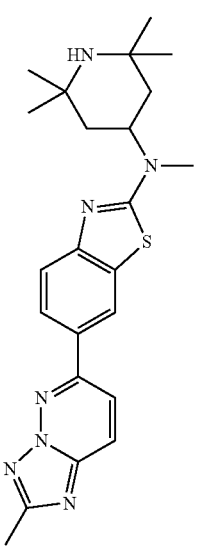
49
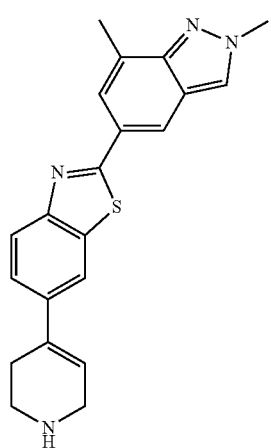
50
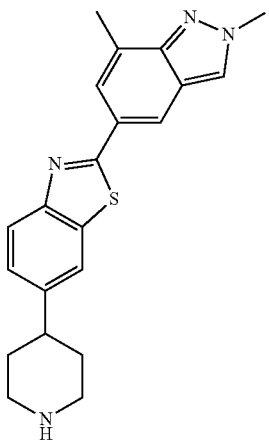
51
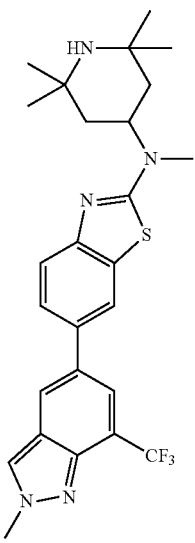
52
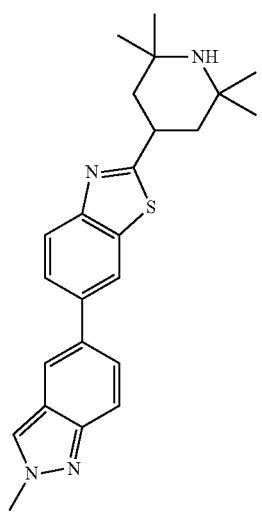

-continued
53
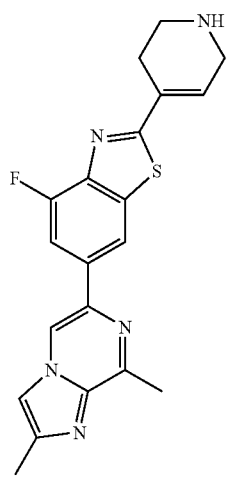
54
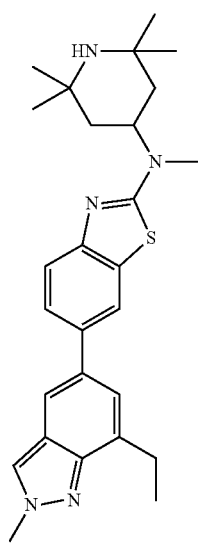
55
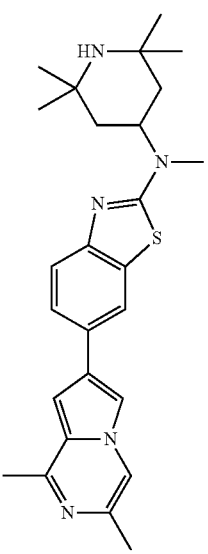
-continued
56
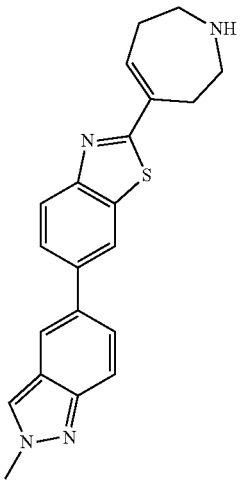
57
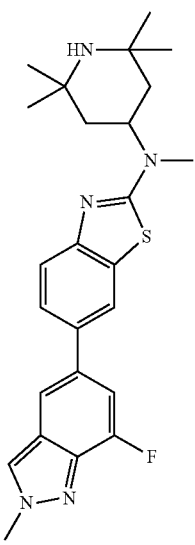
58
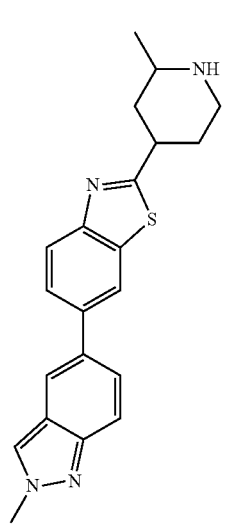

59
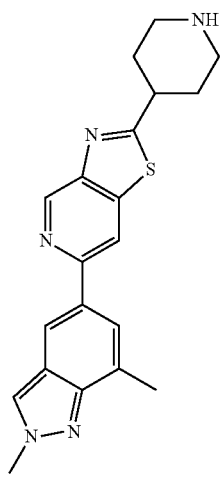
60
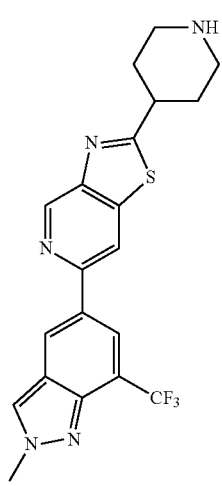
61
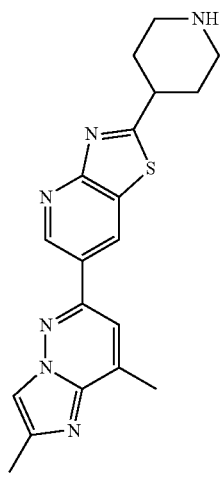
62
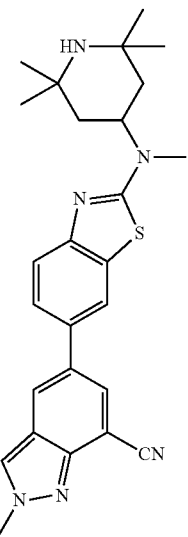
63
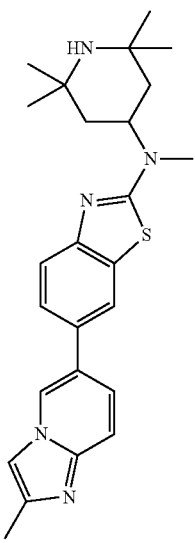
64
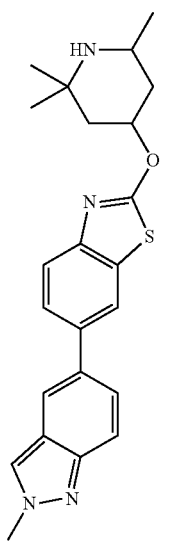

43
-continued
65
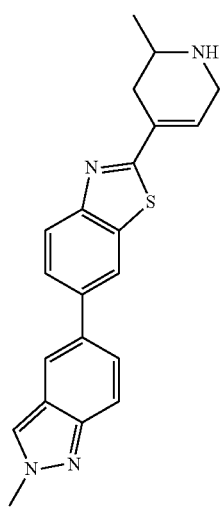
66
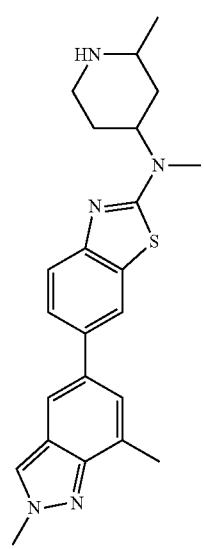
67
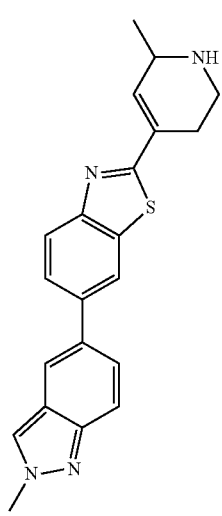
44
-continued
68
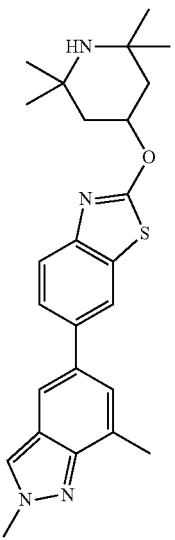
70
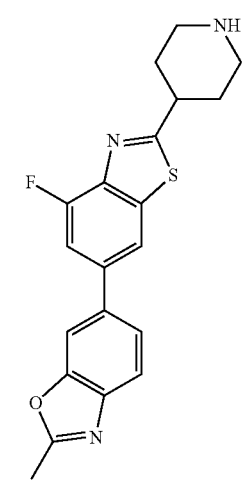
71
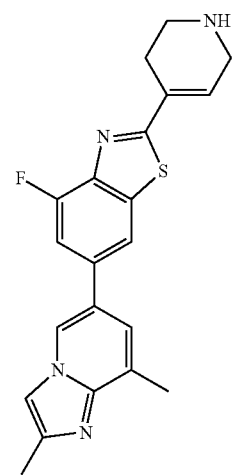

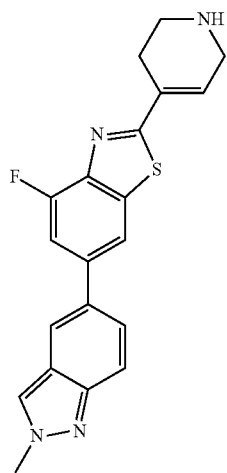
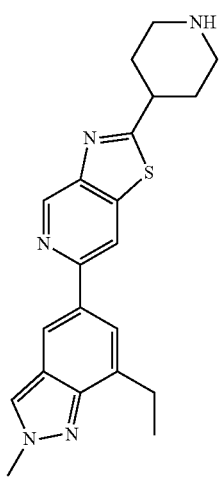

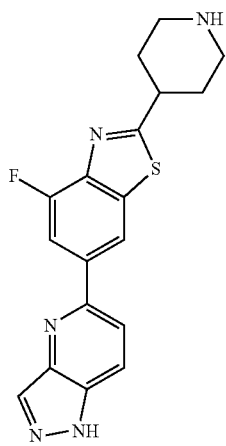
78
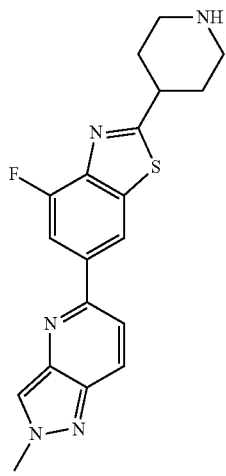
79
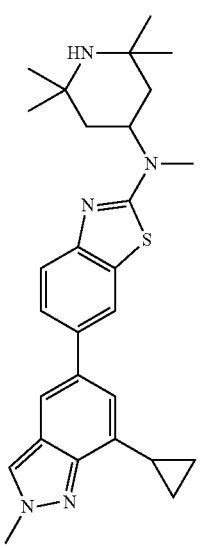
80
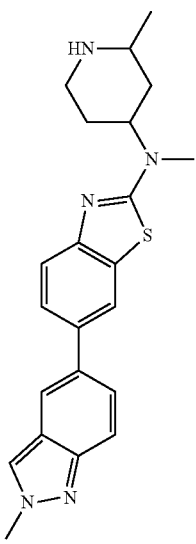
81
82
83

84
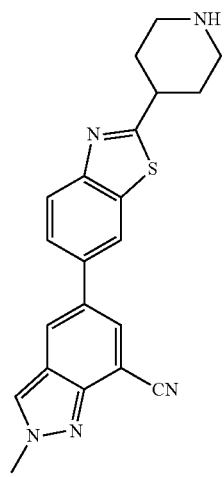
85
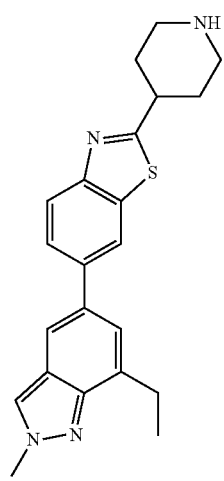
86
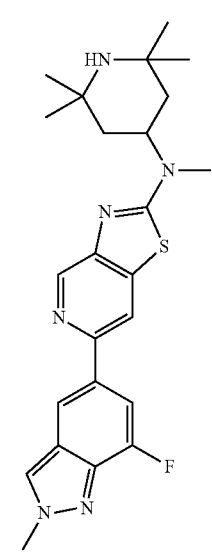
87
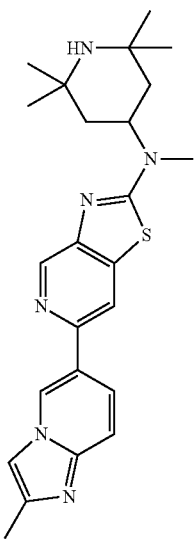
88
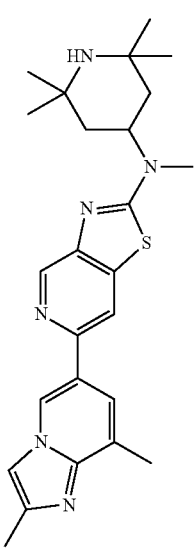
89
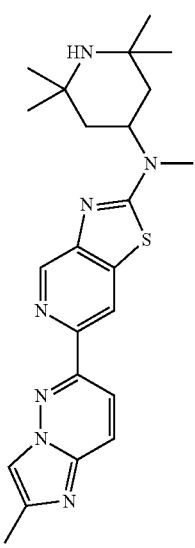

| | |
|---|---|
| 90 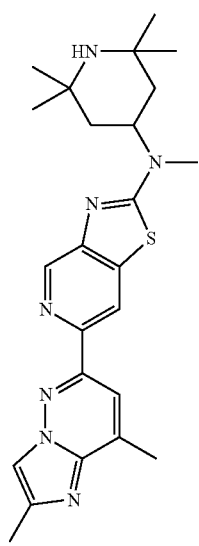 | 93 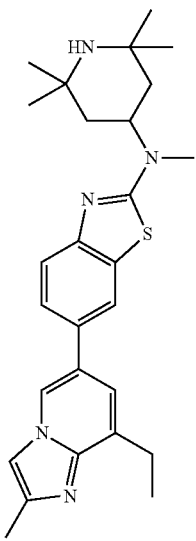 |
| 91 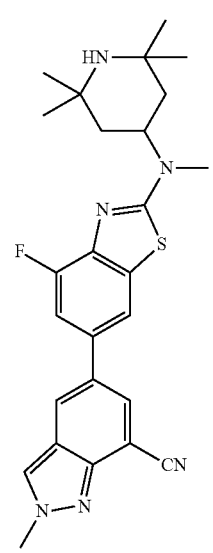 | 94 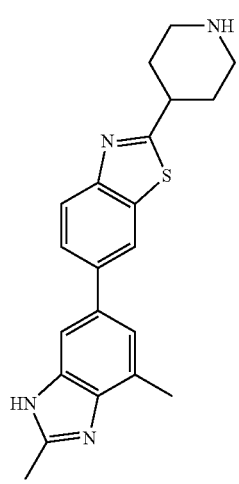 |
| 92 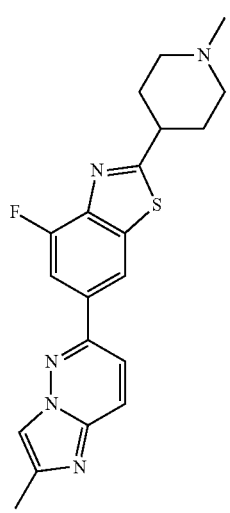 | 95 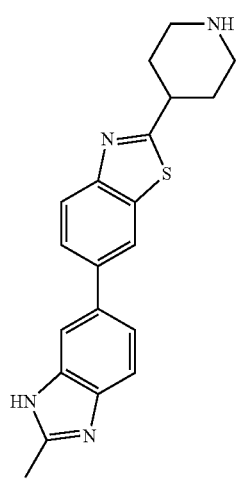 |

96 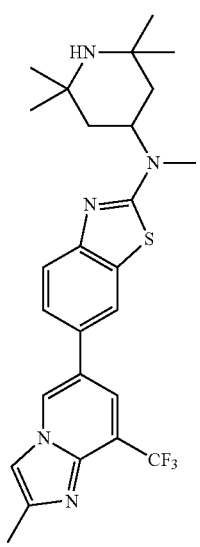
97 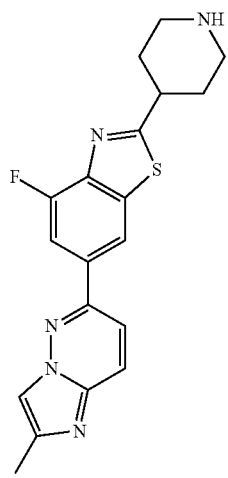
99 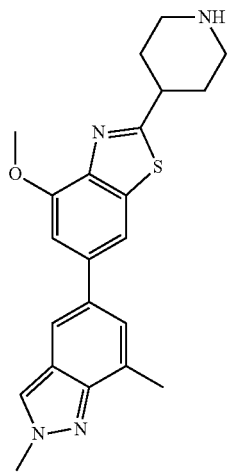
100 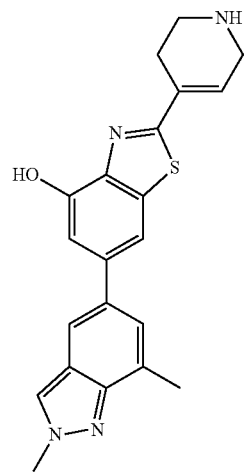
98 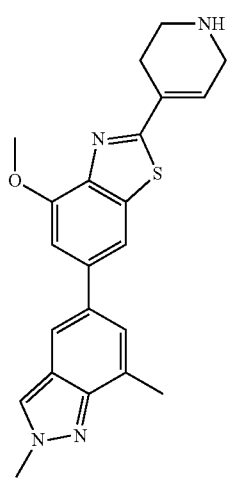
101 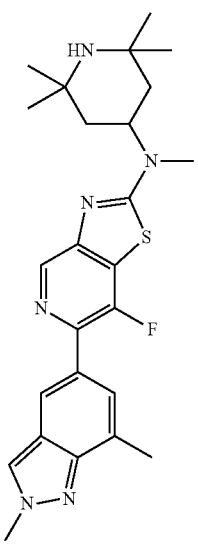

-continued
102
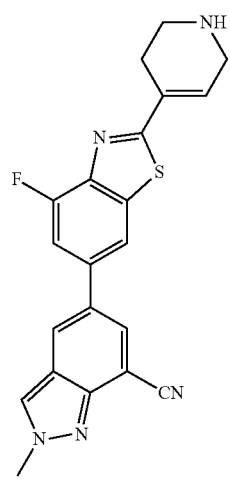
103
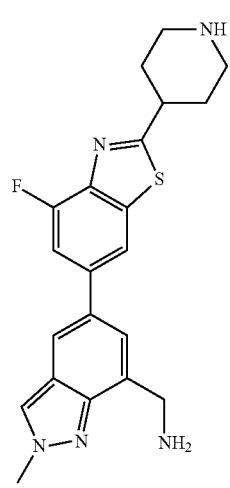
104
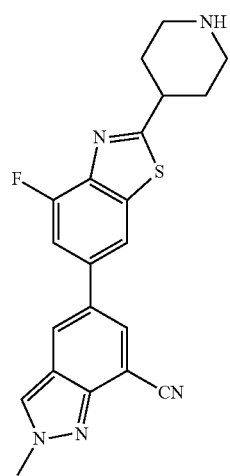
-continued
105
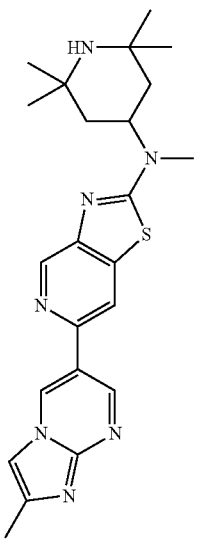
106
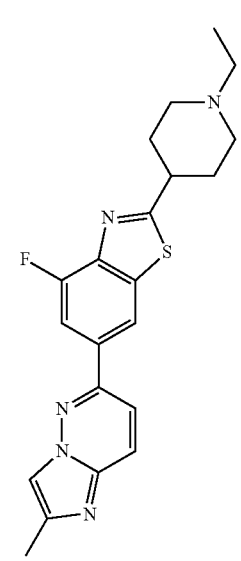
107
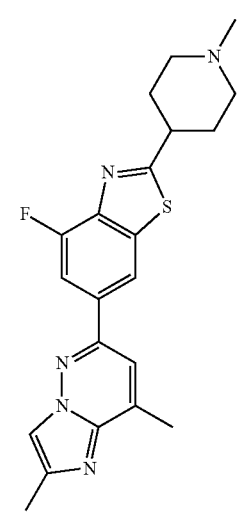

108 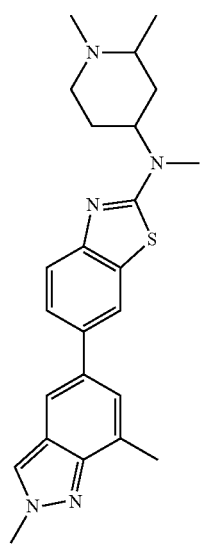
109 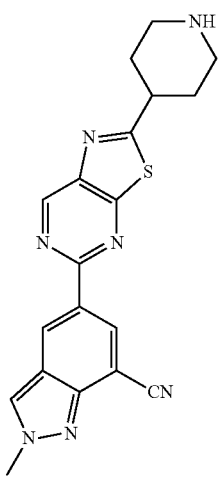
110 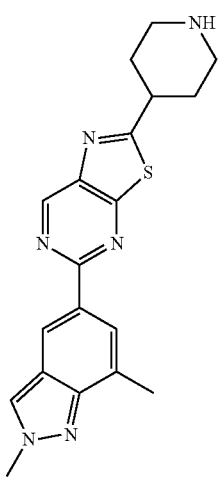
111 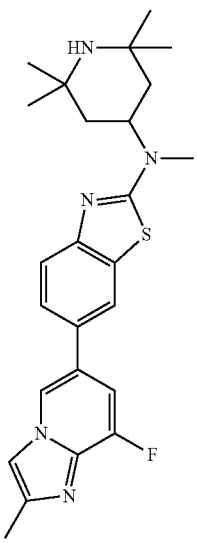
112 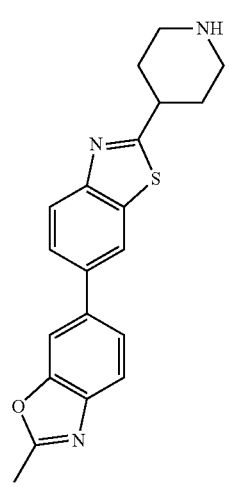
113 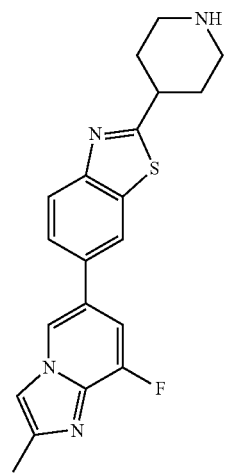

114 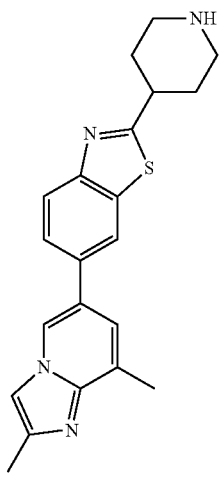
115 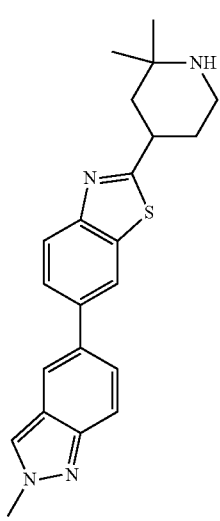
116 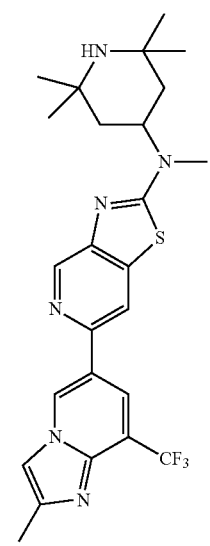
117 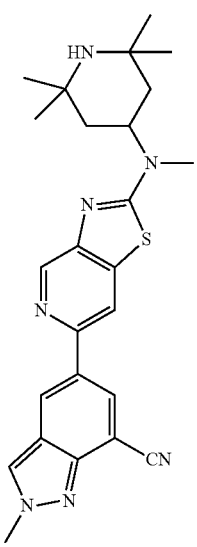
118 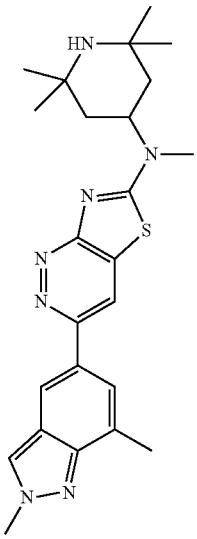
119 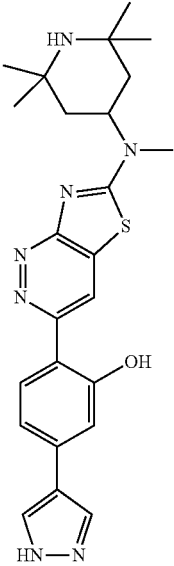

120 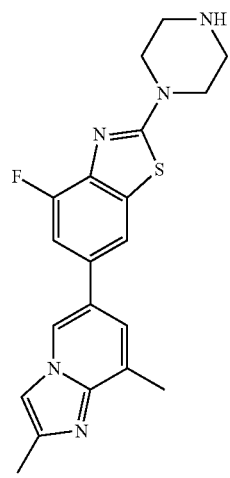
121 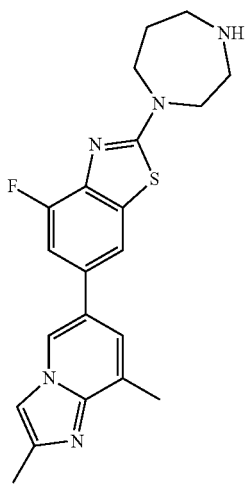
122 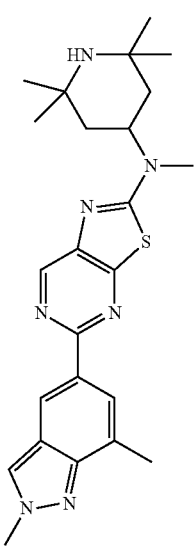
123 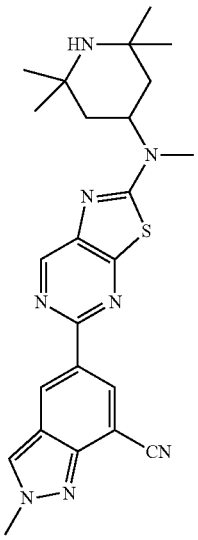
124
125 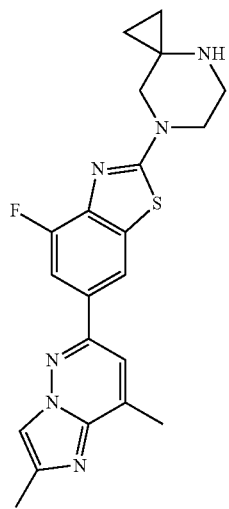

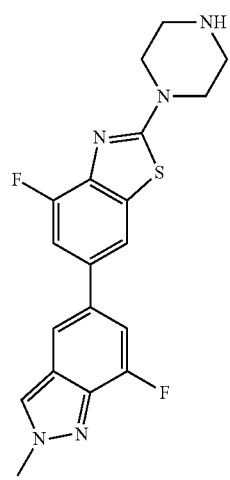
126
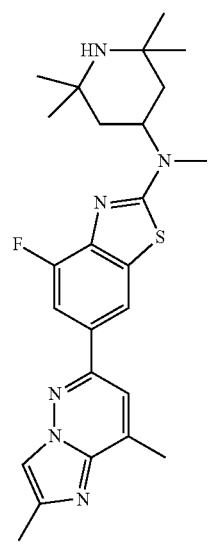
127
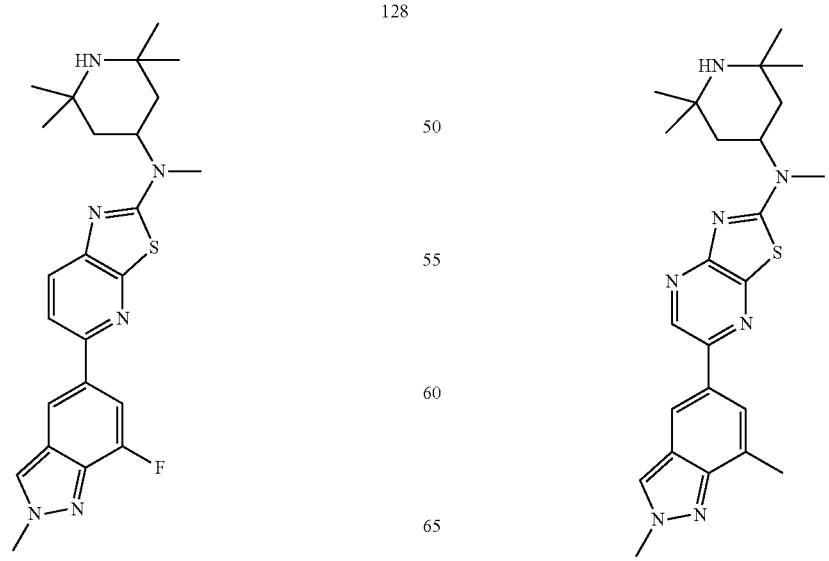
128
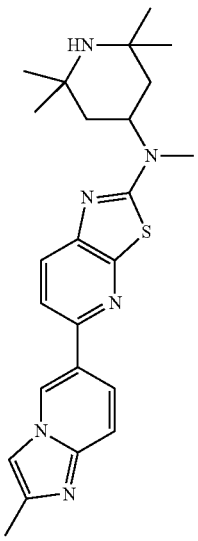
129
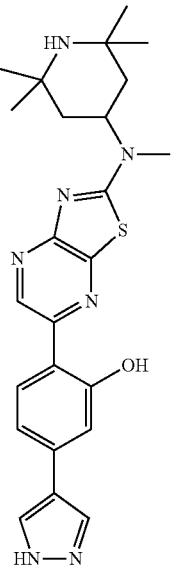
130
131

132
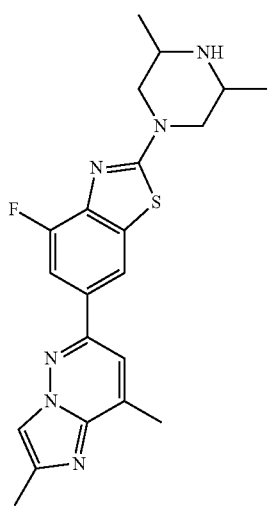
133
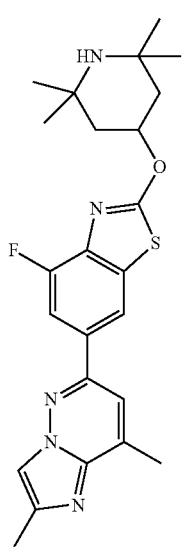
134
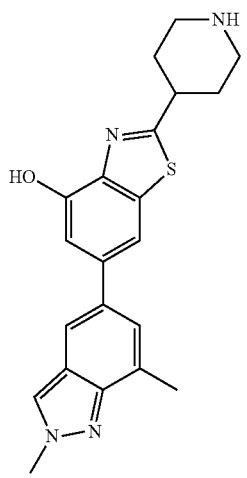
135
136
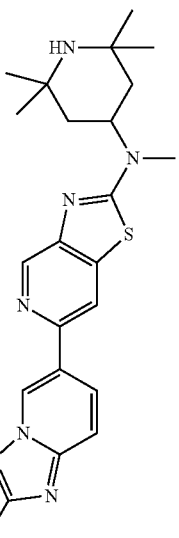
137
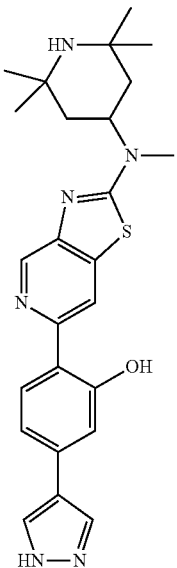

138
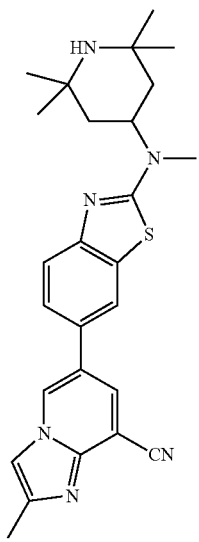
139
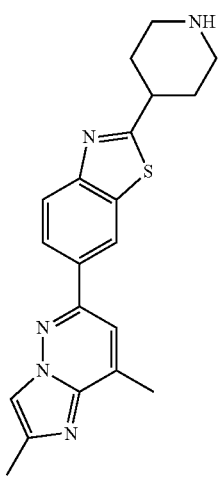
140
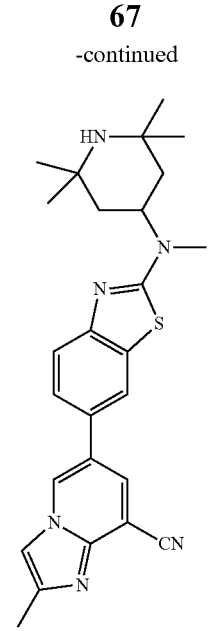
141
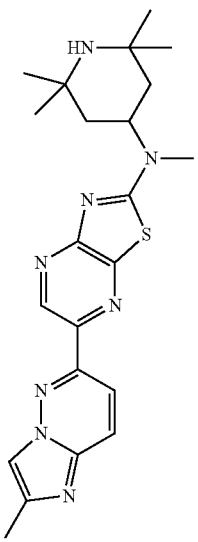
142
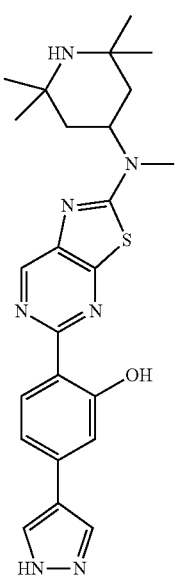
143
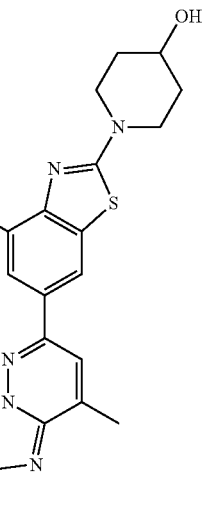

144 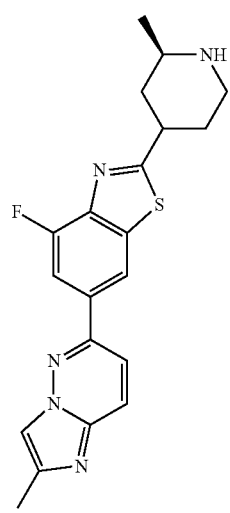
145 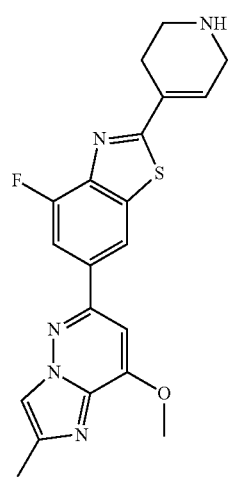
146 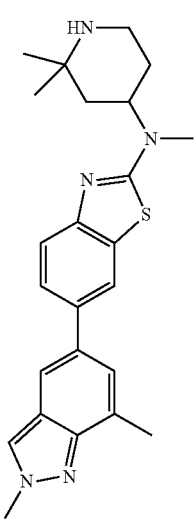
147 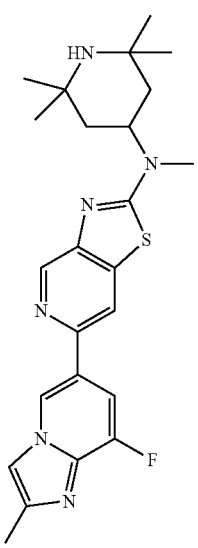
148 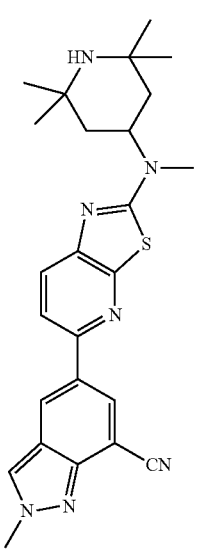
149 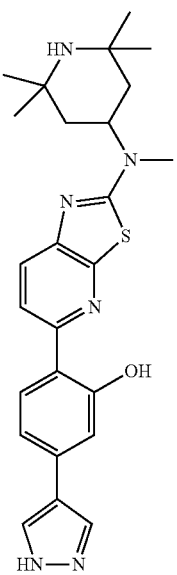

| 150 | 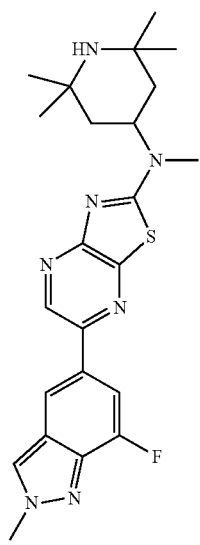 | 153 | 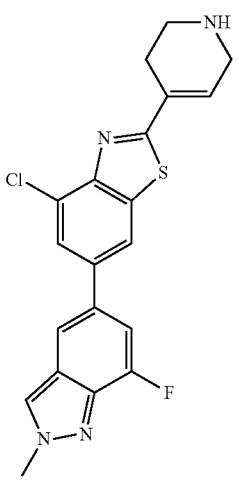 |
| 151 | 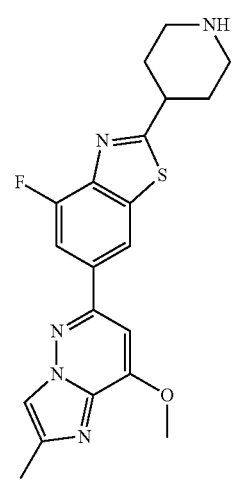 | 154 | 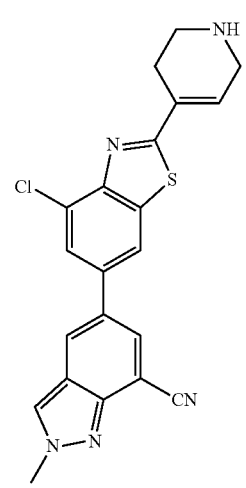 |
| 152 | 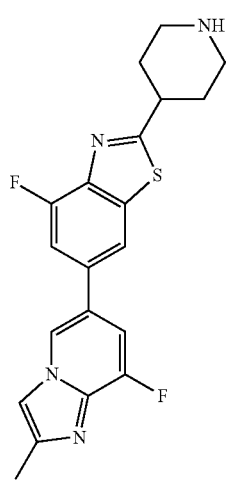 | 155 | 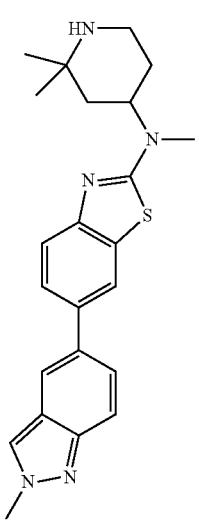 |

156 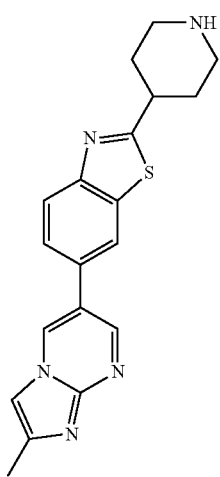
157 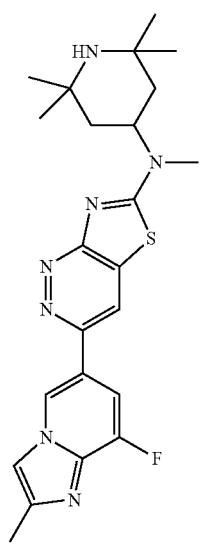
158 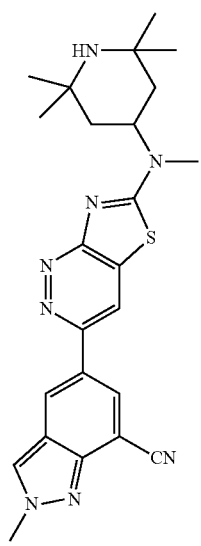
161 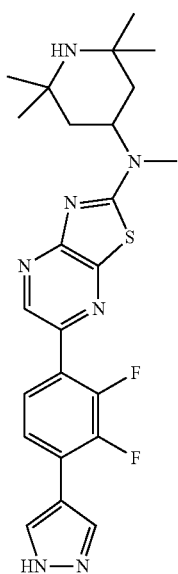
162 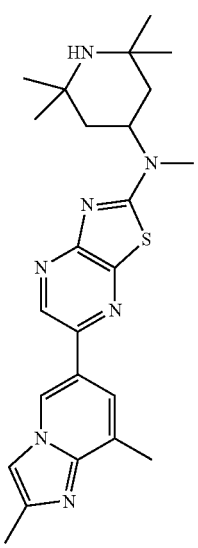
163 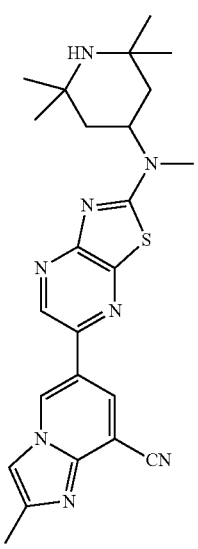

164
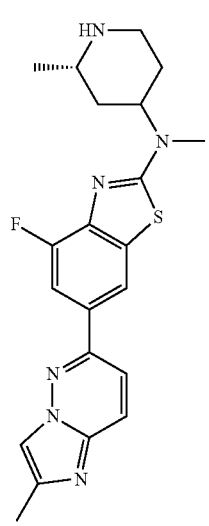
165
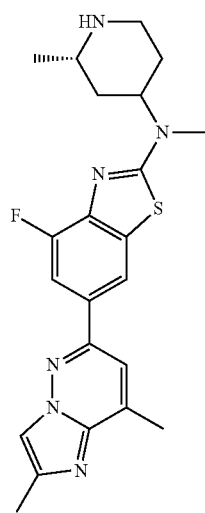
166
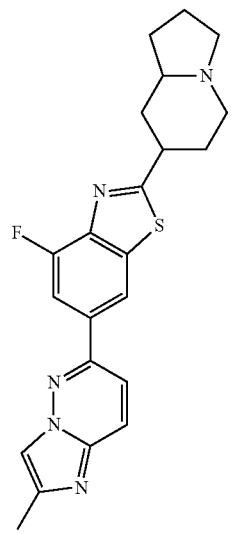
167
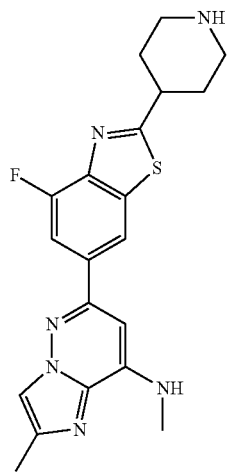
168
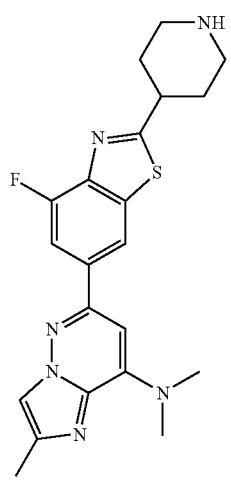
169
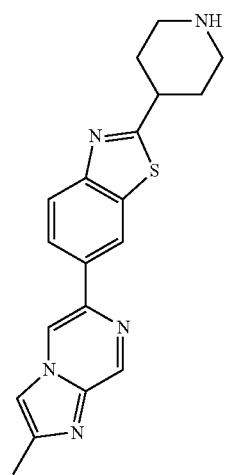

| | |
|---|---|
| 170 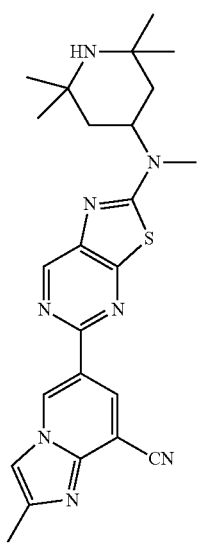 | 173 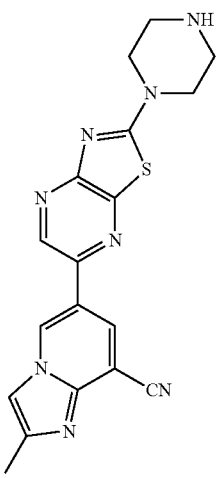 |
| 171 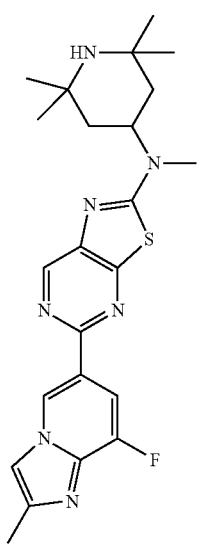 | 174 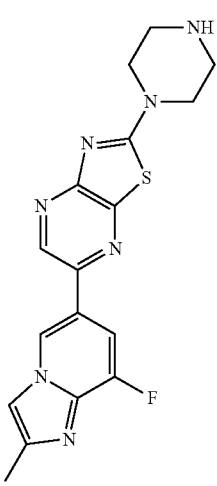 |
| 172 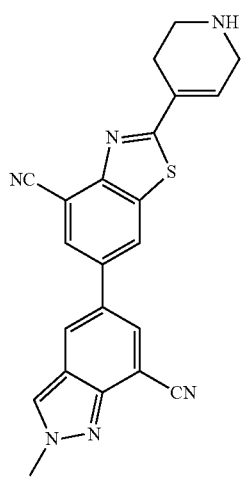 | 175 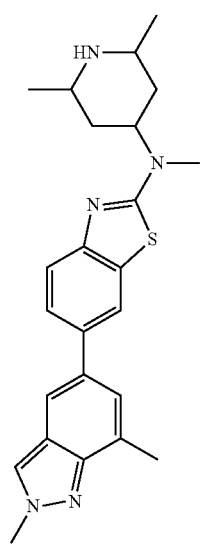 |

176 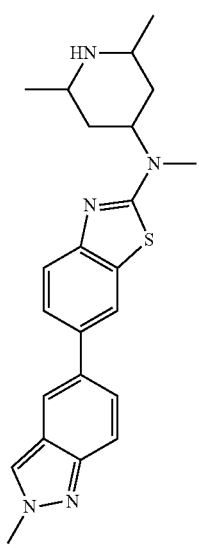
177 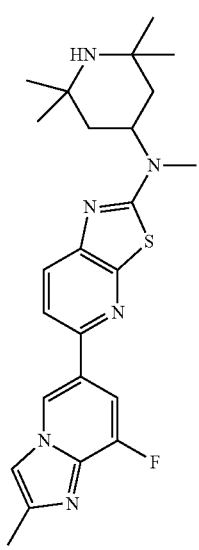
178 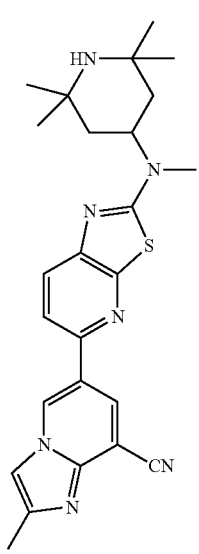
179 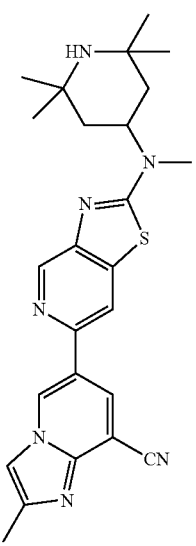
180 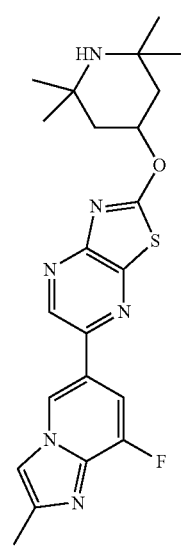
181 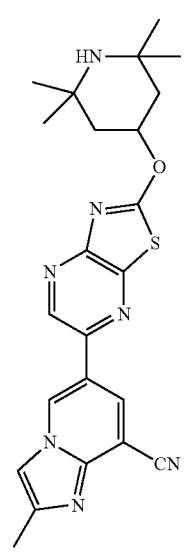

182 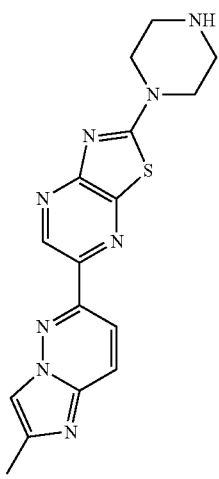
183 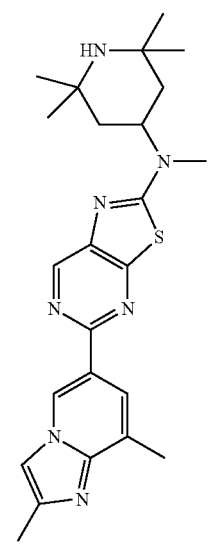
184 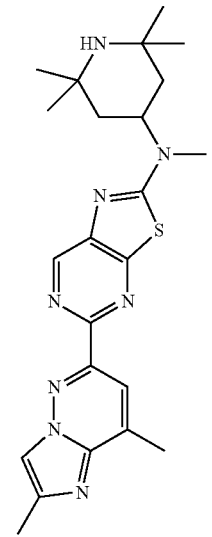
185 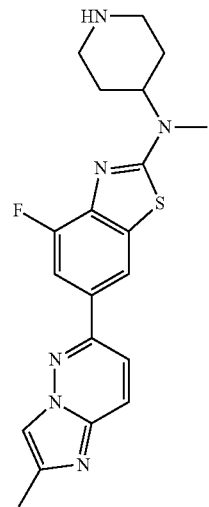
186 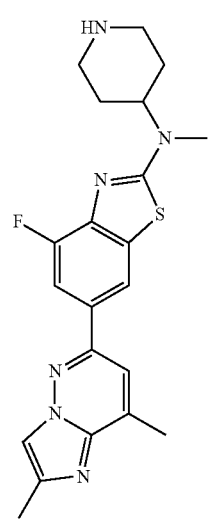
187 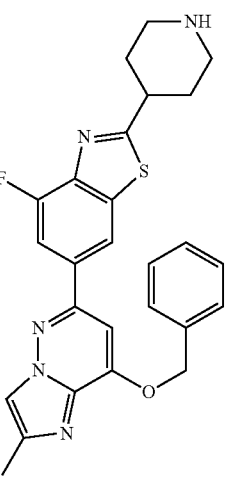

188 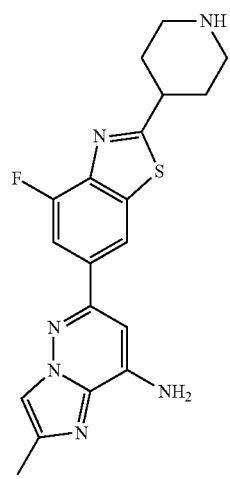
189 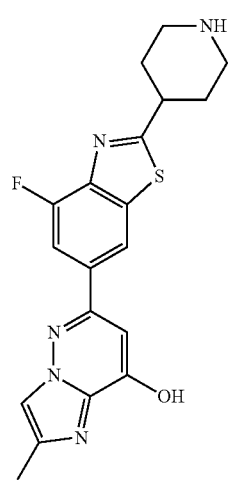
190 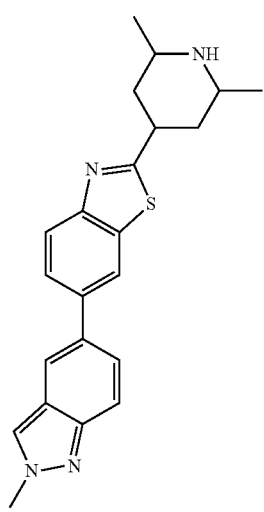
191 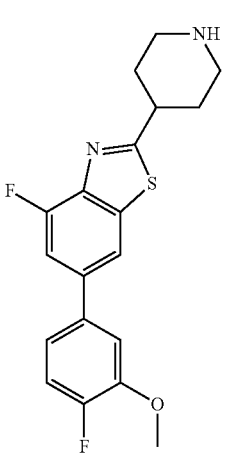
192 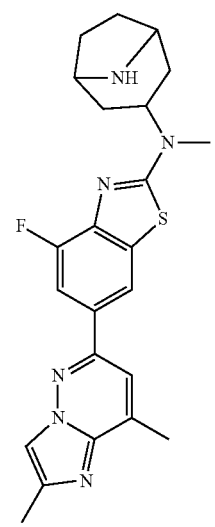
193 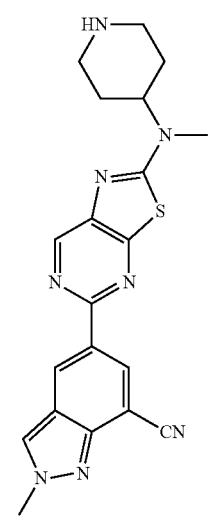

194 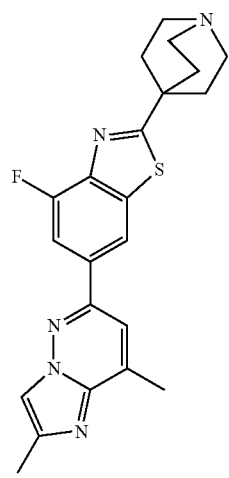
195 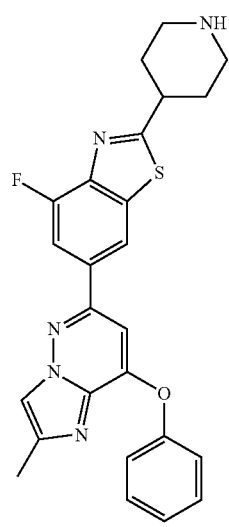
196 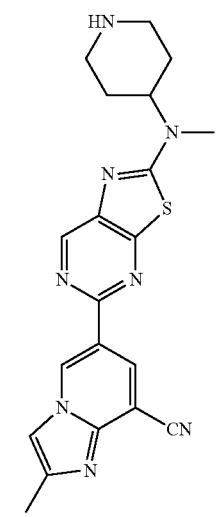
197 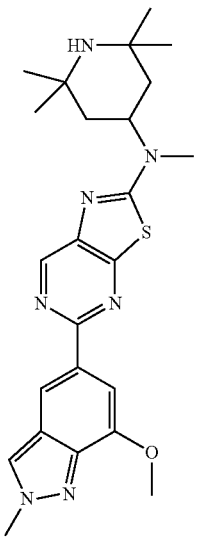
198 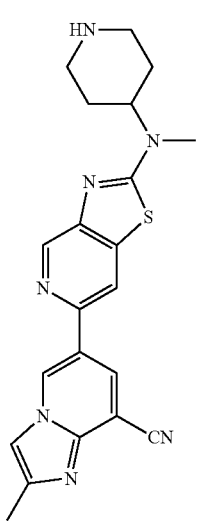
199 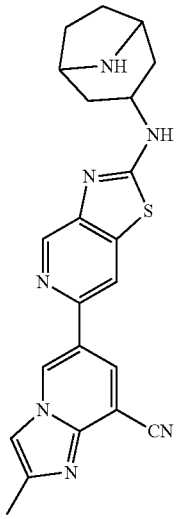

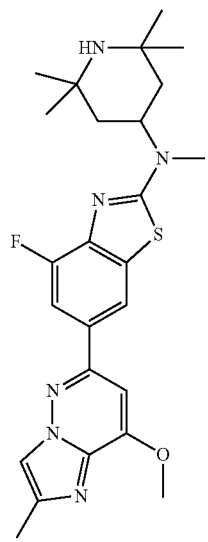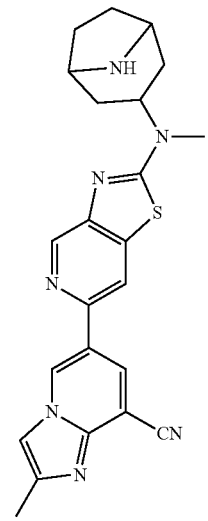

206 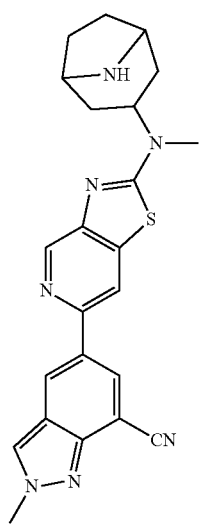
207 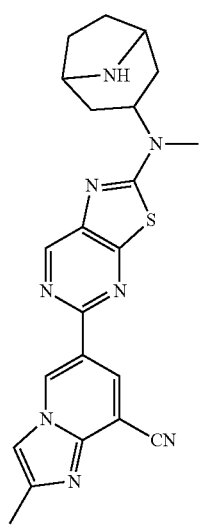
208 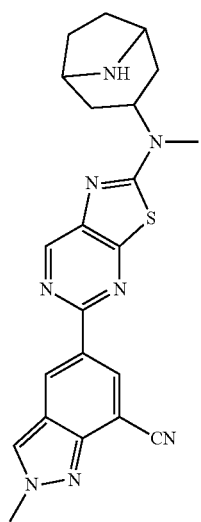
209 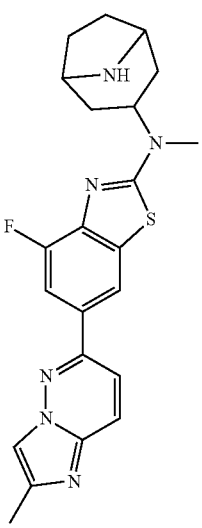
210 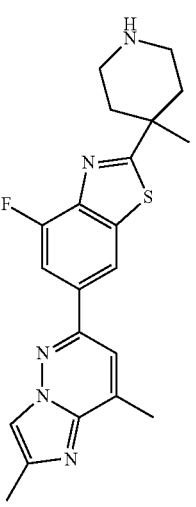
211

| | |
|---|---|
| 212 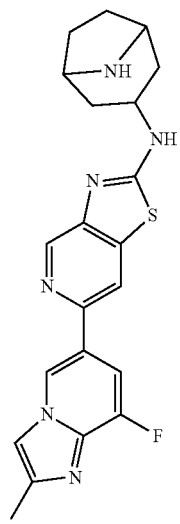 | 215 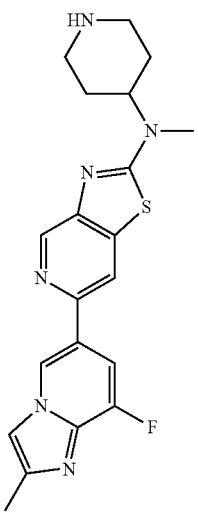 |
| 213 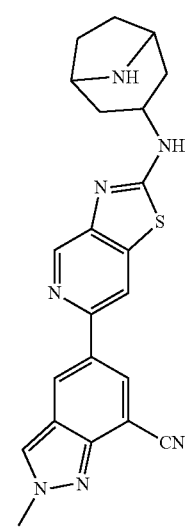 | 216 |
| 214 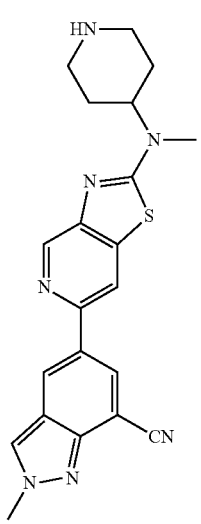 | 217 |

| 218 | 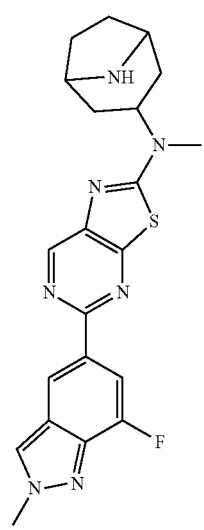 | 221 | 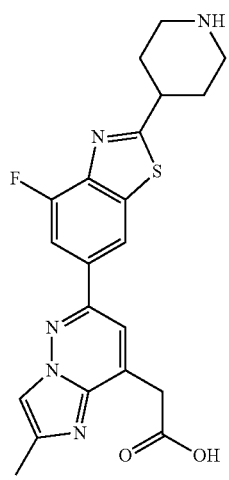 |
| 219 | 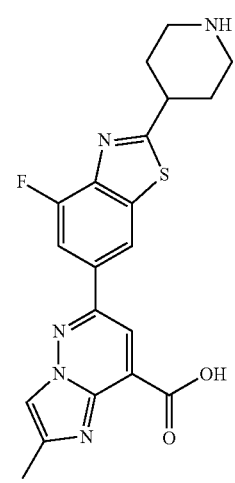 | 222 | 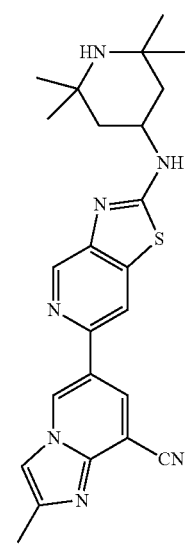 |
| 220 | 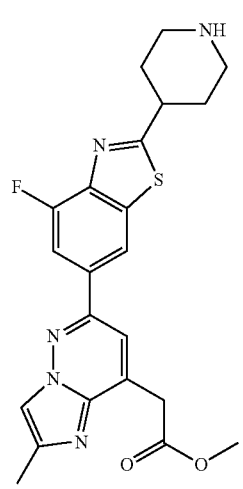 | 223 | 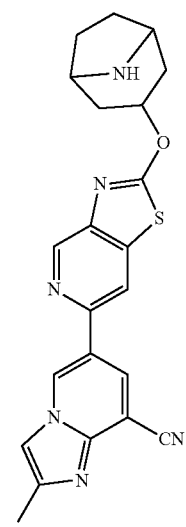 |

224 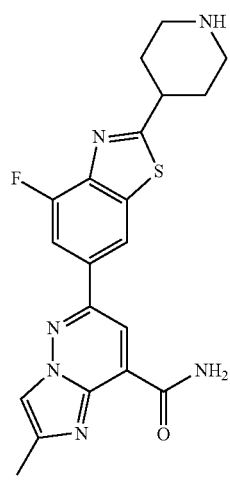
225 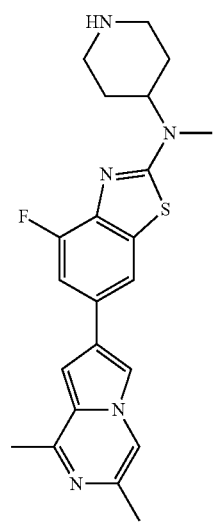
226 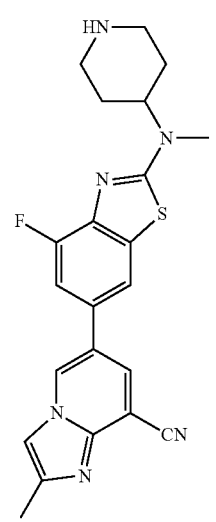
227 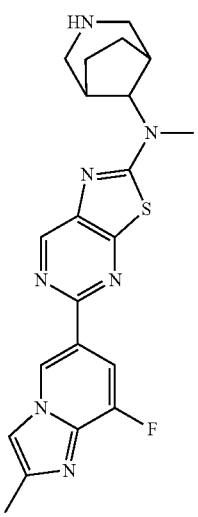
228 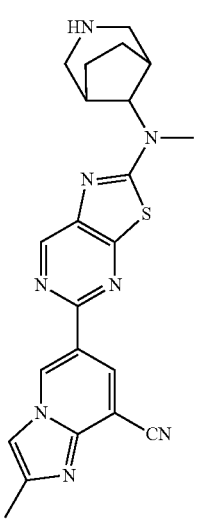
229 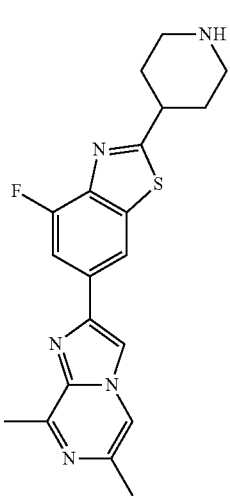

230 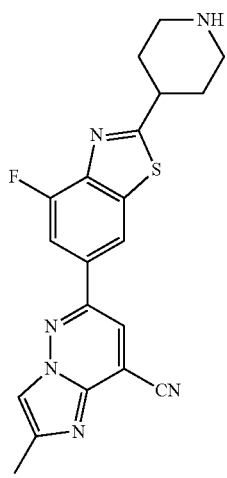
231 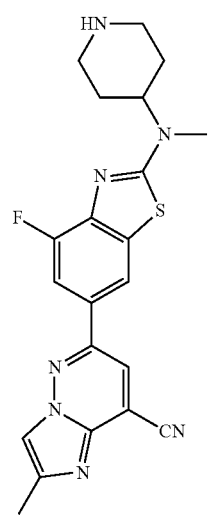
232 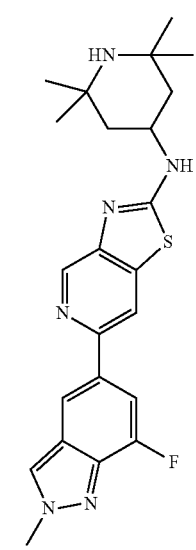
233 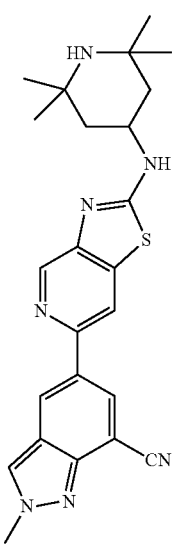
234 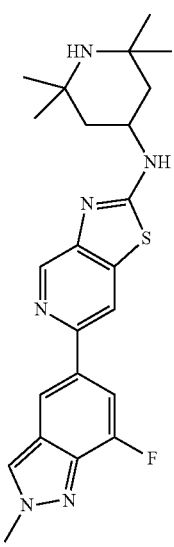
235 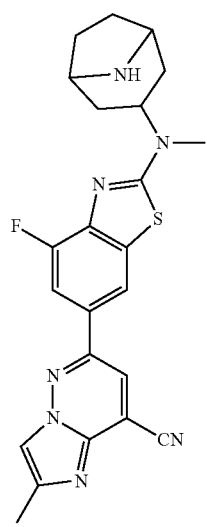

| 236 | 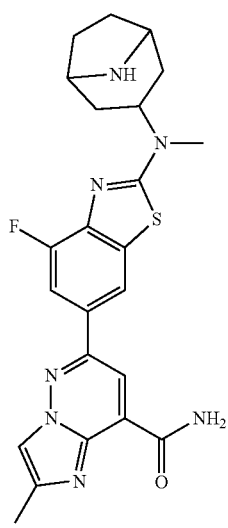 | 239 | 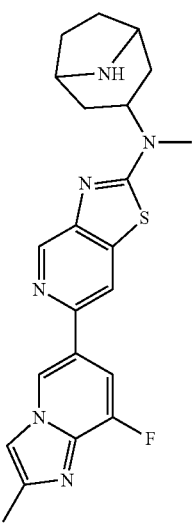 |
| 237 | 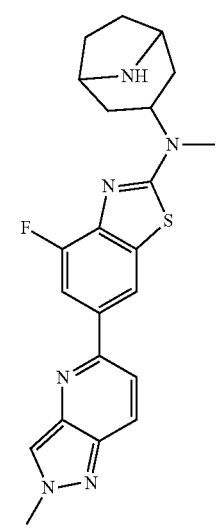 | 240 | 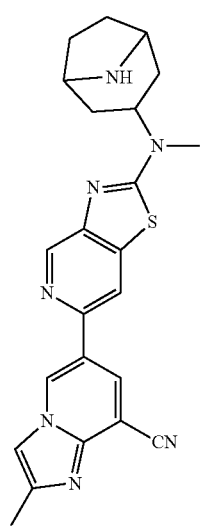 |
| 238 | 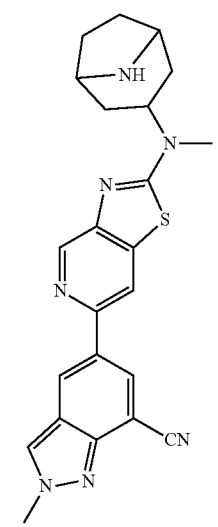 | 241 | 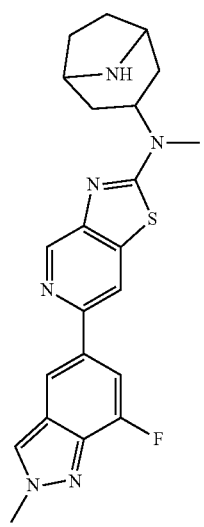 |

| 101 | 102 |
|---|---|
| 242 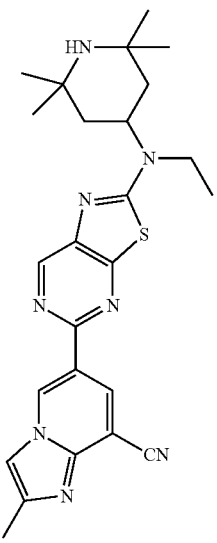 | 245 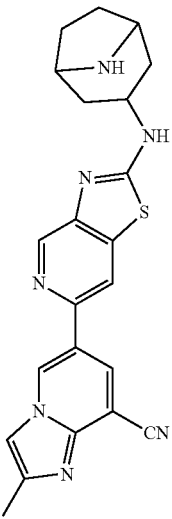 |
| 243 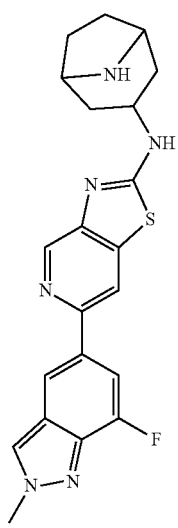 | 246 |
| 244 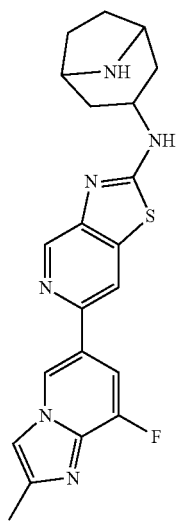 | 247 |

| 248 | 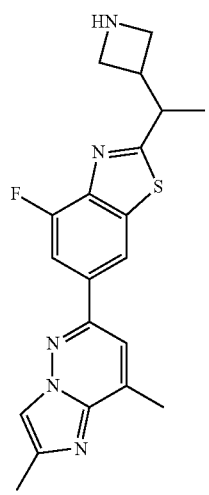 | 251 | 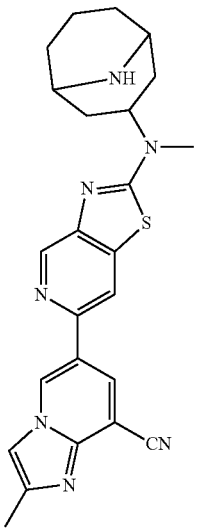 |
|---|---|---|---|
| 249 | 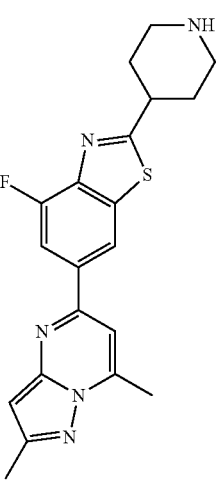 | 252 | 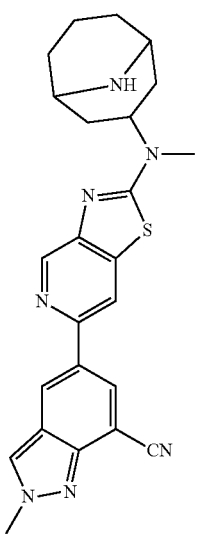 |
| 250 | 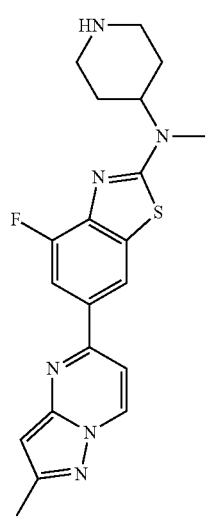 | 253 | 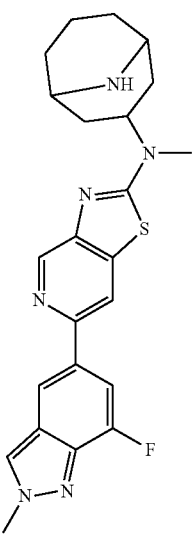 |

254 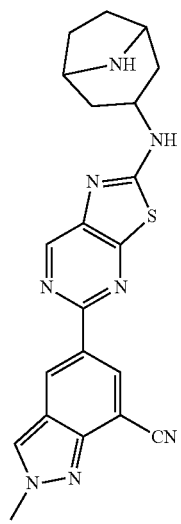
255 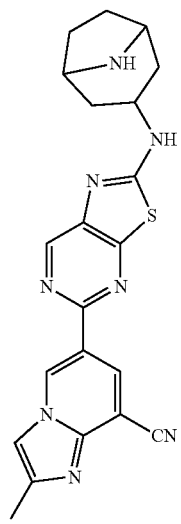
256
257 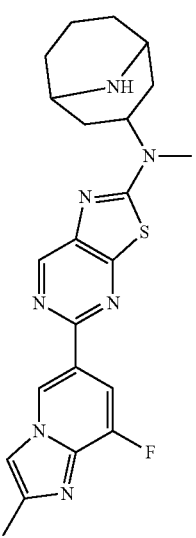
258 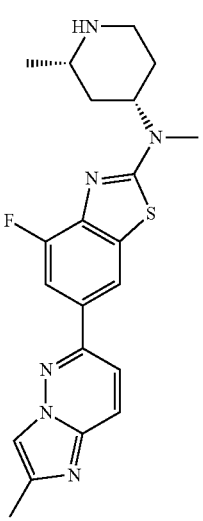
259 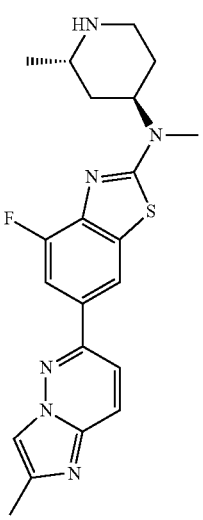

260
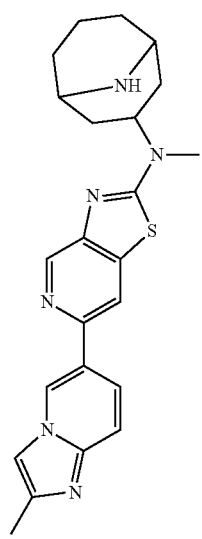
261
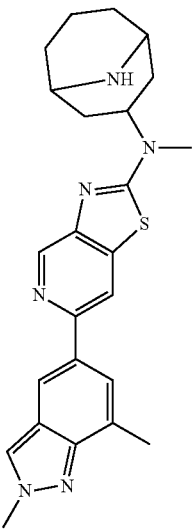
262
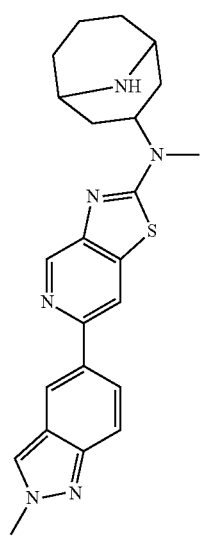
263
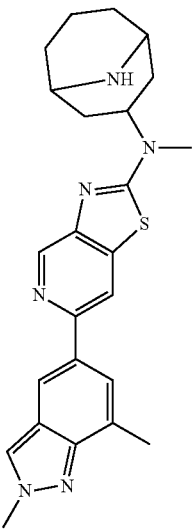
264
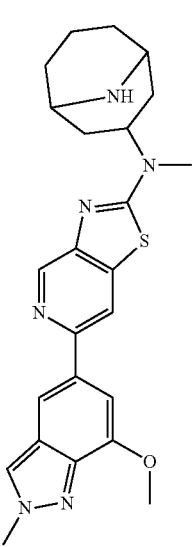
265
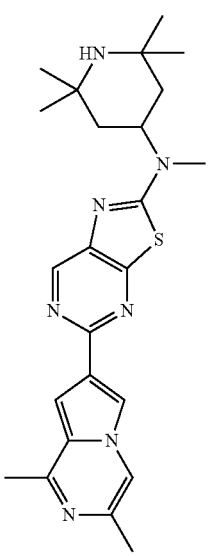

| 266 | 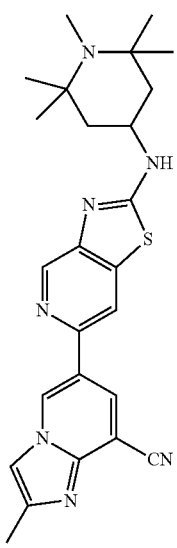 | 269 | 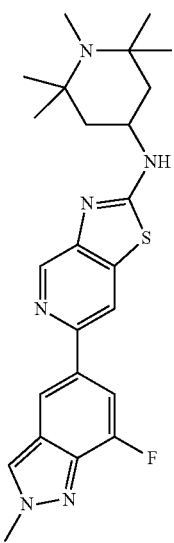 |
| 267 | | 270 | |
| 268 | 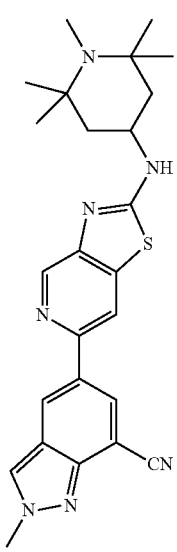 | 271 | 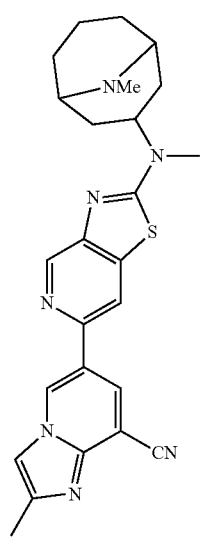 |

| | |
|---|---|
| 272 | 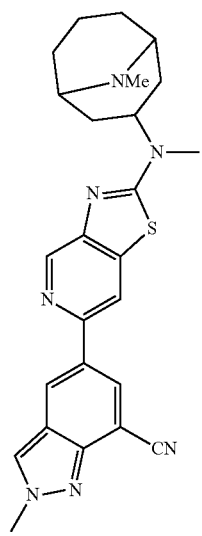 |
| 273 | 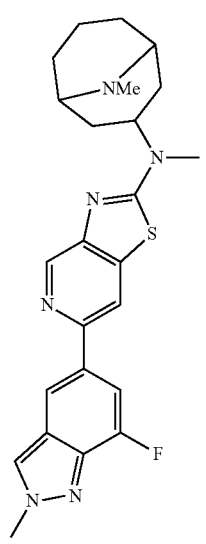 |
| 274 | 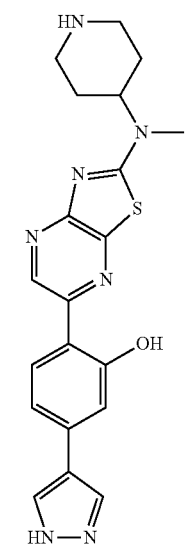 |
| 275 | 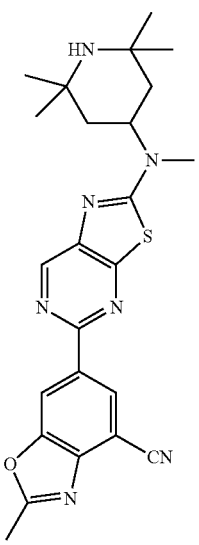 |
| 276 | 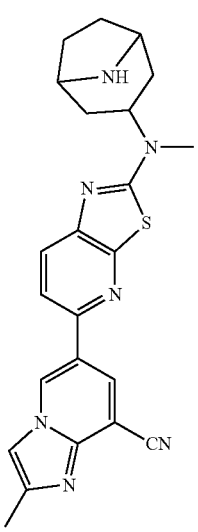 |
| 277 | 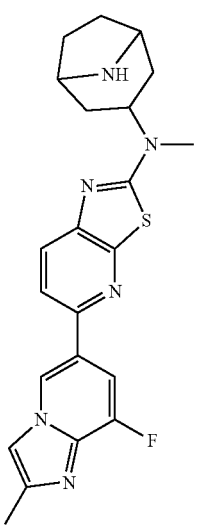 |

| 278 | 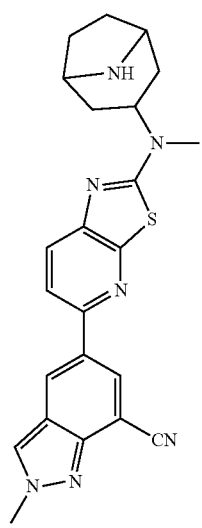 | 281 | 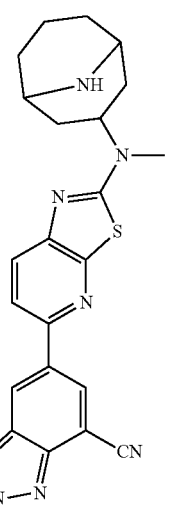 |
| 279 | 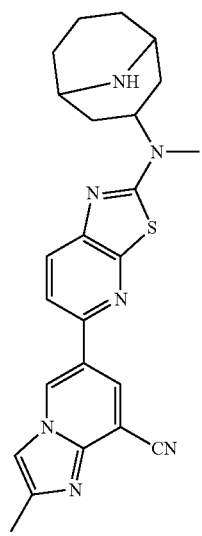 | 282 | 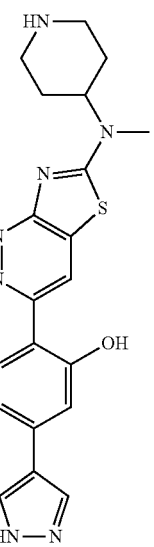 |
| 280 | 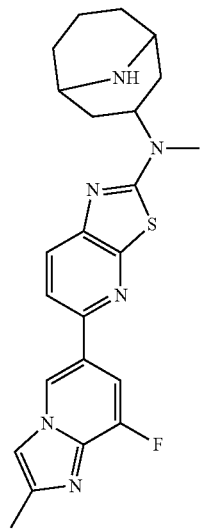 | 283 | 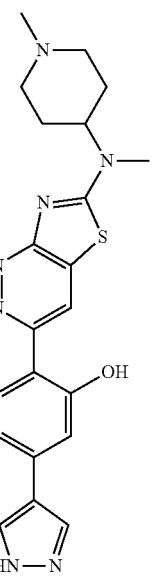 |

284 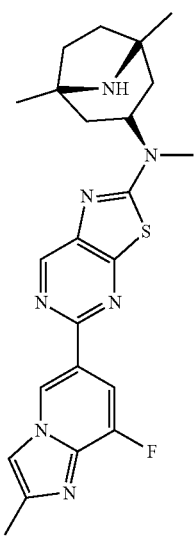
285 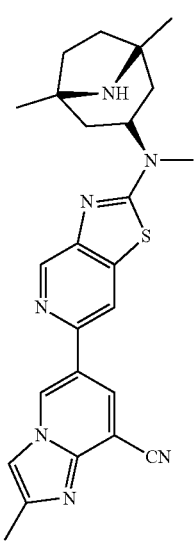
286 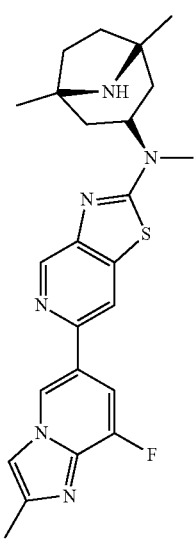
287 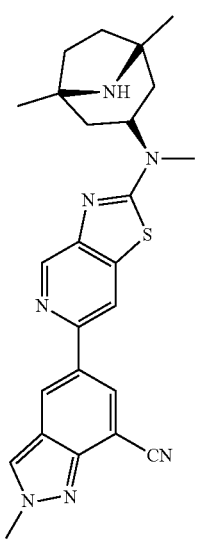
288 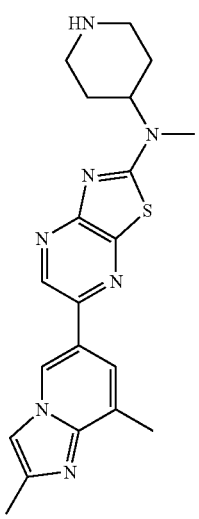
289 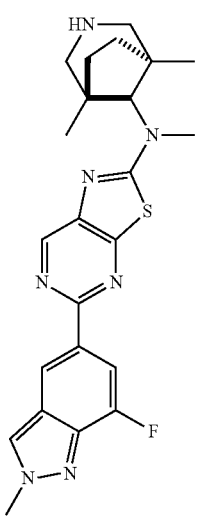

290 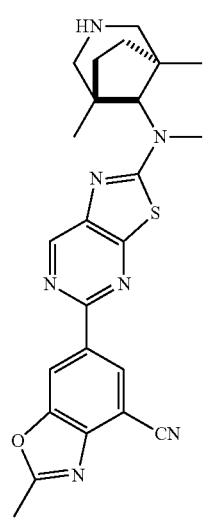
291
292
293 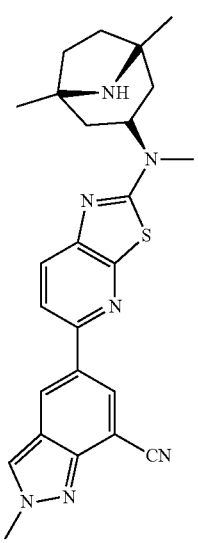
294 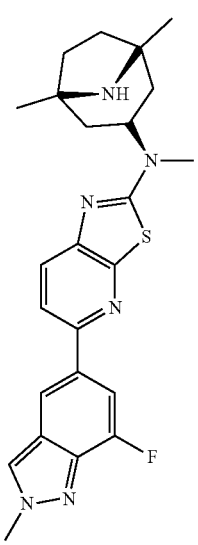
295 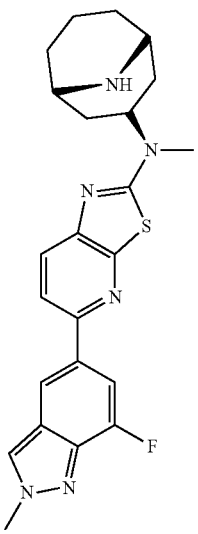

296 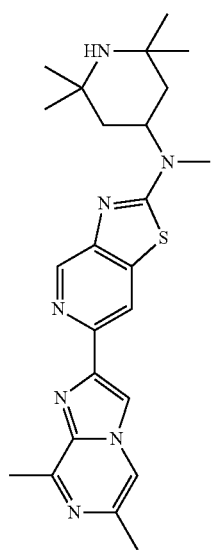
297 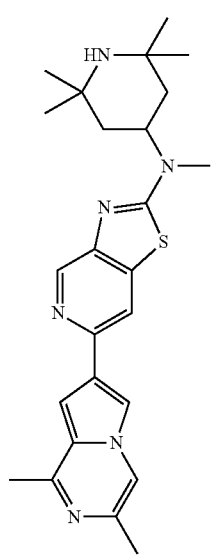
298 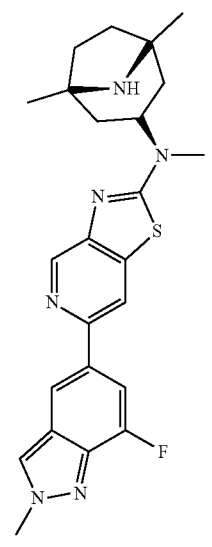
299 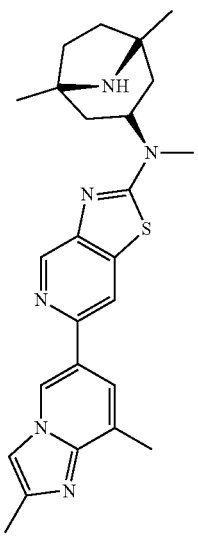
300 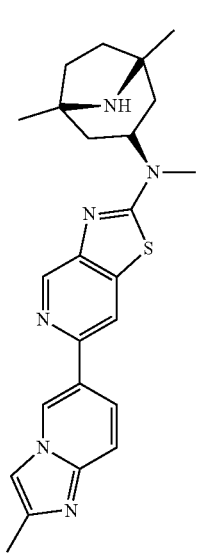
301 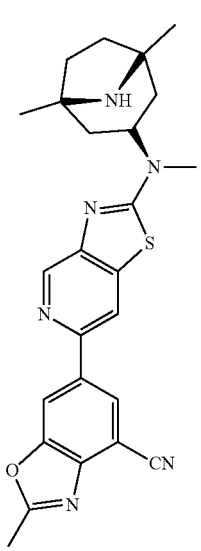

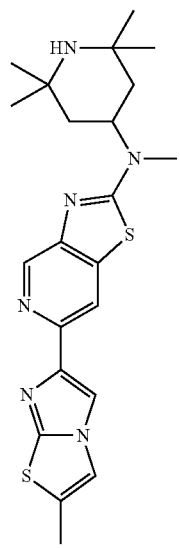
302
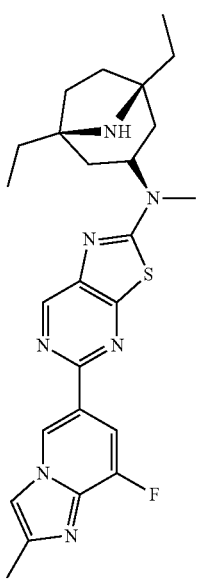
303
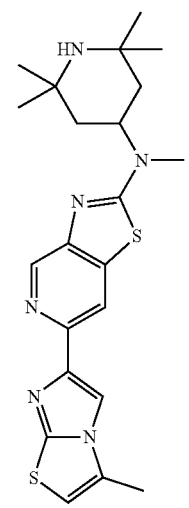
304
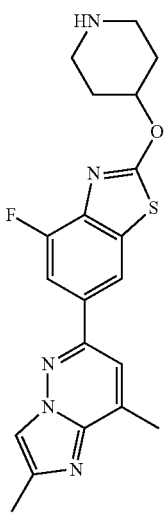
305
306

| 307 | 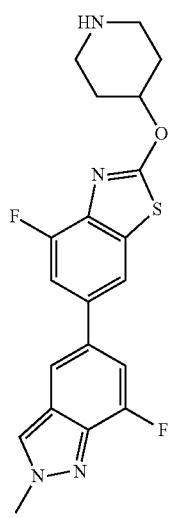 | 310 | 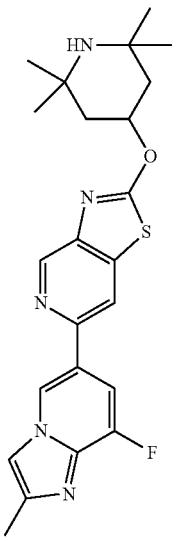 |
| 308 | 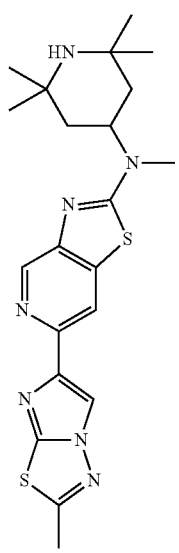 | 311 | 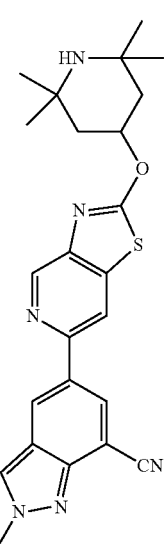 |
| 309 | 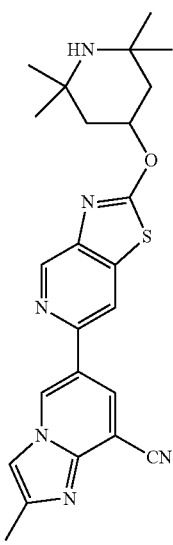 | 312 | 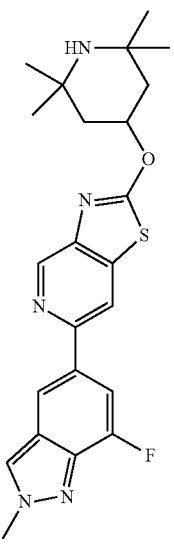 |

| 313 | 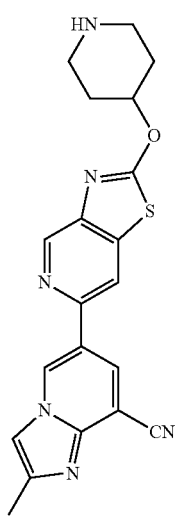 |
| --- | --- |
| 314 | 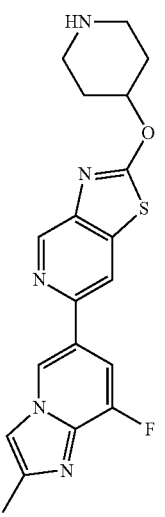 |
| 315 | 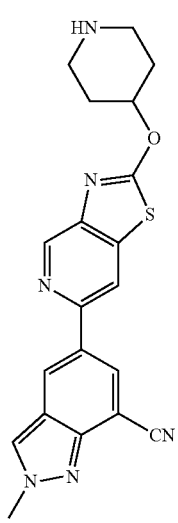 |
| 316 | 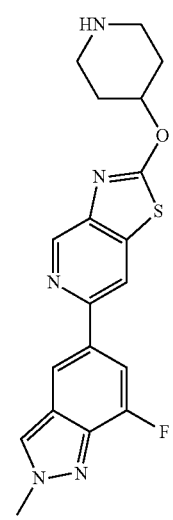 |
| 317 | 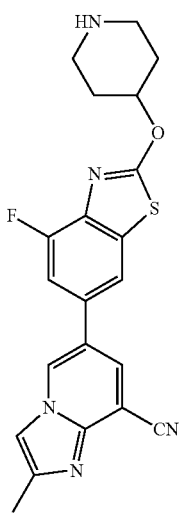 |

127
-continued
319
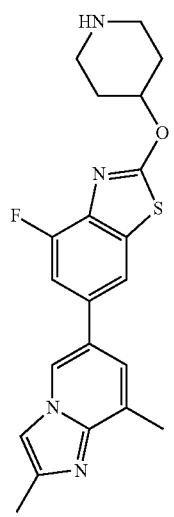
320
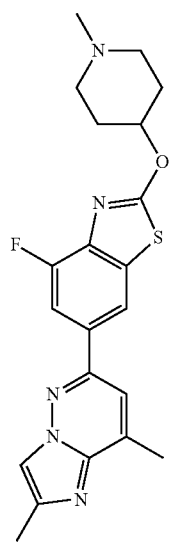
321
128
-continued
322
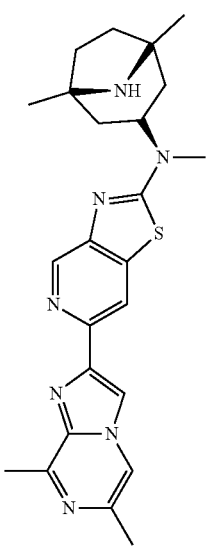
323
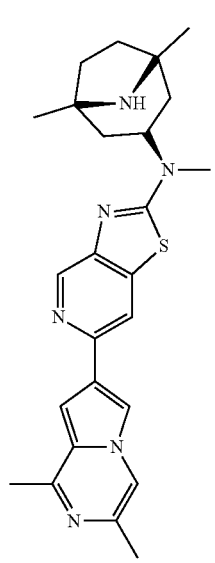
324
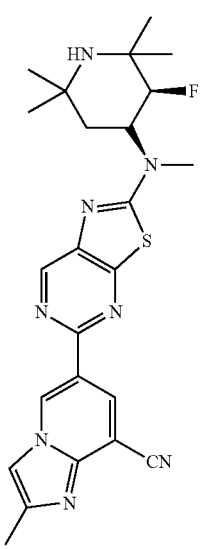

| 129 -continued | | 130 -continued | |
|---|---|---|---|
| 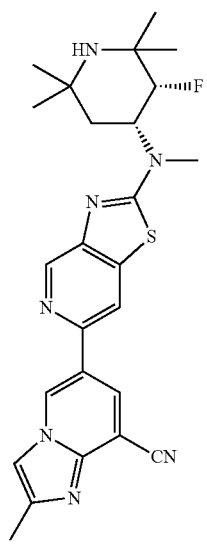 | 325 | 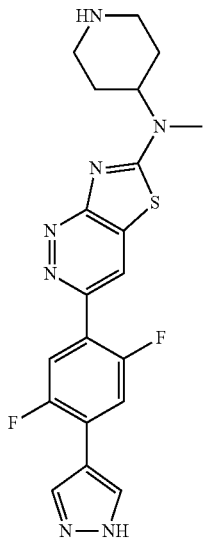 | 328 |
| 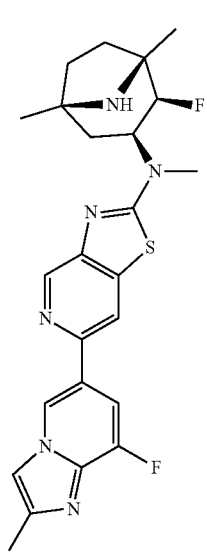 | 326 | 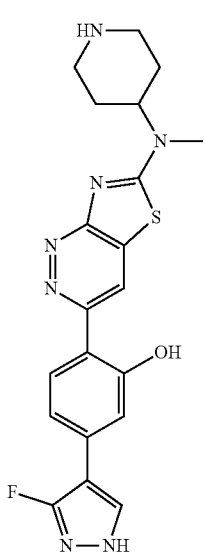 | 329 |
| 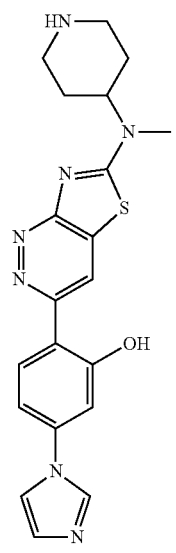 | 327 | 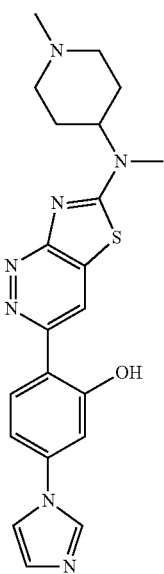 | 330 |

| 331 | 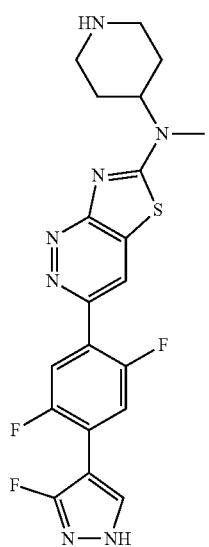 | 334 | 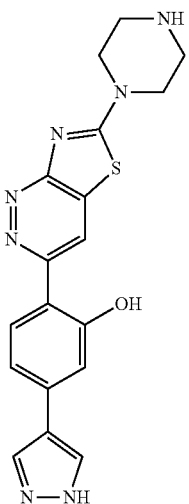 |
| 332 | 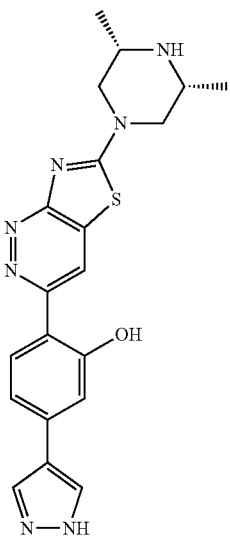 | 335 | 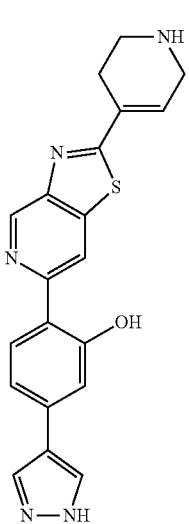 |
| 333 | | 336 | 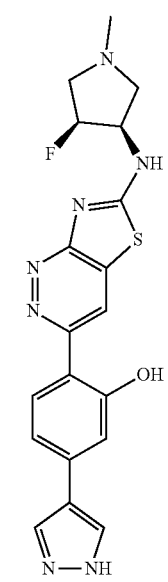 |

337
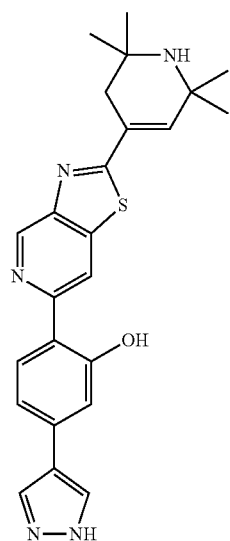
338
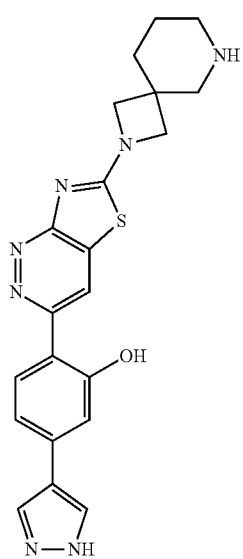
339
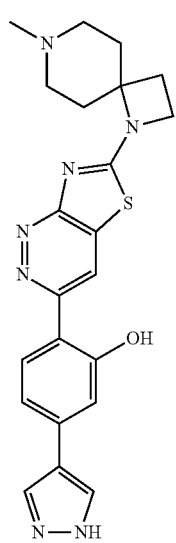
340
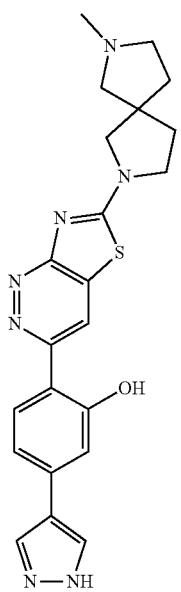
341
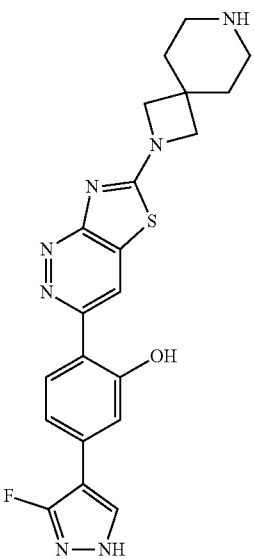

342
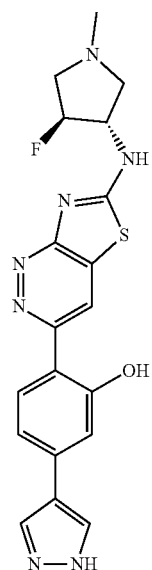
343
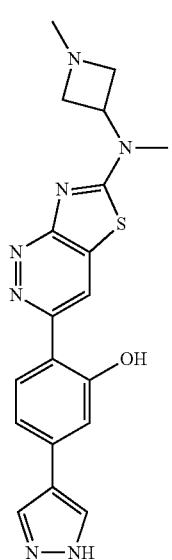
344
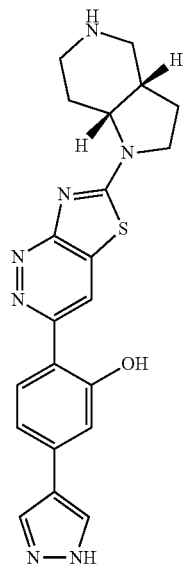
345
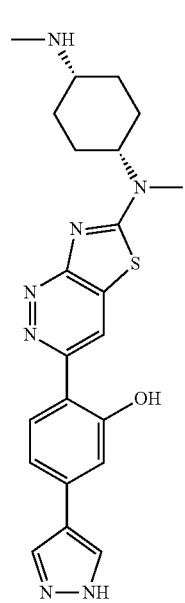

| 137 -continued | | 138 -continued | |
|---|---|---|---|
| 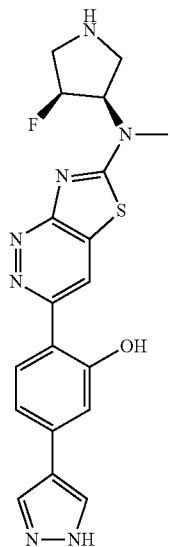 | 346 | 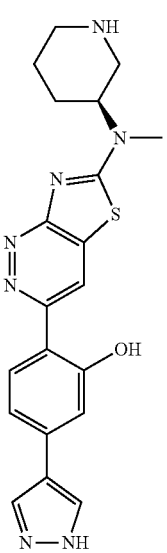 | 349 |
| 347 | | | |
| 348 | | 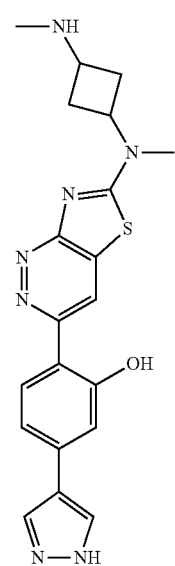 | 350 |

351
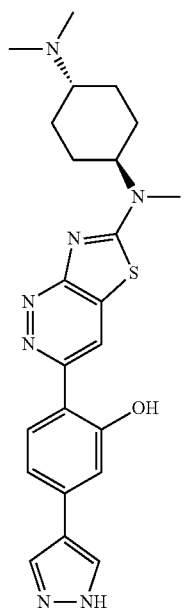
352
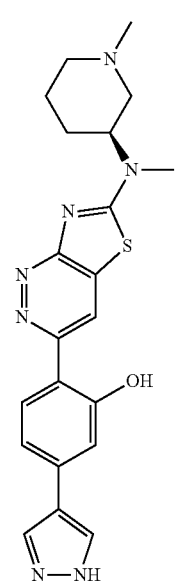
353
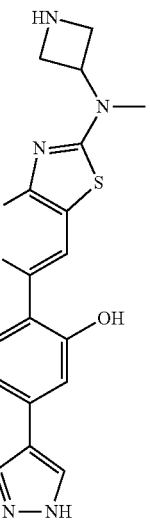
354
355

356
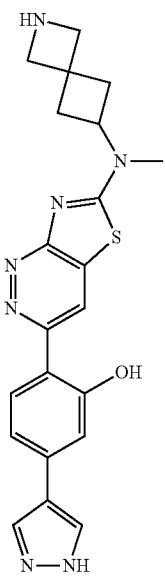
357
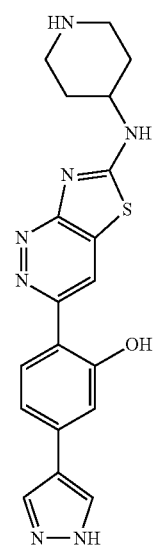
358
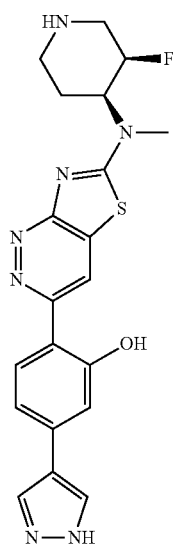
359
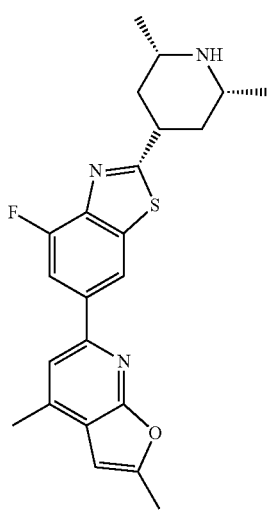
360
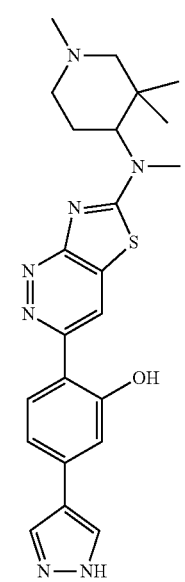
361
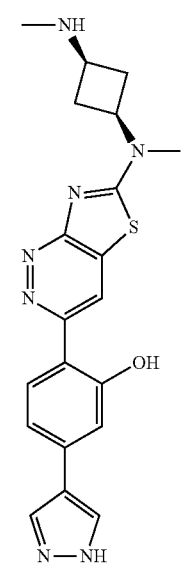

143
-continued
362
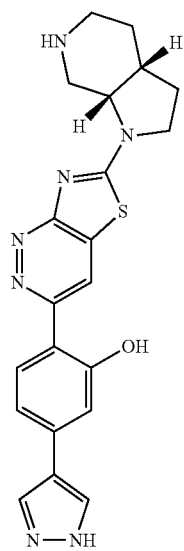
363
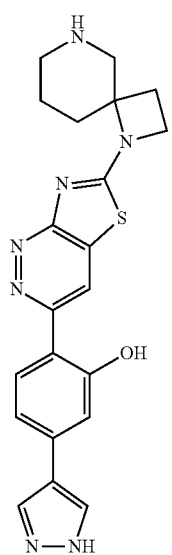
144
-continued
364
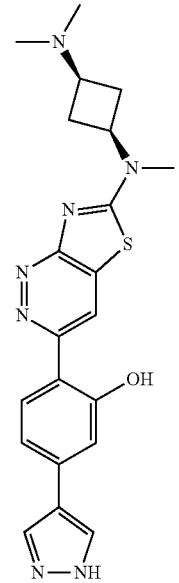
365
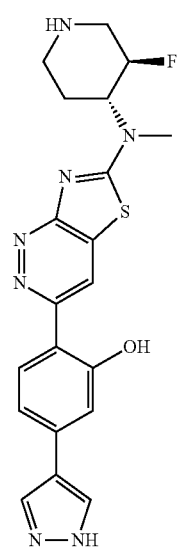

366
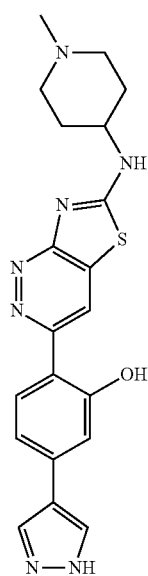
367
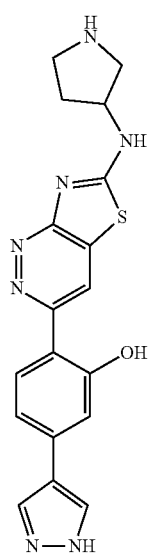
368
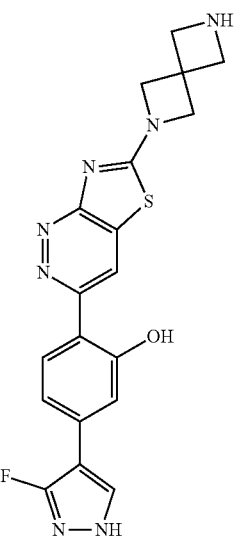
369
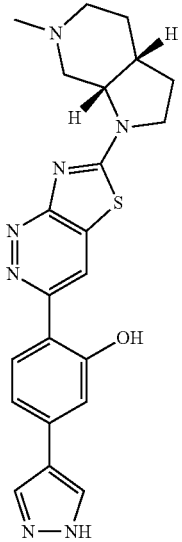
370
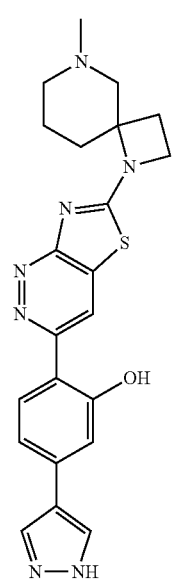

| 147 | 148 |
|---|---|
| -continued | -continued |
| 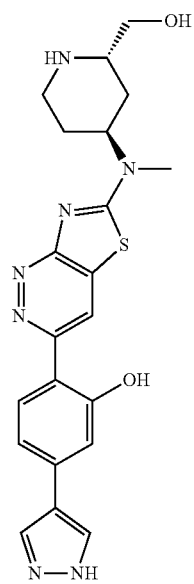 371 | 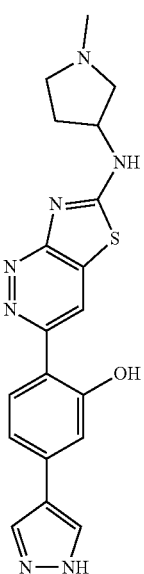 373 |
| 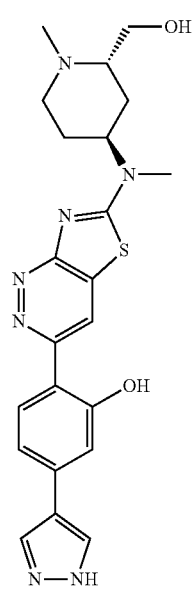 372 | 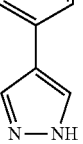 374 |

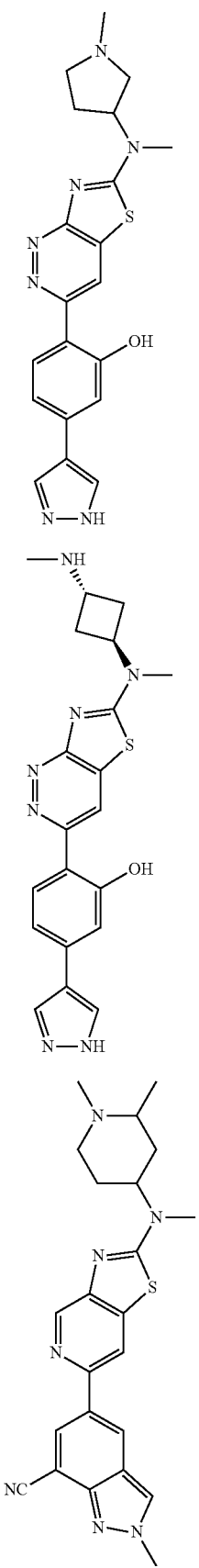
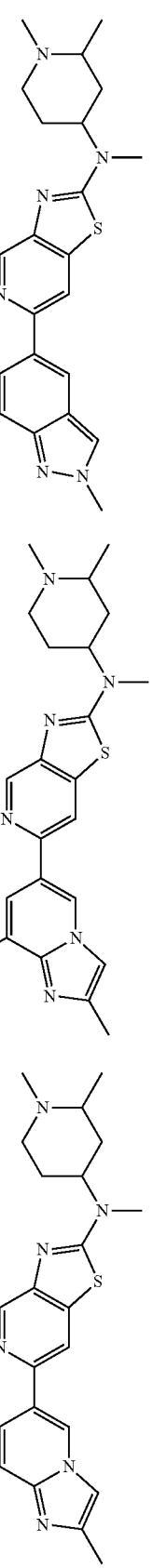

381
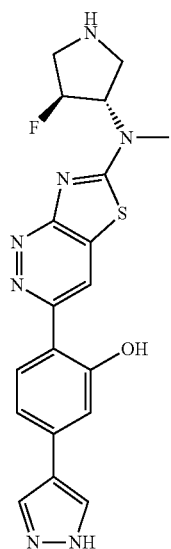
382
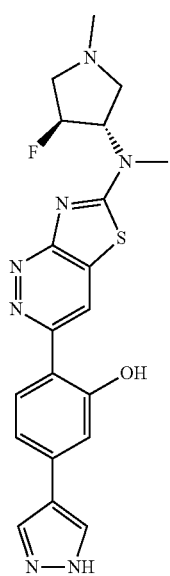
383
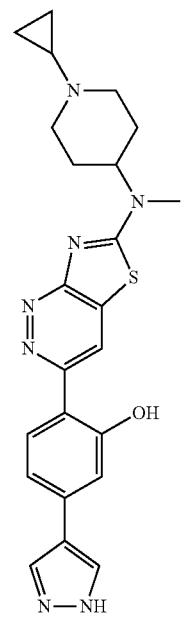
384
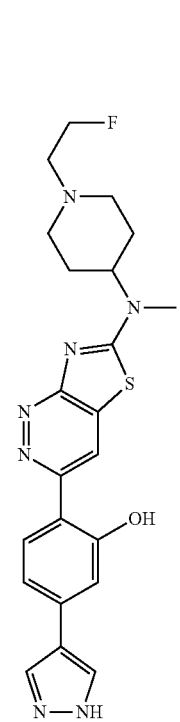

385
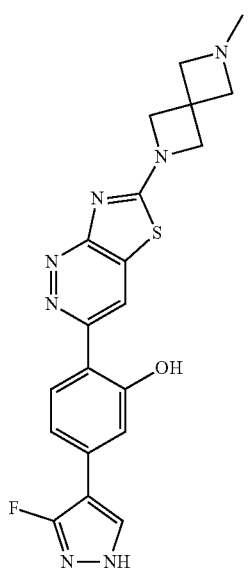
386
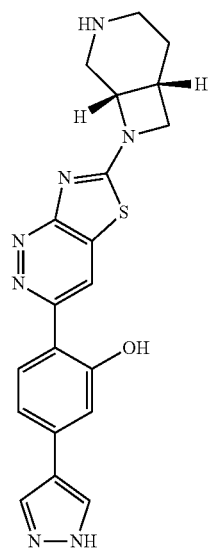
387
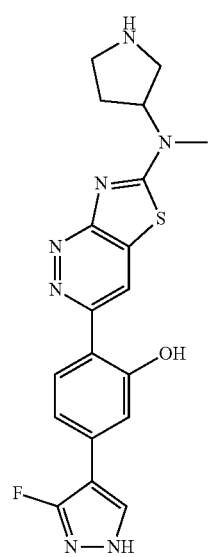
388
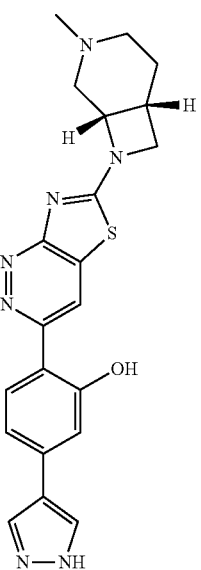
389
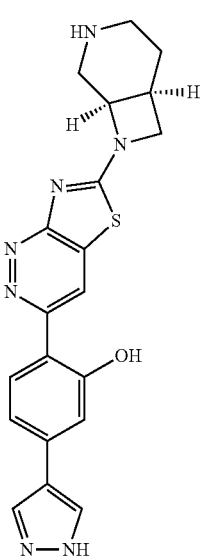

155
-continued
390
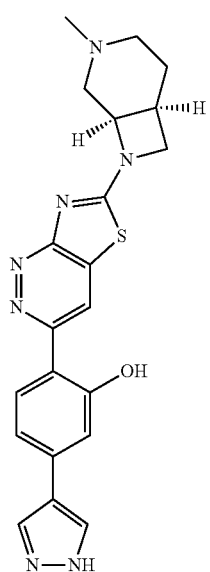
391
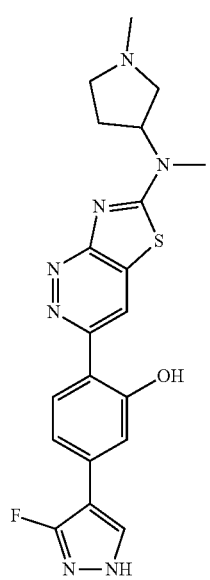
156
-continued
392
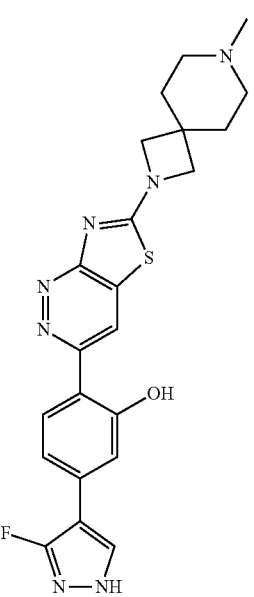
393
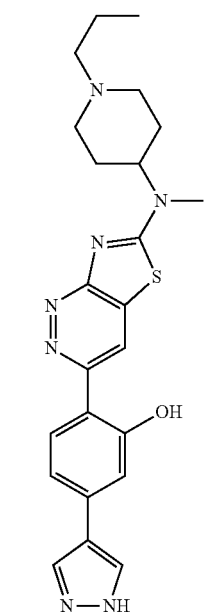

394
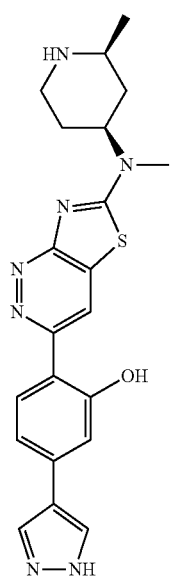
395
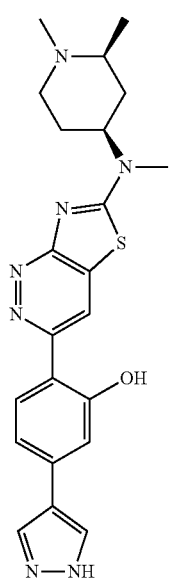
396
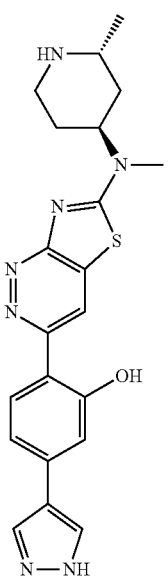
397
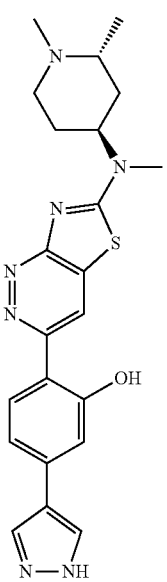

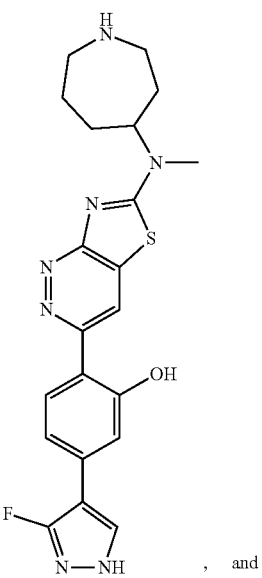, and

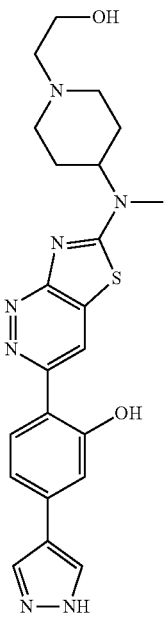;

wherein a form of the compound is selected from the group consisting of a salt, hydrate, solvate, racemate, enantiomer, diastereomer, stereoisomer, and tautomer form thereof.

An aspect the compound of Formula (I) or Formula (II) or a form thereof (wherein compound number (#[1]) indicates that the salt form was isolated) includes a compound selected from the group consisting of:

| Cpd | Name |
|---|---|
| 1 | 6-(2-methyl-2H-indazol-5-yl)-2-(1,2,3,6-tetrahydropyridin-4-yl)-1,3-benzothiazole |
| 2 | 6-(2-methyl-2H-indazol-5-yl)-2-(piperidin-4-yl)-1,3-benzothiazole |
| 3 | 6-(2-methyl-2H-indazol-5-yl)-2-(1-methyl-1,2,3,6-tetrahydropyridin-4-yl)-1,3-benzothiazole |
| 4[1] | 2-(2-methyl-2H-indazol-5-yl)-6-(1,2,3,6-tetrahydropyridin-4-yl)-1,3-benzothiazole |
| 5[1] | 2-(2-methyl-2H-indazol-5-yl)-6-(piperidin-4-yl)-1,3-benzothiazole |
| 6[1] | 2-(2-methyl-2H-indazol-5-yl)-6-(1-methyl-1,2,3,6-tetrahydropyridin-4-yl)-1,3-benzothiazole |
| 7 | 6-(2-methyl-2H-indazol-5-yl)-2-(piperazin-1-yl)-1,3-benzothiazole |
| 8[1] | N-methyl-6-(2-methyl-2H-indazol-5-yl)-N-(piperidin-4-yl)-1,3-benzothiazol-2-amine |
| 9 | 6-(2-methyl-2H-indazol-5-yl)-2-(1-methylpiperidin-4-yl)-1,3-benzothiazole |
| 10[1] | 2-(2-methyl-2H-indazol-5-yl)-6-(1-methylpiperidin-4-yl)-1,3-benzothiazole |
| 11[1] | N-methyl-2-(2-methyl-2H-indazol-5-yl)-N-(piperidin-4-yl)-1,3-benzothiazol-6-amine |
| 12[1] | N-methyl-6-(2-methyl-2H-indazol-5-yl)-N-(piperidin-4-yl)[1,3]thiazolo[4,5-b]pyridine-2-amine |
| 13[1] | 6-(2,7-dimethyl-2H-indazol-5-yl)-N-methyl-N-(piperidin-4-yl)[1,3]thiazolo[4,5-b]pyridin-2-amine |
| 14[1] | 6-(2,7-dimethyl-2H-indazol-5-yl)-N-(piperidin-4-yl)[1,3]thiazolo[4,5-b]pyridin-2-amine |
| 15[1] | 6-(2-methyl-2H-indazol-5-yl)-N-(piperidin-4-yl)[1,3]thiazolo[4,5-b]pyridin-2-amine |
| 16 | N-methyl-6-(2-methyl-2H-indazol-5-yl)-N-(2,2,6,6-tetramethylpiperidin-4-yl)[1,3]thiazolo[4,5-b]pyridin-2-amine |
| 17 | 6-(2,7-dimethyl-2H-indazol-5-yl)-N-methyl-N-(2,2,6,6-tetramethylpiperidin-4-yl)[1,3]thiazolo[4,5-b]pyridin-2-amine |
| 18[1] | 6-(2,7-dimethyl-2H-indazol-5-yl)-2-(1,2,3,6-tetrahydropyridin-4-yl)-1,3-benzothiazole |
| 19[1] | 2-(2-methyl-2H-indazol-5-yl)-6-(1,2,3,6-tetrahydropyridin-4-yl)[1,3]thiazolo[4,5-b]pyridine |
| 20 | N-methyl-6-(2-methyl-2H-indazol-5-yl)-N-(2,2,6,6-tetramethylpiperidin-4-yl)-1,3-benzothiazol-2-amine |
| 21 | 6-(2,7-dimethyl-2H-indazol-5-yl)-N-methyl-N-(2,2,6,6-tetramethylpiperidin-4-yl)-1,3-benzothiazol-2-amine |
| 22[1] | 6-(2,7-dimethyl-2H-indazol-5-yl)-2-(piperidin-4-yl)-1,3-benzothiazole |
| 23 | 4-fluoro-N-methyl-6-(2-methyl-2H-indazol-5-yl)-N-(2,2,6,6-tetramethylpiperidin-4-yl)-1,3-benzothiazol-2-amine |
| 24 | 6-(2,7-dimethyl-2H-indazol-5-yl)-4-fluoro-N-methyl-N-(2,2,6,6-tetramethylpiperidin-4-yl)-1,3-benzothiazol-2-amine |
| 25[1] | N-methyl-5-(2-methyl-2H-indazol-5-yl)-N-(2,2,6,6-tetramethylpiperidin-4-yl)[1,3]thiazolo[5,4-b]pyridin-2-amine |

-continued

| Cpd | Name |
|---|---|
| 26[1] | N-methyl-5-(2-methyl-2H-indazol-5-yl)-N-(piperidin-4-yl)[1,3]thiazolo[5,4-b]pyridin-2-amine |
| 27[1] | N-methyl-6-(2-methyl-2H-indazol-5-yl)-N-(piperidin-4-yl)[1,3]thiazolo[4,5-c]pyridin-2-amine |
| 28[1] | N,N-dimethyl-1-[6-(2-methyl-2H-indazol-5-yl)-1,3-benzothiazol-2-yl]piperidin-4-amine |
| 29[1] | 1-[6-(2-methyl-2H-indazol-5-yl)-1,3-benzothiazol-2-yl]piperidin-4-amine |
| 30[1] | 6-(2,7-dimethyl-2H-indazol-5-yl)-N-methyl-N-(piperidin-4-yl)[1,3]thiazolo[4,5-c]pyridin-2-amine |
| 31 | 6-(2,7-dimethyl-2H-indazol-5-yl)-N-methyl-N-(2,2,6,6-tetramethylpiperidin-4-yl)[1,3]thiazolo[4,5-c]pyridin-2-amine |
| 32 | N-methyl-6-(2-methyl-2H-indazol-5-yl)-N-(2,2,6,6-tetramethylpiperidin-4-yl)[1,3]thiazolo[4,5-c]pyridin-2-amine |
| 33 | 6-(2,8-dimethylimidazo[1,2-a]pyridin-6-yl)-N-methyl-N-(2,2,6,6-tetramethylpiperidin-4-yl)-1,3-benzothiazol-2-amine |
| 34[1] | 6-(1H-indazol-5-yl)-N-methyl-N-(2,2,6,6-tetramethylpiperidin-4-yl)-1,3-benzothiazol-2-amine |
| 35[1] | 6-(2-methyl-2H-indazol-5-yl)-N-(piperidin-4-yl)-1,3-benzothiazol-2-amine |
| 36[1] | 5-(2,7-dimethyl-2H-indazol-5-yl)-N-methyl-N-(piperidin-4-yl)[1,3]thiazolo[5,4-b]pyridin-2-amine |
| 37 | 4-fluoro-N-methyl-6-(2-methylimidazo[1,2-b]pyridazin-6-yl)-N-(2,2,6,6-tetramethylpiperidin-4-yl)-1,3-benzothiazol-2-amine |
| 38[1] | N-methyl-6-(2-methyl-2H-indazol-5-yl)-N-(pyrrolidin-3-yl)-1,3-benzothiazol-2-amine |
| 39 | 6-(2,8-dimethylimidazo[1,2-a]pyridin-6-yl)-4-fluoro-N-methyl-N-(2,2,6,6-tetramethylpiperidin-4-yl)-1,3-benzothiazol-2-amine |
| 40[1] | N-methyl-6-(2-methylimidazo[1,2-b]pyridazin-6-yl)-N-(2,2,6,6-tetramethylpiperidin-4-yl)-1,3-benzothiazol-2-amine |
| 41[1] | 2-(4-fluoropiperidin-4-yl)-6-(2-methyl-2H-indazol-5-yl)-1,3-benzothiazole |
| 42[1] | 2-(azepan-4-yl)-6-(2-methyl-2H-indazol-5-yl)-1,3-benzothiazole |
| 43[1] | 2-(2-methyl-2H-indazol-5-yl)-6-(piperidin-4-yl)[1,3]thiazolo[4,5-b]pyridine |
| 44[1] | 6-[4-fluoro-2-(1,2,3,6-tetrahydropyridin-4-yl)-1,3-benzothiazol-6-yl]-2-methylimidazo[1,2-b]pyridazine |
| 45[1] | 6-[4-fluoro-2-(piperidin-4-yl)-1,3-benzothiazol-6-yl]-2-methylimidazo[1,2-b]pyridazine |
| 46[1] | 6-[4-fluoro-2-(1,2,3,6-tetrahydropyridin-4-yl)-1,3-benzothiazol-6-yl]-2,8-dimethylimidazo[1,2-b]pyridazine |
| 47[1] | 6-[4-fluoro-2-(piperidin-4-yl)-1,3-benzothiazol-6-yl]-2,8-dimethylimidazo[1,2-b]pyridazine |
| 48 | N-methyl-6-(2-methyl[1,2,4]triazolo[1,5-b]pyridazin-6-yl)-N-(2,2,6,6-tetramethylpiperidin-4-yl)-1,3-benzothiazol-2-amine |
| 49[1] | 2-(2,7-dimethyl-2H-indazol-5-yl)-6-(1,2,3,6-tetrahydropyridin-4-yl)-1,3-benzothiazole |
| 50[1] | 2-(2,7-dimethyl-2H-indazol-5-yl)-6-(piperidin-4-yl)-1,3-benzothiazole |
| 51[1] | N-methyl-6-[2-methyl-7-(trifluoromethyl)-2H-indazol-5-yl]-N-(2,2,6,6-tetramethylpiperidin-4-yl)-1,3-benzothiazol-2-amine |
| 52 | 6-(2-methyl-2H-indazol-5-yl)-2-(2,2,6,6-tetramethylpiperidin-4-yl)-1,3-benzothiazole |
| 53[1] | 6-[4-fluoro-2-(1,2,3,6-tetrahydropyridin-4-yl)-1,3-benzothiazol-6-yl]-2,8-dimethylimidazo[1,2-a]pyrazine |
| 54 | 6-(7-ethyl-2-methyl-2H-indazol-5-yl)-N-methyl-N-(2,2,6,6-tetramethylpiperidin-4-yl)-1,3-benzothiazol-2-amine |
| 55[1] | 6-(1,3-dimethylpyrrolo[1,2-a]pyrazin-7-yl)-N-methyl-N-(2,2,6,6-tetramethylpiperidin-4-yl)-1,3-benzothiazol-2-amine |
| 56 | 6-(2-methyl-2H-indazol-5-yl)-2-(2,3,6,7-tetrahydro-1H-azepin-4-yl)-1,3-benzothiazole |
| 57[1] | 6-(7-fluoro-2-methyl-2H-indazol-5-yl)-N-methyl-N-(2,2,6,6-tetramethylpiperidin-4-yl)-1,3-benzothiazol-2-amine |
| 58[1] | 6-(2-methyl-2H-indazol-5-yl)-2-(2-methylpiperidin-4-yl)-1,3-benzothiazole |
| 59[1] | 6-(2,7-dimethyl-2H-indazol-5-yl)-2-(piperidin-4-yl)[1,3]thiazolo[4,5-c]pyridine |
| 60[1] | 6-[2-methyl-7-(trifluoromethyl)-2H-indazol-5-yl]-2-(piperidin-4-yl)[1,3]thiazolo[4,5-c]pyridine |
| 61[1] | 6-(2,8-dimethylimidazo[1,2-b]pyridazin-6-yl)-2-(piperidin-4-yl)[1,3]thiazolo[4,5-b]pyridine |
| 62[1] | 2-methyl-5-{2-[methyl(2,2,6,6-tetramethylpiperidin-4-yl)amino]-1,3-benzothiazol-6-yl}-2H-indazole-7-carbonitrile |
| 63[1] | N-methyl-6-(2-methylimidazo[1,2-a]pyridin-6-yl)-N-(2,2,6,6-tetramethylpiperidin-4-yl)-1,3-benzothiazol-2-amine |
| 64 | 6-(2-methyl-2H-indazol-5-yl)-2-[(2,2,6,6-tetramethylpiperidin-4-yl)oxy]-1,3-benzothiazole |
| 65[1] | 6-(2-methyl-2H-indazol-5-yl)-2-(2-methyl-1,2,3,6-tetrahydropyridin-4-yl)-1,3-benzothiazole |
| 66[1] | 6-(2,7-dimethyl-2H-indazol-5-yl)-N-methyl-N-(2-methylpiperidin-4-yl)-1,3-benzothiazol-2-amine |
| 67[1] | 6-(2-methyl-2H-indazol-5-yl)-2-(6-methyl-1,2,3,6-tetrahydropyridin-4-yl)-1,3-benzothiazole |
| 68[1] | 6-(2,7-dimethyl-2H-indazol-5-yl)-2-[(2,2,6,6-tetramethylpiperidin-4-yl)oxy]-1,3-benzothiazole |
| 70[1] | 6-[4-fluoro-2-(piperidin-4-yl)-1,3-benzothiazol-6-yl]-2-methyl-1,3-benzoxazole |
| 71[1] | 6-(2,8-dimethylimidazo[1,2-a]pyridin-6-yl)-4-fluoro-2-(1,2,3,6-tetrahydropyridin-4-yl)-1,3-benzothiazole |
| 72[1] | 4-fluoro-6-(2-methyl-2H-indazol-5-yl)-2-(1,2,3,6-tetrahydropyridin-4-yl)-1,3-benzothiazole |

| Cpd | Name |
|---|---|
| 73[1] | 4-fluoro-6-(2-methyl-2H-indazol-5-yl)-2-(piperidin-4-yl)-1,3-benzothiazole |
| 74[1] | 2-methyl-5-[2-(piperidin-4-yl)[1,3]thiazolo[4,5-c]pyridin-6-yl]-2H-indazole-7-carbonitrile |
| 75[1] | 6-(7-ethyl-2-methyl-2H-indazol-5-yl)-2-(piperidin-4-yl)[1,3]thiazolo[4,5-c]pyridine |
| 76[1] | 6-(7-fluoro-2-methyl-2H-indazol-5-yl)-2-(piperidin-4-yl)[1,3]thiazolo[4,5-c]pyridine |
| 77[1] | 6-(2-methylimidazo[1,2-a]pyridin-6-yl)-2-(piperidin-4-yl)[1,3]thiazolo[4,5-c]pyridine |
| 78[1] | 5-[4-fluoro-2-(piperidin-4-yl)-1,3-benzothiazol-6-yl]-1H-pyrazolo[4,3-b]pyridine |
| 79[1] | 5-[4-fluoro-2-(piperidin-4-yl)-1,3-benzothiazol-6-yl]-2-methyl-2H-pyrazolo[4,3-b]pyridine |
| 80[1] | 6-(7-cyclopropyl-2-methyl-2H-indazol-5-yl)-N-methyl-N-(2,2,6,6-tetramethylpiperidin-4-yl)-1,3-benzothiazol-2-amine |
| 81[1] | N-methyl-6-(2-methyl-2H-indazol-5-yl)-N-(2-methylpiperidin-4-yl)-1,3-benzothiazol-2-amine |
| 82 | 6-(2-methylimidazo[1,2-a]pyridin-6-yl)-2-(piperidin-4-yl)-1,3-benzothiazole |
| 83 | 6-(7-fluoro-2-methyl-2H-indazol-5-yl)-2-(piperidin-4-yl)-1,3-benzothiazole |
| 84[1] | 2-methyl-5-[2-(piperidin-4-yl)-1,3-benzothiazol-6-yl]-2H-indazole-7-carbonitrile |
| 85 | 6-(7-ethyl-2-methyl-2H-indazol-5-yl)-2-(piperidin-4-yl)-1,3-benzothiazole |
| 86 | 6-(7-fluoro-2-methyl-2H-indazol-5-yl)-N-methyl-N-(2,2,6,6-tetramethylpiperidin-4-yl)[1,3]thiazolo[4,5-c]pyridin-2-amine |
| 87 | N-methyl-6-(2-methylimidazo[1,2-a]pyridin-6-yl)-N-(2,2,6,6-tetramethylpiperidin-4-yl)[1,3]thiazolo[4,5-c]pyridin-2-amine |
| 88 | 6-(2,8-dimethylimidazo[1,2-a]pyridin-6-yl)-N-methyl-N-(2,2,6,6-tetramethylpiperidin-4-yl)[1,3]thiazolo[4,5-c]pyridin-2-amine |
| 89 | N-methyl-6-(2-methylimidazo[1,2-b]pyridazin-6-yl)-N-(2,2,6,6-tetramethylpiperidin-4-yl)[1,3]thiazolo[4,5-c]pyridin-2-amine |
| 90 | 6-(2,8-dimethylimidazo[1,2-b]pyridazin-6-yl)-N-methyl-N-(2,2,6,6-tetramethylpiperidin-4-yl)[1,3]thiazolo[4,5-c]pyridin-2-amine |
| 91 | 5-{4-fluoro-2-[methyl(2,2,6,6-tetramethylpiperidin-4-yl)amino]-1,3-benzothiazol-6-yl}-2-methyl-2H-indazole-7-carbonitrile |
| 92 | 6-[4-fluoro-2-(1-methylpiperidin-4-yl)-1,3-benzothiazol-6-yl]-2-methylimidazo[1,2-b]pyridazine |
| 93[1] | 6-(8-ethyl-2-methylimidazo[1,2-a]pyridin-6-yl)-N-methyl-N-(2,2,6,6-tetramethylpiperidin-4-yl)-1,3-benzothiazol-2-amine |
| 94[1] | 6-(2,4-dimethyl-1H-benzimidazol-6-yl)-2-(piperidin-4-yl)-1,3-benzothiazole |
| 95[1] | 6-(2-methyl-1H-benzimidazol-6-yl)-2-(piperidin-4-yl)-1,3-benzothiazole |
| 96 | N-methyl-6-[2-methyl-8-(trifluoromethyl)imidazo[1,2-a]pyridin-6-yl]-N-(2,2,6,6-tetramethylpiperidin-4-yl)-1,3-benzothiazol-2-amine |
| 97[1] | 2-methyl-6-[2-(piperidin-4-yl)-1,3-benzothiazol-6-yl]imidazo[1,2-b]pyridazine |
| 98[1] | 6-(2,7-dimethyl-2H-indazol-5-yl)-4-methoxy-2-(1,2,3,6-tetrahydropyridin-4-yl)-1,3-benzothiazole |
| 99[1] | 6-(2,7-dimethyl-2H-indazol-5-yl)-4-methoxy-2-(piperidin-4-yl)-1,3-benzothiazole |
| 100[1] | 6-(2,7-dimethyl-2H-indazol-5-yl)-2-(1,2,3,6-tetrahydropyridin-4-yl)-1,3-benzothiazol-4-ol |
| 101 | 6-(2,7-dimethyl-2H-indazol-5-yl)-7-fluoro-N-methyl-N-(2,2,6,6-tetramethylpiperidin-4-yl)[1,3]thiazolo[4,5-c]pyridin-2-amine |
| 102[1] | 5-[4-fluoro-2-(1,2,3,6-tetrahydropyridin-4-yl)-1,3-benzothiazol-6-yl]-2-methyl-2H-indazole-7-carbonitrile |
| 103[1] | 1-{5-[4-fluoro-2-(piperidin-4-yl)-1,3-benzothiazol-6-yl]-2-methyl-2H-indazol-7-yl}methanamine |
| 104[1] | 5-[4-fluoro-2-(piperidin-4-yl)-1,3-benzothiazol-6-yl]-2-methyl-2H-indazole-7-carbonitrile |
| 105 | N-methyl-6-(2-methylimidazo[1,2-a]pyrimidin-6-yl)-N-(2,2,6,6-tetramethylpiperidin-4-yl)[1,3]thiazolo[4,5-c]pyridin-2-amine |
| 106 | 6-[2-(1-ethylpiperidin-4-yl)-4-fluoro-1,3-benzothiazol-6-yl]-2-methylimidazo[1,2-b]pyridazine |
| 107 | 6-[4-fluoro-2-(1-methylpiperidin-4-yl)-1,3-benzothiazol-6-yl]-2,8-dimethylimidazo[1,2-b]pyridazine |
| 108 | 6-(2,7-dimethyl-2H-indazol-5-yl)-N-(1,2-dimethylpiperidin-4-yl)-N-methyl-1,3-benzothiazol-2-amine |
| 109[1] | 2-methyl-5-[2-(piperidin-4-yl)[1,3]thiazolo[5,4-d]pyrimidin-5-yl]-2H-indazole-7-carbonitrile |
| 110[1] | 5-(2,7-dimethyl-2H-indazol-5-yl)-2-(piperidin-4-yl)[1,3]thiazolo[5,4-d]pyrimidine |
| 111[1] | 6-(8-fluoro-2-methylimidazo[1,2-a]pyridin-6-yl)-N-methyl-N-(2,2,6,6-tetramethylpiperidin-4-yl)-1,3-benzothiazol-2-amine |
| 112 | 2-methyl-6-[2-(piperidin-4-yl)-1,3-benzothiazol-6-yl]-1,3-benzoxazole |
| 113[1] | 6-(8-fluoro-2-methylimidazo[1,2-a]pyridin-6-yl)-2-(piperidin-4-yl)-1,3-benzothiazole |
| 114[1] | 6-(2,8-dimethylimidazo[1,2-a]pyridin-6-yl)-2-(piperidin-4-yl)-1,3-benzothiazole |
| 115[1] | 2-(2,2-dimethylpiperidin-4-yl)-6-(2-methyl-2H-indazol-5-yl)-1,3-benzothiazole |
| 116 | N-methyl-6-[2-methyl-8-(trifluoromethyl)imidazo[1,2-a]pyridin-6-yl]-N-(2,2,6,6-tetramethylpiperidin-4-yl)[1,3]thiazolo[4,5-c]pyridin-2-amine |
| 117 | 2-methyl-5-{2-[methyl(2,2,6,6-tetramethylpiperidin-4-yl)amino][1,3]thiazolo[4,5-c]pyridin-6-yl}-2H-indazole-7-carbonitrile |
| 118 | 3-(2,7-dimethyl-2H-indazol-5-yl)-N-methyl-N-(2,2,6,6-tetramethylpiperidin-4-yl)[1,3]thiazolo[4,5-c]pyridazin-6-amine |
| 119[1] | 2-{6-[methyl(2,2,6,6-tetramethylpiperidin-4-yl)amino][1,3]thiazolo[4,5-c]pyridazin-3-yl}-5-(1H-pyrazol-4-yl)phenol |
| 120 | 6-[4-fluoro-2-(piperazin-1-yl)-1,3-benzothiazol-6-yl]-2,8-dimethylimidazo[1,2-b]pyridazine |

-continued

| Cpd | Name |
|---|---|
| 121 | 6-[2-(1,4-diazepan-1-yl)-4-fluoro-1,3-benzothiazol-6-yl]-2,8-dimethylimidazo[1,2-b]pyridazine |
| 122 | 5-(2,7-dimethyl-2H-indazol-5-yl)-N-methyl-N-(2,2,6,6-tetramethylpiperidin-4-yl)[1,3]thiazolo[5,4-d]pyrimidin-2-amine |
| 123 | 2-methyl-5-{2-[methyl(2,2,6,6-tetramethylpiperidin-4-yl)amino][1,3]thiazolo[5,4-d]pyrimidin-5-yl}-2H-indazole-7-carbonitrile |
| 124 | 5-(7-fluoro-2-methyl-2H-indazol-5-yl)-N-methyl-N-(2,2,6,6-tetramethylpiperidin-4-yl)[1,3]thiazolo[5,4-d]pyrimidin-2-amine |
| 125 | 6-[2-(4,7-diazaspiro[2.5]oct-7-yl)-4-fluoro-1,3-benzothiazol-6-yl]-2,8-dimethylimidazo[1,2-b]pyridazine |
| 126 | 4-fluoro-6-(7-fluoro-2-methyl-2H-indazol-5-yl)-2-(piperidin-4-yl)-1,3-benzothiazole |
| 127 | 6-(2,8-dimethylimidazo[1,2-b]pyridazin-6-yl)-4-fluoro-N-methyl-N-(2,2,6,6-tetramethylpiperidin-4-yl)-1,3-benzothiazol-2-amine |
| 128 | 5-(7-fluoro-2-methyl-2H-indazol-5-yl)-N-methyl-N-(2,2,6,6-tetramethylpiperidin-4-yl)[1,3]thiazolo[5,4-b]pyridin-2-amine |
| 129 | N-methyl-5-(2-methylimidazo[1,2-a]pyridin-6-yl)-N-(2,2,6,6-tetramethylpiperidin-4-yl)[1,3]thiazolo[5,4-b]pyridin-2-amine |
| 130[1] | 2-{2-[methyl(2,2,6,6-tetramethylpiperidin-4-yl)amino][1,3]thiazolo[4,5-b]pyrazin-6-yl}-5-(1H-pyrazol-4-yl)phenol |
| 131 | 6-(2,7-dimethyl-2H-indazol-5-yl)-N-methyl-N-(2,2,6,6-tetramethylpiperidin-4-yl)[1,3]thiazolo[4,5-b]pyrazin-2-amine |
| 132[1] | 6-[2-(3,5-dimethylpiperazin-1-yl)-4-fluoro-1,3-benzothiazol-6-yl]-2,8-dimethylimidazo[1,2-b]pyridazine |
| 133[1] | 6-{4-fluoro-2-[(2,2,6,6-tetramethylpiperidin-4-yl)oxy]-1,3-benzothiazol-6-yl}-2,8-dimethylimidazo[1,2-b]pyridazine |
| 134 | 6-(2,7-dimethyl-2H-indazol-5-yl)-2-(piperidin-4-yl)-1,3-benzothiazol-4-ol |
| 135[1] | 6-{2-[(2,6-dimethylpiperidin-4-yl)oxy]-4-fluoro-1,3-benzothiazol-6-yl}-2,8-dimethylimidazo[1,2-b]pyridazine |
| 136 | N-methyl-6-(2-methyl[1,2,4]triazolo[1,5-a]pyridin-6-yl)-N-(2,2,6,6-tetramethylpiperidin-4-yl)[1,3]thiazolo[4,5-c]pyridin-2-amine |
| 137[1] | 2-{2-[methyl(2,2,6,6-tetramethylpiperidin-4-yl)amino][1,3]thiazolo[4,5-c]pyridin-6-yl}-5-(1H-pyrazol-4-yl)phenol |
| 138[1] | 2-methyl-6-{2-[methyl(2,2,6,6-tetramethylpiperidin-4-yl)amino]-1,3-benzothiazol-6-yl}imidazo[1,2-a]pyridine-8-carbonitrile |
| 139[1] | 2,8-dimethyl-6-[2-(piperidin-4-yl)-1,3-benzothiazol-6-yl]imidazo[1,2-b]pyridazine |
| 140 | 2-methyl-5-{2-[methyl(2,2,6,6-tetramethylpiperidin-4-yl)amino][1,3]thiazolo[4,5-b]pyrazin-6-yl}-2H-indazole-7-carbonitrile |
| 141 | N-methyl-6-(2-methylimidazo[1,2-b]pyridazin-6-yl)-N-(2,2,6,6-tetramethylpiperidin-4-yl)[1,3]thiazolo[4,5-b]pyrazin-2-amine |
| 142[1] | 2-{2-[methyl(2,2,6,6-tetramethylpiperidin-4-yl)amino][1,3]thiazolo[5,4-d]pyrimidin-5-yl}-5-(1H-pyrazol-4-yl)phenol |
| 143 | 1-[6-(2,8-dimethylimidazo[1,2-b]pyridazin-6-yl)-4-fluoro-1,3-benzothiazol-2-yl]piperidin-4-ol |
| 144[1] | 6-{4-fluoro-2-[(2R)-2-methylpiperidin-4-yl]-1,3-benzothiazol-6-yl}-2-methylimidazo[1,2-b]pyridazine |
| 145[1] | 6-[4-fluoro-2-(1,2,3,6-tetrahydropyridin-4-yl)-1,3-benzothiazol-6-yl]-8-methoxy-2-methylimidazo[1,2-b]pyridazine |
| 146[1] | 6-(2,7-dimethyl-2H-indazol-5-yl)-N-(2,2-dimethylpiperidin-4-yl)-N-methyl-1,3-benzothiazol-2-amine |
| 147 | 6-(8-fluoro-2-methylimidazo[1,2-a]pyridin-6-yl)-N-methyl-N-(2,2,6,6-tetramethylpiperidin-4-yl)[1,3]thiazolo[4,5-c]pyridin-2-amine |
| 148 | 2-methyl-5-{2-[methyl(2,2,6,6-tetramethylpiperidin-4-yl)amino][1,3]thiazolo[5,4-b]pyridin-5-yl}-2H-indazole-7-carbonitrile |
| 149[1] | 2-{2-[methyl(2,2,6,6-tetramethylpiperidin-4-yl)amino][1,3]thiazolo[5,4-b]pyridin-5-yl}-5-(1H-pyrazol-4-yl)phenol |
| 150 | 6-(7-fluoro-2-methyl-2H-indazol-5-yl)-N-methyl-N-(2,2,6,6-tetramethylpiperidin-4-yl)[1,3]thiazolo[4,5-b]pyrazin-2-amine |
| 151[1] | 6-[4-fluoro-2-(piperidin-4-yl)-1,3-benzothiazol-6-yl]-8-methoxy-2-methylimidazo[1,2-b]pyridazine |
| 152[1] | 4-fluoro-6-(8-fluoro-2-methylimidazo[1,2-a]pyridin-6-yl)-2-(piperidin-4-yl)-1,3-benzothiazole |
| 153[1] | 4-chloro-6-(7-fluoro-2-methyl-2H-indazol-5-yl)-2-(1,2,3,6-tetrahydropyridin-4-yl)-1,3-benzothiazole |
| 154[1] | 5-[4-chloro-2-(1,2,3,6-tetrahydropyridin-4-yl)-1,3-benzothiazol-6-yl]-2-methyl-2H-indazole-7-carbonitrile |
| 155[1] | N-(2,2-dimethylpiperidin-4-yl)-N-methyl-6-(2-methyl-2H-indazol-5-yl)-1,3-benzothiazol-2-amine |
| 156 | 2-methyl-6-[2-(piperidin-4-yl)-1,3-benzothiazol-6-yl]imidazo[1,2-a]pyrimidine |
| 157 | 3-(8-fluoro-2-methylimidazo[1,2-a]pyridin-6-yl)-N-methyl-N-(2,2,6,6-tetramethylpiperidin-4-yl)[1,3]thiazolo[4,5-c]pyridazin-6-amine |
| 158 | 2-methyl-5-{6-[methyl(2,2,6,6-tetramethylpiperidin-4-yl)amino][1,3]thiazolo[4,5-c]pyridazin-3-yl}-2H-indazole-7-carbonitrile |
| 161[1] | 6-[2,3-difluoro-4-(1H-pyrazol-4-yl)phenyl]-N-methyl-N-(2,2,6,6-tetramethylpiperidin-4-yl)[1,3]thiazolo[4,5-b]pyrazin-2-amine |
| 162 | 6-(2,8-dimethylimidazo[1,2-b]pyridazin-6-yl)-N-methyl-N-(2,2,6,6-tetramethylpiperidin-4-yl)[1,3]thiazolo[4,5-b]pyrazin-2-amine |

| Cpd | Name |
|---|---|
| 163 | 2-methyl-6-{2-[methyl(2,2,6,6-tetramethylpiperidin-4-yl)amino][1,3]thiazolo[4,5-b]pyrazin-6-yl}imidazo[1,2-a]pyridine-8-carbonitrile |
| 164[1] | 4-fluoro-N-methyl-6-(2-methylimidazo[1,2-b]pyridazin-6-yl)-N-[(2S)-2-methylpiperidin-4-yl]-1,3-benzothiazol-2-amine |
| 165[1] | 6-(2,8-dimethylimidazo[1,2-b]pyridazin-6-yl)-4-fluoro-N-methyl-N-[(2S)-2-methylpiperidin-4-yl]-1,3-benzothiazol-2-amine |
| 166[1] | 6-[4-fluoro-2-(octahydroindolizin-7-yl)-1,3-benzothiazol-6-yl]-2-methylimidazo[1,2-b]pyridazine |
| 167[1] | 6-[4-fluoro-2-(piperidin-4-yl)-1,3-benzothiazol-6-yl]-N,2-dimethylimidazo[1,2-b]pyridazin-8-amine |
| 168[1] | 6-[4-fluoro-2-(piperidin-4-yl)-1,3-benzothiazol-6-yl]-N,N,2-trimethylimidazo[1,2-b]pyridazin-8-amine |
| 169 | 2-methyl-6-[2-(piperidin-4-yl)-1,3-benzothiazol-6-yl]imidazo[1,2-a]pyrazine |
| 170 | 2-methyl-6-{2-[methyl(2,2,6,6-tetramethylpiperidin-4-yl)amino][1,3]thiazolo[5,4-d]pyrimidin-5-yl}imidazo[1,2-a]pyridine-8-carbonitrile |
| 171 | 5-(8-fluoro-2-methylimidazo[1,2-a]pyridin-6-yl)-N-methyl-N-(2,2,6,6-tetramethylpiperidin-4-yl)[1,3]thiazolo[5,4-d]pyrimidin-2-amine |
| 172[1] | 6-(7-cyano-2-methyl-2H-indazol-5-yl)-2-(1,2,3,6-tetrahydropyridin-4-yl)-1,3-benzothiazole-4-carbonitrile |
| 173[1] | 2-methyl-6-[2-(piperazin-1-yl)[1,3]thiazolo[4,5-b]pyrazin-6-yl]imidazo[1,2-a]pyridine-8-carbonitrile |
| 174[1] | 6-(8-fluoro-2-methylimidazo[1,2-a]pyridin-6-yl)-2-(piperazin-1-yl)[1,3]thiazolo[4,5-b]pyrazine |
| 175[1] | 6-(2,7-dimethyl-2H-indazol-5-yl)-N-(2,6-dimethylpiperidin-4-yl)-N-methyl-1,3-benzothiazol-2-amine |
| 176[1] | N-(2,6-dimethylpiperidin-4-yl)-N-methyl-6-(2-methyl-2H-indazol-5-yl)-1,3-benzothiazol-2-amine |
| 177 | 5-(8-fluoro-2-methylimidazo[1,2-a]pyridin-6-yl)-N-methyl-N-(2,2,6,6-tetramethylpiperidin-4-yl)[1,3]thiazolo[5,4-b]pyridin-2-amine |
| 178 | 2-methyl-6-{2-[methyl(2,2,6,6-tetramethylpiperidin-4-yl)amino][1,3]thiazolo[5,4-b]pyridin-5-yl}imidazo[1,2-a]pyridine-8-carbonitrile |
| 179 | 2-methyl-6-{2-[methyl(2,2,6,6-tetramethylpiperidin-4-yl)amino][1,3]thiazolo[4,5-c]pyridin-6-yl}imidazo[1,2-a]pyridine-8-carbonitrile |
| 180 | 6-(8-fluoro-2-methylimidazo[1,2-a]pyridin-6-yl)-2-[(2,2,6,6-tetramethylpiperidin-4-yl)oxy][1,3]thiazolo[4,5-b]pyrazine |
| 181 | 2-methyl-6-{2-[(2,2,6,6-tetramethylpiperidin-4-yl)oxy][1,3]thiazolo[4,5-b]pyrazin-6-yl}imidazo[1,2-a]pyridine-8-carbonitrile |
| 182[1] | 6-(2-methylimidazo[1,2-b]pyridazin-6-yl)-2-(piperazin-1-yl)[1,3]thiazolo[4,5-b]pyrazine |
| 183 | 5-(2,8-dimethylimidazo[1,2-a]pyridin-6-yl)-N-methyl-N-(2,2,6,6-tetramethylpiperidin-4-yl)[1,3]thiazolo[5,4-d]pyrimidin-2-amine |
| 184 | 5-(2,8-dimethylimidazo[1,2-b]pyridazin-6-yl)-N-methyl-N-(2,2,6,6-tetramethylpiperidin-4-yl)[1,3]thiazolo[5,4-d]pyrimidin-2-amine |
| 185[1] | 4-fluoro-N-methyl-6-(2-methylimidazo[1,2-b]pyridazin-6-yl)-N-(piperidin-4-yl)-1,3-benzothiazol-2-amine |
| 186[1] | 6-(2,8-dimethylimidazo[1,2-b]pyridazin-6-yl)-4-fluoro-N-methyl-N-(piperidin-4-yl)-1,3-benzothiazol-2-amine |
| 187[1] | 8-(benzyloxy)-6-[4-fluoro-2-(piperidin-4-yl)-1,3-benzothiazol-6-yl]-2-methylimidazo[1,2-b]pyridazine |
| 188[1] | 6-[4-fluoro-2-(piperidin-4-yl)-1,3-benzothiazol-6-yl]-2-methylimidazo[1,2-b]pyridazin-8-amine |
| 189[1] | 6-[4-fluoro-2-(piperidin-4-yl)-1,3-benzothiazol-6-yl]-2-methylimidazo[1,2-b]pyridazin-8-ol |
| 190[1] | 2-(2,6-dimethylpiperidin-4-yl)-6-(2-methyl-2H-indazol-5-yl)-1,3-benzothiazole |
| 191[1] | 4-fluoro-6-(4-fluoro-3-methoxyphenyl)-2-(piperidin-4-yl)-1,3-benzothiazole |
| 192[1] | N-[(3-exo)-8-azabicyclo[3.2.1]oct-3-yl]-6-(2,8-dimethylimidazo[1,2-b]pyridazin-6-yl)-4-fluoro-N-methyl-1,3-benzothiazol-2-amine |
| 193[1] | 2-methyl-5-{2-[methyl(piperidin-4-yl)amino][1,3]thiazolo[5,4-d]pyrimidin-5-yl}-2H-indazole-7-carbonitrile |
| 194[1] | 6-[2-(1-azabicyclo[2.2.2]oct-4-yl)-4-fluoro-1,3-benzothiazol-6-yl]-2,8-dimethylimidazo[1,2-b]pyridazine |
| 195[1] | 6-[4-fluoro-2-(piperidin-4-yl)-1,3-benzothiazol-6-yl]-2-methyl-8-phenoxyimidazo[1,2-b]pyridazine |
| 196[1] | 2-methyl-6-{2-[methyl(piperidin-4-yl)amino][1,3]thiazolo[5,4-d]pyrimidin-5-yl}imidazo[1,2-a]pyridine-8-carbonitrile |
| 197 | 5-(7-methoxy-2-methyl-2H-indazol-5-yl)-N-methyl-N-(2,2,6,6-tetramethylpiperidin-4-yl)[1,3]thiazolo[5,4-d]pyrimidin-2-amine |
| 198[1] | 2-methyl-6-{2-[methyl(piperidin-4-yl)amino][1,3]thiazolo[4,5-c]pyridin-6-yl}imidazo[1,2-a]pyridine-8-carbonitrile |
| 199[1] | 6-{2-[(3-exo)-8-azabicyclo[3.2.1]oct-3-ylamino][1,3]thiazolo[4,5-c]pyridin-6-yl}-2-methylimidazo[1,2-a]pyridine-8-carbonitrile |
| 200 | 4-fluoro-6-(8-methoxy-2-methylimidazo[1,2-b]pyridazin-6-yl)-N-methyl-N-(2,2,6,6-tetramethylpiperidin-4-yl)-1,3-benzothiazol-2-amine |
| 201[1] | 6-{4-fluoro-2-[methyl(2,2,6,6-tetramethylpiperidin-4-yl)amino]-1,3-benzothiazol-6-yl}-2-methylimidazo[1,2-b]pyridazin-8-amine |
| 202[1] | 4-fluoro-6-(8-methoxy-2-methylimidazo[1,2-b]pyridazin-6-yl)-N-methyl-N-(piperidin-4-yl)-1,3-benzothiazol-2-amine |

-continued

| Cpd | Name |
|---|---|
| 203[1] | 6-{2-[(3-exo)-8-azabicyclo[3.2.1]oct-3-yl(methyl)amino][1,3]thiazolo[4,5-c]pyridin-6-yl}-2-methylimidazo[1,2-a]pyridine-8-carbonitrile |
| 204[1] | N-[(3-exo)-8-azabicyclo[3.2.1]oct-3-yl]-6-(8-fluoro-2-methylimidazo[1,2-a]pyridin-6-yl)-N-methyl[1,3]thiazolo[4,5-c]pyridin-2-amine |
| 205[1] | N-[(3-exo)-8-azabicyclo[3.2.1]oct-3-yl]-6-(7-fluoro-2-methyl-2H-indazol-5-yl)-N-methyl[1,3]thiazolo[4,5-c]pyridin-2-amine |
| 206[1] | 5-{2-[(3-exo)-8-azabicyclo[3.2.1]oct-3-yl(methyl)amino][1,3]thiazolo[4,5-c]pyridin-6-yl}-2-methyl-2H-indazole-7-carbonitrile |
| 207[1] | 6-{2-[(3-exo)-8-azabicyclo[3.2.1]oct-3-yl(methyl)amino][1,3]thiazolo[5,4-d]pyrimidin-5-yl}-2-methylimidazo[1,2-a]pyridine-8-carbonitrile |
| 208[1] | 5-{2-[(3-exo)-8-azabicyclo[3.2.1]oct-3-yl(methyl)amino][1,3]thiazolo[5,4-d]pyrimidin-5-yl}-2-methyl-2H-indazole-7-carbonitrile |
| 209[1] | N-[(3-exo)-8-azabicyclo[3.2.1]oct-3-yl]-4-fluoro-N-methyl-6-(2-methylimidazo[1,2-b]pyridazin-6-yl)-1,3-benzothiazol-2-amine |
| 210[1] | 6-[4-fluoro-2-(4-methylpiperidin-4-yl)-1,3-benzothiazol-6-yl]-2,8-dimethylimidazo[1,2-b]pyridazine |
| 211[1] | N-[(3-exo)-8-azabicyclo[3.2.1]oct-3-yl]-6-(7-fluoro-2-methyl-2H-indazol-5-yl)[1,3]thiazolo[4,5-c]pyridin-2-amine |
| 212[1] | N-[(3-exo)-8-azabicyclo[3.2.1]oct-3-yl]-6-(8-fluoro-2-methylimidazo[1,2-a]pyridin-6-yl)[1,3]thiazolo[4,5-c]pyridin-2-amine |
| 213[1] | 5-{2-[(3-exo)-8-azabicyclo[3.2.1]oct-3-ylamino][1,3]thiazolo[4,5-c]pyridin-6-yl}-2-methyl-2H-indazole-7-carbonitrile |
| 214[1] | 2-methyl-5-{2-[methyl(piperidin-4-yl)amino][1,3]thiazolo[4,5-c]pyridin-6-yl}-2H-indazole-7-carbonitrile |
| 215[1] | 6-(8-fluoro-2-methylimidazo[1,2-a]pyridin-6-yl)-N-methyl-N-(piperidin-4-yl)[1,3]thiazolo[4,5-c]pyridin-2-amine |
| 216[1] | 6-(7-fluoro-2-methyl-2H-indazol-5-yl)-N-methyl-N-(piperidin-4-yl)[1,3]thiazolo[4,5-c]pyridin-2-amine |
| 217[1] | N-[(3-exo)-8-azabicyclo[3.2.1]oct-3-yl]-5-(8-fluoro-2-methylimidazo[1,2-a]pyridin-6-yl)-N-methyl[1,3]thiazolo[5,4-d]pyrimidin-2-amine |
| 218[1] | N-[(3-exo)-8-azabicyclo[3.2.1]oct-3-yl]-5-(7-fluoro-2-methyl-2H-indazol-5-yl)-N-methyl[1,3]thiazolo[5,4-d]pyrimidin-2-amine |
| 219[1] | 6-[4-fluoro-2-(piperidin-4-yl)-1,3-benzothiazol-6-yl]-2-methylimidazo[1,2-b]pyridazine-8-carboxylic acid |
| 220[1] | methyl {6-[4-fluoro-2-(piperidin-4-yl)-1,3-benzothiazol-6-yl]-2-methylimidazo[1,2-b]pyridazin-8-yl}acetate |
| 221[1] | {6-[4-fluoro-2-(piperidin-4-yl)-1,3-benzothiazol-6-yl]-2-methylimidazo[1,2-b]pyridazin-8-yl}acetic acid |
| 222 | 2-methyl-6-{2-[(2,2,6,6-tetramethylpiperidin-4-yl)amino][1,3]thiazolo[4,5-c]pyridin-6-yl}imidazo[1,2-a]pyridine-8-carbonitrile |
| 223[1] | 6-{2-[(3-exo)-8-azabicyclo[3.2.1]oct-3-yloxy][1,3]thiazolo[4,5-c]pyridin-6-yl}-2-methylimidazo[1,2-a]pyridine-8-carbonitrile |
| 224[1] | 6-[4-fluoro-2-(piperidin-4-yl)-1,3-benzothiazol-6-yl]-2-methylimidazo[1,2-b]pyridazine-8-carboxamide |
| 225 | 6-(1,3-dimethylpyrrolo[1,2-a]pyrazin-7-yl)-4-fluoro-N-methyl-N-(piperidin-4-yl)-1,3-benzothiazol-2-amine |
| 226[1] | 6-{4-fluoro-2-[methyl(piperidin-4-yl)amino]-1,3-benzothiazol-6-yl}-2-methylimidazo[1,2-a]pyridine-8-carbonitrile |
| 227[1] | N-[(8-anti)-3-azabicyclo[3.2.1]oct-8-yl]-5-(8-fluoro-2-methylimidazo[1,2-a]pyridin-6-yl)-N-methyl[1,3]thiazolo[5,4-d]pyrimidin-2-amine |
| 228[1] | 6-{2-[(8-anti)-3-azabicyclo[3.2.1]oct-8-yl(methyl)amino][1,3]thiazolo[5,4-d]pyrimidin-5-yl}-2-methylimidazo[1,2-a]pyridine-8-carbonitrile |
| 229[1] | 2-[4-fluoro-2-(piperidin-4-yl)-1,3-benzothiazol-6-yl]-6,8-dimethylimidazo[1,2-a]pyrazine |
| 230[1] | 6-[4-fluoro-2-(piperidin-4-yl)-1,3-benzothiazol-6-yl]-2-methylimidazo[1,2-b]pyridazine-8-carbonitrile |
| 231[1] | 6-{4-fluoro-2-[methyl(piperidin-4-yl)amino]-1,3-benzothiazol-6-yl}-2-methylimidazo[1,2-b]pyridazine-8-carbonitrile |
| 232[1] | 6-(7-fluoro-2-methyl-2H-indazol-5-yl)-N-(2,2,6,6-tetramethylpiperidin-4-yl)[1,3]thiazolo[4,5-c]pyridin-2-amine |
| 233 | 2-methyl-5-{2-[(2,2,6,6-tetramethylpiperidin-4-yl)amino][1,3]thiazolo[4,5-c]pyridin-6-yl}-2H-indazole-7-carbonitrile |
| 234 | 6-(8-fluoro-2-methylimidazo[1,2-a]pyridin-6-yl)-N-(2,2,6,6-tetramethylpiperidin-4-yl)[1,3]thiazolo[4,5-c]pyridin-2-amine |
| 235[1] | 6-{2-[(3-exo)-8-azabicyclo[3.2.1]oct-3-yl(methyl)amino]-4-fluoro-1,3-benzothiazol-6-yl}-2-methylimidazo[1,2-b]pyridazine-8-carbonitrile |
| 236[1] | 6-{2-[(3-exo)-8-azabicyclo[3.2.1]oct-3-yl(methyl)amino]-4-fluoro-1,3-benzothiazol-6-yl}-2-methylimidazo[1,2-b]pyridazine-8-carboxamide |
| 237[1] | N-[(3-exo)-8-azabicyclo[3.2.1]oct-3-yl]-4-fluoro-N-methyl-6-(2-methyl-2H-pyrazolo[4,3-b]pyridin-5-yl)-1,3-benzothiazol-2-amine |
| 238 | 2-methyl-5-(2-{methyl[(3-exo)-8-methyl-8-azabicyclo[3.2.1]oct-3-yl]amino}[1,3]thiazolo[4,5-c]pyridin-6-yl)-2H-indazole-7-carbonitrile |
| 239 | 6-(8-fluoro-2-methylimidazo[1,2-a]pyridin-6-yl)-N-methyl-N-[(3-exo)-8-methyl-8-azabicyclo[3.2.1]oct-3-yl][1,3]thiazolo[4,5-c]pyridin-2-amine |
| 240 | 2-methyl-6-(2-{methyl[(3-exo)-8-methyl-8-azabicyclo[3.2.1]oct-3-yl]amino}[1,3]thiazolo[4,5-c]pyridin-6-yl)imidazo[1,2-a]pyridine-8-carbonitrile |

| Cpd | Name |
|---|---|
| 241 | 6-(7-fluoro-2-methyl-2H-indazol-5-yl)-N-methyl-N-[(3-exo)-8-methyl-8-azabicyclo[3.2.1]oct-3-yl][1,3]thiazolo[4,5-c]pyridin-2-amine |
| 242 | 6-{2-[ethyl(2,2,6,6-tetramethylpiperidin-4-yl)amino][1,3]thiazolo[5,4-d]pyrimidin-5-yl)-2-methylimidazo[1,2-a]pyridine-8-carbonitrile |
| 243 | N-ethyl-5-(8-fluoro-2-methylimidazo[1,2-a]pyridin-6-yl)-N-(2,2,6,6-tetramethylpiperidin-4-yl)[1,3]thiazolo[5,4-d]pyrimidin-2-amine |
| 244 | 2-methyl-5-(2-{[(3-exo)-8-methyl-8-azabicyclo[3.2.1]oct-3-yl]amino}[1,3]thiazolo[4,5-c]pyridin-6-yl)-2H-indazole-7-carbonitrile |
| 245 | 2-methyl-6-(2-{[(3-exo)-8-methyl-8-azabicyclo[3.2.1]oct-3-yl]amino}[1,3]thiazolo[4,5-c]pyridin-6-yl)imidazo[1,2-a]pyridine-8-carbonitrile |
| 246 | 6-(7-fluoro-2-methyl-2H-indazol-5-yl)-N-[(3-exo)-8-methyl-8-azabicyclo[3.2.1]oct-3-yl][1,3]thiazolo[4,5-c]pyridin-2-amine |
| 247 | 6-(8-fluoro-2-methylimidazo[1,2-a]pyridin-6-yl)-N-[(3-exo)-8-methyl-8-azabicyclo[3.2.1]oct-3-yl][1,3]thiazolo[4,5-c]pyridin-2-amine |
| 248[1] | N-(azetidin-3-yl)-6-(2,8-dimethylimidazo[1,2-b]pyridazin-6-yl)-4-fluoro-N-methyl-1,3-benzothiazol-2-amine |
| 249[1] | 5-[4-fluoro-2-(piperidin-4-yl)-1,3-benzothiazol-6-yl]-2-methylpyrazolo[1,5-a]pyrimidine |
| 250[1] | 4-fluoro-N-methyl-6-(2-methylpyrazolo[1,5-a]pyrimidin-5-yl)-N-(piperidin-4-yl)-1,3-benzothiazol-2-amine |
| 251[1] | 6-{2-[9-azabicyclo[3.3.1]non-3-yl(methyl)amino][1,3]thiazolo[4,5-c]pyridin-6-yl}-2-methylimidazo[1,2-a]pyridine-8-carbonitrile |
| 252[1] | 5-{2-[9-azabicyclo[3.3.1]non-3-yl(methyl)amino][1,3]thiazolo[4,5-c]pyridin-6-yl}-2-methyl-2H-indazole-7-carbonitrile |
| 253[1] | N-(9-azabicyclo[3.3.1]non-3-yl)-6-(7-fluoro-2-methyl-2H-indazol-5-yl)-N-methyl[1,3]thiazolo[4,5-c]pyridin-2-amine |
| 254 | 5-{2-[(1,5-dimethyl-8-azabicyclo[3.2.1]oct-3-yl)(methyl)amino][1,3]thiazolo[5,4-d]pyrimidin-5-yl)-2-methyl-2H-indazole-7-carbonitrile |
| 255 | 6-(2-{[(1R)-1,5-dimethyl-8-azabicyclo[3.2.1]oct-3-yl](methyl)amino}[1,3]thiazolo[5,4-d]pyrimidin-5-yl)-2-methylimidazo[1,2-a]pyridine-8-carbonitrile |
| 256[1] | 6-{2-[(1R,5S)-9-azabicyclo[3.3.1]non-3-yl(methyl)amino][1,3]thiazolo[5,4-d]pyrimidin-5-yl}-2-methylimidazo[1,2-a]pyridine-8-carbonitrile |
| 257[1] | N-[(1R,5S)-9-azabicyclo[3.3.1]non-3-yl]-5-(8-fluoro-2-methylimidazo[1,2-a]pyridin-6-yl)-N-methyl[1,3]thiazolo[5,4-d]pyrimidin-2-amine |
| 258[1] | 4-fluoro-N-methyl-6-(2-methylimidazo[1,2-b]pyridazin-6-yl)-N-[(2S,4S)-2-methylpiperidin-4-yl]-1,3-benzothiazol-2-amine |
| 259[1] | 4-fluoro-N-methyl-6-(2-methylimidazo[1,2-b]pyridazin-6-yl)-N-[(2S,4R)-2-methylpiperidin-4-yl]-1,3-benzothiazol-2-amine |
| 260[1] | N-(9-azabicyclo[3.3.1]non-3-yl)-N-methyl-6-(2-methylimidazo[1,2-a]pyridin-6-yl)[1,3]thiazolo[4,5-c]pyridin-2-amine |
| 261[1] | N-(9-azabicyclo[3.3.1]non-3-yl)-6-(2,8-dimethylimidazo[1,2-a]pyridin-6-yl)-N-methyl[1,3]thiazolo[4,5-c]pyridin-2-amine |
| 262[1] | N-(9-azabicyclo[3.3.1]non-3-yl)-N-methyl-6-(2-methyl-2H-indazol-5-yl)[1,3]thiazolo[4,5-c]pyridin-2-amine |
| 263[1] | N-(9-azabicyclo[3.3.1]non-3-yl)-6-(2,7-dimethyl-2H-indazol-5-yl)-N-methyl[1,3]thiazolo[4,5-c]pyridin-2-amine |
| 264[1] | N-(9-azabicyclo[3.3.1]non-3-yl)-6-(7-methoxy-2-methyl-2H-indazol-5-yl)-N-methyl[1,3]thiazolo[4,5-c]pyridin-2-amine |
| 265 | 5-(1,3-dimethylpyrrolo[1,2-a]pyrazin-7-yl)-N-methyl-N-(2,2,6,6-tetramethylpiperidin-4-yl)[1,3]thiazolo[5,4-d]pyrimidin-2-amine |
| 266[1] | 2-methyl-6-{2-[(1,2,2,6,6-pentamethylpiperidin-4-yl)amino][1,3]thiazolo[4,5-c]pyridin-6-yl}imidazo[1,2-a]pyridine-8-carbonitrile |
| 267[1] | 6-(8-fluoro-2-methylimidazo[1,2-a]pyridin-6-yl)-N-(1,2,2,6,6-pentamethylpiperidin-4-yl)[1,3]thiazolo[4,5-c]pyridin-2-amine |
| 268[1] | 2-methyl-5-{2-[(1,2,2,6,6-pentamethylpiperidin-4-yl)amino][1,3]thiazolo[4,5-c]pyridin-6-yl}-2H-indazole-7-carbonitrile |
| 269[1] | 6-(7-fluoro-2-methyl-2H-indazol-5-yl)-N-(1,2,2,6,6-pentamethylpiperidin-4-yl)[1,3]thiazolo[4,5-c]pyridin-2-amine |
| 270 | 2-methyl-6-{2-[methyl(9-methyl-9-azabicyclo[3.3.1]non-3-yl)amino][1,3]thiazolo[4,5-c]pyridin-6-yl}imidazo[1,2-a]pyridine-8-carbonitrile |
| 271 | 6-(8-fluoro-2-methylimidazo[1,2-a]pyridin-6-yl)-N-methyl-N-(9-methyl-9-azabicyclo[3.3.1]non-3-yl)[1,3]thiazolo[4,5-c]pyridin-2-amine |
| 272 | 2-methyl-5-{2-[methyl(9-methyl-9-azabicyclo[3.3.1]non-3-yl)amino][1,3]thiazolo[4,5-c]pyridin-6-yl}-2H-indazole-7-carbonitrile |
| 273 | 6-(7-fluoro-2-methyl-2H-indazol-5-yl)-N-methyl-N-(9-methyl-9-azabicyclo[3.3.1]non-3-yl)[1,3]thiazolo[4,5-c]pyridin-2-amine |
| 274[1] | 2-{2-[methyl(piperidin-4-yl)amino][1,3]thiazolo[4,5-b]pyrazin-6-yl}-5-(1H-pyrazol-yl)phenol |
| 275 | 2-methyl-6-{2-[methyl(2,2,6,6-tetramethylpiperidin-4-yl)amino][1,3]thiazolo[5,4-d]pyrimidin-5-yl}-1,3-benzoxazole-4-carbonitrile |
| 276[1] | 6-{2-[(3-exo)-8-azabicyclo[3.2.1]oct-3-yl(methyl)amino][1,3]thiazolo[5,4-b]pyridin-5-yl}-2-methylimidazo[1,2-a]pyridine-8-carbonitrile |
| 277[1] | N-[(3-exo)-8-azabicyclo[3.2.1]oct-3-yl]-5-(8-fluoro-2-methylimidazo[1,2-a]pyridin-6-yl)-N-methyl[1,3]thiazolo[5,4-b]pyridin-2-amine |
| 278[1] | 5-{2-[(3-exo)-8-azabicyclo[3.2.1]oct-3-yl(methyl)amino][1,3]thiazolo[5,4-b]pyridin-5-yl}-2-methyl-2H-indazole-7-carbonitrile |

| Cpd | Name |
|---|---|
| 279[1] | 6-{2-[(3-exo)-9-azabicyclo[3.3.1]non-3-yl(methyl)amino][1,3]thiazolo[5,4-b]pyridin-5-yl}-2-methylimidazo[1,2-a]pyridine-8-carbonitrile |
| 280[1] | N-[(3-exo)-9-azabicyclo[3.3.1]non-3-yl]-5-(8-fluoro-2-methylimidazo[1,2-a]pyridin-6-yl)-N-methyl[1,3]thiazolo[5,4-b]pyridin-2-amine |
| 281[1] | 5-{2-[(3-exo)-9-azabicyclo[3.3.1]non-3-yl(methyl)amino][1,3]thiazolo[5,4-b]pyridin-5-yl}-2-methyl-2H-indazole-7-carbonitrile |
| 282[1] | 2-{6-[methyl(piperidin-4-yl)amino][1,3]thiazolo[4,5-c]pyridazin-3-yl}-5-(1H-pyrazol-4-yl)phenol |
| 283[1] | 2-{6-[methyl(1-methylpiperidin-4-yl)amino][1,3]thiazolo[4,5-c]pyridazin-3-yl}-5-(1H-pyrazol-4-yl)phenol |
| 284 | N-[(1R,3s,5S)-1,5-dimethyl-8-azabicyclo[3.2.1]octan-3-yl]-5-(8-fluoro-2-methylimidazo[1,2-a]pyridin-6-yl)-N-methyl[1,3]thiazolo[5,4-d]pyrimidin-2-amine |
| 285 | 6-(2-{[(1R,3s,5S)-1,5-dimethyl-8-azabicyclo[3.2.1]octan-3-yl](methyl)amino}[1,3]thiazolo[4,5-c]pyridin-6-yl)-2-methylimidazo[1,2-a]pyridine-8-carbonitrile |
| 286[1] | N-[(1R,3s,5S)-1,5-dimethyl-8-azabicyclo[3.2.1]octan-3-yl]-6-(8-fluoro-2-methylimidazo[1,2-a]pyridin-6-yl)-N-methyl[1,3]thiazolo[4,5-c]pyridin-2-amine |
| 287 | 5-(2-{[(1R,3s,5S)-1,5-dimethyl-8-azabicyclo[3.2.1]octan-3-yl](methyl)amino}[1,3]thiazolo[4,5-c]pyridin-6-yl)-2-methyl-2H-indazole-7-carbonitrile |
| 288[1] | 6-(2,8-dimethylimidazo[1,2-a]pyridin-6-yl)-N-methyl-N-(piperidin-4-yl)[1,3]thiazolo[4,5-b]pyrazin-2-amine |
| 289 | N-[(1R)-1,5-dimethyl-8-azabicyclo[3.2.1]octan-3-yl]-5-(7-fluoro-2-methyl-2H-indazol-5-yl)-N-methyl[1,3]thiazolo[5,4-d]pyrimidin-2-amine |
| 290 | 6-(2-{[(1R)-1,5-dimethyl-8-azabicyclo[3.2.1]octan-3-yl](methyl)amino}[1,3]thiazolo[5,4-d]pyrimidin-5-yl)-2-methyl-1,3-benzoxazole-4-carbonitrile |
| 291 | 6-(2-{[(1R,3s,5S)-1,5-dimethyl-8-azabicyclo[3.2.1]octan-3-yl](methyl)amino}[1,3]thiazolo[5,4-b]pyridin-5-yl)-2-methylimidazo[1,2-a]pyridine-8-carbonitrile |
| 292 | N-[(1R,3s,5S)-1,5-dimethyl-8-azabicyclo[3.2.1]octan-3-yl]-5-(8-fluoro-2-methylimidazo[1,2-a]pyridin-6-yl)-N-methyl[1,3]thiazolo[5,4-b]pyridin-2-amine |
| 293 | 5-(2-{[(1R,3s,5S)-1,5-dimethyl-8-azabicyclo[3.2.1]octan-3-yl](methyl)amino}[1,3]thiazolo[5,4-b]pyridin-5-yl)-2-methyl-2H-indazole-7-carbonitrile |
| 294 | N-[(1R,3s,5S)-1,5-dimethyl-8-azabicyclo[3.2.1]octan-3-yl]-5-(7-fluoro-2-methyl-2H-indazol-5-yl)-N-methyl[1,3]thiazolo[5,4-b]pyridin-2-amine |
| 295[1] | N-(9-azabicyclo[3.3.1]nonan-3-yl)-5-(7-fluoro-2-methyl-2H-indazol-5-yl)-N-methyl[1,3]thiazolo[5,4-b]pyridin-2-amine |
| 296[1] | 6-(6,8-dimethylimidazo[1,2-a]pyrazin-2-yl)-N-methyl-N-(2,2,6,6-tetramethylpiperidin-4-yl)[1,3]thiazolo[4,5-c]pyridin-2-amine |
| 297[1] | 6-(1,3-dimethylpyrrolo[1,2-a]pyrazin-7-yl)-N-methyl-N-(2,2,6,6-tetramethylpiperidin-4-yl)[1,3]thiazolo[4,5-c]pyridin-2-amine |
| 298 | N-[(1R,3s,5S)-1,5-dimethyl-8-azabicyclo[3.2.1]octan-3-yl]-6-(7-fluoro-2-methyl-2H-indazol-5-yl)-N-methyl[1,3]thiazolo[4,5-c]pyridin-2-amine |
| 299 | N-[(1R,3s,5S)-1,5-dimethyl-8-azabicyclo[3.2.1]octan-3-yl]-6-(2,8-dimethylimidazo[1,2-a]pyridin-6-yl)-N-methyl[1,3]thiazolo[4,5-c]pyridin-2-amine |
| 300 | N-[(1R,3s,5S)-1,5-dimethyl-8-azabicyclo[3.2.1]octan-3-yl]-N-methyl-6-(2-methylimidazo[1,2-a]pyridin-6-yl)[1,3]thiazolo[4,5-c]pyridin-2-amine |
| 301[1] | 6-(2-{[(1R,3s,5S)-1,5-dimethyl-8-azabicyclo[3.2.1]octan-3-yl](methyl)amino)[1,3]thiazolo[4,5-c]pyridin-6-yl)-2-methyl-1,3-benzoxazole-4-carbonitrile |
| 302[1] | N-methyl-6-(2-methylimidazo[2,1-b][1,3]thiazol-6-yl)-N-(2,2,6,6-tetramethylpiperidin-4-yl)[1,3]thiazolo[4,5-c]pyridin-2-amine |
| 303 | 6-(2-{[(1R,3r,5S)-1,5-diethyl-8-azabicyclo[3.2.1]octan-3-yl](methyl)amino}[1,3]thiazolo[5,4-d]pyrimidin-5-yl)-2-methylimidazo[1,2-a]pyridine-8-carbonitrile |
| 304 | N-[(1R,3r,5S)-1,5-diethyl-8-azabicyclo[3.2.1]octan-3-yl]-5-(8-fluoro-2-methylimidazo[1,2-a]pyridin-6-yl)-N-methyl[1,3]thiazolo[5,4-d]pyrimidin-2-amine |
| 305 | N-methyl-6-(3-methylimidazo[2,1-b][1,3]thiazol-6-yl)-N-2,2,6,6-tetramethylpiperidin-4-yl)[1,3]thiazolo[4,5-c]pyridin-2-amine |
| 306[1] | 6-{4-fluoro-2-[(piperidin-4-yl)oxy]-1,3-benzothiazol-6-yl}-2,8-dimethylimidazo[1,2-b]pyridazine |
| 307[1] | 4-fluoro-6-(7-fluoro-2-methyl-2H-indazol-5-yl)-2-[(piperidin-4-yl)oxy]-1,3-benzothiazole |
| 308[1] | N-methyl-6-(2-methylimidazo[2,1-b][1,3,4]thiadiazol-6-yl)-N-(2,2,6,6-tetramethylpiperidin-4-yl)[1,3]thiazolo[4,5-c]pyridin-2-amine |
| 309 | 2-methyl-6-{2-[(2,2,6,6-tetramethylpiperidin-4-yl)oxy][1,3]thiazolo[4,5-c]pyridin-6-yl}imidazo[1,2-a]pyridine-8-carbonitrile |
| 310 | 6-(8-fluoro-2-methylimidazo[1,2-a]pyridin-6-yl)-2-[(2,2,6,6-tetramethylpiperidin-4-yl)oxy][1,3]thiazolo[4,5-c]pyridine |
| 311 | 2-methyl-5-{2-[(2,2,6,6-tetramethylpiperidin-4-yl)oxy][1,3]thiazolo[4,5-c]pyridin-6-yl}-2H-indazole-7-carbonitrile |
| 312 | 6-(7-fluoro-2-methyl-2H-indazol-5-yl)-2-[(2,2,6,6-tetramethylpiperidin-4-yl)oxy][1,3]thiazolo[4,5-c]pyridine |
| 313[1] | 2-methyl-6-{2-[(piperidin-4-yl)oxy][1,3]thiazolo[4,5-c]pyridin-6-yl}imidazo[1,2-a]pyridine-8-carbonitrile |

-continued

| Cpd | Name |
|---|---|
| 314[1] | 6-(8-fluoro-2-methylimidazo[1,2-a]pyridin-6-yl)-2-[(piperidin-4-yl)oxy][1,3]thiazolo[4,5-c]pyridine |
| 315[1] | 2-methyl-5-{2-[(piperidin-4-yl)oxy][1,3]thiazolo[4,5-c]pyridin-6-yl}-2H-indazole-7-carbonitrile |
| 316[1] | 6-(7-fluoro-2-methyl-2H-indazol-5-yl)-2-[(piperidin-4-yl)oxy][1,3]thiazolo[4,5-c]pyridine |
| 317[1] | 6-{4-fluoro-2-[(piperidin-4-yl)oxy]-1,3-benzothiazol-6-yl}-2-methylimidazo[1,2-a]pyridine-8-carbonitrile |
| 318[1] | 5-{4-fluoro-2-[(piperidin-4-yl)oxy]-1,3-benzothiazol-6-yl}-2-methyl-2H-indazole-7-carbonitrile |
| 319[1] | 6-(2,8-dimethylimidazo[1,2-a]pyridin-6-yl)-4-fluoro-2-[(piperidin-4-yl)oxy]-1,3-benzothiazole |
| 320 | 6-{4-fluoro-2-[(1-methylpiperidin-4-yl)oxy]-1,3-benzothiazol-6-yl}-2,8-dimethylimidazo[1,2-b]pyridazine |
| 321 | 6-{2-[(1-ethylpiperidin-4-yl)oxy]-4-fluoro-1,3-benzothiazol-6-yl}-2,8-dimethylimidazo[1,2-b]pyridazine |
| 322 | N-[(1R,3s,5S)-1,5-dimethyl-8-azabicyclo[3.2.1]octan-3-yl]-6-(6,8-dimethylimidazo[1,2-a]pyrazin-2-yl)-N-methyl[1,3]thiazolo[4,5-c]pyridin-2-amine |
| 323 | N-[(1R,3s,5S)-1,5-dimethyl-8-azabicyclo[3.2.1]octan-3-yl]-5-(1,3-dimethylpyrrolo[1,2-a]pyrazin-7-yl)-N-methyl[1,3]thiazolo[5,4-d]pyrimidin-2-amine |
| 324[1] | 6-(2-{[(3R,4R)-3-fluoro-2,2,6,6-tetramethylpiperidin-4-yl](methyl)amino}[1,3]thiazolo[5,4-d]pyrimidin-5-yl)-2-methylimidazo[1,2-a]pyridine-8-carbonitrile |
| 325[1] | 6-(2-{[(3R,4R)-3-fluoro-2,2,6,6-tetramethylpiperidin-4-yl](methyl)amino}[1,3]thiazolo[4,5-c]pyridin-6-yl)-2-methylimidazo[1,2-a]pyridine-8-carbonitrile |
| 326[1] | N-(1R,2S,3S,5S)-2-fluoro-1,5-dimethyl-8-azabicyclo[3.2.1]octan-3-yl]-6-(8-fluoro-2-methylimidazo[1,2-a]pyridin-6-yl)-N-methyl[1,3]thiazolo[4,5-c]pyridin-2-amine |
| 327[1] | 5-(1H-imidazol-1-yl)-2-{6-[methyl(piperidin-4-yl)amino][1,3]thiazolo[4,5-c]pyridazin-3-yl}phenol |
| 328[1] | 3-[2,5-difluoro-4-(1H-pyrazol-4-yl)phenyl]-N-methyl-N-(piperidin-4-yl)[1,3]thiazolo[4,5-c]pyridazin-6-amine |
| 329 | 5-(3-fluoro-1H-pyrazol-4-yl)-2-{6-[methyl(piperidin-4-yl)amino][1,3]thiazolo[4,5-c]pyridazin-3-yl}phenol |
| 330 | 5-(1H-imidazol-1-yl)-2-{6-[methyl(1-methylpiperidin-4-yl)amino][1,3]thiazolo[4,5-c]pyridazin-3-yl}phenol |
| 331[1] | 3-[2,5-difluoro-4-(3-fluoro-1H-pyrazol-4-yl)phenyl]-N-methyl-N-(piperidin-4-yl)[1,3]thiazolo[4,5-c]pyridazin-6-amine |
| 332 | 5-(3-fluoro-1H-pyrazol-4-yl)-2-{6-[methyl(1-methylpiperidin-4-yl)amino][1,3]thiazolo[4,5-c]pyridazin-3-yl}phenol |
| 333 | 2-{6-[(3R,5S)-3,5-dimethylpiperazin-1-yl][1,3]thiazolo[4,5-c]pyridazin-3-yl}-5-(1H-pyrazol-4-yl)phenol |
| 334[1] | 2-[6-(piperazin-1-yl)[1,3]thiazolo[4,5-c]pyridazin-3-yl]-5-(1H-pyrazol-4-yl)phenol |
| 335[1] | 5-(1H-pyrazol-4-yl)-2-[6-(1,2,3,6-tetrahydropyridin-4-yl)[1,3]thiazolo[4,5-c]pyridin-2-yl]phenol |
| 336[1] | 2-(6-{[(3R,4S)-4-fluoro-1-methylpyrrolidin-3-yl]amino}[1,3]thiazolo[4,5-c]pyridazin-3-yl)-5-(1H-pyrazol-4-yl)phenol |
| 337[1] | 5-(1H-pyrazol-4-yl)-2-[6-(2,2,6,6-tetramethyl-1,2,3,6-tetrahydropyridin-4-yl)[1,3]thiazolo[4,5-c]pyridin-2-yl]phenol |
| 338[1] | 2-[6-(2,6-diazaspiro[3.5]nonan-2-yl)[1,3]thiazolo[4,5-c]pyridazin-3-yl]-5-(1H-pyrazol-4-yl)phenol |
| 339[1] | 2-[6-(7-methyl-1,7-diazaspiro[3.5]nonan-1-yl)[1,3]thiazolo[4,5-c]pyridazin-3-yl]-5-(1H-pyrazol-4-yl)phenol |
| 340[1] | 2-[6-(7-methyl-2,7-diazaspiro[4.4]nonan-2-yl)[1,3]thiazolo[4,5-c]pyridazin-3-yl]-5-(1H-pyrazol-4-yl)phenol |
| 341[1] | 2-[6-(2,7-diazaspiro[3.5]nonan-2-yl)[1,3]thiazolo[4,5-c]pyridazin-3-yl]-5-(3-fluoro-1H-pyrazol-4-yl)phenol |
| 342[1] | 2-(6-{[(3S,4S)-4-fluoro-1-methylpyrrolidin-3-yl]amino}[1,3]thiazolo[4,5-c]pyridazin-3-yl)-5-(1H-pyrazol-4-yl)phenol |
| 343 | 2-{6-[methyl(1-methylazetidin-3-yl)amino][1,3]thiazolo[4,5-c]pyridazin-3-yl}-5-(1H-pyrazol-4-yl)phenol |
| 344[1] | 2-{6-[(3aS,7aR)-octahydro-1H-pyrrolo[3,2-c]pyridin-1-yl][1,3]thiazolo[4,5-c]pyridazin-3-yl}-5-(1H-pyrazol-4-yl)phenol |
| 345[1] | 2-(6-{methyl[(1s,4s)-4-(methylamino)cyclohexyl]amino}[1,3]thiazolo[4,5-c]pyridazin-3-yl)-5-(1H-pyrazol-4-yl)phenol |
| 346[1] | 2-(6-{[(3R,4S)-4-fluoropyrrolidin-3-yl](methyl)amino}[1,3]thiazolo[4,5-c]pyridazin-3-yl)-5-(1H-pyrazol-4-yl)phenol |
| 347[1] | 2-{6-[(3aS,7aR)-5-methyloctahydro-1H-pyrrolo[3,2-c]pyridin-1-yl][1,3]thiazolo[4,5-c]pyridazin-3-yl}-5-(1H-pyrazol-4-yl)phenol |
| 348[1] | 2-(6-{methyl[(3R)-piperidin-3-yl]amino}[1,3]thiazolo[4,5-c]pyridazin-3-yl)-5-(1H-pyrazol-4-yl)phenol |
| 349[1] | 2-(6-{methyl[(3S)-piperidin-3-yl]amino}[1,3]thiazolo[4,5-c]pyridazin-3-yl)-5-(1H-pyrazol-4-yl)phenol |
| 350[1] | 2-(6-{methyl[3-(methylamino)cyclobutyl]amino}[1,3]thiazolo[4,5-c]pyridazin-3-yl)-5-(1H-pyrazol-4-yl)phenol |
| 351[1] | 2-(6-{[(1r,4r)-4-(dimethylamino)cyclohexyl](methyl)amino}[1,3]thiazolo[4,5-c]pyridazin-3-yl)-5-(1H-pyrazol-4-yl)phenol |

-continued

| Cpd | Name |
|---|---|
| 352[1] | 2-(6-{methyl[(3S)-1-methylpiperidin-3-yl]amino}[1,3]thiazolo[4,5-c]pyridazin-3-yl)-5-(1H-pyrazol-4-yl)phenol |
| 353[1] | 2-{6-[(azetidin-3-yl)(methyl)amino][1,3]thiazolo[4,5-c]pyridazin-3-yl}-5-(1H-pyrazol-4-yl)phenol |
| 354[1] | 2-[6-(1,7-diazaspiro[3.5]nonan-1-yl)[1,3]thiazolo[4,5-c]pyridazin-3-yl]-5-(1H-pyrazol-4-yl)phenol |
| 355[1] | 2-{6-[(3,3-dimethylpiperidin-4-yl)(methyl)amino][1,3]thiazolo[4,5-c]pyridazin-3-yl}-5-(1H-pyrazol-4-yl)phenol |
| 356[1] | 2-{6-[(2-azaspiro[3.3]heptan-6-yl)(methyl)amino][1,3]thiazolo[4,5-c]pyridazin-3-yl}-5-(1H-pyrazol-4-yl)phenol |
| 357 | 2-{6-[(piperidin-4-yl)amino][1,3]thiazolo[4,5-c]pyridazin-3-yl)-5-(1H-pyrazol-4-yl)phenol |
| 358 | 2-(6-{[(3R,4S)-3-fluoropiperidin-4-yl](methyl)amino}[1,3]thiazolo[4,5-c]pyridazin-3-yl)-5-(1H-pyrazol-4-yl)phenol |
| 359[1] | 5-{2-[(2R,4r,6S)-2,6-dimethylpiperidin-4-yl]-4-fluoro-1,3-benzothiazol-6-yl}-2,7-dimethyl[1,3]oxazolo[5,4-b]pyridine |
| 360[1] | 2-{6-[methyl(1,3,3-trimethylpiperidin-4-yl)amino][1,3]thiazolo[4,5-c]pyridazin-3-yl}-5-(1H-pyrazol-4-yl)phenol |
| 361[1] | 2-(6-{methyl[(1s,3s)-3-(methylamino)cyclobutyl]amino}[1,3]thiazolo[4,5-c]pyridazin-3-yl)-5-(1H-pyrazol-4-yl)phenol |
| 362[1] | 2-{6-[(3aR,7aS)-octahydro-1H-pyrrolo[2,3-c]pyridin-1-yl][1,3]thiazolo[4,5-c]pyridazin-3-yl}-5-(1H-pyrazol-4-yl)phenol |
| 363[1] | 2-[6-(1,6-diazaspiro[3.5]nonan-1-yl)[1,3]thiazolo[4,5-c]pyridazin-3-yl]-5-(1H-pyrazol-4-yl)phenol |
| 364[1] | 2-(6-{[(1s,3s)-3-(dimethylamino)cyclobutyl](methyl)amino}[1,3]thiazolo[4,5-c]pyridazin-3-yl)-5-(1H-pyrazol-4-yl)phenol |
| 365[1] | 2-(6-{[(3R,4R)-3-fluoropiperidin-4-yl](methyl)amino}[1,3]thiazolo[4,5-c]pyridazin-3-yl)-5-(1H-pyrazol-4-yl)phenol |
| 366 | 2-{6-[(1-methylpiperidin-4-yl)amino][1,3]thiazolo[4,5-c]pyridazin-3-yl}-5-(1H-pyrazol-4-yl)phenol |
| 367[1] | 5-(1H-pyrazol-4-yl)-2-{6-[(pyrrolidin-3-yl)amino][1,3]thiazolo[4,5-c]pyridazin-3-yl}phenol |
| 368[1] | 2-[6-(2,6-diazaspiro[3.3]heptan-2-yl)[1,3]thiazolo[4,5-c]pyridazin-3-yl]-5-(3-fluoro-1H-pyrazol-4-yl)phenol |
| 369[1] | 2-{6-[(3aR,7aS)-6-methyloctahydro-1H-pyrrolo[2,3-c]pyridin-1-yl][1,3]thiazolo[4,5-c]pyridazin-3-yl}-5-(1H-pyrazol-4-yl)phenol |
| 370[1] | 2-[6-(6-methyl-1,6-diazaspiro[3.5]nonan-1-yl)[1,3]thiazolo[4,5-c]pyridazin-3-yl]-5-(1H-pyrazol-4-yl)phenol |
| 371[1] | 2-(6-{[(2S,4S)-2-(hydroxymethyl)piperidin-4-yl](methyl)amino}[1,3]thiazolo[4,5-c]pyridazin-3-yl)-5-(1H-pyrazol-4-yl)phenol |
| 372[1] | 2-(6-{[(2S,4S)-2-(hydroxymethyl)-1-methylpiperidin-4-yl](methyl)amino}[1,3]thiazolo[4,5-c]pyridazin-3-yl)-5-(1H-pyrazol-4-yl)phenol |
| 373 | 2-{6-[(1-methylpyrrolidin-3-yl)amino][1,3]thiazolo[4,5-c]pyridazin-3-yl}-5-(1H-pyrazol-4-yl)phenol |
| 374 | 2-{6-[methyl(pyrrolidin-3-yl)amino][1,3]thiazolo[4,5-c]pyridazin-3-yl}-5-(1H-pyrazol-4-yl)phenol |
| 375 | 2-{6-[methyl(1-methylpyrrolidin-3-yl)amino][1,3]thiazolo[4,5-c]pyridazin-3-yl}-5-(1H-pyrazol-4-yl)phenol |
| 376[1] | 2-(6-{methyl[(1r,3r)-3-(methylamino)cyclobutyl]amino}[1,3]thiazolo[4,5-c]pyridazin-3-yl)-5-(1H-pyrazol-4-yl)phenol |
| 377 | 5-{2-[(1,2-dimethylpiperidin-4-yl)(methyl)amino][1,3]thiazolo[4,5-c]pyridin-6-yl}-2-methyl-2H-indazole-7-carbonitrile |
| 378 | N-(1,2-dimethylpiperidin-4-yl)-6-(7-fluoro-2-methyl-2H-indazol-5-yl)-N-methyl[1,3]thiazolo[4,5-c]pyridin-2-amine |
| 379 | 6-{2-[(1,2-dimethylpiperidin-4-yl)(methyl)amino][1,3]thiazolo[4,5-c]pyridin-6-yl}-2-methylimidazo[1,2-a]pyridine-8-carbonitrile |
| 380[1] | N-(1,2-dimethylpiperidin-4-yl)-6-(8-fluoro-2-methylimidazo[1,2-a]pyridin-6-yl)-N-methyl[1,3]thiazolo[4,5-c]pyridin-2-amine |
| 381 | 2-(6-{[(3S,4S)-4-fluoropyrrolidin-3-yl](methyl)amino}[1,3]thiazolo[4,5-c]pyridazin-3-yl)-5-(1H-pyrazol-4-yl)phenol |
| 382 | 2-(6-{[(3S,4S)-4-fluoro-1-methylpyrrolidin-3-yl](methyl)amino}[1,3]thiazolo[4,5-c]pyridazin-3-yl)-5-(1H-pyrazol-4-yl)phenol |
| 383 | 2-{6-[(1-cyclopropylpiperidin-4-yl)(methyl)amino][1,3]thiazolo[4,5-c]pyridazin-3-yl}-5-(1H-pyrazol-4-yl)phenol |
| 384 | 2-(6-{[1-(2-fluoroethyl)piperidin-4-yl](methyl)amino}[1,3]thiazolo[4,5-c]pyridazin-3-yl)-5-(1H-pyrazol-4-yl)phenol |
| 385 | 5-(3-fluoro-1H-pyrazol-4-yl)-2-[6-(6-methyl-2,6-diazaspiro[3.3]heptan-2-yl)[1,3]thiazolo[4,5-c]pyridazin-3-yl]phenol |
| 386[1] | 2-{6-[(1S,6R)-3,8-diazabicyclo[4.2.0]octan-8-yl][1,3]thiazolo[4,5-c]pyridazin-3-yl}-5-(1H-pyrazol-4-yl)phenol |
| 387 | 5-(3-fluoro-1H-pyrazol-4-yl)-2-[6-[methyl(pyrrolidin-3-yl)amino][1,3]thiazolo[4,5-c]pyridazin-3-yl}phenol |
| 388[1] | 2-{6-[(1S,6R)-3-methyl-3,8-diazabicyclo[4.2.0]octan-8-yl][1,3]thiazolo[4,5-c]pyridazin-3-yl}-5-(1H-pyrazol-4-yl)phenol |
| 389[1] | 2-{6-[(1R,6S)-3,8-diazabicyclo[4.2.0]octan-8-yl][1,3]thiazolo[4,5-c]pyridazin-3-yl}-5-(1H-pyrazol-4-yl)phenol |

| Cpd | Name |
|---|---|
| 390[1] | 2-{6-[(1R,6S)-3-methyl-3,8-diazabicyclo[4.2.0]octan-8-yl][1,3]thiazolo[4,5-c]pyridazin-3-yl}-5-(1H-pyrazol-4-yl)phenol |
| 391 | 5-(3-fluoro-1H-pyrazol-4-yl)-2-{6-[methyl(1-methylpyrrolidin-3-yl)amino][1,3]thiazolo[4,5-c]pyridazin-3-yl}phenol |
| 392 | 5-(3-fluoro-1H-pyrazol-4-yl)-2-[6-(7-methyl-2,7-diazaspiro[3.5]nonan-2-yl)[1,3]thiazolo[4,5-c]pyridazin-3-yl]phenol |
| 393 | 2-{6-[methyl(1-propylpiperidin-4-yl)amino][1,3]thiazolo[4,5-c]pyridazin-3-yl}-5-(1H-pyrazol-4-yl)phenol |
| 394[1] | 2-(6-{methyl[(2S,4S)-2-methylpiperidin-4-yl]amino}[1,3]thiazolo[4,5-c]pyridazin-3-yl)-5-(1H-pyrazol-4-yl)phenol |
| 395[1] | 2-(6-{[(2S,4S)-1,2-dimethylpiperidin-4-yl](methyl)amino}[1,3]thiazolo[4,5-c]pyridazin-3-yl)-5-(1H-pyrazol-4-yl)phenol |
| 396[1] | 2-(6-{methyl[(2R,4S)-2-methylpiperidin-4-yl]amino}[1,3]thiazolo[4,5-c]pyridazin-3-yl)-5-(1H-pyrazol-4-yl)phenol |
| 397[1] | 2-(6-{[(2R,4S)-1,2-dimethylpiperidin-4-yl](methyl)amino}[1,3]thiazolo[4,5-c]pyridazin-3-yl)-5-(1H-pyrazol-4-yl)phenol |
| 398 | 2-{6-[(azepan-4-yl)(methyl)amino][1,3]thiazolo[4,5-c]pyridazin-3-yl}-5-(3-fluoro-1H-pyrazol-4-yl)phenol, and |
| 399 | 2-(6-{[1-(2-hydroxyethyl)piperidin-4-yl](methyl)amino}[1,3]thiazolo[4,5-c]pyridazin-3-yl)-5-(1H-pyrazol-4-yl)phenol; |

| Cpd | Name |
|---|---|
| 4 | 2-(2-methyl-2H-indazol-5-yl)-6-(1,2,3,6-tetrahydropyridin-4-yl)-1,3-benzothiazole hydrochloride |
| 5 | 2-(2-methyl-2H-indazol-5-yl)-6-(piperidin-4-yl)-1,3-benzothiazole hydrochloride |
| 6 | 2-(2-methyl-2H-indazol-5-yl)-6-(1-methyl-1,2,3,6-tetrahydropyridin-4-yl)-1,3-benzothiazole hydrochloride |
| 8 | N-methyl-6-(2-methyl-2H-indazol-5-yl)-N-(piperidin-4-yl)-1,3-benzothiazol-2-amine hydrochloride |
| 10 | 2-(2-methyl-2H-indazol-5-yl)-6-(1-methylpiperidin-4-yl)-1,3-benzothiazole hydrochloride |
| 11 | N-methyl-2-(2-methyl-2H-indazol-5-yl)-N-(piperidin-4-yl)-1,3-benzothiazol-6-amine hydrochloride |
| 12 | N-methyl-6-(2-methyl-2H-indazol-5-yl)-N-(piperidin-4-yl)[1,3]thiazolo[4,5-b]pyridin-2-amine hydrochloride |
| 13 | 6-(2,7-dimethyl-2H-indazol-5-yl)-N-methyl-N-(piperidin-4-yl)[1,3]thiazolo[4,5-b]pyridin-2-amine hydrochloride |
| 14 | 6-(2,7-dimethyl-2H-indazol-5-yl)-N-(piperidin-4-yl)[1,3]thiazolo[4,5-b]pyridin-2-amine hydrochloride |
| 15 | 6-(2-methyl-2H-indazol-5-yl)-N-(piperidin-4-yl)[1,3]thiazolo[4,5-b]pyridin-2-amine hydrochloride |
| 18 | 6-(2,7-dimethyl-2H-indazol-5-yl)-2-(1,2,3,6-tetrahydropyridin-4-yl)-1,3-benzothiazole hydrochloride |
| 19 | 2-(2-methyl-2H-indazol-5-yl)-6-(1,2,3,6-tetrahydropyridin-4-yl)[1,3]thiazolo[4,5-b]pyridine hydrochloride |
| 22 | 6-(2,7-dimethyl-2H-indazol-5-yl)-2-(piperidin-4-yl)-1,3-benzothiazole hydrochloride |
| 25 | N-methyl-5-(2-methyl-2H-indazol-5-yl)-N-(2,2,6,6-tetramethylpiperidin-4-yl)[1,3]thiazolo[5,4-b]pyridin-2-amine hydrochloride |
| 26 | N-methyl-5-(2-methyl-2H-indazol-5-yl)-N-(piperidin-4-yl)[1,3]thiazolo[5,4-b]pyridin-2-amine hydrochloride |
| 27 | N-methyl-6-(2-methyl-2H-indazol-5-yl)-N-(piperidin-4-yl)[1,3]thiazolo[4,5-c]pyridin-2-amine hydrochloride |
| 28 | N,N-dimethyl-1-[6-(2-methyl-2H-indazol-5-yl)-1,3-benzothiazol-2-yl]piperidin-4-amine hydrochloride |
| 29 | 1-[6-(2-methyl-2H-indazol-5-yl)-1,3-benzothiazol-2-yl]piperidin-4-amine hydrochloride |
| 30 | 6-(2,7-dimethyl-2H-indazol-5-yl)-N-methyl-N-(piperidin-4-yl)[1,3]thiazolo[4,5-c]pyridin-2-amine hydrochloride |
| 34 | 6-(1H-indazol-5-yl)-N-methyl-N-(2,2,6,6-tetramethylpiperidin-4-yl)-1,3-benzothiazol-2-amine hydrochloride |
| 35 | 6-(2-methyl-2H-indazol-5-yl)-N-(piperidin-4-yl)-1,3-benzothiazol-2-amine hydrochloride |
| 36 | 5-(2,7-dimethyl-2H-indazol-5-yl)-N-methyl-N-(piperidin-4-yl)[1,3]thiazolo[5,4-b]pyridin-2-amine hydrochloride |
| 38 | N-methyl-6-(2-methyl-2H-indazol-5-yl)-N-(pyrrolidin-3-yl)-1,3-benzothiazol-2-amine hydrochloride |
| 40 | N-methyl-6-(2-methylimidazo[1,2-b]pyridazin-6-yl)-N-(2,2,6,6-tetramethylpiperidin-4-yl)-1,3-benzothiazol-2-amine hydrochloride |
| 41 | 2-(4-fluoropiperidin-4-yl)-6-(2-methyl-2H-indazol-5-yl)-1,3-benzothiazole hydrochloride |
| 42 | 2-(azepan-4-yl)-6-(2-methyl-2H-indazol-5-yl)-1,3-benzothiazole hydrochloride |
| 43 | 2-(2-methyl-2H-indazol-5-yl)-6-(piperidin-4-yl)[1,3]thiazolo[4,5-b]pyridine hydrochloride |
| 44 | 6-[4-fluoro-2-(1,2,3,6-tetrahydropyridin-4-yl)-1,3-benzothiazol-6-yl]-2-methylimidazo[1,2-b]pyridazine hydrochloride |

-continued

| Cpd | Name |
| --- | --- |
| 45 | 6-[4-fluoro-2-(piperidin-4-yl)-1,3-benzothiazol-6-yl]-2-methylimidazo[1,2-b]pyridazine hydrochloride |
| 46 | 6-[4-fluoro-2-(1,2,3,6-tetrahydropyridin-4-yl)-1,3-benzothiazol-6-yl]-2,8-dimethylimidazo[1,2-b]pyridazine hydrochloride |
| 47 | 6-[4-fluoro-2-(piperidin-4-yl)-1,3-benzothiazol-6-yl]-2,8-dimethylimidazo[1,2-b]pyridazine hydrochloride |
| 49 | 2-(2,7-dimethyl-2H-indazol-5-yl)-6-(1,2,3,6-tetrahydropyridin-4-yl)-1,3-benzothiazole hydrochloride |
| 50 | 2-(2,7-dimethyl-2H-indazol-5-yl)-6-(piperidin-4-yl)-1,3-benzothiazole hydrochloride |
| 51 | N-methyl-6-[2-methyl-7-(trifluoromethyl)-2H-indazol-5-yl]-N-(2,2,6,6-tetramethylpiperidin-4-yl)-1,3-benzothiazol-2-amine hydrochloride |
| 53 | 6-[4-fluoro-2-(1,2,3,6-tetrahydropyridin-4-yl)-1,3-benzothiazol-6-yl]-2,8-dimethylimidazo[1,2-a]pyrazine hydrochloride |
| 55 | 6-(1,3-dimethylpyrrolo[1,2-a]pyrazin-7-yl)-N-methyl-N-(2,2,6,6-tetramethylpiperidin-4-yl)-1,3-benzothiazol-2-amine hydrochloride |
| 57 | 6-(7-fluoro-2-methyl-2H-indazol-5-yl)-N-methyl-N-(2,2,6,6-tetramethylpiperidin-4-yl)-1,3-benzothiazol-2-amine hydrochloride |
| 58 | 6-(2-methyl-2H-indazol-5-yl)-2-(2-methylpiperidin-4-yl)-1,3-benzothiazole hydrochloride |
| 59 | 6-(2,7-dimethyl-2H-indazol-5-yl)-2-(piperidin-4-yl)[1,3]thiazolo[4,5-c]pyridine hydrochloride |
| 60 | 6-[2-methyl-7-(trifluoromethyl)-2H-indazol-5-yl]-2-(piperidin-4-yl)[1,3]thiazolo[4,5-c]pyridine hydrochloride |
| 61 | 6-(2,8-dimethylimidazo[1,2-b]pyridazin-6-yl)-2-(piperidin-4-yl)[1,3]thiazolo[4,5-b]pyridine hydrochloride |
| 62 | 2-methyl-5-{2-[methyl(2,2,6,6-tetramethylpiperidin-4-yl)amino]-1,3-benzothiazol-6-yl}-2H-indazole-7-carbonitrile hydrochloride |
| 63 | N-methyl-6-(2-methylimidazo[1,2-a]pyridin-6-yl)-N-(2,2,6,6-tetramethylpiperidin-4-yl)-1,3-benzothiazol-2-amine hydrochloride |
| 65 | 6-(2-methyl-2H-indazol-5-yl)-2-(2-methyl-1,2,3,6-tetrahydropyridin-4-yl)-1,3-benzothiazole hydrochloride |
| 66 | 6-(2,7-dimethyl-2H-indazol-5-yl)-N-methyl-N-(2-methylpiperidin-4-yl)-1,3-benzothiazol-2-amine hydrochloride |
| 67 | 6-(2-methyl-2H-indazol-5-yl)-2-(6-methyl-1,2,3,6-tetrahydropyridin-4-yl)-1,3-benzothiazole hydrochloride |
| 68 | 6-(2,7-dimethyl-2H-indazol-5-yl)-2-[(2,2,6,6-tetramethylpiperidin-4-yl)oxy]-1,3-benzothiazole hydrochloride |
| 70 | 6-[4-fluoro-2-(piperidin-4-yl)-1,3-benzothiazol-6-yl]-2-methyl-1,3-benzoxazole hydrochloride |
| 71 | 6-(2,8-dimethylimidazo[1,2-a]pyridin-6-yl)-4-fluoro-2-(1,2,3,6-tetrahydropyridin-4-yl)-1,3-benzothiazole hydrochloride |
| 72 | 4-fluoro-6-(2-methyl-2H-indazol-5-yl)-2-(1,2,3,6-tetrahydropyridin-4-yl)-1,3-benzothiazole hydrochloride |
| 73 | 4-fluoro-6-(2-methyl-2H-indazol-5-yl)-2-(piperidin-4-yl)-1,3-benzothiazole hydrochloride |
| 74 | 2-methyl-5-[2-(piperidin-4-yl)[1,3]thiazolo[4,5-c]pyridin-6-yl]-2H-indazole-7-carbonitrile hydrochloride |
| 75 | 6-(7-ethyl-2-methyl-2H-indazol-5-yl)-2-(piperidin-4-yl)[1,3]thiazolo[4,5-c]pyridine hydrochloride |
| 76 | 6-(7-fluoro-2-methyl-2H-indazol-5-yl)-2-(piperidin-4-yl)[1,3]thiazolo[4,5-c]pyridine hydrochloride |
| 77 | 6-(2-methylimidazo[1,2-a]pyridin-6-yl)-2-(piperidin-4-yl)[1,3]thiazolo[4,5-c]pyridine hydrochloride |
| 78 | 5-[4-fluoro-2-(piperidin-4-yl)-1,3-benzothiazol-6-yl]-1H-pyrazolo[4,3-b]pyridine hydrochloride |
| 79 | 5-[4-fluoro-2-(piperidin-4-yl)-1,3-benzothiazol-6-yl]-2-methyl-2H-pyrazolo[4,3-b]pyridine hydrochloride |
| 80 | 6-(7-cyclopropyl-2-methyl-2H-indazol-5-yl)-N-methyl-N-(2,2,6,6-tetramethylpiperidin-4-yl)-1,3-benzothiazol-2-amine hydrochloride |
| 81 | N-methyl-6-(2-methyl-2H-indazol-5-yl)-N-(2-methylpiperidin-4-yl)-1,3-benzothiazol-2-amine hydrochloride |
| 84 | 2-methyl-5-[2-(piperidin-4-yl)-1,3-benzothiazol-6-yl]-2H-indazole-7-carbonitrile hydrochloride |
| 93 | 6-(8-ethyl-2-methylimidazo[1,2-a]pyridin-6-yl)-N-methyl-N-(2,2,6,6-tetramethylpiperidin-4-yl)-1,3-benzothiazol-2-amine hydrochloride |
| 94 | 6-(2,4-dimethyl-1H-benzimidazol-6-yl)-2-(piperidin-4-yl)-1,3-benzothiazole hydrochloride |
| 95 | 6-(2-methyl-1H-benzimidazol-6-yl)-2-(piperidin-4-yl)-1,3-benzothiazole dihydrochloride |
| 97 | 2-methyl-6-[2-(piperidin-4-yl)-1,3-benzothiazol-6-yl]imidazo[1,2-b]pyridazine hydrochloride |
| 98 | 6-(2,7-dimethyl-2H-indazol-5-yl)-4-methoxy-2-(1,2,3,6-tetrahydropyridin-4-yl)-1,3-benzothiazole hydrochloride |
| 99 | 6-(2,7-dimethyl-2H-indazol-5-yl)-4-methoxy-2-(piperidin-4-yl)-1,3-benzothiazole hydrochloride |
| 100 | 6-(2,7-dimethyl-2H-indazol-5-yl)-2-(1,2,3,6-tetrahydropyridin-4-yl)-1,3-benzothiazol-4-ol hydrobromide |

-continued

| Cpd | Name |
|---|---|
| 102 | 5-[4-fluoro-2-(1,2,3,6-tetrahydropyridin-4-yl)-1,3-benzothiazol-6-yl]-2-methyl-2H-indazole-7-carbonitrile hydrochloride |
| 103 | 1-{5-[4-fluoro-2-(piperidin-4-yl)-1,3-benzothiazol-6-yl]-2-methyl-2H-indazol-7-yl}methanamine dihydrochloride |
| 104 | 5-[4-fluoro-2-(piperidin-4-yl)-1,3-benzothiazol-6-yl]-2-methyl-2H-indazole-7-carbonitrile hydrochloride |
| 109 | 2-methyl-5-[2-(piperidin-4-yl)[1,3]thiazolo[5,4-d]pyrimidin-5-yl]-2H-indazole-7-carbonitrile hydrochloride |
| 110 | 5-(2,7-dimethyl-2H-indazol-5-yl)-2-(piperidin-4-yl)[1,3]thiazolo[5,4-d]pyrimidine hydrochloride |
| 111 | 6-(8-fluoro-2-methylimidazo[1,2-a]pyridin-6-yl)-N-methyl-N-(2,2,6,6-tetramethylpiperidin-4-yl)-1,3-benzothiazol-2-amine hydrochloride |
| 113 | 6-(8-fluoro-2-methylimidazo[1,2-a]pyridin-6-yl)-2-(piperidin-4-yl)-1,3-benzothiazole hydrochloride |
| 114 | 6-(2,8-dimethylimidazo[1,2-a]pyridin-6-yl)-2-(piperidin-4-yl)-1,3-benzothiazole hydrochloride |
| 115 | 2-(2,2-dimethylpiperidin-4-yl)-6-(2-methyl-2H-indazol-5-yl)-1,3-benzothiazole hydrochloride |
| 119 | 2-{6-[methyl(2,2,6,6-tetramethylpiperidin-4-yl)amino][1,3]thiazolo[4,5-c]pyridazin-3-yl}-5-(1H-pyrazol-4-yl)phenol hydrochloride |
| 130 | 2-{2-[methyl(2,2,6,6-tetramethylpiperidin-4-yl)amino][1,3]thiazolo[4,5-b]pyrazin-6-yl}-5-(1H-pyrazol-4-yl)phenol hydrochloride |
| 132 | 6-[2-(3,5-dimethylpiperazin-1-yl)-4-fluoro-1,3-benzothiazol-6-yl]-2,8-dimethylimidazo[1,2-b]pyridazine hydrochloride |
| 133 | 6-{4-fluoro-2-[(2,2,6,6-tetramethylpiperidin-4-yl)oxy]-1,3-benzothiazol-6-yl}-2,8-dimethylimidazo[1,2-b]pyridazine hydrochloride |
| 135 | 6-{2-[(2,6-dimethylpiperidin-4-yl)oxy]-4-fluoro-1,3-benzothiazol-6-yl}-2,8-dimethylimidazo[1,2-b]pyridazine hydrochloride |
| 137 | 2-{2-[methyl(2,2,6,6-tetramethylpiperidin-4-yl)amino][1,3]thiazolo[4,5-c]pyridin-6-yl}-5-(1H-pyrazol-4-yl)phenol hydrochloride |
| 138 | 2-methyl-6-{2-[methyl(2,2,6,6-tetramethylpiperidin-4-yl)amino]-1,3-benzothiazol-6-yl}imidazo[1,2-a]pyridine-8-carbonitrile hydrochloride |
| 139 | 2,8-dimethyl-6-[2-(piperidin-4-yl)-1,3-benzothiazol-6-yl]imidazo[1,2-b]pyridazine hydrochloride |
| 142 | 2-{2-[methyl(2,2,6,6-tetramethylpiperidin-4-yl)amino][1,3]thiazolo[5,4-d]pyrimidin-5-yl}-5-(1H-pyrazol-4-yl)phenol hydrochloride |
| 144 | 6-{4-fluoro-2-[(2R)-2-methylpiperidin-4-yl]-1,3-benzothiazol-6-yl}-2-methylimidazo[1,2-b]pyridazine hydrochloride |
| 145 | 6-[4-fluoro-2-(1,2,3,6-tetrahydropyridin-4-yl)-1,3-benzothiazol-6-yl]-8-methoxy-2-methylimidazo[1,2-b]pyridazine hydrochloride |
| 146 | 6-(2,7-dimethyl-2H-indazol-5-yl)-N-(2,2-dimethylpiperidin-4-yl)-N-methyl-1,3-benzothiazol-2-amine hydrochloride |
| 149 | 2-{2-[methyl(2,2,6,6-tetramethylpiperidin-4-yl)amino][1,3]thiazolo[5,4-b]pyridin-5-yl}-5-(1H-pyrazol-4-yl)phenol hydrochloride |
| 151 | 6-[4-fluoro-2-(piperidin-4-yl)-1,3-benzothiazol-6-yl]-8-methoxy-2-methylimidazo[1,2-b]pyridazine hydrochloride |
| 152 | 4-fluoro-6-(8-fluoro-2-methylimidazo[1,2-a]pyridin-6-yl)-2-(piperidin-4-yl)-1,3-benzothiazole hydrochloride |
| 153 | 4-chloro-6-(7-fluoro-2-methyl-2H-indazol-5-yl)-2-(1,2,3,6-tetrahydropyridin-4-yl)-1,3-benzothiazole hydrochloride |
| 154 | 5-[4-chloro-2-(1,2,3,6-tetrahydropyridin-4-yl)-1,3-benzothiazol-6-yl]-2-methyl-2H-indazole-7-carbonitrile hydrochloride |
| 155 | N-(2,2-dimethylpiperidin-4-yl)-N-methyl-6-(2-methyl-2H-indazol-5-yl)-1,3-benzothiazol-2-amine hydrochloride |
| 161 | 6-[2,3-difluoro-4-(1H-pyrazol-4-yl)phenyl]-N-methyl-N-(2,2,6,6-tetramethylpiperidin-4-yl)[1,3]thiazolo[4,5-b]pyrazin-2-amine hydrochloride |
| 164 | 4-fluoro-N-methyl-6-(2-methylimidazo[1,2-b]pyridazin-6-yl)-N-[(2S)-2-methylpiperidin-4-yl]-1,3-benzothiazol-2-amine hydrochloride |
| 165 | 6-(2,8-dimethylimidazo[1,2-b]pyridazin-6-yl)-4-fluoro-N-methyl-N-[(2S)-2-methylpiperidin-4-yl]-1,3-benzothiazol-2-amine hydrochloride |
| 166 | 6-[4-fluoro-2-(octahydroindolizin-7-yl)-1,3-benzothiazol-6-yl]-2-methylimidazo[1,2-b]pyridazine hydrochloride |
| 167 | 6-[4-fluoro-2-(piperidin-4-yl)-1,3-benzothiazol-6-yl]-N,2-dimethylimidazo[1,2-b]pyridazin-8-amine hydrochloride |
| 168 | 6-[4-fluoro-2-(piperidin-4-yl)-1,3-benzothiazol-6-yl]-N,N,2-trimethylimidazo[1,2-b]pyridazin-8-amine hydrochloride |
| 172 | 6-(7-cyano-2-methyl-2H-indazol-5-yl)-2-(1,2,3,6-tetrahydropyridin-4-yl)-1,3-benzothiazole-4-carbonitrile hydrochloride |
| 173 | 2-methyl-6-[2-(piperazin-1-yl)[1,3]thiazolo[4,5-b]pyrazin-6-yl]imidazo[1,2-a]pyridine-8-carbonitrile hydrochloride |
| 174 | 6-(8-fluoro-2-methylimidazo[1,2-a]pyridin-6-yl)-2-(piperazin-1-yl)[1,3]thiazolo[4,5-b]pyrazine hydrochloride |
| 175 | 6-(2,7-dimethyl-2H-indazol-5-yl)-N-(2,6-dimethylpiperidin-4-yl)-N-methyl-1,3-benzothiazol-2-amine hydrochloride |
| 176 | N-(2,6-dimethylpiperidin-4-yl)-N-methyl-6-(2-methyl-2H-indazol-5-yl)-1,3-benzothiazol-2-amine hydrochloride |

| Cpd | Name |
|---|---|
| 182 | 6-(2-methylimidazo[1,2-b]pyridazin-6-yl)-2-(piperazin-1-yl)[1,3]thiazolo[4,5-b]pyrazine hydrochloride |
| 185 | 4-fluoro-N-methyl-6-(2-methylimidazo[1,2-b]pyridazin-6-yl)-N-(piperidin-4-yl)-1,3-benzothiazol-2-amine hydrochloride |
| 186 | 6-(2,8-dimethylimidazo[1,2-b]pyridazin-6-yl)-4-fluoro-N-methyl-N-(piperidin-4-yl)-1,3-benzothiazol-2-amine hydrochloride |
| 187 | 8-(benzyloxy)-6-[4-fluoro-2-(piperidin-4-yl)-1,3-benzothiazol-6-yl]-2-methylimidazo[1,2-b]pyridazine hydrochloride |
| 188 | 6-[4-fluoro-2-(piperidin-4-yl)-1,3-benzothiazol-6-yl]-2-methylimidazo[1,2-b]pyridazin-8-amine hydrochloride |
| 189 | 6-[4-fluoro-2-(piperidin-4-yl)-1,3-benzothiazol-6-yl]-2-methylimidazo[1,2-b]pyridazin-8-ol hydrochloride |
| 190 | 2-(2,6-dimethylpiperidin-4-yl)-6-(2-methyl-2H-indazol-5-yl)-1,3-benzothiazole hydrochloride |
| 191 | 4-fluoro-6-(4-fluoro-3-methoxyphenyl)-2-(piperidin-4-yl)-1,3-benzothiazole hydrochloride |
| 192 | N-[(3-exo)-8-azabicyclo[3.2.1]oct-3-yl]-6-(2,8-dimethylimidazo[1,2-b]pyridazin-6-yl)-4-fluoro-N-methyl-1,3-benzothiazol-2-amine hydrochloride |
| 193 | 2-methyl-5-{2-[methyl(piperidin-4-yl)amino][1,3]thiazolo[5,4-d]pyrimidin-5-yl}-2H-indazole-7-carbonitrile hydrochloride |
| 194 | 6-[2-(1-azabicyclo[2.2.2]oct-4-yl)-4-fluoro-1,3-benzothiazol-6-yl]-2,8-dimethylimidazo[1,2-b]pyridazine hydrochloride |
| 195 | 6-[4-fluoro-2-(piperidin-4-yl)-1,3-benzothiazol-6-yl]-2-methyl-8-phenoxylmidazo[1,2-b]pyridazine hydrochloride |
| 196 | 2-methyl-6-{2-[methyl(piperidin-4-yl)amino][1,3]thiazolo[5,4-d]pyrimidin-5-yl}imidazo[1,2-a]pyridine-8-carbonitrile hydrochloride |
| 198 | 2-methyl-6-{2-[methyl(piperidin-4-yl)amino][1,3]thiazolo[4,5-c]pyridin-6-yl}imidazo[1,2-a]pyridine-8-carbonitrile hydrochloride |
| 199 | 6-{2-[(3-exo)-8-azabicyclo[3.2.1]oct-3-ylamino][1,3]thiazolo[4,5-c]pyridin-6-yl}-2-methylimidazo[1,2-a]pyridine-8-carbonitrile hydrochloride |
| 201 | 6-{4-fluoro-2-[methyl(2,2,6,6-tetramethylpiperidin-4-yl)amino]-1,3-benzothiazol-6-yl}-2-methylimidazo[1,2-b]pyridazin-8-amine hydrochloride |
| 202 | 4-fluoro-6-(8-methoxy-2-methylimidazo[1,2-b]pyridazin-6-yl)-N-methyl-N-(piperidin-4-yl)-1,3-benzothiazol-2-amine hydrochloride |
| 203 | 6-{2-[(3-exo)-8-azabicyclo[3.2.1]oct-3-yl(methyl)amino][1,3]thiazolo[4,5-c]pyridin-6-yl}-2-methylimidazo[1,2-a]pyridine-8-carbonitrile hydrochloride |
| 204 | N-[(3-exo)-8-azabicyclo[3.2.1]oct-3-yl]-6-(8-fluoro-2-methylimidazo[1,2-a]pyridin-6-yl)-N-methyl[1,3]thiazolo[4,5-c]pyridin-2-amine hydrochloride |
| 205 | N-[(3-exo)-8-azabicyclo[3.2.1]oct-3-yl]-6-(7-fluoro-2-methyl-2H-indazol-5-yl)-N-methyl[1,3]thiazolo[4,5-c]pyridin-2-amine hydrochloride |
| 206 | 5-{2-[(3-exo)-8-azabicyclo[3.2.1]oct-3-yl(methyl)amino][1,3]thiazolo[4,5-c]pyridin-6-yl}-2-methyl-2H-indazole-7-carbonitrile hydrochloride |
| 207 | 6-{2-[(3-exo)-8-azabicyclo[3.2.1]oct-3-yl(methyl)amino][1,3]thiazolo[5,4-d]pyrimidin-5-yl}-2-methylimidazo[1,2-a]pyridine-8-carbonitrile hydrochloride |
| 208 | 5-{2-[(3-exo)-8-azabicyclo[3.2.1]oct-3-yl(methyl)amino][1,3]thiazolo[5,4-d]pyrimidin-5-yl}-2-methyl-2H-indazole-7-carbonitrile hydrochloride |
| 209 | N-[(3-exo)-8-azabicyclo[3.2.1]oct-3-yl]-4-fluoro-N-methyl-6-(2-methylimidazo[1,2-b]pyridazin-6-yl)-1,3-benzothiazol-2-amine hydrochloride |
| 210 | 6-[4-fluoro-2-(4-methylpiperidin-4-yl)-1,3-benzothiazol-6-yl]-2,8-dimethylimidazo[1,2-b]pyridazine hydrochloride |
| 211 | N-[(3-exo)-8-azabicyclo[3.2.1]oct-3-yl]-6-(7-fluoro-2-methyl-2H-indazol-5-yl)[1,3]thiazolo[4,5-c]pyridin-2-amine hydrochloride |
| 212 | N-[(3-exo)-8-azabicyclo[3.2.1]oct-3-yl]-6-(8-fluoro-2-methylimidazo[1,2-a]pyridin-6-yl)[1,3]thiazolo[4,5-c]pyridin-2-amine hydrochloride |
| 213 | 5-{2-[(3-exo)-8-azabicyclo[3.2.1]oct-3-ylamino][1,3]thiazolo[4,5-c]pyridin-6-yl}-2-methyl-2H-indazole-7-carbonitrile hydrochloride |
| 214 | 2-methyl-5-{2-[methyl(piperidin-4-yl)amino][1,3]thiazolo[4,5-c]pyridin-6-yl}-2H-indazole-7-carbonitrile hydrochloride |
| 215 | 6-(8-fluoro-2-methylimidazo[1,2-a]pyridin-6-yl)-N-methyl-N-(piperidin-4-yl)[1,3]thiazolo[4,5-c]pyridin-2-amine hydrochloride |
| 216 | 6-(7-fluoro-2-methyl-2H-indazol-5-yl)-N-methyl-N-(piperidin-4-yl)[1,3]thiazolo[4,5-c]pyridin-2-amine hydrochloride |
| 217 | N-[(3-exo)-8-azabicyclo[3.2.1]oct-3-yl]-5-(8-fluoro-2-methylimidazo[1,2-a]pyridin-6-yl)-N-methyl[1,3]thiazolo[5,4-d]pyrimidin-2-amine hydrochloride |
| 218 | N-[(3-exo)-8-azabicyclo[3.2.1]oct-3-yl]-5-(7-fluoro-2-methyl-2H-indazol-5-yl)-N-methyl}1,3]thiazolo[5,4-d]pyrimidin-2-amine hydrochloride |
| 219 | 6-}4-fluoro-2-(piperidin-4-yl)-1,3-benzothiazol-6-yl]-2-methylimidazo[1,2-b]pyridazine-8-carboxylic acid hydrochloride |
| 220 | methyl {6-[4-fluoro-2-(piperidin-4-yl)-1,3-benzothiazol-6-yl]-2-methylimidazo[1,2-b]pyridazin-8-yl}acetate hydrochloride |
| 221 | {6-[4-fluoro-2-(piperidin-4-yl)-1,3-benzothiazol-6-yl]-2-methylimidazo[1,2-b]pyridazin-8-yl}acetic acid hydrochloride |
| 223 | 6-{2-[(3-exo)-8-azabicyclo[3.2.1]oct-3-yloxy][1,3]thiazolo[4,5-c]pyridin-6-yl}-2-methylimidazo[1,2-a]pyridine-8-carbonitrile hydrochloride |
| 224 | 6-}4-fluoro-2-(piperidin-4-yl)-1,3-benzothiazol-6-yl]-2-methylimidazo[1,2-b]pyridazine-8-carboxamide trifluoroacetate |

-continued

| Cpd | Name |
|---|---|
| 226 | 6-{4-fluoro-2-[methyl(piperidin-4-yl)amino]-1,3-benzothiazol-6-yl}-2-methylimidazo[1,2-a]pyridine-8-carbonitrile hydrochloride |
| 227 | N-[(8-anti)-3-azabicyclo[3.2.1]oct-8-yl]-5-(8-fluoro-2-methylimidazo[1,2-a]pyridin-6-yl)-N-methyl[1,3]thiazolo[5,4-d]pyrimidin-2-amine hydrochloride |
| 228 | 6-{2-[(8-anti)-3-azabicyclo[3.2.1]oct-8-yl(methyl)amino][1,3]thiazolo[5,4-d]pyrimidin-5-yl}-2-methylimidazo[1,2-a]pyridine-8-carbonitrile hydrochloride |
| 229 | 2-[4-fluoro-2-(piperidin-4-yl)-1,3-benzothiazol-6-yl]-6,8-dimethylimidazo[1,2-a]pyrazine hydrochloride |
| 230 | 6-[4-fluoro-2-(piperidin-4-yl)-1,3-benzothiazol-6-yl]-2-methylimidazo[1,2-b]pyridazine-8-carbonitrile hydrochloride |
| 231 | 6-{4-fluoro-2-[methyl(piperidin-4-yl)amino]-1,3-benzothiazol-6-yl}-2-methylimidazo[1,2-b]pyridazine-8-carbonitrile hydrochloride |
| 232 | 6-(7-fluoro-2-methyl-2H-indazol-5-yl)-N-(2,2,6,6-tetramethylpiperidin-4-yl)[1,3]thiazolo[4,5-c]pyridin-2-amine hydrochloride |
| 235 | 6-{2-[(3-exo)-8-azabicyclo[3.2.1]oct-3-yl(methyl)amino]-4-fluoro-1,3-benzothiazol-6-yl}-2-methylimidazo[1,2-b]pyridazine-8-carbonitrile hydrochloride |
| 236 | 6-{2-[(3-exo)-8-azabicyclo[3.2.1]oct-3-yl(methyl)amino]-4-fluoro-1,3-benzothiazol-6-yl}-2-methylimidazo[1,2-b]pyridazine-8-carboxamide hydrochloride |
| 237 | N-[(3-exo)-8-azabicyclo[3.2.1]oct-3-yl]-4-fluoro-N-methyl-6-(2-methyl-2H-pyrazolo[4,3-b]pyridin-5-yl)-1,3-benzothiazol-2-amine hydrochloride |
| 248 | N-(azetidin-3-yl)-6-(2,8-dimethylimidazo[1,2-b]pyridazin-6-yl)-4-fluoro-N-methyl-1,3-benzothiazol-2-amine hydrochloride |
| 249 | 5-[4-fluoro-2-(piperidin-4-yl)-1,3-benzothiazol-6-yl]-2-methylpyrazolo[1,5-a]pyrimidine hydrochloride |
| 250 | 4-fluoro-N-methyl-6-(2-methylpyrazolo[1,5-a]pyrimidin-5-yl)-N-(piperidin-4-yl)-,3-benzothiazol-2-amine hydrochloride |
| 251 | 6-{2-[9-azabicyclo[3.3.1]non-3-yl(methyl)amino][1,3]thiazolo[4,5-c]pyridin-6-yl}-2-methylimidazo[1,2-a]pyridine-8-carbonitrile hydrochloride |
| 252 | 5-{2-[9-azabicyclo[3.3.1]non-3-yl(methyl)amino][1,3]thiazolo[4,5-c]pyridin-6-yl}-2-methyl-2H-indazole-7-carbonitrile hydrochloride |
| 253 | N-(9-azabicyclo[3.3.1]non-3-yl)-6-(7-fluoro-2-methyl-2H-indazol-5-yl)-N-methyl[1,3]thiazolo[4,5-c]pyridin-2-amine hydrochloride |
| 256 | 6-{2-[(1R,5S)-9-azabicyclo[3.3.1]non-3-yl(methyl)amino][1,3]thiazolo[5,4-d]pyrimidin-5-yl}-2-methylimidazo[1,2-a]pyridine-8-carbonitrile hydrochloride |
| 257 | N-[(1R,5S)-9-azabicyclo[3.3.1]non-3-yl]-5-(8-fluoro-2-methylimidazo[1,2-a]pyridin-6-yl)-N-methyl[1,3]thiazolo[5,4-d]pyrimidin-2-amine hydrochloride |
| 258 | 4-fluoro-N-methyl-6-(2-methylimidazo[1,2-b]pyridazin-6-yl)-N-[(2S,4S)-2-methylpiperidin-4-yl]-1,3-benzothiazol-2-amine hydrochloride |
| 259 | 4-fluoro-N-methyl-6-(2-methylimidazo[1,2-b]pyridazin-6-yl)-N-[(2S,4R)-2-methylpiperidin-4-yl]-1,3-benzothiazol-2-amine hydrochloride |
| 260 | N-(9-azabicyclo[3.3.1]non-3-yl)-N-methyl-6-(2-methylimidazo[1,2-a]pyridin-6-yl)[1,3]thiazolo[4,5-c]pyridin-2-amine hydrochloride |
| 261 | N-(9-azabicyclo[3.3.1]non-3-yl)-6-(2,8-dimethylimidazo[1,2-a]pyridin-6-yl)-N-methyl[1,3]thiazolo[4,5-c]pyridin-2-amine hydrochloride |
| 262 | N-(9-azabicyclo[3.3.1]non-3-yl)-N-methyl-6-(2-methyl-2H-indazol-5-yl)[1,3]thiazolo[4,5-c]pyridin-2-amine hydrochloride |
| 263 | N-(9-azabicyclo[3.3.1]non-3-yl)-6-(2,7-dimethyl-2H-indazol-5-yl)-N-methyl[1,3]thiazolo[4,5-c]pyridin-2-amine hydrochloride |
| 264 | N-(9-azabicyclo[3.3.1]non-3-yl)-6-(7-methoxy-2-methyl-2H-indazol-5-yl)-N-methyl[1,3]thiazolo[4,5-c]pyridin-2-amine hydrochloride |
| 266 | 2-methyl-6-{2-[(1,2,2,6,6-pentamethylpiperidin-4-yl)amino][1,3]thiazolo[4,5-c]pyridin-6-yl}imidazo[1,2-a]pyridine-8-carbonitrile hydrochloride |
| 267 | 6-(8-fluoro-2-methylimidazo[1,2-a]pyridin-6-yl)-N-(1,2,2,6,6-pentamethylpiperidin-4-yl)[1,3]thiazolo[4,5-c]pyridin-2-amine hydrochloride |
| 268 | 2-methyl-5-{2-[(1,2,2,6,6-pentamethylpiperidin-4-yl)amino][1,3]thiazolo[4,5-c]pyridin-6-yl}-2H-indazole-7-carbonitrile hydrochloride |
| 269 | 6-(7-fluoro-2-methyl-2H-indazol-5-yl)-N-(1,2,2,6,6-pentamethylpiperidin-4-yl)[1,3]thiazolo[4,5-c]pyridin-2-amine hydrochloride |
| 274 | 2-{2-[methyl(piperidin-4-yl)amino][1,3]thiazolo[4,5-b]pyrazin-6-yl}-5-(1H-pyrazol-4-yl)phenol hydrochloride |
| 276 | 6-{2-[(3-exo)-8-azabicyclo[3.2.1]oct-3-yl(methyl)amino][1,3]thiazolo[5,4-b]pyridin-5-yl}-2-methylimidazo[1,2-a]pyridine-8-carbonitrile hydrochloride |
| 2H | N-[(3-exo)-8-azabicyclo[3.2.1]oct-3-yl]-5-(8-fluoro-2-methylimidazo[1,2-a]pyridin-6-yl)-N-methyl[1,3]thiazolo[5,4-b]pyridin-2-amine hydrochloride |
| 278 | 5-{2-[(3-exo)-8-azabicyclo[3.2.1]oct-3-yl(methyl)amino][1,3]thiazolo[5,4-b]pyridin-5-yl}-2-methyl-2H-indazole-7-carbonitrile hydrochloride |
| 279 | 6-{2-[(3-exo)-9-azabicyclo[3.3.1]non-3-yl(methyl)amino][1,3]thiazolo[5,4-b]pyridin-5-yl}-2-methylimidazo[1,2-a]pyridine-8-carbonitrile hydrochloride |
| 280 | N-[(3-exo)-9-azabicyclo[3.3.1]non-3-yl]-5-(8-fluoro-2-methylimidazo[1,2-a]pyridin-6-yl)-N-methyl[1,3]thiazolo[5,4-b]pyridin-2-amine hydrochloride |
| 281 | 5-{2-[(3-exo)-9-azabicyclo[3.3.1]non-3-yl(methyl)amino][1,3]thiazolo[5,4-b]pyridin-5-yl}-2-methyl-2H-indazole-7-carbonitrile hydrochloride |
| 282 | 2-{6-[methyl(piperidin-4-yl)amino][1,3]thiazolo[4,5-c]pyridazin-3-yl}-5-(1H-pyrazol-4-yl)phenol hydrochloride |
| 283 | 2-{6-[methyl(1-methylpiperidin-4-yl)amino][1,3]thiazolo[4,5-c]pyridazin-3-yl}-5-(1H-pyrazol-4-yl)phenol hydrochloride |

-continued

| Cpd | Name |
|---|---|
| 286 | N-[(1R,3s,5S)-1,5-dimethyl-8-azabicyclo[3.2.1]octan-3-yl]-6-(8-fluoro-2-methylimidazo[1,2-a]pyridin-6-yl)-N-methyl[1,3]thiazolo[4,5-c]pyridin-2-amine hydrochloride |
| 288 | 6-(2,8-dimethylimidazo[1,2-a]pyridin-6-yl)-N-methyl-N-(piperidin-4-yl)[1,3]thiazolo[4,5-b]pyrazin-2-amine hydrochloride |
| 295 | N-(9-azabicyclo[3.3.1]nonan-3-yl)-5-(7-fluoro-2-methyl-2H-indazol-5-yl)-N-methyl[1,3]thiazolo[5,4-b]pyridin-2-amine hydrochloride |
| 296 | 6-(6,8-dimethylimidazo[1,2-a]pyrazin-2-yl)-N-methyl-N-(2,2,6,6-tetramethylpiperidin-4-yl)[1,3]thiazolo[4,5-c]pyridin-2-amine hydrochloride |
| 297 | 6-(1,3-dimethylpyrrolo[1,2-a]pyrazin-7-yl)-N-methyl-N-(2,2,6,6-tetramethylpiperidin-4-yl)[1,3]thiazolo[4,5-c]pyridin-2-amine hydrochloride |
| 301 | 6-(2-{[(1R,3s,5S)-1,5-dimethyl-8-azabicyclo[3.2.1]octan-3-yl](methyl)amino}[1,3]thiazolo[4,5-c]pyridin-6-yl)-2-methyl-1,3-benzoxazole-4-carbonitrile trifluoroacetate |
| 302 | N-methyl-6-(2-methylimidazo[2,1-b][1,3]thiazol-6-yl)-N-(2,2,6,6-tetramethylpiperidin-4-yl)[1,3]thiazolo[4,5-c]pyridin-2-amine hydrochloride |
| 306 | 6-{4-fluoro-2-[(piperidin-4-yl)oxy]-1,3-benzothiazol-6-yl}-2,8-dimethylimidazo[1,2-b]pyridazine hydrochloride |
| 307 | 4-fluoro-6-(7-fluoro-2-methyl-2H-indazol-5-yl)-2-[(piperidin-4-yl)oxy]-1,3-benzothiazole hydrochloride |
| 308 | N-methyl-6-(2-methylimidazo[2,1-b][1,3,4]thiadiazol-6-yl)-N-(2,2,6,6-tetramethylpiperidin-4-yl)[1,3]thiazolo[4,5-c]pyridin-2-amine hydrochloride |
| 313 | 2-methyl-6-{2-[(piperidin-4-yl)oxy][1,3]thiazolo[4,5-c]pyridin-6-yl}imidazo[1,2-a]pyridine-8-carbonitrile hydrochloride |
| 314 | 6-(8-fluoro-2-methylimidazo[1,2-a]pyridin-6-yl)-2-[(piperidin-4-yl)oxy][1,3]thiazolo[4,5-c]pyridine hydrochloride |
| 315 | 2-methyl-5-{2-[(piperidin-4-yl)oxy][1,3]thiazolo[4,5-c]pyridin-6-yl}-2H-indazole-7-carbonitrile hydrochloride |
| 316 | 6-(7-fluoro-2-methyl-2H-indazol-5-yl)-2-[(piperidin-4-yl)oxy][1,3]thiazolo[4,5-c]pyridine hydrochloride |
| 317 | 6-{4-fluoro-2-[(piperidin-4-yl)oxy]-1,3-benzothiazol-6-yl}-2-methylimidazo[1,2-a]pyridine-8-carbonitrile hydrochloride |
| 318 | 5-{4-fluoro-2-[(piperidin-4-yl)oxy]-1,3-benzothiazol-6-yl}-2-methyl-2H-indazole-7-carbonitrile hydrochloride |
| 319 | 6-(2,8-dimethylimidazo[1,2-a]pyridin-6-yl)-4-fluoro-2-[(piperidin-4-yl)oxy]-1,3-benzothiazole hydrochloride |
| 324 | 6-(2-{[(3R,4R)-3-fluoro-2,2,6,6-tetramethylpiperidin-4-yl](methyl)amino)[1,3]thiazolo[5,4-d]pyrimidin-5-yl)-2-methylimidazo[1,2-a]pyridine-8-carbonitrile dihydrochloride |
| 325 | 6-(2-{[(3R,4R)-3-fluoro-2,2,6,6-tetramethylpiperidin-4-yl](methyl)amino}[1,3]thiazolo[4,5-c]pyridin-6-yl)-2-methylimidazo[1,2-a]pyridine-8-carbonitrile dihydrochloride |
| 326 | N-[(1R,2S,3S,5S)-2-fluoro-1,5-dimethyl-8-azabicyclo[3.2.1]octan-3-yl]-6-(8-fluoro-2-methylimidazo[1,2-a]pyridin-6-yl)-N-methyl[1,3]thiazolo[4,5-c]pyridin-2-amine dihydrochloride |
| 327 | 5-(1H-imidazol-1-yl)-2-{6-[methyl(piperidin-4-yl)amino][1,3]thiazolo[4,5-c]pyridazin-3-yl}phenol formate |
| 328 | 3-[2,5-difluoro-4-(1H-pyrazol-4-yl)phenyl]-N-methyl-N-(piperidin-4-yl)[1,3]thiazolo[4,5-c]pyridazin-6-amine formate |
| 331 | 3-[2,5-difluoro-4-(3-fluoro-1H-pyrazol-4-yl)phenyl]-N-methyl-N-(piperidin-4-yl)[1,3]thiazolo[4,5-c]pyridazin-6-amine formate |
| 334 | 2-[6-(piperazin-1-yl)[1,3]thiazolo[4,5-c]pyridazin-3-yl]-5-(1H-pyrazol-4-yl)phenol formate |
| 335 | 5-(1H-pyrazol-4-yl)-2-[6-(1,2,3,6-tetrahydropyridin-4-yl)[1,3]thiazolo[4,5-c]pyridin-2-yl]phenol hydrochloride |
| 336 | 2-(6-{[(3R,4S)-4-fluoro-1-methylpyrrolidin-3-yl]amino}[1,3]thiazolo[4,5-c]pyridazin-3-yl)-5-(1H-pyrazol-4-yl)phenol formate |
| 337 | 5-(1H-pyrazol-4-yl)-2-[6-(2,2,6,6-tetramethyl-1,2,3,6-tetrahydropyridin-4-yl)[1,3]thiazolo[4,5-c]pyridin-2-yl]phenol hydrochloride |
| 338 | 2-[6-(2,6-diazaspiro[3.5]nonan-2-yl)[1,3]thiazolo[4,5-c]pyridazin-3-yl]-5-(1H-pyrazol-4-yl)phenol dihydrochloride |
| 339 | 2-[6-(7-methyl-1,7-diazaspiro[3.5]nonan-1-yl)[1,3]thiazolo[4,5-c]pyridazin-3-yl]-5-(1H-pyrazol-4-yl)phenol dihydrochloride |
| 340 | 2-[6-(7-methyl-2,7-diazaspiro[4.4]nonan-2-yl)[1,3]thiazolo[4,5-c]pyridazin-3-yl]-5-(1H-pyrazol-4-yl)phenol dihydrochloride |
| 341 | 2-[6-(2,7-diazaspiro[3.5]nonan-2-yl)[1,3]thiazolo[4,5-c]pyridazin-3-yl]-5-(3-fluoro-1H-pyrazol-4-yl)phenol formate |
| 342 | 2-(6-{[(3S,4S)-4-fluoro-1-methylpyrrolidin-3-yl]amino}[1,3]thiazolo[4,5-c]pyridazin-3-yl)-5-(1H-pyrazol-4-yl)phenol formate |
| 344 | 2-{6-[(3aS,7aR)-octahydro-1H-pyrrolo[3,2-c]pyridin-1-yl][1,3]thiazolo[4,5-c]pyridazin-3-yl}-5-(1H-pyrazol-4-yl)phenol dihydrochloride |
| 345 | 2-(6-{methyl[(1s,4s)-4-(methylamino)cyclohexyl]amino}[1,3]thiazolo[4,5-c]pyridazin-3-yl)-5-(1H-pyrazol-4-yl)phenol dihydrochloride |
| 346 | 2-(6-{[(3R,4S)-4-fluoropyrrolidin-3-yl](methyl)amino}[1,3]thiazolo[4,5-c]pyridazin-3-yl)-5-(1H-pyrazol-4-yl)phenol formate |
| 347 | 2-{6-[(3aS,7aR)-5-methyloctahydro-1H-pyrrolo[3,2-c]pyridin-1-yl][1,3]thiazolo[4,5-c]pyridazin-3-yl}-5-(1H-pyrazol-4-yl)phenol dihydrochloride |

-continued

| Cpd | Name |
|---|---|
| 348 | 2-(6-{methyl[(3R)-piperidin-3-yl]amino}[1,3]thiazolo[4,5-c]pyridazin-3-yl)-5-(1H-pyrazol-4-yl)phenol dihydrochloride |
| 349 | 2-(6-{methyl[(3S)-piperidin-3-yl]amino}[1,3]thiazolo[4,5-c]pyridazin-3-yl)-5-(1H-pyrazol-4-yl)phenol dihydrochloride |
| 350 | 2-(6-{methyl[3-(methylamino)cyclobutyl]amino}[1,3]thiazolo[4,5-c]pyridazin-3-yl)-5-(1H-pyrazol-4-yl)phenol ditrifluoroacetate |
| 351 | 2-(6-{[(1r,4r)-4-(dimethylamino)cyclohexyl](methyl)amino}[1,3]thiazolo[4,5-c]pyridazin-3-yl)-5-(1H-pyrazol-4-yl)phenol dihydrochloride |
| 352 | 2-(6-{methyl[(3S)-1-methylpiperidin-3-yl]amino}[1,3]thiazolo[4,5-c]pyridazin-3-yl)-5-(1H-pyrazol-4-yl)phenol dihydrochloride |
| 353 | 2-{6-[(azetidin-3-yl)(methyl)amino][1,3]thiazolo[4,5-c]pyridazin-3-yl}-5-(1H-pyrazol-4-yl)phenol dihydrochloride |
| 354 | 2-[6-(1,7-diazaspiro[3.5]nonan-1-yl)[1,3]thiazolo[4,5-c]pyridazin-3-yl]-5-(1H-pyrazol-4-yl)phenol dihydrochloride |
| 355 | 2-{6-[(3,3-dimethylpiperidin-4-yl)(methyl)amino][1,3]thiazolo[4,5-c]pyridazin-3-yl}-5-(1H-pyrazol-4-yl)phenol dihydrochloride |
| 356 | 2-{6-[(2-azaspiro[3.3]heptan-6-yl)(methyl)amino][1,3]thiazolo[4,5-c]pyridazin-3-yl}-5-(1H-pyrazol-4-yl)phenol dihydrochloride |
| 359 | 5-{2-[(2R,4r,6S)-2,6-dimethylpiperidin-4-yl]-4-fluoro-1,3-benzothiazol-6-yl}-2,7-dimethyl[1,3]oxazolo[5,4-b]pyridine hydrochloride |
| 360 | 2-{6-[methyl(1,3,3-trimethylpiperidin-4-yl)amino][1,3]thiazolo[4,5-c]pyridazin-3-yl}-5-(1H-pyrazol-4-yl)phenol dihydrochloride |
| 361 | 2-(6-{methyl[(1s,3s)-3-(methylamino)cyclobutyl]amino}[1,3]thiazolo[4,5-c]pyridazin-3-yl)-5-(1H-pyrazol-4-yl)phenol dihydrochloride |
| 362 | 2-{6-[(3aR,7aS)-octahydro-1H-pyrrolo[2,3-c]pyridin-1-yl][1,3]thiazolo[4,5-c]pyridazin-3-yl}-5-(1H-pyrazol-4-yl)phenol dihydrochloride |
| 363 | 2-[6-(1,6-diazaspiro[3.5]nonan-1-yl)[1,3]thiazolo[4,5-c]pyridazin-3-yl]-5-(1H-pyrazol-4-yl)phenol dihydrochloride |
| 364 | 2-(6-{[(1s,3s)-3-(dimethylamino)cyclobutyl](methyl)amino}[1,3]thiazolo[4,5-c]pyridazin-3-yl)-5-(1H-pyrazol-4-yl)phenol dihydrochloride |
| 365 | 2-(6-{[(3R,4R)-3-fluoropiperidin-4-yl](methyl)amino}[1,3]thiazolo[4,5-c]pyridazin-3-yl)-5-(1H-pyrazol-4-yl)phenol formate |
| 367 | 5-(1H-pyrazol-4-yl)-2-{6-[(pyrrolidin-3-yl)amino][1,3]thiazolo[4,5-c]pyridazin-3-yl}phenol formate |
| 368 | 2-[6-(2,6-diazaspiro[3.3]heptan-2-yl)[1,3]thiazolo[4,5-c]pyridazin-3-yl]-5-(3-fluoro-1H-pyrazol-4-yl)phenol formate |
| 369 | 2-{6-[(3aR,7aS)-6-methyloctahydro-1H-pyrrolo[2,3-c]pyridin-1-yl][1,3]thiazolo[4,5-c]pyridazin-3-yl}-5-(1H-pyrazol-4-yl)phenol dihydrochloride |
| 370 | 2-[6-(6-methyl-1,6-diazaspiro[3.5]nonan-1-yl)[1,3]thiazolo[4,5-c]pyridazin-3-yl]-5-(1H-pyrazol-4-yl)phenol dihydrochloride |
| 371 | 2-(6-{[(2S,4S)-2-(hydroxymethyl)piperidin-4-yl](methyl)amino}[1,3]thiazolo[4,5-c]pyridazin-3-yl)-5-(1H-pyrazol-4-yl)phenol dihydrochloride |
| 372 | 2-(6-{[(2S,4S)-2-(hydroxymethyl)-1-methylpiperidin-4-yl](methyl)amino}[1,3]thiazolo[4,5-c]pyridazin-3-yl)-5-(1H-pyrazol-4-yl)phenol dihydrochloride |
| 376 | 2-(6-{methyl[(1r,3r)-3-(methylamino)cyclobutyl]amino}[1,3]thiazolo[4,5-c]pyridazin-3-yl)-5-(1H-pyrazol-4-yl)phenol dihydrochloride |
| 380 | N-(1,2-dimethylpiperidin-4-yl)-6-(8-fluoro-2-methylimidazo[1,2-a]pyridin-6-yl)-N-methyl[1,3]thiazolo[4,5-c]pyridin-2-amine trifluoroacetate |
| 386 | 2-{6-[(1S,6R)-3,8-diazabicyclo[4.2.0]octan-8-yl][1,3]thiazolo[4,5-c]pyridazin-3-yl}-5-(1H-pyrazol-4-yl)phenol trifluoroacetate |
| 388 | 2-{6-[(1S,6R)-3-methyl-3,8-diazabicyclo[4.2.0]octan-8-yl][1,3]thiazolo[4,5-c]pyridazin-3-yl}-5-(1H-pyrazol-4-yl)phenol trifluoroacetate |
| 389 | 2-{6-[(1R,6S)-3,8-diazabicyclo[4.2.0]octan-8-yl][1,3]thiazolo[4,5-c]pyridazin-3-yl}-5-(1H-pyrazol-4-yl)phenol trifluoroacetate |
| 390 | 2-{6-[(1R,6S)-3-methyl-3,8-diazabicyclo[4.2.0]octan-8-yl][1,3]thiazolo[4,5-c]pyridazin-3-yl}-5-(1H-pyrazol-4-yl)phenol trifluoroacetate |
| 394 | 2-(6-{methyl[(2S,4S)-2-methylpiperidin-4-yl]amino}[1,3]thiazolo[4,5-c]pyridazin-3-yl)-5-(1H-pyrazol-4-yl)phenol trifluoroacetate |
| 395 | 2-(6-{[(2S,4S)-1,2-dimethylpiperidin-4-yl](methyl)amino}[1,3]thiazolo[4,5-c]pyridazin-3-yl)-5-(1H-pyrazol-4-yl)phenol trifluoroacetate |
| 396 | 2-(6-{methyl[(2R,4S)-2-methylpiperidin-4-yl]amino}[1,3]thiazolo[4,5-c]pyridazin-3-yl)-5-(1H-pyrazol-4-yl)phenol trifluoroacetate, and |
| 397 | 2-(6-{[(2R,4S)-1,2-dimethylpiperidin-4-yl](methyl)amino}[1,3]thiazolo[4,5-c]pyridazin-3-yl)-5-(1H-pyrazol-4-yl)phenol trifluoroacetate; | wherein the form of the compound salt is selected from the group consisting of hydrate, solvate, racemate, enantiomer, diastereomer, stereoisomer, and tautomer form thereof.

An aspect of the present description includes a method for preventing, treating or ameliorating HD in a subject in need thereof comprising, administering to the subject an effective amount of a compound of Formula (I) or Formula (II) or a form thereof.

An aspect of the present description includes a method for treating or ameliorating HD in a subject in need thereof comprising, administering to the subject an effective amount of a compound of Formula (I) or Formula (II) or a form thereof.

Another aspect of the present description includes a method for treating or ameliorating HD in a subject in need thereof comprising, administering to the subject an effective amount of a compound salt of Formula (I) or Formula (II) or a form thereof.

An aspect of the present description includes a method for use of a compound of Formula (I) or Formula (II) or a form or composition thereof for treating or ameliorating HD in a subject in need thereof comprising, administering to the subject an effective amount of the compound of Formula (I) or Formula (II) or a form or composition thereof.

Another aspect of the present description includes a method for use of a compound salt of Formula (I) or Formula (II) or a form or composition thereof for treating or ameliorating HD in a subject in need thereof comprising, administering to the subject an effective amount of the compound salt of Formula (I) or Formula (II) or a form thereof.

An aspect of the present description includes a use for a compound of Formula (I) or Formula (II) or a form thereof for treating or ameliorating HD in a subject in need thereof comprising, administering to the subject an effective amount of the compound of Formula (I) or Formula (II) or a form thereof.

Another aspect of the present description includes a use for a compound salt of Formula (I) or Formula (II) or a form thereof for treating or ameliorating HD in a subject in need thereof comprising, administering to the subject an effective amount of the compound salt of Formula (I) or Formula (II) or a form thereof.

An aspect of the present description includes a use for a compound of Formula (I) or Formula (II) or a form thereof in the manufacture of a medicament for treating or ameliorating HD in a subject in need thereof comprising, administering to the subject an effective amount of the medicament.

Another aspect of the present description includes a use for a compound salt of Formula (I) or Formula (II) or a form thereof in the manufacture of a medicament for treating or ameliorating HD in a subject in need thereof comprising, administering to the subject an effective amount of the medicament.

An aspect of the present description includes a use for a compound of Formula (I) or Formula (II) or a form thereof in a combination product with one or more therapeutic agents for treating or ameliorating HD in a subject in need thereof comprising, administering to the subject an effective amount of the compound of Formula (I) or Formula (II) or a form thereof in combination with an effective amount of the one or more agents.

Another aspect of the present description includes a use for a compound salt of Formula (I) or Formula (II) or a form thereof in a combination product with one or more therapeutic agents for treating or ameliorating HD in a subject in need thereof comprising, administering to the subject an effective amount of the compound salt of Formula (I) or Formula (II) or a form thereof in combination with an effective amount of the one or more agents.

Chemical Definitions

The chemical terms used above and throughout the description herein, unless specifically defined otherwise, shall be understood by one of ordinary skill in the art to have the following indicated meanings.

As used herein, the term "$C_{1-6}$alkyl" generally refers to saturated hydrocarbon radicals having from one to eight carbon atoms in a straight or branched chain configuration, including, but not limited to, methyl, ethyl, n-propyl (also referred to as propyl or propanyl), isopropyl, n-butyl (also referred to as butyl or butanyl), isobutyl, sec-butyl, tert-butyl, n-pentyl (also referred to as pentyl or pentanyl), n-hexyl (also referred to as hexyl or hexanyl), and the like. In certain aspects, $C_{1-6}$alkyl includes, but is not limited to, $C_{1-4}$alkyl, $C_{1-2}$alkyl and the like. A $C_{1-6}$alkyl radical is optionally substituted with substituent species as described herein where allowed by available valences.

As used herein, the term "$C_{2-8}$alkenyl" generally refers to partially unsaturated hydrocarbon radicals having from two to eight carbon atoms in a straight or branched chain configuration and one or more carbon-carbon double bonds therein, including, but not limited to, ethenyl (also referred to as vinyl), allyl, propenyl and the like. In certain aspects, $C_{2-8}$alkenyl includes, but is not limited to, $C_{2-6}$alkenyl, $C_{2-4}$alkenyl and the like. A $C_{2-8}$alkenyl radical is optionally substituted with substituent species as described herein where allowed by available valences.

As used herein, the term "$C_{2-8}$alkynyl" generally refers to partially unsaturated hydrocarbon radicals having from two to eight carbon atoms in a straight or branched chain configuration and one or more carbon-carbon triple bonds therein, including, but not limited to, ethynyl, propynyl, butynyl and the like. In certain aspects, $C_{2-8}$alkynyl includes, but is not limited to, $C_{2-6}$alkynyl, $C_{2-4}$alkynyl and the like. A $C_{2-8}$alkynyl radical is optionally substituted with substituent species as described herein where allowed by available valences.

As used herein, the term "$C_{1-6}$alkoxy" generally refers to saturated hydrocarbon radicals having from one to eight carbon atoms in a straight or branched chain configuration of the formula: —O—$C_{1-68}$alkyl, including, but not limited to, methoxy, ethoxy, n-propoxy, isopropoxy, n-butoxy, isobutoxy, sec-butoxy, tert-butoxy, n-pentoxy, n-hexoxy and the like. In certain aspects, $C_{1-6}$alkoxy includes, but is not limited to, $C_{1-4}$alkoxy, $C_{1-2}$alkoxy and the like. A $C_{1-6}$alkoxy radical is optionally substituted with substituent species as described herein where allowed by available valences.

As used herein, the term "$C_{3-10}$cycloalkyl" generally refers to a saturated or partially unsaturated monocyclic, bicyclic or polycyclic hydrocarbon radical, including, but not limited to, cyclopropyl, cyclobutyl, cyclopentyl, cyclohexyl, cyclohexenyl, cycloheptyl, cyclooctyl, 1H-indanyl, indenyl, tetrahydro-naphthalenyl and the like. In certain aspects, $C_{3-10}$cycloalkyl includes, but is not limited to, $C_{3-8}$cycloalkyl, $C_{5-8}$cycloalkyl, and the like. A $C_{3-10}$cycloalkyl radical is optionally substituted with substituent species as described herein where allowed by available valences.

As used herein, the term "aryl" generally refers to a monocyclic, bicyclic or polycyclic aromatic carbon atom ring structure radical, including, but not limited to, phenyl, naphthyl, anthracenyl, fluorenyl, azulenyl, phenanthrenyl and the like. An aryl radical is optionally substituted with substituent species as described herein where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including, but not limited to, furanyl, thienyl, pyrrolyl, pyrazolyl, imidazolyl, isoxazolyl, isothiazolyl, oxazolyl, 1,3-thiazolyl, triazolyl, oxadiazolyl, thiadiazolyl, tetrazolyl, pyridinyl, pyrimidinyl, pyrazinyl, pyridazinyl, triazinyl, indolyl, indazolyl, indolizinyl, isoindolyl, benzofuranyl, benzothienyl, benzoimidazolyl, 1,3-benzothiazolyl, 1,3-benzoxazolyl, purinyl, quinolinyl, isoquinolinyl, quinazolinyl, quinoxalinyl, 1,3-diazinyl, 1,2-diazinyl, 1,2-diazolyl, 1,4-diazanaphthalenyl, acridinyl, furo[3,2-b]pyridinyl, furo[3,2-c]pyridinyl, furo[2,3-c]pyridinyl, 6H-thieno[2,3-b]pyrrolyl, thieno[3,2-c]pyridinyl, thieno[2,3-d]pyrimidinyl, 1H-pyrrolo[2,3-b]pyridinyl, 1H-pyrrolo[2,3-c]pyridinyl, 1H-pyrrolo[3,2-b]pyridinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, 3H-imidazo[4,5-b]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,2,4]triazolo[1,5-a]pyridinyl, [1,2,4]triazolo[4,3-a]pyridinyl and the like. A heteroaryl radical is optionally substituted on a carbon or nitrogen atom ring member with substituent species as described herein where allowed by available valences.

In certain aspects, the nomenclature for a heteroaryl radical may differ, such as in non-limiting examples where furanyl may also be referred to as furyl, thienyl may also be referred to as thiophenyl, pyridinyl may also be referred to as pyridyl, benzothienyl may also be referred to as benzothiophenyl and 1,3-benzoxazolyl may also be referred to as 1,3-benzooxazolyl.

In certain other aspects, the term for a heteroaryl radical may also include other regioisomers, such as in non-limiting examples where the term pyrrolyl may also include 2H-pyrrolyl, 3H-pyrrolyl and the like, the term pyrazolyl may also include 1H-pyrazolyl and the like, the term imidazolyl may also include 1H-imidazolyl and the like, the term triazolyl may also include 1H-1,2,3-triazolyl and the like, the term oxadiazolyl may also include 1,2,4-oxadiazolyl, 1,3,4-oxadiazolyl and the like, the term tetrazolyl may also include 1H-tetrazolyl, 2H-tetrazolyl and the like, the term indolyl may also include 1H-indolyl and the like, the term indazolyl may also include 1H-indazolyl, 2H-indazolyl and the like, the term benzoimidazolyl may also include 1H-benzoimidazolyl and the term purinyl may also include 9H-purinyl and the like.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, but not limited to, oxiranyl, oxetanyl, azetidinyl, tetrahydrofuranyl, pyrrolinyl, pyrrolidinyl, pyrazolinyl, pyrazolidinyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, pyranyl, dihydro-2H-pyranyl, thiopyranyl, 1,3-dioxanyl, 1,2,5,6-tetrahydropyridinyl, 1,2,3,6-tetrahydropyridinyl, piperidinyl, piperazinyl, morpholinyl, thiomorpholinyl, 1,4-diazepanyl, 1,3-benzodioxolyl, 1,4-benzodioxanyl, 2,3-dihydro-1,4-benzodioxinyl, hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, (3aR,6aR)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, (3aR,6aR)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4R,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(1H)-yl, (7R,8aS)-hexahydropyrrolo[1,2-c]pyrazin-(1H)-yl, (8aS)-hexahydropyrrolo[1,2-c]pyrazin-(1H)-yl, (8aR)-hexahydropyrrolo[1,2-c]pyrazin-(1H)-yl, (8aS)-octahydropyrrolo[1,2-c]pyrazin-(1H)-yl, (8aR)-octahydropyrrolo[1,2-c]pyrazin-(1H)-yl, hexahydropyrrolo[1,2-a]pyrazin-(2H)-one, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,7-diazaspiro[3.5]nonyl, 5,8-diazaspiro[3.5]nonyl, 2,7-diazaspiro[4.4]nonyl, 6,9-diazaspiro[4.5]decyl and the like. A heterocyclyl radical is optionally substituted on a carbon or nitrogen atom ring member with substituent species as described herein where allowed by available valences.

In certain aspects, the nomenclature for a heterocyclyl radical may differ, such as in non-limiting examples where 1,3-benzodioxolyl may also be referred to as benzo[d][1,3]dioxolyl and 2,3-dihydro-1,4-benzodioxinyl may also be referred to as 2,3-dihydrobenzo[b][1,4]dioxinyl.

As used herein, the term "$C_{1-6}$alkoxy-$C_{1-6}$alkyl" refers to a radical of the formula: —$C_{1-6}$alkyl-O—$C_{1-6}$alkyl.

As used herein, the term "$C_{1-6}$alkoxy-carbonyl" refers to a radical of the formula: —C(O)—O—$C_{1-6}$alkyl.

As used herein, the term "$C_{1-6}$alkoxy-carbonyl-$C_{1-6}$alkyl" refers to a radical of the formula: —$C_{1-6}$alkyl-C(O)—O—$C_{1-6}$alkyl.

As used herein, the term "$C_{1-6}$alkoxy-carbonyl-amino" refers to a radical of the formula: —NH—C(O)—O—$C_{1-6}$alkyl.

As used herein, the term "$C_{1-6}$alkyl-amino" refers to a radical of the formula: —NH—$C_{1-6}$alkyl.

As used herein, the term "($C_{1-6}$alkyl)$_2$-amino" refers to a radical of the formula: —N($C_{1-6}$alkyl)$_2$.

As used herein, the term "$C_{1-6}$alkyl-carbonyl" refers to a radical of the formula: —C(O)—$C_{1-6}$alkyl.

As used herein, the term "$C_{1-6}$alkyl-carbonyl-amino" refers to a radical of the formula: —NH—C(O)—$C_{1-6}$alkyl.

As used herein, the term "amino-$C_{1-6}$alkyl" refers to a radical of the formula: —$C_{1-6}$alkyl-NH$_2$.

As used herein, the term "amino-carbonyl" refers to a radical of the formula: —C(O)—NH$_2$.

As used herein, the term "aryl-$C_{1-6}$alkoxy" refers to a radical of the formula: —O—$C_{1-6}$alkyl-aryl.

As used herein, the term "aryl-oxy" refers to a radical of the formula: —O-aryl.

As used herein, the term "aryl-$C_{1-6}$alkyl" refers to a radical of the formula: —$C_{1-6}$alkyl-aryl. As used herein, the term "benzoxy-carbonyl" refers to a radical of the formula: —C(O)—O—CH$_2$-phenyl.

As used herein, the term "halo" or "halogen" generally refers to a halogen atom radical, including fluoro, chloro, bromo and iodo.

As used herein, the term "halo-$C_{1-6}$alkoxy" refers to a radical of the formula: —O—$C_{1-6}$alkyl-halo, wherein $C_{1-6}$alkyl is partially or completely substituted with one or more halogen atoms where allowed by available valences.

As used herein, the term "halo-$C_{1-6}$alkyl" refers to a radical of the formula: —$C_{1-6}$alkyl-halo, wherein $C_{1-6}$alkyl is partially or completely substituted with one or more halogen atoms where allowed by available valences.

As used herein, the term "carboxyl" refers to a radical of the formula: —COOH, —C(O)OH or —CO$_2$H.

As used herein, the term "$C_{1-6}$alkyl-carboxyl" refers to a radical of the formula: —$C_{1-6}$alkyl-COOH, —$C_{1-6}$alkyl-C(O)OH or —$C_{1-6}$alkyl-CO$_2$H.

As used herein, the term "hydroxy" refers to a radical of the formula: —OH.

As used herein, the term "hydroxy-$C_{1-6}$alkoxy-$C_{1-6}$alkyl" refers to a radical of the formula: —$C_{1-6}$alkyl-O—$C_{1-6}$alkyl-OH.

As used herein, the term "hydroxy-$C_{1-6}$alkyl" refers to a radical of the formula: —$C_{1-6}$alkyl-OH, wherein $C_{1-6}$alkyl is partially or completely substituted with one or more hydroxy radicals where allowed by available valences.

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. A person of ordinary skill in the art should note that any carbon as well as heteroatom with valences that appear to be unsatisfied as described or shown herein is assumed to have a sufficient number of hydrogen atom(s) to satisfy the valences described or shown. In certain instances, one or more substituents having a double bond (e.g., "oxo" or "=O") as the point of attachment may be described, shown or listed herein within a substituent group, wherein the structure may only show a single bond as the point of attachment to the core structure of Formula (I) or Formula (II). A person of ordinary skill in the art would understand that, while only a single bond is shown, a double bond is intended for those substituents.

As used herein, the term "and the like," with reference to the definitions of chemical terms provided herein, means that variations in chemical structures that could be expected by one skilled in the art include, without limitation, isomers (including chain, branching or positional structural isomers), hydration of ring systems (including saturation or partial unsaturation of monocyclic, bicyclic or polycyclic ring structures) and all other variations where allowed by available valences which result in a stable compound.

For the purposes of this description, where one or more substituent variables for a compound of Formula (I) or Formula (II) or a form thereof encompass functionalities incorporated into a compound of Formula (I) or Formula (II), each functionality appearing at any location within the disclosed compound may be independently selected, and as appropriate, independently and/or optionally substituted.

As used herein, the terms "independently selected," or "each selected" refer to functional variables in a substituent list that may occur more than once on the structure of Formula (I) or Formula (II), the pattern of substitution at each occurrence is independent of the pattern at any other occurrence. Further, the use of a generic substituent variable on any formula or structure for a compound described herein is understood to include the replacement of the generic substituent with species substituents that are included within the particular genus, e.g., aryl may be replaced with phenyl or naphthalenyl and the like, and that the resulting compound is to be included within the scope of the compounds described herein.

As used herein, the terms "each instance of" or "in each instance, when present," when used preceding a phrase such as " . . . $C_{3-10}$cycloalkyl, $C_{3-10}$cycloalkyl-$C_{1-4}$alkyl, aryl, aryl-$C_{1-4}$alkyl, heteroaryl, heteroaryl-$C_{1-4}$alkyl, heterocyclyl and heterocyclyl-$C_{1-4}$alkyl," are intended to refer to the $C_{3-10}$cycloalkyl, aryl, heteroaryl and heterocyclyl ring systems when each are present either alone or as a substituent.

As used herein, the term "optionally substituted" means optional substitution with the specified substituent variables, groups, radicals or moieties.

Compound Forms

As used herein, the term "form" means a compound of Formula (I) or Formula (II) having a form selected from the group consisting of a free acid, free base, prodrug, salt, hydrate, solvate, clathrate, isotopologue, racemate, enantiomer, diastereomer, stereoisomer, polymorph and tautomer form thereof.

In certain aspects described herein, the form of the compound of Formula (I) or Formula (II) is a free acid, free base or salt thereof.

In certain aspects described herein, the form of the compound of Formula (I) or Formula (II) is a salt thereof.

In certain aspects described herein, the form of the compound of Formula (I) or Formula (II) is an isotopologue thereof.

In certain aspects described herein, the form of the compound of Formula (I) or Formula (II) is a stereoisomer, racemate, enantiomer or diastereomer thereof.

In certain aspects described herein, the form of the compound of Formula (I) or Formula (II) is a tautomer thereof.

In certain aspects described herein, the form of the compound of Formula (I) or Formula (II) is a pharmaceutically acceptable form.

In certain aspects described herein, the compound of Formula (I) or Formula (II) or a form thereof is isolated for use.

As used herein, the term "isolated" means the physical state of a compound of Formula (I) or Formula (II) or a form thereof after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterized by standard analytical techniques described herein or well known to the skilled artisan.

As used herein, the term "protected" means that a functional group in a compound of Formula (I) or Formula (II) or a form thereof is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, methoxymethanol, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters. In certain instances, the protecting group may also be a polymer resin, such as a Wang resin or a 2-chlorotrityl-chloride resin. Protecting groups may be added or removed in accordance with standard techniques, which are well-known to those skilled in the art and as described herein. It will also be appreciated by those skilled in the art, although such protected derivatives of compounds described herein may not possess pharmacological activity as such, they may be administered to a subject and thereafter metabolized in the body to form compounds described herein which are pharmacologically active. Such derivatives may therefore be described as "prodrugs". All prodrugs of compounds described herein are included within the scope of the use described herein.

As used herein, the term "prodrug" means a form of an instant compound (e.g., a drug precursor) that is transformed in vivo to yield an active compound of Formula (I) or Formula (II) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In one example, when a compound of Formula (I) or Formula (II) or a form thereof contains a carboxylic acid functional group, a prodrug can comprise an ester formed by the replacement of the hydrogen atom of the acid group with a functional group such as alkyl and the like. In another example, when a compound of Formula (I) or Formula (II) or a form thereof contains a hydroxyl functional group, a prodrug form can be prepared by replacing the hydrogen atom of the hydroxyl with another functional group such as alkyl, alkylcarbonyl or a phosphonate ester and the like. In another example, when a compound of Formula (I) or Formula (II) or a form thereof contains an amine functional group, a prodrug form can be prepared by replacing one or more amine hydrogen atoms with a functional group such as alkyl or substituted carbonyl. Pharmaceutically acceptable prodrugs of compounds of Formula (I) or Formula (II) or a form thereof include those compounds substituted with one or more of the following groups: carboxylic acid esters, sulfonate esters, amino acid esters, phosphonate esters and mono-, di- or triphosphate esters or alkyl substituents, where appropriate. As described herein, it is understood by a person of ordinary skill in the art that one or more of such substituents may be used to provide a compound of Formula (I) or Formula (II) or a form thereof as a prodrug.

One or more compounds described herein may exist in unsolvated as well as solvated forms with pharmaceutically acceptable solvents such as water, ethanol, and the like, and the description herein is intended to embrace both solvated and unsolvated forms.

As used herein, the term "solvate" means a physical association of a compound described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

As used herein, the term "hydrate" means a solvate wherein the solvent molecule is water.

The compounds of Formula (I) or Formula (II) can form salts, which are intended to be included within the scope of this description. Reference to a compound of Formula (I) or Formula (II) or a form thereof herein is understood to include reference to salt forms thereof, unless otherwise indicated. The term "salt(s)", as employed herein, denotes acidic salts formed with inorganic and/or organic acids, as well as basic salts formed with inorganic and/or organic bases. In addition, when a compound of Formula (I) or Formula (II) or a form thereof contains both a basic moiety, such as, without limitation an amine moiety, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds described herein that are safe and effective (i.e., non-toxic, physiologically acceptable) for use in mammals and that possess biological activity, although other salts are also useful. Salts of the compounds of the Formula (I) or Formula (II) may be formed, for example, by reacting a compound of Formula (I) or Formula (II) or a form thereof with an amount of acid or base, such as an equivalent amount, in a medium such as one in which the salt precipitates or in an aqueous medium followed by lyophilization.

Pharmaceutically acceptable salts include one or more salts of acidic or basic groups present in compounds described herein. Particular aspects of acid addition salts include, and are not limited to, acetate, ascorbate, benzoate, benzenesulfonate, bisulfate, bitartrate, borate, bromide, butyrate, chloride, citrate, camphorate, camphorsulfonate, ethanesulfonate, formate, fumarate, gentisinate, gluconate, glucaronate, glutamate, iodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate salts and the like. Certain particular aspects of acid addition salts include chloride or dichloride.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66 (1) 1-19; P. Gould, *International J. of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Suitable basic salts include, but are not limited to, aluminum, ammonium, calcium, lithium, magnesium, potassium, sodium and zinc salts.

All such acid salts and base salts are intended to be included within the scope of pharmaceutically acceptable salts as described herein. In addition, all such acid and base salts are considered equivalent to the free forms of the corresponding compounds for purposes of this description.

Compounds of Formula (I) or Formula (II) and forms thereof, may further exist in a tautomeric form. All such tautomeric forms are contemplated and intended to be included within the scope of the compounds of Formula (I) or Formula (II) or a form thereof as described herein.

The compounds of Formula (I) or Formula (II) or a form thereof may contain asymmetric or chiral centers, and, therefore, exist in different stereoisomeric forms. The present description is intended to include all stereoisomeric forms of the compounds of Formula (I) or Formula (II) as well as mixtures thereof, including racemic mixtures.

The compounds described herein may include one or more chiral centers, and as such may exist as racemic mixtures (R/S) or as substantially pure enantiomers and diastereomers. The compounds may also exist as substantially pure (R) or (S) enantiomers (when one chiral center is present). In one particular aspect, the compounds described herein are (S) isomers and may exist as enantiomerically pure compositions substantially comprising only the (S) isomer. In another particular aspect, the compounds described herein are (R) isomers and may exist as enantiomerically pure compositions substantially comprising only the (R) isomer. As one of skill in the art will recognize, when more than one chiral center is present, the compounds described herein may also exist as a (R,R), (R,S), (S,R) or (S,S) isomer, as defined by IUPAC Nomenclature Recommendations.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the description, a compound of Formula (I) or Formula (II) or a form thereof is a substantially pure (S) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the description, a compound of Formula (I) or Formula (II) or a form thereof is a substantially pure (R) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, or about 80/20.

In addition, the present description embraces all geometric and positional isomers. For example, if a compound of Formula (I) or Formula (II) or a form thereof incorporates a double bond or a fused ring, both the cis- and trans-forms, as well as mixtures, are embraced within the scope of the description. Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art. Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) or Formula (II) may be atropisomers (e.g., substituted biaryls) and are considered as part of this description.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this description, as are positional isomers (such as, for example, 4-pyridyl and 3-pyridyl). Individual stereoisomers of the compounds described herein may, for example, be substantially free of other isomers, or may be present in a racemic mixture, as described supra.

The use of the terms "salt", "solvate", "ester", "prodrug" and the like, is intended to equally apply to the salt, solvate, ester and prodrug of enantiomers, stereoisomers, rotamers, tautomers, positional isomers, racemates or isotopologues of the instant compounds.

The term "isotopologue" refers to isotopically-enriched compounds described herein which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, $^{35}Cl$ and $^{36}Cl$, respectively, each of which are also within the scope of this description.

Certain isotopically-enriched compounds described herein (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances.

Polymorphic crystalline and amorphous forms of the compounds of Formula (I) or Formula (II) and of the salts, solvates, hydrates, esters and prodrugs of the compounds of Formula (I) or Formula (II) are further intended to be included in the present description.

Compound Uses

In accordance with the intended scope of the present description, aspects of the present description include compounds that have been identified and have been demonstrated to be useful in selectively preventing, treating or ameliorating HD and have been provided for use for preventing, treating or ameliorating HD.

An aspect of the present description includes a method for preventing, treating or ameliorating HD in a subject in need thereof comprising, administering to the subject an effective amount of a compound of Formula (I) or Formula (II) or a form thereof.

An aspect of the present description includes a method for treating or ameliorating HD in a subject in need thereof comprising, administering to the subject an effective amount of a compound of Formula (I) or Formula (II) or a form thereof.

An aspect of the present description includes a method for preventing HD in a subject in need thereof comprising, administering to the subject an effective amount of a compound of Formula (I) or Formula (II) or a form thereof.

An aspect of the present description includes a method for treating HD in a subject in need thereof comprising, administering to the subject an effective amount of a compound of Formula (I) or Formula (II) or a form thereof.

An aspect of the present description includes a method for ameliorating HD in a subject in need thereof comprising, administering to the subject an effective amount of a compound of Formula (I) or Formula (II) or a form thereof.

Another aspect of the present description includes a method for treating or ameliorating HD in a subject in need thereof comprising, administering to the subject an effective amount of a compound salt of Formula (I) or Formula (II) or a form thereof.

An aspect of the present description includes a method for use of a compound of Formula (I) or Formula (II) or a form or composition thereof for treating or ameliorating HD in a subject in need thereof comprising, administering to the subject an effective amount of the compound of Formula (I) or Formula (II) or a form or composition thereof.

Another aspect of the present description includes a method for use of a compound salt of Formula (I) or Formula (II) or a form or composition thereof for treating or ameliorating HD in a subject in need thereof comprising, administering to the subject an effective amount of the compound salt of Formula (I) or Formula (II) or a form thereof.

An aspect of the present description includes a use for a compound of Formula (I) or Formula (II) or a form thereof for treating or ameliorating HD in a subject in need thereof comprising, administering to the subject an effective amount of the compound of Formula (I) or Formula (II) or a form thereof.

Another aspect of the present description includes a use for a compound salt of Formula (I) or Formula (II) or a form thereof for treating or ameliorating HD in a subject in need thereof comprising, administering to the subject an effective amount of the compound salt of Formula (I) or Formula (II) or a form thereof.

An aspect of the present description includes a use for a compound of Formula (I) or Formula (II) or a form thereof in the manufacture of a medicament for treating or ameliorating HD in a subject in need thereof comprising, administering to the subject an effective amount of the medicament.

Another aspect of the present description includes a use for a compound salt of Formula (I) or Formula (II) or a form thereof in the manufacture of a medicament for treating or ameliorating HD in a subject in need thereof comprising, administering to the subject an effective amount of the medicament.

An aspect of the present description includes in vitro or in vivo use of the compound of Formula (I) or Formula (II) or a form thereof having activity toward HD.

An aspect of the present description includes a use of the compound of Formula (I) or Formula (II) or a form thereof in a combination therapy to provide additive or synergistic activity, thus enabling the development of a combination product for treating or ameliorating HD.

Another aspect of the present description includes a combination therapy comprising compounds described herein in combination with one or more known drugs or one or more known therapies may be used to treat HD regardless of whether HD is responsive to the known drug.

An aspect of the present description includes a use for a compound of Formula (I) or Formula (II) or a form thereof in a combination product with one or more therapeutic agents for treating or ameliorating HD in a subject in need thereof comprising, administering to the subject an effective amount of the compound of Formula (I) or Formula (II) or a form thereof in combination with an effective amount of the one or more agents.

Another aspect of the present description includes a use for a compound salt of Formula (I) or Formula (II) or a form thereof in a combination product with one or more therapeutic agents for treating or ameliorating HD in a subject in need thereof comprising, administering to the subject an effective amount of the compound salt of Formula (I) or Formula (II) or a form thereof in combination with an effective amount of the one or more agents.

In an aspect of a use or method provided herein, compounds of Formula (I) or Formula (II) or a form thereof used in combination with one or more additional agents can be administered to a subject or contacted with a subject or patient cell(s) prior to, concurrently with, or subsequent to administering to the subject or patient or contacting the cell with an additional agent(s). A compound(s) of Formula (I) or Formula (II) or a form thereof and an additional agent(s) can be administered to a subject or contacted with a cell in single composition or different compositions. In a specific aspect, a compound(s) of Formula (I) or Formula (II) or a form thereof is used in combination with gene therapy to inhibit HTT expression (using, e.g., viral delivery vectors) or the administration of another small molecule HTT inhibitor. In another specific aspect, a compound(s) of Formula (I) or Formula (II) or a form thereof are used in combination with cell replacement using differentiated non-mutant HTT stem cells. In another specific aspect, a compound(s) of Formula (I) or Formula (II) or a form thereof are used in combination with cell replacement using differentiated HTT stem cells.

In one aspect, provided herein is the use of compounds of Formula (I) or Formula (II) or a form thereof in combination with supportive standard of care therapies, including palliative care.

An aspect of the present description includes a use for a compound of Formula (I) or Formula (II) or a form thereof in the preparation of a kit for treating or ameliorating HD in a subject in need thereof comprising, the compound of Formula (I) or Formula (II) or a form thereof and instructions for administering an effective amount of the compound of Formula (I) or Formula (II) or a form thereof.

An aspect of the present description includes a use for a compound of Formula (I) or Formula (II) or a form thereof in the preparation of a kit for treating or ameliorating HD in a subject in need thereof comprising, the compound of Formula (I) or Formula (II) or a form thereof and instructions for administering an effective amount of the compound of Formula (I) or Formula (II) or a form thereof; and optionally, for administering to the subject an effective amount of the compound of Formula (I) or Formula (II) or a form thereof in a combination product with an effective amount of one or more therapeutic agents.

An aspect of the present description includes a use for a compound of Formula (I) or Formula (II) or a form thereof in the preparation of a kit for treating or ameliorating HD in a subject in need thereof comprising, the compound of Formula (I) or Formula (II) or a form thereof and instructions for administering an effective amount of the compound of Formula (I) or Formula (II) or a form thereof; and optionally, for administering to the subject an effective amount of the compound of Formula (I) or Formula (II) or a form thereof in a combination product with an effective amount of the one or more therapeutic agents; and optionally, for administering to the subject an effective amount of the compound of Formula (I) or Formula (II) or a form thereof in a combination product with an effective amount of the one or more therapeutic agents in a combination therapy with a standard of care supportive therapy, wherein the standard of care supportive therapy is palliative care.

In one respect, for each of such aspects, the subject is treatment naive. In another respect, for each of such aspects, the subject is not treatment naive.

As used herein, the term "preventing" refers to keeping a disease, disorder or condition from occurring in a subject that may be predisposed to the disease, disorder and/or condition but has not yet been diagnosed as having the disease, disorder and/or condition.

As used herein, the term "treating" refers to inhibiting the progression of a disease, disorder or condition in a subject already exhibiting the symptoms of the disease, disorder and/or condition, i.e., arresting the development of a disease, disorder and/or condition that has already affected the subject.

As used herein, the term "ameliorating" refers to relieving the symptoms of a disease, disorder or condition in a subject already exhibiting the symptoms of the disease, disorder and/or condition, i.e., causing regression of the disease, disorder and/or condition that has already affected the subject.

As used herein, the term "subject" refers to an animal or any living organism having sensation and the power of voluntary movement, and which requires oxygen and organic food. Nonlimiting examples include members of the human, primate, equine, porcine, bovine, murine, rattus, canine and feline specie. In certain aspects, the subject is a mammal or a warm-blooded vertebrate animal. In other aspects, the subject is a human. As used herein, the term "patient" may be used interchangeably with "subject" and "human".

As used herein, the terms "effective amount" or "therapeutically effective amount" mean an amount of compound of Formula (I) or Formula (II) or a form, composition or medicament thereof that achieves a target plasma concentration that is effective in treating or ameliorating HD as described herein and thus producing the desired therapeutic, ameliorative, inhibitory or preventative effect in a subject in need thereof. In one aspect, the effective amount may be the amount required to treat HD in a subject or patient, more specifically, in a human.

In another aspect, the concentration-biological effect relationships observed with regard to a compound of Formula (I) or Formula (II) or a form thereof indicate a target plasma concentration ranging from approximately 0.001 µg/mL to approximately 50 µg/mL, from approximately 0.01 µg/mL to approximately 20 µg/mL, from approximately 0.05 µg/mL to approximately 10 µg/mL, or from approximately 0.1 µg/mL to approximately 5 µg/mL. To achieve such plasma concentrations, the compounds described herein may be administered at doses that vary, such as, for example, without limitation, from 1.0 ng to 10,000 mg.

In one aspect, the dose administered to achieve an effective target plasma concentration may be administered based upon subject or patient specific factors, wherein the doses administered on a weight basis may be in the range of from about 0.001 mg/kg/day to about 3500 mg/kg/day, or about 0.001 mg/kg/day to about 3000 mg/kg/day, or about 0.001 mg/kg/day to about 2500 mg/kg/day, or about 0.001 mg/kg/day to about 2000 mg/kg/day, or about 0.001 mg/kg/day to about 1500 mg/kg/day, or about 0.001 mg/kg/day to about 1000 mg/kg/day, or about 0.001 mg/kg/day to about 500 mg/kg/day, or about 0.001 mg/kg/day to about 250 mg/kg/day, or about 0.001 mg/kg/day to about 200 mg/kg/day, or about 0.001 mg/kg/day to about 150 mg/kg/day, or about 0.001 mg/kg/day to about 100 mg/kg/day, or about 0.001 mg/kg/day to about 75 mg/kg/day, or about 0.001 mg/kg/day to about 50 mg/kg/day, or about 0.001 mg/kg/day to about 25 mg/kg/day, or about 0.001 mg/kg/day to about 10 mg/kg/day, or about 0.001 mg/kg/day to about 5 mg/kg/day, or about 0.001 mg/kg/day to about 1 mg/kg/day, or about 0.001 mg/kg/day to about 0.5 mg/kg/day, or about 0.001 mg/kg/day to about 0.1 mg/kg/day, or from about 0.01 mg/kg/day to about 3500 mg/kg/day, or about 0.01 mg/kg/day to about 3000 mg/kg/day, or about 0.01 mg/kg/day to about 2500 mg/kg/day, or about 0.01 mg/kg/day to about 2000 mg/kg/day, or about 0.01 mg/kg/day to about 1500 mg/kg/day, or about 0.01 mg/kg/day to about 1000 mg/kg/day, or about 0.01 mg/kg/day to about 500 mg/kg/day, or about 0.01 mg/kg/day to about 250 mg/kg/day, or about 0.01 mg/kg/day to about 200 mg/kg/day, or about 0.01 mg/kg/day to about 150 mg/kg/day, or about 0.01 mg/kg/day to about 100 mg/kg/day, or about 0.01 mg/kg/day to about 75 mg/kg/day, or about 0.01 mg/kg/day to about 50 mg/kg/day, or about 0.01 mg/kg/day to about 25 mg/kg/day, or about 0.01 mg/kg/day to about 10 mg/kg/day, or about 0.01 mg/kg/day to about 5 mg/kg/day, or about 0.01 mg/kg/day to about 1 mg/kg/day, or about 0.01 mg/kg/day to about 0.5 mg/kg/day, or about 0.01 mg/kg/day to about 0.1 mg/kg/day, or from about 0.1 mg/kg/day to about 3500 mg/kg/day, or about 0.1 mg/kg/day to about 3000 mg/kg/day, or about 0.1 mg/kg/day to about 2500 mg/kg/day, or about 0.1 mg/kg/day to about 2000 mg/kg/day, or about 0.1 mg/kg/day to about 1500 mg/kg/day, or about 0.1 mg/kg/day to about 1000 mg/kg/day, or about 0.1 mg/kg/day to about 500 mg/kg/day, or about 0.1 mg/kg/day to about 250 mg/kg/day, or about 0.1 mg/kg/day to about 200 mg/kg/day, or about 0.1 mg/kg/day to about 150 mg/kg/day, or about 0.1 mg/kg/day to about 100 mg/kg/day, or about 0.1 mg/kg/day to about 75 mg/kg/day, or about 0.1 mg/kg/day to about 50 mg/kg/day, or about 0.1 mg/kg/day to about 25 mg/kg/day, or about 0.1 mg/kg/day to about 10 mg/kg/day, or about 0.1 mg/kg/day to about 5 mg/kg/day, or about 0.1 mg/kg/day to about 1 mg/kg/day, or about 0.1 mg/kg/day to about 0.5 mg/kg/day.

Effective amounts for a given subject may be determined by routine experimentation that is within the skill and judgment of a clinician or a practitioner skilled in the art in light of factors related to the subject. Dosage and administration may be adjusted to provide sufficient levels of the active agent(s) or to maintain the desired effect. Factors which may be taken into account include genetic screening, severity of the disease state, status of disease progression, general health of the subject, ethnicity, age, weight, gender, diet, time of day and frequency of administration, drug combination(s), reaction sensitivities, experience with other therapies, and tolerance/response to therapy.

The dose administered to achieve an effective target plasma concentration may be orally administered once (once in approximately a 24 hour period; i.e., "q.d."), twice (once in approximately a 12 hour period; i.e., "b.i.d." or "q.12 h"), thrice (once in approximately an 8 hour period; i.e., "t.i.d." or "q.8 h"), or four times (once in approximately a 6 hour period; i.e., "q.d.s.", "q.i.d." or "q.6 h") daily.

In certain aspects, the dose administered to achieve an effective target plasma concentration may also be administered in a single, divided, or continuous dose for a patient or subject having a weight in a range of between about 40 to about 200 kg (which dose may be adjusted for patients or subjects above or below this range, particularly children under 40 kg). The typical adult subject is expected to have a median weight in a range of about 70 kg. Long-acting pharmaceutical compositions may be administered every 2, 3 or 4 days, once every week, or once every two weeks depending on half-life and clearance rate of the particular formulation.

The compounds and compositions described herein may be administered to the subject via any drug delivery route known in the art. Nonlimiting examples include oral, ocular, rectal, buccal, topical, nasal, sublingual, transdermal, subcutaneous, intramuscular, intraveneous (bolus and infusion), intracerebral, and pulmonary routes of administration.

In another aspect, the dose administered may be adjusted based upon a dosage form described herein formulated for delivery at about 0.02, 0.025, 0.03, 0.05, 0.06, 0.075, 0.08, 0.09, 0.10, 0.20, 0.25, 0.30, 0.50, 0.60, 0.75, 0.80, 0.90, 1.0, 1.10, 1.20, 1.25, 1.50, 1.75, 2.0, 3.0, 5.0, 10, 20, 30, 40, 50, 100, 150, 200, 250, 300, 400, 500, 1000, 1500, 2000, 2500, 3000 or 4000 mg/day.

For any compound, the effective amount can be estimated initially either in cell culture assays or in relevant animal models, such as a mouse, guinea pig, chimpanzee, marmoset or tamarin animal model. Relevant animal models may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is therapeutic index, and can be expressed as the ratio, $LD_{50}/ED_{50}$. In certain aspects, the effective amount is such that a large therapeutic index is achieved. In further particular aspects, the dosage is within a range of circulating concentrations that include an $ED_{50}$ with little or no toxicity. The dosage may vary within this range depending upon the dosage form employed, sensitivity of the patient, and the route of administration.

In one aspect, provided herein are methods for modulating the amount of HTT (huntingtin protein), comprising contacting a human cell with a compound of Formula (I) or Formula (II) or a form thereof. In a specific aspect, provided herein are methods for modulating the amount of HTT, comprising contacting a human cell with a compound of Formula (I) or Formula (II) or a form thereof that modulates the expression of HTT. The human cell can be contacted with a compound of Formula (I) or Formula (II) or a form thereof in vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of HTT expression and/or function. In another aspect, the human cell is from a human with HD. In another aspect, the human cell is in a human with HD. In one aspect, the compound is a form of the compound of Formula (I) or Formula (II).

In a specific aspect, provided herein is a method for enhancing the inhibition of mutant HTT transcribed from the Htt gene, comprising contacting a human cell with a compound of Formula (I) or Formula (II) or a form thereof. The human cell can be contacted with a compound of Formula (I) or Formula (II) or a form thereof in vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of wild-type "normal" HTT expression and/or function. In another aspect, the human cell is from a human with HD. In another aspect, the human cell is in a human with HD. In one aspect, the compound is a form of the compound of Formula (I) or Formula (II).

In another aspect, provided herein is a method for modulating the inhibition of mutant HTT transcribed from the Htt gene, comprising administering to a non-human animal model for HD a compound of Formula (I) or Formula (II) or a form thereof. In a specific aspect, provided herein is a method for modulating the inhibition of mutant HTT transcribed from the Htt gene, comprising administering to a non-human animal model for HD a compound of Formula (I) or Formula (II) or a form thereof. In a specific aspect, the compound is a form of the compound of Formula (I) or Formula (II).

In another aspect, provided herein is a method for decreasing the amount of mutant HTT, comprising contacting a human cell with a compound of Formula (I) or Formula (II) or a form thereof. In a specific aspect, provided herein is a method for decreasing the amount of mutant HTT, comprising contacting a human cell with a compound of Formula (I) or Formula (II) that inhibits the transcription of mutant HTT (huntingtin mRNA) from the Htt gene. In another specific aspect, provided herein is a method for decreasing the amount of HTT, comprising contacting a human cell with a compound of Formula (I) or Formula (II) that inhibits the expression of mutant HTT transcribed from the Htt gene. The human cell can be contacted with a compound of Formula (I) or Formula (II) or a form thereof in vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of HTT expression and/or function. In another aspect, the human cell is from a human with HD. In another aspect, the human cell is in a human with HD. In one aspect, the compound is a form of the compound of Formula (I) or Formula (II).

In certain aspects, treating or ameliorating HD with a compound of Formula (I) or Formula (II) or a form thereof (alone or in combination with an additional agent) has a therapeutic effect and/or beneficial effect. In a specific aspect, treating HD with a compound of Formula (I) or Formula (II) or a form thereof (alone or in combination with an additional agent) results in one, two or more of the following effects: (i) reduces or ameliorates the severity of HD; (ii) delays onset of HD; (iii) inhibits the progression of HD; (iv) reduces hospitalization of a subject; (v) reduces hospitalization length for a subject; (vi) increases the survival of a subject; (vii) improves the quality of life for a subject; (viii) reduces the number of symptoms associated with HD; (ix) reduces or ameliorates the severity of a symptom(s) associated with HD; (x) reduces the duration of a symptom associated with HD; (xi) prevents the recurrence of a symptom associated with HD; (xii) inhibits the development or onset of a symptom of HD; and/or (xiii) inhibits of the progression of a symptom associated with HD.

Metabolites

Another aspect included within the scope of the present description are the use of in vivo metabolic products of the compounds described herein. Such products may result, for example, from the oxidation, reduction, hydrolysis, amidation, esterification and the like of the administered compound, primarily due to enzymatic processes. Accordingly, the description includes the use of compounds produced by a process comprising contacting a compound described herein with a mammalian tissue or a mammal for a period of time sufficient to yield a metabolic product thereof.

Such products typically are identified by preparing a radio-labeled isotopologue (e.g., $^{14}C$ or $^3H$) of a compound described herein, administering the radio-labeled compound in a detectable dose (e.g., greater than about 0.5 mg/kg) to a mammal such as a rat, mouse, guinea pig, dog, monkey or human, allowing sufficient time for metabolism to occur (typically about 30 seconds to about 30 hours), and identifying the metabolic conversion products from urine, bile, blood or other biological samples. The conversion products are easily isolated since they are "radiolabeled" by virtue of being isotopically-enriched (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds described herein even if they possess no biological activity of their own.

Pharmaceutical Compositions

In accordance with the intended scope of the present description, aspects of the present description include compounds that have been identified and have been demonstrated to be useful in selectively preventing, treating or ameliorating HD and have been provided for use as one or more pharmaceutical compositions for preventing, treating or ameliorating HD.

An aspect of the present description includes a use for a compound of Formula (I) or Formula (II) or a form thereof in the preparation of a pharmaceutical composition for treating or ameliorating HD in a subject in need thereof comprising, administering to the subject an effective amount of the compound of Formula (I) or Formula (II) or a form thereof in admixture with one or more pharmaceutically acceptable excipients.

An aspect of the present description includes a use for a pharmaceutical composition of the compound of Formula (I) or Formula (II) or a form thereof in the preparation of a kit for treating or ameliorating HD in a subject in need thereof comprising, the pharmaceutical composition of the compound of Formula (I) or Formula (II) or a form thereof and instructions for administering the pharmaceutical composition.

As used herein, the term "composition" means a product comprising the specified ingredients in the specified amounts, as well as any product which results, directly or indirectly, from combination of the specified ingredients in the specified amounts.

The pharmaceutical composition may be formulated to achieve a physiologically compatible pH, ranging from about pH 3 to about pH 11. In certain aspects, the pharmaceutical composition is formulated to achieve a pH of from about pH 3 to about pH 7. In other aspects, the pharmaceutical composition is formulated to achieve a pH of from about pH 5 to about pH 8.

The term "pharmaceutically acceptable excipient" refers to an excipient for administration of a pharmaceutical agent, such as the compounds described herein. The term refers to any pharmaceutical excipient that may be administered without undue toxicity. Pharmaceutically acceptable excipients may be determined in part by the particular composition being administered, as well as by the particular mode of administration and/or dosage form. Nonlimiting examples of pharmaceutically acceptable excipients include carriers, solvents, stabilizers, adjuvants, diluents, etc. Accordingly, there exists a wide variety of suitable formulations of pharmaceutical compositions for the instant compounds described herein (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive antibodies. Other exemplary excipients include antioxidants such as ascorbic acid; chelating agents such as EDTA; carbohydrates such as dextrin, hydroxyalkylcellulose, hydroxyalkylmethylcellulose (e.g., hydroxypropylmethylcellulose, also known as HPMC), stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended use described herein. Suitable formulations for oral administration include solids, liquid solutions, emulsions and suspensions, while suitable inhalable formulations for pulmonary administration include liquids and powders. Alternative formulations include syrups, creams, ointments, tablets, and lyophilized solids which can be reconstituted with a physiologically compatible solvent prior to administration.

When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents, and preserving agents, in order to provide a palatable preparation.

Pharmaceutically acceptable excipients suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid, or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate, or kaolin, or as soft gelatin capsules wherein the active ingredient is mixed with non-aqueous or oil medium, such as glycerin, propylene glycol, polyethylene glycol, peanut oil, liquid paraffin, or olive oil.

In other aspects, pharmaceutical compositions described herein may be formulated as suspensions comprising a compound of Formula (I) or Formula (II) or a form thereof in admixture with one or more pharmaceutically acceptable excipients suitable for the manufacture of a suspension. In yet other aspects, pharmaceutical compositions described herein may be formulated as dispersible powders and granules suitable for preparation of a suspension by the addition of one or more excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin, or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions described herein may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions described herein may be in the form of a sterile injectable preparation, such as a sterile injectable aqueous emulsion or oleaginous suspension. Such emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propanediol. The sterile injectable preparation may also be prepared as a lyophilized powder. Among the acceptable vehicles and solvents that may be employed are water, Ringer's solution and isotonic sodium chloride solution. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

The compounds described herein may be substantially insoluble in water and sparingly soluble in most pharmaceutically acceptable protic solvents and vegetable oils, but generally soluble in medium-chain fatty acids (e.g., caprylic and capric acids) or triglycerides and in propylene glycol esters of medium-chain fatty acids. Thus, contemplated in the description are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In certain aspects, the compound described herein is formulated for oral administration in a lipid-based composition suitable for low solubility compounds. Lipid-based formulations can generally enhance the oral bioavailability of such compounds. As such, pharmaceutical compositions described herein may comprise a effective amount of a compound of Formula (I) or Formula (II) or a form thereof, together with at least one pharmaceutically acceptable excipient selected from medium chain fatty acids or propylene glycol esters thereof (e.g., propylene glycol esters of edible fatty acids such as caprylic and capric fatty acids) and pharmaceutically acceptable surfactants, such as polysorbate 20 or 80 (also referred to as Tween® 20 or Tween® 80, respectively) or polyoxyl 40 hydrogenated castor oil.

In other aspects, the bioavailability of low solubility compounds may be enhanced using particle size optimization techniques including the preparation of nanoparticles or nanosuspensions using techniques known to those skilled in the art. The compound forms present in such preparations include amorphous, partially amorphous, partially crystalline or crystalline forms.

In alternative aspects, the pharmaceutical composition may further comprise one or more aqueous solubility enhancer(s), such as a cyclodextrin. Nonlimiting examples of cyclodextrin include hydroxypropyl, hydroxyethyl, glucosyl, maltosyl and maltotriosyl derivatives of α-, β-, and γ-cyclodextrin, and hydroxypropyl-β-cyclodextrin (HPBC). In certain aspects, the pharmaceutical composition further comprises HPBC in a range of from about 0.1% to about 20%, from about 1% to about 15%, or from about 2.5% to about 10%. The amount of solubility enhancer employed may depend on the amount of the compound in the composition.

Preparation of Compounds

General Synthetic Methods

As disclosed herein, general methods for preparing the compounds of Formula (I) or Formula (II) or a form thereof as described herein are available via standard, well-known synthetic methodology. Many of the starting materials are commercially available or, when not available, can be prepared using the routes described below using techniques known to those skilled in the art. The synthetic schemes provided herein comprise multiple reaction steps, each of which is intended to stand on its own and can be carried out with or without any preceding or succeeding step(s). In other words, each of the individual reaction steps of the synthetic schemes provided herein in isolation is contemplated.

Scheme A: Compounds of Formula (I) or Formula (II), wherein $R_1$ and $R_2$ independently selected from $C_{3-10}$cycloalkyl, heterocyclyl, phenyl, or heteroaryl ring systems, may be prepared as described in Scheme A below.

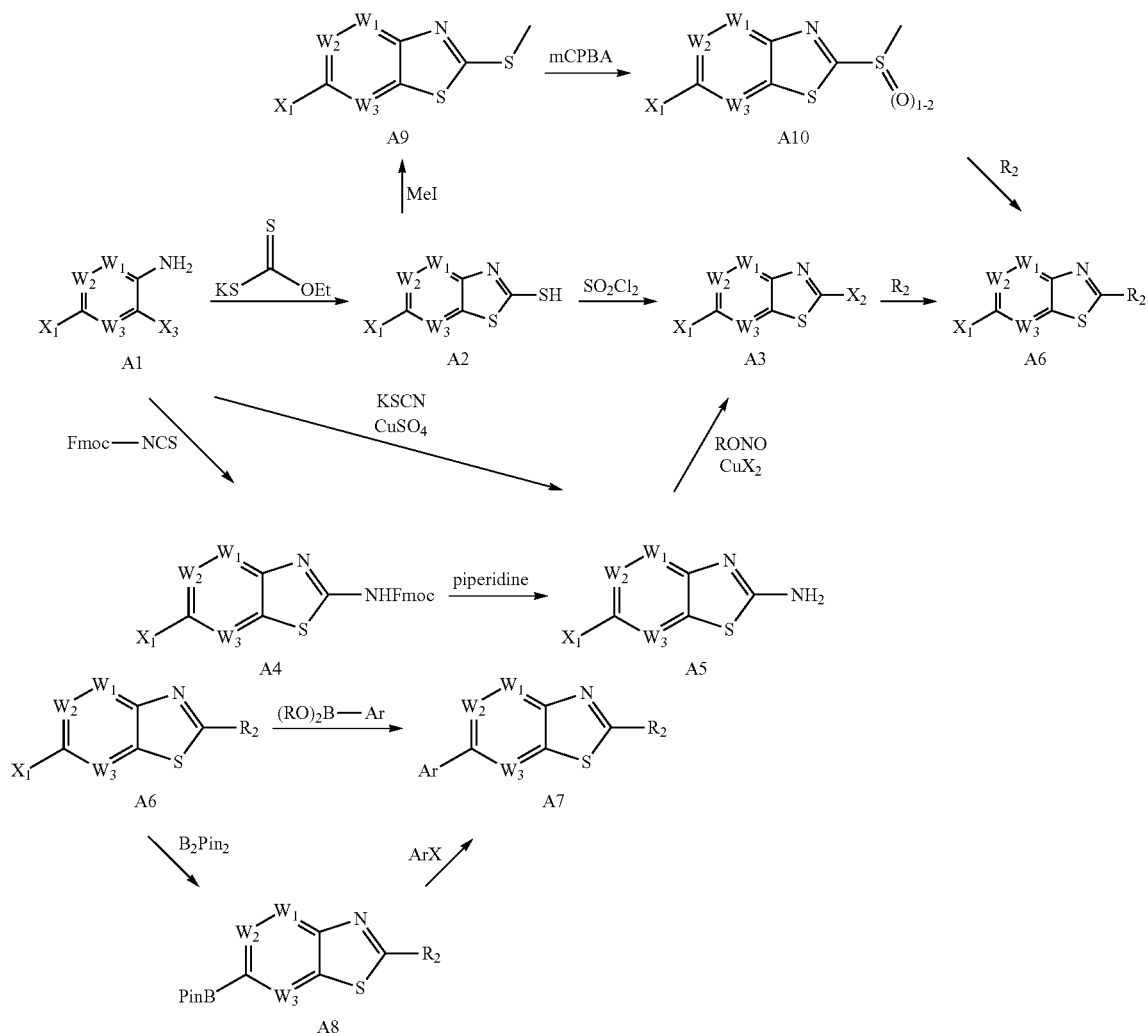

Compound A1 (where $X_1$ and $X_3$ are independently bromine, chlorine, fluorine and the like; $W_1$, $W_2$, and $W_3$ are independently C—$R_a$ or N, where $R_a$ can be functional substituents for further derivatization using techniques known to a person of ordinary skill in the art) is converted to Compound A2 by reacting with potassium ethyl xanthate in a suitable solvent (such as DMF and the like) at elevated temperature (such as 130° C.), which is further reacted with sulfuryl chloride to give Compound A3 ($X_2$=Cl). Alternatively, Compound A1 is reacted with Fmoc-NCS to give Compound A4 which is deprotected by an amine (such as piperidine and the like) to afford Compound A5. Alternatively, Compound A1 is reacted with KNCS in the presence of $CuSO_4$ in a suitable solvent (such as MeOH and the like) to give Compound A5. Compound A5 is then converted to A3 ($X_2$=Cl, Br) by a Sandmeyer reaction using alkyl nitrite (such as t-butyl nitrite and the like) and copper (II) halide in a suitable solvent (such as acetonitrile and the like). Compound A3 is converted to A6 by a nucleophilic substitution with a primary or secondary amine or an alcohol in the presence of a suitable base (such as NaH, $K_2CO_3$ and the like) in a suitable solvent (such as DMF and the like).

Alternatively, Compound A2 can be reacted with iodomethane to give Compound A9, which can be oxidized by an oxidant like mCPBA to give Compound A10. Compound A10 is converted to A6 by a nucleophilic substitution with a primary or secondary amine or an alcohol in the presence of a suitable base (such as NaH, $K_2CO_3$ and the like) in a suitable solvent (such as DMF and the like). Compound A6 is converted to Compound A7 by a Suzuki coupling with an aryl- or heteroaryl-boronic acid (or pinacol boronic ester) in the presence of a catalyst (such as Pd(dppf)$Cl_2$ and the like) and base (such as aqueous $K_2CO_3$ and the like) in a suitable solvent (such as 1,4-dioxane and the like). Alternatively, compound A6 is converted to compound A8 by coupling with $B_2Pin_2$ in the presence of a catalyst (such as Pd(dppf)$Cl_2$ and the like) and base (such as KOAc and the like) in a suitable solvent (such as 1,4-dioxane and the like). Compound A8 is further coupled with an aryl halide or heteroaryl halide in the presence of a catalyst (such as Pd(dppf)$Cl_2$ and the like) and base (such as aqueous $K_2CO_3$ and the like) in a suitable solvent (such as 1,4-dioxane and the like) to give Compound A7.

Scheme B: Compounds of Formula (II), wherein $R_1$ and $R_2$ independently selected from $C_{3-10}$cycloalkyl, heterocyclyl, phenyl, or heteroaryl ring systems, may be prepared as described in Scheme B below.

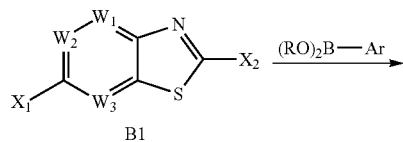

B1 son of ordinary skill in the art) is converted to B2 by a Suzuki coupling with an aryl- or heteroaryl-boronic acid (or pinacol boronic ester) in the presence of a catalyst (such as Pd(dppf)Cl$_2$ and the like) and base (such as aqueous K$_2$CO$_3$ and the like) in a suitable solvent (such as 1,4-dioxane and the like). Compound B2 is converted to Compound B3 by a nucleophilic substitution with a primary or secondary amine in the presence of a suitable base (such as K$_2$CO$_3$ and the like) in a suitable solvent (such as DMF and the like), or by a Hartwig-Buchwald coupling in the presence of a catalyst (such as Pd$_2$(dba)$_3$/RuPhos and the like) and base (such as t-BuONa and the like) in a suitable solvent (such as 1,4-dioxane and the like).

Scheme C: Compounds of Formula (I) or Formula (II), wherein $R_1$ and $R_2$ independently selected from $C_{3-10}$cycloalkyl, heterocyclyl, phenyl, or heteroaryl ring systems, may be prepared as described in Scheme C below.

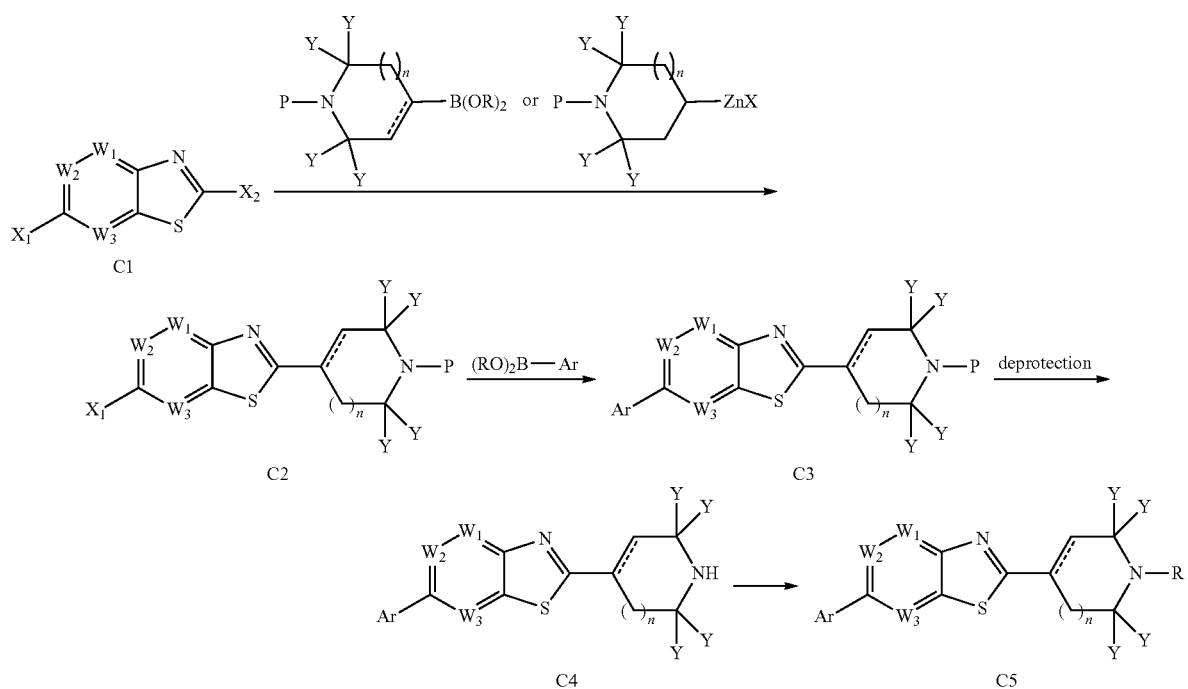

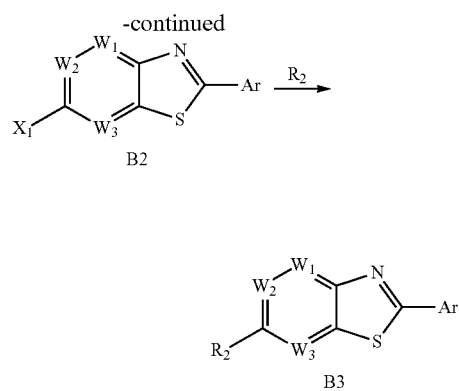

Compound B1 (where $X_1$ and $X_2$ are independently bromine, chlorine and the like; $W_1$, $W_2$, and $W_3$ are independently C—$R_a$ or N, where $R_a$ can be functional substituents for further derivatization using techniques known to a person of ordinary skill in the art) is converted to Compound C2 by a Suzuki coupling with an optionally substituted and appropriately protected amino-containing cycloalkyl/cycloalkenyl pinacol boronic ester (where Y is hydrogen or an optionally substituted alkyl group and P is a protecting group such as Boc and the like) in the presence of a catalyst (such as Pd(dppf)Cl$_2$ and the like) and base (such as aqueous K$_2$CO$_3$ and the like) in a suitable solvent (such as 1,4-dioxane and the like). Alternatively, Compound C1 is converted to Compound C2 by a Negishi coupling with an optionally substituted and appropriately protected amino-containing cycloalkyl zinc halide in the presence of a catalyst (such as Pd(dppf)Cl$_2$ and the like) in a suitable solvent (such as 1,4-dioxane and the like). Compound C2 is converted to Compound C3 by a Suzuki coupling with an aryl- or heteroaryl-boronic acid (or pinacol boronic ester) in the presence of a catalyst (such as Pd(dppf)Cl$_2$ and the like) and base (such as aqueous K$_2$CO$_3$ and the like) in a suitable solvent (such as 1,4-dioxane and the like). Upon treatment with a deprotecting agent appropriate for the protecting group (such as HCl in dioxane for a Boc protecting group), Compound C3 is converted to Compound C4. Compound C4 is converted to Compound C5 by reductive amination with a suitable aldehyde and reducing agent (such as NaBH(OAc)$_3$ and the like) in a suitable solvent (such as 1,2-dichloroethane and the like). Alternatively, Compound C4 is converted to Compound C5 by alkylation with an alkyl halide (such as 2-iodopropane and the like) in the presence of an appropriate base (such as K$_2$CO$_3$ and the like). In cases where unsaturation exists in the ring containing the basic amino group, the compound may be converted to the fully saturated analog under an atmosphere of H$_2$ in a suitable solvent (such as methanol and the like) and in the presence of catalyst (such as 10% Pd/C and the like).

Scheme D: Compounds of Formula (II), wherein R$_1$ and R$_2$ independently selected from C$_{3-10}$cycloalkyl, heterocyclyl, phenyl, or heteroaryl ring systems, may be prepared as described in Scheme D below.

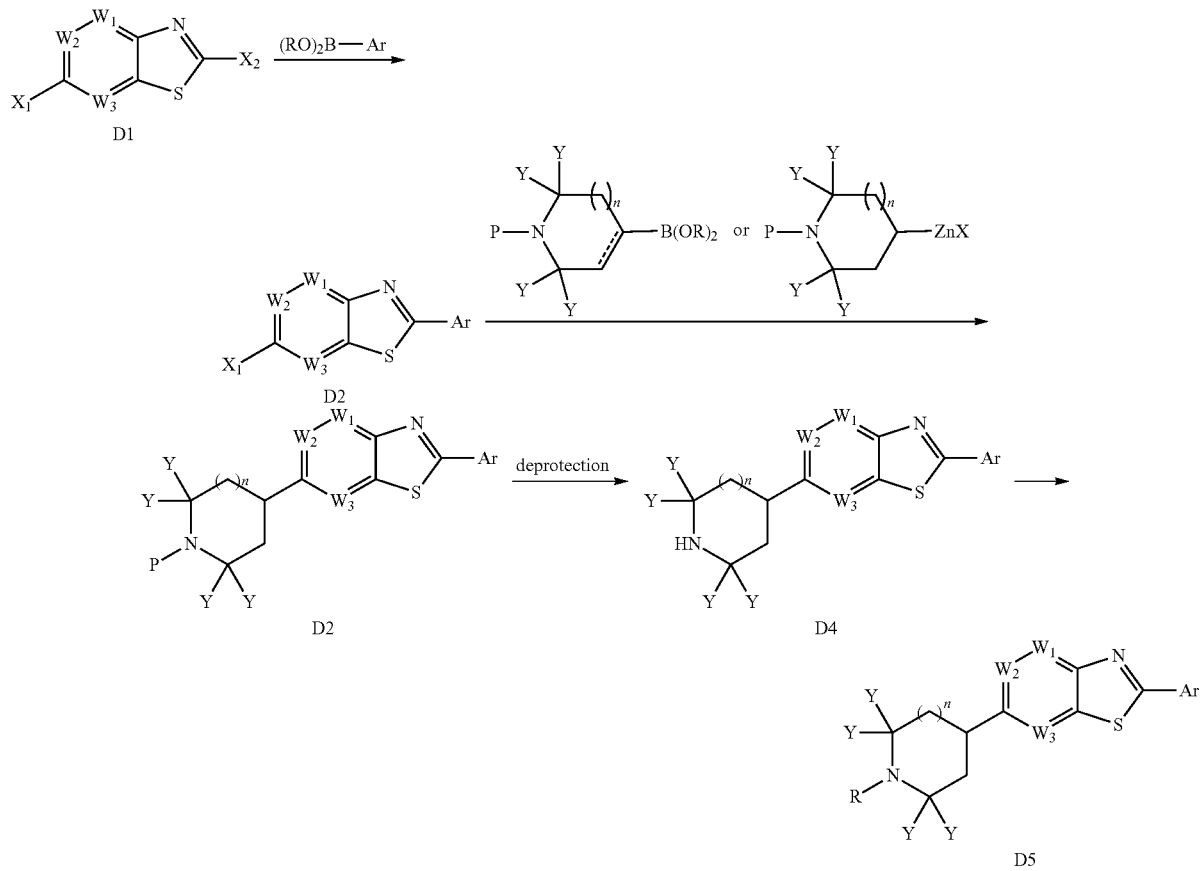

Compound D1 can be converted to Compound D4 and D5 using the conditions described in Scheme C where steps 1 and 2 are reversed.

Scheme E: Compounds of Formula (I) or Formula (II), wherein R$_1$ and R$_2$ independently selected from C$_{3-10}$cycloalkyl, heterocyclyl, phenyl, or heteroaryl ring systems, may be prepared as described in Scheme E below.

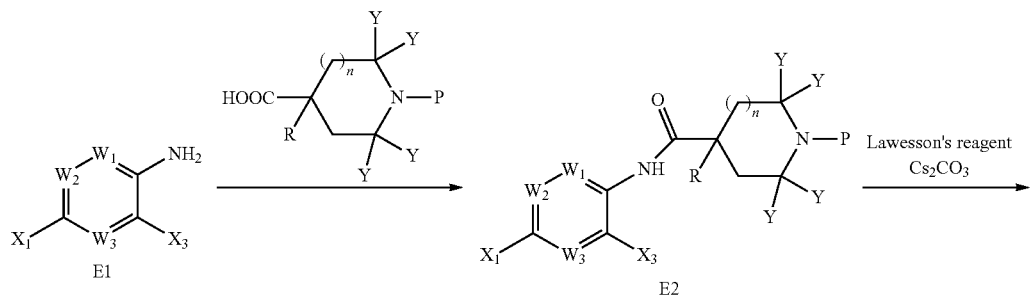

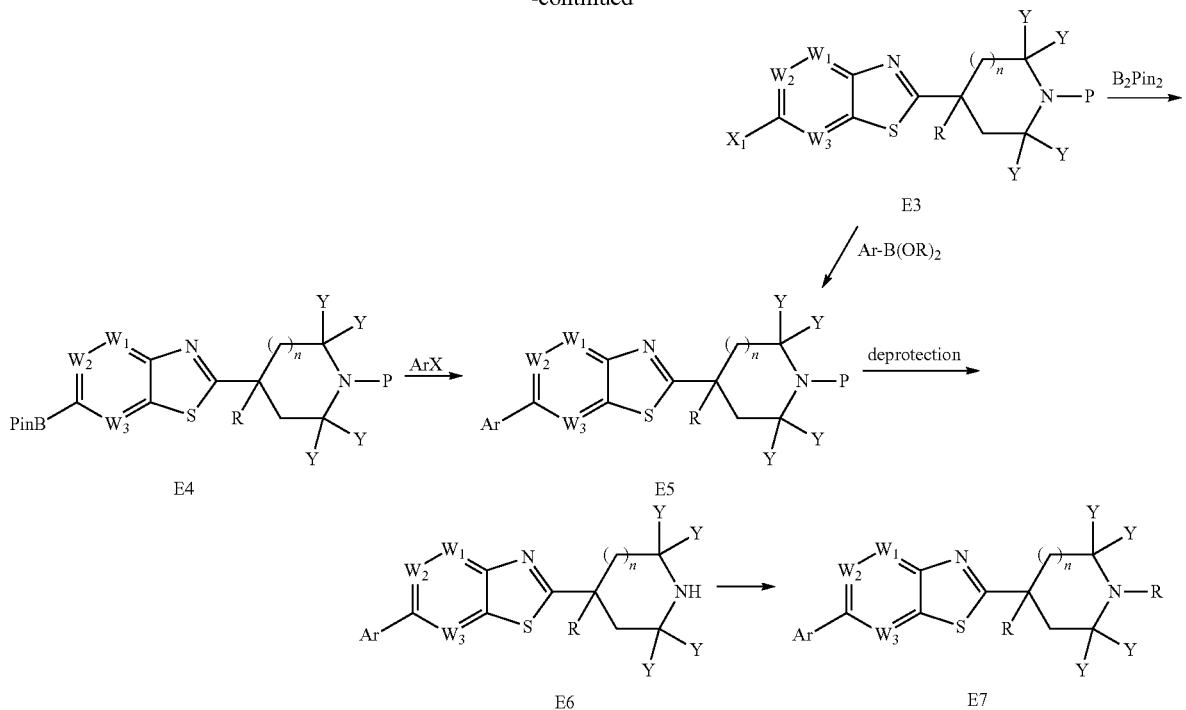

Compound E1 (where $X_1$ and $X_3$ are independently bromine, chlorine, fluorine and the like; $W_1$, $W_2$, and $W_3$ are independently C—$R_a$ or N, where $R_a$ can be functional substituents for further derivatization using techniques known to a person of ordinary skill in the art) is converted to Compound E2 by reacting with an optionally substituted and appropriately protected amino-containing cycloalkyl/cycloalkenyl carboxylic acid (where Y is hydrogen or an optionally substituted alkyl group, P is a protecting group such as Boc and the like and R is H, halogen or an optionally substituted alkyl group) in the presence of an activating reagent (such as oxalyl chloride and the like) and base (such as aqueous pyridine and the like) in a suitable solvent (such as dichloromethane and the like). Compound E2 can be treated with Lawesson's Reagent in the presence of base (such as $Cs_2CO_3$ and the like) in a suitable solvent (such as toluene and the like) to give Compound E3. Compound E3 is converted to compound E4 by coupling with $B_2Pin_2$ in the presence of a catalyst (such as Pd(dppf)$Cl_2$ and the like) and base (such as KOAc and the like) in a suitable solvent (such as 1,4-dioxane and the like). Compound E4 is further coupled with an aryl halide or heteroaryl halide in the presence of a catalyst (such as Pd(dppf)$Cl_2$ and the like) and base (such as aqueous $K_2CO_3$ and the like) in a suitable solvent (such as 1,4-dioxane and the like) to give Compound E5. Alternatively, Compound E3 is converted to Compound E5 by a Suzuki coupling with an aryl- or heteroaryl-boronic acid (or pinacol boronic ester) in the presence of a catalyst (such as Pd(dppf)$Cl_2$ and the like) and base (such as aqueous $K_2CO_3$ and the like) in a suitable solvent (such as 1,4-dioxane and the like). Upon treatment with a deprotecting agent appropriate for the protecting group (such as HCl in dioxane for a Boc protecting group), Compound E5 is converted to Compound E6. Compound E6 is converted to Compound E7 by reductive amination with a suitable aldehyde and reducing agent (such as NaBH(OAc)$_3$ and the like) in a suitable solvent (such as 1,2-dichloroethane and the like).

Scheme F: Compounds of Formula (I) or Formula (II), wherein $R_1$ and $R_2$ independently selected from $C_{3-10}$cycloalkyl, heterocyclyl, phenyl, or heteroaryl ring systems, may be prepared as described in Scheme F below.

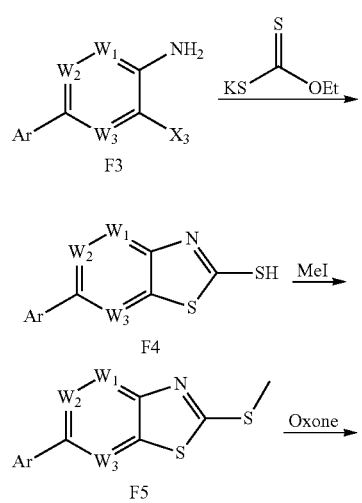

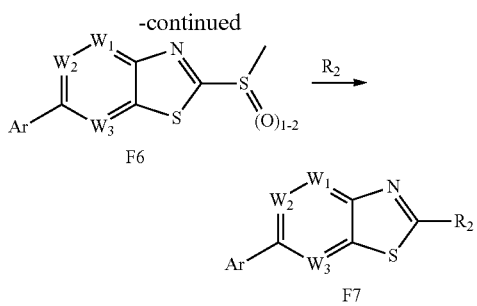

F6

F7

Compound F1 (where $X_1$ and $X_3$ are independently bromine, chlorine, fluorine and the like; $W_1$, $W_2$, and $W_3$ are independently C—$R_a$ or N, where $R_a$ can be functional substituents for further derivatization using techniques known to a person of ordinary skill in the art) is converted to Compound F2 by coupling with $B_2Pin_2$ in the presence of a catalyst (such as Pd(dppf)Cl$_2$ and the like) and base (such as KOAc and the like) in a suitable solvent (such as 1,4-dioxane and the like), which was further coupled with an aryl halide or heteroaryl halide in the presence of a catalyst (such as Pd(dppf)Cl$_2$ and the like) and base (such as aqueous $K_2CO_3$ and the like) in a suitable solvent (such as 1,4-dioxane and the like) to give Compound F3. Compound F3 is converted to Compound F4 by reacting with potassium ethyl xanthate in a suitable solvent (such as DMF and the like) at elevated temperature (such as 130° C.), which is further reacted with iodomethane to give Compound F5. Oxidation of Compound F5 by Oxone affords Compound F6. Compound F6 is converted to Compound F7 by a nucleophilic substitution with a primary or secondary amine in the presence of a suitable base (such as $K_2CO_3$ and the like) in a suitable solvent (such as DMF and the like).

SPECIFIC SYNTHETIC EXAMPLES

To describe in more detail and assist in understanding, the following non-limiting examples are offered to more fully illustrate the scope of compounds described herein and are not to be construed as specifically limiting the scope thereof. Such variations of the compounds described herein that may be now known or later developed, which would be within the purview of one skilled in the art to ascertain, are considered to fall within the scope of the compounds as described herein and hereinafter claimed. These examples illustrate the preparation of certain compounds. Those of skill in the art will understand that the techniques described in these examples represent techniques, as described by those of ordinary skill in the art, that function well in synthetic practice, and as such constitute preferred modes for the practice thereof. However, it should be appreciated that those of skill in the art should, in light of the present disclosure, appreciate that many changes can be made in the specific methods that are disclosed and still obtain a like or similar result without departing from the spirit and scope of the present description.

Other than in the following examples of the embodied compounds, unless indicated to the contrary, all numbers expressing quantities of ingredients, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and rounding techniques used by those of skill in the art.

While the numerical ranges and parameters setting forth the broad scope of the present description are approximations, the numerical values set forth in the examples set forth below are reported as precisely as possible. Any numerical value, however, inherently contains certain errors necessarily resulting from the standard deviation found in their respective testing measurements.

COMPOUND EXAMPLES

As used above, and throughout the present description, the following abbreviations, unless otherwise indicated, shall be understood to have the following meanings:

| Abbreviation | Meaning |
| --- | --- |
| Δ | heating (chemistry) or deletion (biology) |
| AcOH or HOAc | acetic acid |
| Ac$_2$O | acetic anhydride |
| Ag$_2$SO$_4$ | silver sulfate |
| Ar | argon |
| ACN or CH$_3$CN | acetonitrile |
| atm | atmosphere(s) |
| BBr$_3$ | boron tribromide |
| BnNHMe | benzyl methylamine |
| BnOH | benzyl alcohol |
| Boc | tert-butoxy-carbonyl |
| Boc$_2$O | di-tert-butyl dicarbonate |
| B$_2$pin$_2$ | bis(pinacolato)diboron |
| BPin | 4,4,5,5-tetramethyl-1,3,2-dioxaborolanyl |
| Br$_2$ | bromine |
| Burgess Reagent | methyl N-(triethylammoniosulfonyl)carbamate |
| nBuLi or BuLi | n-butyl lithium |
| t-BuNH$_2$ | t-butyl amine |
| BuOH | n-butanol |
| t-BuONa | sodium t-butoxide |
| (t-Bu)$_3$P HBF$_4$ | Tri-t-butylphosphonium tetrafluoroborate |

| Abbreviation | Meaning |
| --- | --- |
| ° C. | degrees Centigrade |
| Cbz—Cl | benzyl chloroformate |
| CDI | 1,1-carbonyldiimidazole or N,N'-carbonyldiimidazole |
| Celite ® or Celite | diatomaceous earth |
| (COCl)$_2$ | oxalyl chloride |
| CO(OMe)$_2$ | dimethyl carbonate |
| CPME | cyclopropyl methyl ether |
| CS$_2$ | carbon disulfide |
| Cs$_2$CO$_3$ | cesium carbonate |
| CuI | copper(I) iodide |
| CuBr$_2$ | copper(II) bromide |
| CuCl$_2$ | copper(II) chloride |
| CuSO$_4$ | copper(II) sulfate |
| d/h/hr/hrs/min/s | day(d)/hour(h, hr or hrs)/minute(min)/second(s) |
| DAST | (diethylamino)sulfur trifluoride |
| DCE | 1,2-dichloroethane |
| DCM or CH$_2$Cl$_2$ | dichloromethane |
| DDQ | 2,3-dichloro-5,6-dicyano-p-benzoquinone |
| DIAD | diisopropyl azodicarboxylate |
| DIEA or DIPEA | N,N-diisopropylethylamine |
| DMA | dimethylacetamide |
| DMAP | 4-(dimethylamino)pyridine |
| DME | 1,2-dimethoxyethane |
| DMF | dimethylformamide |
| DMSO | dimethylsulfoxide |
| EDC or EDCI | N-(3-dimethylaminopropyl)-N'-ethylcarbodiimide hydrochloride |
| EtI | iodoethane |
| EtOAc | ethyl acetate |
| EtOH | ethanol |
| Et$_2$O | diethyl ether |
| Fmoc—NCS | 2-(9H-fluoren-9-yloxy)acetyl isothiocyanate |
| H$_2$ | hydrogen |
| HCl | hydrochloric acid |
| H$_2$SO$_4$ | sulfuric acid |
| HATU | 1-[bis(dimethylamino)methylene]-1H-1,2,3-triazolo[4,5-b]pyridinium 3-oxid hexafluorophosphate |
| iPrI | 2-iodopropane, isopropyl iodide |
| K$_2$CO$_3$ | potassium carbonate |
| KOAc | potassium acetate |
| KOtBu | Potassium t-butoxide |
| KOH | potassium hydroxide |
| KSCN | potassium thiocyanate |
| Lawesson's Reagent | 2,4-bis(4-methoxyphenyl)-2,4-dithioxo-1,3,2,4-dithiadiphosphetane, 2,4-Bis-(4-methoxyphenyl)-1,3-dithia-2,4-diphosphetane 2,4-disulfide |
| LAH | lithium aluminum hydride |
| LC/MS, LCMS or LC-MS | liquid chromatographic mass spectroscopy |
| LDA | lithium diisopropylamine |
| LHMDS | lithium bis(trimethylsilyl)amide or lithium hexamethyldisilazide |
| LiOH | lithium hydroxide |
| MeOH | methanol |
| MeI | iodomethane |
| MeSO$_3$H | methanesulfonic acid |
| Me—THF | 2-methyltetrahydrofuran |
| MgSO$_4$ | magnesium sulfate |
| MS | mass spectroscopy |
| NBS | N-bromosuccinimide |
| NCS | N-chlorosuccinimide |
| NFSI | N-fluorobenzenesulfonimide |
| NH$_4$Cl | ammonium chloride |
| NH$_4$OAc | ammonium acetate |
| NaBH$_4$ | sodium borohydride |
| NaBH(OAc)$_3$ | sodium triacetoxyborohydride |
| NaH | sodium hydride |
| NaHCO$_3$ | sodium bicarbonate |
| NaHMDS | sodium bis(trimethylsilyl)amide or sodium hexamethyldisilazide |
| NaH | sodium hydride |
| NaOAc | sodium acetate |
| NaOH | sodium hydroxide |
| NaOMe | sodium methoxide |
| Na$_2$SO$_4$ | sodium sulfate |
| N$_2$ | nitrogen |
| NH$_4$Cl | ammoniuim chloride |

| Abbreviation | Meaning |
| --- | --- |
| NMP | N-methylpyrrolidone |
| NMR | nuclear magnetic resonance |
| Pb(OAc)$_4$ | lead(IV) acetate or lead tetracetate |
| Pd | palladium |
| Pd/C | palladium on carbon |
| Pd(dba)$_2$ | bis(dibenzylideneacetone)palladium |
| Pd$_2$(dba)$_3$ or Pd$_2$dba$_3$ | tris(dibenzylideneacetone)dipalladium(0) |
| PdCl$_2$(PhCN)$_2$ | trans-bis(benzonitrile)dichloropalladium(II) |
| Pd(dppf)Cl$_2$ or Pd(dppf)Cl$_2$—CH$_2$Cl$_2$ | [1,1'-bis(diphenylphosphino)ferrocene]dichloropalladium(II), complex with dichloromethane |
| Pd(OAc)$_2$ | palladium(II) acetate |
| Pd(OH)$_2$ | palladium hydroxide |
| Pd(PPh$_3$)$_4$ or Pd(Ph$_3$P)$_4$ | tetrakis(triphenylphosphine)palladium(0) |
| Pd(PPh$_3$)$_2$Cl$_2$, PdCl$_2$(PPh$_3$)$_2$ or PdCl$_2$(Ph$_3$P)$_2$ | bis(triphenylphosphine)palladium(II) dichloride |
| PHBu$_3$BF$_4$ or tBu$_3$PHBF$_4$ | tri-tert-butylphosphonium tetrafluoroborate |
| PhI | iodobenzene |
| PhI(OTFA)$_2$ | [bis(trifluoroacetoxy)iodo]benzene |
| PhMe | toluene |
| Ph—N(Tf)$_2$ or PhN(Tf)$_2$ | N-phenyl triflimide, also referred to as N-phenyl-bis(trifluoromethanesulfonimide) |
| POCl$_3$ | phosphoryl chloride or phosphorous(V) oxychloride |
| PPh$_3$ | triphenylphosphine |
| P$_2$S$_5$ | phosphorous pentasulfide |
| PhMe | toluene |
| Psi | pounds per square inch pressure |
| RT | retention time |
| RuPhos | 2-dicyclohexylphosphino-2',6'-diisopropoxybiphenyl |
| SOCl$_2$ | thionly chloride |
| SO$_2$Cl$_2$ | sulfuryl chloride |
| S-Phos, SPhos or Sphos | 2-dicyclohexylphosphino-2',6'-dimethoxybiphenyl |
| S-Phos-Pd G$_2$ | chloro(2-dicyclohexylphosphino-2',6'-dimethoxy-1,1'-biphenyl)(2'-amino-1,1'-biphenyl-2-yl) palladium(II) |
| T$_3$P | propylphosphonic anhydride |
| TEA, Et$_3$N or NEt$_3$ | triethylamine |
| Ti(OiPr)$_4$ | titanium(IV) isopropoxide |
| Tf$_2$O | triflic anhydride |
| TFA | trifluoroacetic acid |
| THF | tetrahydrofuran |
| TIPS | tiisopropylsilane |
| TLC | thin layer chromatography |
| TMEDA | tetramethylethylenediamine |
| TMS | trimethylsilane |
| TMSCl | trimethylchlorosilane or trimethylsilyl chloride |
| t-Bu | tert-butyl |
| TsOH, p-TsOH or pTSA | tosylic acid or p-toluenesulfonic acid |
| X-Phos | 2-dicyclohexylphosphino-2',4',6'-triisopropylbiphenyl |
| ZnCN | zinc cyanide |

Intermediate 1

Benzyl (1R,5S,8S)-8-(Methylamino)-3-azabicyclo[3.2.1]octane-3-carboxylate

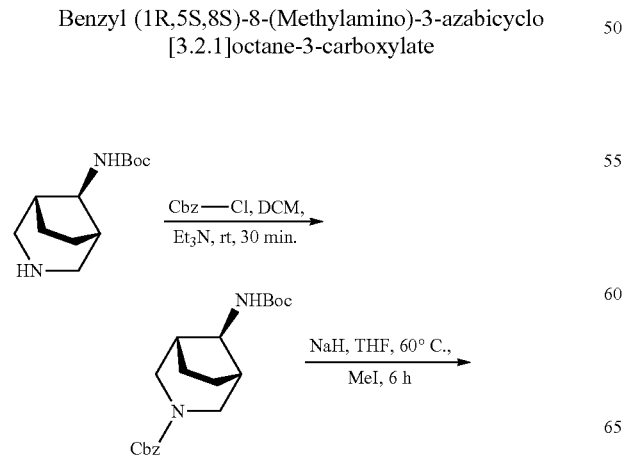

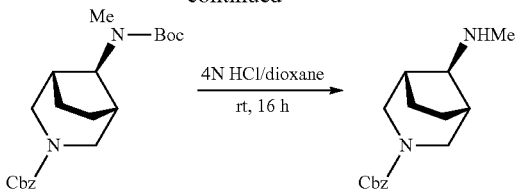

Step 1: tert-Butyl (1R,5S,8S)-3-azabicyclo[3.2.1]octan-8-yl)carbamate (500 mg, 2.21 mmol) was dissolved in CH$_2$Cl$_2$ (2.5 mL) and Et$_3$N (0.36 mL, 2.58 mmol) at 0° C. Benzyl chloroformate (0.36 mL, 2.44 mmol) was added dropwise. The reaction mixture was then stirred at room temperature for 30 min. The precipitated triethylammonium hydrochloride was filtered off. The filtrate was purified by silica gel chromatography (10-20% EtOAc in CH$_2$Cl$_2$), yielding benzyl (1R,5S,8S)-8-((tert-butoxycarbonyl)amino)-3-azabicyclo[3.2.1]octane-3-carboxylate (718 mg, 90%) as a white solid.

¹H NMR (acetone-d₆) δ: 7.30-7.45 (m, 5H), 5.86 (br s, 1H), 5.08-5.18 (m, 2H), 3.90-3.96 (m, 2H), 3.61 (m, 1H), 3.09 (d, J=12 Hz, 1H), 2.97 (d, J=12 Hz, 1H), 2.22-2.27 (m, 2H), 1.86-1.89 (m, 2H), 1.43-1.49 (m, 2H), 1.41 (s, 9H).

Step 2: Benzyl (1R,5S,8S)-8-((tert-butoxycarbonyl)amino)-3-azabicyclo[3.2.1]octane-3-carboxylate (716 mg, 1.99 mmol), THF (12 mL), and NaH (60% oil suspension, 160 mg, 4 mmol) were stirred at room temperature for 30 min. MeI (375 μL, 6 mmol) was added. This mixture was heated at 60° C. for 6 h. This mixture was partitioned between EtOAc and H₂O. The organic layer was dried over MgSO₄, filtered, and concentrated under vacuum. Purification by silica gel chromatography (10-20% EtOAc in CH₂Cl₂) yielded benzyl (1R,5S,8S)-8-((tert-butoxycarbonyl)(methyl)amino)-3-azabicyclo[3.2.1]octane-3-carboxylate (546 mg, 73%) as a clear oil.

¹H NMR (acetone-d₆) δ: 7.30-7.45 (m, 5H), 5.10-5.16 (m, 2H), 3.92-3.97 (m, 2H), 3.78 (s, 1H), 3.13 (d, J=12 Hz, 1H), 3.02 (d, J=12 Hz, 1H), 2.84 (s, 3H), 2.42-2.46 (m, 2H), 1.78-1.83 (m, 2H), 1.53-1.59 (m, 2H), 1.47 (s, 9H).

Step 3: Benzyl (1R,5S,8S)-8-((tert-butoxycarbonyl)(methyl)amino)-3-azabicyclo[3.2.1]octane-3-carboxylate (510 mg, 1.36 mmol) was stirred in 4N HCl in dioxane (2 mL, 8 mmol) at room temperature for 16 h. The reaction mixture was diluted with ether and filtered to yield benzyl (1R,5S,8S)-8-(methylamino)-3-azabicyclo[3.2.1]octane-3-carboxylate hydrochloride (374 mg, 88%) as a white solid.

¹H NMR (methanol-d₄) δ: 7.31-7.41 (m, 5H), 5.11-5.20 (m, 2H), 4.04 (dd, J=13 Hz, 3 Hz, 2H), 3.37 (s, 1H), 3.11 (d, J=13 Hz, 1H), 3.01 (d, J=13 Hz, 1H), 2.75 (s, 3H), 2.46-2.54 (m, 2H), 1.82-1.86 (m, 2H), 1.61-1.69 (m, 2H).

Intermediate 2

N-Ethyl-2,2,6,6-tetramethylpiperidin-4-amine Dihydrochloride

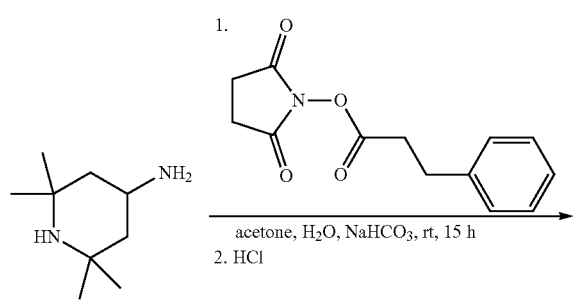

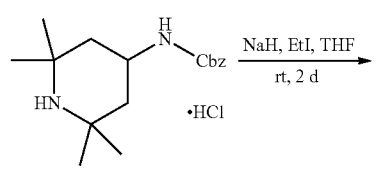

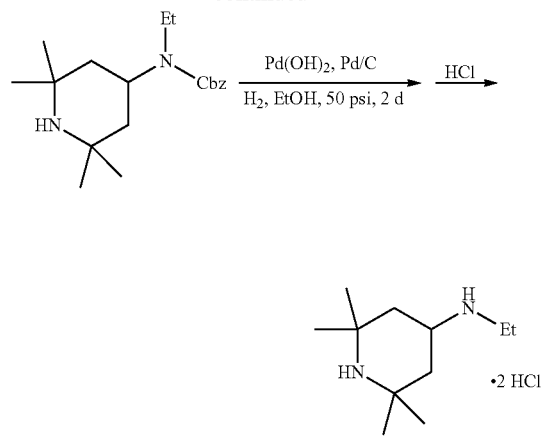

Step 1: 2,2,6,6-Tetramethylpiperidin-4-amine (1 g, 6.4 mmol), benzyl (2,5-dioxopyrrolidin-1-yl) carbonate (1.82 g, 7.3 mmol), NaHCO₃ (1M in H₂O, 14 mL, 14 mmol), and acetone (20 mL) were stirred at room temperature for 15 h. The product, which was very water-soluble, was extracted from the reaction mixture with ethyl acetate. The organic layer was dried over MgSO₄, filtered, and concentrated under vacuum. The concentrate was treated with HCl in ether and filtered to yield benzyl (2,2,6,6-tetramethylpiperidin-4-yl)carbamate hydrochloride (1.93 g, 92%) as a white solid.

¹H NMR (methanol-d₄) δ: 7.30-7.42 (m, 5H), 5.11 (s, 2H), 4.0-4.06 (m, 1H), 2.08 (dd, J=14 Hz, 3.5 Hz, 2H), 1.54 (br s, 6H), 1.47 (m, 2H), 1.41 (s, 6H).

Step 2: Benzyl (2,2,6,6-tetramethylpiperidin-4-yl)carbamate hydrochloride (1.9 g, 5.8 mmol), THF (19 mL) and 60% NaH suspension (1.9 g, 48 mmol) were stirred at room temperature for 30 min. This was followed by addition of EtI (1.5 mL, 19 mmol). The reaction mixture was stirred at room temperature for 2 days. This mixture was partitioned between EtOAc and H₂O. The organic layer was dried over MgSO₄, filtered, and concentrated under vacuum. Purification by silica gel chromatography (5-10% MeOH in CH₂Cl₂, with 0.1% NH₄OH modifier) was done. The product was dissolved in ether and was filtered to remove particulate impurities. The filtrate was concentrated to yield benzyl ethyl(2,2,6,6-tetramethylpiperidin-4-yl)carbamate (701 mg, 38%) as a clear oil.

¹H NMR (acetone-d₆) δ: 7.30-7.50 (m, 5H), 5.15 (s, 2H), 4.48 (m, 1H), 3.25 (q, J=7 Hz, 2H), 1.53-1.59 (m, 2H), 1.38 (t, J=12 Hz, 2H), 1.21 (br 2, 6H), 1.13 (t, J=7 Hz, 3H), 1.10 (s, 6H).

Step 3: Benzyl ethyl(2,2,6,6-tetramethylpiperidin-4-yl)carbamate (700 mg, 2.2 mmol), ethanol (12 mL), 20% Pd(OH)₂ on carbon (100 mg) and 10% Pd/C (100 mg) were hydrogenated at 50 psi for 2 days. The reaction mixture was filtered through Celite®. The filtrate was concentrated and then treated with ethereal HCl. The precipitates that formed were filtered and washed with ether to yield N-ethyl-2,2,6,6-tetramethylpiperidin-4-amine dihydrochloride (525 mg, 93%) as a white solid.

¹H NMR (methanol-d₄) δ: 8.48 (s, 1H), 3.69 (m, 1H), 3.12 (q, J=7 Hz, 2H), 2.26 (dd, J=14 Hz, 3.5 Hz, 2H), 1.67 (t, J=13 Hz, 2H), 1.51 (s, 12H), 1.35 (t, J=7 Hz, 3H).

Intermediate 3

(1R,3S,5S)—N,1,5-Trimethyl-8-azabicyclo[3.2.1]octan-3-amine Dihydrochloride

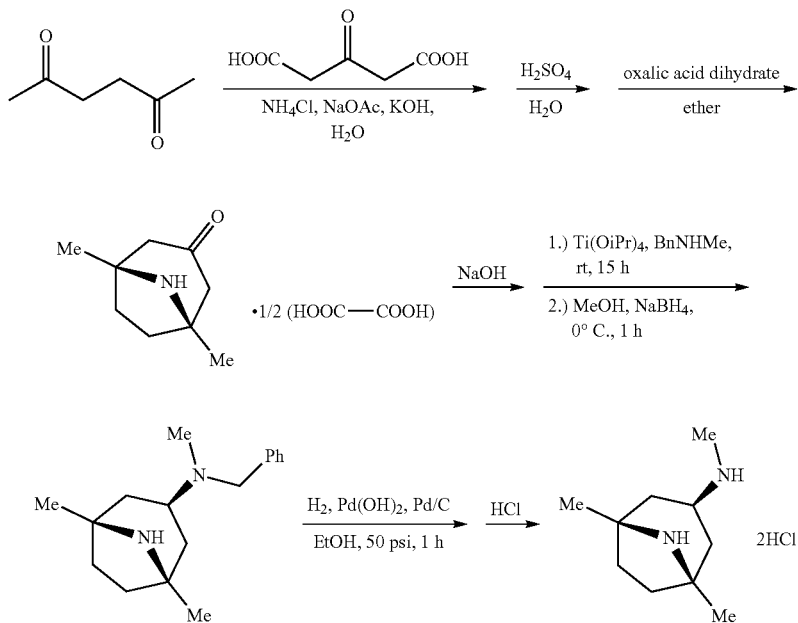

Step 1: Hexane-2,5-dione (10.8 mL, 92.1 mmol) and 3-oxopentanedioic acid (26 g, 178 mmol) were dissolved in $H_2O$ (75 mL) at 0° C. A solution of KOH (23.2 g, 414 mmol) in $H_2O$ (15 mL) was added dropwise, followed by a solution of NaOAc (9 g, 109.7 mmol) and $NH_4Cl$ (15 g, 280.4 mmol) in $H_2O$ (135 mL). Aqueous 50% w/w KOH (8 mL) was added to adjust the pH to 9. More $H_2O$ (60 mL) was added. This was stirred at room temperature over 5 days. The reaction mixture was then re-cooled to 0° C. 50% w/w $H_2SO_4$ (120 mL) was added slowly until the pH was 2, resulting in $CO_2$ evolution. This mixture was then washed with $CH_2Cl_2$ (2×300 mL). The aqueous layer was made basic with solid KOH. This was extracted into EtOAc (5×300 mL). The EtOAc layer was back-washed with brine, dried over $MgSO_4$, filtered, and concentrated under vacuum, yielding crude amine. This was treated with a solution of oxalic acid dihydrate (5.4 g) in 600 mL of ether. The solid was filtered off, washed with ether, then EtOH, then ether again to yield (1R,5S)-1,5-dimethyl-8-azabicyclo[3.2.1]octan-3-one hemi-oxalate (6.085 g, 27.2%) as an off-white solid.

$^1H$ NMR ($D_2O$) δ: 2.79 (d, J=12.5 Hz, 2H), 2.59 (d, J=12.5 Hz, 2H), 1.98-2.06 (m, 4H), 1.50 (s, 6H).

Step 2: (1R,5S)-1,5-Dimethyl-8-azabicyclo[3.2.1]octan-3-one hemi-oxalate (500 mg) was partitioned between dilute aqueous NaOH and $CH_2Cl_2$. The organic layer was dried over $MgSO_4$, filtered, and concentrated under vacuum to yield free base (1R,5S)-1,5-dimethyl-8-azabicyclo[3.2.1]octan-3-one (330 mg, 2.15 mmol) as a clear light orange liquid. This was dissolved in titanium isopropoxide (2.15 mL, 7.25 mmol) and benzyl methylamine (0.42 mL, 3.3 mmol), and stirred at room temperature for 15 h. The mixture was cooled to 0° C. MeOH (8.4 mL) was added, followed by $NaBH_4$ (195 mg, 5.15 mmol) in one portion. This was stirred at 0° C. for 1 h. A 50% solution (w/w) of KOH (0.8 mL) was added, and the mixture was then diluted in $CH_2Cl_2$ and filtered through Celite. $CH_2Cl_2$/MeOH was used to wash the product off the Celite pad. The filtrate was concentrated under vacuum. Purification by silica gel chromatography (9/1/0.1 $CH_2Cl_2$/MeOH/$NH_4OH$) yielded (1R,3S,5S)—N-benzyl-N,1,5-trimethyl-8-azabicyclo[3.2.1]octan-3-amine (413 mg, 74%).

$^1H$ NMR (methanol-$d_4$) δ: 7.25-7.40 (m, 5H), 3.61 (s, 2H), 2.92 (m, 1H), 2.23 (s, 3H), 1.72-1.77 (m, 2H), 1.55-1.70 (m, 4H), 1.48 (t, J=12 Hz, 2H), 1.29 (s, 6H).

Step 3: (1R,3S,5S)—N-Benzyl-N,1,5-trimethyl-8-azabicyclo[3.2.1]octan-3-amine (395 mg, 1.53 mmol) was dissolved in EtOH (10 mL). Pd/C (10%, 100 mg) and Pd(OH)$_2$ (20% on carbon, 100 mg) were added, and the mixture was hydrogenated at 50 psi for 1 h. The reaction mixture was then filtered through Celite. The filtrate was concentrated under vacuum. The concentrate was triturated with ethereal HCl, and the resultant solids were filtered and washed with ether to yield (1R,3s,5S)—N,1,5-trimethyl-8-azabicyclo[3.2.1]octan-3-amine dihydrochloride (281 mg, 76%) as a white solid.

$^1H$ NMR (methanol-$d_4$) δ: 3.66 (m, 1H), 2.77 (s, 3H), 2.31 (dd, J=14 Hz, 5.5 Hz, 2H), 2.10-2.20 (m, 2H), 1.97-2.07 (m, 2H), 1.94 (t, J=13 Hz, 2H), 1.58 (s, 6H).

Intermediate 3a

(1R,3r,5S)-1,5-Diethyl-N-methyl-8-azabicyclo[3.2.1]octan-3-amine

Intermediate 3a was prepared in a similar manner to Intermediate 3.

$^1H$ NMR (methanol-$d_4$) δ: 3.64 (m, 1H), 2.80 (s, 3H), 2.36 (dd, J=13.5, 4.5 Hz, 2H), 2.14 (m, 2H), 1.85-2.0 (m, 8H), 1.09 (t, J=7.5 Hz, 6H).

Intermediate 4

8-(Benzyloxy)-6-chloro-2-methylimidazo[1,2-b]pyridazine

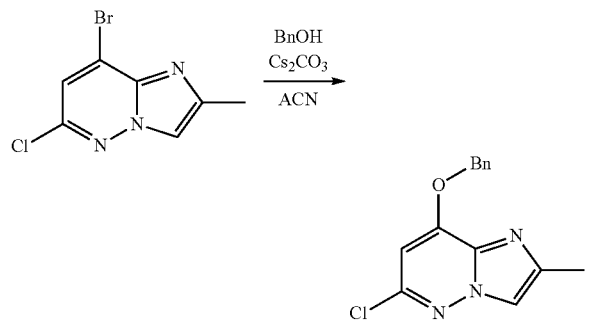

A mixture of 8-bromo-6-chloro-2-methyl-imidazo[1,2-b]pyridazine (100 mg, 0.41 mmol, 1.0 eq.), benzyl alcohol (89 mg, 0.085 mL, 0.81 mmol, 2.0 eq.) and $Cs_2CO_3$ (400 mg, 1.2 mmol, 3.0 eq.) in acetonitrile (1.0 mL) was stirred at 88° C. overnight, then cooled, diluted with ethyl acetate and filtered through Celite. The filtrate was concentrated and purified over silica with ethyl acetate in $CH_2Cl_2$ (0 to 10% gradient) to give 8-benzyloxy-6-chloro-2-methyl-imidazo[1,2-b]pyridazine (81 mg, 73%).

$^1$H NMR (CDCl$_3$) δ: 7.62 (d, J=0.6 Hz, 1H), 7.46-7.53 (m, 2H), 7.36-7.44 (m, 3H), 6.41 (s, 1H), 5.39 (s, 2H), 2.48 (d, J=0.6 Hz, 3H).

Using the procedures described above, additional intermediates described herein may be prepared by substituting the appropriate starting material, suitable reagents and reaction conditions, obtaining compounds such as those selected from:

| Structure | Name and Data |
|---|---|
| | 6-Chloro-N-(2,4-dimethoxybenzyl)-2-methylimidazo[1,2-b]pyridazin-8-amine<br>$^1$H NMR (CDCl$_3$) δ: 7.49 (d, J = 0.6 Hz, 1H), 7.18 (d, J = 8.2 Hz, 1H), 6.50 (d, J = 2.2 Hz, 1H), 6.46 (dd, J = 8.2, 2.2 Hz, 1H), 6.11 (br. s., 1H), 6.08 (s, 1H), 4.41 (d, J = 6.0 Hz, 2H), 3.86 (s, 3H), 3.83 (s, 3H), 2.41 (d, J = 0.9 Hz, 3H). |
| | 6-Chloro-8-methoxy-2-methylimidazo[1,2-b]pyridazine<br>$^1$H NMR (CDCl$_3$) δ: 7.61 (d, J = 0.9 Hz, 1H), 6.38 (s, 1H), 4.09 (s, 3H), 2.47 (d, J = 0.6 Hz, 3H). |
| | 6-Chloro-N,2-dimethylimidazo[1,2-b]pyridazin-8-amine<br>$^1$H NMR (CDCl$_3$) δ: 7.50 (d, J = 0.6 Hz, 1H), 5.90-6.04 (m, 2H), 3.03 (d, J = 5.0 Hz, 3H), 2.42 (d, J = 0.6 Hz, 3H). |
| | 6-Chloro-N,N,2-trimethylimidazo[1,2-b]pyridazin-8-amine<br>$^1$H NMR (CDCl$_3$) δ: 7.49 (d, J = 0.9 Hz, 1H), 5.84 (s, 1H), 3.50 (s, 6H), 2.42 (d, J = 0.6 Hz, 3H) |

233
Intermediate 5

Methyl 2-(6-chloro-2-methylimidazo[1,2-b]pyridazin-8-yl)acetate

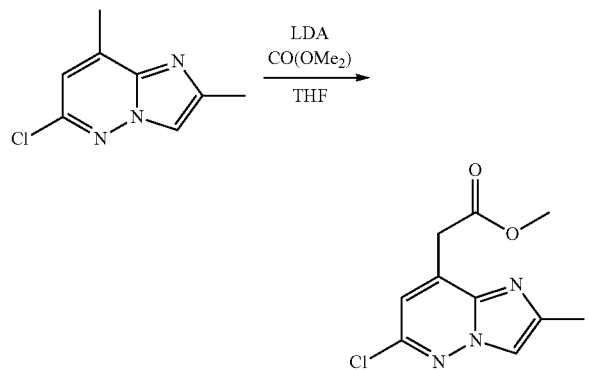

To a solution of 6-chloro-2,8-dimethyl-imidazo[1,2-b]pyridazine (50 mg, 0.28 mmol, 1.0 eq.) in THF (1.2 mL) cooled at −45° C. was added LDA (2.0 M) (0.17 mL, 0.33 mmol, 1.2 eq.) and the mixture was stirred at −45° C. for 30 min before dimethyl carbonate (38 mg, 0.035 mL, 0.41 mmol, 1.5 eq.) was added. After 30 min, the temperature was raised to 0° C. and the mixture was stirred for 2 h before being quenched with saturated NH$_4$Cl. The mixture was extracted with ethyl acetate, then dried and evaporated. The residue was purified over silica gel with methanol in dichloromethane (0 to 5% gradient) to give methyl 2-(6-chloro-2-methyl-imidazo[1,2-b]pyridazin-8-yl)acetate (48 mg, 0.20 mmol, 0.73 eq., 73%).

$^1$H NMR (CDCl$_3$) δ: 7.63 (d, J=0.6 Hz, 1H), 6.97 (s, 1H), 4.00 (d, J=0.6 Hz, 2H), 3.70 (s, 3H), 2.42 (s, 3H).

Intermediate 6

6-Chloro-2-methylimidazo[1,2-b]pyridazine-8-carbonitrile

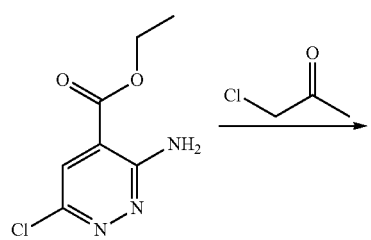

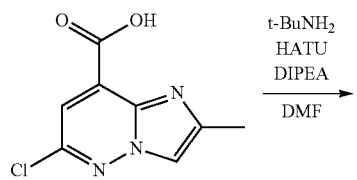

234

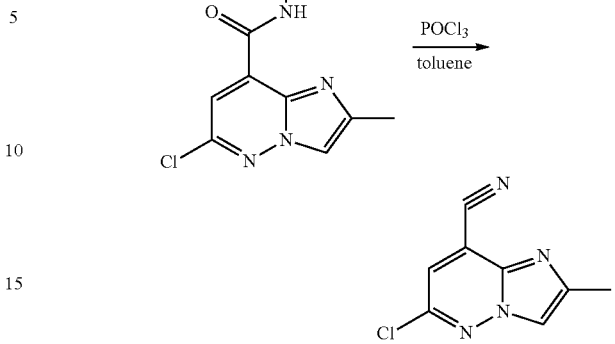

Step 1: A mixture of ethyl 3-amino-6-chloro-pyridazine-4-carboxylate (360 mg, 1.8 mmol, 1.0 eq.) and chloroacetone (3.0 mL) was stirred at 100° C. for 48 h, then cooled, diluted with ether and filtered. The solid was dissolved in methanol and purified with a C18 column to give 6-chloro-2-methyl-imidazo[1,2-b]pyridazine-8-carboxylic acid (150 mg, 40%).

$^1$H NMR (methanol-d$_4$) δ: 8.36 (br s, 1H), 8.24 (d, J=7.6 Hz, 1H), 2.64 (s, 3H).

Step 2: To a solution of 6-chloro-2-methyl-imidazo[1,2-b]pyridazine-8-carboxylic acid (150 mg, 0.71 mmol, 1.0 eq.) in DMF (4.0 mL) was added HATU (560 mg, 1.4 mmol, 2.0 eq.). After 10 min, tert-butylamine (78 mg, 0.11 mL, 1.1 mmol, 1.5 eq.) was added followed by DIPEA (280 mg, 0.37 mL, 2.1 mmol, 3.0 eq.). The mixture was then stirred at room temperature for 5 min at which time LC/MS showed a complete reaction. Aqueous work up followed by purification over silica gel with ethyl acetate in hexanes (2 to 20% gradient) provided N-tert-butyl-6-chloro-2-methyl-imidazo[1,2-b]pyridazine-8-carboxamide (111 mg, 59%).

$^1$H NMR (CDCl$_3$) δ: 9.82-9.95 (br. s., 1H), 7.81 (s, 1H), 7.76 (d, J=0.6 Hz, 1H), 2.52 (d, J=0.6 Hz, 3H), 1.56 (s, 9H).

Step 3: A mixture of N-tert-butyl-6-chloro-2-methyl-imidazo[1,2-b]pyridazine-8-carboxamide (102 mg, 0.382 mmol, 0.54 eq.) and POCl$_3$ (0.80 mL, 8.5 mmol, 12 eq.) in toluene (2.0 mL) was stirred at 110° C. for 48 h and then cooled and filtered. The solid was collected as pure 6-chloro-2-methyl-imidazo[1,2-b]pyridazine-8-carbonitrile (110 mg, 81%).

$^1$H NMR (CDCl$_3$) δ: 7.88 (s, 1H), 7.36 (s, 1H), 2.60 (d, J=0.6 Hz, 3H).

Intermediate 7 rac (3R,4R)-3-Fluoro-N,2,2,6,6-pentamethylpiperidin-4-amine

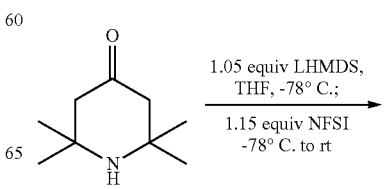

-continued

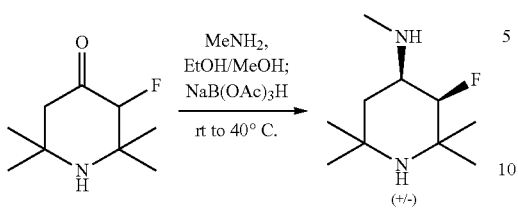

Step 1: To an oven-dried vial was added 2,2,6,6-tetramethylpiperidin-4-one (2.60 g, 16.78 mmol), which was cycled under nitrogen. THF (10 mL) was added, and the stirred reaction was cooled to −78° C. LHMDS (1 mol/L) in THF (17.7 mL, 17.7 mmol) was added dropwise over 5 min. The solution was stirred at −78° C. for 30 min. N-Fluorobenzenesulfonimide (6.13 g, 19.45 mmol) was added to the stirred solution at −78° C. portionwise over 5 min. Stirring was continued for 4 h at −78° C. then the reaction was allowed to warm slowly to 23° C. over 16 h. Methanol (20 mL) was added and the reaction was concentrated to dryness. The residue was purified by silica gel flash column chromatography with dichloromethane in methanol (0-10% gradient) to afford a white solid (1.26 g, 43%).

MS m/z 174.3 [M+H]$^+$; $^1$H NMR (methanol-d$_4$) δ: 4.77 (d, J=0.9 Hz, 1H), 2.60 (d, J=12.5 Hz, 1H), 2.42 (dd, J=12.8, 4.6 Hz, 1H), 1.32 (s, 3H), 1.29 (s, 3H), 1.22 (s, 3H), 1.15 (d, J=3.4 Hz, 3H).

Step 2: To an oven-dried vial was added 3-fluoro-2,2,6,6-tetramethyl-piperidin-4-one (601.4 mg, 3.47 mmol), followed by methanol (15 mL) and methylamine (33 mass % in ethanol) (6 mL, 48.2 mmol). This solution was stirred at 23° C. for 45 min. To this solution was added sodium triacetoxyborohydride (3.01 g, 14.2 mmol) portionwise at room temperature and the solution was stirred for 3 h. The temperature was increased to 40° C. and another portion of sodium triacetoxyborohydride (4.0 equiv., 13.8 mmol) was added portionwise, followed by another 3 h of stirring at 40° C. A third portion of sodium triacetoxyborohydride (4.0 equiv., 13.8 mmol) was added portionwise while stirring at 40° C. and the reaction was allowed to continue stirring at 40° C. for 16 h. The reaction was concentrated to dryness. The residue was partitioned between dichloromethane/methanol (9/1) and sodium hydroxide solution (1.0 N, aqueous). The layers were separated, and the aqueous layer was subsequently extracted once with dichloromethane/methanol (9/1) and then twice with dichloromethane. The combined organic layers were dried over sodium sulfate, filtered and concentrated to afford a light tan solid in a brown liquid that solidified completely after sitting for 2-3 weeks (519.3 mg, 79%).

MS m/z 189.3 [M+H]$^+$; $^1$H NMR (methanol-d$_4$) δ: 4.42 (dd, J=50.7, 1.2 Hz, 1H), 3.01 (dddd, J=30.2, 12.5, 4.3, 1.5 Hz, 1H), 2.48 (s, 3H), 1.70 (dd, J=12.8, 4.3 Hz, 1H), 1.36 (t, J=12.7 Hz, 1H), 1.24 (s, 3H), 1.23 (d, J=1.8 Hz, 3H), 1.20 (d, J=2.4 Hz, 3H), 1.19 (s, 3H), NH protons not observed.

Intermediate 8

Rac (1S,2R,3R,5R)-2-Fluoro-N,1,5-trimethyl-8-azabicyclo[3.2.1]octan-3-amine

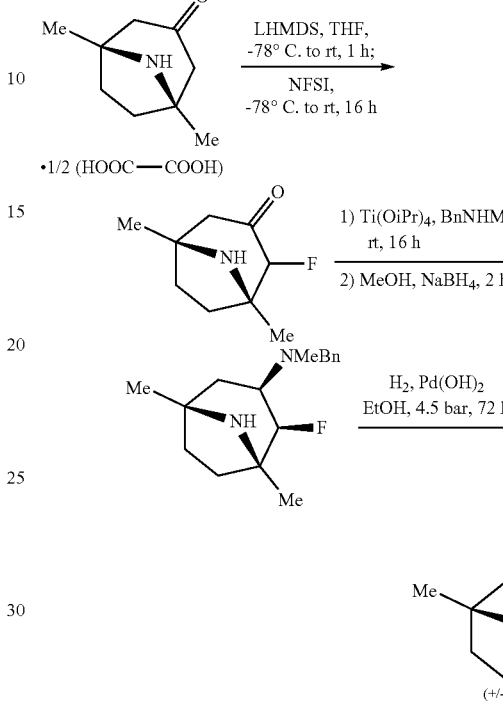

Step 1: To an oven-dried vial was added 1,5-dimethyl-8-azabicyclo[3.2.1]octan-3-one ½ oxalate (491 mg, 2.87 mmol, 1.0 eq.) and THF (5 mL), which was cooled to −78° C. Lithium bis(trimethylsilyl)amide (1.0 M in THF, 11 mL, 11.0 mmol, 3.83 eq.) was added dropwise, and then the suspension was allowed to warm to room temperature over 1 h. The suspension was cooled to −78° C. and then N-fluorobenzenesulfonimide (1.98 g, 6.27 mmol, 2.18 eq.) was added portionwise. After complete addition, the reaction was warmed to room temperature over 16 h. The reaction was concentrated under reduced pressure, and then the solid was triturated with CH$_2$Cl$_2$/MeOH (1:1). The suspension was filtered and the orange filtrate was concentrated. The residue was purified by column chromatography eluting with 0-40% MeOH in CH$_2$Cl$_2$ to yield impure racemic 4-fluoro-1,5-dimethyl-8-azabicyclo[3.2.1]octan-3-one (491.3 mg, 57% by mass). MS m/z 172.3 [M+H]$^+$.

Step 2: To an oven-dried vial was added impure racemic 4-fluoro-1,5-dimethyl-8-azabicyclo[3.2.1]octan-3-one (373 mg, 2.18 mmol, 1.0 eq.), followed by titanium(IV) isopropoxide (3.4 mL, 11 mmol, 5.2 eq.) and N-methyl-1-phenylmethylamine (0.71 mL, 5.5 mmol, 2.5 eq.). The reaction was stirred at room temperature for 16 h. Methanol (10 mL) was added, followed by sodium borohydride (802 mg, 20.7 mmol, 9.53 eq.). Stirring was continued for 2 h at room temperature. The reaction was quenched with aqueous sodium hydroxide (0.2 N, 35 mL). The reaction was then diluted with CH$_2$Cl$_2$/MeOH (9:1) and filtered through Celite to remove the emulsions. The layers were then separated, and the aqueous layer was extracted twice with CH$_2$Cl$_2$/MeOH (9:1). The combined organic phases were dried over sodium sulfate, filtered and concentrated. The residue was purified by column chromatography, eluting with 0-15% MeOH in CH₂Cl₂ to yield rac (1S,3S,4S,5R)—N-benzyl-4-fluoro-N,1,5-trimethyl-8-azabicyclo[3.2.1]octan-3-amine (40.5 mg, 7%).

MS m/z 277.4 [M+H]⁺; ¹H NMR (methanol-d₄) δ: 7.23-7.42 (m, 5H), 4.60 (dd, J=50.7, 2.4 Hz, 1H), 3.78 (d, J=13.1 Hz, 1H), 3.70 (d, J=13.4 Hz, 1H), 2.85 (dddd, J=36.0, 10.1, 8.2, 2.4 Hz, 1H), 2.34 (s, 3H), 1.77 (br d, J=9.2 Hz, 2H), 1.65-1.71 (m, 2H), 1.56-1.64 (m, 2H), 1.33 (d, J=2.4 Hz, 6H); 1 NH not observed.

Step 3: Rac (1S,3S,4S,5R)—N-Benzyl-4-fluoro-N,1,5-trimethyl-8-azabicyclo[3.2.1]octan-3-amine (40.5 mg, 0.147 mmol, 1.0 eq.), palladium hydroxide (20% w/w on carbon)(19.4 mg, 0.0276 mmol, 0.19 eq.), and ethanol (5 mL) were combined and shaken under a hydrogen atmosphere at 4.5 atm for 72 h. The reaction was filtered through Celite, and rinsed with EtOH. The filtrate was concentrated to yield rac (1S,3S,4S,5R)-4-fluoro-N,1,5-trimethyl-8-azabicyclo[3.2.1]octan-3-amine (23.3 mg, 85%).

MS m/z 187.3 [M+H]⁺; ¹H NMR (methanol-d₄) δ: 4.40 (dd, J=50.7, 3.1 Hz, 1H), 2.93 (dddd, J=30.5, 12.2, 6.1, 3.1 Hz, 1H), 2.41 (s, 3H), 1.77 (dd, J=13.0, 6.0 Hz, 1H), 1.62-1.71 (m, 2H), 1.53-1.61 (m, 2H), 1.27-1.32 (m, 1H), 1.24 (s, 3H), 1.19 (s, 3H); 2 NHs not observed.

Intermediate 9

(±) 2,4-trans tert-Butyl 2-[[tert-butyl(dimethyl)silyl]oxymethyl]-4-(methylamino)piperidine-1-carboxylate

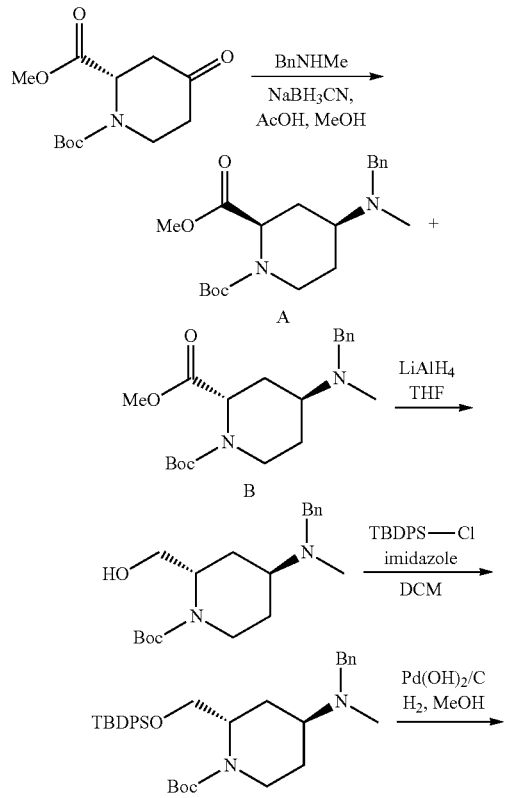

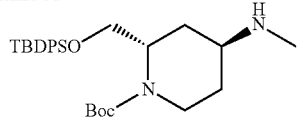

Step 1: (±) 1-(tert-Butyl) 2-methyl (R)-4-oxopiperidine-1,2-dicarboxylate (10 g, 38.9 mmol) was dissolved in MeOH (50 mL). N-Methylbenzylamine (8 mL, 62 mmol) was added, followed by acetic acid (1 mL, 17.4 mmol). The reaction was stirred at room temperature for 1 h. After cooling the mixture to 0° C., NaBH₃CN (3.7 g, 59 mmol) was added in one portion. The reaction was warmed to room temperature and stirred for 15 h. The mixture was partitioned between EtOAc and H₂O. The organic layer was dried over MgSO₄, filtered, and then concentrated under vacuum. Purification by silica chromatography (20-50% EtOAc in hexanes) yielded (±)1-(tert-butyl) 2-methyl (cis)-4-(benzyl(methyl)amino)piperidine-1,2-dicarboxylate (A) (3.96 g, 28%) as the second-highest major component on TLC (when visualized with iodine stain), and (±) 1-(tert-butyl) 2-methyl (trans)-4-(benzyl(methyl)amino)piperidine-1,2-dicarboxylate (B) (2.49 g, 18%) as the lowest major non-baseline TLC component.

A: ¹H NMR (methanol-d₄) δ: 7.20-7.40 (m, 5H), 4.49 (m, 1H), 3.70-3.85 (m, 2H), 3.67 (s, 3H), 3.35-3.50 (m, 1H), 3.30 (m, 1H), 2.45-2.60 (m, 2H), 2.10 (m, 1H), 2.07 (s, 3H), 1.93-2.00 (m, 1H), 1.70-1.78 (m, 1H), 1.47 (s, 9H).

B: ¹H NMR (methanol-d₄) 1:1 mixture of rotamers δ: 7.33 (d, J=4.3 Hz, 4H), 7.23-7.29 (m, 1H), 4.89-4.99 (m, 1H), 4.03-4.09 (m, 1H), 3.67-3.72 (m, 3H), 3.63 (s, 2H), 2.84-3.05 (m, 1H), 2.39-2.50 (m, 2H), 2.23 (s, 3H), 1.70-1.92 (m, 2H), 1.51-1.57 (m, 1H), 1.46 (br d, 9H)

Step 2: The (±) 2,4-trans 01-tert-butyl 02-methyl 4-[benzyl(methyl)amino]piperidine-1,2-dicarboxylate (2.49 g, 6.87 mmol) was dissolved in anhydrous THF (45 mL) in an oven-dried 100-mL round-bottomed flask. An oven-dried Teflon-coated stir bar was added. The tube was fitted with a septum cap and the headspace was swept with dry N₂. The flask was then submerged in an ice bath and the reaction mixture was cooled to 0° C. A 1.0 M solution of LiAlH₄ in THF (6.3 mL, 6.3 mmol, 0.92 eq.) was added dropwise, under N₂, at room temperature and the reaction mixture (a clear solution) was stirred at 0° C. for 1 h. The reaction mixture was then diluted with anhydrous Et₂O (20 mL) and quenched by the Fieser method with vigorous stirring, at 0° C., under sweeping N₂. The reaction mixture was then stirred at room temperature for 1 h. The reaction mixture was then filtered through Celite (45×15 mm bed), and the Celite was washed with 1:1 Et₂O/EtOAc (150 mL). The clear, colorless filtrate was concentrated on a rotovap, then under high vacuum (0.3 mm Hg, room temperature) to afford crude (±) 2,4-trans tert-butyl 4-[benzyl(methyl)amino]-2-(hydroxymethyl)piperidine-1-carboxylate (2.22 g, 97% yield) as a clear, light-amber, flowing oil.

¹H NMR (CDCl₃) δ: 7.34-7.27 (m, 4H), 7.26-7.21 (m, 1H), 4.49 (d, J=50.4 Hz, 1H), 4.13 (d, J=56.5 Hz, 1H), 3.73 (t, J=10.0 Hz, 1H), 3.63-3.48 (m, 3H), 2.95-2.77 (m, 1H), 2.71 (t, J=11.8 Hz, 1H), 2.18 (s, 3H), 1.89 (d, J=13.1 Hz, 1H), 1.81 (d, J=10.5 Hz, 1H), 1.65 (td, J=12.8, 6.2 Hz, 1H), 1.52-1.40 (m, 10H); OH proton not observed.

Step 3: A 100-mL, round-bottom flask was charged with a solution of (±) 2,4-trans tert-butyl 4-[benzyl(methyl)amino]-2-(hydroxymethyl)piperidine-1-carboxylate (2.22 g, 6.64 mmol) in CH₂Cl₂ (50 mL), a Teflon-coated stir bar, and crystalline imidazole (0.610 g, 8.96 mmol, 1.35 eq.). Once the imidazole had completely dissolved, tert-butyldiphenylchlorosilane (1.90 mL, 7.33 mmol, 1.10 eq.) was added to the solution, eliciting precipitation within ~5 minutes. The reaction mixture was stirred gently at room temperature for 1 h. After this time, the reaction mixture was diluted with $CH_2Cl_2$ (30 mL), transferred to a 125 mL separatory funnel, and washed with water (50 mL) and sat. aq. $NaHCO_3$ (50 mL). The organic phase was then dried over anhydrous $Na_2SO_4$, filtered, and the clear colorless filtrate was concentrated on a rotovap to afford a thick, clear, colorless oil. The crude product was purified by silica gel column chromatography on an ISCO system: 80-g silica gel cartridge ($CH_2Cl_2$-equilibrated), $CH_2Cl_2$ isocratic elution (10 minutes) followed by $CH_2Cl_2$/EtOAc gradient elution (1:0 to 1:9 over 40 minutes, 60 mL/min), 50-mL fractions. The product-containing fractions were combined and concentrated on a rotovap and further dried under high vacuum (0.3 mm Hg, room temperature, overnight) to afford (±) 2,4-trans tert-butyl 4-[benzyl(methyl)amino]-2-[[tert-butyl(diphenyl)silyl]oxymethyl]piperidine-1-carboxylate (2.76 g, 73% yield) as a clear, colorless, viscous oil.

$^1$H NMR (CDCl$_3$) δ: 7.66 (d, J=7.0 Hz, 4H), 7.45-7.36 (m, 6H), 7.36-7.26 (m, 4H), 7.26-7.20 (m, 1H), 4.74-4.36 (m, 1H), 4.24-3.93 (m, 1H), 3.73-3.45 (m, 4H), 2.88-2.59 (m, 2H), 2.32-2.05 (m, 4H), 1.86-1.68 (m, 1H), 1.68-1.54 (m, 1H), 1.53-1.37 (m, 10H), 1.06 (s, 9H).

Step 4: The (±) 2,4-trans tert-butyl 4-[benzyl(methyl)amino]-2-[[tert-butyl(diphenyl)silyl]oxymethyl]piperidine-1-carboxylate (2.35 g, 4.10 mmol), was dissolved in MeOH (30 mL) in a 100-mL Parr bomb reactor. The solution was sparged with argon for 5 minutes, then 20% Pd(OH)$_2$/C (0.30 g, 0.43 mmol, 0.10 eq.) was added. The bomb was fitted to a Parr shaker apparatus, purged with H$_2$ (5×20 psi), then charged to a final H$_2$ pressure of 50 psi. The reaction mixture was shaken at room temperature for 50 h. The reaction mixture was then filtered through a 45×20 mm bed of Celite, and the Celite bed was washed with MeOH (200 mL). The clear, colorless filtrate was concentrated on a rotovap to afford a clear, very light amber oil. The crude product was purified by Kugelrohr distillation (260° C., 0.8 mm Hg) to afford the desired (±) 2,4-trans tert-butyl 2-[[tert-butyl(dimethyl)silyl]oxymethyl]-4-(methylamino)piperidine-1-carboxylate (1.22 g, 83% yield) as a clear, colorless, thick oil.

$^1$H NMR (CDCl$_3$) δ 7.70-7.60 (m, 4H), 7.47-7.34 (m, 6H), 4.63-4.31 (m, 1H), 4.20-3.87 (m, 1H), 3.73-3.59 (m, 2H), 2.70 (br s, 1H), 2.56 (br s, 1H), 2.41 (s, 3H), 2.20 (br s, 1H), 1.83 (br s, 1H), 1.42 (s, 9H), 1.31-1.19 (m, 2H), 1.05 (s, 9H).

Example 1

Preparation of Compound 186

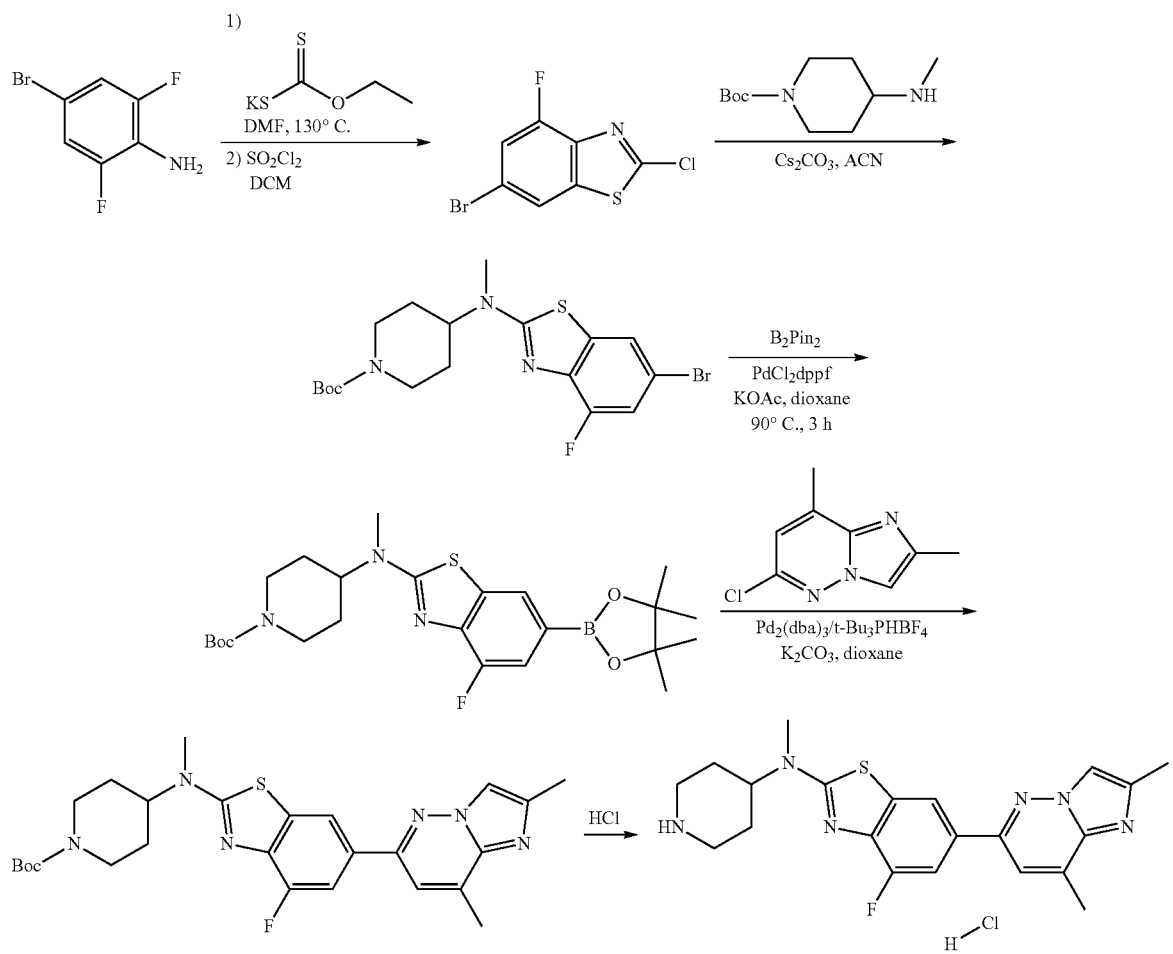

Step 1: A mixture of 4-bromo-2,6-difluoro-aniline (4.16 g, 20.0 mmol, 1.00 eq.) and ethoxycarbothioylsulfanyl potassium (7.69 g, 48.0 mmol, 2.40 eq.) in DMF (25 mL) was stirred at 130° C. overnight, then cooled to room temperature, diluted with 1 N HCl (150 mL) and stirred at room temperature for 1 h. The resulting solid was filtered and washed with water and dried. The resulting material was suspended in $CH_2Cl_2$ (25 mL) and $SO_2Cl_2$ (27.5 g, 16.5 mL, 200 mmol, 10.0 eq.) was added slowly and stirred at room temperature for 48 h. Water was added slowly at 0° C. to quenched the reaction. The resulting precipitate was collected by filtration and purified over silica with ethyl acetate in hexanes (2 to 10% gradient) to give 6-bromo-2-chloro-4-fluoro-1,3-benzothiazole (5.08 g, 95.3%). MS m/z 266.1, 268.0, 270.0 $[M+H]^+$.

Step 2: A mixture of 4-(methylamino)piperidine-1-carboxylate (88 mg, 0.41 mmol, 1.1 eq.), 6-bromo-2-chloro-4-fluoro-1,3-benzothiazole (100 mg, 0.38 mmol, 1.0 eq.) and $Cs_2CO_3$ (240 mg, 0.75 mmol, 2.0 eq.) in acetonitrile (1.0 mL) was stirred at 90° C. overnight, then cooled, diluted with ethyl acetate and concentrated. The residue was purified over silica with ethyl acetate in hexanes (2 to 10% gradient) to give tert-butyl 4-[(6-bromo-4-fluoro-1,3-benzothiazol-2-yl)-methyl-amino]piperidine-1-carboxylate (94 mg, 56%). MS m/z 388.2, 390.0 $[M+H]^+$.

Step 3: A mixture of tert-butyl 4-[(6-bromo-4-fluoro-1,3-benzothiazol-2-yl)-methyl-amino]piperidine-1-carboxylate (94 mg, 0.21 mmol, 1.0 eq.), $B_2Pin_2$ (81 mg, 0.32 mmol, 1.5 eq.), $PdCl_2(dppf)$ (16 mg, 0.021 mmol, 0.10 eq.) and KOAc (63 mg, 0.63 mmol, 3.0 eq.) in dioxane (2.0 mL) was stirred at 90° C. for 3 h under an Ar atmosphere, then cooled, diluted with ethyl acetate and concentrated. The residue was purified over silica with ethyl acetate in hexanes (3 to 50% gradient) to give tert-butyl 4-[[4-fluoro-6-(4,4,5,5-tetramethyl-1,3,2-dioxaborolan-2-yl)-1,3-benzothiazol-2-yl]-methyl-amino]piperidine-1-carboxylate (96 mg, 92%). MS m/z 492.1 $[M+H]^+$.

Step 4: A mixture of tert-butyl 4-[[4-fluoro-6-(4,4,5,5-tetramethyl-1,3,2-dioxaborolan-2-yl)-1,3-benzothiazol-2-yl]-methyl-amino]piperidine-1-carboxylate (48 mg, 0.1 mmol, 1.1 eq.), 6-chloro-2,8-dimethyl-imidazo[1,2-b]pyridazine (16 mg, 0.088 mmol, 1.0 eq.), $Pd_2(dba)_3$ (4.1 mg, 0.0044 mmol, 0.05 eq.), $(t-Bu)_3P·HBF_4$ (2.6 mg, 0.0088 mmol, 0.1 eq.) and 2.0 M aq. $K_2CO_3$ (0.13 mL, 0.26 mmol, 3.0 eq.) in dioxane (1.0 mL) was stirred at 90° C. for 3 h under an Ar atmosphere, then cooled and diluted with ethyl acetate. The mixture was washed with water, brine and the organic layer was dried over sodium sulfate and evaporated. The residue was purified over silica gel with ethyl acetate in dichloromethane (10 to 100% gradient) to provide tert-butyl 4-[[6-(2,8-dimethylimidazo[1,2-b]pyridazin-6-yl)-4-fluoro-1,3-benzothiazol-2-yl]-methyl-amino]piperidine-1-carboxylate (12 mg, 27%). MS m/z 511.4 $[M+H]^+$.

Step 5: To a solution of tert-butyl 4-[[6-(2,8-dimethylimidazo[1,2-b]pyridazin-6-yl)-4-fluoro-1,3-benzothiazol-2-yl]-methyl-amino]piperidine-1-carboxylate in $CH_2Cl_2$ (1.0 mL) was added TFA (1.0 mL). The mixture was stirred at room temperature for 1 h and then the organic volatiles were removed by a stream of nitrogen. The residue was purified by C18 chromatography to give 6-(2,8-dimethylimidazo[1,2-b]pyridazin-6-yl)-4-fluoro-N-methyl-N-(4-piperidyl)-1,3-benzothiazol-2-amine hydrochloride (24 mg) after treatment with HCl in ether.

MS m/z 411.4 $[M+H]^+$; $^1H$ NMR (methanol-$d_4$) δ: 8.41 (s, 1H), 8.31 (d, J=0.9 Hz, 1H), 8.28 (d, J=0.9 Hz, 1H), 7.95-8.01 (m, 1H), 4.67-4.77 (m, 1H), 3.57-3.64 (m, 2H), 3.24-3.31 (m, 2H), 3.23 (s, 3H), 2.80 (d, J=0.6 Hz, 3H), 2.67 (d, J=0.9 Hz, 3H), 2.09-2.29 (m, 4H).

Using the procedure described for Example 1, above, additional compounds described herein were prepared by substituting the appropriate starting material, suitable reagents and reaction conditions, obtaining compounds such as those selected from:

| Cpd | Data |
|-----|------|
| 132 | MS m/z 411.2 $[M + H]^+$; $^1H$ NMR (DMSO-$d_6$) δ: 9.59-9.70 (m, 1H), 9.22-9.34 (m, 1H), 8.51 (d, J = 1.6 Hz, 1H), 8.36 (s, 1H), 8.21 (br. s., 1H), 7.96 (dd, J = 12.3, 1.6 Hz, 1H), 4.20-4.32 (m, 2H), 3.50 (br. s., 2H), 3.31 (dd, J = 13.6, 11.7 Hz, 2H), 2.70 (d, J = 0.6 Hz, 3H), 2.54 (s, 3H), 1.37 (d, J = 6.6 Hz, 6H). |
| 164 | MS m/z 411.3 $[M + H]^+$; $^1H$ NMR (methanol-$d_4$) δ: 8.23 (s, 1H), 8.18 (s, 1H), 8.12 (s, 1H), 7.76-7.81 (m, 1H), 7.61 (s, 1H), 4.60-4.67 (m, 1H), 3.40-3.48 (m, 1H), 3.28-3.39 (m, 1H), 3.09-3.17 (m, 1H), 3.05 (s, 3H), 2.53 (s, 3H), 1.98-2.05 (m, 3H), 1.79-1.89 (m, 1H), 1.31 (d, J = 6.3 Hz, 3H). |
| 165 | MS m/z 425.4 $[M + H]^+$; $^1H$ NMR (methanol-$d_4$) δ: 8.23 (d, J = 1.6 Hz, 1H), 8.15 (d, J = 0.9 Hz, 1H), 8.11 (d, J = 1.3 Hz, 1H), 7.80 (dd, J = 12.1, 1.7 Hz, 1H), 4.57-4.68 (m, 1H), 3.43-3.48 (m, 1H), 3.32-3.40 (m, 1H), 3.10-3.17 (m, 1H), 3.05 (s, 3H), 2.65 (d, J = 0.9 Hz, 3H), 2.52 (d, J = 0.9 Hz, 3H), 1.96-2.09 (m, 3H), 1.77-1.87 (m, 1H), 1.30 (d, J = 6.3 Hz, 3H). |
| 185 | MS m/z 397.3 $[M + H]^+$; $^1H$ NMR (methanol-$d_4$) δ: 8.27-8.34 (m, 3H), 8.21 (s, 1H), 7.88 (d, J = 11.7 Hz, 1H), 4.51 (br. s., 1H), 3.42-3.52 (m, 2H), 3.10-3.20 (m, 5H), 2.53 (s, 3H), 2.01-2.22 (m, 4H). |
| 192 | MS m/z 437.4 $[M + H]^+$; $^1H$ NMR (methanol-$d_4$) δ: 8.29 (s, 1H), 8.17 (s, 1H), 8.14 (s, 1H), 7.85 (d, J = 12.0 Hz, 1H), 4.60-4.72 (m, 1H), 4.05 (br s, 2H), 3.11 (s, 3H), 2.66 (s, 3H), 2.51-2.59 (m, 5H), 2.04-2.17 (m, 4H), 1.90-1.98 (m, 2H). |
| 202 | MS m/z 427.2 $[M + H]^+$; $^1H$ NMR (methanol-$d_4$) δ: 8.28 (d, J = 1.6 Hz, 1H), 8.11 (d, J = 1.3 Hz, 1H), 7.83 (dd, J = 12.0, 1.6 Hz, 1H), 7.65 (s, 1H), 4.55-4.64 (m, 1H), 4.24 (s, 3H), 3.46 (d, J = 12.9 Hz, 2H), 3.14 (td, J = 12.9, 3.2 Hz, 2H), 3.07 (s, 3H), 2.49 (d, J = 0.9 Hz, 3H), 1.97-2.15 (m, 4H). |
| 209 | MS m/z 423.4 $[M + H]^+$; $^1H$ NMR (methanol-$d_4$) δ: 8.25 (d, J = 1.9 Hz, 1H), 8.23 (s, 2H), 8.16 (d, J = 0.9 Hz, 1H), 7.83 (dd, J = 12.0, 1.6 Hz, 1H), 4.75 (m, 1H), 4.06 (br. s., 2H), 3.04 (s, 3H), 2.47 (d, J = 0.9 Hz, 3H), 2.13-2.25 (m, 2H), 2.08 (br s, 4H), 1.86-1.95 (m, 2H). |
| 225 | MS m/z 410.4 $[M + H]^+$; $^1H$ NMR (CDCl$_3$) δ: 7.66 (d, J = 1.6 Hz, 1H), 7.55 (d, J = 1.3 Hz, 2H), 7.35 (dd, J = 12.0, 1.6 Hz, 1H), 6.94 (s, 1H), 4.18-4.35 (m, 1H), 3.30 (d, J = 12.3 Hz, 2H), 3.14 (s, 3H), 2.86 (td, J = 12.1, 2.8 Hz, 2H), 2.70 (s, 3H), 2.41 (d, J = 0.6 Hz, 3H), 1.83-1.94 (m, 4H). |

| Cpd | Data |
|---|---|
| 226 | MS m/z 421.3 [M + H]⁺; ¹H NMR (methanol-d₄) δ: 9.18 (d, J = 1.6 Hz, 1H), 8.66 (d, J = 1.6 Hz, 1H), 7.99 (d, J = 1.3 Hz, 1H), 7.84 (d, J = 1.6 Hz, 1H), 7.41-7.47 (m, 1H), 4.44-4.54 (m, 1H), 3.37-3.45 (m, 2H), 3.04-3.11 (m, 2H), 3.03 (s, 3H), 2.45 (d, J = 0.9 Hz, 3H), 1.94-2.09 (m, 4H). |
| 231 | MS m/z 422.4 [M + H]⁺; ¹H NMR (methanol-d₄) δ: 8.80-8.84 (m, 1H), 8.41-8.43 (m, 1H), 8.38-8.40 (m, 1H), 7.93-8.00 (m, 1H), 4.70-4.77 (m, 1H), 3.56-3.63(m, 2H), 3.23-3.30 (m, 2H), 3.21 (s, 3H), 2.67 (s, 3H), 2.13-2.27 (m, 4H). |
| 235 | MS m/z 448.5 [M + H]⁺; ¹H NMR (methanol-d₄) δ: 8.81-9.09 (m, 1H), 8.46 (br s, 2H), 7.98 (br s, 1H), 4.90 (m, 1H), 4.23 (br s, 2H), 3.20 (br s, 3H), 2.71 (br s, 3H), 1.92-2.44 (m, 8H). |
| 236 | MS m/z 466.4 [M + H]⁺; ¹H NMR (methanol-d₄) δ: 8.67 (s, 1H), 8.31-8.34 (m, 1H), 8.24-8.27 (m, 1H), 7.86-7.92 (m, 1H), 4.84-4.95 (m, 1H), 4.07-4.14 (m, 2H), 3.05 (s, 3H), 2.55 (d, J = 0.6 Hz, 3H), 2.14 (br s, 6H), 1.92-1.99 (m, 2H). |
| 237 | MS m/z 423.4 [M + H]⁺; ¹H NMR (methanol-d₄) δ: 8.88 (d, J = 8.8 Hz, 1H), 8.82 (s, 1H), 8.36 (s, 1H), 8.21 (d, J = 8.8 Hz, 1H), 7.92 (d, J = 11.3 Hz, 1H), 4.95 (m, 1H), 4.43 (s, 3H), 4.24 (br s, 2H), 3.22 (s, 3H), 2.39 (br s, 2H), 2.26 (s, 4H), 2.08 (d, J = 10.7 Hz, 2H). |
| 248 | MS m/z 383.3 [M + H]⁺; ¹H NMR (methanol-d₄) δ: 8.43 (d, J = 1.9 Hz, 1H), 8.30 (d, J = 0.9 Hz, 1H), 8.26 (d, J = 1.3 Hz, 1H), 7.97 (dd, J = 11.8, 1.7 Hz, 1H), 5.24 (t, J = 8.0 Hz, 1H), 4.62-4.72 (m, 2H), 4.39-4.51 (m, 2H), 3.33 (s, 3H), 2.79 (d, J = 0.9 Hz, 3H), 2.60-2.71 (m, 3H). |
| 250 | MS m/z 397.1 [M + H]⁺; ¹H NMR (methanol-d₄) δ: 8.72 (d, J = 7.6 Hz, 1H), 8.28 (d, J = 1.6 Hz, 1H), 7.85-7.91 (m, 1H), 7.41 (d, J = 7.6 Hz, 1H), 6.45 (s, 1H), 4.45-4.56 (m, 1H), 3.42-3.50 (m, 2H), 3.10 (s, 5H), 2.39 (s, 3H), 2.00-2.14 (m, 4H). |
| 258 | MS m/z 411.2 [M + H]⁺; ¹H NMR (methanol-d₄) δ: 8.25-8.32 (m, 3H), 8.20 (s, 1H), 7.86 (d, J = 12.0 Hz, 1H), 4.54 (br. s., 1H), 3.45 (m, 1H), 3.33-3.42 (m, 1H), 3.07-3.16 (m, 4H), 2.52 (s, 3H), 1.99-2.11 (m, 3H), 1.88 (m, 1H), 1.31 (d, J = 6.3 Hz, 3H). |
| 259 | MS m/z 411.2 [M + H]⁺; ¹H NMR (methanol-d₄) δ: 8.26-8.32 (m, 3H), 8.21 (s, 1H), 7.86 (dd, J = 12.0, 0.9 Hz, 1H), 4.54 (br s, 1H), 3.89 (br s, 1H), 3.37 (d, J = 2.8 Hz, 1H), 3.30 (br. s., 1H), 3.09 (s, 3H), 2.53 (s, 3H), 2.26 (m, 1H), 2.04 (m, 2H), 1.89 (d, J = 13.9 Hz, 1H), 1.47 (d, J = 6.9 Hz, 3H). |

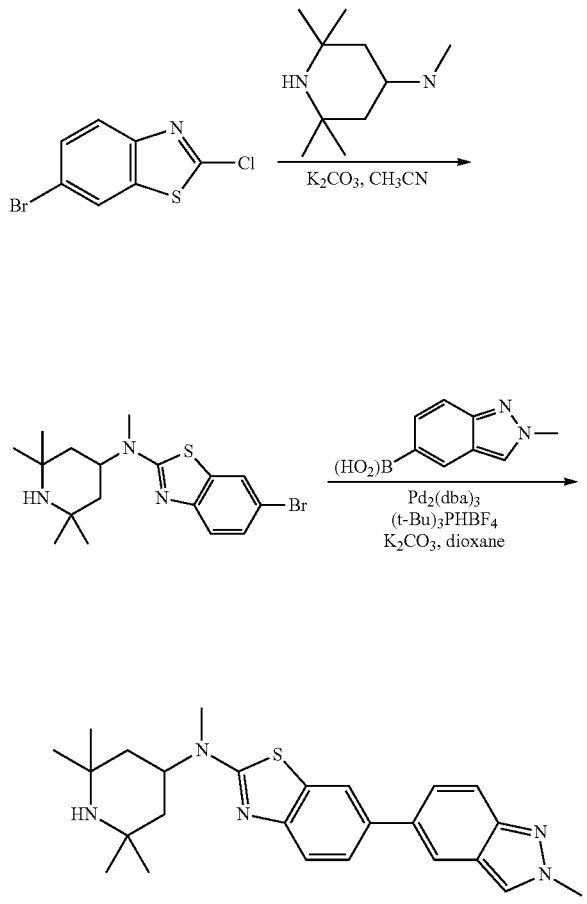

Example 2

Preparation of Compound 20

Step 1: A mixture of 6-bromo-2-chloro-1,3-benzothiazole (600 mg, 2.4 mmol, 1.0 eq.), N,2,2,6,6-pentamethylpiperidin-4-amine (490 mg, 0.54 mL, 2.9 mmol, 1.2 eq.) and K₂CO₃ (1000 mg, 7.2 mmol, 3.0 eq.) in acetonitrile (6.0 mL) was stirred at 100° C. overnight, and then cooled, diluted with ethyl acetate and filtered. The filtrate was concentrated to give 6-bromo-N-methyl-N-(2,2,6,6-tetramethyl-4-piperidyl)-1,3-benzothiazol-2-amine, which was used without further purification.

Step 2: A mixture of 6-bromo-N-methyl-N-(2,2,6,6-tetramethyl-4-piperidyl)-1,3-benzothiazol-2-amine (60 mg, 0.16 mmol, 1.0 eq.), (2-methylindazol-5-yl)boronic acid (36 mg, 0.20 mmol, 1.3 eq.), Pd₂(dba)₃ (7.3 mg, 0.0078 mmol, 0.050 eq.), (t-Bu)₃P HBF₄ (4.6 mg, 0.016 mmol, 0.10 eq.) and K₂CO₃ (2.0 M aq.) (0.24 mL, 0.47 mmol, 3.0 eq.) in dioxane (1.0 mL) was stirred at 100° C. for 1 h, and then cooled, diluted with ethyl acetate and washed with water and brine. The organic layer was separated, dried over sodium sulfate and evaporated. The residue was purified over basic alumina with ethyl acetate in hexanes (10 to 100% gradient) to provide N-methyl-6-(2-methylindazol-5-yl)-N-(2,2,6,6-tetramethyl-4-piperidyl)-1,3-benzothiazol-2-amine (57 mg, 84%).

MS m/z 434.4 [M+H]⁺; ¹H NMR (CDCl₃) δ: 7.85 (s, 1H), 7.78 (d, J=1.3 Hz, 1H), 7.73-7.75 (m, 1H), 7.68 (d, J=9.1 Hz, 1H), 7.47-7.55 (m, 3H), 4.20-4.34 (m, 1H), 4.17 (s, 3H), 3.04 (s, 3H), 1.74 (dd, J=12.5, 3.3 Hz, 2H), 1.36 (d, J=10.7 Hz, 2H), 1.27-1.33 (m, 6H), 1.10-1.21 (m, 6H).

Using the procedure described for Example 2, above, additional compounds described herein were prepared by substituting the appropriate starting material, suitable reagents and reaction conditions, obtaining compounds such as those selected from:

| Cpd | Data |
|---|---|
| 7 | ¹H NMR (DMSO-d$_6$) δ: 8.36 (s, 1H), 8.10 (d, J = 1.9 Hz, 1H), 7.94 (d, J = 0.6 Hz, 1H), 7.63-7.68 (m, 1H), 7.59 (ddd, J = 10.8, 8.7, 1.9 Hz, 2H), 7.50 (d, J = 8.2 Hz, 1H), 4.18 (s, 3H), 3.47-3.54 (m, 4H), 2.79-2.86 (m, 4H). |
| 8 | MS m/z 378.0 [M + H]⁺; ¹H NMR (DMSO-d$_6$) δ: 9.27 (br s, 2H), 8.44 (s, 1H), 8.28 (d, J = 1.5 Hz, 1H), 8.00 (s, 1H), 7.67-7.83 (m, 3H), 7.61 (dd, J = 9.0, 1.6 Hz, 1H), 4.57 (br. s., 1H), 4.20 (s, 3H), 3.42 (d, J = 12.0 Hz, 2H), 3.04-3.22 (m, 5H), 2.15-2.30 (m, 2H), 2.01 (d, J = 11.7 Hz, 2H). |
| 21 | MS m/z 448.4 [M + H]⁺; ¹H NMR (CDCl$_3$) δ: 7.93 (s, 1H), 7.87 (d, J = 1.3 Hz, 1H), 7.68 (d, J = 0.9 Hz, 1H), 7.57-7.64 (m, 2H), 7.35-7.40 (m, 1H), 4.30-4.41 (m, 1H), 4.27 (s, 3H), 3.14 (s, 3H), 2.71 (s, 3H), 1.83 (dd, J = 12.5, 3.3 Hz, 2H), 1.35-1.50 (m, 8H), 1.24 (br s, 6H). |
| 23 | MS m/z 452.0 [M + H]⁺; ¹H NMR (CDCl$_3$) δ: 7.86 (s, 1H), 7.71-7.75 (m, 1H), 7.68 (d, J = 8.8 Hz, 1H), 7.55 (d, J = 1.6 Hz, 1H), 7.45-7.49 (m, 1H), 7.26 (dd, J = 12.0, 1.6 Hz, 1H), 4.29 (br. s., 1H), 4.17 (s, 3H), 3.07 (s, 3H), 1.75 (dd, J = 12.5, 3.3 Hz, 2H), 1.43-1.54 (m, 2H), 1.31-1.37 (m, 6H), 1.21 (d, J = 4.1 Hz, 6H). |
| 24 | MS m/z 466.0 [M + H]⁺; ¹H NMR (CDCl$_3$) δ: 7.93 (s, 1H), 7.65 (dd, J = 6.3, 1.3 Hz, 2H), 7.31-7.38 (m, 2H), 4.25-4.37 (m, 4H), 3.17 (s, 3H), 2.71 (s, 3H), 1.83 (dd, J = 12.5, 3.3 Hz, 2H), 1.42-1.52 (m, 2H), 1.39 (s, 6H), 1.21-1.28 (m, 6H). |
| 28 | MS m/z 392.1 [M + H]⁺; ¹H NMR (DMSO-d$_6$) δ: 9.23-9.93 (m, 1H), 8.37 (s, 1H), 8.13 (d, J = 1.6 Hz, 1H), 7.95 (s, 1H), 7.64-7.68 (m, 1H), 7.62 (dd, J = 8.5, 1.6 Hz, 1H), 7.56-7.60 (m, 1H), 7.52 (d, J = 8.2 Hz, 1H), 4.18 (s, 5H), 3.21 (t, J = 12.0 Hz, 3H), 2.70 (br s, 6H), 2.09 (d, J = 11.7 Hz, 2H), 1.68 (d, J = 8.2 Hz, 2H). |
| 29 | MS m/z 364.1 [M + H]⁺; ¹H NMR (DMSO-d$_6$) δ: 8.39 (s, 1H), 8.28 (br s, 3H), 8.17 (d, J = 1.6 Hz, 1H), 7.96 (s, 1H), 7.64-7.69 (m, 2H), 7.59 (dd, J = 9.1, 1.6 Hz, 1H), 7.56 (d, J = 8.5 Hz, 1H), 4.19 (s, 3H), 4.14 (d, J = 12.9 Hz, 2H), 3.27-3.42 (m, 3H), 2.08 (d, J = 10.7 Hz, 2H), 1.67 (dd, J = 11.8, 3.6 Hz, 2H). |
| 33 | MS m/z 448.5 [M + H]⁺; ¹H NMR (CDCl$_3$) δ: 8.11 (d, J = 0.9 Hz, 1H), 7.78 (d, J = 1.9 Hz, 1H), 7.61 (d, J = 8.2 Hz, 1H), 7.48 (dd, J = 8.2, 1.9 Hz, 1H), 7.38 (d, J = 0.6 Hz, 1H), 7.23 (dd, J = 1.6, 0.9 Hz, 1H), 4.29-4.44 (m, 1H), 3.13 (s, 3H), 2.67 (s, 3H), 2.51 (s, 3H), 1.83 (dd, J = 12.5, 3.3 Hz, 2H), 1.46 (t, J = 12.0 Hz, 2H), 1.39 (d, J = 2.5 Hz, 6H), 1.24 (br s, 6H). |
| 34 | MS m/z 420.4 [M + H]⁺; ¹H NMR (DMSO-d$_6$) δ: 9.41 (d, J = 9.8 Hz, 1H), 8.38 (d, J = 10.7 Hz, 1H), 8.02-8.18 (m, 2H), 7.96 (s, 1H), 7.50-7.69 (m, 4H), 4.60 (br s, 1H), 3.03 (s, 3H), 2.05 (t, J = 12.5 Hz, 2H), 1.81 (d, J = 11.7 Hz, 2H), 1.37-1.55 (m, 12H). |
| 35 | MS m/z 364.1 [M + H]⁺; ¹H NMR (DMSO-d$_6$) δ: 10.25-10.81 (m, 1H), 9.09 (br s, 2H), 8.42 (s, 1H), 8.21 (s, 1H), 7.97 (s, 1H), 7.75 (d, J = 8.5 Hz, 1H), 7.66-7.72 (m, 2H), 7.57 (dd, J = 9.0, 1.4 Hz, 1H), 4.28 (br s, 1H), 4.19 (s, 3H), 3.32-3.44 (m, 2H), 3.04 (br s, 2H), 2.22 (d, J = 10.7 Hz, 2H), 1.79-1.96 (m, 2H). |
| 38 | MS m/z 364.2 [M + H]⁺; ¹H NMR (DMSO-d$_6$) δ: 10.02 (br s, 1H), 9.71 (br s, 1H), 8.44 (br s, 1H), 8.25 (br s, 1H), 7.99 (br s, 1H), 7.56-7.78 (m, 4H), 5.10 (br s, 1H), 4.20 (br s, 3H), 3.13-3.60 (m, 7H), 2.33 (br s, 1H), 2.18 (br s, 1H). |
| 51 | MS m/z 502.2 [M + H]⁺; ¹H NMR (DMSO-d$_6$) δ: 8.82-8.90 (m, 1H), 8.61 (s, 1H), 8.30 (s, 1H), 8.23 (d, J = 1.9 Hz, 1H), 7.94 (s, 1H), 7.84-7.91 (m, 1H), 7.67 (d, J = 1.9 Hz, 1H), 7.55 (d, J = 8.5 Hz, 1H), 4.56-4.70 (m, 1H), 4.26 (s, 3H), 3.06 (s, 3H), 1.90-1.96 (m, 4H), 1.52 (s, 6H), 1.44 (s, 6H). |
| 54 | MS m/z 462.3 [M + H]⁺; ¹H NMR (DMSO-d$_6$) δ: 8.33 (s, 1H), 8.09-8.13 (m, 1H), 7.75 (s, 1H), 7.58-7.62 (m, 1H), 7.48-7.52 (m, 1H), 7.36 (s, 1H), 4.39-4.55 (m, 1H), 4.18 (s, 3H), 3.04 (s, 3H), 2.94-3.01 (m, 2H), 1.68-1.83 (m, 4H), 1.34-1.44 (m, 9H), 1.30 (br s, 6H). |
| 55 | MS m/z 448.3 [M + H]⁺; ¹H NMR (DMSO-d$_6$) δ: 8.81-8.90 (m, 1H), 8.63-8.70 (m, 1H), 8.31-8.43 (m, 2H), 8.09-8.17 (m, 1H), 7.86-7.95 (m, 1H), 7.79-7.85 (m, 1H), 7.52-7.60 (m, 1H), 4.59-4.73 (m, 1H), 3.06 (s, 3H), 2.88 (s, 3H), 2.43 (s, 3H), 1.84-1.98 (m, 4H), 1.51 (s, 6H), 1.44 (s, 6H). |
| 57 | MS m/z 452.1 [M + H]⁺; ¹H NMR (DMSO-d$_6$) δ: 8.87-8.95 (m, 1H), 8.49-8.53 (m, 1H), 8.17-8.19 (m, 1H), 7.81-7.84 (m, 1H), 7.64-7.68 (m, 1H), 7.50-7.54 (m, 1H), 7.39-7.45 (m, 1H), 4.55-4.66 (m, 1H), 4.21 (s, 3H), 3.06 (s, 3H), 1.86-1.99 (m, 4H), 1.51 (s, 6H), 1.45 (s, 6H). |
| 62 | MS m/z 459.2 [M + H]⁺; ¹H NMR (DMSO-d$_6$) δ: 8.81-8.88 (m, 1H), 8.65 (s, 1H), 8.38 (s, 1H), 8.26 (s, 2H), 7.81-7.89 (m, 1H), 7.68-7.72 (m, 1H), 7.52-7.56 (m, 1H), 4.58-4.68 (m, 1H), 4.26 (s, 3H), 3.06 (s, 3H), 1.88-1.96 (m, 4H), 1.52 (s, 6H), 1.44 (s, 6H). |
| 63 | MS m/z 434.1 [M + H]⁺; ¹H NMR (DMSO-d$_6$) δ: 9.23-9.26 (m, 1H), 9.04-9.11 (m, 1H), 8.23-8.29 (m, 2H), 8.03-8.08 (m, 2H), 7.96-8.00 (m, 1H), 7.69-7.73 (m, 1H), 7.60-7.64 (m, 1H), 4.57-4.72 (m, 1H), 3.07 (s, 3H), 2.52 (s, 3H), 1.95-2.03 (m, 2H), 1.86-1.93 (m, 2H), 1.52 (s, 6H), 1.47 (s, 6H). |
| 64 | MS m/z 421.2 [M + H]⁺; ¹H NMR (methanol-d$_4$) δ: 8.26 (s, 1H), 8.04 (s, 1H), 7.95 (s, 1H), 7.63-7.76 (m, 4H), 5.59-5.69 (m, 1H), 4.25 (s, 3H), 2.30 (dd, J = 12.3, 3.5 Hz, 2H), 1.51 (br. s., 2H), 1.40 (s, 6H), 1.30 (s, 6H). |
| 68 | MS m/z 435.0 [M + H]⁺; ¹H NMR (methanol-d$_4$) δ: 8.94 (s, 1H), 8.14 (s, 1H), 8.09 (s, 1H), 7.95 (s, 1H), 7.78 (d, J = 3.2 Hz, 2H), 5.69-5.81 (m, 1H), 4.48 (s, 3H), 2.72 (s, 3H), 2.54 (dd, J = 13.7, 3.9 Hz, 2H), 1.96 (dd, J = 13.4, 10.9 Hz, 2H), 1.63-1.69 (m, 6H), 1.56-1.62 (m, 6H). |
| 80 | MS m/z 474.3 [M + H]⁺; ¹H NMR (DMSO-d$_6$) δ: 8.77-8.84 (m, 1H), 8.32 (s, 1H), 8.13 (s, 1H), 7.79-7.87 (m, 1H), 7.70 (s, 1H), 7.60 (s, 1H), 7.50 (d, J = 8.5 Hz, 1H), 7.11 (s, 1H), 4.55-4.66 (m, 1H), 4.18 (s, 3H), 3.05 (s, 3H), 2.40-2.44 (m, 1H), 1.89-1.95 (m, 4H), 1.51 (s, 6H), 1.43 (s, 6H), 0.98-1.18 (m, 4H). |
| 81 | MS m/z 392.0 [M + H]⁺; ¹H NMR (DMSO-d$_6$) δ: 9.09-9.25 (m, 2H), 8.40 (s, 1H), 8.20 (s, 1H), 7.97 (s, 1H), 7.65-7.72 (m, 2H), 7.60 (dd, J = 8.5, 5.0 Hz, 2H), 4.54 (br. s., |

| Cpd | Data |
|---|---|
|  | 1H), 4.19 (s, 3H), 3.38 (d, J = 10.4 Hz, 2H), 3.05-3.17 (m, 4H), 2.15 (dd, J = 12.5, 3.6 Hz, 1H), 1.90-2.02 (m, 3H), 1.32 (d, J = 6.3 Hz, 3H). |
| 91 | MS m/z 477.4 [M + H]$^+$; $^1$H NMR (CDCl$_3$) δ: 8.10 (s, 1H), 8.06 (d, J = 1.6 Hz, 1H), 7.99 (d, J = 1.6 Hz, 1H), 7.60 (d, J = 1.6 Hz, 1H), 7.29 (dd, J = 10.0, 1.6 Hz, 1H), 4.35-4.50 (br s, 1H), 4.34 (s, 3H), 3.17 (s, 3H), 1.84 (dd, J = 12.5, 3.3 Hz, 2H), 1.45-1.60 (m, 2H), 1.42 (br s, 6H), 1.30 (br s, 6H). |
| 93 | MS m/z 462.0 [M + H]$^+$; $^1$H NMR (DMSO-d$_6$) δ: 9.10 (s, 1H), 8.99 (d, J = 11.3 Hz, 1H), 8.28 (s, 1H), 8.09-8.20 (m, 2H), 8.06 (s, 1H), 7.73 (d, J = 8.5 Hz, 1H), 7.61 (d, J = 8.2 Hz, 1H), 4.61-4.74 (m, 1H), 3.08 (s, 3H), 3.01 (q, J = 7.6 Hz, 2H), 2.53 (s, 3H), 1.96-2.05 (m, 2H), 1.87-1.94 (m, 2H), 1.52 (s, 6H), 1.45 (s, 6H), 1.36 (t, J = 7.6 Hz, 3H). |
| 96 | MS m/z 502.2 [M + H]$^+$; $^1$H NMR (DMSO-d$_6$) δ: 9.09-9.12 (m, 1H), 8.19-8.22 (m, 1H), 7.92-7.95 (m, 1H), 7.84-7.87 (m, 1H), 7.63-7.67 (m, 1H), 7.51-7.55 (m, 1H), 4.26-4.33 (m, 1H), 3.04 (s, 3H), 2.40 (s, 3H), 1.60-1.65 (m, 2H), 1.43-1.50 (m, 2H), 1.24 (s, 6H), 1.10 (s, 6H). |
| 111 | MS m/z 452.0 [M + H]$^+$; $^1$H NMR (DMSO-d$_6$) δ: 8.92-9.08 (m, 2H), 8.25 (d, J = 1.6 Hz, 1H), 8.00-8.18 (m, 3H), 7.71 (dd, J = 8.5, 1.9 Hz, 1H), 7.60 (d, J = 8.5 Hz, 1H), 4.56-4.75 (m, 1H), 3.07 (s, 3H), 2.49 (s, 3H), 1.86-2.03 (m, 4H), 1.52 (s, 6H), 1.45 (s, 6H). |
| 127 | $^1$H NMR (DMSO-d$_6$) δ: 9.37-9.48 (m, 1H), 8.47 (d, J = 1.6 Hz, 1H), 8.39 (br. s., 2H), 8.20-8.31 (m, 1H), 7.95 (dd, J = 12.3, 1.6 Hz, 1H), 4.55-4.83 (m, 1H), 3.11 (s, 3H), 2.71 (s, 3H), 2.55 (s, 3H), 2.04-2.13 (m, 2H), 1.89 (d, J = 10.1 Hz, 2H), 1.49-1.56 (m, 12H). |
| 138 | MS m/z 459.8 [M + H]$^+$; $^1$H NMR (DMSO-d$_6$) δ: 9.20 (s, 1H), 8.75-8.84 (m, 1H), 8.37 (s, 1H), 8.22 (s, 1H), 7.89 (s, 1H), 7.79-7.87 (m, 1H), 7.69 (d, J = 8.5 Hz, 1H), 7.57 (d, J = 8.2 Hz, 1H), 4.59-4.70 (m, 1H), 3.06 (s, 3H), 2.42 (s, 3H), 1.87-1.98 (m, 4H), 1.51 (s, 6H), 1.43 (s, 6H). |
| 146 | MS m/z 420.2 [M + H]$^+$; $^1$H NMR (DMSO-d$_6$) δ: 9.40 (br s, 1H), 9.24 (d, J = 9.1 Hz, 1H), 8.38 (s, 1H), 8.22 (s, 1H), 7.79 (s, 1H), 7.70-7.75 (m, 1H), 7.64-7.69 (m, 1H), 7.38 (s, 1H), 4.56-4.77 (m, 1H), 4.19 (s, 3H), 3.34 (d, J = 11.7 Hz, 1H), 3.22-3.29 (m, 1H), 3.12 (s, 3H), 2.57 (s, 3H), 2.18 (dd, J = 12.0, 4.1 Hz, 1H), 2.10 (t, J = 12.9 Hz, 1H), 1.95 (d, J = 13.9 Hz, 1H), 1.85 (d, J = 11.0 Hz, 1H), 1.47 (s, 3H), 1.44 (s, 3H). |
| 155 | MS m/z 406.2 [M + H]$^+$; $^1$H NMR (DMSO-d$_6$) δ: 9.46 (br s, 1H), 9.30 (br s, 1H), 8.42 (s, 1H), 8.26 (s, 1H), 7.98 (s, 1H), 7.73-7.78 (m, 1H), 7.67-7.73 (m, 2H), 7.60 (d, J = 8.8 Hz, 1H), 4.69 (br s, 1H), 4.19 (s, 3H), 3.30-3.40 (m, 1H), 3.25 (d, J = 10.4 Hz, 1H), 3.13 (s, 3H), 2.08-2.25 (m, 2H), 1.96 (d, J = 12.0 Hz, 1H), 1.86 (d, J = 12.6 Hz, 1H), 1.48 (s, 3H), 1.45 (s, 3H). |
| 175 | MS m/z 420.0 [M + H]$^+$; $^1$H NMR (DMSO-d$_6$) δ: 9.20-9.62 (m, 2H), 8.40 (s, 1H), 8.23-8.29 (m, 1H), 7.66-7.82 (m, 3H), 7.40 (s, 1H), 4.48-4.90 (m, 1H), 4.20 (s, 3H), 3.34-3.88 (m, 2H), 3.16 (s, 3H), 2.57 (s, 3H), 1.80-2.43 (m, 4H), 1.30-1.53 (m, 6H). |
| 176 | MS m/z 406.0 [M + H]$^+$; $^1$H NMR (DMSO-d$_6$) δ: 9.15-9.63 (m, 2H), 8.42 (d, J = 2.5 Hz, 1H), 8.22-8.29 (m, 1H), 7.98 (s, 1H), 7.63-7.79 (m, 3H), 7.60 (d, J = 8.8 Hz, 1H), 4.54-4.83 (m, 1H), 4.19 (s, 3H), 3.37-3.89 (m, 2H), 3.13 (s, 3H), 1.77-2.41 (m, 4H), 1.31-1.49 (m, 6H). |

Example 3

Preparation of Compound 37

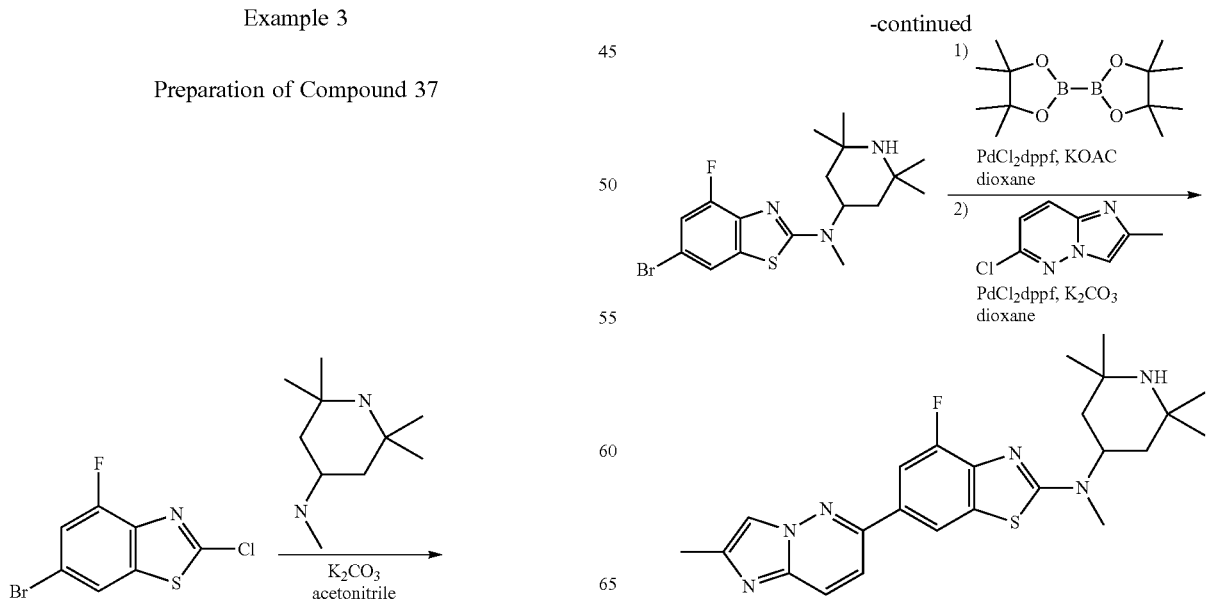

Step 1: A mixture of 6-bromo-2-chloro-4-fluoro-1,3-benzothiazole (530 mg, 2.0 mmol, 1.0 eq.), N,2,2,6,6-pentamethylpiperidin-4-amine (410 mg, 0.45 mL, 2.4 mmol, 1.2 eq.) and K$_2$CO$_3$ (840 mg, 6.0 mmol, 3.0 eq.) in acetonitrile (5.0 mL) was stirred at 100° C. for 4 h, and then cooled, diluted with ethyl acetate and filtered through Celite. The filtrate was concentrated to give 6-bromo-4-fluoro-N-methyl-N-(2,2,6,6-tetramethyl-4-piperidyl)-1,3-benzothiazol-2-amine (840 mg, 100%), which was used directly in next step without further purification.

Step 2: A mixture of 6-bromo-4-fluoro-N-methyl-N-(2,2,6,6-tetramethyl-4-piperidyl)-1,3-benzothiazol-2-amine (78 mg, 0.19 mmol, 1.0 eq.), 4,4,5,5-tetramethyl-2-(4,4,5,5-tetramethyl-1,3,2-dioxaborolan-2-yl)-1,3,2-dioxaborolane (54 mg, 0.21 mmol, 1.1 eq.), PdCl$_2$dppf dichloromethane complex (16 mg, 0.019 mmol, 0.10 eq.) and KOAc (58 mg, 0.58 mmol, 3.0 eq.) in dioxane (1.0 mL) was stirred at 90° C. for 4 h. LC/MS showed a complete conversion to the pinacol boronate. To the mixture was added 6-chloro-2-methyl-imidazo[1,2-b]pyridazine (26 mg, 0.16 mmol, 0.80 eq.) and PdCl$_2$dppf dichloromethane complex (16 mg, 0.019 mmol, 0.10 eq.), followed by K$_2$CO$_3$ (2.0 M aq.) (0.29 mL, 0.58 mmol, 3.0 eq.). The mixture was heated at 90° C. overnight, and then cooled, diluted with ethyl acetate and washed with water and brine. The organic layer was separated, dried over sodium sulfate, and evaporated. The residue was purified over basic alumina with ethyl acetate in hexanes (10 to 100% gradient) to provide 4-fluoro-N-methyl-6-(2-methylimidazo[1,2-b]pyridazin-6-yl)-N-(2,2,6,6-tetramethyl-4-piperidyl)-1,3-benzothiazol-2-amine (40 mg, 45%).

MS m/z 453.4 [M+H]$^+$; $^1$H NMR (CDCl$_3$) δ: 7.92 (d, J=1.9 Hz, 1H), 7.80 (d, J=9.5 Hz, 1H), 7.70 (s, 1H), 7.59 (dd, J=11.8, 1.7 Hz, 1H), 7.33 (d, J=9.5 Hz, 1H), 4.19-4.49 (m, 1H), 3.09 (s, 3H), 2.46 (s, 3H), 1.76 (dd, J=12.3, 3.2 Hz, 2H), 1.40-1.70 (m, 2H), 1.29-1.39 (m, 6H), 1.18-1.28 (m, 6H).

Using the procedure described for Example 3, above, additional compounds described herein were prepared by substituting the appropriate starting material, suitable reagents and reaction conditions, obtaining compounds such as those selected from:

| Cpd | Data |
|---|---|
| 39 | MS m/z 466.4 [M + H]$^+$; $^1$H NMR (CDCl$_3$) δ: 8.10 (d, J = 0.9 Hz, 1H), 7.56 (d, J = 1.6 Hz, 1H), 7.39 (s, 1H), 7.24 (dd, J = 11.8, 1.7 Hz, 1H), 7.19 (d, J = 0.9 Hz, 1H), 4.22-4.44 (m, 1H), 3.17 (s, 3H), 2.67 (s, 3H), 2.52 (s, 3H), 1.83 (dd, J = 12.5, 3.3 Hz, 2H), 1.40-1.52 (m, 2H), 1.35-1.41 (m, 6H), 1.21-1.30 (m, 6H). |
| 40 | MS m/z 435.4 [M + H]$^+$; $^1$H NMR (DMSO-d$_6$) δ: 9.72 (br s, 1H), 8.32-8.82 (m, 5H), 8.08 (br s, 1H), 7.66 (br s, 1H), 4.71 (br s, 1H), 3.09 (br s, 3H), 2.55 (br s, 3H), 2.16 (br s, 2H), 1.81 (br s, 2H), 1.53 (br s, 12H). |
| 48 | MS m/z 436.4 [M + H]$^+$; $^1$H NMR (CDCl$_3$) δ: 8.39 (d, J = 1.6 Hz, 1H), 8.05 (d, J = 9.5 Hz, 1H), 7.94 (dd, J = 8.5, 1.9 Hz, 1H), 7.84 (d, J = 9.5 Hz, 1H), 7.65 (d, J = 8.2 Hz, 1H), 4.34-4.53 (m, 1H), 3.15 (s, 3H), 2.70 (s, 3H), 1.83 (dd, J = 12.5, 3.3 Hz, 2H), 1.49 (br s, 2H), 1.41 (s, 6H), 1.27 (br s, 6H). |
| 200 | MS m/z 483.4 [M + H]$^+$; $^1$H NMR (CDCl$_3$) δ: 8.00 (d, J = 1.6 Hz, 1H), 7.71 (d, J = 0.6 Hz, 1H), 7.64 (dd, J = 11.8, 1.7 Hz, 1H), 6.71 (s, 1H), 4.17 (s, 3H), 3.51 (s, 1H), 3.18 (s, 3H), 2.52 (d, J = 0.6 Hz, 3H), 1.86 (dd, J = 12.3, 2.8 Hz, 2H), 1.22-1.72 (m, 14H). |

Example 4

Preparation of Compound 47

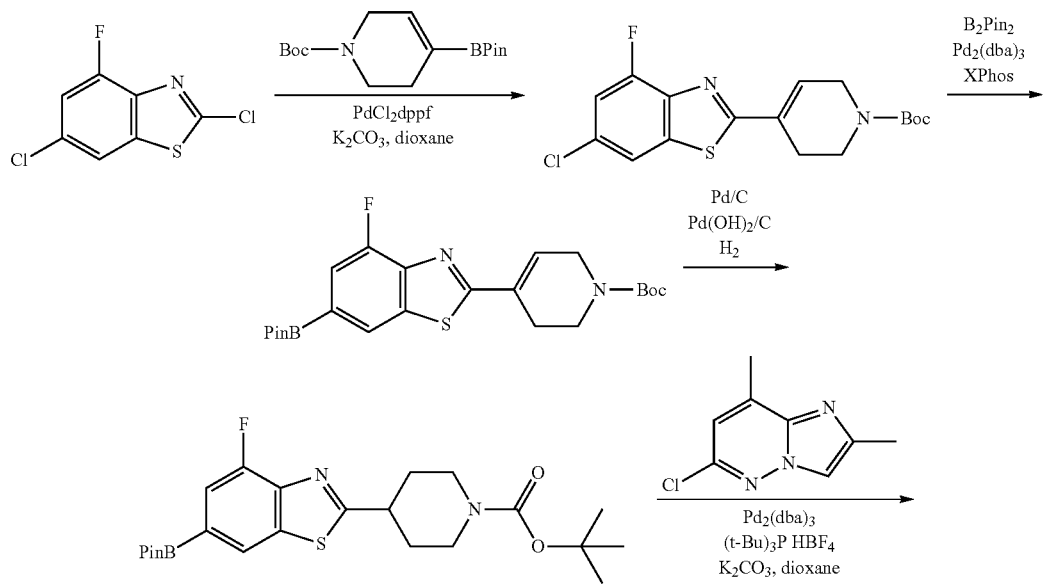

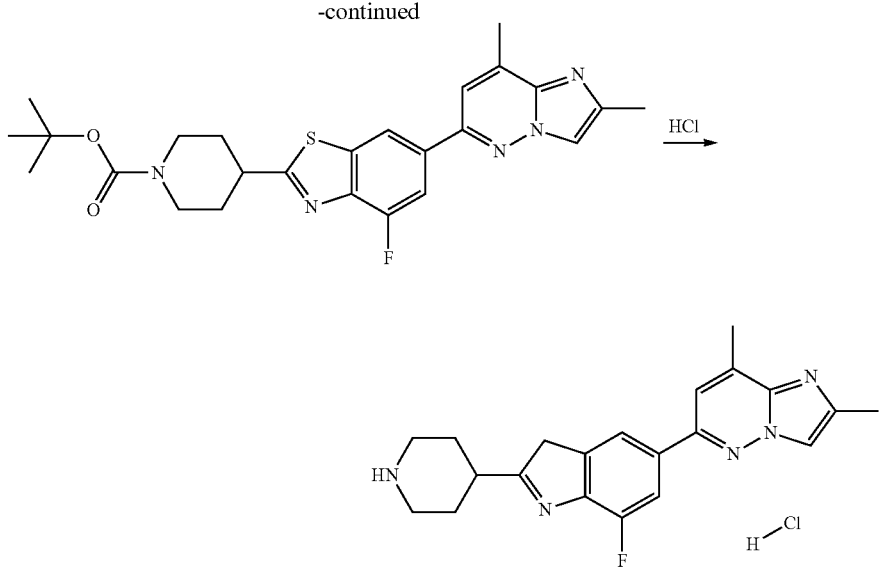

Step 1: A mixture of 2,6-dichloro-4-fluoro-1,3-benzothiazole (3.54 g, 15.9 mmol, 1.00 eq., prepared according to Example 1 step 1 starting from 4-chloro-2,6-difluoroaniline), tert-butyl 4-(4,4,5,5-tetramethyl-1,3,2-dioxaborolan-2-yl)-3,6-dihydro-2H-pyridine-1-carboxylate (5.91 g, 19.1 mmol, 1.20 eq.), PdCl$_2$(dppf) (1.2 g, 1.59 mmol, 0.1 eq.) and K$_2$CO$_3$ (2.0 M aq.) (24 mL, 47.8 mmol, 3.00 eq.) in dioxane (50 mL) was heated at 90° C. for 2 h, and then cooled, diluted with ethyl acetate and washed with water and brine. The organic layer was separated, dried over sodium sulfate and evaporated. The residue was purified over silica gel with ethyl acetate and hexanes (3 to 20%) to give tert-butyl 4-(6-chloro-4-fluoro-1,3-benzothiazol-2-yl)-3,6-dihydro-2H-pyridine-1-carboxylate (5.58 g, 94.9%).

$^1$H NMR (CDCl$_3$) δ: 7.63 (dd, J=1.7, 0.8 Hz, 1H), 7.21 (dd, J=9.8, 1.9 Hz, 1H), 6.72 (br. s., 1H), 4.21 (d, J=2.5 Hz, 2H), 3.68 (t, J=5.5 Hz, 2H), 2.84 (dd, J=4.3, 2.7 Hz, 2H), 1.52 (s, 9H).

Step 2: A mixture of tert-butyl 4-(6-chloro-4-fluoro-1,3-benzothiazol-2-yl)-3,6-dihydro-2H-pyridine-1-carboxylate (4.0 g, 10.8 mmol, 1.0 eq.), 4,4,5,5-tetramethyl-2-(4,4,5,5-tetramethyl-1,3,2-dioxaborolan-2-yl)-1,3,2-dioxaborolane (5.5 g, 21.7 mmol, 2.0 eq.), Pd$_2$(dba)$_3$ (0.5 g, 0.542 mmol, 0.05 eq.), X-Phos (1.06 g, 2.17 mmol, 0.2 eq.) and KOAc (3.23 g, 32.5 mmol, 3.0 eq.) in dioxane (100 mL) was heated at 110° C. overnight, and then cooled, diluted with ethyl acetate, filtered, and concentrated. The crude product was purified over silica gel to give tert-butyl 4-[4-fluoro-6-(4,4,5,5-tetramethyl-1,3,2-dioxaborolan-2-yl)-1,3-benzothiazol-2-yl]-3,6-dihydro-2H-pyridine-1-carboxylate (5.1 g, 100%).

$^1$H NMR (CDCl$_3$) δ: 8.09 (d, J=0.6 Hz, 1H), 7.57 (dd, J=10.7, 0.6 Hz, 1H), 6.76 (s, 1H), 4.21 (br. s., 4H), 3.68 (br. s., 2H), 2.86 (d, J=1.6 Hz, 2H), 1.52 (s, 9H), 1.39 (s, 12H).

Step 3: A mixture of tert-butyl 4-[4-fluoro-6-(4,4,5,5-tetramethyl-1,3,2-dioxaborolan-2-yl)-1,3-benzothiazol-2-yl]-3,6-dihydro-2H-pyridine-1-carboxylate (1.0 g, 2.2 mmol, 1.0 eq.), 5% Pd/C (0.5 g, 0.2 mmol, 0.1 eq.) and 10% Pd(OH)$_2$/C (0.5 g, 0.4 mmol, 0.2 eq.) in MeOH (200 mL) and CH$_2$Cl$_2$ (20 mL) was hydrogenated overnight at 60 psi. The mixture was then filtered thru Celite and purified over silica gel with ethyl acetate in hexanes (5 to 20% gradient) to give tert-butyl 4-[4-fluoro-6-(4,4,5,5-tetramethyl-1,3,2-dioxaborolan-2-yl)-1,3-benzothiazol-2-yl]piperidine-1-carboxylate (0.75 g, 75%).

$^1$H NMR (CDCl$_3$) δ: 8.12 (d, J=0.9 Hz, 1H), 7.57 (d, J=10.7 Hz, 1H), 4.19-4.34 (m, 2H), 3.28-3.38 (m, 1H), 2.86-2.99 (m, 2H), 2.15-2.25 (m, 2H), 1.81-1.94 (m, 2H), 1.50 (s, 9H), 1.39 (s, 12H).

Step 4: tert-Butyl 4-[4-fluoro-6-(4,4,5,5-tetramethyl-1,3,2-dioxaborolan-2-yl)-1,3-benzothiazol-2-yl]piperidine-1-carboxylate (520 mg, 1.1 mmol, 1.0 eq.) was combined with 6-chloro-2,8-dimethyl-imidazo[1,2-b]pyridazine (204 mg, 1.1 mmol, 1.0 eq.), Pd$_2$(dba)$_3$ (52 mg, 0.056 mmol, 0.05 eq.) and (t-Bu)$_3$P HBF$_4$ (33 mg, 0.11 mmol, 0.1 equiv.). The vessel was purged with N$_2$. To the vessel was added dioxane (7.0 mL) and K$_2$CO$_3$ (2.0 M aq.) (3.5 mL, 7.0 mmol). The mixture was heated at 80° C. for 1 h, then cooled and partitioned between EtOAc and H$_2$O. The organic layer was concentrated and chromatographed on silica gel, eluting with 30-100% EtOAc in CH$_2$Cl$_2$ to give the desired tert-butyl 4-[6-(2,8-dimethylimidazo[1,2-b]pyridazin-6-yl)-4-fluoro-1,3-benzothiazol-2-yl]piperidine-1-carboxylate (500 mg, 92%). MS m/z 482.2 [M+H]$^+$.

Step 5: tert-Butyl 4-[6-(2,8-dimethylimidazo[1,2-b]pyridazin-6-yl)-4-fluoro-1,3-benzothiazol-2-yl]piperidine-1-carboxylate (500 mg, 1.0 mmol) was suspended in 4.0 M HCl in 1,4-dioxane (3 mL, 12 mmol). The mixture was stirred for 30 min, then diluted with Et$_2$O (10 mL) and filtered. The solid was partitioned between CH$_2$Cl$_2$ and aqueous K$_2$CO$_3$ (1M). The organic layer was then separated and concentrated. The residue was chromatographed on silica gel, eluting with 0-10% MeOH (2 N NH$_3$) in CH$_2$Cl$_2$. The purified material was dissolved in 1.25 M HCl in MeOH (3 mL) followed by the removal of volatiles to give 6-(2,8-dimethylimidazo[1,2-b]pyridazin-6-yl)-4-fluoro-2-(piperidin-4-yl)benzo[d]thiazole hydrochloride (340 mg, 72%).

MS m/z 382.3 [M+H]$^+$. $^1$H NMR (methanol-d$_4$) δ: 8.49 (d, J=1.9 Hz, 1H), 7.98 (dd, J=11.9, 1.9 Hz, 1H), 7.95 (s, 1H), 7.66 (d, J=1.3 Hz, 1H), 3.52 (m, 1H), 3.44 (m, 2H), 3.09 (td, J=12.6, 3.2 Hz, 2H), 2.69 (s, 3H), 2.51 (s, 3H), 2.38 (m, 2H), 2.09 (m, 2H).

Using the procedure described for Example 4, above, additional compounds described herein were prepared by substituting the appropriate starting material, suitable reagents and reaction conditions, obtaining compounds such as those selected from:

| Cpd | Data |
|---|---|
| 78 | MS m/z 354.2 [M + H]+; 1H NMR (methanol-$d_4$) δ: 8.42 (d, J = 1.6 Hz, 1H), 8.21 (d, J = 0.9 Hz, 1H), 8.05 (dd, J = 9.0, 1.1 Hz, 1H), 7.91-7.97 (m, 2H), 3.45-3.55 (m, 3H), 3.12-3.22 (m, 2H), 2.34-2.41 (m, 2H), 2.06-2.16 (m, 2H). |
| 79 | MS m/z 368.3 [M + H]+; 1H NMR (methanol-$d_4$) δ: 8.73-8.84 (m, 2H), 8.60 (d, J = 1.6 Hz, 1H), 8.20 (d, J = 9.1 Hz, 1H), 8.04 (dd, J = 11.3, 1.9 Hz, 1H), 4.44 (s, 3H), 3.65-3.73 (m, 1H), 3.61 (d, J = 13.2 Hz, 2H), 3.28-3.35 (m, 2H), 2.46-2.55 (m, 2H), 2.20-2.30 (m, 2H). |
| 126 | MS m/z 385.3 [M + H]+; 1H NMR (CDCl$_3$) δ: 8.04 (d, J = 2.5 Hz, 1H), 7.86 (d, J = 1.6 Hz, 1H), 7.66 (d, J = 1.3 Hz, 1H), 7.45 (dd, J = 11.3, 1.6 Hz, 1H), 7.25 (dd, J = 12.3, 1.3 Hz, 1H), 4.31 (s, 3H), 3.32-3.42 (m, 3H), 2.91 (td, J = 12.0, 2.5 Hz, 2H), 2.30 (dd, J = 13.1, 2.4 Hz, 2H), 1.96-2.04 (m, 2H). |
| 151 | MS m/z 398.3 [M + H]+; 1H NMR (methanol-$d_4$) δ: 8.73 (s, 1H), 8.31 (s, 1H), 8.13 (d, J = 11.3 Hz, 1H), 7.88 (s, 1H), 4.40 (s, 3H), 3.63-3.72 (m, 1H), 3.60 (d, J = 12.9 Hz, 2H), 3.28 (t, J = 7.4 Hz, 2H), 2.64 (s, 3H), 2.50 (d, J = 12.3 Hz, 2H), 2.20-2.30 (m, 2H). |
| 152 | MS m/z 385.3 [M + H]+; 1H NMR (methanol-$d_4$) δ: 8.93 (d, J = 1.3 Hz, 1H), 8.10-8.18 (m, 2H), 8.03 (d, J = 1.3 Hz, 1H), 7.61 (dd, J = 11.5, 1.7 Hz, 1H), 3.42-3.56 (m, 3H), 3.14 (td, J = 12.6, 2.8 Hz, 2H), 2.50 (d, J = 0.9 Hz, 3H), 2.35 (dd, J = 14.5, 2.8 Hz, 2H), 2.05-2.15 (m, 2H). |
| 167 | MS m/z 397.4 [M + H]+; 1H NMR (methanol-$d_4$) δ: 8.61 (br. s., 1H), 8.12 (s, 1H), 8.04 (d, J = 11.7 Hz, 1H), 7.18 (s, 1H), 3.65-3.70 (m, 1H), 3.59 (d, J = 11.3 Hz, 2H), 3.20-3.30 (m, 2H), 3.24 (s, 3H), 2.63 (s, 3H), 2.50 (d, J = 13.9 Hz, 2H), 2.18-2.30 (m, 2H). |
| 168 | MS m/z 411.4 [M + H]+; 1H NMR (methanol-$d_4$) δ: 8.60 (br. s., 1H), 8.15 (br s, 1H), 8.00 (d, J = 11.3 Hz, 1H), 7.14 (br. s., 1H), 3.52-3.60 (m, 3H), 3.46 (s, 6H), 3.20-3.26 (m, 2H), 2.62 (s, 3H), 2.40-2.50 (m, 2H), 2.23 (br s, 2H). |
| 187 | MS m/z 474.3 [M + H]+; 1H NMR (methanol-$d_4$) δ: 8.72 (d, J = 1.3 Hz, 1H), 8.31 (d, J = 1.3 Hz, 1H), 8.14 (dd, J = 11.7, 1.6 Hz, 1H), 8.01 (s, 1H), 7.67 (dd, J = 8.0, 1.4 Hz, 2H), 7.46-7.54 (m, 3H), 5.69 (s, 2H), 3.65-3.70 (m, 1H), 3.58-3.63 (m, 2H), 3.25-3.31 (m, 2H), 2.61 (d, J = 0.9 Hz, 3H), 2.45-2.53 (m, 2H), 2.20-2.30 (m, 2H). |
| 191 | MS m/z 361.3 [M + H]+; 1H NMR (methanol-$d_4$) δ: 8.08 (s, 1H), 7.55-7.61 (m, 1H), 7.38-7.43 (m, 1H), 7.18-7.28 (m, 2H), 3.99 (s, 3H), 3.55-3.65 (m, 3H), 3.23-3.30 (m, 2H), 2.43-2.51 (m, 2H), 2.16-2.27 (m, 2H). |
| 195 | MS m/z 460.3 [M + H]+; 1H NMR (methanol-$d_4$) δ: 8.41 (dd, J = 4.1, 0.9 Hz, 2H), 7.92 (dd, J = 11.7, 0.9 Hz, 1H), 7.61-7.69 (m, 2H), 7.44-7.54 (m, 3H), 7.33 (s, 1H), 3.53-3.67 (m, 3H), 3.20-3.24 (m, 2H), 2.69 (s, 3H), 2.40-2.46 (m, 2H), 2.14-2.25 (m, 2H). |
| 219 | MS m/z 412.4 [M + H]+; 1H NMR (methanol-$d_4$) δ: 8.69 (s, 1H), 8.57 (d, J = 1.3 Hz, 1H), 8.31 (d, J = 0.9 Hz, 1H), 7.94-8.02 (m, 1H), 3.44-3.52 (m, 1H), 3.37-3.44 (m, 2H), 3.04-3.11 (m, 2H), 2.52 (d, J = 0.9 Hz, 3H), 2.26-2.34 (m, 2H), 2.00-2.10 (m, 2H). |
| 220 | MS m/z 440.4 [M + H]+; 1H NMR (methanol-$d_4$) δ: 8.54 (d, J = 1.6 Hz, 1H), 8.32 (s, 1H), 8.27 (d, J = 0.9 Hz, 1H), 7.94-8.00 (m, 1H), 4.18 (s, 2H), 3.69 (s, 3H), 3.48-3.56 (m, 1H), 3.40-3.45 (m, 2H), 3.13-3.18 (m, 2H), 2.54 (d, J = 0.9 Hz, 3H), 2.31-2.38 (m, 2H), 2.04-2.15 (m, 2H). |
| 221 | MS m/z 426.4 [M + H]+; 1H NMR (methanol-$d_4$) δ: 8.66 (s, 1H), 8.44 (s, 1H), 8.38 (s, 1H), 8.06-8.14 (m, 1H), 4.27 (s, 2H), 3.62-3.70 (m, 1H), 3.54-3.61 (m, 2H), 3.22-3.29 (m, 2H), 2.66 (s, 3H), 2.44-2.51 (m, 2H), 2.18-2.28 (m, 2H). |
| 230 | MS m/z 393.3 [M + H]+; 1H NMR (methanol-$d_4$) δ: 8.85 (s, 1H), 8.57 (s, 1H), 8.38 (s, 1H), 7.97-8.04 (m, 1H), 3.51-3.59 (m, 1H), 3.42-3.50 (m, 2H), 3.11-3.17 (m, 2H), 2.57 (s, 3H), 2.33-2.40 (m, 2H), 2.06-2.17 (m, 2H). |
| 249 | MS m/z 368.0 [M + H]+; 1H NMR (methanol-$d_4$) δ: 8.88 (d, J = 7.3 Hz, 1H), 8.66 (d, J = 1.6 Hz, 1H), 8.11-8.17 (m, 1H), 7.61 (d, J = 7.3 Hz, 1H), 6.60 (s, 1H), 3.55-3.69 (m, 3H), 3.23-3.31 (m, 2H), 2.54 (s, 3H), 2.45-2.52 (m, 2H), 2.18-2.28 (m, 2H). |

Example 5

Preparation of Compound 201

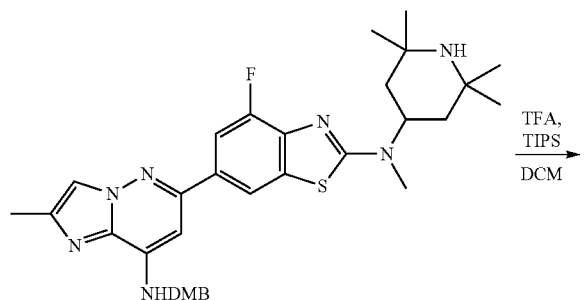

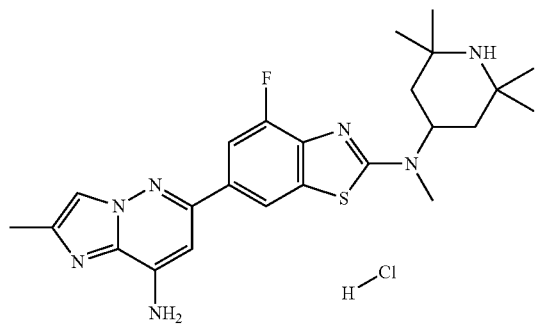

A mixture of 6-[8-[(2,4-dimethoxyphenyl)methylamino]-2-methyl-imidazo[1,2-b]pyridazin-6-yl]-4-fluoro-N-methyl-N-(2,2,6,6-tetramethyl-4-piperidyl)-1,3-benzothi azol-2-amine (10 mg, 0.016 mmol, 1.0 eq., prepared according to the procedure in Example 3) and triisopropylsilane (0.2 mL) in CH$_2$Cl$_2$ (1.0 mL) and TFA (1.0 mL) was stirred at room temperature for 1 h. The mixture was then concentrated and purified with a C18 column to give 6-(8-amino-2-methyl-imidazo[1,2-b]pyridazin-6-yl)-4-fluoro-N-methyl-N-(2,2,6,6-tetramethyl-4-piperidyl)-1,3-benzothiazol-2-amine hydrochloride (5.0 mg, 61%) after treatment with HCl in MeOH.

MS m/z 468.4 [M+H]$^+$. $^1$H NMR (methanol-d$_4$) δ: 8.23 (d, J=1.3 Hz, 1H), 8.11 (s, 1H), 7.75-7.83 (m, 1H), 7.25 (s, 1H), 4.98-5.08 (m, 1H), 3.19 (s, 3H), 2.63 (s, 3H), 2.01-2.13 (m, 4H), 1.68 (s, 6H), 1.57 (s, 6H).

Using the procedure described for Example 5, above, additional compounds described herein were prepared by substituting the appropriate starting material, suitable reagents and reaction conditions, obtaining compounds such as those selected from:

| Cpd | Data |
|---|---|
| 188 | MS m/z 383.5 [M + H]$^+$; $^1$H NMR (methanol-d$_4$) δ: 8.34 (d, J = 1.6 Hz, 1H), 7.98 (d, J = 0.9 Hz, 1H), 7.80 (dd, J = 11.7, 1.3 Hz, 1H), 7.11 (s, 1H), 3.41-3.54 (m, 3H), 3.09-3.17 (m, 2H), 2.49 (d, J = 0.9 Hz, 3H), 2.35 (dd, J = 14.3, 2.4 Hz, 2H), 2.09 (d, J = 12.0 Hz, 2H). |
| 189 | MS m/z 384.3 [M + H]$^+$; $^1$H NMR (methanol-d$_4$) δ: 8.41 (br s, 1H), 8.07 (br s, 1H), 7.79-7.89 (m, 1H), 7.30 (br. s., 1H), 3.43-3.57 (m, 3H), 3.15 (td, J = 12.5, 2.5 Hz, 2H), 2.49 (s, 3H), 2.32-2.39 (m, 2H), 2.05-2.17 (m, 2H). |

Example 6

Preparation of Compound 224

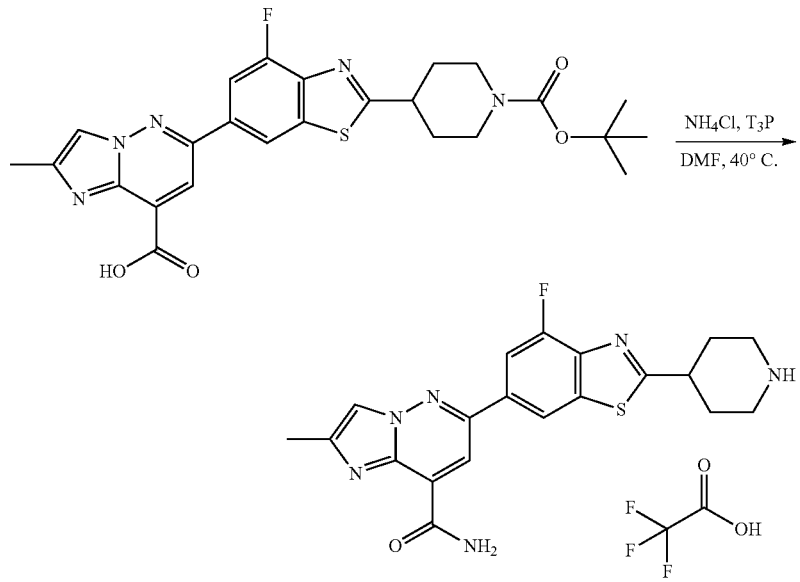

To a solution of 6-[2-(1-tert-butoxycarbonyl-4-piperidyl)-4-fluoro-1,3-benzothiazol-6-yl]-2-methyl-imidazo[1,2-b]pyridazine-8-carboxylic acid (17 mg, 0.033 mmol, 1.0 eq.) in DMF (0.5 mL) was added TEA (20 mg, 0.028 mL, 0.20 mmol, 6.0 eq.), after 10 min ammonium chloride (5.4 mg, 0.10 mmol, 3.0 eq.) was added followed by 1-propanephosphonic anhydride (50 mass %) in DMF (63 mg, 0.10 mmol, 3.0 eq.). The mixture was stirred at 40° C. overnight, then basified with aq. K$_2$CO$_3$, filtered, and the solid was collected and was further purified over C18 to give 6-[4-fluoro-2-(4-piperidyl)-1,3-benzothiazol-6-yl]-2-methyl-imidazo[1,2-b]pyridazine-8-carboxamide; 2,2,2-trifluoroacetic acid (10.0 mg, 57%).

MS m/z 411.3 [M+H]$^+$. $^1$H NMR (methanol-d$_4$) δ: 8.50 (d, J=5.7 Hz, 2H), 8.17 (s, 1H), 7.94 (d, J=11.3 Hz, 1H), 3.43-3.55 (m, 3H), 3.10-3.18 (m, 2H), 2.51 (s, 3H), 2.32-2.40 (m, 2H), 2.05-2.15 (m, 2H).

Example 7

Preparation of Compound 44

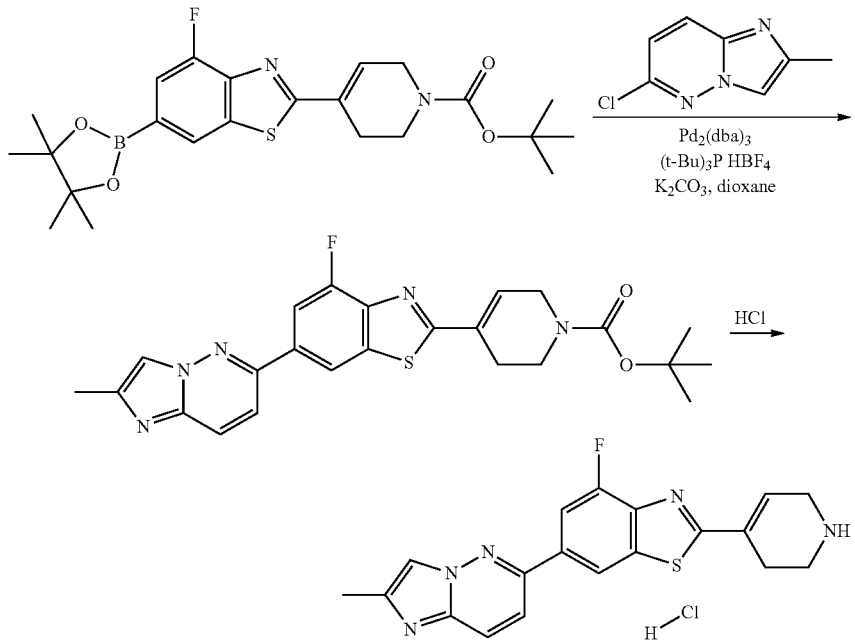

Step 1: A mixture of tert-butyl 4-[4-fluoro-6-(4,4,5,5-tetramethyl-1,3,2-dioxaborolan-2-yl)-1,3-benzothiazol-2-yl]-3,6-dihydro-2H-pyridine-1-carboxylate (prepared in example 4 step 2, 66 mg, 0.14 mmol, 1.2 eq.), 6-chloro-2-methyl-imidazo[1,2-b]pyridazine (20 mg, 0.12 mmol, 1.0 eq.), $Pd_2(dba)_3$ (5.5 mg, 0.0060 mmol, 0.05 eq.), $(t\text{-}Bu)_3P$ $HBF_4$ (3.5 mg, 0.012 mmol, 0.10 eq.) and $K_2CO_3$ (2.0 M aq.) (0.18 mL, 0.36 mmol, 3.0 eq.) in dioxane (1.0 mL) was stirred at 100° C. for 1 h. The reaction mixture was then cooled, diluted with ethyl acetate and washed with brine and then dried over sodium sulfate and concentrated. The residue was purified over silica gel with methanol in dichloromethane (0 to 8% gradient) to give tert-butyl 4-[4-fluoro-6-(2-methylimidazo[1,2-b]pyridazin-6-yl)-1,3-benzothiazol-2-yl]-3,6-dihydro-2H-pyridine-1-carboxylate (59 mg, 100%). MS m/z 466.2 [M+H]$^+$.

Step 2: To a suspension of tert-butyl 4-[4-fluoro-6-(2-methylimidazo[1,2-b]pyridazin-6-yl)-1,3-benzothiazol-2-yl]-3,6-dihydro-2H-pyridine-1-carboxylate (15 mg, 0.032 mmol, 1.0 eq.) in dioxane (0.2 mL) was added HCl (4 M in dioxane) (1.0 mL). The mixture was stirred at room temperature for 1 h, then diluted with ether and filtered to give 4-fluoro-6-(2-methylimidazo[1,2-b]pyridazin-6-yl)-2-(1,2,3,6-tetrahydropyridin-4-yl)-1,3-benzothiazole hydrochloride (12 mg, 85%).

MS m/z 366.3 [M+H]$^+$; $^1$H NMR (DMSO-d$_6$) δ: 9.70 (br s, 1H), 9.61 (br s, 1H), 8.80 (d, J=1.3 Hz, 1H), 8.49 (d, J=9.5 Hz, 1H), 8.42 (s, 1H), 8.30 (d, J=9.5 Hz, 1H), 8.13 (dd, J=12.0, 1.3 Hz, 1H), 6.94 (br s, 1H), 3.90 (br s, 2H), 3.37 (d, J=4.4 Hz, 2H), 2.95 (br s, 2H), 2.54 (s, 3H).

Using the procedure described for Example 7, above, additional compounds described herein were prepared by substituting the appropriate starting material, suitable reagents and reaction conditions, obtaining compounds such as those selected from:

| Cpd | Data |
|---|---|
| 1 | MS m/z 347.1 [M + H]$^+$; $^1$H NMR (DMSO-d$_6$) δ: 8.41 (s, 1H), 8.38 (s, 1H), 8.06 (s, 1H), 8.00 (d, J = 8.5 Hz, 1H), 7.82 (d, J = 8.5 Hz, 1H), 7.62-7.73 (m, 2H), 6.83 (br s, 1H), 4.19 (s, 3H), 3.49 (br s, 2H), 2.96 (t, J = 5.5 Hz, 2H), 2.59 (br s, 2H). |
| 18 | MS m/z 361.1 [M + H]$^+$; $^1$H NMR (DMSO-d$_6$) δ: 9.09 (br s, 2H), 8.43 (d, J = 1.6 Hz, 1H), 8.39 (s, 1H), 8.04 (d, J = 8.5 Hz, 1H), 7.88 (s, 1H), 7.86 (dd, J = 8.5, 1.9 Hz, 1H), 7.45 (s, 1H), 6.81 (br s, 1H), 4.20 (s, 3H), 3.91 (br s, 2H), 3.40 (d, J = 4.4 Hz, 2H), 2.92 (br s, 2H), 2.58 (s, 3H). |
| 46 | MS m/z 380.1 [M + H]$^+$; $^1$H NMR (DMSO-d$_6$) δ: 9.57 (br s, 2H), 8.68 (s, 1H), 8.34 (s, 1H), 8.22 (br s, 1H), 8.03 (d, J = 11.7 Hz, 1H), 6.86 (br s, 1H), 3.82 (br s, 2H), 3.24-3.35 (m, 2H), 2.87 (br s, 2H), 2.66 (s, 3H), 2.49 (s, 3H). |
| 53 | MS m/z 380.3 [M + H]$^+$; $^1$H NMR (DMSO-d$_6$) δ: 9.57 (br s, 2H), 9.43 (s, 1H), 8.68 (s, 1H), 8.12 (s, 1H), 8.05 (d, J = 12.3 Hz, 1H), 6.88 (br s, 1H), 3.89 (br s, 2H), 3.37 (d, J = 6.9 Hz, 2H), 2.85-2.95 (m, 2H), 2.91 (s, 3H), 2.55 (s, 3H). |
| 71 | MS m/z 379.3 [M + H]$^+$; $^1$H NMR (DMSO-d$_6$) δ: 9.56 (br s, 2H), 9.20 (s, 1H), 8.36 (d, J = 1.6 Hz, 1H), 8.15 (s, 1H), 8.02 (d, J = 0.9 Hz, 1H), 7.81 (dd, J = 12.0, 1.6 Hz, 1H), |

-continued

| Cpd | Data |
|---|---|
| | 6.80-6.86 (m, 1H), 3.88-3.92 (m, 2H), 3.24-3.33 (m, 2H), 2.87 (br. s., 2H), 2.60 (s, 3H), 2.48 (d, J = 0.9 Hz, 3H). |
| 72 | MS m/z 365.3 [M + H]+; 1H NMR (DMSO-d6) δ: 9.22-9.35 (m, 2H), 8.38 (s, 1H), 8.25 (d, J = 1.6 Hz, 1H), 8.07 (s, 1H), 7.71 (dd, J = 12.3, 1.6 Hz, 1H), 7.59-7.67 (m, 2H), 6.78 (br s, 1H), 4.13 (s, 3H), 3.78-3.85 (m, 2H), 3.25-3.33 (m, 2H), 2.87 (br s, 2H). |
| 102 | MS m/z 390.3 [M + H]+; 1H NMR (methanol-d4) δ: 8.37-8.42 (m, 1H), 8.23-8.28 (m, 1H), 8.05-8.08 (m, 1H), 7.97-8.00 (m, 1H), 7.49-7.55 (m, 1H), 6.71-6.76 (m, 1H), 4.23 (s, 3H), 3.86-3.93 (m, 2H), 3.41-3.46 (m, 2H), 3.00-3.06 (m, 2H). |
| 145 | MS m/z 396.3 [M + H]+; 1H NMR (methanol-d4) δ: 8.72 (d, J = 1.6 Hz, 1H), 8.31 (d, J = 0.9 Hz, 1H), 8.14 (dd, J = 11.7, 1.6 Hz, 1H), 7.88 (s, 1H), 6.96 (s, 1H), 4.40 (s, 3H), 4.04 (d, J = 3.2 Hz, 2H), 3.58 (t, J = 6.1 Hz, 2H), 3.15 (d, J = 1.9 Hz, 2H), 2.64 (d, J = 0.6 Hz, 3H). |

Example 8

Preparation of Compound 65 and Compound 67

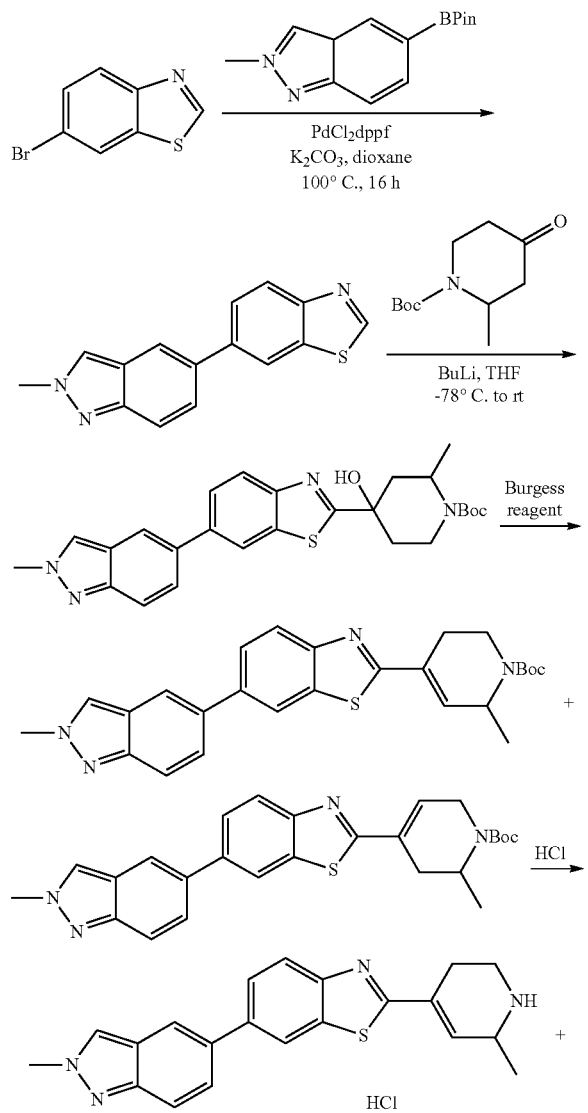

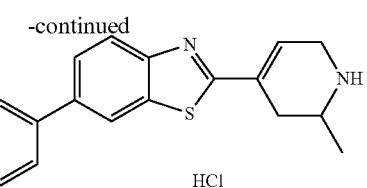

Step 1: A mixture of 6-bromobenzo[d]thiazole (2.12 g), 2-methyl-5-(4,4,5,5-tetramethyl-1,3,2-dioxaborolan-2-yl)-2H-indazole (1.2 eq.), PdCl2dppf (0.1 eq.) and K2CO3 (2.5 eq.) in dioxane and water was heated at 100° C. for 16 h under N2 atmosphere, then cooled, diluted with ethyl acetate and washed with water and brine. The organic layer was separated, dried over sodium sulfate and concentrated. The residue was purified by flash silica gel chromatography to afford 6-(2-methyl-2H-indazol-5-yl)benzo[d]thiazole (1.3 g, 48%). MS m/z 266.1, 268.1 [M+H]+.

Step 2: To a solution of 6-(2-methyl-2H-indazol-5-yl)benzo[d]thiazole (700 mg) in THF at −78° C. was added slowly a solution of n-BuLi (3.0 eq.) in hexanes. After 30 min, a solution of tert-butyl 2-methyl-4-oxopiperidine-1-carboxylate (2.0 eq.) in THF was added and the temperature was allowed to rise slowly to room temperature over 16 h. The mixture was treated with saturated NH4Cl solution and extracted with ethyl acetate. The organic extracts were combined, dried over sodium sulfate and evaporated. The residue was purified by silica gel flash column chromatography to afford tert-butyl 4-hydroxy-2-methyl-4-(6-(2-methyl-2H-indazol-5-yl)benzo[d]thiazol-2-yl)piperidine-1-carboxylate (0.56 g, 43%). MS m/z 479.2 [M+H]+.

Step 3: A mixture of tert-butyl 4-hydroxy-2-methyl-4-(6-(2-methyl-2H-indazol-5-yl)benzo[d]thiazol-2-yl)piperidine-1-carboxylate (0.56 g) and Burgess reagent (2.0 eq.) in THF was stirred at 90° C. for 48 h, then cooled, diluted with ice-water, and basified with concentrated ammonium hydroxide. The mixture was extracted with ethyl acetate. The organic extracts were combined, dried over sodium sulfate and then concentrated. The residue was purified by silica gel flash column chromatography to give a mixture of tert-butyl 6-methyl-4-(6-(2-methyl-2H-indazol-5-yl)benzo[d]thiazol-2-yl)-3,6-dihydropyridine-1(2H)-carboxylate and tert-butyl 2-methyl-4-(6-(2-methyl-2H-indazol-5-yl)benzo[d]thiazol-2-yl)-3,6-dihydropyridine-1(2H)-carboxylate (410 mg, 76%). MS m/z 461.2 [M+H]+.

Step 4: The mixture of tert-butyl 6-methyl-4-(6-(2-methyl-2H-indazol-5-yl)benzo[d]thiazol-2-yl)-3,6-dihydropyridine-1(2H)-carboxylate and tert-butyl 2-methyl-4-(6-(2-methyl-2H-indazol-5-yl)benzo[d]thiazol-2-yl)-3,6-dihydropyridine-1(2H)-carboxylate (300 mg) was stirred in 4.0 N HCl in dioxane for 16 h, then concentrated and the residue was purified over chiral prep-HPLC and C18 prep-HPLC to give 2-(6-methyl-1,2,3,6-tetrahydropyridin-4-yl)-6-(2-methyl-2H-indazol-5-yl)benzo[d]thiazole hydrochloride (21 mg).

MS m/z 361.1 [M+H]+; 1H NMR (DMSO-d6) δ: 9.81-9.93 (m, 1H), 9.25-9.38 (m, 1H), 8.45 (d, J=8.5 Hz, 2H), 8.02-8.12 (m, 2H), 7.87 (dd, J=8.7, 1.7 Hz, 1H), 7.64-7.74 (m, 2H), 6.74 (br s, 1H), 4.20 (br s, 3H), 3.44-3.54 (m, 1H), 3.20-3.33 (m, 1H), 2.93 (br s, 2H), 1.47 (d, J=7.3 Hz, 3H)

and 2-(2-methyl-1,2,3,6-tetrahydropyridin-4-yl)-6-(2-methyl-2H-indazol-5-yl)benzo[d]thiazole hydrochloride (11 mg).

MS m/z 361.2 [M+H]+; 1H NMR (DMSO-d6) δ: 9.73-9.83 (m, 1H), 9.46-9.56 (m, 1H), 8.44 (d, J=1.9 Hz, 2H), 8.08 (s, 1H), 8.05 (d, J=8.5 Hz, 1H), 7.83-7.90 (m, 1H), 7.69-7.73 (m, 1H), 7.65-7.69 (m, 1H), 6.80 (br s, 1H), 4.20 (s, 3H), 3.89 (br s, 2H), 3.45-3.55 (m, 1H), 3.11 (d, J=14.8 Hz, 1H), 2.60-2.69 (m, 1H), 1.44 (d, J=6.3 Hz, 3H).

Using the procedure described for Example 8, above, additional compounds described herein were prepared by substituting the appropriate starting material, suitable reagents and reaction conditions, obtaining compounds such as those selected from:

to example 7 step 1, 48 mg, 0.10 mmol, 1.0 eq.) in MeOH (30 mL) was added 10% Pd/C (40 mg, 0.038 mmol, 0.36 eq.) and 10% Pd(OH)2/C (30 mg, 0.021 mmol, 0.21 eq.) followed by one drop of 1N HCl. The mixture was shaken under a H2 atmosphere at 50 psi in a Parr shaker for 16 h. LC/MS indicated complete reaction. The mixture was filtered through Celite, concentrated and purified over silica gel with methanol in dichloromethane (0 to 6% gradient) to give tert-butyl 4-[4-fluoro-6-(2-methylimidazo[1,2-b]pyridazin-6-yl)-1,3-benzothiazol-2-yl]piperidine-1-carboxylate (39 mg, 81%). MS m/z 468.1 [M+H]+.

Step 2: To a suspension of tert-butyl 4-[4-fluoro-6-(2-methylimidazo[1,2-b]pyridazin-6-yl)-1,3-benzothiazol-2-yl]piperidine-1-carboxylate (15 mg, 0.032 mmol, 1.0 eq.) in dioxane (0.2 mL) was added HCl (4 M in dioxane) (1.0 mL). The mixture was stirred at room temperature for 1 h, then diluted with ether and filtered to give 4-fluoro-6-(2-methylimidazo[1,2-b]pyridazin-6-yl)-2-(4-piperidyl)-1,3-benzothiazole hydrochloride (25 mg, 74%).

MS m/z 368.3 [M+H]+. 1H NMR (DMSO-d6) δ: 9.33 (br s, 1H), 9.20 (br s, 1H), 8.82 (d, J=1.3 Hz, 1H), 8.56 (d, J=9.5 Hz, 1H), 8.50 (s, 1H), 8.40 (d, J=9.8 Hz, 1H), 8.13 (dd, J=11.8, 1.1 Hz, 1H), 3.57-3.65 (m, 1H), 3.33-3.42 (m, 2H),

| Cpd | Data |
|---|---|
| 56 | MS m/z 361.2 [M + H]+; 1H NMR (DMSO-d6) δ: 8.42 (s, 1H), 8.38 (d, J = 1.3 Hz, 1H), 8.07 (s, 1H), 7.99 (d, J = 8.5 Hz, 1H), 7.82 (dd, J = 8.5, 1.6 Hz, 1H), 7.68-7.73 (m, 1H), 7.63-7.68 (m, 1H), 6.97 (t, J = 6.1 Hz, 1H), 4.20 (s, 3H), 3.16 (d, J = 4.7 Hz, 2H), 3.08-3.13 (m, 2H), 3.01-3.07 (m, 2H), 2.64 (d, J = 4.1 Hz, 2H). |

Example 9

Preparation of Compound 45

3.02-3.12 (m, 2H), 2.56 (s, 3H), 2.31 (d, J=12.3 Hz, 2H), 2.06-2.17 (m, 2H).

Using the procedure described for Example 9, above, additional compounds described herein were prepared by

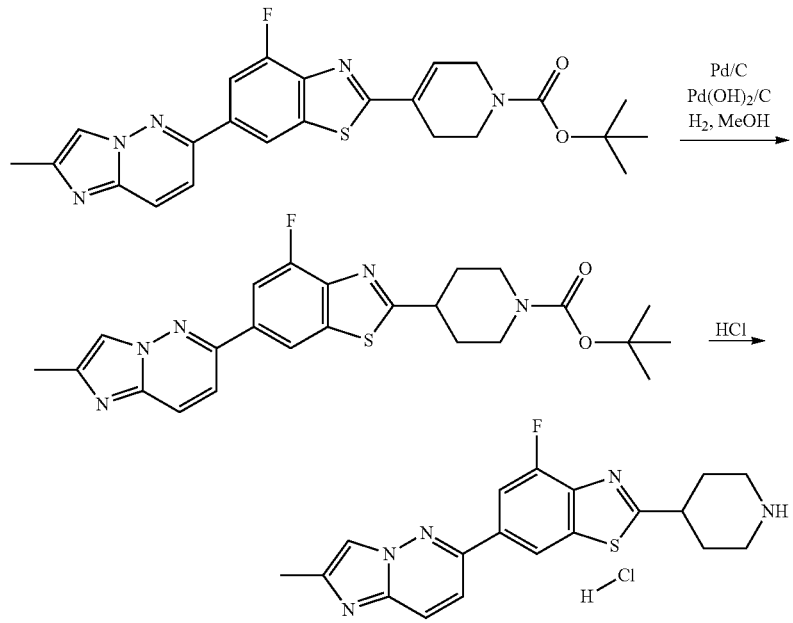

Step 1: To a solution of tert-butyl 4-[4-fluoro-6-(2-methylimidazo[1,2-b]pyridazin-6-yl)-1,3-benzothiazol-2-yl]-3,6-dihydro-2H-pyridine-1-carboxylate (prepared according substituting the appropriate starting material, suitable reagents and reaction conditions, obtaining compounds such as those selected from:

| Cpd | Data |
|---|---|
| 2 | MS m/z 349.1 [M + H]⁺; $^1$H NMR (methanol-d$_4$) δ: 8.16 (s, 2H), 7.87-7.94 (m, 2H), 7.73 (dd, J = 8.5, 1.6 Hz, 1H), 7.59 (d, J = 3.5 Hz, 2H), 4.14 (s, 3H), 3.41-3.50 (m, 3H), 3.13 (td, J = 12.5, 2.7 Hz, 2H), 2.34 (d, J = 12.0 Hz, 2H), 2.07 (d, J = 12.0 Hz, 2H). |
| 22 | MS m/z 363.1 [M + H]⁺; $^1$H NMR (DMSO-d$_6$) δ: 8.93-9.11 (m, 1H), 8.72-8.90 (m, 1H), 8.41 (d, J = 1.6 Hz, 1H), 8.38 (s, 1H), 8.01 (d, J = 8.5 Hz, 1H), 7.86 (s, 1H), 7.83 (dd, J = 8.5, 1.9 Hz, 1H), 7.43 (s, 1H), 4.20 (s, 3H), 3.52 (s, 1H), 3.39 (d, J = 12.6 Hz, 2H), 3.03-3.14 (m, 2H), 2.58 (s, 3H), 2.29 (d, J = 11.3 Hz, 2H), 2.05 (d, J = 11.3 Hz, 2H). |
| 42 | MS m/z 363.1 [M + H]⁺; $^1$H NMR (DMSO-d$_6$) δ: 9.37 (br s, 1H), 9.22 (br s, 1H), 8.40-8.45 (m, 2H), 8.05 (s, 1H), 8.00 (d, J = 8.5 Hz, 1H), 7.83 (dd, J = 8.5, 1.9 Hz, 1H), 7.68-7.72 (m, 1H), 7.63-7.67 (m, 1H), 4.20 (s, 3H), 3.50-3.58 (m, 1H), 3.33 (s, 1H), 3.10-3.27 (m, 3H), 2.41 (d, J = 14.8 Hz, 1H), 2.24-2.33 (m, 2H), 1.89-2.05 (m, 3H). |
| 52 | MS m/z 405.2 [M + H]⁺; $^1$H NMR (methanol-d$_4$) δ: 8.29 (s, 1H), 8.26-8.27 (m, 1H), 7.99-8.03 (m, 2H), 7.82-7.86 (m, 1H), 7.69-7.74 (m, 2H), 4.26 (s, 3H), 3.69-3.81 (m, 1H), 2.11-2.21 (m, 2H), 1.60-1.70 (m, 2H), 1.41 (s, 6H), 1.30 (s, 6H). |
| 58 | MS m/z 363.2 [M + H]⁺; $^1$H NMR (DMSO-d$_6$) δ: 8.94-9.71 (m, 2H), 8.43 (d, 7 = 3.2 Hz, 2H), 8.05 (s, 1H), 8.02 (d, J = 8.5 Hz, 1H), 7.84 (dd, J = 8.5, 1.6 Hz, 1H), 7.68-7.73 (m, 1H), 7.62-7.67 (m, 1H), 4.20 (s, 3H), 3.50-3.59 (m, 1H), 3.02-3.12 (m, 1H), 2.51 (br s, 2H), 2.23-2.36 (m, 2H), 2.05 (dd, J = 12.8, 3.3 Hz, 1H), 1.88 (d, J = 12.9 Hz, 1H), 1.35 (d, J = 6.3 Hz, 3H). |
| 66 | MS m/z 406.2 [M + H]⁺; $^1$H NMR (DMSO-d$_6$) δ: 8.74-8.99 (m, 2H), 8.33 (s, 1H), 8.11 (s, 1H), 7.75 (s, 1H), 7.60 (d, J = 9.8 Hz, 1H), 7.49 (d, J = 8.5 Hz, 1H), 7.37 (s, 1H), 4.43-4.58 (m, 1H), 4.18 (s, 3H), 3.35-3.43 (m, 2H), 3.08-3.17 (m, 1H), 3.03 (s, 3H), 2.56 (s, 3H), 2.00-2.12 (m, 1H), 1.85-1.98 (m, 3H), 1.29 (d, J = 6.3 Hz, 3H). |
| 70 | MS m/z 368.3 [M + H]⁺; $^1$H NMR (DMSO-d$_6$) δ: 8.65-8.78 (m, 1H), 8.39-8.53 (m, 1H), 8.29 (d, J = 1.6 Hz, 1H), 8.04 (t, J = 1.1 Hz, 1H), 7.72-7.78 (m, 1H), 7.69 (d, J = 1.3 Hz, 2H), 3.45-3.53 (m, 1H), 3.32-3.38 (m, 2H), 2.97-3.08 (m, 2H), 2.59 (s, 3H), 2.20-2.28 (m, 2H), 1.91-2.02 (m, 2H). |
| 73 | MS m/z 367.3 [M + H]⁺; $^1$H NMR (DMSO-d$_6$) δ: 8.96-9.07 (m, 1H), 8.69-8.83 (m, 1H), 8.45 (s, 1H), 8.31 (d, J = 1.6 Hz, 1H), 8.09-8.13 (m, 1H), 7.76 (dd, J = 12.3, 1.6 Hz, 1H), 7.70-7.73 (m, 1H), 7.68 (d, J = 1.9 Hz, 1H), 4.21 (s, 3H), 3.53-3.60 (m, 1H), 3.38-3.43 (m, 2H), 3.03-3.15 (m, 2H), 2.27-2.35 (m, 2H), 2.00-2.12 (m, 2H). |
| 82 | MS m/z 349.2 [M + H]⁺; $^1$H NMR (DMSO-d$_6$) δ: 8.91 (s, 1H), 8.41 (d, J = 1.3 Hz, 1H), 8.03 (d, J = 8.5 Hz, 1H), 7.81 (dd, J = 8.5, 1.6 Hz, 1H), 7.71 (s, 1H), 7.58-7.63 (m, 1H), 7.52-7.57 (m, 1H), 3.25 (br. s., 1H), 3.08 (d, J = 12.3 Hz, 2H), 2.68 (t, J = 11.3 Hz, 2H), 2.36 (s, 3H), 2.07 (d, J = 11.3 Hz, 2H), 1.72 (dd, J = 12.0, 3.5 Hz, 2H). |
| 83 | MS m/z 367.1 [M + H]⁺; $^1$H NMR (DMSO-d$_6$) δ: 8.55 (br s, 1H), 8.42 (br s, 1H), 7.99 (d, J = 7.6 Hz, 1H), 7.91 (br s, 1H), 7.84 (d, J = 7.3 Hz, 1H), 7.49 (d, J = 12.9 Hz, 1H), 4.23 (br. s., 3H), 3.22 (br s, 1H), 3.05 (d, J = 10.1 Hz, 2H), 2.64 (t, J = 11.0 Hz, 2H), 2.04 (d, J = 11.3 Hz, 2H), 1.69 (d, J = 10.4 Hz, 2H). |
| 84 | MS m/z 374.2 [M + H]⁺; $^1$H NMR (DMSO-d$_6$) δ: 8.71 (s, 2H), 8.53 (d, J = 1.6 Hz, 1H), 8.49 (d, J = 1.6 Hz, 2H), 8.33 (d, J = 1.6 Hz, 1H), 8.06 (d, J = 8.5 Hz, 1H), 7.92 (dd, J = 8.4, 1.7 Hz, 1H), 4.28 (s, 3H), 3.50-3.58 (m, 1H), 3.42 (d, J = 12.6 Hz, 2H), 3.05-3.17 (m, 2H), 2.31 (d, J = 12.6 Hz, 2H), 1.95-2.06 (m, 2H). |
| 85 | MS m/z 377.2 [M + H]⁺; $^1$H NMR (DMSO-d$_6$) δ: 8.38 (br s, 2H), 7.98 (d, J = 7.6 Hz, 1H), 7.83 (d, J = 18.6 Hz, 2H), 7.42 (br s, 1H), 4.20 (br s, 3H), 3.20 (br s, 1H), 2.94-3.10 (m, 4H), 2.62 (t, J = 10.4 Hz, 2H), 2.03 (d, J = 10.7 Hz, 2H), 1.67 (d, J = 11.0 Hz, 2H), 1.37 (br s, 3H). |
| 94 | MS m/z 363.2 [M + H]⁺; $^1$H NMR (DMSO-d$_6$) δ: 15.14-15.48 (m, 2H), 9.39 (br. s., 1H), 9.28 (br s, 1H), 8.49 (s, 1H), 8.06 (d, J = 8.5 Hz, 1H), 7.79-7.93 (m, 2H), 7.72 (s, 1H), 3.54 (t, J = 11.2 Hz, 1H), 3.33-3.41 (m, 2H), 3.08 (q, J = 11.6 Hz, 2H), 2.86 (s, 3H), 2.67 (s, 3H), 2.29 (d, J = 12.9 Hz, 2H), 2.04-2.18 (m, 2H). |
| 95 | MS m/z 349.2 [M + H]⁺; $^1$H NMR (DMSO-d$_6$) δ: 15.18 (br s, 2H), 9.23 (br s, 1H), 9.11 (d, J = 8.8 Hz, 1H), 8.53 (s, 1H), 8.02-8.13 (m, 2H), 7.81-7.95 (m, 3H), 3.48-3.60 (m, 1H), 3.38 (d, J = 10.7 Hz, 2H), 3.00-3.14 (m, 2H), 2.84 (s, 3H), 2.29 (d, J = 12.6 Hz, 2H), 2.00-2.17 (m, 2H). |
| 97 | MS m/z 350.0 [M + H]⁺; $^1$H NMR (DMSO-d$_6$) δ: 9.19-9.28 (m, 1H), 9.08-9.18 (m, 1H), 8.96 (s, 1H), 8.59 (d, J = 9.5 Hz, 1H), 8.54 (s, 1H), 8.45 (d, J = 9.8 Hz, 1H), 8.28 (d, J = 8.8 Hz, 1H), 8.19 (d, J = 8.5 Hz, 1H), 3.58 (t, J = 11.2 Hz, 1H), 3.33-3.43 (m, 2H), 3.02-3.13 (m, 2H), 2.57 (s, 3H), 2.26-2.34 (m, 2H), 2.03-2.15 (m, 2H). |
| 103 | MS m/z 396.3 [M + H]⁺; $^1$H NMR (methanol-d$_4$) δ: 8.23 (s, 1H), 7.95 (dd, J = 13.9, 1.3 Hz, 2H), 7.58 (s, 1H), 7.43-7.49 (m, 2H), 4.39 (s, 2H), 4.13 (s, 3H), 3.36-3.47 (m, 3H), 3.03-3.11 (m, 2H), 2.23-2.34 (m, 2H), 1.97-2.11 (m, 2H). |
| 104 | MS m/z 392.3 [M + H]⁺; $^1$H NMR (methanol-d$_4$) δ: 8.53 (d, J = 1.6 Hz, 1H), 8.19 (d, J = 1.9 Hz, 1H), 8.14 (d, J = 1.6 Hz, 1H), 7.63-7.67 (m, 1H), 4.33 (s, 3H), 3.57-3.66 (m, 3H), 3.23-3.31 (m, 2H), 2.44-2.52 (m, 2H), 2.17-2.28 (m, 2H). |
| 112 | MS m/z 350.2 [M + H]⁺; $^1$H NMR (DMSO-d$_6$) δ: 8.46 (s, 1H), 8.00-8.08 (m, 2H), 7.82-7.88 (m, 1H), 7.70-7.78 (m, 2H), 3.17-3.25 (m, 1H), 3.00-3.08 (m, 2H), 2.66 (s, 3H), 2.60-2.64 (m, 2H), 2.02-2.08 (m, 2H), 1.62-1.74 (m, 2H). |
| 113 | MS m/z 367.2 [M + H]⁺; $^1$H NMR (methanol-d$_4$) δ: 9.02 (s, 1H), 8.48 (s, 1H), 8.26 (d, J = 11.0 Hz, 1H), 8.13-8.18 (m, 2H), 7.92 (d, J = 8.5 Hz, 1H), 3.58-3.67 (m, 2H), 3.27-3.25 (m, 3H), 2.62 (s, 3H), 2.43-2.52 (m, 2H), 2.14-2.25 (m, 2H). |
| 114 | MS m/z 363.2 [M + H]⁺; $^1$H NMR (DMSO-d$_6$) δ: 9.18 (s, 1H), 8.84 (br s, 1H), 8.61 (d, J = 10.1 Hz, 1H), 8.56 (s, 1H), 8.20 (s, 1H), 8.14 (d, J = 8.8 Hz, 1H), 8.08 (s, 1H), 7.92 |

| Cpd | Data |
|---|---|
|  | (d, J = 8.5 Hz, 1H), 3.35-3.43 (d, J = 12.6 Hz, 1H), 3.05-3.16 (m, 2H), 2.65 (s, 3H), 2.54 (s, 3H), 2.31 (d, J = 12.3 Hz, 2H), 1.96-2.08 (m, 2H). |
| 115 | MS m/z 377.0 [M + H]$^+$; $^1$H NMR (DMSO-d$_6$) δ: 9.51 (d, J = 10.1 Hz, 1H), 9.35 (br s, 1H), 8.44 (d, J = 9.5 Hz, 2H), 8.07 (s, 1H), 8.02 (d, J = 8.5 Hz, 1H), 7.84 (d, J = 8.8 Hz, 1H), 7.64-7.74 (m, 2H), 4.21 (s, 3H), 3.63-3.73 (m, 1H), 3.22 (br s, 2H), 2.23 (d, J = 12.6 Hz, 1H), 2.16 (d, J = 13.2 Hz, 1H), 1.94-2.10 (m, 2H), 1.45 (d, J = 3.2 Hz, 6H). |
| 139 | MS m/z 364.2 [M + H]$^+$; $^1$H NMR (DMSO-d$_6$) δ: 9.18 (br s, 1H), 9.08 (br s, 1H), 8.90 (s, 1H), 8.43 (br s, 1H), 8.29 (br s, 1H), 8.22-8.27 (m, 1H), 8.17 (d, J = 8.8 Hz, 1H), 3.54-3.61 (m, 1H), 3.34-3.43 (m, 2H), 3.02-3.14 (m, 2H), 2.73 (s, 3H), 2.56 (s, 3H), 2.24-2.35 (m, 2H), 2.03-2.15 (m, 2H). |
| 144 | MS m/z 382.1 [M + H]$^+$; $^1$H NMR (methanol-d$_4$) δ: 8.57 (d, J = 1.6 Hz, 1H), 8.35 (m, 2H), 8.27 (s, 1H), 7.98-8.02 (m, 1H), 3.46-3.51 (m, 1H), 3.31-3.38 (m, 2H), 3.11-3.16 (m, 2H), 2.55 (d, J = 0.9 Hz, 3H), 2.34-2.41 (m, 2H), 1.96-2.08 (m, 1H), 1.32 (d, J = 6.6 Hz, 3H). |
| 156 | MS m/z 350.2 [M + H]$^+$; $^1$H NMR (methanol-d$_4$) δ: 9.12 (d, J = 2.2 Hz, 1H), 8.88 (d, J = 2.2 Hz, 1H), 8.34 (s, 1H), 8.07 (d, J = 8.5 Hz, 1H), 7.82-7.87 (m, 1H), 7.67 (s, 1H), 3.35-3.41 (m, 1H), 3.20-3.27 (m, 2H), 2.81-2.89 (m, 2H), 2.49 (s, 3H), 2.18-2.27 (m, 2H), 1.85-1.97 (m, 2H). |
| 166 | MS m/z 408.2 [M + H]$^+$; $^1$H NMR (methanol-d$_4$) δ: 8.55 (d, J = 1.3 Hz, 1H), 8.31 (d, J = 0.9 Hz, 2H), 8.24 (s, 1H), 7.99 (dd, J = 11.7, 1.3 Hz, 1H), 3.72-3.88 (m, 1H), 3.50-3.65 (m, 2H), 3.23-3.49 (m, 2H), 2.96-3.15 (m, 2H), 2.54 (s, 3H), 2.19-2.33 (m, 2H), 2.05-2.17 (m, 3H), 1.94-2.04 (m, 2H). |
| 169 | MS m/z 350.1 [M + H]$^+$; $^1$H NMR (methanol-d$_4$) δ: 8.96-9.00 (m, 2H), 8.62 (d, J = 1.6 Hz, 1H), 8.09-8.14 (m, 1H), 8.03 (s, 1H), 7.86 (s, 1H), 3.36-3.45 (m, 1H), 3.29-3.32 (m, 2H), 2.91-2.99 (m, 2H), 2.52 (s, 3H), 2.24-2.32 (m, 2H), 1.92-2.04 (m, 2H). |
| 190 | MS m/z 377.0 [M + H]$^+$; $^1$H NMR (DMSO-d$_6$) δ: 8.95-9.71 (m, 2H), 8.42-8.46 (m, 2H), 8.06 (s, 1H), 8.02 (d, J = 8.5 Hz, 1H), 7.84 (dd, J = 8.4, 1.7 Hz, 1H), 7.69-7.73 (m, 1H), 7.64-7.68 (m, 1H), 4.21 (s, 3H), 3.48-3.85 (m, 2H), 3.34 (br s, 1H), 2.18-2.35 (m, 2H), 1.77-2.14 (m, 2H), 1.31-1.50 (m, 6H). |

Example 10

Preparation of Compound 106

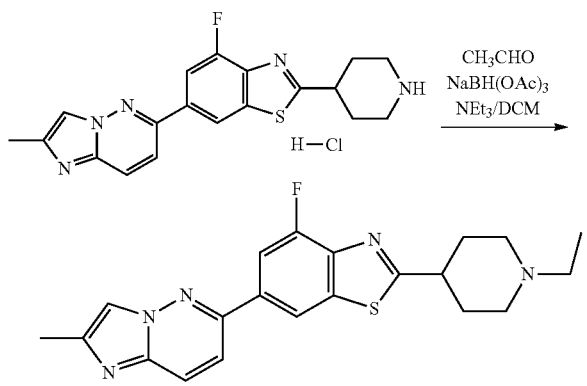

To a mixture of 4-fluoro-6-(2-methylimidazo[1,2-b]pyridazin-6-yl)-2-(4-piperidyl)-1,3-benzothiazole hydrochloride (prepared according to Example 9 step 2, 100 mg, 0.25 mmol, 1.0 eq.) in CH$_2$Cl$_2$ (5.0 mL) was added NEt$_3$ (25 mg, 0.035 mL, 0.25 mmol, 1.0 eq.) followed by acetaldehyde (0.36 mL, 2.5 mmol, 10 eq.) followed by NaBH(OAc)$_3$ (160 mg, 0.74 mmol, 3.0 eq.). The mixture was stirred at room temperature for 2 h, after which LC/MS showed complete conversion. The mixture was treated with aq. K$_2$CO$_3$, and then extracted with ethyl acetate, dried and concentrated. The residue was purified over silica gel with methanol in CH$_2$Cl$_2$ (3 to 20% gradient) to give 2-(1-ethyl-4-piperidyl)-4-fluoro-6-(2-methylimidazo[1,2-b]pyridazin-6-yl)-1,3-benzothiazole (80 mg, 82%).

MS m/z 396.2 [M+H]$^+$; $^1$H NMR (CDCl$_3$) δ: 8.26 (d, J=1.3 Hz, 1H), 7.94 (d, J=9.5 Hz, 1H), 7.80-7.86 (m, 2H), 7.47 (d, J=9.5 Hz, 1H), 3.51 (d, J=5.4 Hz, 3H), 3.28 (br s, 1H), 3.18 (d, J=10.1 Hz, 2H), 2.50-2.65 (m, 2H), 2.01-2.41 (m, 6H), 1.14-1.25 (m, 3H).

Using the procedure described for Example 10, above, additional compounds described herein were prepared by substituting the appropriate starting material, suitable reagents and reaction conditions, obtaining compounds such as those selected from:

| Cpd | Data |
|---|---|
| 3 | MS m/z 361.0 [M + H]$^+$; $^1$H NMR (methanol-d$_4$) δ: 8.28 (s, 2H), 8.01-8.08 (m, 2H), 7.83-7.88 (m, 1H), 7.71 (s, 2H), 6.76-6.81 (m, 1H), 4.25 (s, 3H), 3.96-4.19 (m, 2H), 3.47-3.79 (m, 2H), 3.13-3.25 (m, 2H), 3.07 (s, 3H). |
| 6 | MS m/z 361.0 [M + H]$^+$; $^1$H NMR (DMSO-d$_6$) δ: 11.00-11.13 (m, 1H), 8.57 (s, 1H), 8.52 (s, 1H), 8.26 (d, J = 1.3 Hz, 1H), 7.95-8.05 (m, 2H), 7.75 (d, J = 9.1 Hz, 1H), 7.70 (dd, J = 8.5, 1.6 Hz, 1H), 6.34 (br s, 1H), 4.23 (s, 3H), 3.95-4.02 (m, 1H), 3.74-3.83 (m, 1H), 3.58-3.66 (m, 1H), 3.23-3.35 (m, 1H), 2.93-3.05 (m, 1H), 2.87 (m, 4H). |
| 9 | MS m/z 363.1 [M + H]$^+$; $^1$H NMR (methanol-d$_4$) δ: 8.23-8.33 (m, 2H), 7.98-8.07 (m, 2H), 7.85 (dd, J = 8.5, 1.9 Hz, 1H), 7.66-7.76 (m, 2H), 4.26 (s, 3H), 3.72 (d, J = 12.8 Hz, 2H), 3.47-3.58 (m, 1H), 3.25 (d, J = 2.5 Hz, 2H), 2.98 (s, 3H), 2.51 (br. s., 2H), 2.13-2.28 (m, 2H). |

| Cpd | Data |
|---|---|
| 10 | MS m/z 363.2 [M + H]⁺; ¹H NMR (DMSO-d₆) δ: 8.97-9.35 (m, 1H), 8.42 (s, 1H), 8.37 (s, 1H), 7.82-7.91 (m, 3H), 7.62 (d, J = 9.1 Hz, 1H), 7.29 (d, J = 7.9 Hz, 1H), 4.09 (s, 3H), 3.32-3.48 (m, 2H), 2.99 (br. s., 2H), 2.79-2.88 (m, 1H), 2.71 (s, 3H), 1.91-2.03 (m, 2H), 1.71-1.85 (m, 2H). |
| 92 | MS m/z 382.3 [M + H]⁺; ¹H NMR (CDCl₃) δ: 8.27 (d, J = 1.3 Hz, 1H), 7.95 (d, J = 9.5 Hz, 1H), 7.82-7.88 (m, 2H), 7.48 (d, J = 9.5 Hz, 1H), 3.11-3.38 (m, 3H), 2.57 (s, 3H), 2.10-2.53 (m, 9H). |
| 107 | MS m/z 396.3 [M + H]⁺; ¹H NMR (CDCl₃) δ: 8.25 (d, J = 1.6 Hz, 1H), 7.82 (dd, J = 11.3, 1.6 Hz, 1H), 7.80 (d, J = 0.9 Hz, 1H), 7.30 (d, J = 0.9 Hz, 1H), 3.20-3.31 (m, 1H), 2.75 (d, J = 0.9 Hz, 3H), 2.56 (d, J = 0.6 Hz, 3H), 2.44 (br. s., 3H), 2.04-2.40 (m, 8H). |
| 108 | MS m/z 420.4 [M + H]⁺; ¹H NMR (CDCl₃) δ: 7.93 (s, 1H), 7.88 (t, 7 = 1.1 Hz, 1H), 7.67 (d, J = 0.9 Hz, 1H), 7.60 (d, J = 0.9 Hz, 2H), 7.36-7.39 (m, 1H), 4.37-4.58 (m, 1H), 4.27 (s, 3H), 3.19-3.34 (m, 1H), 3.11 (s, 3H), 2.71 (s, 3H), 2.55 (br. s., 5H), 2.22-2.45 (m, 1H), 1.96 (d, J = 10.4 Hz, 3H), 1.37 (br. s., 3H). |
| 330 | MS [M + H]⁺ 422.1; ¹H NMR (methanol-d₄) δ: 8.76 (s, 1H), 8.26 (s, 1H), 8.03 (d, J = 8.4 Hz, 1H), 7.67 (s, 1H), 7.23-7.19 (m, 2H), 3.24 (s, 3H), 3.33 (m, 1H), 3.14 (d, J = 12.0 Hz, 2H), 2.45 (s, 3H), 2.44-2.40 (m, 2H), 2.11-2.04 (m, 2H), 1.97-1.95 (m, 2H), OH proton not observed. |
| 332 | MS [M + H]⁺ 440.2; ¹H NMR (DMSO-d₆) δ: 13.79 (s, 1H), 12.69 (s, 1H), 8.95 (s, 1H), 8.30 (s, 1H), 7.94 (d, J = 8.8 Hz, 1H), 7.24-7.18 (m, 2H), 3.35-3.31 (m, 1H), 3.16 (s, 3H), 3.05 (d, J = 12 Hz, 2H), 2.36-2.32 (m, 5H), 2.01-1.93 (m, 2H),1.83-1.81 (m, 2H). |
| 336 | MS [M + H]⁺ 412.0; ¹H NMR (DMSO-d₆) δ: 8.76 (s, 1H), 8.14 (s, 2H), 7.88 (d, J = 8.4 Hz, 1H), 7.31 (d, J = 6.8 Hz, 1H), 7.26 (s, 1H), 5.64-5.51 (m, 1H), 5.15 (br s, 1H), 4.30-3.54 (m, 4H), 3.01 (s, 3H), 2 NH and OH protons not observed. |
| 339 | MS [M + H]⁺ 434.4; ¹H NMR (DMSO-d₆) δ: 10.45 (s, 1H), 9.10 (s, 1H), 8.15 (s, 2H), 7.75 (d, J = 8.2 Hz, 1H), 7.33 (s, 1H), 7.29 (d, J = 8.1 Hz, 1H), 4.25 (s, 2H), 3.49 (d, J = 11.2 Hz, 2H), 3.09 (q, J = 11.6, 11.1 Hz, 2H), 2.84-2.70 (m, 5H), 2.49-2.46 (m, 2H), 2.24 (d, J = 12.7 Hz, 2H), NH proton not observed. |
| 340 | MS [M + H]⁺ 434.4; ¹H NMR (DMSO-d₆) δ: 11.42-11.05 (m, 1H), 9.05 (s, 1H), 8.14 (s, 2H), 7.83-7.76 (m, 1H), 7.32-7.25 (m, 2H), 4.00-3.81 (m, 2H), 3.75-3.56 (m, 4H), 3.27-3.06 (m, 2H), 2.82 (d, J = 4.5 Hz, 3H), 2.35-1.98 (m, 4H), 1 NH not observed. |
| 342 | MS [M + H]⁺ 412.2; ¹H NMR (DMSO-d₆) δ: 8.74 (s, 1H), 8.17 (s, 1H), 8.10 (s, 2H), 7.85 (d, J = 8.3 Hz, 1H), 7.28-7.18 (m, 2H), 5.10 (d, J = 53.2 Hz, 1H), 4.63-4.41 (m, 1H), 3.23 (m, 1H), 2.95-2.74 (m, 2H), 2.41 (m, 1H), 2.32 (s, 3H), NH proton not observed. |
| 343 | MS [M + H]⁺ 494.3; ¹H NMR (DMSO-d₆) δ: 2:1 mixture of rotamers δ: 11.08 (br s, 0.3H), 10.93 (br s, 0.7H), 9.09 (s, 1H), 8.16 (s, 2H), 7.83 (d, J = 8.3 Hz, 1H), 7.31-7.26 (m, 2H), 5.58 (bs, 0.3H), 5.12 (s, 0.7H), 4.70-4.59 (m, 1H), 4.52-4.36 (m, 3H), 4.32-4.22 (m, 1H), 3.45 (s, 1H), 3.32 (s, 2H), 2.96-2.91 (m, 3H). |
| 347 | MS [M + H]⁺ 434.3; ¹H NMR (DMSO-d₆) δ: 10.50 (br s, 1H), 9.03 (s, 1H), 8.15 (s, 2H), 7.90-7.75 (m, 1H), 7.27 (s, 2H), 4.61-4.04 (m, 1H), 4.02-3.53 (m, 3H), 3.49-3.23 (m, 2H), 3.26-2.84 (m, 1H), 2.77 (s, 6H), 2.12 (d, J = 6.2 Hz, 1H), 1.97-1.76 (m, 1H), NH proton not observed. |
| 351 | MS [M + H]⁺ 450.4; ¹H NMR (DMSO-d₆) δ: 11.29 (br s, 1H), 9.11 (s, 1H), 8.14 (s, 2H), 7.72 (d, J = 8.1 Hz, 1H), 7.35 (s, 1H), 7.28 (d, J = 8.0 Hz, 1H), 4.61 (br s, 1H), 3.33-3.07 (m, 4H), 2.69 (d, J = 4.0 Hz, 6H), 2.22 (d, J = 9.7 Hz, 2H), 1.99-1.90 (m, 2H), 1.90-1.80 (m, 2H), 1.79-1.66 (m, 2H), 1 NH proton not observed. |
| 352 | MS [M + H]⁺ 422.4; ¹H NMR (DMSO-d₆) δ: 9.11 (s, 1H), 8.16 (s, 2H), 7.81 (d, J = 7.1 Hz, 1H), 7.33-7.25 (m, 2H), 5.02 (br s, 1H), 3.52-3.33 (m, 3H), 3.23 (s, 3H), 2.99-2.88 (m, 1H), 2.79 (s, 3H), 2.06-1.86 (m, 4H), NH and OH protons not observed. |
| 360 | MS [M + H]⁺ 450.4; ¹H NMR (DMSO-d₆) δ: 10.06 (s, 1H), 9.04 (s, 1H), 8.15 (s, 2H), 7.86 (d, J = 8.4 Hz, 1H), 7.27 (s, 2H), 5.03-4.90 (m, 1H), 3.47 (d, J = 16.1 Hz, 1H), 3.33-3.08 (m, 6H), 2.75 (s, 3H), 2.47-2.38 (m, 1H), 1.98 (d, J = 16.1 Hz, 1H), 1.29 (s, 3H), 1.02 (s, 3H), NH proton not observed. |
| 364 | MS [M + H]⁺ 422.3; ¹H NMR (DMSO-d₆) δ: 11.40 (br s, 1H), 9.04 (s, 1H), 8.15 (s, 2H), 7.83 (d, J = 8.7 Hz, 1H), 7.35-7.22 (m, 2H), 4.80 (br s, 1H), 3.59-3.48 (m, 1H), 3.38 (s, 3H), 2.78 (q, J = 9.4 Hz, 2H), 2.69 (d, J = 4.8 Hz, 6H), 2.69-2.63 (m, 2H), 1 NH proton not observed. |
| 366 | MS [M + H]⁺ 408.0; ¹H NMR (DMSO-d₆) δ: 8.83 (s, 1H), 8.29 (br s, 1H), 8.01 (br s, 1H), 7.86 (d, J = 8.8 Hz, 1H), 7.28-7.22 (m, 2H), 3.89 (br s, 1H), 3.44 (m, 1H), 2.80-2.68 (m, 2H), 2.18 (s, 3H), 2.12-1.94 (m, 3H), 1.63-1.50 (m, 2H), 2 NH and OH protons not observed. |
| 369 | MS [M + H]⁺ 434.4; ¹H NMR (DMSO-d₆) δ: 1:1 mixture of rotamers δ: 11.19-10.61 (m, 2H), 9.07 (s, 1H), 8.15 (s, 2H), 7.81 (d, J = 8.3 Hz, 1H), 7.31-7.26 (m, 2H), 4.79-4.48 (m, 1H), 3.86-3.59 (m, 3H), 3.36-3.28 (m, 1H), 3.20-3.09 (m, 1H), 3.08-2.95 (m, 1H), 2.83-2.72 (m, 3H), 2.72-2.59 (m, 1H), 2.44-2.23 (m, 2H), 2.21-2.03 (m, 1H), 1.96 (d, J = 14.9 Hz, 1H). |
| 370 | MS [M + H]⁺ 434.4; ¹H NMR (DMSO-d₆) δ: 11.07 (s, 1H), 9.05 (s, 1H), 8.16 (s, 2H), 7.80 (d, J = 8.2 Hz, 1H), 7.30 (s, 1H), 7.28 (d, J = 8.2 Hz, 1H), 4.29-4.16 (m, 2H), 3.93 (d, J = 11.5 Hz, 1H), 3.61 (dd, J = 10.5 Hz, 1H), 3.31 (d, J = 11.1 Hz, 1H), 3.06-2.91 (m, 2H), 2.81 (d, J = 4.3 Hz, 3H), 2.45-2.33 (m, 2H), 2.16 (d, J = 12.3 Hz, 1H), 2.03-1.93 (m, 1H), 1.90-1.77 (m, 1H), NH proton not observed. |

-continued

| Cpd | Data |
|---|---|
| 372 | MS m/z [M + H]⁺ 452.3; ¹H NMR (methanol-d₄) δ: 1:1 mixture of rotamers δ: 9.08 (s, 0.5H), 9.07 (s, 0.5H), 8.30 (s, 2H), 7.77 (d, J = 8.1 Hz, 1H), 7.38 (d, J = 8.1 Hz, 1H), 7.31 (s, 1H), 5.41 (br s, 0.5H), 4.22 (br s, 0.5H), 4.15-3.89 (m, 2H), 3.83-3.68 (m, 2H), 3.60-3.32 (m, 4H), 3.17 (s, 1.5H), 3.01 (s, 1.5H), 2.72-2.15 (m, 3H), 2.15-2.07 (m, 1H), NH and OH protons not observed. |
| 373 | MS m/z [M + H]⁺ 393.9; ¹H NMR (DMSO-d₆) δ: 8.82 (s, 1H), 8.14 (s, 2H), 7.86 (d, J = 8.8 Hz, 1H), 7.28-7.21 (m, 2H), 4.50 (br s, 1H), 3.45 (m, 1H), 2.77-2.55 (m, 3H), 2.37-2.29 (m, 2H), 2.28 (s, 3H), 1.80-1.66 (m, 1H), NH and OH protons not observed. |
| 375 | MS m/z [M + H]⁺ 408.1; ¹H NMR (DMSO-d₆) δ: 8.91 (s, 1H), 8.29 (br s, 1H), 8.00 (br s, 1H), 7.88 (d, J = 8.8 Hz, 1H), 7.28-7.22 (m, 2H), 3.50 (m, 1H), 3.23 (s, 3H), 2.91-2.81 (m, 2H), 2.55 (m, 1H), 2.36-2.14 (m, 2H), 2.27 (s, 3H), 1.93-1.82 (m, 1H), NH and OH protons not observed. |
| 382 | MS m/z [M + H]⁺ 426.0; ¹H NMR (DMSO-d₆) δ: 8.88 (s, 1H), 8.12 (s, 2H), 7.87 (d, J = 8.4 Hz, 1H), 7.51 (m, 1H), 7.35-7.19 (m, 2H), 5.53-5.30 (m, 1H), 3.56 (m, 1H), 3.21 (s, 3H), 3.04 (m, 1H), 2.98-2.73 (m, 2H), 2.64 (m, 1H), 2.29 (s, 3H), NH not observed. |
| 383 | MS m/z [M + H]⁺ 448.0; ¹H NMR (DMSO-d₆) δ: 8.93 (s, 1H), 8.30 (s, 1H), 8.01 (s, 1H), 7.89 (d, J = 8.8 Hz, 1H), 7.28-7.23 (m, 2H), 3.50 (m, 1H), 3.25-2.90 (m, 5H), 2.45-2.22 (m, 1H), 2.10-1.60 (m, 6H), 1.00-0.20 (m, 4H), NH and OH protons not observed. |
| 384 | MS m/z [M + H]⁺ 453.9; ¹H NMR (DMSO-d₆) δ: 8.91 (s, 1H), 8.29 (br s, 1H), 8.01 (br s, 1H), 7.88 (d, J = 8.8 Hz, 1H), 7.28-7.22 (m, 2H), 4.61 (d, J = 47.2 Hz, 2H), 3.35-2.65 (m, 8H), 2.44-2.15 (m, 2H), 2.06-1.72 (m, 4H), NH and OH protons not observed. |
| 385 | MS m/z [M + H]⁺ 424.2; ¹H NMR (DMSO-d₆) δ: 8.91 (s, 1H), 8.34 (d, J = 2.4 Hz, 1H), 8.28 (d, J = 2.4 Hz, 1H), 7.91 (dd, J = 8.8, 6.4 Hz, 1H), 7.19 (d, J = 11.2 Hz, 2H), 4.37 (s, 4H), 3.56 (s, 4H), 2.21 (s, 3H), NH proton not observed. |
| 388 | MS m/z [M + H]⁺ 420.3; ¹H NMR (methanol-d₄) δ: 8.75 (s, 1H), 8.01 (s, 2H), 7.82 (d, J = 8.2 Hz, 1H), 7.25-7.15 (m, 2H), 5.03-4.95 (m, 1H), 4.43-4.36 (m, 1H), 4.37-4.26 (m, 1H), 3.88-3.78 (m, 1H), 3.73-3.60 (m, 1H), 3.42-3.33 (m, 1H), 3.10 (d, J = 18.5 Hz, 1H), 3.02 (s, 3H), 2.97 (d, J = 16.4 Hz, 1H), 2.66-2.53 (m, 1H), 2.27-2.15 (m, 1H), NH and OH protons not observed. |
| 390 | MS m/z [M + H]⁺ 420.3; ¹H NMR (methanol-d₄) δ: 8.67 (br s, 1H), 8.00 (s, 2H), 7.72 (d, J = 7.9 Hz, 1H), 7.16-7.09 (m, 2H), 5.03-4.93 (m, 1H), 4.43-4.26 (m, 2H), 3.82 (br s, 1H), 3.76-3.66 (m, 1H), 3.42-3.36 (m, 1H), 3.12 (br s, 1H), 3.04 (s, 3H), 3.00 (br s, 1H), 2.59 (br s, 1H), 2.28-2.17 (m, 1H), NH and OH protons not observed. |
| 391 | MS m/z [M + H]⁺ 426.0; ¹H NMR (DMSO-d₆) δ: 8.82 (s, 1H), 8.25-8.19 (m, 2H), 7.90 (d, J = 8.4 Hz, 1H), 7.22-7.14 (m, 2H), 3.77 (m, 1H), 3.20 (s, 3H), 3.00-2.88 (m, 2H), 2.75-2.67 (m, 1H), 2.44-2.24 (m, 2H), 2.34 (s, 3H), 1.99-1.87 (m, 1H), NH proton not observed. |
| 392 | MS m/z [M + H]⁺ 451.9; ¹H NMR (DMSO-d₆) δ: 8.96 (s, 1H), 8.26 (d, J = 2.0 Hz, 1H), 8.13 (s, 1H), 7.84 (d, J = 8.8 Hz, 1H), 7.26-7.20 (m, 2H), 4.14 (d, J = 30.8 Hz, 4H), 3.40 (d, J = 12.0 Hz, 2H), 3.00 (t, J = 12.0 Hz, 2H), 2.76 (s, 3H), 2.25 (d, J = 13.6 Hz, 2H), 1.92 (t, J = 12.0 Hz, 2H), NH or OH proton not observed. |
| 393 | MS m/z [M + H]⁺ 450.0; ¹H NMR (DMSO-d₆) δ: 8.91 (s, 1H), 8.29 (s, 1H), 8.00 (s, 1H), 7.88 (d, J = 8.8 Hz, 1H), 7.28-7.23 (m, 2H), 3.48 (m, 1H), 3.15 (s, 3H), 2.98 (d, J = 12.0 Hz, 2H), 2.27 (t, J = 7.2 Hz, 2H), 2.04 (t, J = 11.2 Hz, 2H), 1.95-1.82 (m, 2H), 1.80-1.71 (m, 2H), 1.50-1.39 (m, 2H), 0.86 (t, J = 7.2 Hz, 3H), NH and OH protons not observed. |
| 395 | MS m/z [M + H]⁺ 436.4; ¹H NMR (methanol-d₄) δ: 8.79 (s, 1H), 8.03 (s, 2H), 7.87 (d, J = 7.9 Hz, 1H), 7.27-7.22 (m, 2H), 4.80 (br s, 1H), 3.75-3.68 (m, 2H), 3.60-3.55 (m, 1H), 3.25 (s, 3H), 2.98 (s, 3H), 2.34-2.22 (m, 3H), 2.19-2.07 (m, 1H), 1.48 (d, J = 6.4 Hz, 3H), NH and OH protons not observed. |
| 397 | MS m/z [M + H]⁺ 436.4; ¹H NMR (methanol-d₄) δ: 8.80 (s, 1H), 8.12-8.00 (m, 2H), 7.90 (d, J = 8.4 Hz, 1H), 7.33-7.23 (m, 2H), 4.03-3.94 (m, 1H), 3.57-3.46 (m, 2H), 3.25 (s, 3H), 3.23-3.12 (m, 1H), 2.92 (s, 3H), 2.52-2.43 (m, 1H), 2.30 (d, J = 8.8 Hz, 1H), 2.25-2.12 (m, 2H), 1.60 (d, J = 6.9 Hz, 3H), NH and OH protons not observed. |
| 399 | MS m/z [M + H]⁺ 451.9; ¹H NMR (DMSO-d₆) δ: 14.50-13.45 (br s, 1H), 13.01 (s, 1H), 8.94 (s, 1H), 8.46-7.98 (br s, 2H), 7.88 (d, J = 8.8 Hz, 1H), 7.28-7.22 (m, 2H), 4.43 (s, 1H), 3.54-3.48 (m, 2H), 3.16 (s, 3H), 3.01 (d, J = 11.2 Hz, 2H), 2.43 (t, J = 6.4 Hz, 2H), 2.14 (t, J = 11.2 Hz, 2H), 1.96-1.83 (m, 2H), 1.79-1.70 (m, 2H), NH proton not observed. |

Example 11

Preparation of Compound 12

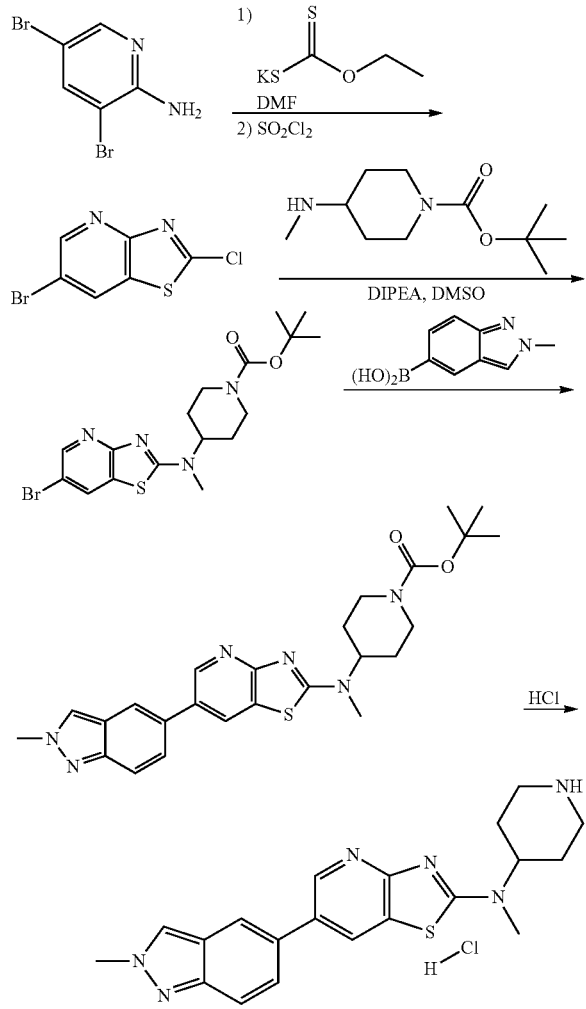

Step 1: A mixture of 3,5-dibromopyridin-2-amine (2.5 g, 9.92 mmol, 1.00 eq.) and ethoxycarbothioylsulfanyl potassium (3.8 g, 24 mmol, 2.4 eq.) in DMF (12 mL) was stirred at 130° C. overnight. The reaction mixture was then cooled to room temperature, diluted with 1 N HCl (75 mL) and stirred at room temperature for 1 h. The resulting solid was filtered and washed with water and dried. The resulting material was suspended in dichloromethane (15 mL) and SO$_2$Cl$_2$ (14 g, 8.5 mL, 100 mmol, 10 eq.) was added slowly. After 2 h, water was added slowly at 0° C. to quench the reaction. The resulting precipitate was collected by filtration and dried to give 6-bromo-2-chloro-thiazolo[4,5-b]pyridine (1.7 g, 69%).

$^1$H NMR (CDCl$_3$) δ: 8.79 (br s, 1H), 8.33 (s, 1H).

Step 2: A mixture of 6-bromo-2-chloro-thiazolo[4,5-b]pyridine (250 mg, 1.0 mmol, 1.0 eq.), tert-butyl 4-(methylamino)piperidine-1-carboxylate (260 mg, 1.2 mmol, 1.2 eq.) and DIPEA (200 mg, 0.26 mL, 1.5 mmol, 1.5 eq.) in DMSO (2.0 mL) was stirred at 100° C. for 1 h. LC/MS indicated complete reaction. The mixture was cooled to room temperature, diluted with ethyl acetate and washed with water and brine, and then dried over sodium sulfate and concentrated. The residue was purified over silica gel with ethyl acetate in hexanes (5 to 15% gradient) to provide tert-butyl 4-[(6-bromothiazolo[4,5-b]pyridin-2-yl)-methyl-amino]piperidine-1-carboxylate (280 mg, 65%).

$^1$H NMR (CDCl$_3$) δ: 8.41 (d, J=2.2 Hz, 1H), 7.96 (d, J=2.2 Hz, 1H), 4.42-4.74 (m, 1H), 4.15-4.41 (m, 2H), 3.04 (s, 3H), 2.75-2.93 (m, 2H), 1.82 (d, J=1.6 Hz, 2H), 1.63-1.77 (m, 2H), 1.48 (s, 9H).

Step 3: A mixture of tert-butyl 4-[(6-bromothiazolo[4,5-b]pyridin-2-yl)-methyl-amino]piperidine-1-carboxylate (75 mg, 0.18 mmol, 1.0 eq.), (2-methylindazol-5-yl)boronic acid (37 mg, 0.21 mmol, 1.2 eq.), Pd$_2$(dba)$_3$ (16 mg, 0.018 mmol, 0.10 eq.), (t-Bu)$_3$P HBF$_4$ (10 mg, 0.035 mmol, 0.20 eq.) and K$_2$CO$_3$ (2.0 M aq.) (0.26 mL, 0.53 mmol, 3.0 eq.) in dioxane (1.0 mL) was stirred at 90° C. for 1 h and then diluted with ethyl acetate and washed with brine, dried and concentrated. The residue was purified over silica gel with ethyl acetate in dichloromethane (0 to 20% gradient) to give tert-butyl 4-[methyl-[6-(2-methylindazol-5-yl)thiazolo[4,5-b]pyridin-2-yl]amino]piperidine-1-carboxylate. MS m/z 479.4 [M+H]$^+$.

Step 4: To a solution of tert-butyl 4-[methyl-[6-(2-methylindazol-5-yl)thiazolo[4,5-b]pyridin-2-yl]amino]piperidine-1-carboxylate (30 mg, 0.063 mmol, 1.0 eq.) in dioxane (0.25 mL) was added HCl (4 M in dioxane) (1.0 mL). The mixture was then stirred at room temperature for 1 h and then diluted with ether, filtered and dried to give N-methyl-6-(2-methylindazol-5-yl)-N-(4-piperidyl)thiazolo[4,5-b]pyridin-2-amine hydrochloride.

MS m/z 379.3 [M+H]$^+$; $^1$H NMR (DMSO-d$_6$) δ: 9.05-9.18 (m, 2H), 9.03 (br s, 1H), 8.72 (d, J=1.9 Hz, 1H), 8.48 (s, 1H), 8.13 (d, J=0.9 Hz, 1H), 7.75 (d, J=9.1 Hz, 1H), 7.65 (dd, J=9.1, 1.9 Hz, 1H), 4.21 (s, 3H), 3.43 (d, J=12.3 Hz, 2H), 3.19 (m, 6H), 2.17-2.28 (m, 2H), 1.97 (d, J=12.6 Hz, 2H).

Using the procedure described for Example 11, above, additional compounds described herein were prepared by substituting the appropriate starting material, suitable reagents and reaction conditions, obtaining compounds such as those selected from:

| Cpd | Data |
|---|---|
| 13 | MS m/z 393.3 [M + H]$^+$; $^1$H NMR (DMSO-d$_6$) δ: 9.12-9.28 (m, 2H), 9.08 (s, 1H), 8.70 (d, J = 1.9 Hz, 1H), 8.45 (s, 1H), 7.95 (d, J = 0.9 Hz, 1H), 7.46 (s, 1H), 4.21 (br s, 4H), 3.39-3.46 (m, 2H), 3.20 (s, 3H), 3.12 (d, J = 11.3 Hz, 2H), 2.59 (s, 3H), 2.15-2.30 (m, 2H), 1.90-2.00 (m, 2H). |
| 14 | MS m/z 379.3 [M + H]$^+$; $^1$H NMR (DMSO-d$_6$) δ: 10.34-10.44 (m, 1H), 9.06-9.22 (m, 2H), 9.01 (s, 1H), 8.63 (d, J = 1.9 Hz, 1H), 8.46 (s, 1H), 7.93 (d, J = 0.9 Hz, 1H), 7.43 (s, 1H), 4.21 (br s, 4H), 3.33-3.40 (m, 2H), 3.09 (d, J = 10.7 Hz, 2H), 2.58 (s, 3H), 2.14-2.24 (m, 2H), 1.84-1.95 (m, 2H). |
| 15 | MS m/z 365.3 [M + H]$^+$; $^1$H NMR (DMSO-d$_6$) δ: 10.47 (br s, 1H), 9.09-9.28 (m, 2H), 9.02 (br s, 1H), 8.63 (s, 1H), 8.49 (s, 1H), 8.12 (s, 1H), 7.74 (d, J = 8.8 Hz, 1H), 7.62 |

| Cpd | Data |
|---|---|
|  | (d, J = 8.8 Hz, 1H), 4.20 (br s, 4H), 3.31-3.38 (m, 2H), 3.08 (d, J = 7.3 Hz, 2H), 2.18 (d, J = 11.0 Hz, 2H), 1.90 (d, J = 9.8 Hz, 2H). |
| 16 | MS m/z 435.4 [M + H]$^+$; $^1$H NMR (CDCl$_3$) δ: 8.69 (d, J = 2.2 Hz, 1H), 8.12 (d, J = 2.2 Hz, 1H), 7.97 (s, 1H), 7.85 (dd, J = 1.6, 0.9 Hz, 1H), 7.79-7.83 (m, 1H), 7.56 (dd, J = 8.8, 1.6 Hz, 1H), 4.46-4.76 (m, 1H), 4.28 (s, 3H), 3.16 (s, 3H), 1.84 (dd, J = 12.3, 3.5 Hz, 2H), 1.46-1.56 (m, 2H), 1.41 (br s, 6H), 1.27 (br s, 6H). |
| 17 | MS m/z 449.4 [M + H]$^+$; $^1$H NMR (CDCl$_3$) δ: 8.68 (d, J = 2.2 Hz, 1H), 8.12 (d, J = 2.2 Hz, 1H), 7.95 (s, 1H), 7.68 (d, J = 0.9 Hz, 1H), 7.31-7.35 (m, 1H), 4.42-4.80 (m, 1H), 4.28 (s, 3H), 3.12-3.19 (m, 3H), 2.72 (s, 3H), 1.83 (dd, J = 12.6, 3.5 Hz, 2H), 1.47 (d, J = 18.6 Hz, 2H), 1.36-1.43 (br s, 6H), 1.26 (br s, 6H). |

Example 12

Preparation of Compound 101

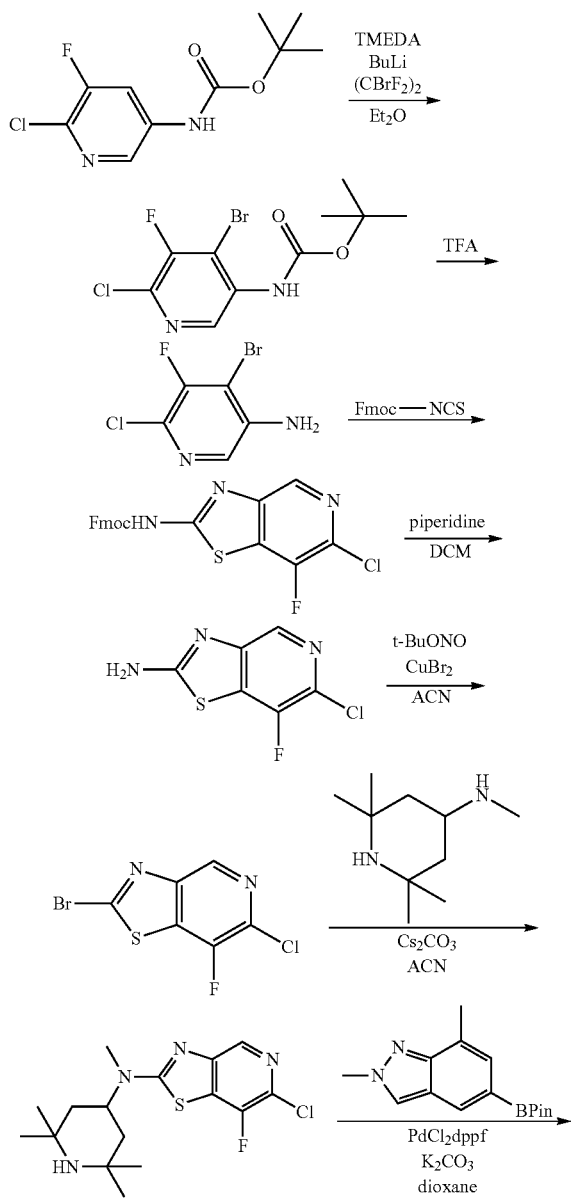

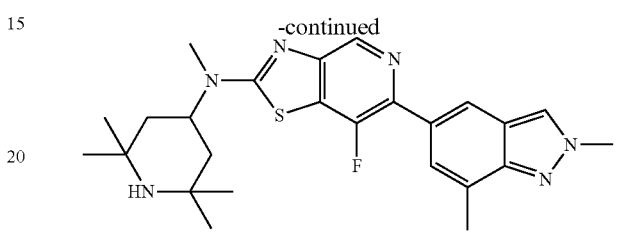

Step 1: To a solution of tert-butyl N-(6-chloro-5-fluoro-3-pyridyl)carbamate (500 mg, 2.0 mmol, 1.0 eq.) and TMEDA (710 mg, 0.93 mL, 6.1 mmol, 3.0 eq.) in Et$_2$O (10 mL) at −78° C. was added dropwise BuLi (1.6 M in hexane) (3.8 mL, 6.1 mmol, 3.0 eq.) while maintaining the temperature below −60° C. The solution became purple. Upon complete addition, the temperature was allowed to rise to −20° C. and the mixture was stirred at that temperature for 90 min and a turbid mixture was formed. The mixture was cooled to −78° C. again, to which C$_2$Br$_2$F$_4$ (1700 mg, 0.77 mL, 6.4 mmol, 3.1 eq.) was added dropwise and the temperature was allowed to rise to room temperature slowly over 1 h. The reaction was quenched by 1N HCl (5.0 mL) and ice water. The mixture was diluted with ether, washed with water, sodium bicarbonate and brine, dried over sodium sulfate and then concentrated to give a solid tert-butyl N-(4-bromo-6-chloro-5-fluoro-3-pyridyl)carbamate (660 mg, 100%), which was used in the next step without further purification.

Step 2: To a solution of tert-butyl N-(4-bromo-6-chloro-5-fluoro-3-pyridyl)carbamate (660 mg, 2.0 mmol, 1.0 eq.) in CH$_2$Cl$_2$ (10.0 mL) was added TFA (5.0 mL). The mixture was stirred at room temperature for 1 h and then concentrated and treated with ethyl acetate. The mixture was washed with aqueous sodium bicarbonate and brine, and dried and concentrated to give 4-bromo-6-chloro-5-fluoro-pyridin-3-amine, which was used without further purification.

Step 3: A mixture of 4-bromo-6-chloro-5-fluoro-pyridin-3-amine (108 mg, 0.479 mmol, 1.00 eq.) and 2-(9H-fluoren-9-yloxy)acetyl isothiocyanate (148 mg, 0.527 mmol, 1.10 eq.) in acetone (1.0 mL) was stirred at 50° C. overnight and then cooled and treated with ether and filtered to give 9H-fluoren-9-ylmethyl N-(6-chloro-7-fluoro-thiazolo[4,5-c]pyridin-2-yl)carbamate as a solid. MS m/z 426.2, 428.3 [M+H]$^+$.

Step 4: To a suspension of 9H-fluoren-9-ylmethyl N-(6-chloro-7-fluoro-thiazolo[4,5-c]pyridin-2-yl)carbamate (210 mg, 0.49 mmol, 1.0 eq.) in CH$_2$Cl$_2$ (7.0 mL) was added piperidine (427 mg, 0.5 mL, 4.9 mmol, 10 eq.) and the mixture was stirred at room temperature for 2 h. LC/MS showed complete reaction. The mixture was diluted with ethyl acetate, washed with aq NH$_4$Cl and brine, dried and then concentrated. The residue was purified over silica gel with methanol in dichloromethane (0 to 10% gradient) to give 6-chloro-7-fluoro-thiazolo[4,5-c]pyridin-2-amine (100 mg, 100%)

$^1$H NMR (methanol-$d_4$) δ: 8.52 (s, 1H).

Step 5: To a suspension of 6-chloro-7-fluoro-thiazolo[4, 5-c]pyridin-2-amine (100 mg, 0.49 mmol, 1.0 eq.) in acetonitrile (3.0 mL) was added tert-butyl nitrite (110 mg, 0.13 mL, 0.98 mmol, 2.0 eq.) followed by cupric bromide (120 mg, 0.54 mmol, 1.1 eq.). The solid was slowly dissolved and the mixture was stirred at 60° C. for 1 h. The mixture was diluted with ethyl acetate, washed with NH$_4$Cl and brine, and then dried and concentrated. The residue was purified with ethyl acetate in hexanes to give 2-bromo-6-chloro-7-fluoro-thiazolo[4,5-c]pyridine in almost quantitative yield.

$^1$H NMR (CDCl$_3$) δ: 8.82 (d, J=0.9 Hz, 1H).

Step 6: A mixture of 2-bromo-6-chloro-7-fluoro-thiazolo[4,5-c]pyridine (32 mg, 0.12 mmol, 1.0 eq.), N,2,2,6,6-pentamethylpiperidin-4-amine; dihydrochloride (32 mg, 0.13 mmol, 1.1 eq.) and Cs$_2$CO$_3$ (160 mg, 0.48 mmol, 4.0 eq.) in acetonitrile (0.5 mL) was stirred at 80° C. overnight and then cooled to room temperature, diluted with ethyl acetate, filtered and evaporated to give 6-chloro-7-fluoro-N-methyl-N-(2,2,6,6-tetramethyl-4-piperidyl)thiazolo[4,5-c]pyridin-2-amine (45 mg, 110%) which was used in the next step without further purification.

$^1$H NMR (CDCl$_3$) δ: 8.32 (d, J=0.9 Hz, 1H), 4.21-4.46 (m, 1H), 3.03 (s, 3H), 1.71 (dd, J=12.6, 3.5 Hz, 2H), 1.33-1.43 (m, 2H), 1.29 (s, 6H), 1.15 (s, 6H).

Step 7: A mixture of 6-chloro-7-fluoro-N-methyl-N-(2,2, 6,6-tetramethyl-4-piperidyl)thiazolo[4,5-c]pyridin-2-amine (39 mg, 0.11 mmol, 1.0 eq.), 2,7-dimethyl-5-(4,4,5,5-tetramethyl-1,3,2-dioxaborolan-2-yl)indazole (45 mg, 0.16 mmol, 1.5 eq.), PdCl$_2$dppf DCM complex (9.0 mg, 0.011 mmol, 0.1 eq.) and aqueous K$_2$CO$_3$ (2.0 M, 0.16 mL, 3.0 eq.) in dioxane (1.0 mL) was heated at 100° C. overnight, then cooled, diluted with ethyl acetate, washed with water and brine, dried over sodium sulfate and concentrated. The residue was purified over basic alumina with ethyl acetate in hexanes (10 to 100% gradient) followed by methanol in dichloromethane (0 to 10% gradient) to provide 6-(2,7-dimethylindazol-5-yl)-7-fluoro-N-methyl-N-(2,2,6,6-tetramethyl-4-piperidyl)thiazolo[4,5-c]pyridin-2-amine (7.0 mg, 14%).

MS m/z 467.4 [M+H]$^+$; $^1$H NMR (CDCl$_3$) δ: 8.76 (d, J=2.2 Hz, 1H), 8.09 (s, 1H), 7.98 (s, 1H), 7.75 (d, J=0.9 Hz, 1H), 4.29 (br. s., 4H), 3.16 (s, 3H), 2.73 (s, 3H), 1.89 (d, J=11.7 Hz, 2H), 1.50-1.85 (m, 14H).

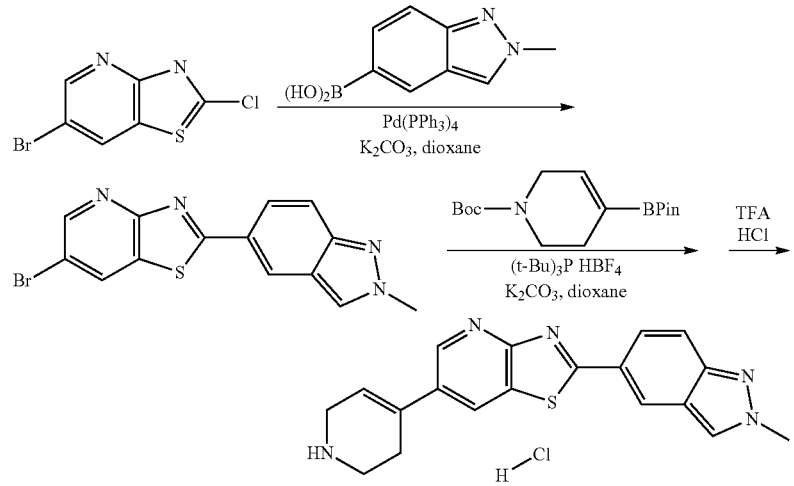

Example 13

Preparation of Compound 19

Step 1: A mixture of 6-bromo-2-chloro-thiazolo[4,5-b] pyridine (500 mg, 2.0 mmol, 1.0 eq.), (2-methylindazol-5-yl)boronic acid (390 mg, 2.2 mmol, 1.1 eq.), Pd(PPh$_3$)$_4$ (230 mg, 0.20 mmol, 0.10 eq.) and K$_2$CO$_3$ (2.0 M aq.) (3.0 mL, 6.0 mmol, 3.0 eq.) in dioxane (8.0 mL) was stirred at 100° C. overnight. The mixture was then treated with water, acidified with HCl and filtered. The filter cake was washed with acetonitrile and ether, and then dried to give 6-bromo-2-(2-methylindazol-5-yl)thiazolo[4,5-b]pyridine (100 mg, 14%), which was used in the next step without further purification.

Step 2: A mixture of 6-bromo-2-(2-methylindazol-5-yl) thiazolo[4,5-b]pyridine (100 mg, 0.29 mmol, 1.0 eq.), tert-butyl 4-(4,4,5,5-tetramethyl-1,3,2-dioxaborolan-2-yl)-3,6-dihydro-2H-pyridine-1-carboxylate (110 mg, 0.35 mmol, 1.2 eq.), (t-Bu)$_3$P HBF$_4$ (8.5 mg, 0.029 mmol, 0.10 eq.) and K$_2$CO$_3$ (2.0 M aq.) (0.43 mL, 0.87 mmol, 3.0 eq.) in dioxane (1.0 mL) was stirred at 100° C. for 2 h then cooled, diluted with water and filtered. The filter cake was washed with acetonitrile and ether. The solid was treated with TFA, concentrated and purified by C18 ISCO and further purified with prep-HPLC to give 2-(2-methylindazol-5-yl)-6-(1,2,3, 6-tetrahydropyridin-4-yl)thiazolo[4,5-b]pyridine hydrochloride (22 mg, 20%) after treatment with HCl in ether.

MS m/z 348.3 [M+H]$^+$; $^1$H NMR (DMSO-$d_6$) δ: 9.30 (br s, 2H), 8.79 (d, J=1.9 Hz, 1H), 8.68 (d, J=2.2 Hz, 1H), 8.55 (d, J=11.7 Hz, 2H), 7.96 (dd, J=9.0, 1.4 Hz, 1H), 7.71 (d, J=8.8 Hz, 1H), 6.39 (br s, 1H), 4.17 (s, 3H), 3.74 (br s, 2H), 3.23-3.36 (m, 2H), 2.75 (br s, 2H).

Using the procedure described for Example 13, above, additional compounds described herein were prepared by substituting the appropriate starting material, suitable reagents and reaction conditions, obtaining compounds such as those selected from:

| Cpd | Data |
|---|---|
| 335 | MS m/z [M + H]+ 376.2; ¹H NMR (methanol-d₄) δ: 9.15-9.28 (m, 1H), 8.21-8.29 (m, 1H), 8.09-8.17 (m, 1H), 7.80-7.88 (m, 2H), 7.23-7.35 (m, 2H), 6.75-6.86 (m, 1H), 3.94 (br s, 2H), 3.51 (br s, 2H), 3.0 (br s, 2H), 2 NH and OH protons not observed. |
| 337 | MS m/z [M + H]+ 432.3; ¹H NMR (methanol-d₄) δ: 9.22 (s, 1H), 8.33 (d, 7 = 0.8 Hz, 1H), 8.09-8.20 (m, 1H), 7.96-8.06 (m, 2H), 7.27-7.35 (m, 2H), 6.71 (s, 1H), 2.92 (d, J = 1.2 Hz, 2H), 1.68 (s, 6H), 1.58-1.63 (m, 6H), 2 NH and OH protons not observed. |

Example 14

Preparation of Compound 43

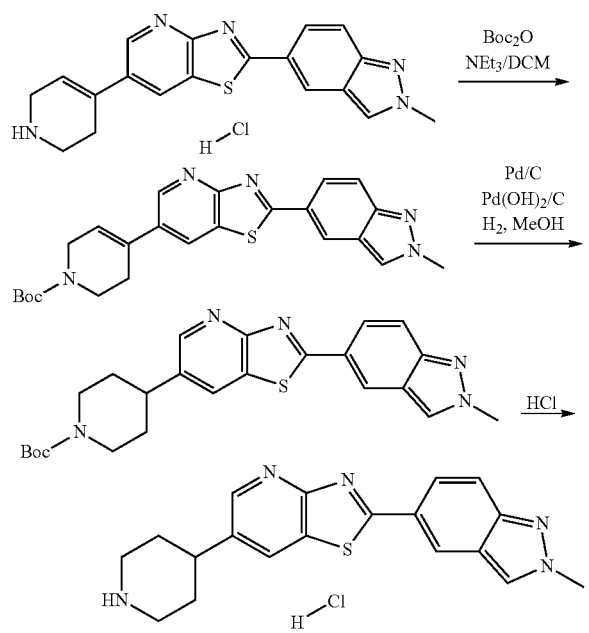

Step 1: A mixture of 2-(2-methylindazol-5-yl)-6-(1,2,3,6-tetrahydropyridin-4-yl)thiazolo[4,5-b]pyridine hydrochloride (31 mg, 0.081 mmol, 1.0 eq., prepared in Example 13), Boc₂O (36 mg, 0.16 mmol, 2.0 eq.) and NEt₃ (25 mg, 0.034 mL, 0.24 mmol, 3.0 eq.) in CH₂Cl₂ (3.0 mL) was stirred at room temperature for three days. The mixture was then diluted with CH₂Cl₂, washed with water and brine, dried over sodium sulfate and concentrated to provide crude tert-butyl 4-[2-(2-methylindazol-5-yl)thiazolo[4,5-b]pyridin-6-yl]-3,6-dihydro-2H-pyridine-1-carboxylate (32 mg, 89%). MS m/z 448.4 [M+H]+.

Step 2: A mixture of tert-butyl 4-[2-(2-methylindazol-5-yl)thiazolo[4,5-b]pyridin-6-yl]-3,6-dihydro-2H-pyridine-1-carboxylate (32 mg, 0.071 mmol, 1.0 eq.), 10% Pd/C (30 mg, 0.028 mmol, 0.39 eq.), 10% Pd(OH)₂/C (30 mg, 0.021 mmol, 0.30 eq.) and 2 drops of 1 N HCl in MeOH (25 mL) was hydrogenated at room temperature for 16 h under a H₂ balloon. LC/MS indicated complete reaction. The reaction mixture was treated with Celite and then filtered. The filtrate was concentrated and the product was purified over silica gel with methanol in dichloromethane (0 to 6% gradient) to give tert-butyl 4-[2-(2-methylindazol-5-yl)thiazolo[4,5-b]pyridin-6-yl]piperidine-1-carboxylate (10 mg, 31%). MS m/z 450.4 [M+H]+.

Step 3: To a solution of tert-butyl 4-[2-(2-methylindazol-5-yl)thiazolo[4,5-b]pyridin-6-yl]piperidine-1-carboxylate (10 mg, 0.022 mmol, 1.0 eq.) in dioxane (0.2 mL) was added HCl (4 M in dioxane) (1.0 mL). The mixture was then stirred at room temperature for 30 min, diluted with ether and filtered. The filter cake was collected and dried to give 2-(2-methylindazol-5-yl)-6-(4-piperidyl)thiazolo[4,5-b]pyridine hydrochloride (4.0 mg, 47%).

MS m/z 350.2 [M+H]+; ¹H NMR (DMSO-d₆) δ: 9.38 (br s, 1H), 9.22 (br s, 1H), 8.98-9.08 (m, 3H), 8.93 (d, J=1.9 Hz, 1H), 8.44 (dd, J=9.1, 1.6 Hz, 1H), 8.21 (d, J=9.1 Hz, 1H), 4.66 (s, 3H), 3.84 (d, J=11.7 Hz, 2H), 3.41-3.57 (m, 3H), 2.48 (br s, 2H), 2.31-2.43 (m, 2H).

Using the procedure described for Example 14, above, additional compounds described herein were prepared by substituting the appropriate starting material, suitable reagents and reaction conditions, obtaining compounds such as those selected from:

| Cpd | Data |
|---|---|
| 61 | MS m/z 365.3 [M + H]+; ¹H NMR (DMSO-d₆) δ: 9.10-9.47 (m, 4H), 8.29-8.59 (m, 2H), 3.62 (br. s., 1H), 3.32-3.45 (m, 2H), 3.00-3.15 (m, 2H), 2.76 (br. s., 3H), 2.58 (br. s., 3H), 2.25-2.35 (m, 2H), 2.03-2.20 (m, 2H). |

Example 15

Preparation of Compound 49

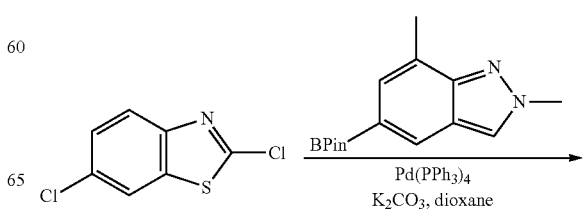

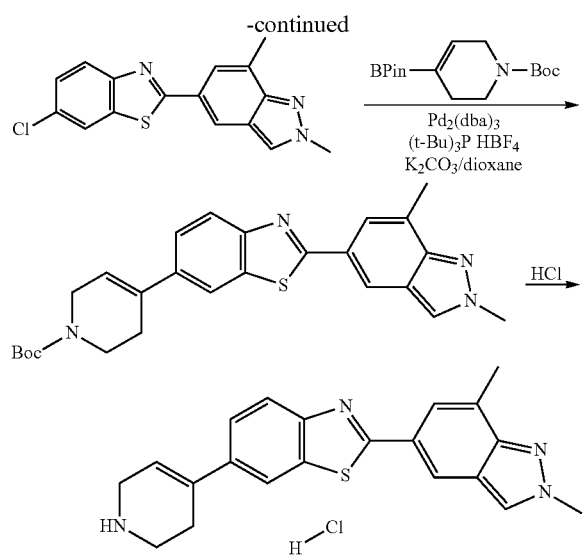

Step 1: A mixture of 2,6-dichloro-1,3-benzothiazole (200 mg, 0.98 mmol, 1.0 eq.), 2,7-dimethyl-5-(4,4,5,5-tetramethyl-1,3,2-dioxaborolan-2-yl)indazole (320 mg, 1.2 mmol, 1.2 eq.), PdCl₂dppf dichloromethane adduct (81 mg, 0.098 mmol, 0.10 eq.) and K₂CO₃ (2.0 M aq.) (1.5 mL, 2.9 mmol, 3.0 eq.) in dioxane (4.0 mL) was stirred at 90° C. for 12 h. After cooling, the reaction mixture was diluted with ethyl acetate, washed with brine, dried and then concentrated. The residue was purified over silica gel with ethyl acetate in dichloromethane (0 to 25% gradient) to give 6-chloro-2-(2,7-dimethylindazol-5-yl)-1,3-benzothiazole (200 mg, 65%).

¹H NMR (CDCl₃) δ: 8.28 (d, J=0.6 Hz, 1H), 8.06 (s, 1H), 8.00 (d, J=8.8 Hz, 1H), 7.90 (d, J=1.9 Hz, 1H), 7.82-7.86 (m, 1H), 7.47 (dd, J=8.7, 2.0 Hz, 1H), 4.31 (s, 3H), 2.74 (s, 3H).

Step 2: A mixture of 6-chloro-2-(2,7-dimethylindazol-5-yl)-1,3-benzothiazole (100 mg, 0.32 mmol, 1.0 eq.), tert-butyl 4-(4,4,5,5-tetramethyl-1,3,2-dioxaborolan-2-yl)-3,6-dihydro-2H-pyridine-1-carboxylate (120 mg, 0.38 mmol, 1.2 eq.), Pd₂(dba)₃ (15 mg, 0.016 mmol, 0.05 eq.), (t-Bu)₃P HBF₄ (9.3 mg, 0.032 mmol, 0.10 eq.) and K₂CO₃ (2.0 M aq.) (0.48 mL, 0.96 mmol, 3.0 eq.) in dioxane (1.5 mL) was stirred at 100° C. for 12 h, then cooled, diluted with ethyl acetate and washed with water and brine, dried over sodium sulfate and evaporated. The residue was purified over silica gel with methanol in dichloromethane (0 to 5% gradient) to give tert-butyl 4-[2-(2,7-dimethylindazol-5-yl)-1,3-benzothiazol-6-yl]-3,6-dihydro-2H-pyridine-1-carboxylate (131 mg, 89%). MS m/z 461.4 [M+H]⁺.

Step 3: To a suspension of tert-butyl 4-[2-(2,7-dimethylindazol-5-yl)-1,3-benzothiazol-6-yl]-3,6-dihydro-2H-pyridine-1-carboxylate (20 mg, 0.043 mmol, 1.0 eq.) in dioxane (0.25 mL) was added HCl (4 M in dioxane) (1.0 mL, 4.0 mmol, 92 eq.). The mixture was stirred at room temperature for 30 min and then diluted with ether and filtered. The solid cake was washed with ether and dried to give 2-(2,7-dimethylindazol-5-yl)-6-(1,2,3,6-tetrahydropyridin-4-yl)-1,3-benzothiazole hydrochloride (14 mg, 81%).

MS m/z 361.3 [M+H]⁺; ¹H NMR (DMSO-d₆) δ: 9.31 (br s, 2H), 8.46 (s, 1H), 8.26 (s, 1H), 8.17 (s, 1H), 7.93 (d, J=8.5 Hz, 1H), 7.72 (s, 1H), 7.61 (d, J=8.2 Hz, 1H), 6.27 (br s, 1H), 4.15 (s, 3H), 3.72 (br s, 2H), 3.27 (br s, 2H), 2.73 (br s, 2H), 2.53 (s, 3H).

Using the procedure described for Example 15, above, additional compounds described herein were prepared by substituting the appropriate starting material, suitable reagents and reaction conditions, obtaining compounds such as those selected from:

| Cpd | Data |
|---|---|
| 4 | MS m/z 347.0 [M + H]⁺; ¹H NMR (DMSO-d₆) δ: 9.01-9.29 (m, 2H), 8.56 (s, 1H), 8.52 (s, 1H), 8.26 (s, 1H), 7.97-8.03 (m, 2H), 7.75 (d, J = 8.8 Hz, 1H), 7.68 (dd, J = 8.7, 1.4 Hz, 1H), 6.35 (br. s., 1H), 4.22 (s, 3H), 3.78 (br. s., 2H), 3.33-3.43 (m, 2H), 2.78 (br. s., 2H). |

Example 16

Preparation of Compound 50

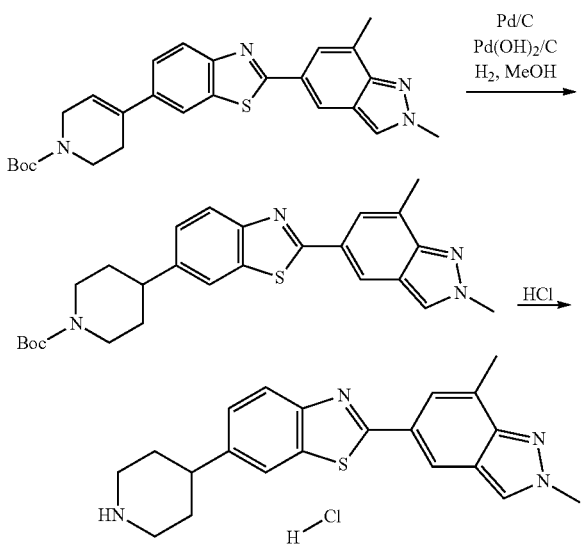

Step 1: A mixture of tert-butyl 4-[2-(2,7-dimethylindazol-5-yl)-1,3-benzothiazol-6-yl]-3,6-dihydro-2H-pyridine-1-carboxylate (65 mg, 0.14 mmol, 1.0 eq., prepared in Example 15 step 2), 10% Pd/C (50 mg, 0.047 mmol, 0.33 eq.) and 10% Pd(OH)₂/C (50 mg, 0.036 mmol, 0.25 eq.) in MeOH (50 mL) and one drop of 1N HCl was shaken for 4 h at 60 psi using a Pan shaker. The mixture was filtered through Celite, concentrated and the residue was purified over silica gel with methanol in dichloromethane (0 to 10% gradient) to give tert-butyl 4-[2-(2,7-dimethylindazol-5-yl)-1,3-benzothiazol-6-yl]piperidine-1-carboxylate (22 mg, 34%). MS m/z 463.4 [M+H]⁺.

Step 2: Applying the procedure of Example 15 step 3 to tert-butyl 4-[2-(2,7-dimethylindazol-5-yl)-1,3-benzothiazol-6-yl]piperidine-1-carboxylate (22 mg, 0.048 mmol, 1.0 eq.) provided 2-(2,7-dimethylindazol-5-yl)-6-(4-piperidyl)-1,3-benzothiazole hydrochloride (14 mg, 74%).

MS m/z 363.3 [M+H]⁺; ¹H NMR (DMSO-d₆) δ: 8.98-9.18 (m, 2H), 8.45 (s, 1H), 8.24 (d, J=0.6 Hz, 1H), 7.84-7.96 (m, 2H), 7.71 (s, 1H), 7.34 (dd, J=8.4, 1.4 Hz, 1H), 4.15 (s, 3H), 3.25-3.37 (m, 2H), 2.84-3.04 (m, 3H), 2.52 (s, 3H), 1.85-1.99 (m, 4H).

Using the procedure described for Example 16, above, additional compounds described herein were prepared by substituting the appropriate starting material, suitable reagents and reaction conditions, obtaining compounds such as those selected from:

C. under nitrogen atmosphere for 16 h, then cooled, diluted with ethyl acetate, washed with water and brine, dried over sodium sulfate and concentrated. The residue was purified over silica gel with ethyl acetate and hexanes (10 to 100% gradient) to give tert-butyl 4-(methyl(2-(2-methyl-2H-indazol-5-yl)benzo[d]thiazol-6-yl)amino)piperidine-1-carboxylate (60 mg, 21.5%). MS m/z 478.1 [M+H]⁺.

Step 2: Applying the procedure of Example 15 step 3 to tert-butyl 4-(methyl(2-(2-methyl-2H-indazol-5-yl)benzo[d]thiazol-6-yl)amino)piperidine-1-carboxylate (60 mg) provided N-methyl-2-(2-methyl-2H-indazol-5-yl)-N-(piperidin-4-yl)benzo[d]thiazol-6-amine hydrochloride (24 mg, 50%).

MS m/z 378.1 [M+H]⁺. ¹H NMR (DMSO-d₆) δ: 8.89-9.01 (m, 1H), 8.67-8.80 (m, 1H), 8.52 (s, 1H), 8.40 (s, 1H), 7.94-7.98 (m, 1H), 7.87-7.93 (m, 1H), 7.64-7.75 (m, 2H), 7.23-7.35 (m, 1H), 4.22 (s, 3H), 4.04-4.15 (m, 1H), 3.37 (d, J=12.6 Hz, 2H), 2.98-3.09 (m, 2H), 2.90 (s, 3H), 1.95-2.07 (m, 2H), 1.83-1.93 (m, 2H).

| Cpd | Data |
|---|---|
| 5 | MS m/z 349.1 [M + H]⁺; ¹H NMR (DMSO-d₆) δ: 8.86-9.44 (m, 2H), 8.56 (s, 1H), 8.49 (s, 1H), 7.95-8.02 (m, 3H), 7.75 (d, J = 8.8 Hz, 1H), 7.41 (d, J = 8.5 Hz, 1H), 4.23 (s, 3H), 3.40-3.55 (m, 2H), 2.96-3.09 (m, 3H), 1.93-2.06 (m, 4H). |

Example 17

Preparation of Compound 11

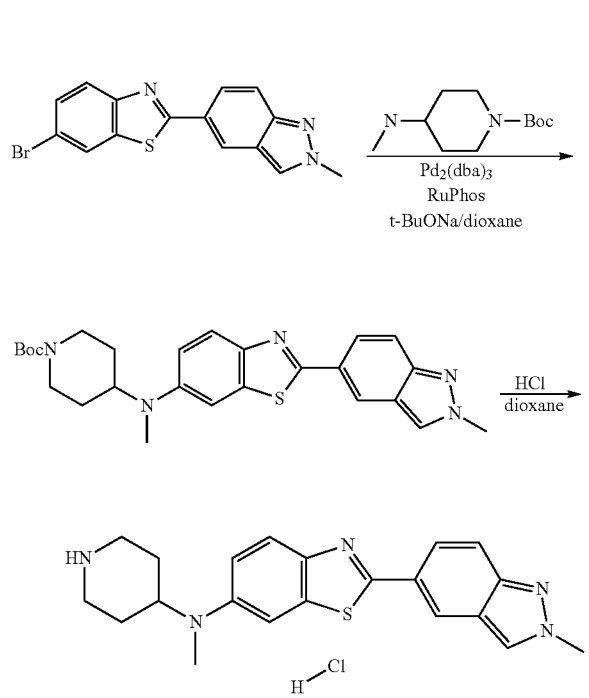

Step 1: A mixture of 6-bromo-2-(2-methyl-2H-indazol-5-yl)benzo[d]thiazole (160 mg, prepared according to Example 15 step 1), tert-butyl 4-(methylamino)piperidine-1-carboxylate (2.0 eq.), Pd₂(dba)₃ (0.1 eq.), RuPhos (0.2 eq.) and t-BuONa (2.5 eq.) in dioxane (1.0 mL) was stirred at 70°

Example 18

Preparation of Compound 120

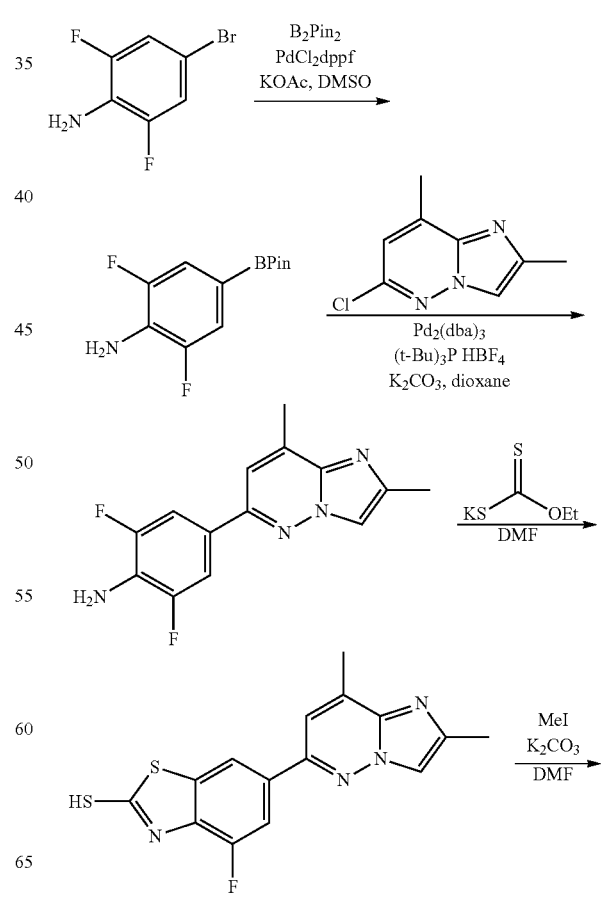

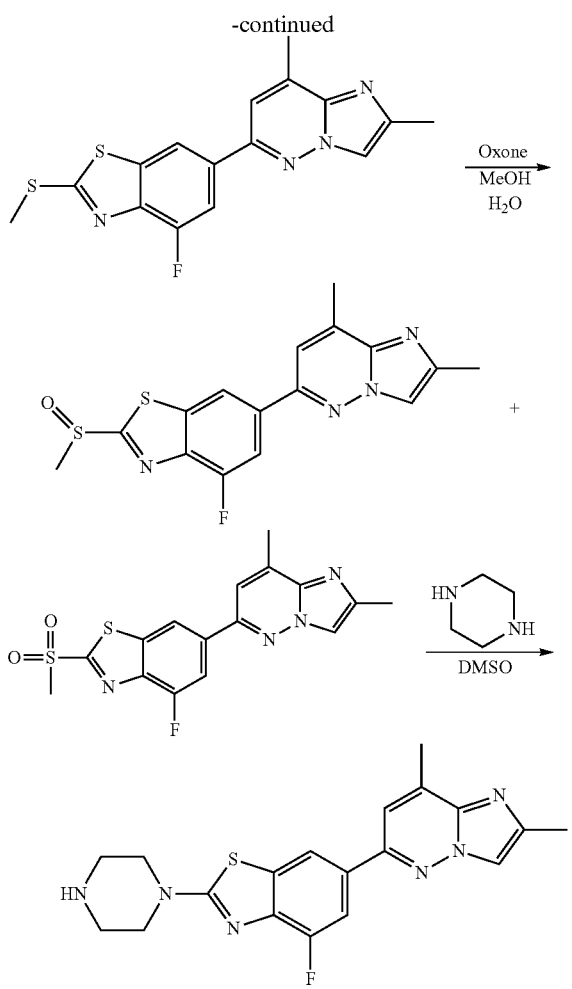

Step 1: A 100 mL round bottom flask was charged with 4-bromo-2,6-difluoro-aniline (2.5 g, 12 mmol), bis(pinacolato)diboron (3.40 g, 13 mmol), Pd(dppf)Cl$_2$ (300 mg, 0.364 mmol), and KOAc (3.50 g, 36 mmol). The reaction vessel was evacuated and purged with N$_2$ (3×). Anhydrous DMSO (15 mL) was added and the reaction was heated at 80° C. for 1.5 h, then cooled and diluted with EtOAc (100 mL) and NaHCO$_3$ (100 mL). The organic layer was separated and washed with brine, dried, and concentrated. The residue was purified by column chromatography on silica gel with ethyl acetate and hexanes (0-10% gradient) to afford a white solid (1.8 g, 59%). MS m/z 256.1 [M+H]$^+$.

Step 2: A 100 mL flask was charged with 6-chloro-2,8-dimethyl-imidazo[1,2-b]pyridazine (0.62 g, 3.41 mmol), boronate ester prepared as above (1.05 g, 4.12 mmol), Pd$_2$(dba)$_3$ (313 mg, 0.342 mmol), tBu$_3$PHBF$_4$ (200 mg, 0.682 mmol), and K$_2$CO$_3$ (1.42 g, 10.3 mmol). The reaction vessel was evacuated and purged with N$_2$ (3×). Dioxane (18 mL) and H$_2$O (6 mL) were added and the reaction was heated at 90° C. for 1.5 h, then cooled and diluted with CH$_2$Cl$_2$ (30 mL) and H$_2$O (15 mL). The organic layer was separated and the aqueous layer was further extracted with CH$_2$Cl$_2$ (2×). The combined organic extracts were washed with brine, dried and concentrated. The residue was purified by trituration with CH$_3$CN to give the desired intermediate as a tan solid (630 mg, 67%). MS m/z 275.3 [M+H]$^+$.

Step 3: A 20 mL vial was charged with 4-(2,8-dimethyl-imidazo[1,2-b]pyridazin-6-yl)-2,6-difluoro-aniline (0.415 g, 1.51 mmol) and ethylxanthic acid potassium salt (0.606 g, 3.63 mmol) and 2.5 mL of anhydrous DMF was added. The resulting brown suspension was heated at 130° C. for 2 h, then cooled to ambient temperature and diluted with 9 mL of 1 N HCl. The resulting suspension was stirred for 1 h and then filtered. The solid cake was washed with H$_2$O, collected and dried to give the desired intermediate as a brown solid (460 mg, 92%). MS m/z 331.1 [M+H]$^+$.

Step 4: To a mixture of 6-(2,8-dimethylimidazo[1,2-b]pyridazin-6-yl)-4-fluoro-1,3-benzothiazole-2-thiol (0.46 g, 1.39 mmol) in 5.5 mL of anhydrous DMF was added K$_2$CO$_3$ (0.462 g, 3.34 mmol) followed by MeI (0.166 mL, 2.65 mmol) dropwise via syringe. The brown mixture was stirred at ambient temperature for 2 h. The resulting precipitate was filtered, washed with H$_2$O, and dried to afford the desired as a tan solid (320 mg, 67%). MS m/z 345.0 [M+H]$^+$.

Step 5: To a suspension of the intermediate prepared above (0.317 g, 0.920 mmol) in MeOH (6.8 mL) was added Oxone (1.77 g, 2.85 mmol) in H$_2$O (6.8 mL) dropwise via syringe. The mixture was stirred overnight at ambient temperature and was then filtered through a phase separator followed by washing with H$_2$O. The solid was dried to afford a mixture of sulfone and sulfoxide at a ratio of 22:70 (330 mg, 95%). MS m/z 361.1, 377.1 [M+H]$^+$.

Step 6: A mixture of the sulfone and sulfoxide (50 mg, 0.13 mmol) and piperizine (17 mg, 0.20 mmol) in 0.17 mL of anhydrous DMSO was treated with DIPEA (0.046 mL, 0.26 mmol) and heated at 90° C. for 2 h. The reaction was then cooled to ambient temperature and diluted with EtOAc and H$_2$O. The phases were separated and the aqueous layer was further extracted with EtOAc (2×). The combined organic extracts were washed with brine, dried over Na$_2$SO$_4$, filtered, and concentrated. The residue was purified by column chromatography on silica gel with dichloromethane and methanol (0-15% gradient). The desired fractions were combined and concentrated and the residue was treated with HCl in Et$_2$O to give the desired product as a yellow solid (28 mg, 49%).

MS m/z 383.1 [M+H]$^+$; $^1$H NMR (DMSO-d$_6$) δ: 9.25-9.44 (m, 2H), 8.49 (d, J=1.3 Hz, 1H), 8.21-8.34 (m, 1H), 7.99-8.15 (m, 1H), 7.88-7.97 (m, 1H), 3.85-3.95 (m, 4H), 3.30 (br s, 4H), 2.68 (s, 3H), 2.45 (s, 3H).

Using the procedure described for Example 18, above, additional compounds described herein were prepared by substituting the appropriate starting material, suitable reagents and reaction conditions, obtaining compounds such as those selected from:

| Cpd | Data |
|---|---|
| 121 | MS m/z 397.4 [M + H]$^+$; $^1$H NMR (CDCl$_3$) δ: 7.92 (d, J = 1.6 Hz, 1H), 7.67 (d, J = 0.6 Hz, 1H), 7.58 (dd, J = 11.8, 1.7 Hz, 1H), 7.15 (d, J = 1.3 Hz, 1H), 3.85 (br s, 2H), 3.78 (br s, 2H), 3.11-3.18 (m, 2H), 2.94-3.01 (m, 2H), 2.63 (d, J = 0.9 Hz, 3H), 2.46 (d, J = 0.6 Hz, 3H), 2.01-2.09 (m, 3H). |
| 125 | MS m/z 409.3 [M + H]$^+$; $^1$H NMR (CDCl$_3$) δ: 7.92 (d, J = 1.6 Hz, 1H), 7.67 (d, J = 0.6 Hz, 1H), 7.59 (dd, J = 12.0, 1.6 Hz, 1H), 7.16 (d, J = 0.9 Hz, 1H), 3.66 (d, J = 5.0 Hz, |

| Cpd | Data |
|---|---|
| | 2H), 3.56 (s, 2H), 3.09-3.14 (m, 2H), 2.63 (d, J = 0.9 Hz, 3H), 2.46 (s, 3H), 0.76 (br s, 2H), 0.68-0.73 (m, 2H). |
| 133 | MS m/z 454.2 [M + H]+; 1H NMR (DMSO-d6) δ: 9.15-9.23 (m, 1H), 8.58 (d, J = 1.3 Hz, 1H), 8.50-8.56 (m, 1H), 8.28-8.36 (m, 1H), 8.08-8.16 (m, 1H), 8.01-8.06 (m, 1H), 5.63-5.72 (m, 1H), 2.69 (s, 3H), 2.50 (s, 3H), 2.40 (dd, J = 13.2, 4.1 Hz, 2H), 1.93 (d, J = 2.8 Hz, 2H), 1.52 (s, 12H). |
| 135 | 1H NMR (DMSO-d6) δ: 9.06-9.17 (m, 1H), 8.73-8.85 (m, 1H), 8.57 (d, J = 1.6 Hz, 1H), 8.24-8.36 (m, 1H), 8.06-8.16 (m, 1H), 7.98-8.05 (m, 1H), 5.46-5.56 (m, 1H), 3.41-3.52 (m, 2H), 2.68 (s, 3H), 2.52 (s, 3H), 2.42-2.47 (m, 2H), 1.66-1.77 (m, 2H), 1.34 (d, J = 6.6 Hz, 6H). |
| 143 | 1H NMR (DMSO-d6) δ: 8.42 (d, J = 1.9 Hz, 1H), 8.33-8.39 (m, 1H), 8.16-8.25 (m, 1H), 7.84-7.96 (m, 1H), 3.87-3.95 (m, 2H), 3.78-3.86 (m, 1H), 3.41-3.52 (m, 2H), 2.68 (s, 3H), 2.54 (s, 3H), 1.84-1.93 (m, 2H), 1.46-1.57 (m, 2H). |

Example 19

Preparation of Compound 210

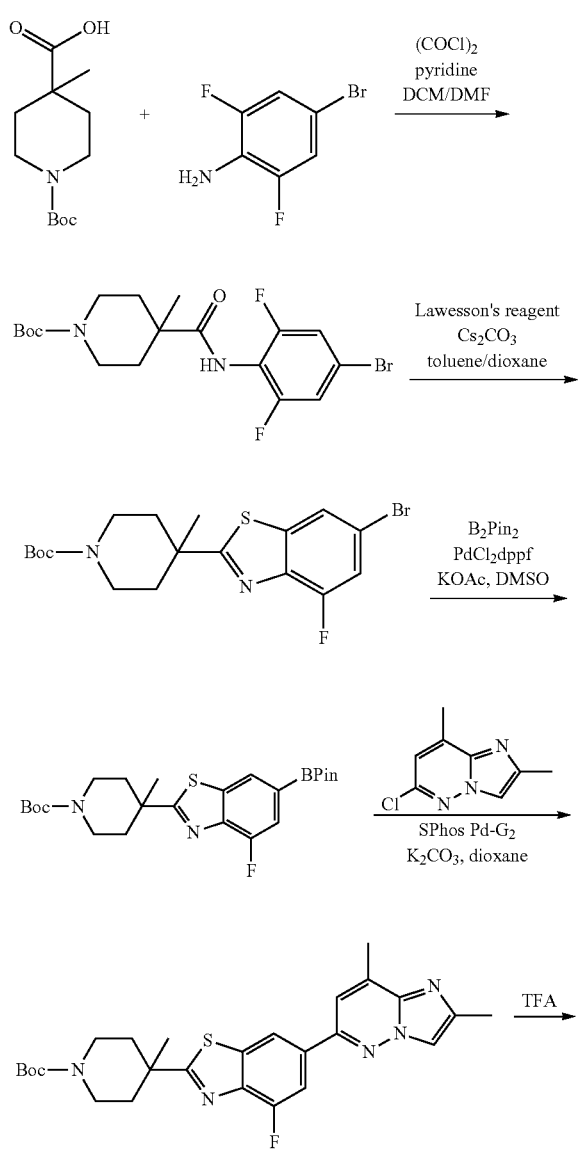

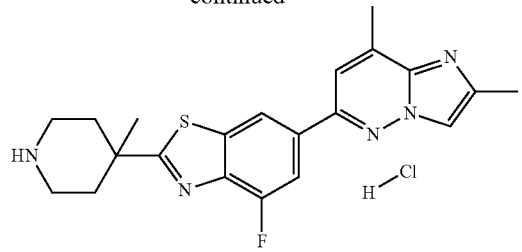

Step 1: To a solution of 1-tert-butoxycarbonyl-4-methyl-piperidine-4-carboxylic acid (240 mg, 0.99 mmol, 1.0 eq.) in CH$_2$Cl$_2$ (8.0 mL) was added pyridine (320 mg, 0.32 mL, 3.9 mmol, 4.0 eq.), (COCl)$_2$ (130 mg, 0.088 mL, 0.99 mmol, 1.0 eq.) followed by 2 drops of DMF. After 1 h at room temperature, 4-bromo-2,6-difluoro-aniline (210 mg, 0.99 mmol, 1.0 eq.) was added and the mixture was stirred at room temperature overnight, after which CH$_2$Cl$_2$ was added and washed with water and brine. The organic layers were dried, evaporated and purified over silica gel with ethyl acetate in hexanes (5 to 50% gradient) to give tert-butyl 4-[(4-bromo-2,6-difluoro-phenyl)carbamoyl]-4-methyl-piperidine-1-carboxylate (350 mg, 82%).

$^1$H NMR (CDCl$_3$) δ: 7.43 (s, 1H), 7.11 (d, J=6.6 Hz, 2H), 3.65-3.81 (m, 2H), 3.14-3.22 (m, 2H), 2.09 (d, J=13.9 Hz, 2H), 1.46-1.52 (m, 2H), 1.45 (s, 9H), 1.32 (s, 3H).

Step 2: A mixture of tert-butyl 4-[(4-bromo-2,6-difluoro-phenyl)carbamoyl]-4-methyl-piperidine-1-carboxylate (350 mg, 0.81 mmol, 1.0 eq.), Lawesson's reagent (200 mg, 0.48 mmol, 0.60 eq.), Cs$_2$CO$_3$ (660 mg, 2.0 mmol, 2.5 eq.) in toluene (4.0 mL) and dioxane (2.0 mL) was stirred at 100° C. overnight. After cooling the reaction mixture was treated with saturated aq. sodium bicarbonate and filtered. The filtrate was dried, concentrated and the residue was purified over silica gel with ethyl acetate in hexanes (5 to 35% gradient) to give tert-butyl 4-(6-bromo-4-fluoro-1,3-benzothiazol-2-yl)-4-methyl-piperidine-1-carboxylate (79 mg, 23%).

$^1$H NMR (CDCl$_3$) δ: 7.81 (dd, J=1.6, 0.6 Hz, 1H), 7.35 (dd, J=9.8, 1.6 Hz, 1H), 3.68-3.76 (m, 2H), 3.33 (s, 2H), 2.29-2.37 (m, 2H), 1.81 (s, 2H), 1.49 (s, 3H), 1.48 (s, 9H).

Step 3: A mixture of tert-butyl 4-(6-bromo-4-fluoro-1,3-benzothiazol-2-yl)-4-methyl-piperidine-1-carboxylate (79 mg, 0.18 mmol, 1.0 eq.), B$_2$Pin$_2$ (71 mg, 0.28 mmol, 1.5 eq.), PdCl$_2$dppf dichloromethane adduct (15 mg, 0.018 mmol, 0.10 eq.) and KOAc (55 mg, 0.55 mmol, 3.0 eq.) in dioxane (1.8 mL) was stirred at 100° C. for 2 h, then cooled, diluted with ethyl acetate and filtered through Celite. The filtrate was concentrated and purified over silica gel with ethyl acetate in hexanes (5 to 50% gradient) to give tert-butyl 4-[4-fluoro-6-(4,4,5,5-tetramethyl-1,3,2-dioxaborolan-2-yl)-1,3-benzothiazol-2-yl]-4-methyl-piperidine-1-carboxylate (60 mg, 68%).

$^1$H NMR (CDCl$_3$) δ: 8.11 (d, J=0.9 Hz, 1H), 7.57 (dd, J=10.9, 0.8 Hz, 1H), 3.68-3.78 (m, 2H), 3.34 (s, 2H), 2.31-2.41 (m, 2H), 1.82 (s, 2H), 1.50 (s, 3H), 1.48 (s, 9H), 1.39 (s, 12H).

Step 4: A mixture of tert-butyl 4-[4-fluoro-6-(4,4,5,5-tetramethyl-1,3,2-dioxaborolan-2-yl)-1,3-benzothiazol-2-yl]-4-methyl-piperidine-1-carboxylate (60 mg, 0.13 mmol, 1.0 eq.), 6-chloro-2,8-dimethyl-imidazo[1,2-b]pyridazine (23 mg, 0.13 mmol, 1.0 eq.), SPhos-Pd G2 (9.3 mg, 0.013 mmol, 0.10 eq.) and K$_2$CO$_3$ (2.0 M aq.) (0.19 mL, 0.38 mmol, 3.0 eq.) in dioxane (1.0 mL) was stirred at 100° C. for 2 h, then cooled to room temperature, diluted with ethyl acetate and washed with brine. The organic layer was dried and evaporated. The residue was purified over silica with ethyl acetate and dichloromethane (10 to 100% gradient) to give tert-butyl 4-[6-(2,8-dimethylimidazo[1,2-b]pyridazin-6-yl)-4-fluoro-1,3-benzothiazol-2-yl]-4-methyl-piperidine-1-carboxylate (35 mg, 56%). MS m/z 496.4 [M+H]$^+$.

Step 5: To tert-Butyl 4-[6-(2,8-dimethylimidazo[1,2-b]pyridazin-6-yl)-4-fluoro-1,3-benzothiazol-2-yl]-4-methyl-piperidine-1-carboxylate (35 mg, 0.071 mmol, 1.0 eq.) was added TFA (1.0 mL). The mixture was stirred for 15 min at room temperature after which the organic volatiles were removed by a stream of nitrogen. The residue was purified over a C18 column to give 6-(2,8-dimethylimidazo[1,2-b]pyridazin-6-yl)-4-fluoro-2-(4-methyl-4-piperidyl)-1,3-benzothiazole hydrochloride (28 mg, 92%) after treatment with HCl.

MS m/z 396.5 [M+H]$^+$; $^1$H NMR (methanol-d$_4$) δ: 8.52 (d, J=1.3 Hz, 1H), 8.14-8.22 (m, 2H), 7.93 (dd, J=11.3, 1.3 Hz, 1H), 3.20-3.27 (m, 2H), 3.08-3.15 (m, 2H), 2.64 (s, 3H), 2.49 (d, J=0.6 Hz, 3H), 2.42-2.48 (m, 2H), 1.92-1.98 (m, 2H), 1.44 (s, 3H).

Using the procedure described for Example 19, above, additional compounds described herein were prepared by substituting the appropriate starting material, suitable reagents and reaction conditions, obtaining compounds such as those selected from:

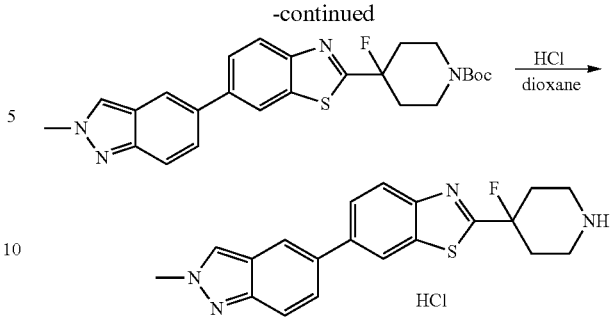

Step 1: To a solution of tert-butyl 4-hydroxy-4-(6-(2-methyl-2H-indazol-5-yl)benzo[d]thiazol-2-yl)piperidine-1-carboxylate (500 mg, prepared according to the procedure in Example 8 step 2) in dichloromethane at 0° C. was added DAST (2.0 eq) and the temperature was allowed to rise to room temperature and stirred for 16 h. The reaction was quenched with saturated sodium bicarbonate. The mixture was extracted with ethyl acetate, dried over sodium sulfate and evaporated. The residue was purified by silica gel flash column chromatography to afford tert-butyl 4-fluoro-4-(6-(2-methyl-2H-indazol-5-yl)benzo[d]thiazol-2-yl)piperidine-1-carboxylate (450 mg, 89%). MS m/z 467.1 [M+H]$^+$.

Step 2: tert-Butyl 4-fluoro-4-(6-(2-methyl-2H-indazol-5-yl)benzo[d]thiazol-2-yl)piperidine-1-carboxylate (450 mg) was treated with 4.0 N HCl in dioxane. The mixture was stirred at room temperature for 16 h then diluted with large amount of ether and filtered. The solid was collected and dried to give 2-(4-fluoropiperidin-4-yl)-6-(2-methyl-2H-indazol-5-yl)benzo[d]thiazole hydrochloride (0.38 g, 98%).

MS m/z 367.1 [M+H]$^+$; $^1$H NMR (DMSO-d$_6$) δ: 9.37 (br s, 2H), 8.53 (d, J=1.6 Hz, 1H), 8.44 (s, 1H), 8.13 (d, J=8.5 Hz, 1H), 8.08 (s, 1H), 7.92 (dd, J=8.7, 1.7 Hz, 1H), 7.64-7.74 (m, 2H), 4.20 (s, 3H), 3.39-3.46 (m, 2H), 3.15-3.28 (m, 2H), 2.54-2.69 (m, 2H), 2.38-2.47 (m, 2H).

| Cpd | Data |
|---|---|
| 194 | MS m/z 408.4 [M + H]$^+$; $^1$H NMR (methanol-d$_4$) δ: 8.70 (d, J = 1.6 Hz, 1H), 8.35 (dd, J = 6.0, 0.9 Hz, 2H), 8.13 (dd, J = 11.5, 1.4 Hz, 1H), 3.58-3.66 (m, 6H), 2.82 (d, J = 1.3 Hz, 3H), 2.68 (d, J = 0.9 Hz, 3H), 2.49-2.56 (m, 6H). |

Example 20

Preparation of Compound 41

Example 21

Preparation of Compound 229

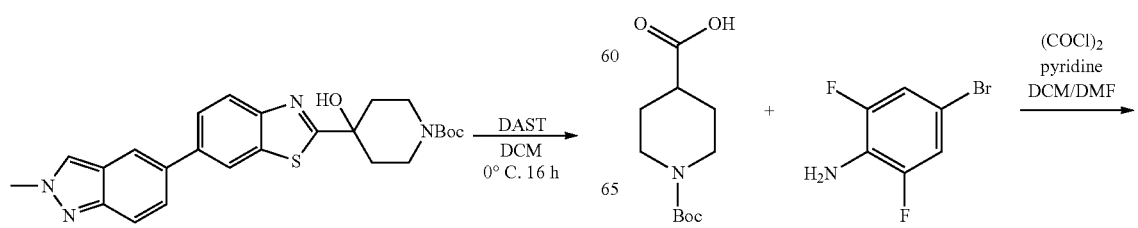

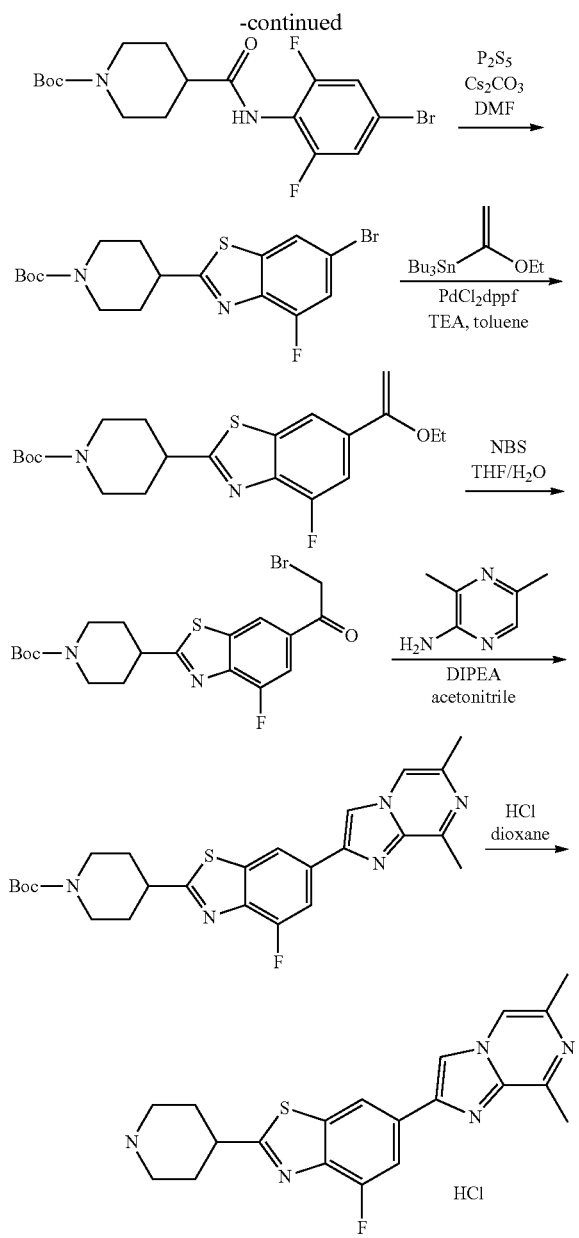

Step 1: To a solution of 1-tert-butoxycarbonyl-piperidine-4-carboxylic acid (2.29 g, 10.0 mmol, 1.00 eq.) in CH$_2$Cl$_2$ (100 mL) at room temperature was added pyridine (3.19 g, 3.26 mL, 40.0 mmol, 4.00 eq.) followed by (COCl)$_2$ (1360 mg, 0.934 mL, 10.5 mmol, 1.05 eq.) and DMF (73 mg, 0.078 mL, 3 mmol, 0.1 eq.). After 1 h, 4-bromo-2,6-difluoro-aniline (2.29 g, 11.0 mmol, 1.10 eq.) was added and the mixture was stirred at room temperature for 3 days. The mixture was then washed with water and brine, and dried and purified over silica gel with ethyl acetate in hexanes (5 to 50% gradient) to give tert-butyl 4-[(4-bromo-2,6-difluoro-phenyl)carbamoyl]piperidine-1-carboxylate (2.0 g, 48%). MS m/z 417.2, 419.2 [M−H]$^-$.

Step 2: A suspension of phosphorus pentasulfide (270 mg, 1.2 mmol, 1.0 eq.) in pyridine (4.0 mL) was stirred at 85° C. for 30 min to give a clear solution, to which was added tert-butyl 4-[(4-bromo-2,6-difluoro-phenyl)carbamoyl]piperidine-1-carboxylate (500 mg, 1.2 mmol, 1.0 eq.). The mixture was stirred at 85° C. overnight, and then cooled, poured into a mixture of saturated sodium bicarbonate and water (1:1), stirred for 2 h and then filtered. The solid was collected and dried, followed by purification over silica gel with ethyl acetate and dichloromethane (0 to 10% gradient). The desired fractions were combined and evaporated. To the residue was added DMF (1.0 mL) and the mixture was heated with Cs$_2$CO$_3$ (390 mg, 1.2 mmol, 1.0 eq.) at 100° C. for 16 h. Aqueous work up followed by purification with ethyl acetate and dichloromethane (0 to 30% gradient) provided tert-butyl 4-(6-bromo-4-fluoro-1,3-benzothiazol-2-yl)piperidine-1-carboxylate (118 mg, 24%).

$^1$H NMR (CDCl$_3$) δ: 7.81 (dd, J=1.7, 0.8 Hz, 1H), 7.36 (dd, J=9.6, 1.7 Hz, 1H), 4.19-4.32 (m, 2H), 3.26-3.35 (m, 1H), 2.85-2.98 (m, 2H), 2.14-2.22 (m, 2H), 1.80-1.90 (m, 2H), 1.50 (s, 9H).

Step 3: A mixture of tert-butyl 4-(6-bromo-4-fluoro-1,3-benzothiazol-2-yl)piperidine-1-carboxylate (118 mg, 0.284 mmol, 1.00 eq.), tributyl(1-ethoxyvinyl)tin (212 mg, 0.198 mL, 0.568 mmol, 2.00 eq.), TEA (86.7 mg, 0.119 mL, 0.852 mmol, 3.00 eq.) and PdCl$_2$dppf dichloromethane adduct (23.4 mg, 0.0284 mmol, 0.100 eq.) in toluene (2.0 mL) was heated at 110° C. overnight, cooled and then purified over basic alumina with ethyl acetate and hexanes (0 to 25% gradient) to give tert-butyl 4-[6-(1-ethoxyvinyl)-4-fluoro-1,3-benzothiazol-2-yl]piperidine-1-carboxylate (57 mg, 49%).

$^1$H NMR (acetone-d$_6$) δ: 8.15 (d, J=1.6 Hz, 1H), 7.55 (dd, J=12.3, 1.3 Hz, 1H), 4.90 (d, J=3.2 Hz, 1H), 4.41 (d, J=2.8 Hz, 1H), 4.15-4.28 (m, 2H), 4.00 (q, J=6.9 Hz, 2H), 3.35-3.46 (m, 1H), 2.90-3.11 (m, 2H), 2.15-2.23 (m, 2H), 1.75-1.87 (m, 2H), 1.48 (s, 9H), 1.45 (t, J=7.1 Hz, 3H).

Step 4: To a solution of tert-butyl 4-[6-(1-ethoxyvinyl)-4-fluoro-1,3-benzothiazol-2-yl]piperidine-1-carboxylate (57 mg, 0.14 mmol, 1.0 eq.) in THF (1.0 mL) and water (0.3 mL) was added NBS (25 mg, 0.14 mmol, 1.0 eq.). The mixture was stirred at room temperature for 1 h then diluted with ethyl acetate, washed with water, NaHCO$_3$ and brine. The organic layer was dried and concentrated, and then purified over silica gel with ethyl acetate and dichloromethane (0 to 20% gradient) to give tert-butyl 4-[6-(2-bromoacetyl)-4-fluoro-1,3-benzothiazol-2-yl]piperidine-1-carboxylate (62 mg, 97%).

$^1$H NMR (CDCl$_3$) δ: 8.35 (d, J=1.6 Hz, 1H), 7.81 (dd, J=10.7, 1.6 Hz, 1H), 4.49 (s, 2H), 4.21-4.35 (m, 2H), 3.30-3.43 (m, 1H), 2.87-3.01 (m, 2H), 2.16-2.28 (m, 2H), 1.82-1.95 (m, 2H), 1.50 (s, 9H).

Step 5: A mixture of tert-butyl 4-[6-(2-bromoacetyl)-4-fluoro-1,3-benzothiazol-2-yl]piperidine-1-carboxylate (62 mg, 0.14 mmol, 1.0 eq.), 3,5-dimethylpyrazin-2-amine (20 mg, 0.16 mmol, 1.2 eq.) and DIPEA (18 mg, 0.024 mL, 0.14 mmol, 1.0 eq.) in acetonitrile (0.5 mL) was heated at 90° C. for 2 h. Aqueous work up followed by purification with ethyl acetate in dichloromethane (0 to 100% gradient) provided tert-butyl 4-[6-(6,8-dimethylimidazo[1,2-a]pyrazin-2-yl)-4-fluoro-1,3-benzothiazol-2-yl]piperidine-1-carboxylate (38 mg, 58%). MS m/z 482.3 [M+H]$^+$.

Step 6: tert-Butyl 4-[6-(6,8-dimethylimidazo[1,2-a]pyrazin-2-yl)-4-fluoro-1,3-benzothiazol-2-yl]piperidine-1-carboxylate (38 mg, 0.079 mmol, 1.0 eq.) was treated with TFA (0.5 mL) then concentrated and purified using a C18 column to give 6-(6,8-dimethylimidazo[1,2-a]pyrazin-2-yl)-4-fluoro-2-(4-piperidyl)-1,3-benzothiazole hydrochloride (26 mg, 79%) after treatment with HCl.

MS m/z 382.3 [M+H]$^+$; $^1$H NMR (methanol-d$_4$) δ: 8.76 (s, 1H), 8.52 (s, 1H), 8.44 (d, J=1.6 Hz, 1H), 7.85-7.91 (m, 1H), 3.36-3.49 (m, 3H), 3.04-3.11 (m, 2H), 2.97 (s, 3H), 2.46 (s, 3H), 2.25-2.33 (m, 2H), 1.98-2.09 (m, 2H).

Example 22

Preparation of Compound 98

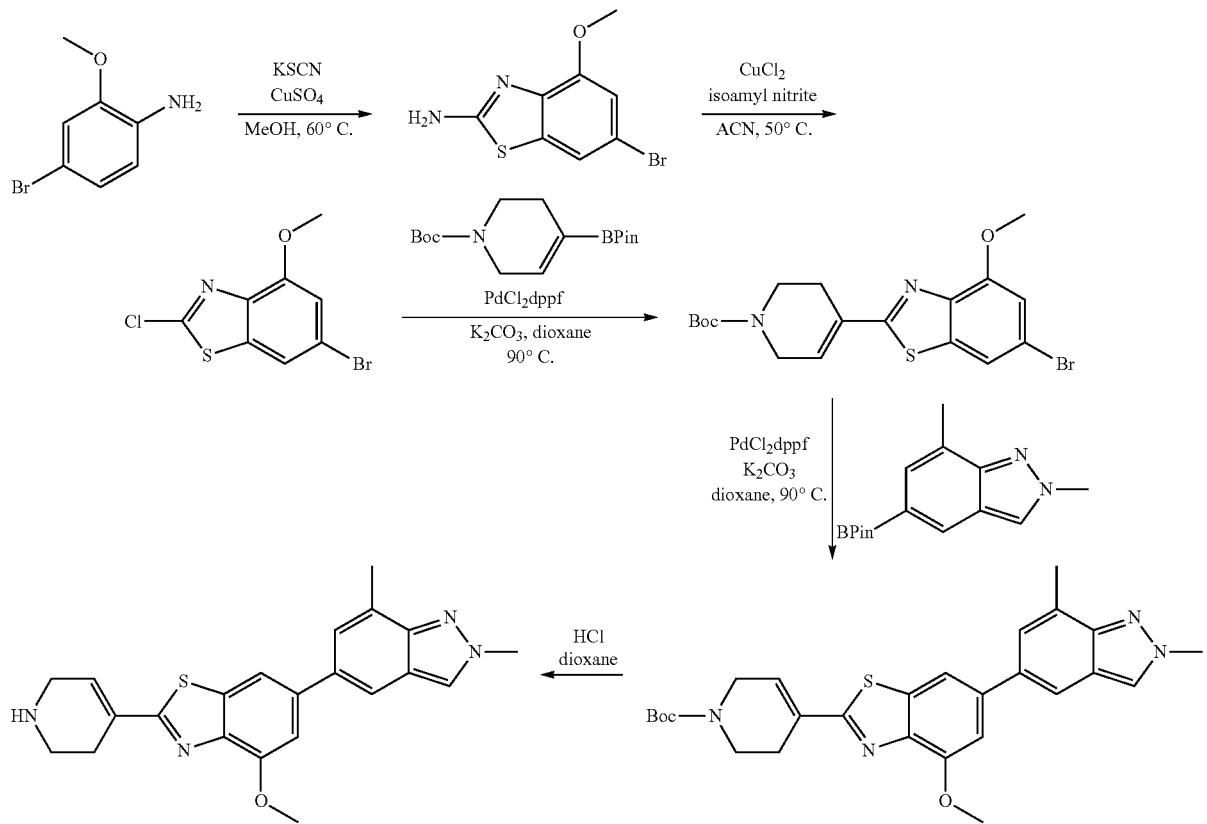

Step 1: A mixture of 4-bromo-2-methoxy-aniline (1 g, 4.94 mmol), KSCN (1.46 g, 14.85 mmol) and CuSO$_4$ (1.19 g, 7.42 mmol) in 50 mL of MeOH was heated to 60° C. for 16 h. The reaction was cooled to room temperature, filtered through Celite, concentrated, and then purified on an ISCO eluting with EtOAc/hexanes (10-70% gradient) to afford 6-bromo-4-methoxy-1,3-benzothiazol-2-amine (1.1 g, 86%) as a dark brown solid, which was used directly in the next step (~85% pure).

Step 2: To a solution of 6-bromo-4-methoxy-1,3-benzothiazol-2-amine (1.1 g, 4.2 mmol) in 200 mL of acetonitrile was added CuCl$_2$ (1.1 g, 8.5 mmol) and isoamyl nitrite (1.2 mL, 8.5 mmol). The reaction mixture was stirred at room temperature for 1 h, and then heated to 50° C. for 3 h. The reaction was cooled to room temperature, filtered through Celite, diluted with water and extracted with EtOAc. The combined organic extracts were dried over Na$_2$SO$_4$, concentrated, and purified on an ISCO eluting with an EtOAc/hexanes (0-40% gradient) to afford 6-bromo-2-chloro-4-methoxy-1,3-benzothiazole (675 mg, 57%) as a white solid.

MS m/z 279.9 [M+H]$^+$; $^1$H NMR (acetone-d$_6$) δ: 7.84 (d, J=1.9 Hz, 1H), 7.27 (d, J=1.9 Hz, 1H), 4.07 (s, 3H).

Step 3: To a round bottom flask was added 6-bromo-2-chloro-4-methoxy-1,3-benzothiazole (298 mg, 1.07 mmol), tert-butyl 4-(4,4,5,5-tetramethyl-1,3,2-dioxaborolan-2-yl)-3,6-dihydro-2H-pyridine-1-carboxylate (331 mg, 1.07 mmol), Pd(dppf)Cl$_2$ (80 mg, 0.1 mmol) and, K$_2$CO$_3$ (448 mg, 3.2 mmol). The reaction was degassed with N$_2$ for 15 min and dioxane (10 mL) and water (2.5 mL) were added. The reaction was heated to 90° C. for 3 h. UPLC showed 90% of the desired product. The reaction was cooled down to room temperature, and partitioned between EtOAc and water. The organic phase was dried over Na$_2$SO$_4$, concentrated under reduced pressure and then purified on an ISCO through silica gel eluting with EtOAc/hexanes (0% to 20% gradient) to provide tert-butyl 4-(6-bromo-4-methoxy-1,3-benzothiazol-2-yl)-3,6-dihydro-2H-pyridine-1-carboxylate (388 mg, 85.3%).

MS m/z 425.2, 427.2 [M+H]$^+$; $^1$H NMR (acetone-d$_6$) δ: 7.79 (d, J=1.9 Hz, 1H), 7.19 (d, J=1.9 Hz, 1H), 6.72-6.82 (m, 1H), 4.12-4.24 (m, 2H), 3.67 (s, 3H), 2.80-2.84 (m, 2H), 2.75-2.79 (m, 2H), 1.50 (s, 9H).

Step 4: To a round bottom flask was added tert-butyl 4-(6-bromo-4-methoxy-1,3-benzothiazol-2-yl)-3,6-dihydro-2H-pyridine-1-carboxylate (70 mg, 0.16 mmol), 2,7-dimethyl-5-(4,4,5,5-tetramethyl-1,3,2-dioxaborolan-2-yl)indazole (54 mg, 0.19 mmol), PddppfCl$_2$ (12 mg, 0.016 mmol) and K$_2$CO$_3$ (69 mg, 0.49 mmol). The reaction was degassed with N$_2$ for 15 min and dioxane (10 mL) and water (2.5 mL) were added and the reaction was heated to 90° C. for 16 h. The reaction was cooled to room temperature, and then partitioned between EtOAc and water. The organic phase was dried over Na$_2$SO$_4$, concentrated under reduced pressure and purified on an ISCO through silica gel eluting with EtOAc/hexanes (0% to 100%), providing tert-butyl 4-[6-(2,7-dimethylindazol-5-yl)-4-methoxy-1,3-benzothiazol-2-yl]-3,6-dihydro-2H-pyridine-1-carboxylate (80 mg, 99%). MS m/z 491.3 [M+H]$^+$.

Step 5: tert-Butyl 4-[6-(2,7-dimethylindazol-5-yl)-4-methoxy-1,3-benzothiazol-2-yl]-3,6-dihydro-2H-pyridine-1-carboxylate (12 mg, 0.025 mmol) was dissolved in 0.5 mL of MeOH and HCl (4 M) in 1,4-dioxane (0.012 mL) was added. The reaction mixture was stirred at room temperature for 1 h until UPLC showed complete consumption of the starting material. The reaction was concentrated, triturated in Et₂O, and the resultant precipitate was filtered to yield 6-(2,7-dimethyl-2H-indazol-5-yl)-4-methoxy-2-(1,2,3,6-tetrahydropyridin-4-yl)benzo[d]thiazole hydrochloride (8 mg, 76.6%) as a yellow solid.

MS m/z 391.5 [M+H]$^+$; $^1$H NMR (DMSO-d$_6$) δ: 8.94-9.14 (m, 1H), 8.40 (s, 1H), 7.96 (d, J=1.9 Hz, 1H), 7.93 (d, J=1.9 Hz, 1H), 7.42-7.55 (m, 1H), 7.31-7.39 (m, 1H), 6.67-6.80 (m, 1H), 4.21 (s, 3H), 4.08 (s, 3H), 3.83-3.91 (m, 2H), 3.33-3.42 (m, 2H), 2.86-3.00 (m, 2H), 2.59 (s, 3H).

Using the procedure described for Example 22, above, additional compounds described herein were prepared by substituting the appropriate starting material, suitable reagents and reaction conditions, obtaining compounds such as those selected from:

tert-Butyl 4-[6-(2,7-dimethylindazol-5-yl)-4-methoxy-1,3-benzothiazol-2-yl]-3,6-dihydro-2H-pyridine-1-carboxylate (46 mg, 0.09 mmol, prepared in Example 23, step 4) was dissolved in 5 mL of MeOH. 10 mg of Pd/C was added and the reaction was subjected to 70 psi H₂ in a Parr shaker for 48 h, then filtered and concentrated to yield crude tert-butyl 4-[6-(2,7-dimethylindazol-5-yl)-4-methoxy-1,3-benzothiazol-2-yl]piperidine-1-carboxylate (30 mg). This was dissolved in 0.5 mL of MeOH and 4M HCl in 1,4-dioxane (30 µL) was added. The reaction mixture was stirred at room temperature for 1 h until UPLC showed complete consumption of the starting material. The reaction mixture was then concentrated, triturated in Et₂O, and the precipitate was filtered to yield 6-(2,7-dimethyl-2H-indazol-5-yl)-4-methoxy-2-(piperidin-4-yl)benzo[d]thiazole hydrochloride (11 mg, 46.0%) as a yellow solid.

MS m/z 393.5 [M+H]$^+$; $^1$H NMR (DMSO-d$_6$): δ 8.88-8.99 (m, 1H), 8.43 (s, 1H), 7.77-7.89 (m, 1H), 7.42-7.55 (m, 1H), 7.31-7.39 (m, 1H), 6.67-6.80 (m, 1H), 4.27 (s, 3H), 4.18 (s, 3H), 3.45-3.52 (m, 2H), 3.25-3.34 (m, 2H), 3.15-3.20 (m, 1H), 2.53 (s, 3H), 2.41-2.48 (m, 2H), 2.18-2.24 (m, 2H).

| Cpd | Data |
|---|---|
| 153 | MS m/z 399.8 [M + H]$^+$; $^1$H NMR (DMSO-d$_6$): δ: 9.11-9.32 (m, 1H), 8.58 (d, J = 2.5 Hz, 1H), 8.49 (d, J = 1.6 Hz, 1H), 8.03 (d, J = 1.6 Hz, 1H), 8.03 (d, J = 1.3 Hz, 1H), 7.56 (dd, J = 13.1, 1.4 Hz, 1H), 6.72-6.95 (m, 1H), 4.24 (s, 3H), 3.77-3.86 (m, 2H), 3.28-3.43 (m, 2H), 2.89-3.02 (m, 2H). |
| 154 | MS m/z 406.9 [M + H]$^+$; $^1$H NMR (DMSO-d$_6$): δ: 9.16-9.27 (m, 1H), 8.73 (s, 1H), 8.57 (d, J = 1.9 Hz, 1H), 8.55 (d, J = 1.6 Hz, 1H), 8.39 (d, J = 1.6 Hz, 1H), 8.11 (d, J = 1.9 Hz, 1H), 6.81-6.94 (m, 1H), 4.29 (s, 3H), 3.88-4.00 (m, 2H), 3.34-3.47 (m, 2H), 2.83-3.01 (m, 2H). |

Example 23

Preparation of Compound 99

Example 24

Preparation of Compound 100

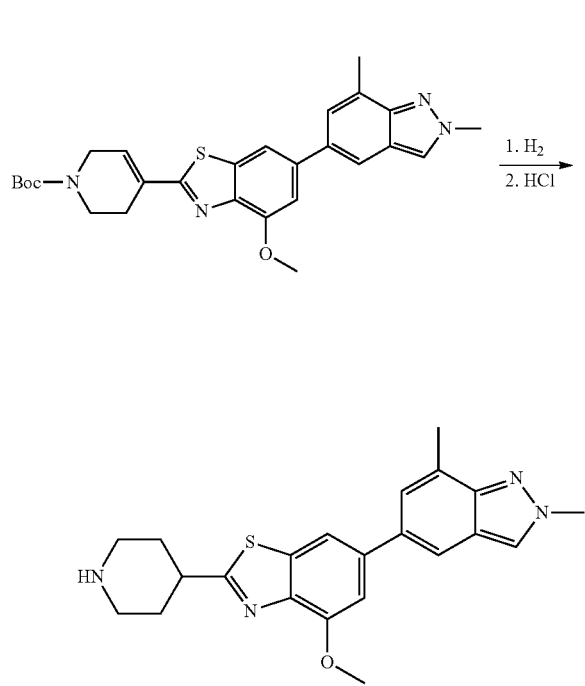

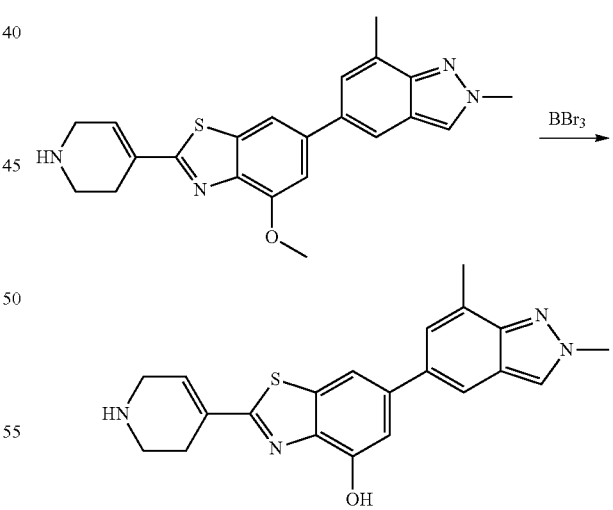

6-(2,7-dimethylindazol-5-yl)-4-methoxy-2-(1,2,3,6-tetrahydropyridin-4-yl)-1,3-benzothiazole (40 mg, 0.10 mmol) was dissolved in 2 mL of CH₂Cl₂ and BBr₃ (1.0 M) in CH₂Cl₂ (0.51 mL) was added dropwise. The reaction mixture was stirred at room temperature for 2 h until UPLC (quenched with MeOH) showed complete consumption of the starting material. The reaction was quenched with MeOH, concentrated to dryness, triturated in CH₂Cl₂, and the precipitate was filtered and dried to yield 6-(2,7-dimethyl-2H-indazol-5-yl)-2-(1,2,3,6-tetrahydropyridin-4-yl)benzo[d]thiazol-4-ol hydrobromide (41 mg, 87.5%) as an orange solid.

MS m/z 377.5 [M+H]+; 1H NMR (DMSO-d6): δ 8.84-9.00 (m, 1H), 8.29-8.46 (m, 1H), 7.80 (d, J=1.6 Hz, 1H), 7.78 (d, J=1.6 Hz, 1H), 7.36 (s, 1H), 7.14-7.26 (m, 1H), 6.64-6.78 (m, 1H), 4.20 (s, 3H), 3.85-3.94 (m, 2H), 3.36-3.46 (m, 2H), 2.83-3.00 (m, 2H), 2.57 (s, 3H).

Example 25

Preparation of Compound 134

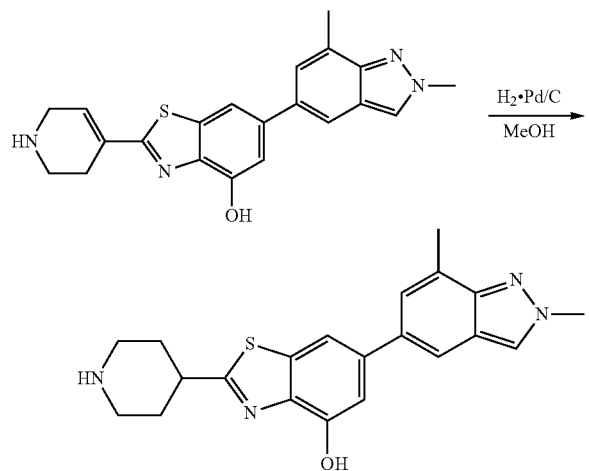

6-(2,7-Dimethyl-2H-indazol-5-yl)-2-(1,2,3,6-tetrahydropyridin-4-yl)benzo[d]thiazol-4-ol (30 mg, 0.07 mmol) was dissolved in 5 mL of MeOH. Approximately 10 mg of Pd/C was added and the reaction was subjected to 70 psi H2 in a Parr shaker for 48 h. The reaction mixture was then filtered and concentrated to yield the desired product (~30 mg, ~80% purity by 1H NMR). The product was purified on an ISCO through silica gel, eluting CH2Cl2/MeOH (0% to 30% gradient) containing NH4OH (2.5%) to provide 6-(2,7-dimethyl-2H-indazol-5-yl)-2-(piperidin-4-yl)benzo[d]thiazol-4-ol (14 mg, 56.4%) as a tan solid.

MS m/z 379.5 [M+H]+; 1H NMR (methanol-d4) δ: 8.42 (br s, 1H), 8.24 (s, 1H), 7.74-7.78 (m, 1H), 7.68 (d, J=1.9 Hz, 1H), 7.40 (d, J=1.9 Hz, 1H), 7.38-7.39 (m, 1H), 7.20 (d, J=1.6 Hz, 1H), 4.26 (s, 3H), 3.52-3.60 (m, 3H), 3.27 (td, J=12.5, 3.0 Hz, 2H), 2.64 (s, 3H), 2.45 (dd, J=14.8, 3.8 Hz, 2H), 2.22 (tdd, J=14.8, 12.5, 3.0 Hz, 2H).

Example 26

Preparation of Compound 172

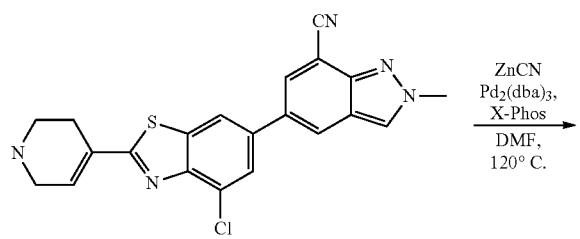

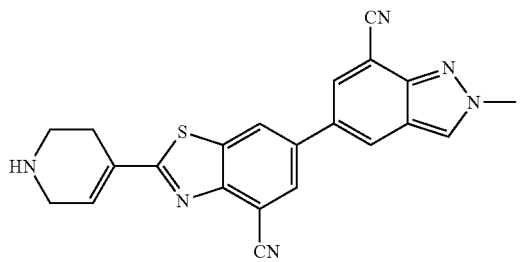

tert-Butyl 4-[4-chloro-6-(7-cyano-2-methyl-indazol-5-yl)-1,3-benzothiazol-2-yl]-3,6-dihydro-2H-pyridine-1-carboxylate (40 mg, 0.08 mmol, prepared as in Example 23), ZnCN (9.5 mg, 0.08 mmol), Pd2dba3 (4 mg, 0.004 mmol) and X-Phos (3.8 mg, 0.008 mmol) were mixed together in dry DMF (1.2 mL) in a microwave tube and heated for 30 min to 120° C. in the microwave. The mixture was poured onto aqueous NaHCO3, and the precipitate was filtered and dried, to provide tert-butyl 4-[4-cyano-6-(7-cyano-2-methyl-indazol-5-yl)-1,3-benzothiazol-2-yl]-3,6-dihydro-2H-pyridine-1-carboxylate (33 mg, 84.1%) as dark greenish-grey solid. The solid was dissolved in 0.5 ml of CH2Cl2 and was treated with a solution of 4M HCl 1,4-dioxane (6 µL) and the reaction was stirred for 2 h. The reaction mixture was concentrated under reduced pressure and dried to provide 6-(7-cyano-2-methyl-indazol-5-yl)-2-(1,2,3,6-tetrahydropyridin-4-yl)-1,3-benzothiazole-4-carbonitrile hydrochloride (3.7 mg, 71%) as a yellow solid.

MS m/z 397.5 [M+H]+; 1H NMR (methanol-d4) δ: 8.64 (d, J=1.9 Hz, 1H), 8.56 (s, 1H), 8.43 (d, J=1.9 Hz, 1H), 8.29 (d, J=1.9 Hz, 1H), 8.23 (d, J=1.9 Hz, 1H), 8.01 (br s, 1H), 6.96-6.99 (m, 1H), 4.34 (s, 3H), 4.05 (dd, J=6.3, 2.5 Hz, 2H), 3.55-3.61 (m, 2H), 3.13-3.18 (m, 2H).

Example 27

Preparation of Compound 86

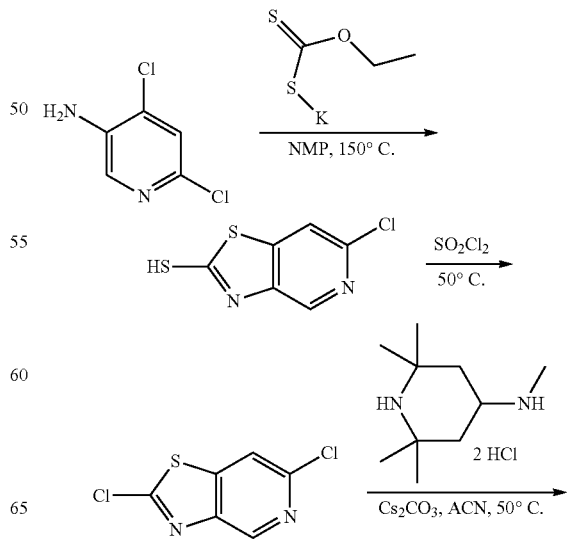

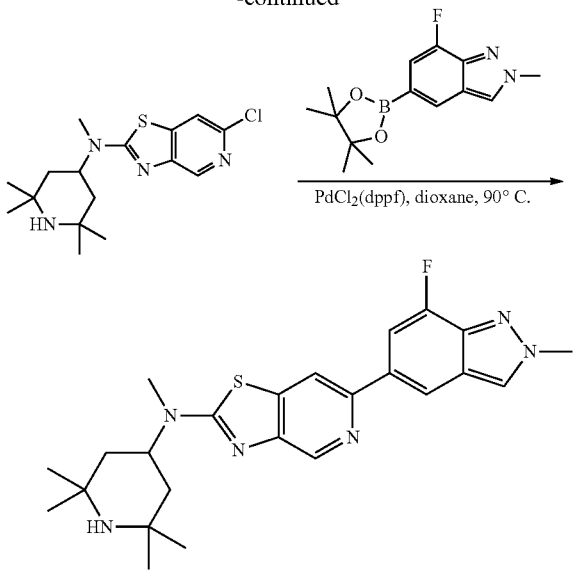

Step 1: A mixture of 4,6-dichloropyridin-3-amine (10 g, 61.35 mmol), potassium O-ethyl carbonodithioate (14.8 g, 92.3 mmol), and NMP (60 mL) was stirred at 150° C. for 6 h. LC/MS showed the disappearance of starting dichloride. The reaction mixture was cooled to room temperature and acetic acid (10 mL) was added and then water (500 mL). The precipitate formed was collected by filtration, washed with water, dried and used directly in the next step. LC-MS m/z 203.2, 205.2 [M+H]$^+$, RT 1.10 min.

Step 2: The above material was treated with sulfuryl dichloride (50 mL) at 50° C. overnight and then added to a stirred mixture of ice-NaHCO$_3$/CH$_2$Cl$_2$ (~1 L). The precipitate was removed by filtration and the filtrate was concentrated. The residue was chromatographed (silica gel, ethyl acetate in hexanes, 0-40%) to provide 2,6-dichlorothiazolo[4,5-c]pyridine (3.62 g, 28.8% for 2 steps). LC-MS m/z 205.1, 207.1, 209.1 [M+H]$^+$, RT 1.27 min.

Step 3: A mixture of 2,6-dichlorothiazolo[4,5-c]pyridine (3.62 g, 17.7 mmol), N,2,2,6,6-pentamethylpiperidin-4-amine dihydrochloride (4.51 g, 18.5 mmol), Cs$_2$CO$_3$ (25.9 g, 79.5 mmol) and acetonitrile (35 mL) was stirred at 50° C. for 24 h. The reaction mixture was then diluted with ethyl acetate and filtered. The filtrate was concentrated and the residue was chromatographed (silica gel, MeOH in CH$_2$Cl$_2$ 0-20%) to provide 6-chloro-N-methyl-N-(2,2,6,6-tetramethyl-4-piperidyl)thiazolo[4,5-c]pyridin-2-amine (4.92 g, 82.2%) as an off white powder.

LC-MS m/z 339.2, 341.3 [M+H]$^+$, RT 0.99 min; $^1$H NMR (CDCl$_3$) δ: 8.54 (d, J=0.6 Hz, 1H), 7.54 (d, J=0.6 Hz, 1H), 4.42 (br s, 1H), 3.09 (s, 3H), 1.79 (dd, J=12.6, 3.5 Hz, 2H), 1.43-1.56 (m, 2H), 1.38 (s, 6H), 1.26 (br s, 6H).

Step 4: To a mixture of 6-chloro-N-methyl-N-(2,2,6,6-tetramethyl-4-piperidyl)thiazolo[4,5-c]pyridin-2-amine (0.169 g, 0.50 mmol), 7-fluoro-2-methyl-5-(4,4,5,5-tetramethyl-1,3,2-dioxaborolan-2-yl)indazole (0.166 g, 0.60 mmol), PdCl$_2$(dppf) (0.042 g, 0.050 mmol) in 1,4-dioxane (2.0 mL) under an argon atmosphere, was added K$_2$CO$_3$ (0.63 mL, 1.3 mmol, 2.0 M). The mixture was stirred at 90° C. for 2 h and then cooled and diluted with ethyl acetate. The precipitate was removed by filtration and the filtrate was concentrated. The residue was chromatographed (silica gel, MeOH in CH$_2$Cl$_2$, 0-20%) to provide, after trituration with ethyl ether, 6-(7-fluoro-2-methyl-indazol-5-yl)-N-methyl-N-(2,2,6,6-tetramethyl-4-piperidyl)thiazolo[4,5-c]pyridin-2-amine (180 mg, 79.8%).

LC-MS m/z 453.4 [M+H]$^+$, RT 0.88 min; $^1$H NMR (CDCl$_3$) δ: 8.87 (d, J=0.9 Hz, 1H), 8.07 (d, J=1.3 Hz, 1H), 8.01 (d, J=1.0 Hz, 1H), 7.98 (d, J=0.9 Hz, 1H), 7.66 (dd, J=12.8, 1.4 Hz, 1H), 4.55 (br s, 1H), 4.27 (s, 3H), 3.14 (s, 3H), 1.02-1.89 (m, 16H).

Using the procedure described for Example 27, above, additional compounds described herein were prepared by substituting the appropriate starting material, suitable reagents and reaction conditions, obtaining compounds such as those selected from:

| Cpd | Data |
|---|---|
| 27 | MS m/z 378.9 [M + H]$^+$; $^1$H NMR (methanol-d$_4$): δ: 8.78 (s, 1H), 8.77 (s, 1H), 8.65 (s, 1H), 8.42 (s, 1H), 7.92 (d, J = 9 Hz, 1H), 7.88 (dd, J = 9 Hz, 1.5 Hz, 1H), 4.10-4.30 (br s, 1H), 4.36 (s, 3H), 3.61-3.68 (m, 2H), 3.24-3.30 (m, 5H), 2.24-2.33 (m, 2H), 2.17-2.21 (m, 2H). |
| 30 | MS m/z 393.0 [M + H]$^+$; $^1$H NMR (methanol-d$_4$): δ: 8.76 (s, 1H), 8.74 (s, 1H), 8.55 (s, 1H), 8.20 (s, 1H), 7.61 (s, 1H), 4.60-4.80 (br s, 1H), 4.34 (s, 3H), 3.61-3.68 (m, 2H), 3.23-3.33 (m, 5H), 2.72 (s, 3H), 2.17-2.31 (m, 4H). |
| 31 | MS m/z 449.0 [M + H]$^+$; $^1$H NMR (methanol-d$_4$): δ: 8.72 (s, 1H), 8.28 (s, 1H), 8.26 (s, 1H), 8.08 (s, 1H), 7.71 (s, 1H), 4.60 (br s, 1H), 4.27 (s, 3H), 3.18 (s, 3H), 2.66 (s, 3H), 2.01-2.06 (m, 2H), 1.90-2.00 (m, 2H), 1.69 (s, 6H), 1.48 (s, 6H). |
| 32 | MS m/z 435.0 [M + H]$^+$; $^1$H NMR (methanol-d$_4$): δ: 8.71 (s, 1H), 8.30 (s, 1H), 8.26 (s, 1H), 8.25 (s, 1H), 7.94 (dd, J = 9 Hz, 1.5 Hz, 1H), 7.70 (d, J = 9 Hz, 1H), 4.58 (br s, 1H), 4.26 (s, 3H), 3.18 (s, 3H), 1.80-1.84 (m, 2H), 1.60-1.65 (m, 2H), 1.41 (s, 6H), 1.28 (s, 6H). |
| 87 | LC-MS m/z 435.4 [M + H]$^+$, RT 0.75 min.; $^1$H NMR (CDCl$_3$) δ: 8.78-8.87 (m, 2H), 7.92 (d, J = 0.6 Hz, 1H), 7.67 (dd, J = 9.5, 1.6 Hz, 1H), 7.56 (d, J = 9.1 Hz, 1H), 7.40 (s, 1H), 4.43 (br s, 1H), 3.13 (s, 3H), 2.48 (s, 3H), 1.81 (dd, J = 12.6, 3.5 Hz, 2H), 1.14-1.64 (m, 14H). |
| 88 | LC-MS m/z 449.5 [M + H]$^+$, RT 0.80 min.; $^1$H NMR (CDCl$_3$) δ: 8.85 (d, J = 0.6 Hz, 1H), 8.67 (s, 1H), 7.94 (s, 1H), 7.52 (t, J = 1.0 Hz, 1H), 7.40 (d, J = 0.9 Hz, 1H), 4.40-4.92 (m, 1H), 3.14 (s, 3H), 2.68 (s, 3H), 2.50 (d, J = 0.6 Hz, 3H), 1.80-1.92 (m, 2H), 1.28-1.78 (m, 14H). |
| 89 | LC-MS m/z 436.4 [M + H]$^+$, RT 0.84 min.; $^1$H NMR (CDCl$_3$) δ: 8.86 (d, J = 0.6 Hz, 1H), 8.60 (d, J = 0.6 Hz, 1H), 8.16 (d, J = 9.5 Hz, 1H), 7.89 (dd, J = 9.5, 0.6 Hz, 1H), 7.76 (s, 1H), 4.53 (br s, 1H), 3.14 (s, 3H), 2.53 (d, J = 0.6 Hz, 3H), 1.83 (dd, J = 12.5, 3.3 Hz, 2H), 1.27-1.71 (m, 14H). |
| 90 | LC-MS m/z 450.4 [M + H]$^+$, RT 0.85 min.; $^1$H NMR (CDCl$_3$) δ: 8.87 (d, J = 0.6 Hz, 1H), 8.61 (d, J = 0.6 Hz, 1H), 7.99 (d, J = 1.3 Hz, 1H), 7.74 (d, J = 0.6 Hz, 1H), 4.78 |

| Cpd | Data |
|---|---|
| | (br s, 1H), 3.15 (s, 3H), 2.72 (d, J = 0.9 Hz, 3H), 2.54 (d, J = 0.6 Hz, 3H), 1.83-1.91 (m, 2H), 1.41-1.81 (m, 14H). |
| 105 | LC-MS m/z 436.4 [M + H]$^+$, RT 0.76 min.; $^1$H NMR (CDCl$_3$) δ: 9.11 (d, J = 2.2 Hz, 1H), 9.02 (d, J = 2.2 Hz, 1H), 8.85 (d, J = 0.6 Hz, 1H), 8.01 (d, J = 0.6 Hz, 1H), 7.36 (d, J = 0.9 Hz, 1H), 4.52 (br s, 1H), 3.12-3.16 (m, 3H), 2.53 (d, J = 0.9 Hz, 3H), 1.83 (br dd, J = 12.5, 3.3 Hz, 2H), 1.23-1.76 (m, 14H). |
| 116 | LC-MS m/z 503.3 [M + H]$^+$, RT 0.96 min.; $^1$H NMR (CDCl$_3$) δ: 8.89 (d, J = 0.6 Hz, 1H), 8.48 (d, J = 0.6 Hz, 1H), 8.32 (s, 1H), 8.07 (s, 1H), 8.03 (d, J = 0.9 Hz, 1H), 4.47 (br s, 1H), 4.31 (s, 3H), 3.14 (s, 3H), 1.83 (dd, J = 12.5, 3.3 Hz, 2H), 1.21-1.69 (m, 14H). |
| 117 | LC-MS m/z 460.4 [M + H]$^+$, RT 0.93 min.; $^1$H NMR (CDCl$_3$) δ: 8.88 (d, J = 0.6 Hz, 1H), 8.54 (d, J = 1.6 Hz, 1H), 8.43 (d, J = 1.6 Hz, 1H), 8.10 (s, 1H), 8.00 (d, J = 0.6 Hz, 2H), 4.48 (br s, 1H), 4.32 (s, 3H), 3.12-3.16 (s, 3H), 1.83 (br dd, J = 12.1, 3.0 Hz, 2H), 1.18-1.73 (m, 14H). |
| 136 | LC-MS m/z 436.3 [M + H]+, RT 0.92 min.; $^1$H NMR (CDCl$_3$) δ: 9.09-9.11 (m, 1H), 8.84 (d, J = 0.6 Hz, 1H), 8.11 (dd, J = 9.3, 1.7 Hz, 1H), 7.91-7.93 (m, 1H), 7.66 (d, J = 9.1 Hz, 1H), 4.41 (br s, 1H), 3.12 (s, 3H), 2.61 (s, 3H), 1.79 (dd, J = 12.5, 3.3 Hz, 2H), 1.19-1.52 (m, 14H). |
| 147 | LC-MS m/z 453.2 [M + H]$^+$, RT 0.85 min.; $^1$H NMR (DMSO-d$_6$) δ: 9.08 (d, J = 1.6 Hz, 1H), 8.73 (s, 1H), 8.45 (s, 1H), 7.89 (d, J = 2.2 Hz, 1H), 7.75 (dd, J = 12.8, 1.4 Hz, 1H), 4.37 (br s, 1H), 3.07 (s, 3H), 2.37 (s, 3H), 1.41-1.80 (m, 4H), 1.01-1.38 (m, 12H). |
| 179 | LC-MS m/z 460.2 [M + H]$^+$, RT 0.94 min.; $^1$H NMR (DMSO-d$_6$) δ: 9.48 (d, J = 1.6 Hz, 1H), 8.72 (s, 1H), 8.48-8.53 (m, 2H), 7.96 (s, 1H), 4.39 (br s, 1H), 3.06 (s, 3H), 2.33-2.46 (m, 3H), 0.90-1.80 (m, 16H). |
| 198 | LC-MS m/z 404.2 [M + H]$^+$, RT 0.84 min.; $^1$H NMR (DMSO-d$_6$) δ: 9.69 (s, 1H), 9.00 (br s, 2H), 8.84 (br s, 1H), 8.80 (s, 1H), 8.65 (s, 1H), 8.13 (s, 1H), 4.48 (br s, 1H), 3.33-3.46 (m, 2H), 3.09 (s, 3H), 2.47 (s, 3H), 2.09-2.24 (m, 2H), 1.86-1.99 (m, 2H), 1.34-1.70 (m, 2H). |
| 199 | LC-MS m/z 416.2 [M + H]$^+$, RT 0.84 min.; $^1$H NMR (DMSO-d$_6$) δ: 9.68 (d, J = 1.3 Hz, 1H), 9.16-9.33 (m, 2H), 8.96 (br d, J = 6.6 Hz, 1H), 8.81 (s, 1H), 8.76 (s, 1H), 8.55 (s, 1H), 8.14 (s, 1H), 4.18-4.34 (m, 1H), 4.05 (br s, 2H), 2.47 (s, 3H), 2.21 (br d, J = 13.6 Hz, 2H), 1.94-2.08 (m, 4H), 1.89 (br t, J = 1.0 Hz, 2H). |
| 203 | LC-MS m/z 430.2 [M + H]$^+$, RT 0.89 min.; $^1$H NMR (DMSO-d$_6$) δ: 9.60-9.73 (m, 2H), 9.11 (br s, 1H), 8.73-8.86 (m, 2H), 8.61 (s, 1H), 8.10 (s, 1H), 4.65 (br s, 1H), 4.11 (br s, 2H), 3.12 (s, 3H), 2.46 (s, 3H), 2.37 (br t, J = 11.5 Hz, 2H), 1.93-2.16 (m, 4H), 1.81-1.92 (m, 2H). |
| 204 | LC-MS m/z 423.2 [M + H]$^+$, RT 0.80 min.; $^1$H NMR (DMSO-d$_6$) δ: 9.52 (br d, J = 9.8 Hz, 1H), 9.34-9.47 (m, 1H), 9.01 (br d, J = 10.7 Hz, 1H), 8.83 (s, 1H), 8.61 (s, 1H), 8.37 (br d, J = 11.0 Hz, 1H), 8.19 (s, 1H), 4.65 (br s, 1H), 4.11 (br s, 2H), 3.12 (s, 3H), 2.47-2.53 (s, 3H, obscured by DMSO-d$_6$), 2.34 (br t, J = 11.5 Hz, 2H), 1.94-2.12 (m, 4H), 1.80-1.91 (m, 2H). |
| 205 | LC-MS m/z 423.2 [M + H]$^+$, RT 0.87 min.; $^1$H NMR (DMSO-d$_6$) δ: 9.82 (br d, J = 8.8 Hz, 1H), 9.19 (br s, 1H), 8.80-8.91 (m, 2H), 8.73 (d, J = 2.8 Hz, 1H), 8.29 (d, J = 0.9 Hz, 1H), 7.74 (dd, J = 12.9, 1.3 Hz, 1H), 4.57-4.84 (m, 1H), 4.25 (s, 3H), 4.02-4.20 (m, 2H), 3.19 (s, 3H), 2.43 (br t, J = 11.7 Hz, 2H), 1.78-2.13 (m, 6H). |
| 206 | LC-MS m/z 430.2 [M + H]$^+$, RT 0.90 min.; $^1$H NMR (DMSO-d$_6$) δ: 9.63 (br d, J = 8.8 Hz, 1H), 9.08 (br d, J = 8.8 Hz, 1H), 8.84 (s, 1H), 8.78 (s, 2H), 8.71 (s, 1H), 8.56 (d, J = 1.6 Hz, 1H), 4.66 (br s, 1H), 4.28 (s, 3H), 4.12 (br s, 2H), 3.14 (s, 3H), 2.37 (br t, J = 11.5 Hz, 2H), 1.93-2.14 (m, 4H), 1.80-1.94 (m, 2H). |
| 211 | LC-MS m/z 409.2 [M + H]$^+$, RT 0.83 min.; $^1$H NMR (DMSO-d$_6$) δ: 8.87-9.23 (m, 2H), 8.70-8.87 (m, 2H), 8.63-8.69 (m, 1H), 8.61 (br s, 1H), 8.24 (d, J = 0.9 Hz, 1H), 7.73 (d, J = 12.9 Hz, 1H), 4.19-4.32 (m, 4H), 4.06 (br s, 2H), 2.16-2.28 (m, 2H), 1.79-2.10 (m, 6H). |
| 212 | LC-MS m/z 409.3 [M + H]$^+$, RT 0.78 min.; $^1$H NMR (DMSO-d$_6$) δ: 9.44 (s, 1H), 9.13-9.31 (m, 2H), 8.90 (br d, J = 6.6 Hz, 1H), 8.75 (s, 1H), 8.54 (s, 1H), 8.41 (d, J = 1.0 Hz, 1H), 8.23 (s, 1H), 4.16-4.31 (m, 1H), 3.95-4.16 (m, 2H), 2.47-2.53 (s, 3H, obscured by DMSO-d$_6$), 2.13-2.29 (m, 2H), 1.77-2.09 (m, 6H). |
| 213 | LC-MS m/z 416.2 [M + H]$^+$, RT 0.87 min.; $^1$H NMR (DMSO-d$_6$) δ: 9.01-9.21 (m, 2H), 8.94 (br s, 1H), 8.69-8.85 (m, 3H), 8.62 (s, 1H), 8.54 (d, J = 1.3 Hz, 1H), 4.19-4.38 (m, 4H), 4.06 (br s, 2H), 2.15-2.29 (m, 2H), 1.79-2.09 (m, 6H). |
| 214 | LC-MS m/z 404.2 [M + H]$^+$, RT 0.88 min.; $^1$H NMR (DMSO-d$_6$) δ: 8.99 (br s, 2H), 8.79-8.82 (m, 2H), 8.77 (s, 1H), 8.71 (s, 1H), 8.58 (d, J = 1.0 Hz, 1H), 4.48 (br s, 1H), 4.28 (s, 3H), 3.33-3.45 (m, 2H), 3.02-3.18 (m, 5H), 2.08-2.24 (m, 2H), 1.87-1.99 (m, 2H). |
| 215 | LC-MS m/z 397.3 [M + H]$^+$, RT 0.77 min.; $^1$H NMR (DMSO-d$_6$) δ: 9.46 (s, 1H), 9.24-9.35 (m, 1H), 9.13-9.22 (m, 1H), 8.80 (s, 1H), 8.65 (s, 1H), 8.45 (br d, J = 12.0 Hz, 1H), 8.24 (s, 1H), 4.47 (br s, 1H), 3.32-3.43 (m, 2H), 3.09 (s, 5H), 2.52 (s, 3H), 2.13-2.32 (m, 2H), 1.84-2.00 (m, 2H). |
| 216 | LC-MS m/z 397.3 [M + H]$^+$, RT 0.84 min.; $^1$H NMR (DMSO-d$_6$) δ: 8.98-9.20 (m, J = 12.9 Hz, 2H), 8.79 (s, 1H), 8.76 (s, 1H), 8.67 (d, J = 2.5 Hz, 1H), 8.28 (d, J = 0.9 Hz, 1H), 7.77 (dd, J = 13.2, 0.9 Hz, 1H), 4.45 (br s, 1H), 4.24 (s, 3H), 3.33-3.49 (m, 2H), 3.01-3.21 (m, 5H), 2.08-2.28 (m, 2H), 1.85-2.02 (m, 2H). |
| 222 | LC-MS 446.4 m/z [M + H]$^+$, RT 0.91 min.; $^1$H NMR (DMSO-d$_6$) δ: 9.50 (d, J = 1.6 Hz, 1H), 8.67 (s, 1H), 8.52 (d, J = 1.6 Hz, 1H), 8.42-8.46 (m, 1H), 8.44 (s, 1H), 8.35-8.41 (m, 1H), 8.40 (br s, 1H), 7.96 (d, J = 0.9 Hz, 1H), 4.22 (br s, 1H), 2.40 (s, 3H), 1.95 (br s, 2H), 0.97-1.41 (m, 14H). |

| Cpd | Data |
|---|---|
| 223 | LC-MS m/z 417.3 [M + H]+, RT 0.90 min.; 1H NMR (DMSO-d6) δ: 9.70 (s, 1H), 9.51 (br d, J = 9.8 Hz, 1H), 9.23-9.45 (m, 1H), 9.03 (s, 1H), 8.77 (s, 1H), 8.71 (s, 1H), 8.12 (s, 1H), 5.44-5.61 (m, 1H), 4.13 (br s, 2H), 2.42-2.48 (m, 5H), 1.95-2.18 (m, 6H). |
| 232 | LC-MS m/z 439.3 [M + H]+, RT 0.87 min.; 1H NMR (DMSO-d6) δ: 9.12 (br d, J = 11.7 Hz, 1H), 8.81 (br s, 1H), 8.72 (s, 1H), 8.62 (br d, J = 2.2 Hz, 1H), 8.55 (s, 1H), 8.23 (d, J = 0.6 Hz, 1H), 8.15 (br d, J = 13.9 Hz, 1H), 7.75 (d, J = 13.6 Hz, 1H), 4.35 (br s, 1H), 4.23 (s, 3H), 2.18(br dd,J = 13.2, 3.2 Hz, 2H), 1.59 (brt, J = 12.6 Hz, 2H), 1.39-1.53 (m, 12H). |
| 233 | LC-MS m/z 446.3 [M + H]+, RT 0.89 min.; 1H NMR (DMSO-d6) δ: 8.93 (br s, 1H), 8.77 (d, J = 1.3 Hz, 1H), 8.65-8.74 (m, 2H), 8.48-8.63 (m, 3H), 7.99 (br s, 1H), 4.23-4.43 (m, 4H), 2.07-2.30 (m, 2H), 1.22-1.79 (m, 14H). |
| 234 | LC-MS m/z 439.3 [M + H]+, RT 0.81 min.; 1H NMR (DMSO-d6) δ: 9.09 (s, 2H), 8.67 (s, 1H), 8.51-8.64 (m, 1H), 8.40 (s, 1H), 7.97-8.23 (m, 1H), 7.84-7.96 (m, 1H), 7.74 (br d, J = 12.9 Hz, 1H), 4.32 (br s, 1H), 2.37 (s, 3H), 2.07-2.23 (m, 2H), 1.23-1.73 (m, 14H). |
| 238 | LC-MS m/z 444.4 [M + H]+, RT 0.91 min.; 1H NMR (CDCl3) δ: 8.86 (d, J = 0.6 Hz, 1H), 8.53 (d, J = 1.6 Hz, 1H), 8.43 (d, J = 1.6 Hz, 1H), 8.10 (s, 1H), 7.99 (d, J = 1.0 Hz, 1H), 4.64 (br s, 1H), 4.31 (s, 3H), 3.49 (br s, 2H), 3.16 (s, 3H), 2.48 (br s, 3H), 2.17-2.33 (m, 2H), 1.42-2.11 (m, 6H). |
| 239 | LC-MS m/z 437.4 [M + H]+, RT 0.89 min.; 1H NMR (CDCl3) δ: 8.82 (d, J = 0.9 Hz, 1H), 8.65 (d, J = 1.3 Hz, 1H), 7.89 (d, J = 0.9 Hz, 1H), 7.41-7.50 (m, 2H), 4.83 (br s, 1H), 3.61 (br s, 2H), 3.21 (s, 3H), 2.59 (br s, 3H), 2.52 (s, 3H), 2.32(br s, 2H), 1.43-2.21 (m, 6H). |
| 240 | LC-MS m/z 444.5 [M + H]+, RT 0.91 min.; 1H NMR (CDCl3) δ: 9.02 (d, J = 1.6 Hz, 1H), 8.81 (d, J = 0.6 Hz, 1H), 8.16 (d, J = 1.6 Hz, 1H), 7.91 (d, J = 0.6 Hz, 1H), 7.52 (d, J = 0.9 Hz, 1H), 4.59 (br s, 1H), 3.45 (br s, 2H), 3.15 (s, 3H), 2.54 (s, 3H), 2.45 (br s, 3H), 2.14-2.35 (m, 2H), 1.66-2.03 (m, 6H). |
| 241 | LC-MS m/z 437.5 [M + H]+, RT 0.88 min.; 1H NMR (CDCl3) δ: 8.85 (d, J = 0.9 Hz, 1H), 8.06 (d, J = 1.3 Hz, 1H), 8.00 (d, J = 2.5 Hz, 1H), 7.97 (d, J = 0.9 Hz, 1H), 7.66 (dd, J = 12.6, 1.3 Hz, 1H), 4.63 (br s, 1H), 4.27 (s, 3H), 3.49 (br s, 2H), 3.15 (s, 3H), 2.48 (br s, 3H), 2.10-2.30 (m, 2H), 1.53-2.08 (m, 6H). |
| 244 | LC-MS m/z 430.5 [M + H]+, RT 0.90 min.; 1H NMR (DMSO-d6) δ: 8.76 (d, J = 1.6 Hz, 1H), 8.70 (s, 1H), 8.68 (d, J = 0.6 Hz, 1H), 8.58 (d, J = 1.6 Hz, 1H), 8.48 (s, 1H), 8.38 (br d, J = 1.0 Hz, 1H), 4.26 (s, 3H), 4.03-4.24 (m, 1H), 3.23-3.61 (m, 5H), 2.30-2.45 (m, 2H), 1.94-2.19 (m, 3H), 1.64-1.89 (m, 3H). |
| 245 | LC-MS m/z 430.4 [M + H]+, RT 0.90 min.; 1H NMR (DMSO-d6) δ: 9.50 (d, J = 1.9 Hz, 1H), 8.70 (s, 1H), 8.60 (br d, J = 5.4 Hz, 1H), 8.52 (d, J = 1.6 Hz, 1H), 8.46 (s, 1H), 7.97 (d, J = 0.6 Hz, 1H), 4.14-4.33 (m, 1H), 3.83 (br s, 2H), 3.32 (s, 3H), 2.58-2.71 (m, 2H), 2.36-2.45 (m, 3H), 2.13-2.28 (m, 3H), 1.84-2.07 (m, 3H). |
| 246 | LC-MS m/z 421.0 [M − H]−, RT 0.86 min.; 1H NMR (DMSO-d6) δ: 8.67 (d, J = 0.6 Hz, 1H), 8.55 (d, J = 2.8 Hz, 1H), 8.39-8.50 (m, 2H), 8.22 (d, J = 0.9 Hz, 1H), 7.78 (dd, J = 13.6, 1.3 Hz, 1H), 4.21 (s, 3H), 3.78 (br s, 1H), 3.27-3.36 (m, 5H), 2.53-2.72 (m, 2H), 2.08-2.34 (m, 3H), 1.75-2.06 (m, 3H). |
| 247 | LC-MS m/z 421.3 [M − H]−, RT 0.82 min.; 1H NMR (DMSO-d6) δ: 9.08 (d, J = 1.6 Hz, 1H), 8.68 (d, J = 0.6 Hz, 1H), 8.59 (br d, J = 5.7 Hz, 1H), 8.39 (d, J = 0.6 Hz, 1H), 7.88-7.90 (m, 1H), 7.74 (dd, J = 12.8, 1.4 Hz, 1H), 4.15-4.33 (m, 1H), 3.85 (br s, 2H), 3.32 (s, 3H), 2.64 (br s, 2H), 2.31-2.43 (m, 3H), 2.12-2.31 (m, 3H), 1.87-2.10 (m, 3H). |
| 251 | LC-MS m/z 444.4 [M + H]+, RT 0.86 min.; 1H NMR (DMSO-d6) δ: 9.71 (br d, J = 11.0 Hz, 1H), 9.65 (d, J = 1.6 Hz, 1H), 9.01 (br d, J = 10.7 Hz, 1H), 8.81 (d, J = 0.9 Hz, 1H), 8.76 (s, 1H), 8.61 (d, J = 0.6 Hz, 1H), 8.10 (s, 1H), 5.30 (br s, 1H), 3.75 (br s, 2H), 3.11 (s, 3H), 2.47-2.53 (m, 2H, obscured by DMSO-d6), 2.46 (d, J = 0.6 Hz, 3H), 1.72-2.15 (m, 8H). |
| 252 | LC-MS m/z 444.4 [M + H]+, RT 0.87 min.; 1H NMR (DMSO-d6) δ: 9.58 (br d, J = 11.0 Hz, 1H), 8.90-9.00 (m, 1H), 8.82 (s, 1H), 8.78 (d, J = 1.9 Hz, 1H), 8.76 (s, 1H), 8.68 (s, 1H), 8.58 (d, J = 1.6 Hz, 1H), 5.27 (br s, 1H), 4.28 (s, 3H), 3.76 (br s, 2H), 3.11 (s, 3H), 2.40-2.48 (m, 2H), 1.72-2.14 (m, 8H). |
| 253 | LC-MS m/z 437.4 [M + H]+, RT 0.83 min.; 1H NMR (DMSO-d6) δ: 9.82 (br d, J = 10.4 Hz, 1H), 9.08 (br d, J = 10.4 Hz, 1H), 8.84 (s, 1H), 8.75 (s, 1H), 8.68 (d, J = 2.8 Hz, 1H), 8.27 (d, J = 1.3 Hz, 1H), 7.75 (dd, J = 13.2, 1.3 Hz, 1H), 5.29 (br s, 1H), 4.24 (s, 3H), 3.75 (br s, 2H), 3.15 (s, 3H), 2.51-2.58 (m, 2H), 1.68-2.19 (m, 8H). |
| 260 | LC-MS m/z 419.4 [M + H]+, RT 0.73 min.; 1H NMR (DMSO-d6) δ: 9.76 (br d, J = 11.3 Hz, 1H), 9.59 (dd, J = 1.6, 0.9 Hz, 1H), 9.04 (br s, 1H), 8.84 (d, J = 0.9 Hz, 1H), 8.64 (d, J = 0.6 Hz, 1H), 8.55 (dd, J = 9.6, 1.7 Hz, 1H), 8.17 (s, 1H), 8.00 (d, J = 9.5 Hz, 1H), 4.92 (br s, 1H), 3.75 (br s, 2H), 3.12 (s, 3H), 2.52 (d, J = 1.3 Hz, 3H), 2.44-2.48 (m, 2H), 1.75-2.15 (m, 8H). |
| 261 | LC-MS m/z 433.5 [M + H]+, RT 0.75 min.; 1H NMR (DMSO-d6) δ: 9.85 (br d, J = 11.3 Hz, 1H), 9.43 (s, 1H), 9.09 (br d, J = 9.5 Hz, 1H), 8.82 (d, J = 0.6 Hz, 1H), 8.61 (s, 1H), 8.41 (s, 1H), 8.16 (d, J = 0.9 Hz, 1H), 5.32 (br s, 1H), 3.74 (br s, 2H), 3.12 (s, 3H), 2.67 (s, 3H), 2.51-2.57 (m, J = 0.9 Hz, 5H), 1.74-2.15 (m, 8H). |
| 262 | LC-MS m/z 419.5 [M + H]+, RT 0.76 min.; 1H NMR (DMSO-d6) δ: 9.71 (br d, J = 10.7 Hz, 1H), 9.00 (br d, J = 8.2 Hz, 1H), 8.86 (s, 1H), 8.76 (br s, 1H), 8.57 (s, 1H), 8.37-8.45 (m, 1H), 7.87 (dd, J = 9.1, 1.3 Hz, 1H), 7.77 (d, J = 9.1 Hz, 1H), 5.27 (br s, 1H), 4.22 (s, 3H), 3.76 (br s, 2H), 3.15 (s, 3H), 2.47-2.53 (m, 2H, obscured by DMSO-d6), 1.68-2.16 (m, 8H). |
| 263 | LC-MS m/z 433.5 [M + H]+, RT 0.79 min.; 1H NMR (DMSO-d6) δ: 10.10 (br d, J = 10.7 Hz, 1H), 9.29 (br d, J = 10.7 Hz, 1H), 8.91 (s, 1H), 8.83 (s, 1H), 8.61 (s, 1H), |

| Cpd | Data |
|---|---|
| | 8.27 (d, J = 0.9 Hz, 1H), 7.61 (s, 1H), 5.37 (br s, 1H), 4.23 (s, 3H), 3.74 (br s, 2H), 3.19 (s, 3H), 2.54-2.66 (m, 5H), 1.75-2.19 (m, 8H). |
| 264 | LC-MS m/z 449.5 [M + H]$^+$, RT 0.77 min.; $^1$H NMR (DMSO-d$_6$) δ: 9.66 (br d, J = 12.0 Hz, 1H), 8.97 (br d, J = 11.7 Hz, 1H), 8.85 (s, 1H), 8.82 (br s, 1H), 8.51 (s, 1H), 7.95 (d, J = 1.3 Hz, 1H), 7.27 (s, 1H), 5.30 (br s, 1H), 4.18 (s, 3H), 3.95-4.11 (m, 3H), 3.77 (br s, 2H), 3.15 (s, 3H), 2.47-2.53 (m, 2H, obscured by DMSO-d$_6$), 1.76-2.16 (m, 8H). |
| 266 | LC-MS m/z 460.5 [M + H]$^+$, RT 0.81 min.; $^1$H NMR (DMSO-d$_6$) δ: 10.29 (br d, J = 5.0 Hz, 1H), 9.68 (d, J = 1.6 Hz, 1H), 8.99 (br d, J = 6.9 Hz, 1H), 8.81 (s, 1H), 8.69-8.77 (m, 1H), 8.56 (s, 1H), 8.13 (d, J = 0.9 Hz, 1H), 4.26-4.45 (m, 1H), 2.69 (d, J = 5.4 Hz, 3H), 2.47 (d, J = 0.9 Hz, 3H), 2.22 (dd, J = 13.2, 3.5 Hz, 2H), 2.06 (br t, J = 12.8 Hz, 2H), 1.55 (s, 6H), 1.43 (s, 6H). |
| 267 | LC-MS m/z 453.5 [M + H]$^+$, RT 0.70 min.; $^1$H NMR (DMSO-d$_6$) δ: 10.42 (br d, J = 5.0 Hz, 1H), 9.48 (d, J = 1.3 Hz, 1H), 9.09 (br d, J = 6.9 Hz, 1H), 8.74 (d, J = 0.6 Hz, 1H), 8.53-8.63 (m, 1H), 8.43-8.51 (m, 1H), 8.17-8.37 (m, 1H), 4.26-4.47 (m, 1H), 2.68 (d, J = 5.0 Hz, 3H), 2.53 (d, J = 0.9 Hz, 3H), 2.22 (dd, J = 13.6, 3.5 Hz, 2H), 2.03-2.15 (m, 2H), 1.55 (s, 6H), 1.43 (s, 6H). |
| 268 | LC-MS m/z 460.6 [M + H]$^+$, RT 0.82 min.; $^1$H NMR (DMSO-d$_6$) δ: 10.21 (br d, J = 5.0 Hz, 1H), 9.18 (br s, 1H), 8.82 (s, 1H), 8.75-8.79 (m, 2H), 8.68 (s, 1H), 8.53 (d, J = 1.3 Hz, 1H), 4.37 (br s, 1H), 4.24-4.33 (m, 3H), 2.70 (d, J = 5.0 Hz, 3H), 2.24 (br dd, J = 13.4, 3.3 Hz, 2H), 2.00-2.12 (m, 2H), 1.54 (s, 6H), 1.43 (s, 6H). |
| 269 | LC-MS m/z 453.5; [M + H]$^+$, RT 0.78 min.; $^1$H NMR (DMSO-d$_6$) δ: 10.31 (br d, J = 4.7 Hz, 1H), 9.40 (br s, 1H), 8.71-8.79 (m, 3H), 8.28 (d, J = 1.3 Hz, 1H), 7.71 (dd, J = 12.9, 1.6 Hz, 1H), 4.39 (br s, 1H), 4.25 (s, 3H), 2.70 (d, J = 5.0 Hz, 3H), 2.24 (dd, J = 13.6, 3.5 Hz, 2H), 2.00-2.19 (m, 2H), 1.55 (s, 6H), 1.43 (s, 6H). |
| 270 | LC-MS m/z 458.5 [M + H]$^+$, RT 0.82 min.; $^1$H NMR (DMSO-d$_6$) δ: 9.49 (d, J = 1.9 Hz, 1H), 8.74 (s, 1H), 8.46-8.55 (m, 2H), 7.96 (d, J = 0.9 Hz, 1H), 5.04 (br s, 1H), 3.32 (br s, 5H), 3.08 (s, 3H), 2.95 (br s, 2H), 2.40 (d, J = 0.6 Hz, 3H), 1.44-2.32 (m, 8H). |
| 271 | LC-MS m/z 451.5 [M + H]$^+$, RT 0.71 min.; $^1$H NMR (CDCl$_3$) δ: 8.82 (d, J = 0.6 Hz, 1H), 8.65 (d, J = 1.3 Hz, 1H), 7.88 (d, J = 0.6 Hz, 1H), 7.40-7.50 (m, 2H), 5.31 (br s, 1H), 3.27 (br s, 2H), 3.13-3.22 (m, 3H), 2.75 (br s, 3H), 2.50 (d, J = 0.6 Hz, 3H), 2.03-2.33 (m, 4H), 1.45-1.97 (m, 6H). |
| 272 | LC-MS m/z 458.5 [M + H]$^+$, RT 0.83 min.; $^1$H NMR (CDCl$_3$) δ: 8.87 (d, J = 0.6 Hz, 1H), 8.53 (d, J = 1.6 Hz, 1H), 8.36-8.49 (m, 1H), 8.10 (s, 1H), 8.00 (d, J = 0.6 Hz, 1H), 5.26 (br s, 1H), 4.32 (s, 3H), 3.26 (br s, 2H), 3.19 (s, 3H), 2.74 (br s, 3H), 2.03-2.34 (m, 4H), 1.46-1.97 (m, 6H). |
| 273 | LC-MS m/z 451.5 [M + H]$^+$, RT 0.80 min.; $^1$H NMR (CDCl$_3$) δ: 8.86 (d, J = 0.6 Hz, 1H), 8.06 (d, J = 1.3 Hz, 1H), 8.00 (d, J = 2.5 Hz, 1H), 7.98 (d, J = 0.6 Hz, 1H), 7.66 (dd, J = 12.9, 1.3 Hz, 1H), 5.19 (br s, 1H), 4.27 (s, 3H), 3.09-3.26 (m, 5H), 2.70 (br s, 3H), 2.02-2.28 (m, 4H), 1.62-1.95 (m, 6H). |
| 285 | MS m/z [M + H]$^+$ 458.4; $^1$H NMR (DMSO-d$_6$) δ: 9.49 (d, J = 1.6 Hz, 1H), 8.73 (d, J = 0.6 Hz, 1H), 8.52 (d, J = 1.6 Hz, 1H), 8.49 (d, J = 0.6 Hz, 1H), 7.96 (d, J = 0.9 Hz, 1H), 4.41 (br s, 1H), 3.25-3.39 (m, 1H), 2.97-3.11 (m, 3H), 2.37-2.45 (m, 3H), 1.46-1.87 (m, 8H), 1.21 (s, 6H). |
| 286 | MS m/z [M + H]$^+$ 451.5; $^1$H NMR (DMSO-d$_6$) δ: 10.05-10.14 (m, 1H), 9.44-9.50 (m, 1H), 9.15-9.24 (m, 1H), 8.81-8.87 (m, 1H), 8.63 (s, 1H), 8.45 (br d, J = 12.0 Hz, 1H), 8.24 (s, 1H), 4.57-4.85 (m, 1H), 3.12-3.19 (m, 3H), 2.51-2.53 (m, 3H), 2.27-2.36 (m, 2H), 2.03-2.14 (m, 2H), 1.83-1.97 (m, 4H), 1.48 (s, 6H). |
| 287 | MS m/z [M + H]$^+$ 458.4; $^1$H NMR (DMSO-d$_6$) δ: 8.77 (d, J = 1.58 Hz, 1H), 8.74 (d, J = 0.63 Hz, 1H), 8.70 (s, 1H), 8.59 (d, J = 1.58 Hz, 1H), 8.55 (d, J = 0.63 Hz, 1H), 4.31-4.52 (m, 1H), 4.24-4.28 (m, 3H), 2.95-3.10 (m, 3H), 1.48-1.86 (m, 8H), 1.20 (s, 6H), NH proton not observed. |
| 296 | MS m/z [M + H]$^+$ 450.5; $^1$H NMR (DMSO-d$_6$) δ: 9.43-9.58 (m, 1H), 8.80 (d, 7 = 0.63 Hz, 3H), 8.54-8.61 (m, 1H), 8.41-8.49 (m, 1H), 4.61-4.88 (m, 1H), 3.03-3.19 (m, 3H), 2.81-2.99 (m, 3H), 2.48 (s, 3H), 2.06-2.18 (m, 2H), 1.82-1.92 (m, 2H), 1.44-1.60 (m, 12H). |
| 297 | MS m/z [M + H]$^+$ 449.5; $^1$H NMR (DMSO-d$_6$) δ: 9.38-9.53 (m, 1H), 8.71-8.87 (m, 2H), 8.57 (s, 1H), 8.34-8.48 (m, 2H), 8.22 (s, 1H), 4.61-4.81 (m, 1H), 3.10 (s, 3H), 2.93 (s, 3H), 2.44 (d, J = 0.95 Hz, 3H), 2.03-2.16 (m, 2H), 1.83-1.95 (m, 2H), 1.48-1.57 (m, 12H). |
| 298 | MS m/z [M + H]$^+$ 451.4; $^1$H NMR (DMSO-d$_6$) δ: 8.72 (d, J = 0.95 Hz, 1H), 8.55 (d, J = 2.84 Hz, 1H), 8.49 (d, J = 0.63 Hz, 1H), 8.24 (d, J = 0.95 Hz, 1H), 7.80 (dd, J = 13.87, 1.26 Hz, 1H), 4.32-4.54 (m, 1H), 4.21 (s, 3H), 3.04 (s, 3H), 1.50-1.88 (m, 8H), 1.22 (s, 6H), NH proton not observed. |
| 299 | MS m/z [M + H]$^+$ 447.5; $^1$H NMR (DMSO-d$_6$) δ: 8.98-9.03 (m, 1H), 8.72 (d, 7 = 0.63 Hz, 1H), 8.40 (s, 1H), 7.70-7.75 (m, 2H), 4.41 (br s, 1H), 2.52 (s, 3H), 3.03 (s, 3H), 2.34 (d, J = 1.00 Hz, 3H), 1.47-1.82 (m, 8H), 1.18 (s, 6H), NH proton not observed. |
| 300 | MS m/z [M + H]$^+$ 433.5; $^1$H NMR (MHz, DMSO-d$_6$) δ: 9.17 (dd, J = 1.89, 0.95 Hz, 1H), 8.73 (d, J = 0.63 Hz, 1H), 8.42 (d, J = 0.63 Hz, 1H), 7.85 (dd, J = 9.46, 1.89 Hz, 1H), 7.76 (s, 1H), 7.50 (d, J = 9.46 Hz, 1H), 4.37 (br s, 1H), 3.04 (s, 3H), 2.27-2.41 (m, 3H), 1.44-1.85 (m, 8H),1.18 (s, 6H), NH proton not observed. |
| 301 | MS m/z [M + H]$^+$ 459.4; $^1$H NMR (methanol-d$_4$) δ: 8.77 (s, 1H), 8.48 (d, 7 = 1.00 Hz, 1H), 8.41 (s, 1H), 8.29-8.38 (m, 1H), 4.90-5.04 (m, 1H), 3.16 (s, 3H), 2.75 (s, 3H), 2.01-2.41 (m, 8H), 1.57 (s, 6H), NH proton not observed. |
| 302 | MS m/z [M + H]$^+$ 441.4; $^1$H NMR (DMSO-d$_6$) δ: 9.36 (br d, J = 12.30 Hz, 1H), 8.62-8.81 (m, 2H), 8.48 (br s, 1H), 8.32 (br d, J = 11.98 Hz, 1H), 7.88 (s, 1H), 4.55-4.83 (m, |

| Cpd | Data |
|---|---|
| | 1H), 3.13 (s, 3H), 2.45 (br d, J = 1.26 Hz, 3H), 2.01-2.15 (m, 2H), 1.81-1.95 (m, 2H), 1.51 (d, J = 10.40 Hz, 12H). |
| 305 | MS m/z [M + H]⁺ 441.4; ¹H NMR (DMSO-d₆) δ: 8.63 (d, J = 0.63 Hz, 1H), 8.35 (d, J = 0.95 Hz, 1H), 8.18 (s, 1H), 6.90 (d, J = 1.26 Hz, 1H), 4.23-4.51 (m, 1H), 3.05 (s, 3H), 2.44 (d, J = 1.26 Hz, 3H), 1.40-1.72 (m, 4H), 1.27 (br s, 6H), 1.12 (br s, 6H), NH proton not observed. |
| 308 | MS m/z [M + H]⁺ 442.5; ¹H NMR (DMSO-d₆) δ: 9.45 (br d, J = 12.30 Hz, 1H), 8.79-8.98 (m, 1H), 8.73 (s, 2H), 8.40 (br d, J = 11.35 Hz, 1H), 4.60-4.80 (m, 1H), 3.12 (s, 3H), 2.77 (s, 3H), 2.01-2.19 (m, 2H), 1.81-1.94 (m, 2H), 1.52 (br d, J = 6.62 Hz, 12H). |
| 322 | MS m/z [M + H]⁺ 448.5; ¹H NMR (DMSO-d₆) δ: 8.69 (s, 1H), 8.56 (s, 1H), 8.41 (s, 1H), 8.28 (s, 1H), 4.27-4.50 (m, 1H), 3.03 (s, 3H), 2.75 (s, 3H), 2.37 (s, 3H), 1.43-1.80 (m, 8H), 1.18 (s, 6H), NH proton not observed. |
| 325 | MS m/z [M + H]⁺ 478.2; ¹H NMR (methanol-d₄) δ: 9.70 (d, J = 1.5 Hz, 1H), 9.10 (d, J = 1.5 Hz, 1H), 8.94 (s, 1H), 8.64 (s, 1H), 8.26 (d, J = 1.2 Hz, 1H), 5.37-5.51 (m, 1H), 5.05 (d, J = 48.5 Hz, 1H), 3.33 (s, 3H), 2.66 (s, 3H), 2.49 (t, J = 13.4 Hz, 1H), 2.10 (dd, J = 13.4, 3.7 Hz, 1H), 1.75 (d, J = 0.9 Hz, 3H), 1.71 (s, 3H), 1.63 (s, 3H), 1.59 (d, J = 2.1 Hz, 3H); 1 NH not observed. |
| 326 | MS m/z [M + H]⁺ 469.2; ¹H NMR (methanol-d₄) δ: 9.30 (d, J = 0.9 Hz, 1H), 8.92 (s, 1H), 8.57 (s, 1H), 8.49 (dd, J = 11.3, 0.9 Hz, 1H), 8.19 (d, J = 0.6 Hz, 1H), 5.17-5.30 (m, 1H), 5.02-5.14 (m, 1H), 3.31 (d, J = 1.5 Hz, 3H), 2.64 (d, J = 0.6 Hz, 3H), 2.50 (br t, J = 13.3 Hz, 1H), 2.33-2.42 (m, 2H), 2.15 (br dd, J = 13.6, 5.6 Hz, 2H), 2.05 (s, 1H), 1.65 (s, 3H), 1.63 (s, 3H); 1NH not observed. |
| 377 | MS m/z [M + H]⁺ 432.4; ¹H NMR (DMSO-d₆) δ: 8.77 (s, 1H), 8.74 (s, 1H), 8.69 (s, 1H), 8.60 (s, 1H), 8.55 (s, 1H), 4.26 (s, 3H), 4.00-4.16 (m, 1H), 3.07 (s, 3H), 2.84-2.95 (m, 1H), 1.97-2.27 (m, 5H), 1.79-1.95 (m, 1H), 1.65-1.79 (m, 2H), 1.49-1.63 (m, 1H), 1.06 (d, J = 6.1 Hz, 3H). |
| 378 | MS m/z [M + H]⁺ 425.4; ¹H NMR (DMSO-d₆) δ: 8.72 (s, 1H), 8.54 (d, 7 = 1.8 Hz, 1H), 8.47 (s, 1H), 8.23 (s, 1H), 7.80 (d, J = 13.7 Hz, 1H), 4.21 (s, 3H), 3.96-4.14 (m, 1H), 3.05 (s, 3H), 2.84-2.93 (m, 1H), 2.09-2.24 (m, 4H), 1.97-2.08 (m, 1H), 1.80-1.93 (m, 1H), 1.65-1.76 (m, 2H), 1.48-1.62 (m, 1H), 1.05 (d, J = 6.1 Hz, 3H). |
| 379 | MS m/z [M + H]⁺ 432.4; ¹H NMR (DMSO-d₆) δ: 9.50 (d, J = 1.5 Hz, 1H), 8.74 (s, 1H), 8.53 (d, J = 1.5 Hz, 1H), 8.50 (s, 1H), 7.96 (s, 1H), 3.98-4.21 (m, 1H), 3.07 (s, 3H), 2.84-2.99 (m, 1H), 2.40 (s, 3H), 1.47-2.31 (m, 9H), 1.08 (br d, J = 5.2 Hz, 3H). |
| 380 | MS m/z [M + H]⁺ 425.4; ¹H NMR (methanol-d₄) δ: 9.21 (s, 1H), 8.78 (s, 1H), 8.37-8.45 (m, 2H), 8.10 (br s, 1H), 4.63-4.74 (m, 1H), 3.66-3.75 (m, 1H), 3.23-3.61 (m, 2H), 3.14-3.22 (m, 3H), 2.96 (s, 3H), 2.59 (s, 3H), 2.00-2.37 (m, 4H), 1.48 (d, J = 6.1 Hz, 3H). |

Example 28

Preparation of Compound 137

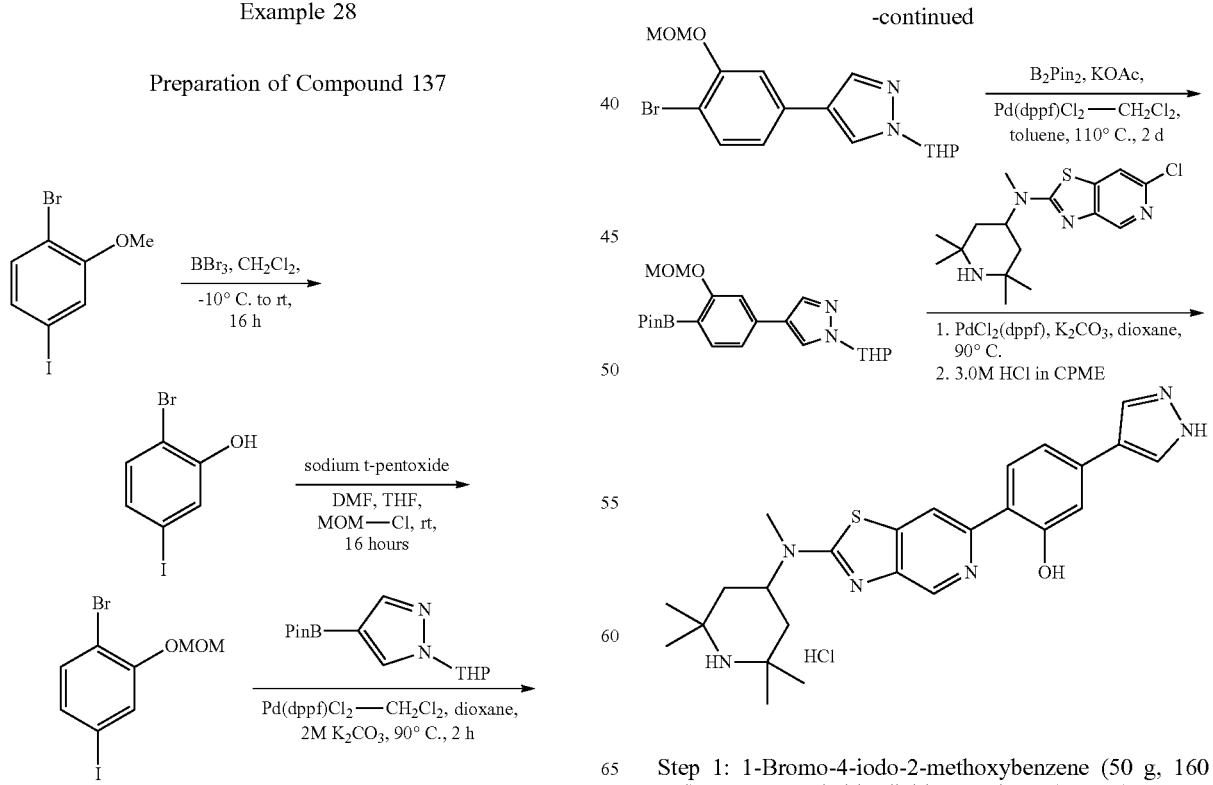

Step 1: 1-Bromo-4-iodo-2-methoxybenzene (50 g, 160 mmol) was suspended in dichloromethane (75 mL) at −10° C. Boron tribromide (250 mL, 250 mmol, 1M in CH₂Cl₂,)

was cannulated in over minutes, with the internal temperature remaining below 0° C. throughout the addition. After the addition, the mixture was stirred at 0° C. for 1 h, and then at room temperature for 16 h. The mixture was cooled in an ice bath and 10% aqueous $Na_2CO_3$ (250 mL) was added in portions. The mixture was then partitioned between $H_2O$ and dichloromethane. The dichloromethane layer was dried over $MgSO_4$ and then filtered. 2-Bromo-5-iodophenol (46 g, 96%) was obtained from the filtrate as a pinkish-white solid.

$^1$H NMR (acetone-$d_6$) δ: 9.24 (br s, 1H), 7.38 (d, J=2 Hz, 1H), 7.31 (d, J=8.5 Hz, 1H), 7.17 (dd, J=8.5 Hz, 2 Hz, 1H).

Step 2: 2-Bromo-5-iodophenol (54.9 g, 184 mmol), was dissolved in DMF (240 mL) at 0° C. Sodium tert-pentoxide (2.5 M in THF, 90 mL, 230 mmol) was then added dropwise. The reaction was stirred at 0° C. for 15 min after the addition was complete. Chloromethyl methyl ether (18 mL, 225 mmol) was added dropwise over 30 min. The mixture was warmed to ambient temperature and was stirred for 16 h. The mixture was diluted with 1.5 L of $H_2O$ and was extracted into EtOAc (2×400 mL). The combined organic layers were washed with $H_2O$ (300 mL), and then with brine. The organic layer was dried over $MgSO_4$, filtered, and concentrated under vacuum. The crude product was flushed through a silica plug using $CH_2Cl_2$ in hexanes (0-10%) to yield 1-bromo-4-iodo-2-(methoxymethoxy)benzene (61 g, 97%) as a clear liquid.

$^1$H NMR (acetone-$d_6$) δ: 7.56 (d, J=2 Hz, 1H), 7.38 (d, J=8 Hz, 1H), 7.33 (dd, J=8 Hz, 2 Hz, 1H), 5.35 (s, 2H), 3.50 (s, 3H).

Step 3: 1-Bromo-4-iodo-2-(methoxymethoxy)benzene (49 g, 143 mmol), 1-(tetrahydro-2H-pyran-2-yl)-4-(4,4,5,5-tetramethyl-1,3,2-dioxaborolan-2-yl)-1H-pyrazole (48.4 g, 174 mmol), $PdCl_2$(dppf)-dichloromethane adduct (3.1 g, 3.6 mmol), dioxane (500 mL), and aqueous $K_2CO_3$ (350 mL, 350 mmol, 1M) were heated at 90° C. for 2 h. The reaction mixture was then partitioned between $H_2O$ and EtOAc. The organic layer was dried over $MgSO_4$, filtered, and concentrated under vacuum. Purification by silica gel chromatography (EtOAc in hexanes, 20-50%), followed by trituration with hexanes, yielded 4-(4-bromo-3-(methoxymethoxy)phenyl)-1-(tetrahydro-2H-pyran-2-yl)-1H-pyrazole (40.4 g, 77%) as an off-white solid.

$^1$H NMR (acetone-$d_6$) δ: 8.22 (s, 1H), 7.88 (s, 1H), 7.55 (d, J=8.5 Hz, 1H), 7.47 (d, J=2 Hz, 1H), 7.23 (dd, J=8.5 Hz, 2 Hz, 1H), 5.44 (dd, J=9.5 Hz, 2.5 Hz, 1H), 5.38 (S, 2H), 4.01 (m, 1H), 3.72 (m, 1H), 3.51 (s, 3H), 2.1-2.23 (m, 1H), 2.0-2.1 (m, 2H), 1.7-1.8 (m, 1H), 1.6-1.7 (m, 2H).

Step 4: Potassium acetate (22 g, 224 mmol) was pumped dry at 180° C. for 2 h, and then the flask was filled with argon. 4-(4-bromo-3-(methoxymethoxy)phenyl)-1-(tetrahydro-2H-pyran-2-yl)-1H-pyrazole (20 g, 54.5 mmol), Pd $Cl_2$(dppf)-dichloromethane adduct (1.22 g, 1.47 mmol), bis(pinacolato)diboron (20.8 g, 81.9 mmol), and dry toluene (200 mL) was added. This mixture was heated at 110° C. for 2 days. The mixture was filtered through Celite, eluting with ether. The filtrate was concentrated under vacuum, re-dissolved in ether, and was filtered again through Celite to remove solid impurities. Purification by silica gel chromatography (EtOAc in hexanes, 20-50%) yielded crude product (12 g) that mostly free of protodeboronated by-product. This was dissolved in ether (100 mL) and washed with aqueous $NaHCO_3$ (2×1.5 L), brine, dried over $MgSO_4$, and then filtered. The filtrate was concentrated to provide pure product (7.05 g, 32%) as a glassy semi-solid.

$^1$H NMR (acetone-$d_6$): δ: 8.24 (s, 1H), 7.90 (s, 1H), 7.65 (d, J=8 Hz, 1H), 7.33 (d, J=1.5 Hz, 1H), 7.29 (dd, J=8 Hz, 1.5 Hz, 1H), 5.45 (dd, J=10 Hz, 2.5 Hz, 1H), 5.25 (s, 2H), 4.01 (m, 1H), 3.69-3.74 (m, 1H), 3.52 (s, 3H), 2.15-2.2 (m, 1H), 2.0-2.1 (m, 2H), 1.7-1.8 (m, 1H), 1.6-1.68 (m, 2H), 1.35 (s, 12H).

Step 5: To a mixture of 6-chloro-N-methyl-N-(2,2,6,6-tetramethyl-4-piperidyl)thiazolo[4,5-c]pyridin-2-amine (169 mg, 0.50 mmol), 3-[3-(methoxymethoxy)-4-(4,4,5,5-tetramethyl-1,3,2-dioxaborolan-2-yl)phenyl]-1-tetrahydro-pyran-2-yl-pyrazole (249 mg, 0.60 mmol), $PdCl_2$(dppf) (50 mg, 0.06 mmol) in 1,4-dioxane (2.0 mL), under argon was added $K_2CO_3$ (0.63 mL, 1.3 mmol, 2.0 M). The mixture was stirred at 90° C. for 2 h, cooled, and then diluted with EtOAc. The precipitate was removed by filtration. The filtrate was concentrated and chromatographed (MeOH in $CH_2Cl_2$, 0-20%) to provide the coupling product, which was treated with HCl (5 mL, 3 M in CPME) at room temperature overnight. The precipitate was collected by filtration and dried to provide 2-[2-[methyl-(2,2,6,6-tetramethyl-4-piperidyl)amino]thiazolo[4,5-c]pyridin-6-yl]-5-(1H-pyrazol-3-yl)phenol hydrochloride (102 mg, 41%).

LC-MS 463.2 m/z [M+H]$^+$, RT 0.95 min; $^1$H NMR (DMSO-$d_6$) δ: 9.50 (br d, J=11.3 Hz, 1H), 8.73-8.88 (m, 2H), 8.44 (br d, J=12.0 Hz, 1H), 8.13 (s, 2H), 7.78 (br d, J=8.5 Hz, 1H), 7.21-7.31 (m, 2H), 4.65 (br s, 1H), 3.13 (s, 3H), 2.12 (br t, J=12.8 Hz, 2H), 1.83-1.94 (m, 2H), 1.42-1.60 (m, 12H).

Example 29

Preparation of Compound 128

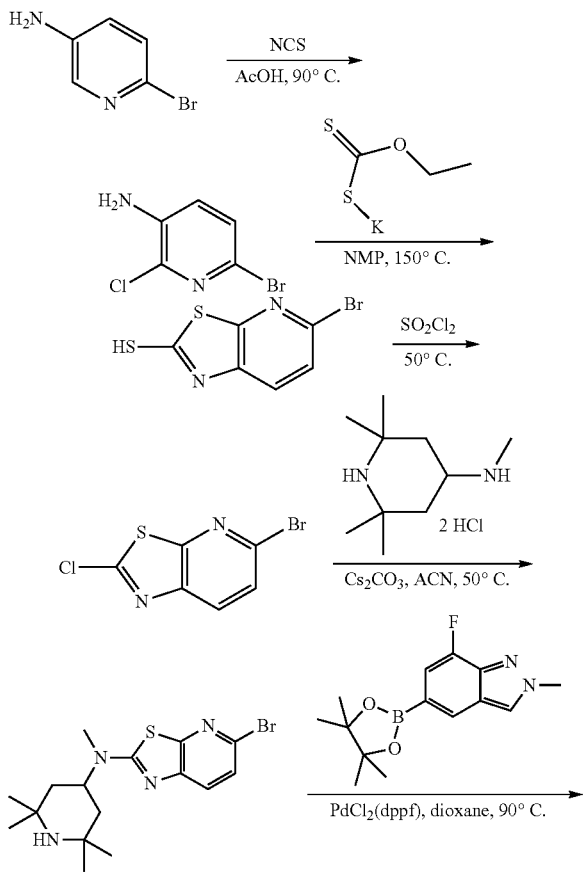

-continued

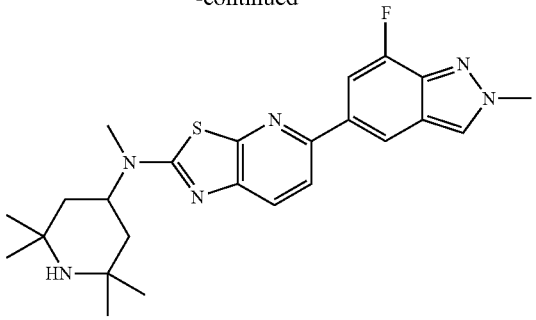

Step 1: A mixture of 6-bromopyridin-3-amine (11.7 g, 67.6 mmol), 1-chloropyrrolidine-2,5-dione (9.93 g, 74.4 mmol) and acetic acid (70 mL) was stirred at 90° C. for 2 h. The solvent was removed on a rotovap and the residue was washed with water and dried to provide 6-bromo-2-chloro-pyridin-3-amine (13.1 g, 93.4%). LC-MS m/z 207.1, 209.1 [M+H]$^+$, RT: 1.12 min.

Step 2: A mixture of 6-bromo-2-chloro-pyridin-3-amine (13.1 g, 63.1 mmol), ethylxanthic acid potassium salt (15.2 g, 94.8 mmol), and NMP (60 mL) was stirred at 150° C. for 6 h. LC/MS showed the disappearance of the starting pyridine. The reaction was then cooled to room temperature and acetic acid (10 mL) was added and then diluted with water (500 mL). The precipitate was collected by filtration, washed with water, dried and used directly in the next step.

Step 3: The above material was treated with sulfuryl chloride (20 mL, 247.9 mmol) and heated at 50° C. overnight and the mixture was then added to an ice and NaHCO$_3$/CH$_2$Cl$_2$ (~0.5 L). The precipitate was removed by filtration and the filtrate was concentrated. The residue was chromatographed (silica gel, ethyl acetate in hexanes, 0-40%) to provide 5-bromo-2-chlorothiazolo[5,4-b]pyridine (3.94 g, 63.5%). LC-MS m/z 251.0 [M+H]$^+$, RT: 1.44 min.

Step 4: A mixture of 6-bromo-2-chloro-thiazolo[4,5-c] pyridine (3.94 g, 15.8 mmol), N,2,2,6,6-pentamethylpiperidin-4-amine (2.82 g, 16.6 mmol), Cs$_2$CO$_3$ (12.9 g, 39.6 mmol) and acetonitrile (32 mL) was heated at 50° C. for 24 h. The reaction mixture was then diluted with ethyl acetate and filtered. The filtrate was concentrated and the residue was chromatographed (silica gel, MeOH in CH$_2$Cl$_2$ 0-20%) to provide 5-bromo-N-methyl-N-(2,2,6,6-tetramethyl-4-piperidyl)thiazolo[5,4-b]pyridin-2-amine (5.41 g, 89.4%) as an off white powder. LC-MS m/z 383.2, 385.1 [M+H]$^+$, RT: 1.02 min.

Step 5: To a mixture of 5-bromo-N-methyl-N-(2,2,6,6-tetramethyl-4-piperidyl)thiazolo[5,4-b]pyridin-2-amine (95.8 mg, 0.25 mmol), 7-fluoro-2-methyl-5-(4,4,5,5-tetramethyl-1,3,2-dioxaborolan-2-yl)indazole (82.8 mg, 0.30 mmol), and PdCl$_2$(dppf) (21 mg, 0.025 mmol) in 1,4-dioxane (1.0 mL), under an argon atmosphere, was added K$_2$CO$_3$ (0.31 mL, 0.62 mmol, 2.0 M). The mixture was heated at 90° C. for 2 h and then cooled and diluted with ethyl acetate. The precipitate was removed by filtration and the filtrate was concentrated and chromatographed (silica gel, MeOH in CH$_2$Cl$_2$, 0-20%) to provide, after trituration with ethyl ether, 5-(7-fluoro-2-methyl-indazol-5-yl)-N-methyl-N-(2,2,6,6-tetramethyl-4-piperidyl)thiazolo[5,4-b] pyridin-2-amine (65 mg, 57.5%).

LC-MS m/z 453.3 [M+H]$^+$, RT 1.04 min.; $^1$H NMR (CDCl$_3$) δ: 8.04 (d, J=0.9 Hz, 1H), 7.99 (d, J=2.5 Hz, 1H), 7.64-7.77 (m, 2H), 7.27 (s, 1H), 4.46 (br s, 1H), 4.26 (s, 3H), 3.12 (s, 3H), 1.82 (dd, J=12.5, 3.3 Hz, 2H), 1.16-1.60 (m, 14H).

Using the procedure described for Example 29, above, additional compounds described herein were prepared by substituting the appropriate starting material, suitable reagents and reaction conditions, obtaining compounds such as those selected from:

| Cpd | Data |
|---|---|
| 25 | MS m/z 435.0 [M + H]$^+$; $^1$H NMR (DMSO-d$_6$): δ: 8.42 (s, 1H), 8.39 (s, 1H), 7.99 (dd, J = 9 Hz, 1.5 Hz, 1H), 7.91 (d, J = 9 Hz, 1H), 7.79 (d, J = 8 Hz, 1H), 7.65 (d, J = 9 Hz, 1H), 4.37 (br s, 1H), 4.19 (s, 3H), 3.04 (s, 3H), 1.61-1.96 (m, 2H), 1.47-1.53 (m, 2H), 1.25 (s, 6H), 1.11 (s, 6H). |
| 26 | MS m/z 378.9 [M + H]$^+$; $^1$H NMR (DMSO-d$_6$): δ: 8.85-9.00 (m, 2H), 8.44 (s, 1H), 8.40 (s, 1H), 7.99 (dd, J = 9 Hz, 1.5 Hz, 1H), 7.93 (d, J = 8.5 Hz, 1H), 7.81 (d, J = 8.5 Hz, 1H), 7.67 (d, J = 8 Hz, 1H), 4.40-4.48 (m, 1H), 4.19 (s, 3H), 3.37-3.42 (m, 2H), 3.10-3.18 (m, 2H), 3.07 (s, 3H), 2.08-2.20 (m, 2H), 1.90-1.95 (m, 2H). |
| 36 | MS m/z 393.3 [M + H]$^+$; $^1$H NMR (DMSO-d$_6$): δ: 8.97-9.12 (m, 2), 8.40 (s, 1H), 8.20 (s, 1H), 7.92 (d, J = 9 Hz, 1H), 7.80 (d, J = 8.5 Hz, 1H), 7.78 (s, 1H), 4.44-4.53 (m, 1H), 4.20 (s, 3H), 3.35-3.45 (m, 2H), 3.10-3.18 (m, 2H), 3.08 (s, 3H), 2.64 (s, 3H), 2.12-2.21 (m, 2H), 1.90-1.95 (m, 2H). |
| 129 | LC-MS m/z 435.3 [M + H]$^+$, RT 0.82 min.; $^1$H NMR (CDCl$_3$) δ: 8.73-8.83 (m, 1H), 7.75 (d, J = 8.5 Hz, 1H), 7.71 (dd, J = 9.5, 1.6 Hz, 1H), 7.60 (d, J = 8.5 Hz, 1H), 7.56 (d, J = 9.1 Hz, 1H), 7.39 (s, 1H), 4.52 (br s, 1H), 3.12 (s, 3H), 2.47 (d, J = 0.6 Hz, 3H), 1.82 (dd, J = 12.5, 3.3 Hz, 2H), 1.28-1.73 (m, 14H). |
| 148 | LC-MS m/z 460.3 [M + H]$^+$, RT 1.04 min.; $^1$H NMR (DMSO-d$_6$) δ: 8.79 (d, J = 1.3 Hz, 1H), 8.69 (s, 1H), 8.59 (d, J = 1.6 Hz, 1H), 8.02 (d, J = 8.5 Hz, 1H), 7.82 (d, J = 8.5 Hz, 1H), 4.43 (br s, 1H), 4.26 (s, 3H), 3.07 (s, 3H), 0.99-1.80 (m, 16H). |
| 149 | LC-MS m/z 463.3 [M + H]$^+$, RT 1.02 min.; $^1$H NMR (DMSO-d$_6$) δ: 9.59 (br d, J = 11.3 Hz, 1H), 8.47 (br d, J = 11.7 Hz, 1H), 8.20 (s, 2H), 8.11 (d, J = 8.8 Hz, 1H), 7.93 (d, J = 8.8 Hz, 2H), 7.13-7.27 (m, 2H), 4.61 (br s, 1H), 3.08 (s, 3H), 2.12 (br t, J = 12.9 Hz, 2H), 1.85 (br dd, J = 12.8, 3.0 Hz, 2H), 1.42-1.65 (m, 12H). |
| 177 | LC-MS m/z 453.2 [M + H]$^+$, RT 0.87 min.; $^1$H NMR (DMSO-d$_6$) δ: 9.09 (d, J = 1.6 Hz, 1H), 7.85-7.92 (m, 2H), 7.81 (d, J = 8.5 Hz, 1H), 7.76 (dd, J = 12.9, 1.3 Hz, 1H), 4.36 (br s, 1H), 3.05 (s, 3H), 2.36 (d, J = 0.6 Hz, 3H), 1.62 (br dd, J = 11.8, 3.0 Hz, 2H), 1.47 (br t, J = 12.1 Hz, 2H), 1.23 (s, 6H), 1.09 (s, 6H). |
| 178 | LC-MS m/z 460.2 [M + H]$^+$, RT 0.98 min.; $^1$H NMR (DMSO-d$_6$) δ: 9.48 (d, J = 1.6 Hz, 1H), 8.53 (d, J = 1.9 Hz, 1H), 7.91-7.97 (m, 2H), 7.82 (d, J = 8.5 Hz, 1H), 4.12-4.65 (m, 1H), 3.05 (s, 3H), 2.36-2.42 (m, 3H), 0.95-1.78 (m, 16H). |
| 276 | LC-MS m/z 430.4 [M + H]$^+$, RT 0.84 min.; $^1$H NMR (DMSO-d$_6$) δ: 9.61 (d, J = 1.6 Hz, 1H), 9.42 (br d, J = 10.4 Hz, 1H), 8.93-9.02 (m, 1H), 8.74 (s, 1H), 8.06 (s, 1H), 8.03 (d, J = 8.5 Hz, 1H), 7.91 (d, J = 8.5 Hz, 1H), 4.67 (br s, 1H), 4.12 (br s, 2H), 3.10 (s, |

-continued

| Cpd | Data |
|---|---|
| | 3H), 2.45 (d, J = 0.9 Hz, 3H), 2.28-2.37 (m, 2H), 1.94-2.14 (m, 4H), 1.82-1.91 (m, 2H). |
| 277 | LC-MS m/z 423.4 [M + H]⁺, RT 0.74 min.; ¹H NMR (DMSO-d₆) δ: 9.68 (br d, J = 10.1 Hz, 1H), 9.46 (s, 1H), 9.11 (br d, J = 8.8 Hz, 1H), 8.46 (br d, J = 12.0 Hz, 1H), 8.22 (s, 1H), 8.05 (d, J = 8.5 Hz, 1H), 7.94 (d, J = 8.5 Hz, 1H), 4.68 (br s, 1H), 4.11 (br s, 2H), 3.13 (s, 3H), 2.51 (d, J = 0.9 Hz, 3H), 2.34-2.43 (m, 2H), 2.04-2.13 (m, 2H), 1.92-2.01 (m, 2H), 1.80-1.90 (m, 2H). |
| 278 | LC-MS m/z 430.4 [M + H]⁺, RT 0.89 min.; ¹H NMR (DMSO-d₆) δ: 9.28 (br d, J = 10.4 Hz, 1H), 8.91 (br d, J = 12.3 Hz, 1H), 8.80 (d, J = 1.6 Hz, 1H), 8.70 (s, 1H), 8.59 (d, J = 1.6 Hz, 1H), 8.04 (d, J = 8.5 Hz, 1H), 7.86 (d, J = 8.5 Hz, 1H), 4.65 (br s, 1H), 4.21-4.33 (m, 3H), 4.12 (br s, 2H), 3.09 (s, 3H), 2.22-2.34 (m, 2H), 1.94-2.13 (m, 4H), 1.79-1.92 (m, 2H). |
| 279 | LC-MS m/z 444.4 [M + H]⁺, RT 0.87 min.; ¹H NMR (DMSO-d₆) δ: 9.57-9.70 (m, 2H), 8.97 (br d, J = 11.0 Hz, 1H), 8.79 (s, 1H), 8.08 (d, J = 0.6 Hz, 1H), 8.03 (d, J = 8.5 Hz, 1H), 7.92 (d, J = 8.5 Hz, 1H), 5.33 (br s, 1H), 3.75 (br s, 2H), 3.09 (s, 3H), 2.39-2.48 (m, 5H), 1.72-2.13 (m, 8H). |
| 280 | LC-MS m/z 437.5 [M + H]⁺, RT 0.76 min.; ¹H NMR (DMSO-d₆) δ: 9.87 (br d, J = 10.1 Hz, 1H), 9.48 (d, J = 0.9 Hz, 1H), 9.11 (br d, J = 10.7 Hz, 1H), 8.49 (br d, J = 12.0 Hz, 1H), 8.23 (d, J = 0.9 Hz, 1H), 8.05 (d, J = 8.5 Hz, 1H), 7.94 (d, J = 8.5 Hz, 1H), 5.34 (br s, 1H), 3.74 (br s, 2H), 3.11 (s, 3H), 2.51-2.58 (m, 5H), 1.72-2.18 (m, 8H). |
| 281 | LC-MS m/z 444.5 [M + H]⁺, RT 0.92 min.; ¹H NMR (DMSO-d₆) δ: 9.26 (br d, J = 11.0 Hz, 1H), 8.77-8.88 (m, 2H), 8.70 (s, 1H), 8.60 (d, J = 1.6 Hz, 1H), 8.04 (d, J = 8.5 Hz, 1H), 7.86 (d, J = 8.5 Hz, 1H), 5.29 (br s, 1H), 4.27 (s, 3H), 3.77 (br s, 2H), 3.07 (s, 3H), 2.33-2.45 (m, 2H), 1.72-2.11 (m, 8H). |
| 291 | MS m/z [M + H]⁺ 458.4; ¹H NMR (DMSO-d₆) δ: 9.47 (d, J = 1.58 Hz, 1H), 8.53 (d, J = 1.58 Hz, 1H), 7.89-8.00 (m, 2H), 7.83 (d, J = 8.51 Hz, 1H), 4.26-4.60 (m, 1H), 3.03 (s, 3H), 2.40 (d, J = 0.63 Hz, 3H), 1.47-1.87 (m, 8H), 1.20 (s, 6H), NH proton not observed. |
| 292 | MS m/z [M + H]⁺ 451.6; ¹H NMR (DMSO-d₆) δ: 9.10 (d, J = 1.58 Hz, 1H), 7.90-7.95 (m, 1H), 7.89 (dd, J = 3.15, 0.95 Hz, 1H), 7.86 (d, J = 8.51 Hz, 1H), 7.77 (dd, J = 12.77, 1.42 Hz, 1H), 4.58-4.76 (m, 1H), 3.09 (s, 3H), 2.37 (d, J = 1.00 Hz, 3H), 1.78-2.21 (m, 8H), 1.43 (br s, 6H), NH proton not observed. |
| 293 | MS m/z [M + H]⁺ 458.5; ¹H NMR (DMSO-d₆) δ: 8.78 (d, J = 1.00 Hz, 1H), 8.69 (s, 1H), 8.59 (d, J = 1.58 Hz, 1H), 8.01 (d, J = 8.51 Hz, 1H), 7.77-7.87 (m, J = 8.51 Hz, 1H), 4.34-4.59 (m, 1H), 4.26 (s, 3H), 3.04 (s, 3H), 1.45-1.96 (m, 8H), 1.22 (br s, 6H), NH proton not observed. |
| 294 | MS m/z [M + H]⁺ 451.4; ¹H NMR (DMSO-d₆) δ: 8.55 (d, J = 2.52 Hz, 1H), 8.25 (s, 1H), 7.95 (d, J = 8.51 Hz, 1H), 7.73-7.82 (m, 2H), 4.50 (br s, 1H), 4.21 (s, 3H), 3.05 (s, 3H), 1.55-2.06 (m, 8H), 1.17-1.44 (m, 6H), NH proton not observed. |
| 295 | MS m/z [M + H]⁺ 437.5; ¹H NMR (DMSO-d₆) δ: 9.47 (br d, J = 11.03 Hz, 1H), 8.91 (br d, J = 11.67 Hz, 1H), 8.55 (d, J = 2.52 Hz, 1H), 8.26 (d, J = 0.95 Hz, 1H), 7.97 (d, J = 8.51 Hz, 1H), 7.83 (d, J = 8.51 Hz, 1H), 7.78 (dd, J = 13.56, 1.26 Hz, 1H), 5.27 (br s, 1H), 4.22 (s, 3H), 3.76 (br s, 2H), 3.08 (s, 3H), 2.39-2.47 (m, 2H), 1.73-2.13 (m, 8H). |

Example 30

Preparation of Compound 59

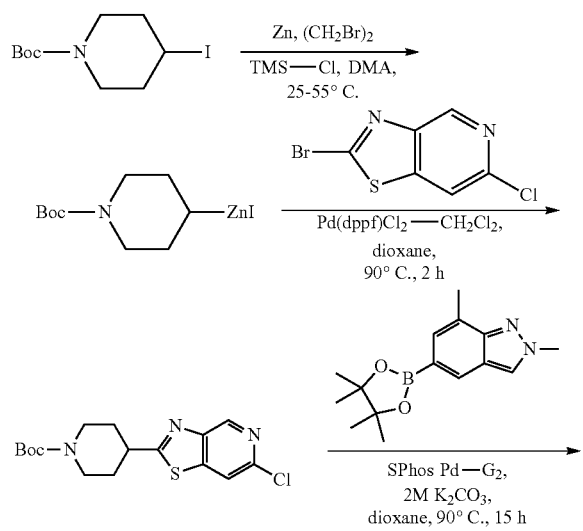

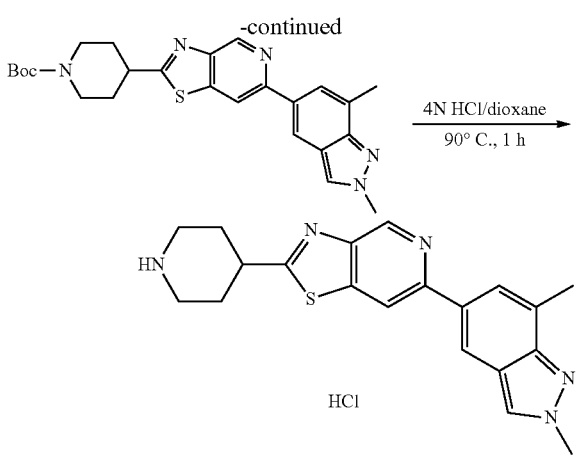

Step 1: Zinc powder (2.11 g, 32.3 mmol) was suspended in dimethylacetamide (5.2 mL) at room temperature under argon. A mixture of 1,2-dibromoethane (260 µL, 3 mmol) and TMSCl (365 µL, 8.22 mmol) was added dropwise to the zinc suspension at such a rate as to keep the internal temperature below 45° C. Once addition was complete, the reaction mixture was stirred for another 15 min, by which time the internal temperature dropped to 30° C. A solution of tert-butyl 4-iodopiperidine-1-carboxylate (8.25 g, 26 mmol) in DMA (13 mL) was added to this mixture at such a rate that the internal temperature did not rise above 55° C. Upon completion of the addition, the mixture was allowed to cool to ambient temperature. The mixture was filtered under an inert argon atmosphere through glass wool to yield 20 mL of ~1M of (1-(tert-butoxycarbonyl)piperidin-4-yl)zinc(II) iodide in DMA.

Step 2: A mixture of 2-bromo-6-chlorothiazolo[4,5-c]pyridine (300 mg, 1.2 mmol), Pd(dppf)Cl$_2$—CH$_2$Cl$_2$ (50 mg, 0.06 mmol), and dioxane (2.5 mL) was stirred under argon, while 1.8 mL of the zinc iodide solution prepared in step 1 was added. The mixture was heated at 90° C. for 2 h. The reaction mixture was then quenched with aqueous NH$_4$Cl, and the mixture was partitioned between EtOAc and H$_2$O. The organic layer was dried over MgSO$_4$, filtered, and then concentrated under vacuum. Purification by silica gel chromatography (20% EtOAc in CH$_2$Cl$_2$), followed by trituration with 1:4 ether/hexane, yielded tert-butyl 4-(6-chlorothiazolo[4,5-c]pyridin-2-yl)piperidine-1-carboxylate (196 mg, 46%) as an off-white solid. $^1$H NMR showed 20 mol % of the des-bromo byproduct 6-chlorothiazolo[4,5-c]pyridine, along with the desired intermediate.

$^1$H NMR (acetone-d$_6$): δ: 8.98 (s, 1H), 8.19 (s, 1H), 4.20 (m, 2H), 3.46 (m, 1H), 3.0 (br s, 2H), 2.18-2.23 (m, 2H), 1.78-1.86 (m, 2H), 1.48 (s, 9H).

Step 3: Crude tert-butyl 4-(6-chlorothiazolo[4,5-c]pyridin-2-yl)piperidine-1-carboxylate (60 mg, 80% purity, 0.17 mmol), 2,7-dimethyl-5-(4,4,5,5-tetramethyl-1,3,2-dioxaborolan-2-yl)-2H-indazole (60 mg, 0.22 mmol), SPhos Pd G2 (10 mg, 0.014 mmol), 2M K$_2$CO$_3$ (0.2 mL, 0.4 mmol), and dioxane (0.6 mL) were heated at 90° C. for 15 h. The mixture was then partitioned between EtOAc and H$_2$O. The organic layer was dried over MgSO$_4$, filtered, and then concentrated under vacuum. Purification by silica gel chromatography (20-50% acetone in CH$_2$Cl$_2$), followed by ether trituration, yielded tert-butyl 4-(6-(2,7-dimethyl-2H-indazol-5-yl)thiazolo[4,5-c]pyridin-2-yl)piperidine-1-carboxylate (58 mg, 73%) as a tan solid. UPLC showed 80% purity, with 20% 6-(2,7-dimethyl-2H-indazol-5-yl)thiazolo[4,5-c]pyridine present.

MS m/z 464.4 [M+H]$^+$.

Step 4: Crude tert-butyl 4-(6-(2,7-dimethyl-2H-indazol-5-yl)thiazolo[4,5-c]pyridin-2-yl)piperidine-1-carboxylate (58 mg, 80% purity, 0.12 mmol) was heated with 4N HCl in dioxane (1.0 mL, 1 mmol) at 90° C. for 1 h. The mixture was diluted in ether and was filtered. The solids were purified by C18 preparatory HPLC. Treatment of the collected fractions with concentrated HCl, followed by concentration under vacuum, yielded the title compound (29 mg, 60%) as a pure yellow solid.

MS m/z 364.3 [M+H]$^+$; $^1$H NMR (DMSO-d$_6$): δ: 9.31 (s, 1H), 8.80 (s, 1H), 8.47 (s, 1H), 8.33 (s, 1H), 7.84 (s, 1H), 4.20 (s, 3H), 3.57-3.63 (m, 1H), 3.39-3.43 (m, 2H), 3.05-3.13 (m, 2H), 2.59 (s, 3H), 2.30-2.36 (m, 2H), 2.00-2.11 (m, 2H).

Using the procedure described for Example 30, above, additional compounds described herein were prepared by substituting the appropriate starting material, suitable reagents and reaction conditions, obtaining compounds such as those selected from:

| Cpd | Data |
| --- | --- |
| 60 | MS m/z 418.3 [M + H]$^+$; $^1$H NMR (methanol-d$_4$) δ: 9.52 (s, 1H), 9.03 (s, 1H), 8.70 (s, 1H), 8.69 (s, 1H), 8.28 (s, 1H), 4.37 (s, 3H), 3.75-3.83 (m, 1H), 3.59-3.64 (m, 2H), 3.25-3.30 (m, 2H), 2.52-2.58 (m, 2H), 2.20-2.35 (m, 2H). |
| 74 | MS m/z 375.3 [M + H]$^+$; $^1$H NMR (DMSO-d$_6$) δ: 9.32 (s, 1H), 8.91 (d, J = 1.5 Hz, 1H), 8.89 (s, 1H), 8.77 (s, 1H), 8.67 (d, J = 1.5 Hz, 1H), 3.57-3.64 (m, 1H), 3.40-3.45 (m, 2H), 3.05-3.12 (m, 2H), 2.30-2.35 (m, 2H), 2.03-2.08 (m, 2H). |
| 75 | MS m/z 378.3 [M + H]$^+$; $^1$H NMR (methanol-d$_4$) δ: 9.51 (s, 1H), 9.08 (s, 1H), 8.55 (s, 1H), 8.29 (d, J = 2 Hz, 1H), 7.66 (s, 1H), 4.34 (s, 3H), 3.76-3.85 (m, 1H), 3.57-3.66 (m, 2H), 3.25-3.32 (m, 2H), 3.18 (q, J = 7.5 Hz, 2H), 2.53-2.60 (m, 2H), 2.23-2.35 (m, 2H), 1.49 (t, J = 7.5 Hz, 3H). |
| 76 | MS m/z 368.1 [M + H]$^+$; $^1$H NMR (DMSO-d$_6$) δ: 9.31 (s, 1H), 8.83 (s, 1H), 8.62 (d, J = 3 Hz, 1H), 8.38 (s, 1H), 7.85 (d, J = 13.5 Hz, 1H), 4.23 (s, 3H), 3.55-3.65 (m, 1H), 3.38-3.43 (m, 2H), 3.06-3.14 (m, 2H), 2.30-2.36 (m, 2H), 2.00-2.12 (m, 2H). |
| 77 | MS m/z 350.1 [M + H]$^+$; $^1$H NMR (methanol-d$_4$) δ: 9.54 (s, 1H), 9.35 (s, 1H), 8.76 (s, 1H), 8.70 (dd, J = 9.5 Hz, 1.5 Hz, 1H), 8.10 (s, 1H), 7.98 (d, J = 9.5 Hz, 1H), 3.64-3.73 (m, 1H), 3.57-3.62 (m, 2H), 3.23-3.32 (m, 2H), 2.62 (s, 3H), 2.46-2.55 (m, 2H), 2.18-2.30 (m, 2H). |
| 109 | MS m/z 376.1 [M + H]$^+$; $^1$H NMR (methanol-d$_4$) δ: 9.34 (s, 1H), 9.23 (d, J = 1.5 Hz, 1H), 8.91 (d, J = 1.5 Hz, 1H), 8.62 (s, 1H), 4.33 (s, 3H), 3.63-3.72 (m, 1H), 3.60 (dt, J = 13 Hz, 3.5 Hz, 2H), 3.28 (td, J = 12.5 Hz, 3 Hz, 2H), 2.48-2.55 (m, 2H), 2.29-2.40 (m, 2H). |
| 110 | MS m/z 365.1 [M + H]$^+$; $^1$H NMR (methanol-d$_4$) δ: 9.40 (s, 1H), 8.97 (s, 1H), 8.86 (s, 1H), 8.62 (m, 1H), 4.43 (s, 3H), 3.65-3.72 (m, 1H), 3.60 (dt, J = 13 Hz, 3.5 Hz, 2H), 3.28 (td, J = 12.5 Hz, 3 Hz, 2H), 2.73 (s, 3H), 2.48-2.55 (m, 2H), 2.29-2.40 (m, 2H). |

Example 31

Preparation of Compound 122

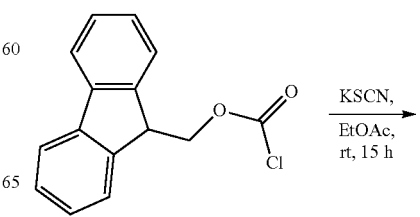

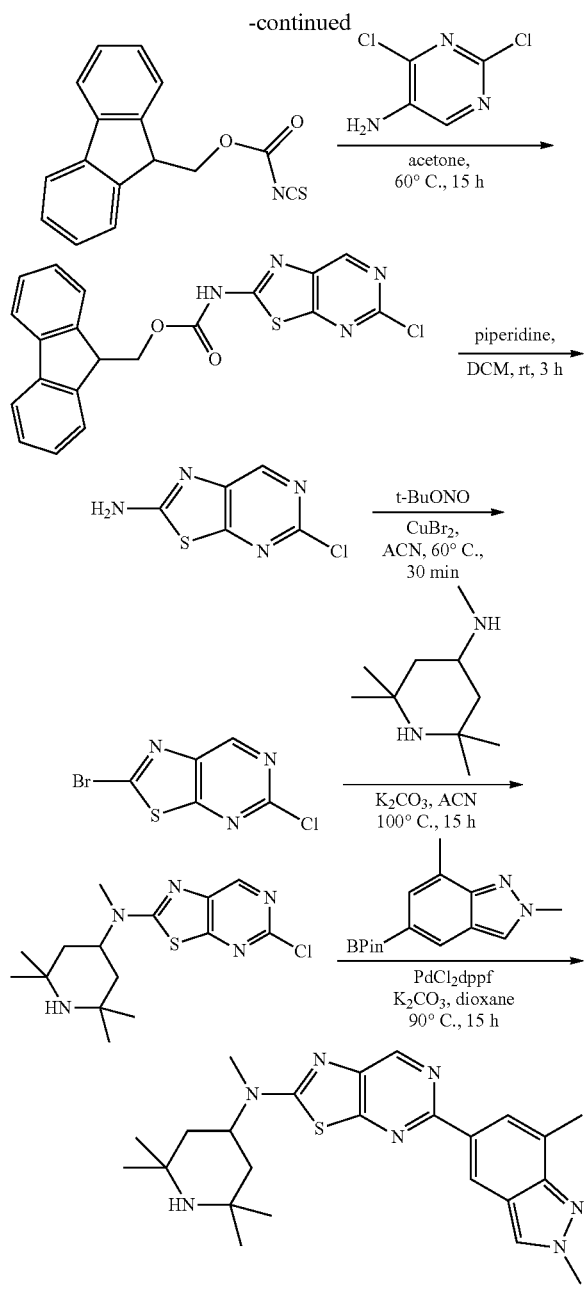

were washed with acetone to yield (9H-fluoren-9-yl)methyl (5-chlorothiazolo[5,4-d]pyrimidin-2-yl)carbamate (716 mg, 88%) as a yellow solid.

$^1$H NMR (DMSO-d$_6$): δ: 12.9 (s, 1H), 9.07 (s, 1H), 7.93 (d, J=7.5 Hz, 2H), 7.81 (d, J=7.5 Hz, 2H), 7.45 (t, J=7.5 Hz, 2H), 7.37 (t, J=7.5 Hz, 2H), 4.62 (d, J=7 Hz, 2H), 4.38 (t, J=7 Hz, 1H).

Step 3: (9H-Fluoren-9-yl)methyl (5-chlorothiazolo[5,4-d] pyrimidin-2-yl)carbamate (650 m, 1.56 mmol) was stirred in CH$_2$Cl$_2$ (25 mL) and piperidine (2.5 mL, 25 mmol) at room temperature for 3 h. After this time, the precipitated solid was filtered and was washed with CH$_2$Cl$_2$ to yield 5-chlorothiazolo[5,4-d]pyrimidin-2-amine (211 mg, 72%) as an off-white solid.

$^1$H NMR (DMSO-d$_6$): δ: 8.55 (s, 1H), 8.30 (br s, 2H).

Step 4: 5-Chlorothiazolo[5,4-d]pyrimidin-2-amine (180 mg, 0.96 mmol), acetonitrile (6.6 mL), t-butyl nitrite (0.25 mL, 2.1 mmol), and CuBr$_2$ (252 mg, 1.14 mmol) were heated at 60° C. for 30 min. The reaction mixture was partitioned between EtOAc and H$_2$O. The organic layer was dried over MgSO$_4$, filtered, and concentrated under vacuum. Purification by silica gel chromatography (0-2% EtOAc in CH$_2$Cl$_2$) yielded 2-bromo-5-chlorothiazolo[5,4-d]pyrimidine (211 mg, 87%) as a white solid.

$^1$H NMR (acetone-d$_6$): δ: 9.29 (s, 1H).

Step 5: 2-Bromo-5-chlorothiazolo[5,4-d]pyrimidine (180 mg, 0.72 mmol), N,2,2,6,6-pentamethylpiperidin-4-amine (204 mg, 0.84 mmol), K$_2$CO$_3$ (490 mg, 3.54 mmol), and acetonitrile (3 mL) were heated at 100° C. for 15 h. The reaction mixture was diluted with ether and was filtered. The filtrate was concentrated under vacuum, re-dissolved in ether and was then filtered to remove orange particulate matter. The filtrate was concentrated under vacuum. Hexane trituration yielded 5-chloro-N-methyl-N-(2,2,6,6-tetramethylpiperidin-4-yl)thiazolo[5,4-d]pyrimidin-2-amine (193 mg, 79%) as a white solid.

$^1$H NMR (acetone-d$_6$): δ: 8.55 (s, 1H), 4.40-4.70 (br s, 1H), 3.18 (s, 3H), 1.75 (dd, J=12.5 Hz, 3.5 Hz, 2H), 1.58 (t, J=12.5 Hz, 2H), 1.31 (s, 6H), 1.16 (s, 6H).

Step 6: 5-Chloro-N-methyl-N-(2,2,6,6-tetramethylpiperidin-4-yl)thiazolo[5,4-d]pyrimidin-2-amine (40 mg, 0.12 mmol), 2,7-dimethyl-5-(4,4,5,5-tetramethyl-1,3,2-dioxaborolan-2-yl)-2H-indazole (44 mg, 0.16 mmol), Pd(dppf)Cl$_2$—CH$_2$Cl$_2$ (10 mg, 0.012 mmol), dioxane (0.45 mL), and 2M K$_2$CO$_3$ (0.15 mL, 0.3 mmol) were heated at 90° C. for 15 h. The reaction mixture was partitioned between H$_2$O and EtOAc. The organic layer was dried over MgSO$_4$, filtered, and then concentrated under vacuum. Purification by silica gel chromatography (20% MeOH in CH$_2$Cl$_2$, followed by 9/1/0.1 H$_2$Cl$_2$/MeOH/NH$_4$OH), followed by ether trituration yielded the title product (34 mg, 64%) as a white solid.

MS m/z 450.5 [M+H]$^+$; $^1$H NMR (DMSO-d$_6$): δ: 8.82 (s, 1H), 8.58 (s, 1H), 8.45 (s, 1H), 8.06 (s, 1H), 4.30-4.70 (br s, 1H), 4.20 (s, 3H), 3.10 (s, 3H), 2.58 (s, 3H), 1.45-1.75 (m, 4H), 1.29 (br s, 6H), 1.17 (br s, 6H).

Step 1: (9H-Fluoren-9-yl)methyl carbonochloridate (2.0 g, 7.77 mmol), potassium thiocyanate (826 mg, 8.51 mmol) and EtOAc (15 mL) were stirred under argon at room temperature for 15 h. The reaction mixture was then flushed through silica with EtOAc to remove inorganics. The filtrate was then concentrated under vacuum. Purification by silica gel chromatography (1:1 hexanes/CH$_2$Cl$_2$), yielded O-((9H-fluoren-9-yl)methyl) carbonisothiocyanatidate (1.71 g, 78%) as a white solid.

$^1$H NMR (CDCl$_3$): δ: 7.81 (d, J=7.5 Hz, 2H), 7.62 (d, J=7.5 Hz, 2H), 7.47 (t, J=7.5 Hz, 2H), 7.37 (t, J=7.5 Hz, 2H), 4.50 (d, J=7.5 Hz, 2H), 4.30 (t, J=7.5 Hz, 1H).

Step 2: O-((9H-Fluoren-9-yl)methyl) carbonisothiocyanatidate (562 mg, 2 mmol), 2,4-dichloropyrimidin-5-amine (328 mg, 2 mmol) and acetone (5 mL) were heated at 60° C. for 15 h. The reaction mixture was filtered and the solids Using the procedure described for Example 31, above, additional compounds described herein were prepared by substituting the indicated intermediate in Step 5, if any, the appropriate starting material, the suitable reagents and reaction conditions, obtaining compounds such as those selected from:

| Cpd | Intermediate and Data |
|---|---|
| 123 | MS m/z 461.3 [M + H]$^+$; $^1$H NMR (DMSO-d$_6$) δ: 9.09 (d, J = 1.5 Hz, 1H), 8.86 (s, 1H), 8.76 (s, 1H), 8.75 (d, J = 1.5 Hz, 1H), 4.3-4.7 (br s, 1H), 4.28 (s, 3H), 3.11 (s, 3H), 1.4-1.8 (m, 4H), 1.28 (br s, 6H), 1.15 (br s, 6H). |
| 124 | MS m/z 454.2 [M + H]$^+$; $^1$H NMR (DMSO-d$_6$) δ: 8.83 (s, 1H), 8.62 (d, J = 3 Hz, 1H), 8.60 (d, J = 1 Hz, 1H), 7.94 (dd, J = 8.5 Hz, 1 Hz, 1H), 4.3-4.7 (br s, 1H), 4.20 (s, 3H), 3.10 (s, 3H), 1.65 (m, 2H), 1.47-1.53 (m, 2H), 1.25 (br s, 6H), 1.11 (br s, 6H). |
| 142 | MS m/z 464.2 [M + H]$^+$; $^1$H NMR (methanol-d$_4$,) δ: 8.81 (s, 1H), 8.57-8.65 (m, 2H), 8.44-8.54 (m, 1H), 7.36 (s, 1H), 4.98-5.17 (m, 1H), 3.26 (s, 3H), 2.05-2.17 (m, 4H), 1.67 (s, 6H), 1.58 ppm (s, 6H). |
| 170 | MS m/z 461.4 [M + H]$^+$; $^1$H NMR (DMSO-d$_6$) δ: 9.69 (d, J = 1.5 Hz, 1H), 8.83 (s, 1H), 8.57 (d, J = 1.5 Hz, 1H), 8.03 (s, 1H), 4.1-4.7 (br s, 1H), 3.09 (s, 3H), 2.41 (s, 3H), 1.63-1.67 (m, 2H), 1.45-1.55 (m, 2H), 1.25 (br s, 6H), 1.11 (br s, 6H). |
| 171 | MS m/z 454.2 [M + H]$^+$; $^1$H NMR (DMSO-d$_6$) δ: 9.33 (d, J = 1.5 Hz, 1H), 8.84 (s, 1H), 7.98 (d, J = 2.5 Hz, 1H), 7.82 (dd, J = 12 Hz, 1.5 Hz, 1H), 4.3-4.7 (br s, 1H), 3.1 (s, 3H), 2.38 (s, 3H), 1.63-1.67 (m, 2H), 1.45-1.55 (m, 2H), 1.25 (br s, 6H), 1.11 (br s, 6H). |
| 183 | MS m/z 450.2 [M + H]$^+$; $^1$H NMR (DMSO-d$_6$) δ: 9.28 (s, 1H), 8.83 (s, 1H), 7.91 (s, 1H), 7.83 (s, 1H), 4.3-4.7 (br s, 1H), 3.10 (s, 3H), 2.53 (s, 3H), 2.40 (s, 3H), 1.0-1.8 (m, 16 H). |
| 184 | MS m/z 451.2 [M + H]$^+$; $^1$H NMR (DMSO-d$_6$) δ: 8.91 (s, 1H), 8.12 (s, 1H), 7.97 (s, 1H), 4.4-4.9 (br s, 1H), 3.13 (s, 3H), 2.64 (s, 3H), 2.43 (s, 3H), 1.0-1.8 (m, 16H). |
| 193 | MS m/z 405.2 [M + H]$^+$; $^1$H NMR (DMSO-d$_6$) δ: 9.09 (d, J = 1.5 Hz, 1H), 8.87-8.95 (m, 2H), 8.86 (s, 1H), 8.77 (s, 1H), 8.75 (d, J = 2 Hz, 1H), 4.51 (br s, 1H), 4.28 (s, 3H), 3.38-3.42 (m, 2H), 3.08-3.17 (m, 5H), 2.10-2.20 (m, 2H), 1.95-1.99 (m, 2H). |
| 196 | MS m/z 405.4 [M + H]$^+$; $^1$H NMR (DMSO-d$_6$) δ: 9.76 (d, J = 1.5 Hz, 1H), 8.88-9.02 (m, 2H), 8.87 (s, 1H), 8.69 (d, J = 1.5 Hz, 1H), 8.11 (1H), 4.51 (br s, 1H), 3.39-3.43 (m, 2H), 3.10-3.18 (m, 5H), 3.27 (s, 3H), 2.14-2.21 (m, 2H), 1.94-1.98 (m, 2H). |
| 197 | MS m/z 466.3 [M + H]$^+$; $^1$H NMR (DMSO-d$_6$) δ: 8.84 (s, 1H), 8.43 (s, 1H), 8.35 (d, J = 1.5 Hz, 1H), 7.63 (d, J = 1.5 Hz, 1H), 4.3-4.7 (br s, 1H), 4.17 (s, 3H), 4.00 (s, 3H), 3.11 (s, 3H), 1.0-1.8 (m, 16H). |
| 207 | Intermediate 3<br>MS m/z 431.2 [M + H]$^+$; $^1$H NMR (DMSO-d$_6$) δ: 9.81 (d, J = 1.5 Hz, 1H), 9.62 (m, 1H), 9.08, (m, 1H), 8.92 (s, 1H), 8.76 (s, 1H), 8.14 (s, 1H), 4.68 (br s, 1H), 4.13 (br s, 2H), 3.16 (s, 3H), 2.46 (s, 3H), 2.31-2.39 (m, 2H), 1.80-2.15 (m, 6H). |
| 208 | Intermediate 3<br>MS m/z 431.2 [M + H]$^+$; $^1$H NMR (DMSO-d$_6$) δ: 9.40 (m, 1H), 9.10 (d, J = 1.5 Hz, 1H), 8.96 (m, 1H), 8.78 (s, 1H), 8.75 (d, J = 1.5 Hz, 1H), 4.70 (br s, 1H), 4.33 (s, 3H), 4.13 (br s, 2H), 3.17 (s, 3H), 2.30-2.36 (m, 2H), 1.95-2.14 (m, 4H), 1.83-1.92 (m, 2H). |
| 217 | Intermediate 3<br>MS m/z 424.4 [M + H]$^+$; $^1$H NMR (methanol-d$_4$) δ: 9.59 (s, 1H), 8.88 (s, 1H), 8.71 (d, J = 11 Hz, 1H), 8.21 (s, 1H), 5.01 (br s, 1H), 4.25 (br s, 2H), 3.22 (s, 3H), 2.63 (s, 3H), 2.32-2.39 (m, 2H), 2.20-2.28 (m, 4H), 2.07-2.11 (m, 2H). |
| 218 | Intermediate 3<br>MS m/z 424.4 [M + H]$^+$; $^1$H NMR (methanol-d$_4$) δ: 8.86 (s, 1H), 8.61 (d, J = 1.5 Hz, 1H), 8.59 (d, J = 2.5 Hz, 1H), 7.94 (dd, J = 13 Hz, 1 Hz, 1H), 4.97 (br s, 1H), 4.32 (s, 3H), 4.26 (br s, 2H), 3.19 (s, 3H), 2.32-2.41(m, 2H), 2.20-2.28 (m, 4H), 2.07-2.11 (m, 2H). |
| 227 | Intermediate 1<br>MS m/z 424.3[M + H]$^+$; $^1$H NMR (methanol-d$_4$) δ: 9.59 (s, 1H), 8.90 (s, 1H), 8.71 (d, J = 11.5 Hz, 1H), 8.21 (s, 1H), 4.39 (s, 1H), 3.49 (d, J = 13 Hz, 2H), 3.40 (dd, J = 13 Hz, 3 Hz, 2H), 3.30 (s, 3H), 3.01 (br s, 2H), 2.63 (s, 3H), 2.16-2.22 (m, 2H), 1.94-2.04 (m, 2H). |
| 228 | Intermediate 1<br>MS m/z 431.3 [M + H]$^+$; $^1$H NMR (methanol-d$_4$) δ: 9.96 (d, J = 1.5 Hz, 1H), 9.37 (d, J = 1.5 Hz, 1H), 8.92 (s, 1H), 8.27 (d, J = 1 Hz, 1H), 4.41 (s, 1H), 3.47-3.52 (m, 2H), 3.38-3.43 (m, 2H), 3.32 (s, 3H), 3.02 (br s, 2H), 2.65 (s, 3H), 2.18-2.24 (m, 2H), 1.95-2.03 (m, 2H). |
| 242 | Intermediate 2<br>MS m/z 475.5 [M + H]$^+$; $^1$H NMR (methanol-d$_4$) δ: 9.56 (d, J = 1.5 Hz, 1H), 8.72 (s, 1H), 8.69 (d, J = 1.5 Hz, 1H), 7.87 (s, 1H), 4.5-4.7 (br s, 1H), 3.66 (q, J = 7 Hz, 2H), 2.49 (s, 3H), 1.93-1.98 (m, 2H), 1.75-1.85 (m, 2H), 1.47 (s, 6H), 1.25-1.40 (m, 9H). |
| 243 | Intermediate 2<br>MS m/z 468.4 [M + H]$^+$; $^1$H NMR (methanol-d$_4$) δ: 9.20 (d, J = 1.5 Hz, 1H), 8.73 (s, 1H), 7.97 (dd, J = 12 Hz, 1.5 Hz, 1H), 7.81 (d, J = 2 Hz, 1H), 4.5-4.7 (br s, 1H), 3.66 (q, J = 7 Hz, 2H), 2.46 (s, 3H), 1.89-1.93 (m, 2H), 1.69-1.79 (m, 2H), 1.38 (s, 6H), 1.36 (t, J = 7 Hz, 3H), 1.31 (s, 6H). |
| 254 | MS m/z 460.4 [M + H]$^+$; $^1$H NMR (DMSO-d$_6$) δ: 9.07 (d, J = 1.5 Hz, 1H), 8.84 (s, 1H), 8.75 (s, 1H), 8.74 (d, J = 1.5 Hz, 1H), 4.3-4.6 (br s, 1H), 4.27 (s, 3H), 3.07 (s, 3H), 1.74-1.77 (m, 2H), 1.50-1.66 (m, 6H), 1.18 (s, 6H). |
| 255 | MS m/z 459.6 [M + H]$^+$; $^1$H NMR (methanol-d$_4$) δ: 9.48 (d, J = 1.5 Hz, 1H), 8.66 (s, 1H), 8.61 (d, J = 1.5 Hz, 1H), 7.84 (d, J = 1 Hz, 1H), 4.5-4.7 (br s, 1H), 3.12 (s, 3H), 2.48 (s, 3H), 1.95-2.00 (m, 2H), 1.70-1.81 (m, 6H), 1.33 (s, 6H). |
| 256 | Intermediate 3<br>MS m/z 445.1 [M + H]$^+$; $^1$H NMR (methanol-d$_4$) δ: 9.95 (d, J = 1.5 Hz, 1H), 9.37 (d, J = 1.5 Hz, 1H), 8.90 (s, 1H), 8.26 (s, 1H), 5.63 (s, 1H), 3.91 (br s, 2H), 3.25 (s, 3H), 2.65 (s, 3H), 2.45-2.52 (m, 2H), 2.05-2.25 (m, 7H), 1.97 (m, 1H). |
| 257 | MS m/z 438.0 [M + H]$^+$; $^1$H NMR (methanol-d$_4$) δ: 9.59 (s, 1H), 8.88 (s, 1H), 8.71 (d, J = 11 Hz, 1H), 8.21 (s, 1H), 5.64 (br s, 1H), 3.91 (br s, 2H), 3.21 (s, 3H), 2.63 (s, 3H), 2.45-2.53 (m, 2H), 2.05-2.25 (m, 7H), 1.97 (m, 1H). |

-continued

| Cpd | Intermediate and Data |
|---|---|
| 275 | MS m/z 462.5 [M + H]⁺; ¹H NMR (DMSO-d₆) δ: 8.87 (s, 1H), 8.80 (d, J = 1.5 Hz, 1H), 8.70 (d, J = 1.5 Hz, 1H), 4.2-4.7 (br s, 1H), 3.11 (s, 3H), 2.75 (s, 3H), 1.64-1.68 (m, 2H), 1.47-1.54 (m, 2H), 1.26 (s, 6H), 1.12 (s, 6H). |
| 284 | MS m/z 452.4 [M + H]⁺; ¹H NMR (methanol-d₄) δ: 9.18 (d, J = 1 Hz, 1H), 8.71 (s, 1H), 7.94 (dd, J = 12, 1 Hz, 1H), 7.80 (d, J = 1 Hz, 1H), 4.55-4.75 (br s, 1H), 3.14 (s, 3H), 2.46 (s, 3H), 2.02 (m, 2H), 1.75-1.85 (m, 6H), 1.37 (s, 6H), NH proton not observed. |
| 289 | MS m/z 452.3 [M + H]⁺. ¹H NMR (methanol-d₄) δ: 8.73 (s, 1H), 8.59 (d, J = 1.5 Hz, 1H), 8.43 (d, J = 3 Hz, 1H), 8.02 (dd, J = 13, 1.5 Hz, 1H), 4.55-4.75 (br s, 1H), 4.27 (s, 3H), 3.14 (s, 3H), 2.05 (m, 2H), 1.79-1.87 (m, 6H), 1.38 (s, 6H), NH proton not observed. |
| 290 | MS m/z 460.2 [M + H]⁺; ¹H NMR (DMSO-d₆) δ: 8.88 (s, 1H), 8.81 (d, J = 1.5 Hz, 1H), 8.70 (d, J = 1.5 Hz, 1H), 4.3-4.7 (br s, 1H), 3.09 (s, 3H), 2.76 (s, 3H), 1.91 (br s, 2H), 1.53-1.70 (m, 6H), 1.22 (s, 6H), NH proton not observed. |
| 303 | Intermediate 3a<br>MS m/z 487.2 [M + H]⁺; ¹H NMR (methanol-d₄) δ: 9.52 (d, J = 1.5 Hz, 1H), 8.69 (s, 1H), 8.64 (d, J = 2 Hz, 1H), 7.86 (s, 1H), 4.5-4.7 (br s, 1H), 3.15 (s, 3H), 2.49 (s, 3H), 1.8-2.1 (m, 4H), 1.6-1.8 (m, 8H), 1.02 (t, J = 7.5 Hz, 6H), NH proton not observed. |
| 304 | Intermediate 3a<br>MS m/z 480.3 [M + H]⁺; ¹H NMR (methanol-d₄) δ: 9.21 (d, J = 1.5 Hz, 1H), 8.75 (s, 1H), 7.97 (dd, J = 12, 1.5 Hz, 1H), 7.82 (s, 1H), 3.19 (s, 3H), 2.46 (s, 3H), 2.12 (m, 2H), 1.99 (m, 2H), 1.7-1.9 (m, 8H), 1.04 (t, J = 7.5 Hz, 6H), CH methyne proton (broad) and NH proton not observed. |
| 324 | Intermediate 7<br>MS m/z 479.6 [M + H]⁺; ¹H NMR (methanol-d₄) δ: 9.98 (s, 1H), 9.38 (s, 1H), 8.92 (s, 1H), 8.27 (s, 1H), 5.47 (dd, J = 32.7, 12.8 Hz, 1H), 5.03 (d, J = 48.5 Hz, 1H), 3.34 (s, 3H), 2.66 (s, 3H), 2.47 (t, J = 13.7 Hz, 1H), 2.09 (d, J = 13.1 Hz, 1H), 1.74 (s, 3H), 1.74 (s, 3H), 1.64 (s, 3H), 1.59 (d, J = 1.8 Hz, 3H), NH proton not observed. |

Example 32

Preparation of Compound 265

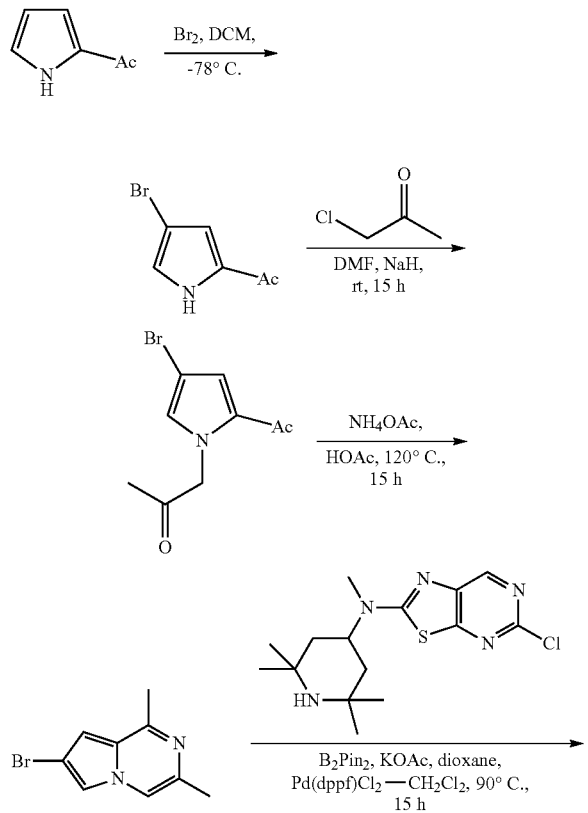

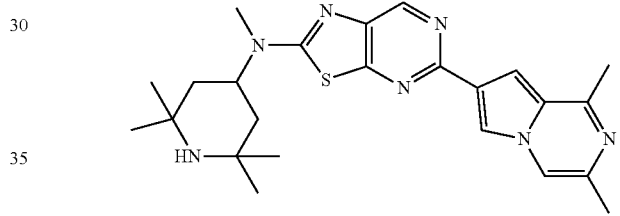

Step 1: 1-(1H-pyrrol-2-yl)ethan-1-one (1.09 g, 10 mmol) was dissolved in CH₂Cl₂ (50 mL) at −78° C. A solution of Br₂ (0.62 mL, 12.1 mmol) in CH₂Cl₂ (12 mL) was added by syringe. After the addition was complete, the mixture was poured onto ice. The bilayer was separated, and then the organic layer was washed with aqueous 1N NaOH to remove the dibrominated byproduct. The organic layer was dried over MgSO₄, filtered, and concentrated under vacuum to yield 1-(4-bromo-1H-pyrrol-2-yl)ethan-1-one (1.42 g, 76%) as a grayish solid.

¹H NMR (acetone-d₆) δ: 11.08 (br s, 1H), 7.19 (t, J=1.5 Hz, 1H), 7.02 (t, J=1.5 Hz, 1H), 2.36 (s, 3H).

Step 2: 1-(4-Bromo-1H-pyrrol-2-yl)ethan-1-one (1.36 g, 7.23 mmol) was dissolved in DMF (15 mL) at 0° C. NaH (60%, 316 mg, 7.9 mmol) was added. The reaction mixture was then stirred at room temperature for 30 minutes. Chloroacetone (0.6 mL, 7 mmol) was then added dropwise. The mixture was stirred at room temperature for 15 h then partitioned between EtOAc and H₂O. The organic layer was dried over MgSO₄, filtered, and concentrated under vacuum. Purification by silica gel chromatography (30% EtOAc in hexanes) yielded 1-(2-acetyl-4-bromo-1H-pyrrol-1-yl)propan-2-one (1.2 g, 68%) as a white solid.

¹H NMR (acetone-d₆) δ: 7.13 (d, J=2 Hz, 1H), 7.10 (d, J=2 Hz, 1H), 5.17 (s, 2H), 2.36 (s, 3H), 2.18 (s, 3H).

Step 3: 1-(2-Acetyl-4-bromo-1H-pyrrol-1-yl)propan-2-one (1.15 g, 4.71 mmol), NH₄OAc (7.2 g, 93 mmol), and HOAc (40 mL) were heated at 120° C. for 15 h. The solvent was then removed under vacuum and the concentrate was treated with aqueous NaOH, and then extracted into EtOAc. The organic layer was dried over MgSO$_4$, filtered, and concentrated under vacuum. Purification by silica gel chromatography (10-50% EtOAc in CH$_2$Cl$_2$) yielded 7-bromo-1,3-dimethylpyrrolo[1,2-a]pyrazine (975 mg, 92%) as a light tan solid.

$^1$H NMR (acetone-d$_6$) δ: 7.86 (s, 1H), 7.63 (d, J=1.5 Hz, 1H), 6.84 (t, J=1 Hz, 1H), 2.56 (s, 3H), 2.31 (s, 3H).

Step 4: 7-Bromo-1,3-dimethylpyrrolo[1,2-a]pyrazine (32 mg, 0.14 mmol), KOAc (46 mg, 0.47 mmol), bis(pinacolato)diboron (46 mg, 0.18 mmol), Pd(dppf)Cl$_2$—CH$_2$Cl$_2$ (8 mg, 0.016 mmol), and dioxane (0.6 mL) were heated at 90° C. for 1 h, then cooled. 5-Chloro-N-methyl-N-(2,2,6,6-tetramethylpiperidin-4-yl)thiazolo[5,4-d]pyrimidin-2-amine (40 mg, 0.12 mmol, prepared as in Example 32, Pd(dppf)Cl$_2$—CH$_2$Cl$_2$ (8 mg, 0.016 mmol), and 2M K$_2$CO$_3$ (0.2 mL, 0.4 mmol) were added. The mixture was heated at 90° C. for 15 h. The mixture was partitioned between CH$_2$Cl$_2$ and H$_2$O. The organic layer was dried over MgSO$_4$, filtered, and concentrated under vacuum. Purification by silica gel chromatography (5% MeOH in CH$_2$Cl$_2$, followed by 9/1/0.1 CH$_2$Cl$_2$/MeOH/NH$_4$OH), followed by ether trituration, yielded the title compound (16 mg, 30%) as a white solid.

MS m/z 450.5 [M+H]$^+$; $^1$H NMR (methanol-d$_4$) δ: 8.68 (s, 1H), 8.15 (d, J=1.5 Hz, 1H), 7.88 (s, 1H), 7.47 (s, 1H), 4.2-4.4 (br s, 1H), 3.19 (s, 3H), 2.67 (s, 3H), 2.36 (s, 3H), 1.87-1.93 (m, 2H), 1.68-1.78 (m, 2H), 1.47 (br s, 6H), 1.35 (s, 6H).

Using the procedure described for Example 32, above, additional compounds described herein were prepared by substituting the appropriate starting material, suitable reagents and reaction conditions, obtaining compounds such as those selected from:

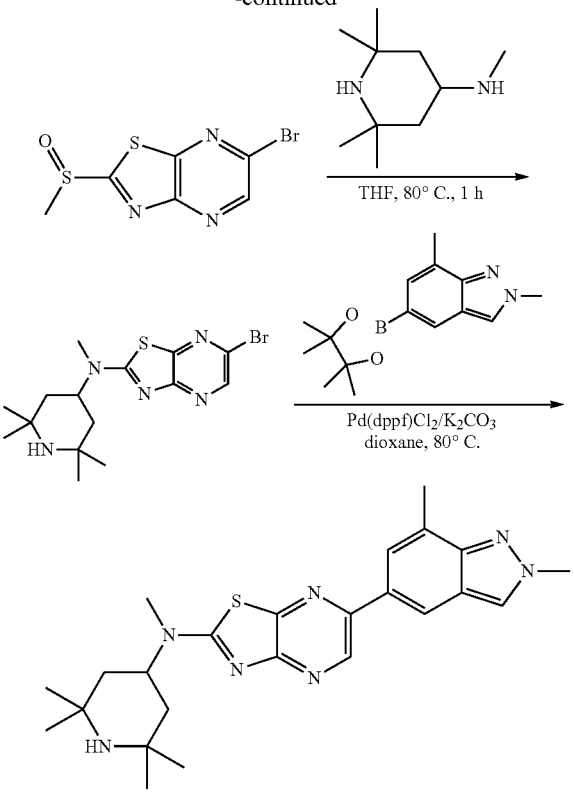

| Cpd | Data |
|---|---|
| 323 | MS m/z 448.5 [M + H]$^+$; $^1$H NMR (methanol-d$_4$) δ: 8.67 (s, 1H), 8.15 (s, 1H), 7.87 (s, 1H), 7.46 (s, 1H), 4.55-4.75 (br s, 1H), 3.14 (s, 3H), 2.67 (s, 3H), 2.36 (s, 3H), 2.02 (m, 2H), 1.75-1.85 (m, 6H), 1.37 (s, 6H), NH proton not observed. |

Example 33

Preparation of Compound 131

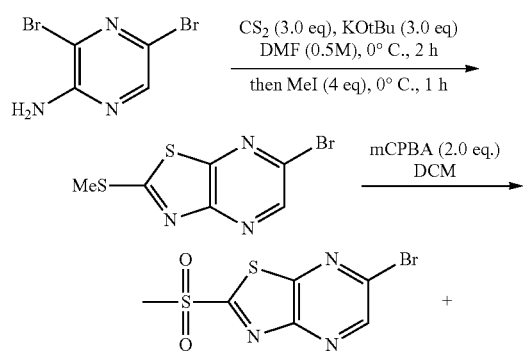

Step 1: 3,5-Dibromopyrazin-2-amine (1.0 g, 4 mmol) was dissolved in DMF (8.0 mL) and CS$_2$ (0.5 mL, 8 mmol, 2 eq.) was added. The solution was cooled and stirred at 0° C. and to the cold solution was added t-BuOK (1M solution, 8 mL, 2 eq) in THF. The resulting solution was stirred for 1 h at 0° C. and added additional CS$_2$ (0.25 mL, 4 mmole, 1 eq) and tBuOK (4 mL, 1 eq) in THF. The solution was stirred for an additional hour and the disappearance of SM was observed by UPLC. MeI (1 mL, 4 eq) was added and the reaction was stirred for 1 h. The reaction was then quenched with ice-cold water. The resulting precipitate was filtered, washed with hexanes and dried to give 6-bromo-2-(methylthio)thiazolo[4,5-b]pyrazine (0.84 g, 81%). MS m/z 262.1, 264.1 [M+H]$^+$.

Step 2: 6-Bromo-2-(methylthio)thiazolo[4,5-b]pyrazine (0.5 g, 1.9 mmol) was dissolved in CH$_2$Cl$_2$ and the solution was cooled to 0° C. To the solution was added mCPBA (0.95 g, 3.8 mmol, 70% purity, 2 eq.). The solution was then stirred at 0° C. for 1 h and then slowly warmed to room temperature. The reaction was then quenched with NaHCO$_3$ and the mixture was extracted with CH$_2$Cl$_2$. The organic layer was dried and evaporated to give a mixture of 6-bromo-2-(methylsulfonyl)thiazolo[4,5-]pyrazine and 6-bromo-2-(methylsulfinyl)thiazolo[4,5-b]pyrazine (600 mg), which was utilized in the next step without any further purification.

Step 3: The mixture of 6-bromo-2-(methylsulfonyl)thiazolo[4,5-]pyrazine and 6-bromo-2-(methylsulfinyl)thiazolo[4,5-b]pyrazine prepared above (0.375 g, 1.28 mmol) was dissolved in THF (4 mL). To the solution was added N-2,2,6,6-pentamethylpiperidin-4-amine (0.45 mL, 2.56 mmol) and the mixture was heated at 80° C. for 1 h. The reaction was complete and the mixture was purified on silica gel, eluting with 0-30% MeOH in dichloromethane to give 6-bromo-N-methyl-N-(2,2,6,6-tetramethylpiperidin-4-yl)thiazolo[4,5-b]pyrazin-2-amine (0.34 g, 70%). MS m/z 384.1, 386.1 $[M+H]^+$.

Step 4: 6-Bromo-N-methyl-N-(2,2,6,6-tetramethylpiperidin-4-yl)thiazolo[4,5-b]pyrazin-2-amine was combined with 2,7-dimethyl-5-(4,4,5,5-tetramethyl-1,3,2-dioxaborolan-2-yl)indazole (50 mg, 0.13 mmol), [1,1'-bis(diphenylphosphino) ferrocene]dichloropalladium(II) dichloromethane complex (10 mg, 0.013 mmol), 1,4-dioxane (2 mL) and aqueous 1 M $K_2CO_3$ (0.4 mL). The mixture was heated at 80° C. for 8 h under an Ar atmosphere, then cooled and partitioned between EtOAc and $H_2O$. The organic layer was washed with brine, dried over $Na_2SO_4$, filtered and then concentrated. The residue was chromatographed on silica gel, eluting with 10-100% EtOAc in hexanes to afford 6-(2,7-dimethyl-2H-indazol-5-yl)-N-methyl-N-(2,2,6,6-tetramethylpiperidin-4-yl)thiazolo[4,5-b]pyrazin-2-amine (35 mg, 60%).

MS m/z 450.4 $[M+H]^+$; $^1H$ NMR (methanol-$d_4$, 500 MHz): δ: 8.86 (s, 1H), 8.30 (s, 1H), 8.22 (d, J=0.6 Hz, 1H), 7.80 (s, 1H), 5.04-5.15 (m, 1H), 4.27 (s, 3H), 3.23 (s, 3H), 2.66 (s, 3H), 2.01-2.16 (m, 4H), 1.67 (s, 6H), 1.56 ppm (s, 6H).

Using the procedure described for Example 33, above, additional compounds described herein were prepared by substituting the appropriate starting material, suitable reagents and reaction conditions, obtaining compounds such as those selected from:

| Cpd | Data |
|---|---|
| 130 | MS m/z 464.2 $[M + H]^+$; $^1H$ NMR (methanol-$d_4$): δ: 9.09 (s, 1H), 8.36 (br s, 2H), 8.02 (d, J = 8.2 Hz, 1H), 7.28 (dd, J = 8.2, 1.9 Hz, 1H), 7.25 (d, J = 1.6 Hz, 1H), 4.99-5.19 (m, 1H), 3.24 (s, 3H), 2.00-2.15 (m, 4H), 1.65 (s, 6H), 1.55 (s, 6H). |
| 140 | MS m/z 461.2 $[M + H]^+$; $^1H$ NMR (methanol-$d_4$, 500 MHz) δ: 8.84 (s, 1H), 8.67 (d, J = 1.6 Hz, 1H), 8.45-8.53 (m, 2H), 4.89-4.97 (m, 1H), 4.29 (s, 3H), 3.19 (s, 3H), 1.72-1.93 (m, 4H), 1.45 (br s, 6H), 1.34 (br s, 6H). |
| 141 | MS m/z 437.2 $[M + H]^+$; $^1H$ NMR (methanol-$d_4$, 500 MHz): δ: 9.25 (s, 1H), 8.12 (d, J = 9.8 Hz, 1H), 7.94-8.02 (m, 2H), 5.10-5.37 (m, 1H), 3.23 (s, 3H), 2.50 (s, 3H), 2.06 (d, J = 7.3 Hz, 4H), 1.63 (s, 6H), 1.52 (s, 6H). |
| 150 | MS m/z 454.3 $[M + H]^+$; $^1H$ NMR (methanol-$d_4$) δ: 8.87 (s, 1H), 8.40 (d, J = 2.8 Hz, 1H), 8.22 (d, J = 1.3 Hz, 1H), 7.75 (dd, J = 12.9, 1.3 Hz, 1H), 4.94-5.29 (m, 1H), 4.26 (s, 3H), 3.21 (s, 3H), 2.07 (d, J = 3.5 Hz, 4H), 1.64 (s, 6H), 1.52 (s, 6H). |
| 161 | MS m/z 484.3 $[M + H]^+$; $^1H$ NMR (methanol-$d_4$) δ: 8.80 (d, J = 1.3 Hz, 1H), 8.34 (s, 2H), 7.87 (dd, J = 8.5, 1.6 Hz, 1H), 7.68 (dd, J = 8.2, 1.6 Hz, 1H), 5.01-5.29 (m, 1H), 3.25 (s, 3H), 2.11 (m, 4H), 1.66 (s, 6H), 1.56 (s, 6H). |
| 162 | MS m/z 451.2 $[M + H]^+$; $^1H$ NMR (methanol-$d_4$) δ: 9.24 (s, 1H), 7.95 (dd, J = 2.7, 1.1 Hz, 2H), 5.01-5.41 (m, 1H), 3.23 (s, 3H), 2.68 (d, J = 0.9 Hz, 3H), 2.50 (s, 3H), 2.02-2.11 (m, 4H), 1.65 (s, 6H), 1.53 (s, 6H). |
| 163 | MS m/z 461.4 $[M + H]^+$; $^1H$ NMR (DMSO-$d_6$) δ: 9.55 (d, J = 1.6 Hz, 1H), 9.02 (s, 1H), 8.61 (d, J = 1.6 Hz, 1H), 7.97 (d, J = 0.9 Hz, 1H), 4.69-5.20 (m, 1H), 3.14 (s, 3H), 2.41 (s, 3H), 1.80-2.01 (m, 4H), 1.47 (br s, 12H). |
| 173 | MS m/z 377.1 $[M + H]^+$; $^1H$ NMR (methanol-$d_4$) δ: 9.39 (d, J = 1.6 Hz, 1H), 8.89 (s, 1H), 8.52 (d, J = 1.6 Hz, 1H), 7.87 (s, 1H), 3.95 (br s, 4H), 3.22-3.27 (m, 4H), 2.50 (s, 3H). |
| 174 | MS m/z 370.3 $[M + H]^+$; $^1H$ NMR (methanol-$d_4$) δ: 9.41 (d, J = 0.9 Hz, 1H), 9.03 (s, 1H), 8.55 (dd, J = 11.3, 1.3 Hz, 1H), 8.10-8.25 (m, 1H), 4.07-4.24 (m, 4H), 3.40-3.56 (m, 4H), 2.64 (d, J = 0.9 Hz, 3H). |
| 180 | MS m/z 441.4 $[M + H]^+$; $^1H$ NMR (methanol-$d_4$) δ: 9.10 (d, J = 8.8 Hz, 2H), 7.84 (s, 2H), 5.85-5.95 (m, 1H), 2.54-2.62 (m, 2H), 2.48 (s, 3H), 1.87-2.01 (m, 2H), 1.63 (s, 6H), 1.56 (s, 6H). |
| 181 | MS m/z 448.4 $[M + H]^+$; $^1H$ NMR (methanol-$d_4$) δ: 9.48 (br. s., 1H), 9.11 (s, 1H), 8.58 (s, 1H), 7.88 (s, 1H), 5.83-5.95 (m, 1H), 2.53-2.62 (m, 2H), 2.49 (s, 3H), 1.84-2.00 (m, 2H), 1.62 (s, 6H), 1.56 (s, 6H). |
| 182 | MS m/z 353.1 $[M + H]^+$; $^1H$ NMR (methanol-$d_4$) δ: 9.41 (s, 1H), 8.75 (d, J = 9.5 Hz, 1H), 8.49 (d, J = 9.8 Hz, 1H), 8.42 (s, 1H), 4.16 (br. s., 4H), 3.47-3.55 (m, 4H), 2.68 (d, J = 0.9 Hz, 3H). |
| 274 | MS m/z 408.4 $[M + H]^+$; $^1H$ NMR (methanol-$d_4$) δ: 8.95 (s, 1H), 7.93-8.06 (m, 2H), 7.89 (d, J = 7.9 Hz, 1H), 7.20 (d, J = 7.9 Hz, 1H), 7.16 (s, 1H), 3.91-4.09 (m, 1H), 3.00 (br s, 2H), 2.41 (br s, 5H), 2.18 (d, J = 12.3 Hz, 2H), 1.74 (d, J = 10.1 Hz, 2H). |
| 282 | MS m/z 408.4 $[M + H]^+$; $^1H$ NMR (methanol-$d_4$) δ: 9.07 (s, 1H), 8.18 (s, 2H), 7.73-7.77 (m, 1H), 7.35-7.39 (m, 1H), 7.29 (d, J = 1.3 Hz, 1H), 4.97-5.06 (m, 1H), 3.57-3.63 (m, 2H), 3.34 (s, 3H), 2.14-2.37 (m, 6H). |
| 283 | MS m/z 422.4 $[M + H]^+$; $^1H$ NMR (methanol-$d_4$) δ: 8.67 (s, 1H), 7.94-8.09 (m, 2H), 7.83 (d, J = 9.1 Hz, 1H), 7.20 (m, 2H), 4.88-4.92 (m, 1H), 3.21 (br s, 3H), 3.07-3.15 (m, 2H), 2.42 (s, 3H), 2.30-2.39 (m, 2H), 2.01-2.12 (m, 2H), 1.85-1.96 (m, 2H). |
| 118 | MS m/z 450.3 $[M + H]^+$; $^1H$ NMR (methanol-$d_4$) δ: 8.53 (s, 1H), 8.33 (s, 1H), 8.18 (s, 1H), 7.82 (d, J = 1.3 Hz, 1H), 5.29-5.43 (m, 1H), 4.28 (s, 3H), 3.24 (s, 3H), 2.68 (s, 3H), 2.05 (d, J = 3.5 Hz, 4H), 1.61 (s, 6H), 1.49 (s, 6H). |
| 119 | MS m/z 464.5 $[M + H]^+$; $^1H$ NMR (methanol-$d_4$) δ: 9.09 (s, 1H), 8.32 (s, 2H), 7.73-7.81 (m, 1H), 7.36-7.42 (m, 1H), 7.25-7.34 (m, 1H), 5.28-5.41 (m, 1H), 3.33 (br. s., 3H), 2.07-2.18 (m, 4H), 1.65 (s, 6H), 1.58 (s, 6H). |
| 157 | MS m/z 454.4 $[M + H]^+$; $^1H$ NMR (methanol-$d_4$) δ: 8.96 (s, 1H), 8.49 (s, 1H), 7.76-7.86 (m, 2H), 5.08-5.44 (m, 1H), 3.19-3.26 (m, 3H), 2.47 (d, J = 0.6 Hz, 3H), 1.79-1.90 (m, 2H), 1.62-1.74 (m, 2H), 1.41 (br s, 6H), 1.28 (br s, 6H). |
| 158 | MS m/z 461.4 $[M + H]^+$; $^1H$ NMR (methanol-$d_4$) δ: 8.68 (d, J = 1.6 Hz, 1H), 8.57 (s, 1H), 8.56 (s, 1H), 8.55 (d, J = 1.6 Hz, 1H), 5.03-5.31 (m, 1H), 4.32 (s, 3H), 3.23 (s, 3H), 2.09 (br s, 4H), 1.64 (s, 6H), 1.52 (s, 6H). |

| Cpd | Data |
|---|---|
| 288 | MS m/z 394.4 [M + H]⁺; ¹H NMR (methanol-d₄) δ: 9.31 (s, 1H), 8.97 (s, 1H), 8.45 (s, 1H), 8.04 (s, 1H), 3.61 (d, J = 15.3 Hz, 2H), 3.27 (m, 6H), 2.74 (s, 3H), 2.62 (s, 3H), 2.27 (td, J = 13.3, 11.1 Hz, 2H), 2.17 (d, J = 15.1 Hz, 2H), NH proton not observed. |

Example 34

Preparation of Compound 312

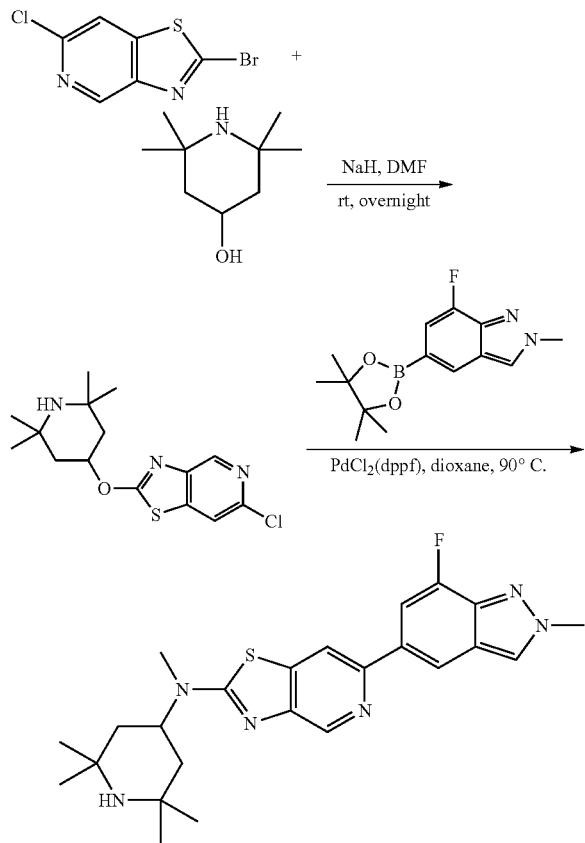

Step 1: To a solution of 2,2,6,6-tetramethylpiperidin-4-ol (472 mg, 3.00 mmol) in DMF (8.5 mL) was added NaH (150 mg, 3.75 mmol, 60 mass % in oil). The mixture was stirred at room temperature for 5 min followed by the addition of 2-bromo-6-chloro-thiazolo[4,5-c]pyridine (624 mg, 2.50 mmol), and then stirred at room temperature overnight. The mixture was diluted with ice water and extracted with EtOAc. The organic phase was washed with water, brine and dried over Na₂SO₄. The solvent was removed and the residue was chromatographed (MeOH in dichloromethane 0-20%) to provide 6-chloro-2-[(2,2,6,6-tetramethyl-4-piperidyl)oxy]thiazolo[4,5-c]pyridine (487 mg, 59.8%) as a white solid.

MS m/z 326.3, 328.2 [M+H]⁺, RT 0.94 min; ¹H NMR (CDCl₃) δ: 8.67-8.72 (m, 1H), 7.61-7.65 (m, 1H), 5.58-5.68 (m, 1H), 2.20-2.44 (m, 2H), 1.08-1.82 (m, 14H), NH proton not observed.

Step 2: The procedure for Example 28 step 4 was followed to give 6-(7-fluoro-2-methyl-2H-indazol-5-yl)-N-methyl-N-(2,2,6,6-tetramethylpiperidin-4-yl)thiazolo[4,5-c]pyridin-2-amine.

MS m/z [M+H]⁺ 440.2; 1H NMR (500 MHz, DMSO-d₆) δ: 8.94 (s, 1H), 8.63 (s, 1H), 8.60 (d, J=1.00 Hz, 1H), 8.30 (d, J=1.26 Hz, 1H), 7.81 (dd, J=13.56, 1.26 Hz, 1H), 5.54-5.68 (m, 1H), 4.22 (s, 3H), 2.15-2.35 (m, 2H), 1.02-1.70 (m, 14H), NH proton not observed.

Using the procedure described for Example 34, above, additional compounds described herein were prepared by substituting the appropriate starting material, suitable reagents and reaction conditions, obtaining compounds such as those selected from:

| Cpd | Data |
|---|---|
| 306 | MS m/z [M + H]⁺ 398.4; ¹H NMR (DMSO-d₆) δ: 8.95 (br d, J = 1.00 Hz, 2H), 8.57 (d, J = 1.58 Hz, 1H), 8.32 (br s, 1H), 8.13 (br s, 1H), 8.02 (dd, J = 11.98, 1.58 Hz, 1H), 5.44-5.57 (m, 1H), 3.08-3.39 (m, 4H), 2.69 (s, 3H), 2.24-2.34 (m, 2H), 2.52 (s, 3H), 2.03-2.16 (m, 2H). |
| 307 | MS m/z [M + H]⁺ 401.3; ¹H NMR (DMSO-d₆) δ: 8.76 (br s, 2H), 8.55 (d, J = 2.84 Hz, 1H), 8.16 (d, J = 1.58 Hz, 1H), 7.92 (d, J = 1.26 Hz, 1H), 7.70 (dd, J = 12.45, 1.73 Hz, 1H), 7.47 (dd, J = 13.24, 1.26 Hz, 1H), 5.43-5.51 (m, 1H), 4.22 (s, 3H), 3.13-3.34 (m, 4H), 2.23-2.35 (m, 2H), 2.00-2.12 (m, 2H). |
| 309 | MS m/z [M + H]⁺ 447.4; ¹H NMR (DMSO-d₆) δ: 9.56 (d, J = 1.89 Hz, 1H), 8.97 (d, J = 0.63 Hz, 1H), 8.64 (s, 1H), 8.54 (d, J = 1.58 Hz, 1H), 8.00 (d, J = 0.95 Hz, 1H), 5.56-5.68 (m, 1H), 2.41 (s, 3H), 2.06-2.36 (m, 2H), 0.83-1.80 (m, 14H), NH proton not observed. |
| 310 | MS m/z [M + H]⁺ 440.5; ¹H NMR (DMSO-d₆) δ: 9.15 (d, J = 1.26 Hz, 1H), 8.96 (d, J = 0.63 Hz, 1H), 8.58 (s, 1H), 7.91-7.96 (m, 1H), 7.76 (dd, J = 12.77, 1.42 Hz, 1H), 5.54-5.70 (m, 1H), 2.36-2.40 (m, 3H), 2.15-2.34 (m, 2H), 1.04-1.70 (m, 14H), NH proton not observed. |

-continued

| Cpd | Data |
|---|---|
| 311 | MS m/z [M + H]⁺ 447.5; ¹H NMR (DMSO-d₆) δ: 8.96 (d, J = 0.63 Hz, 1H), 8.82 (d, J = 1.00 Hz, 1H), 8.68 (s, 1H), 8.74 (s, 1H), 8.60 (d, J = 1.58 Hz, 1H), 5.54-5.67 (m, 1H), 4.27 (s, 3H), 2.14-2.34 (m, 2H), 1.02-1.70 (m, 14H), NH proton not observed. |
| 313 | MS m/z [M + H]⁺ 391.3; ¹H NMR (DMSO-d₆) δ: 9.66 (d, J = 1.58 Hz, 1H), 9.10 (br s, 2H), 9.02 (d, J = 0.95 Hz, 1H), 8.68-8.75 (m, 2H), 8.10 (d, J = 1.00 Hz, 1H), 5.43-5.53 (m, 1H), 3.09-3.36 (m, 4H), 2.45 (d, J = 0.63 Hz, 3H), 2.24-2.35 (m, 2H), 2.04-2.19 (m, 2H). |
| 314 | MS m/z [M + H]⁺ 384.3; ¹H NMR (DMSO-d₆) δ: 9.45 (s, 1H), 9.20 (d, J = 1.00 Hz, 2H), 9.04 (d, J = 0.95 Hz, 1H), 8.73 (d, J = 1.00 Hz, 1H), 8.35 (br d, J = 11.66 Hz, 1H), 8.22 (s, 1H), 5.43-5.52 (m, 1H), 3.09-3.34 (m, 4H), 2.50 (3H, obscured by DMSO-d₆ signal), 2.26-2.36 (m, 2H), 2.03-2.18 (m, 2H). |
| 315 | MS m/z [M + H]⁺ 391.4; ¹H NMR (DMSO-d₆) δ: 9.00 (d, J = 0.95 Hz, 1H), 8.95 (br s, 2H), 8.83 (d, J = 1.58 Hz, 1H), 8.76 (s, 1H), 8.73 (d, J = 0.63 Hz, 1H), 8.61 (d, J = 1.58 Hz, 1H), 5.44-5.51 (m, 1H), 4.27 (s, 3H), 3.12-3.34 (m, 4H), 2.23-2.34 (m, 2H), 2.02-2.15 (m, 2H). |
| 316 | MS m/z [M + H]⁺ 384.4; ¹H NMR (DMSO-d₆) δ: 9.09 (br s, 2H), 8.99 (d, J = 0.63 Hz, 1H), 8.70 (d, J = 0.63 Hz, 1H), 8.63 (d, J = 2.84 Hz, 1H), 8.30 (d, J = 1.26 Hz, 1H), 7.80 (dd, J = 13.56, 1.26 Hz, 1H), 5.43-5.52 (m, 1H), 4.23 (s, 3H), 3.23-3.34 (m, 2H), 3.11-3.22 (m, 2H), 2.24-2.35 (m, 2H), 2.04-2.16 (m, 2H). |
| 317 | MS m/z [M + H]⁺ 408.3; ¹H NMR (DMSO-d₆) δ: 9.32 (s, 1H), 8.83-9.02 (m, 2H), 8.44 (s, 1H), 8.20 (d, J = 1.2 Hz, 1H), 7.93 (s, 1H), 7.78 (dd, J = 12.1, 1.4 Hz, 1H), 5.43-5.53 (m, 1H), 3.11-3.34 (m, 4H), 2.43 (s, 3H), 2.22-2.34 (m, 2H), 2.00-2.15 (m, 2H). |
| 318 | MS m/z [M + H]⁺ 408.4; ¹H NMR (DMSO-d₆) δ: 8.93 (br d, J = 18.92 Hz, 2H), 8.70 (s, 1H), 8.46 (s, 1H), 8.30 (s, 1H), 8.21 (s, 1H), 7.77 (br d, J = 12.21 Hz, 1H), 5.39-5.55 (m, 1H), 4.27 (s, 3H), 3.10-3.33 (m, 4H), 2.22-2.35 (m, 2H), 2.00-2.15 (m, J = 9.20 Hz, 2H). |
| 319 | MS m/z [M + H]⁺ 397.4; ¹H NMR (DMSO-d₆) δ: 9.01-9.24 (m, 3H), 8.23 (s, 1H), 8.16 (s, 1H), 8.06 (s, 1H), 7.78 (br d, J = 11.9 Hz, 1H), 5.44-5.52 (m, 1H), 3.09-3.33 (m, 4H), 2.65 (s, 3H), 2.53 (s, 3H), 2.22-2.35 (m, 2H), 2.01-2.15 (m, 2H). |
| 320 | MS m/z [M + H]⁺ 412.2; ¹H NMR (DMSO-d₆) δ: 8.43 (d, J = 1.22 Hz, 1H), 8.02 (s, 1H), 7.92 (dd, J = 12.21, 1.22 Hz, 1H), 7.67 (s, 1H), 5.18-5.29 (m, 1H), 2.56-2.62 (m, 3H), 2.62-2.76 (m, 2H), 2.31-2.44 (m, 5H), 2.26 (s, 3H), 2.06-2.17 (m, 2H), 1.82-1.95 (m, 2H). |
| 321 | MS m/z [M + H]⁺ 426.2; ¹H NMR (DMSO-d₆) δ: 8.43 (d, J = 1.22 Hz, 1H), 8.02 (s, 1H), 7.92 (dd, J = 12.21, 1.22 Hz, 1H), 7.67 (s, 1H), 5.18-5.29 (m, 1H), 3.31 (m, 2H, obscured by H₂O signal), 2.62-2.76 (m, 2H), 2.59 (s, 3H), 2.31-2.44 (m, 5H), 2.26 (s, 3H), 2.06-2.17 (m, 2H), 1.82-1.95 (m, 2H). |

Example 35

Preparation of Compound 359

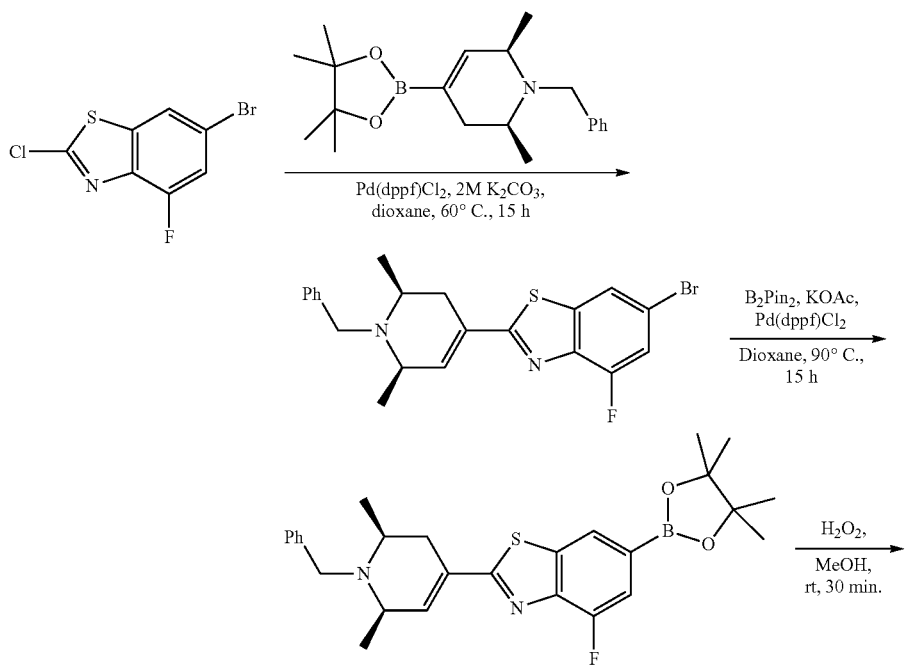

-continued

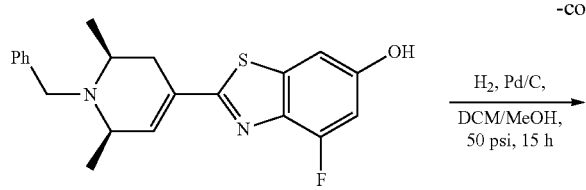 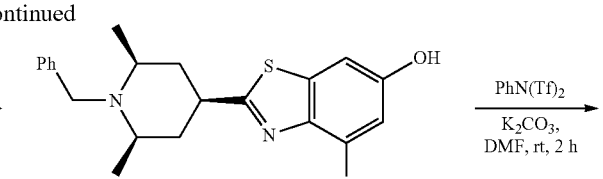

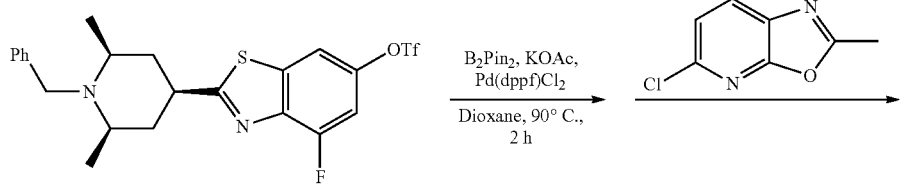

(70%, 2 steps)

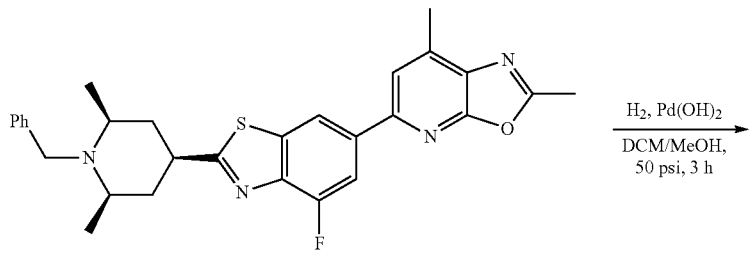

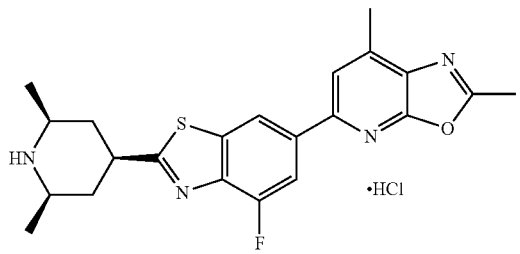

Step 1: 6-Bromo-2-chloro-4-fluorobenzo[d]thiazole (800 mg, 3.0 mmol), (2S,6R)-1-benzyl-2,6-dimethyl-4-(4,4,5,5-tetramethyl-1,3,2-dioxaborolan-2-yl)-1,2,3,6-tetrahydropyridine (1.0 g, 2.75 mmol, 90% purity), Pd(dppf)Cl$_2$—CH$_2$Cl$_2$ (100 mg, 0.12 mmol), dioxane (12 mL), and 2M aqueous K$_2$CO$_3$ (6 mL, 12 mmol) were heated at 60° C. for 15 h. After cooling, the reaction mixture was partitioned between H$_2$O and CH$_2$Cl$_2$. The organic layer was dried over MgSO$_4$, filtered, and then concentrated under vacuum. Purification by silica chromatography (10% EtOAc in hexanes) yielded 2-((2S,6R)-1-benzyl-2,6-dimethyl-1,2,3,6-tetrahydropyridin-4-yl)-6-bromo-4-fluorobenzo[d]thiazole (833 mg, 70%) as a white solid.

$^1$H NMR (methanol-d$_4$) δ: 7.97 (s, 1H), 7.40-7.47 (m, 3H), 7.30-7.35 (m, 2H), 7.20-7.26 (m, 1H), 6.69 (s, 1H), 4.00 (d, J=15.5 Hz, 1H), 3.90 (d, J=15.5 Hz, 1H), 3.50-3.54 (m, 1H), 3.05-3.11 (m, 1H), 2.80-2.86 (m, 1H), 2.48-2.55 (m, 1H), 1.33 (d, J=7 Hz, 3H), 1.26 (d, J=7 Hz, 3H).

Step 2: Potassium acetate (1.25 g, 12.7 mmol) was dried under sweeping argon at 180° C. for 15 minutes and then cooled to room temperature. 2-((2S,6R)-1-benzyl-2,6-dimethyl-1,2,3,6-tetrahydropyridin-4-yl)-6-bromo-4-fluorobenzo[d]thiazole (900 mg, 2.09 mmol), Pd(dppf)Cl$_2$—CH$_2$Cl$_2$ (100 mg, 0.12 mmol), bis(pinacolatodiboron) (800 mg, 3.15 mmol), and dioxane (7 mL) were added. The reaction mixture was heated at 90° C. for 15 h, cooled and then diluted in EtOAc and filtered through Celite. The filtrate was concentrated under vacuum. The crude product was purified by silica chromatography (10-20% EtOAc in CH$_2$Cl$_2$) and then the product was dissolved in ether and filtered to remove red solid impurities. The filtrate was concentrated to provide 2-((2S,6R)-1-benzyl-2,6-dimethyl-1,2,3,6-tetrahydropyridin-4-yl)-4-fluoro-6-(4,4,5,5-tetramethyl-1,3,2-dioxaborolan-2-yl)benzo[d]thiazole (970 mg, 90% purity, 87% yield) as a tan oil.

$^1$H NMR (methanol-d$_4$) δ: 8.10 (s, 1H), 7.49 (d, J=11 Hz, 1H), 7.42-7.46 (m, 2H), 7.31-7.35 (m, 2H), 7.22-7.27 (m, 1H), 6.73 (s, 1H), 4.03 (d, J=15.5 Hz, 1H), 3.91 (d, J=15.5 Hz, 1H), 3.46-3.53 (m, 1H), 3.10 (m, 1H), 2.83-2.89 (m, 1H), 2.52-2.57 (m, 1H), 1.39 (s, 12H), 1.35 (d, J=7 Hz, 3H), 1.27 (d, J=7 Hz, 3H).

Step 3: 2-((2S,6R)-1-Benzyl-2,6-dimethyl-1,2,3,6-tetrahydropyridin-4-yl)-4-fluoro-6-(4,4,5,5-tetramethyl-1,3,2-dioxaborolan-2-yl)benzo[d]thiazole (970 mg, 90% purity, 1.82 mmol) was suspended in MeOH (10 mL) at 0° C. Hydrogen peroxide (0.22 mL, 35%, 2.5 mmol) was added dropwise. The mixture was then stirred at room temperature for 30 min. MeOH was removed under vacuum. Purification by silica chromatography (20-30% EtOAc in CH$_2$Cl$_2$) yielded 2-((2S,6R)-1-benzyl-2,6-dimethyl-1,2,3,6-tetrahydropyridin-4-yl)-4-fluorobenzo[d]thiazol-6-ol (492 mg, 70%) as a light tan solid.

$^1$H NMR (methanol-d$_4$) δ: 7.41-7.45 (m, 2H), 7.31-7.35 (m, 2H), 7.21-7.26 (m, 1H), 7.07 (s, 1H), 6.72 (d, J=12 Hz, 1H), 6.52 (s, 1H), 4.01 (d, J=15.5 Hz, 1H), 3.90 (d, J=15.5 Hz, 1H), 3.45-3.51 (m, 1H), 3.04-3.09 (m, 1H), 2.79-2.84

(m, 1H), 2.45-2.53 (m, 1H), 1.32 (d, J=7 Hz, 3H), 1.27 (d, J=7 Hz, 3H), OH not observed.

Step 4: 2-((2S,6R)-1-Benzyl-2,6-dimethyl-1,2,3,6-tetrahydropyridin-4-yl)-4-fluorobenzo[d]thiazol-6-ol (490 mg, 1.26 mmol), $CH_2Cl_2$ (5 mL), MeOH (5 mL), and 10% palladium on carbon (240 mg) were combined and hydrogenated at 50 psi for 15 h. The mixture was filtered through Celite, using $MeOH/CH_2Cl_2$ to wash the filter pad. The filtrate was concentrated under vacuum. Purification by silica chromatography (95:5:0.5 $CH_2Cl_2/MeOH/NH_4OH$) yielded crude 2-((2S,4r,6R)-1-benzyl-2,6-dimethylpiperidin-4-yl)-4-fluorobenzo[d]thiazol-6-ol (425 mg, ca. 5:1 cis-/trans-).

Step 5: Crude 2-((2S,4r,6R)-1-benzyl-2,6-dimethylpiperidin-4-yl)-4-fluorobenzo[d]thiazol-6-ol (420 mg), $K_2CO_3$ (291 mg, 2.1 mmoL), N,N-bis(trifluoromethylsulfonyl)aniline (593 mg, 1.66 mmol), and DMF (3.8 mL) were stirred at room temperature for 2 h. This was partitioned between $H_2O$ and EtOAc. Purification by silica (10-20% EtOAc in $CH_2Cl_2$) yielded 2-((2S,4r,6R)-1-benzyl-2,6-dimethylpiperidin-4-yl)-4-fluorobenzo[d]thiazol-6-yl trifluoromethanesulfonate (439 mg, 70% over 2 steps) as a brown oil.

$^1H$ NMR (acetone-$d_6$) δ: 8.14 (s, 1H), 7.56 (d, J=13 Hz, 1H), 7.42-7.46 (m, 2H), 7.29-7.33 (m, 2H), 7.17-7.21 (m, 1H), 3.87 (s, 2H), 3.35-3.42 (m, 1H), 2.79-2.83 (m, 2H), 2.15-2.19 (m, 2H), 1.74 (q, J=12 Hz, 2H), 1.13 (d, J=7 Hz, 6H).

Step 6: 2-((2S,4r,6R)-1-Benzyl-2,6-dimethylpiperidin-4-yl)-4-fluorobenzo[d]thiazol-6-yl trifluoromethanesulfonate (100 mg, 0.2 mmol), potassium acetate (70 mg, 0.71 mmol), bis(pinacolatodiboron) (61 mg, 0.24 mmol), $Pd(dppf)Cl_2$—$CH_2Cl_2$ (15 mg, 0.018 mmol), and dioxane (0.8 mL) were heated at 90° C. for 2 h. The reaction mixture was then diluted with EtOAc and was filtered through Celite. The filtrate was then concentrated under vacuum. The product was re-dissolved in $CH_2Cl_2$ and was filtered though celite to remove black insoluble materials. The filtrate was concentrated to afford 160 mg of crude boronic acid. To this boronic acid was added 5-chloro-2,7-dimethyl-oxazolo[5,4-b]pyridine (87 mg, 0.2 mmol), $Pd(dppf)Cl_2$—$CH_2Cl_2$ (10 mg, 0.012 mmol), dioxane (0.7 mL) and 2M aqueous $K_2CO_3$ (0.35 mL, 0.7 mmol). This mixture was heated at 90° C. for 1 h. The reaction mixture was then partitioned between $CH_2Cl_2$ and $H_2O$. The organic layer was dried over $MgSO_4$, filtered, and concentrated under vacuum. Purification by silica chromatography (20-30% EtOAc in $CH_2Cl_2$), followed by trituration with ether/hexanes, yielded 5-(2-((2S,4r,6R)-1-benzyl-2,6-dimethylpiperidin-4-yl)-4-fluorobenzo[d]thiazol-6-yl)-2,7-dimethyloxazolo[5,4-b]pyridine (63 mg, 60%).

$^1H$ NMR (acetone-$d_6$) δ: 8.63 (s, 1H), 8.06 (d, J=12.5 Hz, 1H), 7.98 (s, 1H), 7.48 (m, 2H), 7.31 (m, 2H), 7.19 (m, 1H), 3.87 (s, 2H), 3.32-3.40 (m, 1H), 2.80 (m, 2H, obscured by HDO peak), 2.69 (s, 3H), 2.67 (s, 3H), 2.16-2.20 (m, 2H), 1.75 (q, J=12 Hz, 2H), 1.14 (d, J=6 Hz, 6H).

Step 7: 5-(2-((2S,4r,6R)-1-Benzyl-2,6-dimethylpiperidin-4-yl)-4-fluorobenzo[d]thiazol-6-yl)-2,7-dimethyloxazolo[5,4-b]pyridine (61 mg, 0.12 mmol) was dissolved in $CH_2Cl_2$ (1 mL) and methanol (1 mL). $Pd(OH)_2$ (20% on C, 200 mg) was added. This was hydrogenated at 50 psi for 3 h, during which time HCl is generated from catalytic reduction of dichloromethane. The mixture was filtered through Celite and rinsed with $CH_2Cl_2/MeOH$. The filtrate was concentrated under vacuum and purified by silica chromatography (5-10% MeOH in $CH_2Cl_2$). Trituration with 9:1 $CH_2Cl_2/MeOH$ yielded title product (28 mg, 49% yield) as an off-white solid.

MS m/z 411.3 [M+H]$^+$; $^1H$ NMR (methanol-$d_4$) δ: 8.52 (s, 1H), 8.01 (d, J=12 Hz, 1H), 7.88 (s, 1H), 3.65 (m, 1H), 3.45 (m, 2H), 2.71 (s, 3H), 2.68 (s, 3H), 2.50 (m, 2H), 1.85 (q, J=13 Hz, 2H), 1.45 (d, J=6.5 Hz, 6H).

Example 36

Preparation of Compound 329

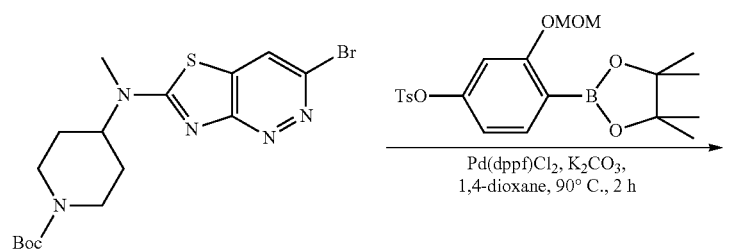

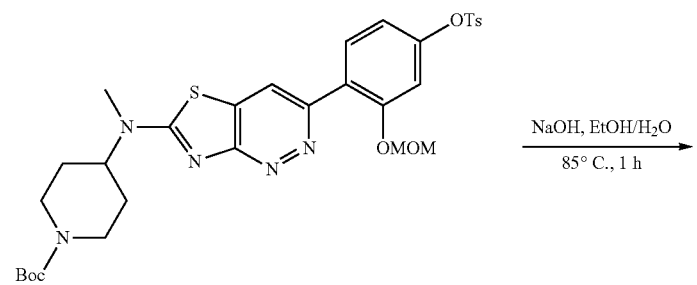

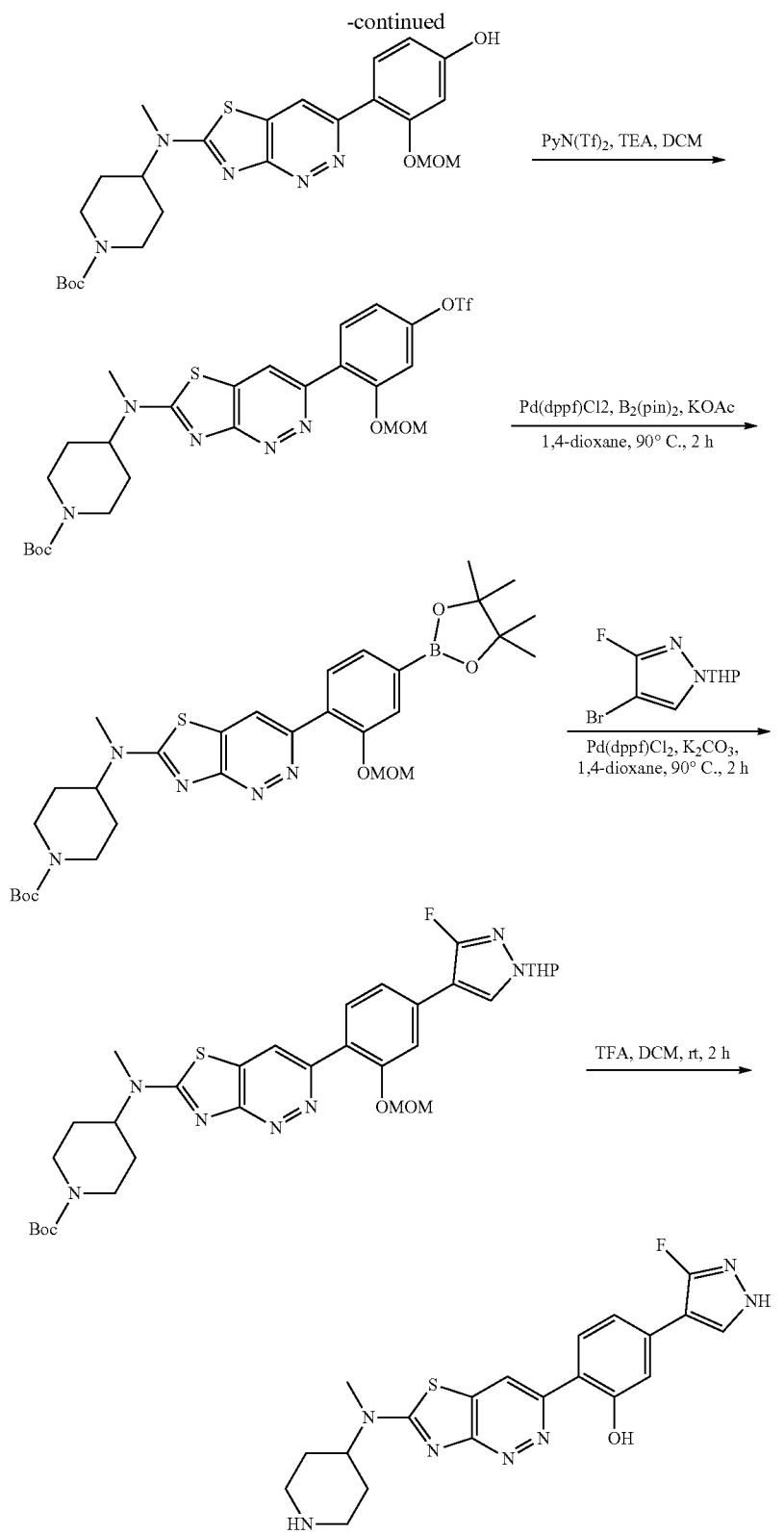

Step 1: A mixture of tert-butyl 4-((3-bromothiazolo[4,5-c]pyridazin-6-yl)(methyl)amino)piperidine-1-carboxylate (427 mg, 1 mmol), prepared according to the procedure starting from 2-amino-6-bromopyridazine described in Example 34, 3-(methoxymethoxy)-4-(4,4,5,5-tetramethyl-1,3,2-dioxaborolan-2-yl)phenyl 4-methylbenzenesulfonate (434 mg, 1 mmol), Pd (dppf)Cl₂ (73 mg, 0.1 mmol) and K₂CO₃ (345 mg, 2.5 mmol) in a mixture of 1,4-dioxane (4 mL) and water (1 mL) was stirred at 90° C. under N₂ for 2 h. The solution was concentrated and the residue was purified by flash column chromatography eluting with 5% MeOH in CH$_2$Cl$_2$ to afford the desired compound tert-butyl 4-((3-(2-(methoxymethoxy)-4-(tosyloxy)phenyl)thiazolo[4,5-c]pyridazin-6-yl)(methyl)amino)piperidine-1-carboxylate (393 mg, 60% yield). MS m/z: 656 [M+H]$^+$.

Step 2: A mixture of tert-butyl 4-((3-(2-(methoxymethoxy)-4-(tosyloxy)phenyl)thiazolo[4,5-c]pyridazin-6-yl)(methyl)amino)piperidine-1-carboxylate (400 mg, 0.61 mmol) and NaOH (122 mg, 3.05 mmol) in EtOH (3 mL) and water (1 mL) was stirred at 85° C. for 1 h. The solution was concentrated and the residue was purified by flash column chromatography eluting with 5%-10% MeOH in CH$_2$Cl$_2$ to afford the desired compound tert-butyl 4-((3-(4-hydroxy-2-(methoxymethoxy)phenyl)thiazolo[4,5-c]pyridazin-6-yl)(methyl)amino)piperidine-1-carboxylate (269 mg, 88% yield) as a white solid. MS m/z: 502 [M+H]$^+$.

Step 3: To a mixture of tert-butyl 4-((3-(4-hydroxy-2-(methoxymethoxy)phenyl)thiazolo[4,5-c]pyridazin-6-yl)(methyl)amino)piperidine-1-carboxylate (269 mg, 0.54 mmol) and Et$_3$N (227 µL, 1.63 mmol) in CH$_2$Cl$_2$ (2 mL) was added PhNTf$_2$ (289 mg, 0.81 mmol). The resulting mixture was stirred at room temperature for 16 h. The solution was concentrated and the residue was purified by flash column chromatography eluting with 5% MeOH in CH$_2$Cl$_2$ to afford the desired compound tert-butyl 4-((3-(2-(methoxymethoxy)-4-(((trifluoromethyl)sulfonyl)oxy)phenyl)thiazolo[4,5-c]pyridazin-6-yl)(methyl)amino)piperidine-1-carboxylate (214 mg, 65% yield) as a white solid. MS m/z: 634 [M+H]$^+$.

Step 4: A mixture of tert-butyl 4-((3-(2-(methoxymethoxy)-4-(((trifluoromethyl)sulfonyl)oxy)phenyl)thiazolo[4,5-c]pyridazin-6-yl)(methyl)amino)piperidine-1-carboxylate (214 mg, 0.34 mmol), B$_2$(pin)$_2$ (104 mg, 0.41 mmol), Pd (dppf)Cl$_2$ (25 mg, 0.034 mmol) and KOAc (100 mg, 1.02 mmol) in dioxane (3 mL) was stirred at 95° C. under N$_2$ for 2 h to afford a mixture containing tert-butyl 4-((3-(2-(methoxymethoxy)-4-(4,4,5,5-tetramethyl-1,3,2-dioxaborolan-2-yl)phenyl)thiazolo[4,5-c]pyridazin-6-yl)(methyl)amino)piperidine-1-carboxylate, which was used in next step without any work-up. MS m/z: 612 [M+H]$^+$.

Step 5: A mixture of tert-butyl 4-((3-(2-(methoxymethoxy)-4-(4,4,5,5-tetramethyl-1,3,2-dioxaborolan-2-yl)phenyl)thiazolo[4,5-c]pyridazin-6-yl)(methyl)amino)piperidine-1-carboxylate obtained in step 4 (1.3 mL mixture from step 4, 0.15 mmol theoretically), 4-bromo-3-fluoro-1-(tetrahydro-2H-pyran-2-yl)-1H-pyrazole (37 mg, 0.15 mmol), Pd (dppf)Cl$_2$ (11 mg, 0.015 mmol) and K$_2$CO$_3$ (62 mg, 0.45 mmol) in a mixture of 1,4-dioxane (0.8 mL) and water (0.2 mL) was stirred at 95° C. under N$_2$ for 2 h. The solution was concentrated and the residue was purified by prep-HPLC to afford tert-butyl 4-((3-(4-(3-fluoro-1-(tetrahydro-2H-pyran-2-yl)-1H-pyrazol-4-yl)-2-(methoxymethoxy)phenyl)thiazolo[4,5-c]pyridazin-6-yl)(methyl)amino)piperidine-1-carboxylate (58 mg, 70% yield). MS m/z: 654 [M+H]$^+$.

Step 6: To a solution of tert-butyl 4-((3-(4-(3-fluoro-1-(tetrahydro-2H-pyran-2-yl)-1H-pyrazol-4-yl)-2-(methoxymethoxy)phenyl)thiazolo[4,5-c]pyridazin-6-yl)(methyl)amino)piperidine-1-carboxylate (58 mg, 0.09 mmol) in CH$_2$Cl$_2$ (1 mL) was added TFA (1 mL). The mixture was stirred at room temperature for 2 h. The solution was concentrated, and the residue was basified by excess NH$_3$ in MeOH. The volatiles were removed again, and the residue was purified by prep-HPLC to afford 5-(3-fluoro-1H-pyrazol-4-yl)-2-(6-(methyl(piperidin-4-yl)amino)thiazolo[4,5-c]pyridazin-3-yl)phenol (17 mg, 46% yield).

MS m/z: 426 [M+H]$^+$; $^1$H NMR (DMSO-d$_6$) δ 8.94 (s, 1H), 8.30 (d, J=2.1 Hz, 1H), 7.94 (d, J=8.5 Hz, 1H), 7.20 (d, J=7.6 Hz, 2H), 3.16 (s, 3H), 3.06 (d, J=13.4 Hz, 2H), 2.95-2.86 (m, 1H), 2.69-2.55 (m, 2H), 1.82-1.64 (m, 4H), 2NH and OH protons not observed.

Using the procedure described for Example 36, above, additional compounds described herein were prepared by substituting the appropriate starting material, suitable reagents and reaction conditions, obtaining compounds such as those selected from:

| Cpd | Data |
|---|---|
| 331 | MS m/z 446.1 [M + H]$^+$; $^1$H NMR (methanol-d$_4$) δ: 8.50 (br s, 1H), 8.33-8.31 (m, 1H), 7.97-7.92 (m, 2H), 7.58 (dd, J = 12.1, 6.2 Hz, 1H), 7.45 (s, 1H), 3.47 (d, J = 13.1 Hz, 2H), 3.32 (s, 1H), 3.29-3.15 (m, 3H), 3.05 (t, J = 12.3 Hz, 2H), 2.26-2.13 (m, 2H), 2.10-1.99 (m, 2H). |
| 333 | MS m/z 408.0 [M + H]$^+$; $^1$H NMR (DMSO-d$_6$) δ: 13.90 (s, 1H), 13.02 (s, 1H), 8.95 (s, 1H), 8.31 (s, 1H), 8.01 (s, 1H), 7.90 (d, 7 = 8.4 Hz, 1H), 7.26-7.22 (m, 2H), 4.90-4.05 (br s, 2H), 2.89-2.72 (m, 4H), 1.07 (d, 7 = 5.6 Hz, 6H), 1 NH proton not observed. |
| 334 | MS m/z 380.1; [M + H]$^+$; $^1$H NMR (DMSO-d$_6$) δ: 13.85 (s, 1H), 13.02 (s, 1H), 8.96 (s, 1H), 8.31 (br s, 1H), 8.01 (br s, 1H), 7.89 (d, J = 9.0 Hz, 1H), 7.32-7.21 (m, 2H), 5.30-4.30 (br s, 1H), 3.74 (s, 4H), 3.02-2.88 (m, 4H). |
| 338 | MS m/z 420.4; [M + H]$^+$; $^1$H NMR (DMSO-d$_6$) δ: 9.41 (s, 2H), 9.07 (s, 1H), 8.14 (s, 2H), 7.76 (d, J = 8.2 Hz, 1H), 7.31 (s, 1H), 7.29 (d, J = 8.2 Hz, 1H), 4.35 (d, J = 8.4 Hz, 2H), 4.10 (d, J = 9.4 Hz, 2H), 3.42-3.29 (m, 2H), 3.03-2.90 (m, 2H), 2.01-1.88 (m, 2H), 1.82-1.71 (m, 2H), 1 NH proton not observed. |
| 341 | MS m/z 438.2 [M + H]$^+$; $^1$H NMR (DMSO-d$_6$) δ: 13.75 (br s, 1H), 12.74 (br s, 1H), 8.95 (s, 1H), 8.39 (s, 1H), 8.29 (d, J = 1.2 Hz, 1H), 7.91 (d, J = 8.4 Hz, 1H), 7.26-7.17 (m, 2H), 4.04 (s, 4H), 2.83 (s, 4H), 1.84 (s, 4H). |
| 344 | MS m/z 420.4 [M + H]$^+$; $^1$H NMR (DMSO-d$_6$) δ: 9.16 (br s, 1H), 9.03 (s, 1H), 8.92 (br s, 1H), 8.14 (s, 2H), 7.82 (d, J = 8.5 Hz, 1H), 7.31-7.24 (m, 2H), 4.46 (br s, 1H), 3.79 (br s, 1H), 3.64 (br s, 1H), 3.39-3.19 (m, 3H), 3.07-2.96 (m, 1H), 2.77-2.68 (m, 1H), 2.53-2.35 (m, 2H), 2.18-2.07 (m, 1H), 1.92 (br s, 1H), 1 NH not observed. |
| 345 | MS m/z 436.3 [M + H]$^+$; $^1$H NMR (DMSO-d$_6$) δ: 9.11 (br s, 2H), 9.05 (s, 1H), 8.14 (s, 2H) 7.77 (d, J = 8.1 Hz, 1H), 7.31-7.26 (m, 2H), 4.56 (br s, 1H), 3.20 (s, 3H), 3.05-2.93 (m, 1H), 2.54 (t, J = 5.4 Hz, 3H), 2.21 (d, J = 11.3 Hz, 2H), 1.96-1.87 (m, 2H), 1.82 (q, J = 11-2, 10.4 Hz, 2H), 1.68-1.55 (m, 2H), 1 NH not observed. |
| 346 | MS m/z 412.1 [M + H]$^+$; $^1$H NMR (DMSO-d$_6$) δ: 8.83 (s, 1H), 8.23 (s, 1H), 8.10 (br s, 2H), 7.87 (d, J = 8.4 Hz, 1H), 7.28-7.19 (m, 2H), 5.56-5.35 (m, 1H), 5.00 (br s, 1H), 3.50-3.24 (m, 4H), 3.22 (s, 3H), 2 NH protons not observed. |

| Cpd | Data |
|---|---|
| 348 | MS m/z 408.3 [M + H]⁺; ¹H NMR (DMSO-d₆) δ: 9.78 (br s, 1H), 9.31 (br s, 1H), 9.11 (s, 1H), 8.15 (s, 2H), 7.78 (d, J = 8.2 Hz, 1H), 7.32 (s, 1H), 7.29 (dd, J = 8.2, 1.7 Hz, 1H), 4.97 (br s, 1H), 3.42-3.12 (m, 6H), 2.86 (q, J = 12.5, 12.1 Hz, 1H), 2.14-1.78 (m, 4H), 1 NH proton not observed. |
| 349 | MS m/z 408.3 [M + H]⁺; ¹H NMR (DMSO-d₆) δ: 9.77 (s, 1H), 9.12 (s, 1H), 8.16 (s, 2H), 7.78 (d, J = 8.2 Hz, 1H), 7.32 (s, 1H), 7.29 (d, J = 8.2 Hz, 1H), 4.97 (br s, 1H), 3.41-3.17 (m, 6H), 2.86 (q, J = 13.5, 13.0 Hz, 1H), 2.07-1.80 (m, 4H), NH and OH protons not observed. |
| 350 | MS m/z 408.3; [M + H]⁺; ¹H NMR (DMSO-d₆) δ: 2:1 mixture of diastereomers δ: 13.78 (br s, 0.7H), 13.11 (br s, 0.3H), 9.04 (br s, 2H), 8.96 (s, 1H), 8.15 (s, 2H), 7.88 (d, J = 7.9 Hz, 1H), 7.29-7.19 (m, 2H), 5.24 (br s, 0.7H), 4.71 (br s, 0.3H), 3.70 (s, 0.7H), 3.56-3.45 (m, 0.3H), 3.28 (s, 2H), 3.26 (s, 1H), 2.89-2.75 (m, 1.7H), 2.69-2.61 (m, 0.3H), 2.61-2.51 (m, 5H), |
| 353 | MS m/z 380.3; [M + H]⁺; ¹H NMR (DMSO-d₆) δ: 2:1 mixture of rotamers δ: 9.28-8.97 (m, 2H), 8.28 (br s, 1H), 8.15 (s, 2H), 7.86 (d, J = 6.5 Hz, 1H), 7.28 (s, 1H), 5.37 (br s, 0.7H), 5.21 (br s, 0.3H), 4.40 (br s, 2H), 4.26 (br s, 2H), 3.38 (s, 2H), 3.22 (s, 1H), 1 NH and OH protons not observed. |
| 354 | MS m/z 420.4 [M + H]⁺; ¹H NMR (DMSO-d₆) δ: 9.36 (br s, 1H), 9.05 (s, 1H), 8.67 (br s, 1H), 8.15 (s, 2H), 7.80 (d, J = 8.2 Hz, 1H), 7.34-7.26 (m, 2H), 4.22 (s, 2H), 3.41 (d, J = 12.6 Hz, 2H), 2.94 (q, J = 11.6, 11.2 Hz, 2H), 2.68 (br s, 2H), 2.50-2.44 (m, 2H), 2.19 (d, J = 13.1 Hz, 2H), 1 NH proton not observed. |
| 355 | MS m/z 436.4 [M + H]⁺; ¹H NMR (DMSO-d₆) δ: 9.51 (br s, 1H), 9.10 (s, 1H), 8.78 (br s, 1H), 8.16 (s, 2H), 7.80 (d, J = 8.1 Hz, 1H), 7.35-7.26 (m, 2H), 4.97 (br s, 1H), 3.39-3.30 (m, 1H), 3.31-3.12 (m, 4H), 3.06 (s, 2H), 2.45-2.28 (m, 1H), 1.93 (d, J = 13.9 Hz, 1H), 1.26 (s, 3H), 1.03 (s, 3H), 1 NH proton not observed. |
| 356 | MS m/z 420.4 [M + H]⁺; ¹H NMR (DMSO-d₆) δ: 9.05 (s, 1H), 8.27 (br s, 2H), 8.14 (s, 2H), 7.89-7.77 (m, 1H), 7.33-7.23 (m, 2H), 4.72 (br s, 1H), 4.14-3.89 (m, 2H), 3.43-3.06 (m, 5H), 2.68-2.55 (m, 2H), 2.49-2.27 (m, 2H), 1 NH proton not observed. |
| 357 | MS m/z 394.1 [M + H]⁺; ¹H NMR (DMSO-d₆) δ: 8.82 (s, 1H), 8.39 (s, 1H), 8.14 (br s, 2H), 7.86 (d, J = 8.8 Hz, 1H), 7.28-7.21 (m, 2H), 4.14 (br s, 1H), 3.28-3.14 (m, 2H), 3.00-2.84 (m, 2H), 2.20-2.15 (m, 2H), 1.75-1.56 (m, 2H), 2 NH protons not observed. |
| 358 | MS m/z 426.0; [M + H]⁺; ¹H NMR (DMSO-d₆) δ: 8.97 (s, 1H), 8.26 (s, 1H), 8.15 (s, 2H), 7.89 (d, J = 8.8 Hz, 1H), 7.29-7.23 (m, 2H), 4.96 (d, J = 50.4 Hz, 1H), 4.95-4.57 (br s, 1H), 3.35-3.30 (m, 1H), 3.22 (s, 3H), 3.20-3.05 (m, 2H), 2.98-2.68 (m, 2H), 2.21-2.07 (m, 1H), 1.76-1.65 (m, 1H), 1NH proton not observed. |
| 361 | MS m/z 408.5 [M + H]⁺; ¹H NMR (DMSO-d₆) δ: 9.67 (br s, 2H), 9.09 (s, 1H), 8.15 (s, 2H), 7.77 (d, J = 8.1 Hz, 1H), 7.31 (s, 1H), 7.29 (d, J = 8.4 Hz, 1H), 5.07-4.23 (m, 1H), 3.54-3.45 (m, 1H), 3.41 (s, 3H), 2.74 (q, J = 9.7, 9.2 Hz, 2H), 2.69-2.59 (m, 2H), 2.49-2.40 (m, 3H), 1 NH proton not observed. |
| 362 | MS m/z 420.3 [M + H]⁺; ¹H NMR (DMSO-d₆) δ: 9.16 (br s, 1H), 9.08 (br s, 1H), 9.05 (s, 1H), 8.15 (s, 2H), 7.83 (d, J = 8.7 Hz, 1H), 7.30-7.26 (m, 2H), 4.52 (br s, 1H), 3.75 (br s, 1H), 3.61 (br s, 1H), 3.53 (br s, 2H), 3.15-3.04 (m, 2H), 2.68 (br s, 1H), 2.21 (br s, 1H), 2.16-2.03 (m, 2H), 1.85 (d, J = 13.5 Hz, 1H), 1 NH not observed. |
| 363 | MS m/z 420.4 [M + H]⁺; ¹H NMR (DMSO-d₆) δ: 9.79 (s, 1H), 9.42 (d, J = 9.8 Hz, 1H), 9.06 (s, 1H), 8.15 (s, 2H), 7.78 (d, J = 8.2 Hz, 1H), 7.30 (d, J = 1.4 Hz, 1H), 7.28 (dd, J = 8.2, 1.6 Hz, 1H), 4.24 (dd, J = 7.7 Hz, 2H), 3.75-3.67 (m, 1H), 3.61-3.52 (m, 1H), 3.21-3.15 (m, 1H), 2.96 (q, J = 11.7 Hz, 1H), 2.76 (dt, J = 11.2, 7.7 Hz, 1H), 2.48-2.40 (m, 1H), 2.37 (dt, J = 11.3, 7.8 Hz, 1H), 2.16 (d, J = 12.8 Hz, 1H), 2.01-1.90 (m, 1H), 1.82-1.70 (m, 1H), 1 NH proton not observed. |
| 365 | MS m/z 426.0; [M + H]⁺; ¹H NMR (DMSO-d₆) δ: 8.90 (s, 1H), 8.29-8.04 (br s, 2H), 8.19 (s, 1H), 7.89 (d, J = 8.8 Hz, 1H), 7.28-7.22 (m, 2H), 4.80 (m, 2H), 3.36-3.15 (m, 4H), 3.00-2.91 (m, 1H), 2.65-2.55 (m, 2H), 1.91-1.79 (m, 2H), NH protons not observed. |
| 367 | MS m/z 380.1 [M + H]⁺; ¹H NMR (DMSO-d₆) δ: 8.87 (s, 1H), 8.35 (s, 1H), 8.15 (br s, 2H), 7.87 (d, J = 8.4 Hz, 1H), 7.29-7.24 (m, 2H), 4.63 (s, 1H), 3.41-3.31 (m, 2H), 3.20-3.07 (m, 3H), 2.25 (m, 1H), 1.99 (m, 1H), NH and OH protons not observed. |
| 368 | MS m/z 410.3 [M + H]⁺; ¹H NMR (DMSO-d₆) δ: 8.85 (s, 1H), 8.39 (s, 2H), 8.23 (s, 1H), 7.92 (d, J = 8 Hz, 1H), 7.21 (s, 1H), 4.48-4.44 (m, 4H), 4.22-3.95 (m, 4H), 2 NH protons not observed. |
| 371 | MS m/z 438.4 [M + H]⁺; ¹H NMR (DMSO-d₆) δ: 9.83 (br s, 1H), 9.10 (s, 1H), 8.78 (br d, J = 10.1 Hz, 1H), 8.16 (s, 2H), 7.78 (d, J = 8.2 Hz, 1H), 7.32 (d, J = 1.5 Hz, 1H), 7.31-7.26 (m, 1H), 4.74 (br s, 1H), 3.94 (dd, J = 11.6, 8.3 Hz, 1H), 3.77 (dd, J = 11.6, 5.1 Hz, 1H), 3.67-3.60(m, 1H), 3.41-3.30 (m, 1H), 3.30-3.18 (m, 4H), 2.42-2.24 (m, 2H), 1.97 (d, J = 12.6 Hz, 2H), NH proton not observed. |
| 374 | MS m/z 394.1; [M + H]⁺; ¹H NMR (DMSO-d₆) δ: 8.98 (s, 1H), 8.15 (s, 2H), 7.88 (d, J = 8.8 Hz, 1H), 7.29-7.24 (m, 2H), 5.23 (br s, 1H), 3.55 (m, 1H), 3.40-3.22 (m, 3H), 3.21 (s, 3H), 2.40-2.28 (m, 1H), 2.25-2.12 (m, 1H), 2 NH and OH protons not observed. |
| 376 | MS m/z 408.5 [M + H]⁺; ¹H NMR (methanol-d₄) δ: 9.05 (s, 1H), 8.15 (s, 2H), 7.74 (d, J = 8.1 Hz, 1H), 7.35 (d, J = 8.3 Hz, 1H), 7.27 (s, 1H), 5.41 (br s, 1H), 3.98-3.84 (m, 1H), 3.46 (br s, 3H), 3.04 (dt, J = 16.0, 8.2 Hz, 2H), 2.82-2.74 (m, 2H), 2.72 (s, 3H), 2 NH and OH protons not observed. |
| 381 | MS m/z 411.9 [M + H]⁺; ¹H NMR (DMSO-d₆) δ: 8.92 (s, 1H), 8.13 (s, 2H), 7.88 (d, J = 8.8 Hz, 1H), 7.29-7.20 (m, 2H), 5.33 (d, J = 52.0 Hz, 1H), 5.12-4.80 (br s, 1H), 3.58-3.25 (m, 5H), 3.15 (s, 3H), NH and OH protons not observed. |

-continued

| Cpd | Data |
|---|---|
| 386 | MS m/z 406.3 [M + H]⁺; ¹H NMR (methanol-d₄) δ: 8.77 (br s, 1H), 8.01 (s, 2H), 7.83 (d, J = 7.2 Hz, 1H), 7.29-7.12 (m, 2H), 5.03-4.96 (m, 1H), 4.51-4.33 (m, 1H), 4.11-3.92 (m, 2H), 3.65-3.54 (m, 1H), 3.47 (d, J = 16.4 Hz, 1H), 3.18-3.03 (m, 2H), 2.44-2.31 (m, 1H), 2.14-2.01 (m, 1H), 2NH and OH protons not observed. |
| 387 | MS m/z 411.9; [M + H]⁺; ¹H NMR (DMSO-d₆) δ: 8.94 (s, 1H), 8.32 (s, 1H), 8.28 (s, 1H), 7.93 (d, J = 8.4 Hz, 1H), 7.24-7.16 (m, 2H), 5.50-4.80 (br s, 1H), 3.35-2.95 (m, 5H), 3.19 (s, 3H), 2.27-2.14 (m, 1H), 2.07-1.92 (m, 1H), 1 NH proton not observed. |
| 389 | MS m/z 406.2 [M + H]⁺; ¹H NMR (methanol-d₄) δ: 8.82 (s, 1H), 8.02 (s, 2H), 7.82 (d, J = 9.2 Hz, 1H), 7.27-7.18 (m, 2H), 5.02-4.97 (m, 1H), 4.47-4.39 (m, 1H), 4.09-3.97 (m, 2H), 3.63-3.55 (m, 1H), 3.48 (d, J = 13.3 Hz, 1H), 3.27-3.23 (m, 1H), 3.16-3.07 (m, 1H), 2.45-2.34 (m, 1H), 2.15-2.03 (m, 1H), 2NH and OH protons not observed. |
| 394 | MS m/z 422.4 [M + H]⁺; ¹H NMR (methanol-d₄) δ: δ: 8.79 (s, 1H), 8.03 (s, 2H), 7.81 (d, J = 8.2 Hz, 1H), 7.24 (d, J = 9.4 Hz, 1H), 7.22 (s, 1H), 4.81 (br s, 1H), 3.63-3.55 (m, 1H), 3.53-3.43 (m, 1H), 3.32-3.27 (m, 1H), 3.25 (s, 3H), 2.27-2.12 (m, 3H), 1.99 (q, J = 12.3 Hz, 1H), 1.42 (d, J = 6.5 Hz, 3H), 2NH and OH protons not observed. |
| 396 | MS m/z 422.4 [M + H]⁺; ¹H NMR (methanol-d₄) δ: δ: 8.83 (s, 1H), 8.03 (s, 2H), 7.81 (d, J = 8.2 Hz, 1H), 7.26 (d, J = 8.2 Hz, 1H), 7.23 (s, 1H), 4.91 (br s, 1H), 4.05-3.95 (m, 1H), 3.52-3.39 (m, 2H), 3.26 (s, 3H), 2.37 (td, J = 12.9, 5.2 Hz, 1H), 2.26-2.12 (m, 2H), 2.03 (d, J = 14.0 Hz, 1H), 1.57 (d, J = 7.1 Hz, 3H), NH and OH protons not observed. |
| 398 | MS m/z 439.2; [M + H]⁺; ¹H NMR (DMSO-d₆) δ: 8.92 (s, 1H), 8.27 (d, J = 2.0 Hz, 1H), 7.93 (d, J = 8.8 Hz, 1H), 7.24-7.16 (m, 2H), 4.83 (br s, 1H), 3.35-3.03 (m, 7H), 2.24-1.76 (m, 6H), 2NH and OH protons not observed. |

Example 37

Preparation of 328

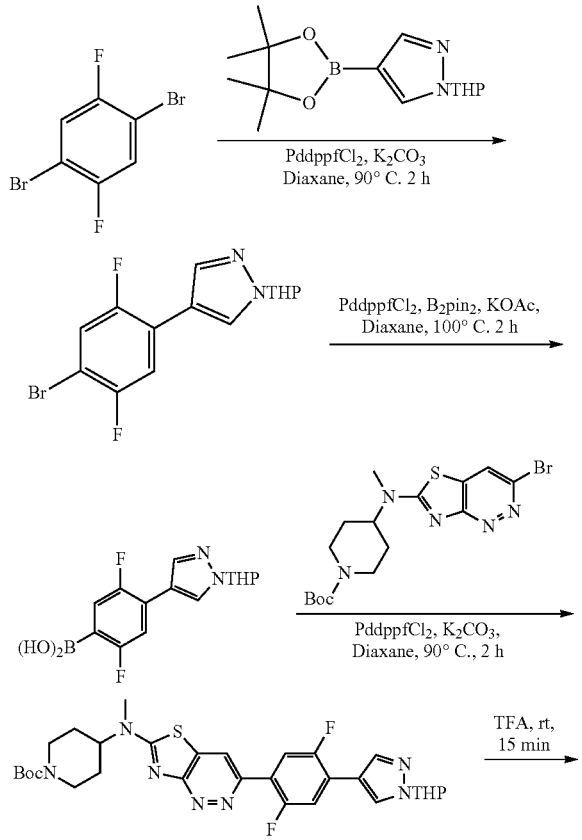

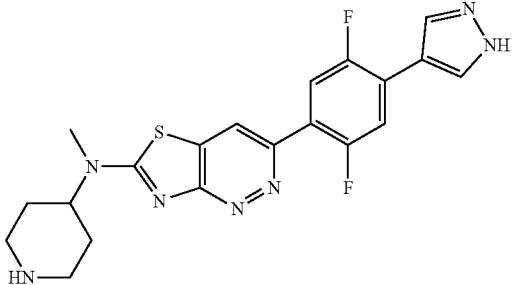

Step 1: A mixture of 4-(4-bromo-2,5-difluorophenyl)-1-(tetrahydro-2H-pyran-2-yl)-1H-pyrazole (1.0 g, 3.7 mmol), 1-(tetrahydro-2H-pyran-2-yl)-4-(4,4,5,5-tetramethyl-1,3,2-dioxaborolan-2-yl)-1H-pyrazole (1.24 g, 4.4 mmol), Pd(dppf)Cl₂ (267 mg, 0.37 mmol) and K₂CO₃ (1.02 mg, 7.4 mmol) in dioxane-H₂O (12 mL, 9/3, v/v) was stirred at 90° C. under N₂ for 2 h. The solution was concentrated, and the residue was purified by silica gel chromatography, eluting with 10%-20% EtOAc in petroleum ether to give 4-(4-bromo-2,5-difluorophenyl)-1-(tetrahydro-2H-pyran-2-yl)-1H-pyrazole as light-yellow solid (470 mg, 37% yield). MS m/z: 343, 345 [M+H]⁺.

Step 2: A mixture of 4-(4-bromo-2,5-difluorophenyl)-1-(tetrahydro-2H-pyran-2-yl)-1H-pyrazole (100 mg, 0.29 mmol), B₂(Pin)₂ (89 mg, 0.35 mmol), Pd (dppf)Cl₂ (22 mg, 0.03 mmol) and KOAc (57 mg, 0.58 mmol) in dioxane (5 mL) was stirred at 90° C. under N₂ for 2 h. The resulting solution was used in the next step without purification. MS m/z: 309 [M+H]⁺.

Step 3: The reaction mixture from step 2 and tert-butyl 4-((3-bromothiazolo[4,5-c]pyridazin-6-yl)(methyl)amino)piperidine-1-carboxylate (139 mg, 0.32 mmol), Pd (dppf)Cl₂ (24 mg, 0.03 mmol) and K₂CO₃ (88 mg, 0.64 mmol) in dioxane-H₂O (5 mL, 9/3, v/v) was stirred at 90° C. under N₂ for 2 h. The solution was concentrated, and the residue was purified by silica gel chromatography eluting with 20%-30%

EtOAc in petroleum ether to give tert-butyl 4-((3-(2,5-difluoro-4-(1-(tetrahydro-2H-pyran-2-yl)-1H-pyrazol-4-yl)phenyl)thiazolo[4,5-c]pyridazin-6-yl)(methyl)amino)piperidine-1-carboxylate as light-yellow solid (50 mg, 35% yield). MS m/z: 612 [M+H]$^+$.

Step 4: tert-Butyl 4-((3-(2,5-difluoro-4-(1-(tetrahydro-2H-pyran-2-yl)-1H-pyrazol-4-yl)phenyl)thiazolo[4,5-c]pyridazin-6-yl)(methyl)amino)piperidine-1-carboxylate (80 mg, 0.13 mmol) was dissolved in TFA (1 mL). After 15 min, the volatiles were removed. To the above residue was added NH$_3$-MeOH (15 ml) and the resultant mixture was stirred at room temperature for 1 h. The volatiles were then removed again under reduced pressure. The residue was purified by Prep-HPLC to afford 3-(2,5-difluoro-4-(1H-pyrazol-4-yl)phenyl)-N-methyl-N-(piperidin-4-yl)thiazolo[4,5-c]pyridazin-6-amine as a white solid (22 mg, 39% yield).

MS m/z: 428 [M+H]$^+$; $^1$H NMR (DMSO-d$_6$) δ: 8.55 (s, 1H), 8.32 (s, 2H), 7.92-7.83 (m, 2H), 3.20-3.14 (m, 6H), 2.77-2.72 (m, 2H), 1.86-1.76 (m, 4H), 2NH protons not observed.

Example 38

Preparation of 327

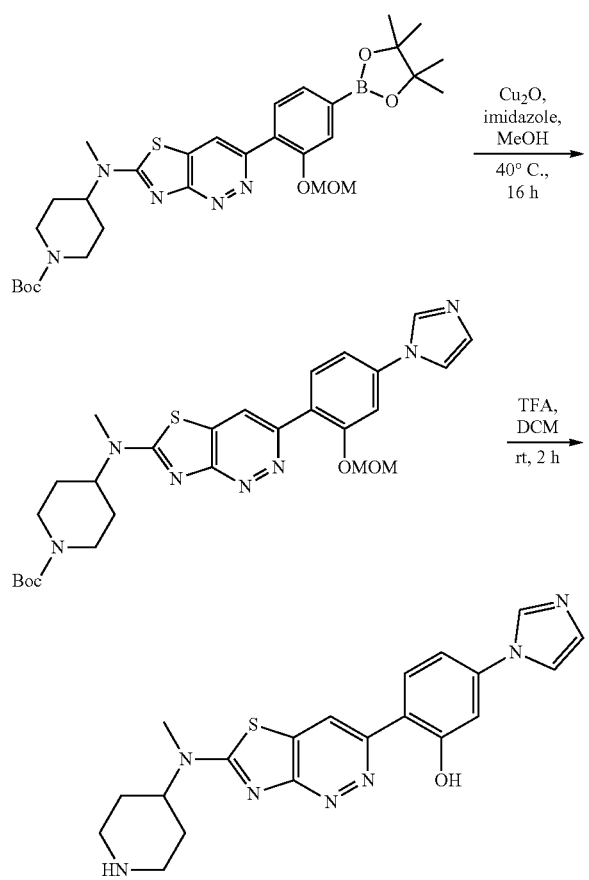

Step 1: A mixture of tert-butyl 4-((3-(2-(methoxymethoxy)-4-(4,4,5,5-tetramethyl-1,3,2-dioxaborolan-2-yl)phenyl)thiazolo[4,5-c]pyridazin-6-yl)(methyl)amino)piperidine-1-carboxylate (90 mg, 0.15 mmol), prepared according to the procedure described in Example 37, imidazole (20 mg, 0.3 mmol) and Cu$_2$O (4 mg, 0.03 mmol) in MeOH (2 mL) was stirred at 40° C. under air for 16 h. The solution was concentrated and the residue was purified by prep-TLC eluting with 7% MeOH in CH$_2$Cl$_2$ to afford tert-butyl 4-((3-(4-(1H-imidazol-1-yl)-2-(methoxymethoxy)phenyl)thiazolo[4,5-c]pyridazin-6-yl)(methyl)amino)piperidine-1-carboxylate (49 mg, 60% yield). MS m/z: 552 [M+H]$^+$.

Step 2: To a solution tert-butyl 4-((3-(4-(1H-imidazol-1-yl)-2-(methoxymethoxy)phenyl)thiazolo[4,5-c]pyridazin-6-yl)(methyl)amino)piperidine-1-carboxylate (49 mg, 0.09 mmol) in CH$_2$Cl$_2$ (1 mL) was added TFA (1 mL). The mixture was stirred at room temperature for 2 h. The solution was concentrated, and the residue was basified by excess of NH$_3$ in MeOH. The volatiles were removed and the residue was purified by prep-HPLC to afford 5-(1H-imidazol-1-yl)-2-(6-(methyl(piperidin-4-yl)amino)thiazolo[4,5-c]pyridazin-3-yl)phenol (15 mg, 42% yield).

MS m/z: 408.2 [M+H]$^+$; $^1$H NMR (DMSO-d$_6$) δ: 9.02 (s, 1H), 8.41 (s, 1H), 8.29 (s, 1H), 8.06 (d, J=8.6 Hz, 1H), 7.88 (s, 1H), 7.42-7.26 (m, 2H), 7.13 (s, 1H), 3.27 (d, J=11.3 Hz, 3H), 3.16 (s, 3H), 2.99-2.87 (m, 2H), 2.03-1.79 (m, 4H), 1NH proton not observed.

BIOLOGICAL EXAMPLES

The following in vitro biological examples demonstrate the usefulness of the compounds of the present description for treating Huntington's disease.

To describe in more detail and assist in understanding the present description, the following non-limiting biological examples are offered to more fully illustrate the scope of the description and are not to be construed as specifically limiting the scope thereof. Such variations of the present description that may be now known or later developed, which would be within the purview of one skilled in the art to ascertain, are considered to fall within the scope of the present description and as hereinafter claimed.

Compounds of Formula (I) or Formula (II) were tested using the Meso Scale Discovery (MSD) Assay provided in International Application No. PCT/US2016/066042, filed on Dec. 11, 2016 and claiming priority to U.S. Provisional Application 62/265,652 filed on Dec. 10, 2015, the entire contents of which are incorporated herein by reference.

The Endogenous Huntingtin Protein assay used in Example 1 was developed using the ELISA-based MSD electrochemiluminescence assay platform.

Example 1

Endogenous Huntingtin Protein Assay

Meso Scale Discovery (MSD) 96-well or 384-well plates were coated overnight at 4° C. with MW1 (expanded polyglutamine) or MAB2166 monoclonal antibody (for capture) at a concentration of 1 μg/mL in PBS (30 μL per well). Plates were then washed three times with 300 μL wash buffer (0.05% Tween-20 in PBS) and blocked (100 μL blocking buffer; 5% BSA in PBS) for 4-5 hours at room temperature with rotational shaking and then washed three times with wash buffer.

Samples (25 μL) were transferred to the antibody-coated MSD plate and incubated overnight at 4° C. After removal of the lysates, the plate was washed three times with wash buffer, and 25 μL of #5656S (Cell signaling; rabbit monoclonal) secondary antibody (diluted to 0.25 μg/mL in 0.05% Tween-20 in blocking buffer) was added to each well and incubated with shaking for 1 Hour at room temperature. Following incubation with the secondary antibody, the wells were rinsed with wash buffer after which 25 µL of goat anti-rabbit SULFO TAG secondary detection antibody (required aspect of the MSD system) (diluted to 0.25 µg/mL in 0.05% Tween-20 in blocking buffer) was added to each well and incubated with shaking for 1 hour at room temperature. After rinsing three times with wash buffer, 150 µL of read buffer T with surfactant (MSD) were added to each empty well, and the plate was imaged on a SI 6000 imager (MSD) according to manufacturers' instructions provided for 96- or 384-well plates. The resulting $IC_{50}$ values (µM) for compounds tested are shown in Table 1.

As shown in Table 1, test compounds described herein had the following $IC_{50}$ values, an $IC_{50}$ value between >3 µM and ≤9 µM is indicated by a single star (*), an $IC_{50}$ value between >1 µM and ≤3 µM is indicated by two stars (), an $IC_{50}$ value between >0.5 µM and ≤1 µM is indicated by three stars (*), an $IC_{50}$ value between >0.1 µM and ≤0.5 µM is indicated by four stars (**) and an $IC_{50}$ value of ≤0.1 µM is indicated by five stars (***).

TABLE 1

| Cpd | $IC_{50}$ |
| --- | --- |
| 1 | **** |
| 2 | **** |
| 3 | *** |
| 4 | **** |
| 5 | *** |
| 6 | ** |
| 7 | ** |
| 8 | **** |
| 9 | ** |
| 10 | ** |
| 11 | ** |
| 12 | ** |
| 13 | *** |
| 14 | ** |
| 15 | ** |
| 16 | *** |
| 17 | **** |
| 18 | **** |
| 19 | **** |
| 20 | ***** |
| 21 | **** |
| 22 | ***** |
| 23 | ***** |
| 24 | ***** |
| 25 | **** |
| 26 | *** |
| 27 | *** |
| 28 | ** |
| 29 | ** |
| 30 | **** |
| 31 | ***** |
| 32 | ***** |
| 33 | ***** |
| 34 | **** |
| 35 | **** |
| 36 | **** |
| 37 | ***** |
| 38 | ** |
| 39 | ***** |
| 40 | ***** |
| 41 | ** |
| 42 | **** |
| 43 | **** |
| 44 | ***** |
| 45 | ***** |
| 46 | ***** |
| 47 | ***** |
| 48 | **** |
| 49 | **** |
| 50 | **** |
| 51 | **** |
| 52 | ** |
| 53 | **** |
| 54 | **** |
| 55 | ***** |
| 56 | *** |
| 57 | ***** |
| 58 | *** |
| 59 | **** |
| 60 | **** |
| 61 | ***** |
| 62 | ***** |
| 63 | **** |
| 64 | ** |
| 65 | **** |
| 66 | ***** |
| 67 | ** |
| 68 | ** |
| 70 | ***** |
| 71 | **** |
| 72 | **** |
| 73 | ***** |
| 74 | ***** |
| 75 | **** |
| 76 | **** |
| 77 | **** |
| 78 | *** |
| 79 | ***** |
| 80 | ** |
| 81 | **** |
| 82 | **** |
| 83 | ***** |
| 84 | ***** |
| 85 | **** |
| 86 | ***** |
| 87 | ***** |
| 88 | ***** |
| 89 | *** |
| 90 | **** |
| 91 | ***** |
| 92 | ***** |
| 93 | **** |
| 94 | ***** |
| 95 | **** |
| 96 | **** |
| 97 | ***** |
| 98 | **** |
| 99 | ** |
| 100 | *** |
| 101 | **** |
| 102 | ***** |
| 103 | ***** |
| 104 | ***** |
| 105 | **** |
| 106 | ***** |
| 107 | ***** |
| 108 | *** |
| 109 | **** |
| 110 | **** |
| 111 | ***** |
| 112 | **** |
| 113 | ***** |
| 114 | ***** |
| 115 | *** |
| 116 | **** |
| 117 | ***** |
| 118 | **** |
| 119 | ***** |
| 120 | ***** |
| 121 | ***** |
| 122 | **** |
| 123 | ***** |
| 124 | ***** |
| 125 | **** |
| 126 | ***** |
| 127 | ***** |
| 128 | **** |
| 129 | *** |
| 130 | ***** |
| 131 | ***** |
| 132 | ***** |

TABLE 1-continued

| Cpd | IC$_{50}$ |
|---|---|
| 133 | ***** |
| 134 | **** |
| 135 | ***** |
| 136 | **** |
| 137 | * |
| 138 | ***** |
| 139 | ***** |
| 140 | ***** |
| 141 | ***** |
| 142 | **** |
| 143 | **** |
| 144 | ***** |
| 145 | ***** |
| 146 | **** |
| 147 | ***** |
| 148 | ***** |
| 149 | **** |
| 150 | ***** |
| 151 | ***** |
| 152 | ***** |
| 153 | ** |
| 154 | ** |
| 155 | **** |
| 156 | ** |
| 157 | ***** |
| 158 | **** |
| 161 | ** |
| 162 | ***** |
| 163 | ***** |
| 164 | ***** |
| 165 | ***** |
| 166 | ***** |
| 167 | ***** |
| 168 | ***** |
| 169 | **** |
| 170 | ***** |
| 171 | ***** |
| 172 | ** |
| 173 | ** |
| 174 | ** |
| 175 | ***** |
| 176 | ***** |
| 177 | ***** |
| 178 | ***** |
| 179 | ***** |
| 180 | **** |
| 181 | **** |
| 182 | *** |
| 183 | ***** |
| 184 | ** |
| 185 | ***** |
| 186 | ***** |
| 187 | ***** |
| 188 | ***** |
| 189 | **** |
| 190 | ** |
| 191 | ** |
| 192 | ***** |
| 193 | ***** |
| 194 | ***** |
| 195 | ***** |
| 196 | ***** |
| 197 | **** |
| 198 | ***** |
| 199 | ***** |
| 200 | ***** |
| 201 | **** |
| 202 | ***** |
| 203 | ***** |
| 204 | ***** |
| 205 | ***** |
| 206 | ***** |
| 207 | ***** |
| 208 | ***** |
| 209 | ***** |
| 210 | *** |
| 211 | ***** |
| 212 | ***** |

TABLE 1-continued

| Cpd | IC$_{50}$ |
|---|---|
| 213 | ***** |
| 214 | ***** |
| 215 | ***** |
| 216 | **** |
| 217 | ***** |
| 218 | **** |
| 219 | ** |
| 220 | ***** |
| 221 | ***** |
| 222 | ***** |
| 223 | **** |
| 224 | ***** |
| 225 | ***** |
| 226 | ***** |
| 227 | ** |
| 228 | *** |
| 229 | ***** |
| 230 | ***** |
| 231 | ***** |
| 232 | ***** |
| 233 | ***** |
| 234 | ***** |
| 235 | ***** |
| 236 | ***** |
| 237 | **** |
| 238 | ***** |
| 239 | **** |
| 240 | **** |
| 241 | **** |
| 242 | **** |
| 243 | **** |
| 244 | ** |
| 245 | ** |
| 246 | ** |
| 247 | **** |
| 248 | **** |
| 249 | ***** |
| 250 | **** |
| 251 | ***** |
| 252 | ***** |
| 253 | ***** |
| 254 | ***** |
| 255 | ***** |
| 256 | ***** |
| 257 | ***** |
| 258 | ***** |
| 259 | ***** |
| 260 | ***** |
| 261 | ***** |
| 262 | ***** |
| 263 | ***** |
| 264 | ***** |
| 265 | ***** |
| 266 | **** |
| 267 | **** |
| 268 | **** |
| 269 | **** |
| 270 | ***** |
| 271 | **** |
| 272 | **** |
| 273 | *** |
| 274 | ***** |
| 275 | ***** |
| 276 | ***** |
| 277 | **** |
| 278 | ***** |
| 279 | ***** |
| 280 | ***** |
| 281 | ***** |
| 282 | ***** |
| 283 | *** |
| 284 | ***** |
| 285 | ***** |
| 286 | ***** |
| 287 | ***** |
| 288 | **** |
| 289 | ***** |
| 290 | ***** |

TABLE 1-continued

| Cpd | IC$_{50}$ |
|---|---|
| 291 | ***** |
| 292 | ***** |
| 293 | ***** |
| 294 | **** |
| 295 | **** |
| 296 | ***** |
| 297 | ***** |
| 298 | ***** |
| 299 | ***** |
| 300 | ***** |
| 301 | ***** |
| 303 | ***** |
| 304 | **** |
| 305 | *** |
| 306 | ***** |
| 307 | ***** |
| 308 | ** |
| 309 | ***** |
| 310 | ***** |
| 311 | ***** |
| 312 | **** |
| 313 | **** |
| 314 | **** |
| 315 | **** |
| 316 | **** |
| 317 | ***** |
| 318 | ***** |
| 319 | ***** |
| 320 | ***** |
| 321 | ***** |
| 322 | ***** |
| 323 | ***** |
| 324 | ***** |
| 325 | ***** |
| 326 | ***** |
| 327 | **** |
| 328 | **** |
| 329 | ***** |
| 332 | ***** |
| 334 | **** |
| 335 | ** |
| 336 | ** |
| 337 | *** |
| 338 | *** |
| 339 | ***** |
| 340 | ** |
| 341 | *** |
| 342 | **** |
| 343 | **** |
| 344 | ***** |
| 345 | **** |
| 346 | **** |
| 347 | ** |
| 348 | **** |
| 349 | ***** |
| 350 | **** |
| 351 | ** |
| 352 | ***** |
| 353 | **** |
| 354 | ***** |
| 355 | ***** |
| 356 | **** |
| 357 | **** |
| 358 | *** |
| 359 | ***** |
| 361 | **** |
| 362 | ***** |
| 363 | ***** |
| 364 | ** |
| 365 | **** |
| 366 | ***** |
| 367 | **** |
| 368 | **** |
| 369 | **** |
| 370 | ***** |
| 371 | ***** |
| 372 | ***** |
| 373 | ***** |

TABLE 1-continued

| Cpd | IC$_{50}$ |
|---|---|
| 374 | ***** |
| 375 | ***** |
| 376 | **** |
| 377 | **** |
| 378 | **** |
| 379 | ***** |
| 380 | **** |
| 381 | **** |
| 382 | **** |
| 383 | ***** |
| 384 | ***** |
| 385 | ***** |
| 386 | ***** |
| 387 | ***** |
| 388 | **** |
| 389 | ***** |
| 390 | ***** |
| 391 | ***** |
| 392 | ** |
| 393 | ** |
| 394 | ***** |
| 395 | ***** |
| 396 | ***** |
| 397 | ***** |
| 398 | ***** |
| 399 | ***** |

Without regard to whether a document cited herein was specifically and individually indicated as being incorporated by reference, all documents referred to herein are incorporated by reference into the present application for any and all purposes to the same extent as if each individual reference was fully set forth herein.

Having now fully described the subject matter of the claims, it will be understood by those having ordinary skill in the art that the same can be performed within a wide range of equivalents without affecting the scope of the subject matter or particular aspects described herein. It is intended that the appended claims be interpreted to include all such equivalents.

What is claimed is:

1. A method for treating or ameliorating Huntington's Disease in a subject in need thereof comprising administering to the subject an effective amount of a compound of Formula (I):

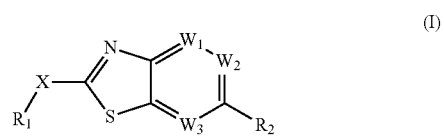

or a form thereof, wherein:
W$_1$, W$_2$ and W$_3$ are independently C—R$_a$ or N;
R$_a$ is, in each instance, independently selected from the group consisting of hydrogen, cyano, halogen, hydroxy, C$_{1-6}$alkyl, halo-C$_{1-6}$alkyl, C$_{1-6}$alkyl-carbonyl, C$_{1-6}$alkoxy, halo-C$_{1-6}$alkoxy, C$_{1-6}$alkoxy-C$_{1-6}$alkyl, C$_{1-6}$alkoxy-carbonyl, amino, C$_{1-6}$alkyl-amino, (C$_{1-6}$alkyl)$_2$-amino, amino-C$_{1-6}$alkyl, and hydroxy-C$_{1-6}$alkyl;
X is selected from the group consisting of N—R$_b$, O, and a bond;
R$_b$ is selected from the group consisting of hydrogen and C$_{1-6}$alkyl;

$R_1$ is selected from the group consisting of $C_{3-10}$cycloalkyl and heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and wherein each instance of $C_{3-10}$cycloalkyl and heterocyclyl is optionally substituted with one, two three, or four $R_3$ substituents and optionally, with one additional $R_4$ substituent, or, wherein, alternatively, each instance of $C_{3-10}$cycloalkyl and heterocyclyl is optionally substituted with one, two, three, four, or five $R_3$ substituents;

$R_2$ is selected from the group consisting of phenyl and heteroaryl, wherein heteroaryl is selected from the group consisting of furanyl, 1H-imidazolyl, 1H-1,2,3-triazolyl, 4H-1,2,4-triazolyl, pyridazinyl, pyrimidinyl, pyrazinyl, 1H-indolyl, 2H-indolyl, 1H-indazolyl, 2H-indazolyl, indolizinyl, benzofuranyl, 1H-benzimidazolyl, 1,3-benzoxazolyl, furo[2,3-b]pyridinyl, furo[2,3-c]pyridinyl, furo[3,2-b]pyridinyl, furo[3,2-c]pyridinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, 1H-pyrazolo[4,3-b]pyridinyl, 2H-pyrazolo[4,3-b]pyridinyl, 2H-pyrazolo[4,3-c]pyridinyl, pyrazolo[1,5-a]pyrazinyl, pyrazolo[1,5-a]pyrimidinyl, imidazo[1,2-a]pyridinyl, imidazo[1,2-a]pyrimidinyl, imidazo[1,2-a]pyraziny, imidazo[1,2-b]pyridazinyl, imidazo[1,2-c]pyrimidinyl, imidazo[1,5-a]pyridinyl, imidazo[2,1-b][1,3]thiazolyl, imidazo[2,1-b][1,3,4]thiadiazoly, [1,3]oxazolo[4,5-b]pyridinyl, [1,2,4]triazolo[1,5-a]pyridinyl, [1,2,4]triazolo[1,5-b]pyridazinyl, and quinolinyl, wherein each instance of phenyl and heteroaryl is optionally substituted with one, two or three $R_5$ substituents and optionally, with one additional $R_6$ substituent, or, wherein, alternatively, each instance of phenyl and heteroaryl is optionally substituted with one, two, three or four $R_5$ substituents;

$R_3$ is, in each instance, independently selected from the group consisting of cyano, halogen, hydroxy, $C_{1-6}$alkyl, halo-$C_{1-6}$alkyl, $C_{1-6}$alkyl-carbonyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, amino-$C_{1-6}$alkyl, and hydroxy-$C_{1-6}$alkyl;

$R_4$ is selected from the group consisting of $C_{3-10}$cycloalkyl, phenyl, heterocyclyl, and heteroaryl;

wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, wherein heteroaryl is a 3-7 membered monocyclic or 6-10 membered bicyclic ring system having 1, 2, 3, or 4 heteroatom ring members independently selected from N, O, or S, and wherein each instance of $C_{3-10}$cycloalkyl, phenyl, heterocyclyl, and heteroaryl is optionally substituted with one, two or three $R_7$ substituents;

$R_5$ is, in each instance, independently selected from the group consisting of cyano, halogen, hydroxy, $C_{1-6}$alkyl, halo-$C_{1-6}$alkyl, $C_{1-6}$alkyl-carbonyl, $C_{1-6}$alkoxy, halo-$C_{1-6}$alkoxy, $C_{1-6}$alkoxy-$C_{1-6}$alkyl, $C_{1-6}$alkoxy-carbonyl, $C_{1-6}$alkoxy-carbonyl-$C_{1-6}$alkyl, carboxyl, $C_{1-6}$alkyl-carboxyl, amino, $C_{1-6}$alkyl-amino, $(C_{1-6}$alkyl$)_2$-amino, amino-$C_{1-6}$alkyl, amino-carbonyl, and hydroxy-$C_{1-6}$alkyl;

$R_6$ is selected from the group consisting of $C_{3-10}$cycloalkyl, phenyl, phenyl-$C_{1-6}$alkoxy, phenyl-oxy, heterocyclyl, and heteroaryl;

wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, wherein heteroaryl is a 3-7 membered monocyclic or 6-10 membered bicyclic ring system having 1, 2, 3, or 4 heteroatom ring members independently selected from N, O, or S, and wherein, each instance of $C_{3-10}$cycloalkyl, phenyl, heterocyclyl, and heteroaryl is optionally substituted with one, two or three $R_7$ substituents; and $R_7$ is, in each instance, independently selected from the group consisting of cyano, halogen, hydroxy, $C_{1-6}$alkyl, halo-$C_{1-6}$alkyl, $C_{1-6}$alkyl-carbonyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, $(C_{1-6}$alkyl$)_2$-amino, amino-$C_{1-6}$alkyl, and hydroxy-$C_{1-6}$alkyl;

wherein a form of the compound is selected from the group consisting of a salt, hydrate, solvate, racemate, enantiomer, diastereomer, stereoisomer, and tautomer form thereof.

2. The method of claim 1, wherein $R_1$ is heterocyclyl selected from the group consisting of azetidinyl, tetrahydrofuranyl, pyrrolidinyl, piperidinyl, piperazinyl, 1H-azepinyl, 2,3,6,7-tetrahydro-1H-azepinyl, azepanyl, 1,4-diazepanyl, 1,2,5,6-tetrahydropyridinyl, 1,2,3,6-tetrahydropyridinyl, octahydroindolizinyl, octahydro-1H-pyrrolo[3,2-c]pyridinyl, (3aS,7aR)-octahydro-1H-pyrrolo[3,2-c]pyridinyl, 1-azabicyclo[2.2.2]octyl, 3-azabicyclo[3.1.0]hexyl, (1R,5S)-3-azabicyclo[3.1.0]hexyl, 3-azabicyclo[3.2.1]octyl, 8-azabicyclo[3.2.1]octyl, (1R,5S)-8-azabicyclo[3.2.1]octyl, 8-azabicyclo[3.2.1]oct-2-en-yl, (1R,5S)-8-azabicyclo[3.2.1]oct-2-en-yl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 1,4-diazabicyclo[3.1.1]heptyl, 3,6-diazabicyclo[3.2.0]heptyl, 2,5-diazabicyclo[2.2.2]octyl, 1,4-diazabicyclo[3.2.1]octyl, 3,8-diazabicyclo[3.2.1]octyl, (1R,5S)-3,8-diazabicyclo[3.2.1]octyl, 1,4-diazabicyclo[3.2.2]nonyl, 3,8-diazabicyclo[4.2.0]octyl, (1S,6R)-3,8-diazabicyclo[4.2.0]octyl, (1R,6S)-3,8-diazabicyclo[4.2.0]octyl, 2-azaspiro[3.3]heptyl, 4,7-diazaspiro[2.5]octyl, 2,6-diazaspiro[3.3]heptyl, 2,6-diazaspiro[3.4]octyl, 1,6-diazaspiro[3.5]nonyl, 1,7-diazaspiro[3.5]nonyl, 2,6-diazaspiro[3.5]nonyl, 2,7-diazaspiro[3.5]nonyl, 5,8-diazaspiro[3.5]nonyl, 1,7-diazaspiro[4.4]nonyl, 2,7-diazaspiro[4.4]nonyl, 2,7-diazaspiro[4.5]decyl, and 6,9-diazaspiro[4.5]decyl, wherein heterocyclyl is optionally substituted with one, two three, or four $R_3$ substituents and optionally, with one additional $R_4$ substituent, or, alternatively, wherein heterocyclyl is optionally substituted with one, two, three, four, or five $R_3$ substituents.

3. The method of claim 1, wherein $R_2$ is heteroaryl selected from the group consisting of furanyl, 1H-imidazolyl, 1H-1,2,3-triazolyl, 4H-1,2,4-triazolyl, pyridazinyl, pyrimidinyl, pyrazinyl, 1H-indolyl, 2H-indolyl, 1H-indazolyl, 2H-indazolyl, indolizinyl, benzofuranyl, 1H-benzimidazolyl, 1,3-benzoxazolyl, furo[2,3-b]pyridinyl, furo[2,3-c]

pyridinyl, furo[3,2-b]pyridinyl, furo[3,2-c]pyridinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, 1H-pyrazolo[4,3-b]pyridinyl, 2H-pyrazolo[4,3-b]pyridinyl, 2H-pyrazolo[4,3-c]pyridinyl, pyrazolo[1,5-a]pyrazinyl, pyrazolo[1,5-a]pyrimidinyl, imidazo[1,2-a]pyridinyl, imidazo[1,2-a]pyrimidinyl, imidazo[1,2-a]pyrazinyl, imidazo[1,2-b]pyridazinyl, imidazo[1,2-c]pyrimidinyl, imidazo[1,5-a]pyridinyl, imidazo[2,1-b][1,3]thiazolyl, imidazo[2,1-b][1,3,4]thiadiazolyl, [1,3]oxazolo[4,5-b]pyridinyl, [1,2,4]triazolo[1,5-a]pyridnyl, [1,2,4]triazolo[1,5-b]pyridazinyl, and quinolinyl, wherein heteroaryl is optionally substituted with one, two or three $R_5$ substituents and optionally, with one additional $R_6$ substituent, or, alternatively, wherein heteroaryl is optionally substituted with one, two, three or four $R_5$ substituents.

4. The method of claim 1, wherein the form of the compound is a compound salt selected from the group consisting of hydrochloride, hydrobromide, trifluoroacetate, formate, and dihydrochloride salts.

5. A method for treating or ameliorating Huntington's Disease in a subject in need thereof comprising administering to the subject an effective amount of a compound, or a form thereof, selected from the group consisting of:

- 6-(2-methyl-2H-indazol-5-yl)-2-(1,2,3,6-tetrahydropyridin-4-yl)-1,3-benzothiazole;
- 6-(2-methyl-2H-indazol-5-yl)-2-(piperidin-4-yl)-1,3-benzothiazole;
- 6-(2-methyl-2H-indazol-5-yl)-2-(1-methyl-1,2,3,6-tetrahydropyridin-4-yl)-1,3-benzothiazole;
- 6-(2-methyl-2H-indazol-5-yl)-2-(piperazin-1-yl)-1,3-benzothiazole;
- N-methyl-6-(2-methyl-2H-indazol-5-yl)-N-(piperidin-4-yl)-1,3-benzothiazol-2-amine;
- 6-(2-methyl-2H-indazol-5-yl)-2-(1-methylpiperidin-4-yl)-1,3-benzothiazole;
- N-methyl-6-(2-methyl-2H-indazol-5-yl)-N-(piperidin-4-yl)[1,3]thiazolo[4,5-b]pyridin-2-amine;
- 6-(2,7-dimethyl-2H-indazol-5-yl)-N-methyl-N-(piperidin-4-yl)[1,3]thiazolo[4,5-b]pyridin-2-amine;
- 6-(2,7-dimethyl-2H-indazol-5-yl)-N-(piperidin-4-yl)[1,3]thiazolo[4,5-b]pyridin-2-amine;
- 6-(2-methyl-2H-indazol-5-yl)-N-(piperidin-4-yl)[1,3]thiazolo[4,5-b]pyridin-2-amine;
- N-methyl-6-(2-methyl-2H-indazol-5-yl)-N-(2,2,6,6-tetramethylpiperidin-4-yl)[1,3]thiazolo[4,5-b]pyridin-2-amine;
- 6-(2,7-dimethyl-2H-indazol-5-yl)-N-methyl-N-(2,2,6,6-tetramethylpiperidin-4-yl)[1,3]thiazolo[4,5-b]pyridin-2-amine;
- 6-(2,7-dimethyl-2H-indazol-5-yl)-2-(1,2,3,6-tetrahydropyridin-4-yl)-1,3-benzothiazole;
- N-methyl-6-(2-methyl-2H-indazol-5-yl)-N-(2,2,6,6-tetramethylpiperidin-4-yl)-1,3-benzothiazol-2-amine;
- 6-(2,7-dimethyl-2H-indazol-5-yl)-N-methyl-N-(2,2,6,6-tetramethylpiperidin-4-yl)-1,3-benzothiazol-2-amine;
- 6-(2,7-dimethyl-2H-indazol-5-yl)-2-(piperidin-4-yl)-1,3-benzothiazole
- 4-fluoro-N-methyl-6-(2-methyl-2H-indazol-5-yl)-N-(2,2,6,6-tetramethylpiperidin-4-yl)-1,3-benzothiazol-2-amine;
- 6-(2,7-dimethyl-2H-indazol-5-yl)-4-fluoro-N-methyl-N-(2,2,6,6-tetramethylpiperidin-4-yl)-1,3-benzothiazol-2-amine;
- N-methyl-5-(2-methyl-2H-indazol-5-yl)-N-(2,2,6,6-tetramethylpiperidin-4-yl)[1,3]thiazolo[5,4-b]pyridin-2-amine;
- N-methyl-5-(2-methyl-2H-indazol-5-yl)-N-(piperidin-4-yl)[1,3]thiazolo[5,4-b]pyridin-2-amine;
- N-methyl-6-(2-methyl-2H-indazol-5-yl)-N-(piperidin-4-yl)[1,3]thiazolo[4,5-c]pyridin-2-amine;
- N,N-dimethyl-1-[6-(2-methyl-2H-indazol-5-yl)-1,3-benzothiazol-2-yl]piperidin-4-amine;
- 1-[6-(2-methyl-2H-indazol-5-yl)-1,3-benzothiazol-2-yl]piperidin-4-amine;
- 6-(2,7-dimethyl-2H-indazol-5-yl)-N-methyl-N-(piperidin-4-yl)[1,3]thiazolo[4,5-c]pyridin-2-amine;
- 6-(2,7-dimethyl-2H-indazol-5-yl)-N-methyl-N-(2,2,6,6-tetramethylpiperidin-4-yl)[1,3]thiazolo[4,5-c]pyridin-2-amine;
- N-methyl-6-(2-methyl-2H-indazol-5-yl)-N-(2,2,6,6-tetramethylpiperidin-4-yl)[1,3]thiazolo[4,5-c]pyridin-2-amine;
- 6-(2,8-dimethylimidazo[1,2-a]pyridin-6-yl)-N-methyl-N-(2,2,6,6-tetramethylpiperidin-4-yl)-1,3-benzothiazol-2-amine;
- 6-(1H-indazol-5-yl)-N-methyl-N-(2,2,6,6-tetramethylpiperidin-4-yl)-1,3-benzothiazol-2-amine;
- 6-(2-methyl-2H-indazol-5-yl)-N-(piperidin-4-yl)-1,3-benzothiazol-2-amine;
- 5-(2,7-dimethyl-2H-indazol-5-yl)-N-methyl-N-(piperidin-4-yl)[1,3]thiazolo[5,4-b]pyridin-2-amine;
- 4-fluoro-N-methyl-6-(2-methylimidazo[1,2-b]pyridazin-6-yl)-N-(2,2,6,6-tetramethylpiperidin-4-yl)-1,3-benzothiazol-2-amine;
- N-methyl-6-(2-methyl-2H-indazol-5-yl)-N-(pyrrolidin-3-yl)-1,3-benzothiazol-2-amine;
- 6-(2,8-dimethylimidazo[1,2-a]pyridin-6-yl)-4-fluoro-N-methyl-N-(2,2,6,6-tetramethylpiperidin-4-yl)-1,3-benzothiazol-2-amine;
- N-methyl-6-(2-methylimidazo[1,2-b]pyridazin-6-yl)-N-(2,2,6,6-tetramethylpiperidin-4-yl)-1,3-benzothiazol-2-amine;
- 2-(4-fluoropiperidin-4-yl)-6-(2-methyl-2H-indazol-5-yl)-1,3-benzothiazole;
- 2-(azepan-4-yl)-6-(2-methyl-2H-indazol-5-yl)-1,3-benzothiazole;
- 6-[4-fluoro-2-(1,2,3,6-tetrahydropyridin-4-yl)-1,3-benzothiazol-6-yl]-2-methylimidazo[1,2-b]pyridazine;
- 6-[4-fluoro-2-(piperidin-4-yl)-1,3-benzothiazol-6-yl]-2-methylimidazo[1,2-b]pyridazine;
- 6-[4-fluoro-2-(1,2,3,6-tetrahydropyridin-4-yl)-1,3-benzothiazol-6-yl]-2,8-dimethylimidazo[1,2-b]pyridazine;
- 6-[4-fluoro-2-(piperidin-4-yl)-1,3-benzothiazol-6-yl]-2,8-dimethylimidazo[1,2-b]pyridazine;
- N-methyl-6-(2-methyl[1,2,4]triazolo[1,5-b]pyridazin-6-yl)-N-(2,2,6,6-tetramethylpiperidin-4-yl)-1,3-benzothiazol-2-amine;
- N-methyl-6-[2-methyl-7-(trifluoromethyl)-2H-indazol-5-yl]-N-(2,2,6,6-tetramethylpiperidin-4-yl)-1,3-benzothiazol-2-amine;
- 6-(2-methyl-2H-indazol-5-yl)-2-(2,2,6,6-tetramethylpiperidin-4-yl)-1,3-benzothiazole;
- 6-[4-fluoro-2-(1,2,3,6-tetrahydropyridin-4-yl)-1,3-benzothiazol-6-yl]-2,8-dimethylimidazo[1,2-a]pyrazine;
- 6-(7-ethyl-2-methyl-2H-indazol-5-yl)-N-methyl-N-(2,2,6,6-tetramethylpiperidin-4-yl)-1,3-benzothiazol-2-amine;
- 6-(1,3-dimethylpyrrolo[1,2-a]pyrazin-7-yl)-N-methyl-N-(2,2,6,6-tetramethylpiperidin-4-yl)-1,3-benzothiazol-2-amine;

6-(2-methyl-2H-indazol-5-yl)-2-(2,3,6,7-tetrahydro-1H-azepin-4-yl)-1,3-benzothiazole;

6-(7-fluoro-2-methyl-2H-indazol-5-yl)-N-methyl-N-(2,2,6,6-tetramethylpiperidin-4-yl)-1,3-benzothiazol-2-amine;

6-(2-methyl-2H-indazol-5-yl)-2-(2-methylpiperidin-4-yl)-1,3-benzothiazole;

6-(2,7-dimethyl-2H-indazol-5-yl)-2-(piperidin-4-yl)[1,3]thiazolo[4,5-c]pyridine;

6-[2-methyl-7-(trifluoromethyl)-2H-indazol-5-yl]-2-(piperidin-4-yl)[1,3]thiazolo[4,5-c]pyridine;

6-(2,8-dimethylimidazo[1,2-b]pyridazin-6-yl)-2-(piperidin-4-yl)[1,3]thiazolo[4,5-b]pyridine;

2-methyl-5-{2-[methyl(2,2,6,6-tetramethylpiperidin-4-yl)amino]-1,3-benzothiazol-6-yl}-2H-indazole-7-carbonitrile;

N-methyl-6-(2-methylimidazo[1,2-a]pyridin-6-yl)-N-(2,2,6,6-tetramethylpiperidin-4-yl)-1,3-benzothiazol-2-amine;

6-(2-methyl-2H-indazol-5-yl)-2-[(2,2,6,6-tetramethylpiperidin-4-yl)oxy]-1,3-benzothiazole;

6-(2-methyl-2H-indazol-5-yl)-2-(2-methyl-1,2,3,6-tetrahydropyridin-4-yl)-1,3-benzothiazole;

6-(2,7-dimethyl-2H-indazol-5-yl)-N-methyl-N-(2-methylpiperidin-4-yl)-1,3-benzothiazol-2-amine;

6-(2-methyl-2H-indazol-5-yl)-2-(6-methyl-1,2,3,6-tetrahydropyridin-4-yl)-1,3-benzothiazole;

6-(2,7-dimethyl-2H-indazol-5-yl)-2-[(2,2,6,6-tetramethylpiperidin-4-yl)oxy]-1,3-benzothiazole;

6-[4-fluoro-2-(piperidin-4-yl)-1,3-benzothiazol-6-yl]-2-methyl-1,3-benzoxazole;

6-(2,8-dimethylimidazo[1,2-a]pyridin-6-yl)-4-fluoro-2-(1,2,3,6-tetrahydropyridin-4-yl)-1,3-benzothiazole;

4-fluoro-6-(2-methyl-2H-indazol-5-yl)-2-(1,2,3,6-tetrahydropyridin-4-yl)-1,3-benzothiazole;

4-fluoro-6-(2-methyl-2H-indazol-5-yl)-2-(piperidin-4-yl)-1,3-benzothiazole;

2-methyl-5-[2-(piperidin-4-yl)[1,3]thiazolo[4,5-c]pyridin-6-yl]-2H-indazole-7-carbonitrile;

6-(7-ethyl-2-methyl-2H-indazol-5-yl)-2-(piperidin-4-yl)[1,3]thiazolo[4,5-c]pyridine;

6-(7-fluoro-2-methyl-2H-indazol-5-yl)-2-(piperidin-4-yl)[1,3]thiazolo[4,5-c]pyridine;

6-(2-methylimidazo[1,2-a]pyridin-6-yl)-2-(piperidin-4-yl)[1,3]thiazolo[4,5-c]pyridine 5-[4-fluoro-2-(piperidin-4-yl)-1,3-benzothiazol-6-yl]-1H-pyrazolo[4,3-b]pyridine 5-[4-fluoro-2-(piperidin-4-yl)-1,3-benzothiazol-6-yl]-2-methyl-2H-pyrazolo[4,3-b]pyridine;

6-(7-cyclopropyl-2-methyl-2H-indazol-5-yl)-N-methyl-N-(2,2,6,6-tetramethylpiperidin-4-yl)-1,3-benzothiazol-2-amine;

N-methyl-6-(2-methyl-2H-indazol-5-yl)-N-(2-methylpiperidin-4-yl)-1,3-benzothiazol-2-amine;

6-(2-methylimidazo[1,2-a]pyridin-6-yl)-2-(piperidin-4-yl)-1,3-benzothiazole;

6-(7-fluoro-2-methyl-2H-indazol-5-yl)-2-(piperidin-4-yl)-1,3-benzothiazole;

2-methyl-5-[2-(piperidin-4-yl)-1,3-benzothiazol-6-yl]-2H-indazole-7-carbonitrile;

6-(7-ethyl-2-methyl-2H-indazol-5-yl)-2-(piperidin-4-yl)-1,3-benzothiazole;

6-(7-fluoro-2-methyl-2H-indazol-5-yl)-N-methyl-N-(2,2,6,6-tetramethylpiperidin-4-yl)[1,3]thiazolo[4,5-c]pyridin-2-amine;

N-methyl-6-(2-methylimidazo[1,2-a]pyridin-6-yl)-N-(2,2,6,6-tetramethylpiperidin-4-yl)[1,3]thiazolo[4,5-c]pyridin-2-amine;

6-(2,8-dimethylimidazo[1,2-a]pyridin-6-yl)-N-methyl-N-(2,2,6,6-tetramethylpiperidin-4-yl)[1,3]thiazolo[4,5-c]pyridin-2-amine;

N-methyl-6-(2-methylimidazo[1,2-b]pyridazin-6-yl)-N-(2,2,6,6-tetramethylpiperidin-4-yl)[1,3]thiazolo[4,5-c]pyridin-2-amine;

6-(2,8-dimethylimidazo[1,2-b]pyridazin-6-yl)-N-methyl-N-(2,2,6,6-tetramethylpiperidin-4-yl)[1,3]thiazolo[4,5-c]pyridin-2-amine;

5-{4-fluoro-2-[methyl(2,2,6,6-tetramethylpiperidin-4-yl)amino]-1,3-benzothiazol-6-yl}-2-methyl-2H-indazole-7-carbonitrile;

6-[4-fluoro-2-(1-methylpiperidin-4-yl)-1,3-benzothiazol-6-yl]-2-methylimidazo[1,2-b]pyridazine;

6-(8-ethyl-2-methylimidazo[1,2-a]pyridin-6-yl)-N-methyl-N-(2,2,6,6-tetramethylpiperidin-4-yl)-1,3-benzothiazol-2-amine;

6-(2,4-dimethyl-1H-benzimidazol-6-yl)-2-(piperidin-4-yl)-1,3-benzothiazole;

6-(2-methyl-1H-benzimidazol-6-yl)-2-(piperidin-4-yl)-1,3-benzothiazole;

N-methyl-6-[2-methyl-8-(trifluoromethyl)imidazo[1,2-a]pyridin-6-yl]-N-(2,2,6,6-tetramethylpiperidin-4-yl)-1,3-benzothiazol-2-amine;

2-methyl-6-[2-(piperidin-4-yl)-1,3-benzothiazol-6-yl]imidazo[1,2-b]pyridazine;

6-(2,7-dimethyl-2H-indazol-5-yl)-4-methoxy-2-(1,2,3,6-tetrahydropyridin-4-yl)-1,3-benzothiazole 6-(2,7-dimethyl-2H-indazol-5-yl)-4-methoxy-2-(piperidin-4-yl)-1,3-benzothiazole;

6-(2,7-dimethyl-2H-indazol-5-yl)-2-(1,2,3,6-tetrahydropyridin-4-yl)-1,3-benzothiazol-4-ol;

6-(2,7-dimethyl-2H-indazol-5-yl)-7-fluoro-N-methyl-N-(2,2,6,6-tetramethylpiperidin-4-yl)[1,3]thiazolo[4,5-c]pyridin-2-amine;

5-[4-fluoro-2-(1,2,3,6-tetrahydropyridin-4-yl)-1,3-benzothiazol-6-yl]-2-methyl-2H-indazole-7-carbonitrile;

1-{5-[4-fluoro-2-(piperidin-4-yl)-1,3-benzothiazol-6-yl]-2-methyl-2H-indazol-7-yl}methanamine;

5-[4-fluoro-2-(piperidin-4-yl)-1,3-benzothiazol-6-yl]-2-methyl-2H-indazole-7-carbonitrile;

N-methyl-6-(2-methylimidazo[1,2-a]pyrimidin-6-yl)-N-(2,2,6,6-tetramethylpiperidin-4-yl)[1,3]thiazolo[4,5-c]pyridin-2-amine;

6-[2-(1-ethylpiperidin-4-yl)-4-fluoro-1,3-benzothiazol-6-yl]-2-methylimidazo[1,2-b]pyridazine;

6-[4-fluoro-2-(1-methylpiperidin-4-yl)-1,3-benzothiazol-6-yl]-2,8-dimethylimidazo[1,2-b]pyridazine;

6-(2,7-dimethyl-2H-indazol-5-yl)-N-(1,2-dimethylpiperidin-4-yl)-N-methyl-1,3-benzothiazol-2-amine;

2-methyl-5-[2-(piperidin-4-yl)[1,3]thiazolo[5,4-d]pyrimidin-5-yl]-2H-indazole-7-carbonitrile;

5-(2,7-dimethyl-2H-indazol-5-yl)-2-(piperidin-4-yl)[1,3]thiazolo[5,4-d]pyrimidine;

6-(8-fluoro-2-methylimidazo[1,2-a]pyridin-6-yl)-N-methyl-N-(2,2,6,6-tetramethylpiperidin-4-yl)-1,3-benzothiazol-2-amine;

2-methyl-6-[2-(piperidin-4-yl)-1,3-benzothiazol-6-yl]-1,3-benzoxazole;

6-(8-fluoro-2-methylimidazo[1,2-a]pyridin-6-yl)-2-(piperidin-4-yl)-1,3-benzothiazole;

6-(2,8-dimethylimidazo[1,2-a]pyridin-6-yl)-2-(piperidin-4-yl)-1,3-benzothiazole;

2-(2,2-dimethylpiperidin-4-yl)-6-(2-methyl-2H-indazol-5-yl)-1,3-benzothiazole;
N-methyl-6-[2-methyl-8-(trifluoromethyl)imidazo[1,2-a]pyridin-6-yl]-N-(2,2,6,6-tetramethylpiperidin-4-yl)[1,3]thiazolo[4,5-c]pyridin-2-amine;
2-methyl-5-{2-[methyl(2,2,6,6-tetramethylpiperidin-4-yl)amino][1,3]thiazolo[4,5-c]pyridin-6-yl}-2H-indazole-7-carbonitrile;
3-(2,7-dimethyl-2H-indazol-5-yl)-N-methyl-N-(2,2,6,6-tetramethylpiperidin-4-yl)[1,3]thiazolo[4,5-c]pyridazin-6-amine;
2-{6-[methyl(2,2,6,6-tetramethylpiperidin-4-yl)amino][1,3]thiazolo[4,5-c]pyridazin-3-yl}-5-(1H-pyrazol-4-yl)phenol;
6-[4-fluoro-2-(piperazin-1-yl)-1,3-benzothiazol-6-yl]-2,8-dimethylimidazo[1,2-b]pyridazine;
6-[2-(1,4-diazepan-1-yl)-4-fluoro-1,3-benzothiazol-6-yl]-2,8-dimethylimidazo[1,2-b]pyridazine;
5-(2,7-dimethyl-2H-indazol-5-yl)-N-methyl-N-(2,2,6,6-tetramethylpiperidin-4-yl)[1,3]thiazolo[5,4-d]pyrimidin-2-amine;
2-methyl-5-{2-[methyl(2,2,6,6-tetramethylpiperidin-4-yl)amino][1,3]thiazolo[5,4-d]pyrimidin-5-yl}-2H-indazole-7-carbonitrile;
5-(7-fluoro-2-methyl-2H-indazol-5-yl)-N-methyl-N-(2,2,6,6-tetramethylpiperidin-4-yl)[1,3]thiazolo[5,4-d]pyrimidin-2-amine;
6-[2-(4,7-diazaspiro[2.5]oct-7-yl)-4-fluoro-1,3-benzothiazol-6-yl]-2,8-dimethylimidazo[1,2-b]pyridazine;
4-fluoro-6-(7-fluoro-2-methyl-2H-indazol-5-yl)-2-(piperidin-4-yl)-1,3-benzothiazole;
6-(2,8-dimethylimidazo[1,2-b]pyridazin-6-yl)-4-fluoro-N-methyl-N-(2,2,6,6-tetramethylpiperidin-4-yl)-1,3-benzothiazol-2-amine;
5-(7-fluoro-2-methyl-2H-indazol-5-yl)-N-methyl-N-(2,2,6,6-tetramethylpiperidin-4-yl)[1,3]thiazolo[5,4-b]pyridin-2-amine;
N-methyl-5-(2-methylimidazo[1,2-a]pyridin-6-yl)-N-(2,2,6,6-tetramethylpiperidin-4-yl)[1,3]thiazolo[5,4-b]pyridin-2-amine;
2-{2-[methyl(2,2,6,6-tetramethylpiperidin-4-yl)amino][1,3]thiazolo[4,5-b]pyrazin-6-yl}-5-(1H-pyrazol-4-yl)phenol;
6-(2,7-dimethyl-2H-indazol-5-yl)-N-methyl-N-(2,2,6,6-tetramethylpiperidin-4-yl)[1,3]thiazolo[4,5-b]pyrazin-2-amine;
6-[2-(3,5-dimethylpiperazin-1-yl)-4-fluoro-1,3-benzothiazol-6-yl]-2,8-dimethylimidazo[1,2-b]pyridazine;
6-{4-fluoro-2-[(2,2,6,6-tetramethylpiperidin-4-yl)oxy]-1,3-benzothiazol-6-yl}-2,8-dimethylimidazo[1,2-b]pyridazine;
6-(2,7-dimethyl-2H-indazol-5-yl)-2-(piperidin-4-yl)-1,3-benzothiazol-4-ol;
6-{2-[(2,6-dimethylpiperidin-4-yl)oxy]-4-fluoro-1,3-benzothiazol-6-yl}-2,8-dimethylimidazo[1,2-b]pyridazine;
N-methyl-6-(2-methyl[1,2,4]triazolo[1,5-a]pyridin-6-yl)-N-(2,2,6,6-tetramethylpiperidin-4-yl)[1,3]thiazolo[4,5-c]pyridin-2-amine;
2-{2-[methyl(2,2,6,6-tetramethylpiperidin-4-yl)amino][1,3]thiazolo[4,5-c]pyridin-6-yl}-5-(1H-pyrazol-4-yl)phenol;
2-methyl-6-{2-[methyl(2,2,6,6-tetramethylpiperidin-4-yl)amino]-1,3-benzothiazol-6-yl}imidazo[1,2-a]pyridine-8-carbonitrile;
2,8-dimethyl-6-[2-(piperidin-4-yl)-1,3-benzothiazol-6-yl]imidazo[1,2-b]pyridazine;
2-methyl-5-{2-[methyl(2,2,6,6-tetramethylpiperidin-4-yl)amino][1,3]thiazolo[4,5-b]pyrazin-6-yl}-2H-indazole-7-carbonitrile;
N-methyl-6-(2-methylimidazo[1,2-b]pyridazin-6-yl)-N-(2,2,6,6-tetramethylpiperidin-4-yl)[1,3]thiazolo[4,5-b]pyrazin-2-amine;
2-{2-[methyl(2,2,6,6-tetramethylpiperidin-4-yl)amino][1,3]thiazolo[5,4-d]pyrimidin-5-yl}-5-(1H-pyrazol-4-yl)phenol;
1-[6-(2,8-dimethylimidazo[1,2-b]pyridazin-6-yl)-4-fluoro-1,3-benzothiazol-2-yl]piperidin-4-ol;
6-{4-fluoro-2-[(2R)-2-methylpiperidin-4-yl]-1,3-benzothiazol-6-yl}-2-methylimidazo[1,2-b]pyridazine;
6-[4-fluoro-2-(1,2,3,6-tetrahydropyridin-4-yl)-1,3-benzothiazol-6-yl]-8-methoxy-2-methylimidazo[1,2-b]pyridazine;
6-(2,7-dimethyl-2H-indazol-5-yl)-N-(2,2-dimethylpiperidin-4-yl)-N-methyl-1,3-benzothiazol-2-amine;
6-(8-fluoro-2-methylimidazo[1,2-a]pyridin-6-yl)-N-methyl-N-(2,2,6,6-tetramethylpiperidin-4-yl)[1,3]thiazolo[4,5-c]pyridin-2-amine;
2-methyl-5-{2-[methyl(2,2,6,6-tetramethylpiperidin-4-yl)amino][1,3]thiazolo[5,4-b]pyridin-5-yl}-2H-indazole-7-carbonitrile;
2-{2-[methyl(2,2,6,6-tetramethylpiperidin-4-yl)amino][1,3]thiazolo[5,4-b]pyridin-5-yl}-5-(1H-pyrazol-4-yl)phenol;
6-(7-fluoro-2-methyl-2H-indazol-5-yl)-N-methyl-N-(2,2,6,6-tetramethylpiperidin-4-yl)[1,3]thiazolo[4,5-b]pyrazin-2-amine;
6-[4-fluoro-2-(piperidin-4-yl)-1,3-benzothiazol-6-yl]-8-methoxy-2-methylimidazo[1,2-b]pyridazine;
4-fluoro-6-(8-fluoro-2-methylimidazo[1,2-a]pyridin-6-yl)-2-(piperidin-4-yl)-1,3-benzothiazole;
4-chloro-6-(7-fluoro-2-methyl-2H-indazol-5-yl)-2-(1,2,3,6-tetrahydropyridin-4-yl)-1,3-benzothiazole;
5-[4-chloro-2-(1,2,3,6-tetrahydropyridin-4-yl)-1,3-benzothiazol-6-yl]-2-methyl-2H-indazole-7-carbonitrile;
N-(2,2-dimethylpiperidin-4-yl)-N-methyl-6-(2-methyl-2H-indazol-5-yl)-1,3-benzothiazol-2-amine;
2-methyl-6-[2-(piperidin-4-yl)-1,3-benzothiazol-6-yl]imidazo[1,2-a]pyrimidine;
3-(8-fluoro-2-methylimidazo[1,2-a]pyridin-6-yl)-N-methyl-N-(2,2,6,6-tetramethylpiperidin-4-yl)[1,3]thiazolo[4,5-c]pyridazin-6-amine;
2-methyl-5-{6-[methyl(2,2,6,6-tetramethylpiperidin-4-yl)amino][1,3]thiazolo[4,5-c]pyridazin-3-yl}-2H-indazole-7-carbonitrile;
6-[2,3-difluoro-4-(1H-pyrazol-4-yl)phenyl]-N-methyl-N-(2,2,6,6-tetramethylpiperidin-4-yl)[1,3]thiazolo[4,5-b]pyrazin-2-amine;
6-(2,8-dimethylimidazo[1,2-b]pyridazin-6-yl)-N-methyl-N-(2,2,6,6-tetramethylpiperidin-4-yl)[1,3]thiazolo[4,5-b]pyrazin-2-amine;
2-methyl-6-{2-[methyl(2,2,6,6-tetramethylpiperidin-4-yl)amino][1,3]thiazolo[4,5-b]pyrazin-6-yl}imidazo[1,2-a]pyridine-8-carbonitrile;
4-fluoro-N-methyl-6-(2-methylimidazo[1,2-b]pyridazin-6-yl)-N-[(2S)-2-methylpiperidin-4-yl]-1,3-benzothiazol-2-amine;
6-(2,8-dimethylimidazo[1,2-b]pyridazin-6-yl)-4-fluoro-N-methyl-N-[(2S)-2-methylpiperidin-4-yl]-1,3-benzothiazol-2-amine;
6-[4-fluoro-2-(octahydroindolizin-7-yl)-1,3-benzothiazol-6-yl]-2-methylimidazo[1,2-b]pyridazine;
6-[4-fluoro-2-(piperidin-4-yl)-1,3-benzothiazol-6-yl]-N,2-dimethylimidazo[1,2-b]pyridazin-8-amine;

6-[4-fluoro-2-(piperidin-4-yl)-1,3-benzothiazol-6-yl]-N,N,2-trimethylimidazo[1,2-b]pyridazin-8-amine;

2-methyl-6-[2-(piperidin-4-yl)-1,3-benzothiazol-6-yl]imidazo[1,2-a]pyrazine;

2-methyl-6-{2-[methyl(2,2,6,6-tetramethylpiperidin-4-yl)amino][1,3]thiazolo[5,4-d]pyrimidin-5-yl}imidazo[1,2-a]pyridine-8-carbonitrile;

5-(8-fluoro-2-methylimidazo[1,2-a]pyridin-6-yl)-N-methyl-N-(2,2,6,6-tetramethylpiperidin-4-yl)[1,3]thiazolo[5,4-d]pyrimidin-2-amine;

6-(7-cyano-2-methyl-2H-indazol-5-yl)-2-(1,2,3,6-tetrahydropyridin-4-yl)-1,3-benzothiazole-4-carbonitrile;

2-methyl-6-[2-(piperazin-1-yl)[1,3]thiazolo[4,5-b]pyrazin-6-yl]imidazo[1,2-a]pyridine-8-carbonitrile;

6-(8-fluoro-2-methylimidazo[1,2-a]pyridin-6-yl)-2-(piperazin-1-yl)[1,3]thiazolo[4,5-b]pyrazine;

6-(2,7-dimethyl-2H-indazol-5-yl)-N-(2,6-dimethylpiperidin-4-yl)-N-methyl-1,3-benzothiazol-2-amine;

N-(2,6-dimethylpiperidin-4-yl)-N-methyl-6-(2-methyl-2H-indazol-5-yl)-1,3-benzothiazol-2-amine;

5-(8-fluoro-2-methylimidazo[1,2-a]pyridin-6-yl)-N-methyl-N-(2,2,6,6-tetramethylpiperidin-4-yl)[1,3]thiazolo[5,4-b]pyridin-2-amine;

2-methyl-6-{2-[methyl(2,2,6,6-tetramethylpiperidin-4-yl)amino][1,3]thiazolo[5,4-b]pyridin-5-yl}imidazo[1,2-a]pyridine-8-carbonitrile;

2-methyl-6-{2-[methyl(2,2,6,6-tetramethylpiperidin-4-yl)amino][1,3]thiazolo[4,5-c]pyridin-6-yl}imidazo[1,2-a]pyridine-8-carbonitrile;

6-(8-fluoro-2-methylimidazo[1,2-a]pyridin-6-yl)-2-[(2,2,6,6-tetramethylpiperidin-4-yl)oxy][1,3]thiazolo[4,5-b]pyrazine;

2-methyl-6-{2-[(2,2,6,6-tetramethylpiperidin-4-yl)oxy][1,3]thiazolo[4,5-b]pyrazin-6-yl}imidazo[1,2-a]pyridine-8-carbonitrile;

6-(2-methylimidazo[1,2-b]pyridazin-6-yl)-2-(piperazin-1-yl)[1,3]thiazolo[4,5-b]pyrazine;

5-(2,8-dimethylimidazo[1,2-a]pyridin-6-yl)-N-methyl-N-(2,2,6,6-tetramethylpiperidin-4-yl)[1,3]thiazolo[5,4-d]pyrimidin-2-amine;

5-(2,8-dimethylimidazo[1,2-b]pyridazin-6-yl)-N-methyl-N-(2,2,6,6-tetramethylpiperidin-4-yl)[1,3]thiazolo[5,4-d]pyrimidin-2-amine;

4-fluoro-N-methyl-6-(2-methylimidazo[1,2-b]pyridazin-6-yl)-N-(piperidin-4-yl)-1,3-benzothiazol-2-amine;

6-(2,8-dimethylimidazo[1,2-b]pyridazin-6-yl)-4-fluoro-N-methyl-N-(piperidin-4-yl)-1,3-benzothiazol-2-amine;

8-(benzyloxy)-6-[4-fluoro-2-(piperidin-4-yl)-1,3-benzothiazol-6-yl]-2-methylimidazo[1,2-b]pyridazine;

6-[4-fluoro-2-(piperidin-4-yl)-1,3-benzothiazol-6-yl]-2-methylimidazo[1,2-b]pyridazin-8-amine;

6-[4-fluoro-2-(piperidin-4-yl)-1,3-benzothiazol-6-yl]-2-methylimidazo[1,2-b]pyridazin-8-ol;

2-(2,6-dimethylpiperidin-4-yl)-6-(2-methyl-2H-indazol-5-yl)-1,3-benzothiazole;

4-fluoro-6-(4-fluoro-3-methoxyphenyl)-2-(piperidin-4-yl)-1,3-benzothiazole;

N-[(3-exo)-8-azabicyclo[3.2.1]oct-3-yl]-6-(2,8-dimethylimidazo[1,2-b]pyridazin-6-yl)-4-fluoro-N-methyl-1,3-benzothiazol-2-amine;

2-methyl-5-{2-[methyl(piperidin-4-yl)amino][1,3]thiazolo[5,4-d]pyrimidin-5-yl}-2H-indazole-7-carbonitrile;

6-[2-(1-azabicyclo[2.2.2]oct-4-yl)-4-fluoro-1,3-benzothiazol-6-yl]-2,8-dimethylimidazo[1,2-b]pyridazine;

6-[4-fluoro-2-(piperidin-4-yl)-1,3-benzothiazol-6-yl]-2-methyl-8-phenoxyimidazo[1,2-b]pyridazine;

2-methyl-6-{2-[methyl(piperidin-4-yl)amino][1,3]thiazolo[5,4-d]pyrimidin-5-yl}imidazo[1,2-a]pyridine-8-carbonitrile;

5-(7-methoxy-2-methyl-2H-indazol-5-yl)-N-methyl-N-(2,2,6,6-tetramethylpiperidin-4-yl)[1,3]thiazolo[5,4-d]pyrimidin-2-amine;

2-methyl-6-{2-[methyl(piperidin-4-yl)amino][1,3]thiazolo[4,5-c]pyridin-6-yl}imidazo[1,2-a]pyridine-8-carbonitrile;

6-{2-[(3-exo)-8-azabicyclo[3.2.1]oct-3-ylamino][1,3]thiazolo[4,5-c]pyridin-6-yl}-2-methylimidazo[1,2-a]pyridine-8-carbonitrile;

4-fluoro-6-(8-methoxy-2-methylimidazo[1,2-b]pyridazin-6-yl)-N-methyl-N-(2,2,6,6-tetramethylpiperidin-4-yl)-1,3-benzothiazol-2-amine;

6-{4-fluoro-2-[methyl(2,2,6,6-tetramethylpiperidin-4-yl)amino]-1,3-benzothiazol-6-yl}-2-methylimidazo[1,2-b]pyridazin-8-amine;

4-fluoro-6-(8-methoxy-2-methylimidazo[1,2-b]pyridazin-6-yl)-N-methyl-N-(piperidin-4-yl)-1,3-benzothiazol-2-amine;

6-{2-[(3-exo)-8-azabicyclo[3.2.1]oct-3-yl(methyl)amino][1,3]thiazolo[4,5-c]pyridin-6-yl}-2-methylimidazo[1,2-a]pyridine-8-carbonitrile;

N-[(3-exo)-8-azabicyclo[3.2.1]oct-3-yl]-6-(8-fluoro-2-methylimidazo[1,2-a]pyridin-6-yl)-N-methyl[1,3]thiazolo[4,5-c]pyridin-2-amine;

N-[(3-exo)-8-azabicyclo[3.2.1]oct-3-yl]-6-(7-fluoro-2-methyl-2H-indazol-5-yl)-N-methyl[1,3]thiazolo[4,5-c]pyridin-2-amine;

5-{2-[(3-exo)-8-azabicyclo[3.2.1]oct-3-yl(methyl)amino][1,3]thiazolo[4,5-c]pyridin-6-yl}-2-methyl-2H-indazole-7-carbonitrile;

6-{2-[(3-exo)-8-azabicyclo[3.2.1]oct-3-yl(methyl)amino][1,3]thiazolo[5,4-d]pyrimidin-5-yl}-2-methylimidazo[1,2-a]pyridine-8-carbonitrile;

5-{2-[(3-exo)-8-azabicyclo[3.2.1]oct-3-yl(methyl)amino][1,3]thiazolo[5,4-d]pyrimidin-5-yl}-2-methyl-2H-indazole-7-carbonitrile;

N-[(3-exo)-8-azabicyclo[3.2.1]oct-3-yl]-4-fluoro-N-methyl-6-(2-methylimidazo[1,2-b]pyridazin-6-yl)-1,3-benzothiazol-2-amine;

6-[4-fluoro-2-(4-methylpiperidin-4-yl)-1,3-benzothiazol-6-yl]-2,8-dimethylimidazo[1,2-b]pyridazine;

N-[(3-exo)-8-azabicyclo[3.2.1]oct-3-yl]-6-(7-fluoro-2-methyl-2H-indazol-5-yl)[1,3]thiazolo[4,5-c]pyridin-2-amine;

N-[(3-exo)-8-azabicyclo[3.2.1]oct-3-yl]-6-(8-fluoro-2-methylimidazo[1,2-a]pyridin-6-yl)[1,3]thiazolo[4,5-c]pyridin-2-amine;

5-{2-[(3-exo)-8-azabicyclo[3.2.1]oct-3-ylamino][1,3]thiazolo[4,5-c]pyridin-6-yl}-2-methyl-2H-indazole-7-carbonitrile;

2-methyl-5-{2-[methyl(piperidin-4-yl)amino][1,3]thiazolo[4,5-c]pyridin-6-yl}-2H-indazole-7-carbonitrile;

6-(8-fluoro-2-methylimidazo[1,2-a]pyridin-6-yl)-N-methyl-N-(piperidin-4-yl)[1,3]thiazolo[4,5-c]pyridin-2-amine;

6-(7-fluoro-2-methyl-2H-indazol-5-yl)-N-methyl-N-(piperidin-4-yl)[1,3]thiazolo[4,5-c]pyridin-2-amine;

N-[(3-exo)-8-azabicyclo[3.2.1]oct-3-yl]-5-(8-fluoro-2-methylimidazo[1,2-a]pyridin-6-yl)-N-methyl[1,3]thiazolo[5,4-d]pyrimidin-2-amine;

N-[(3-exo)-8-azabicyclo[3.2.1]oct-3-yl]-5-(7-fluoro-2-methyl-2H-indazol-5-yl)-N-methyl[1,3]thiazolo[5,4-d]pyrimidin-2-amine;

6-[4-fluoro-2-(piperidin-4-yl)-1,3-benzothiazol-6-yl]-2-methylimidazo[1,2-b]pyridazine-8-carboxylic acid;

methyl {6-[4-fluoro-2-(piperidin-4-yl)-1,3-benzothiazol-6-yl]-2-methylimidazo[1,2-b]pyridazin-8-yl}acetate;

{6-[4-fluoro-2-(piperidin-4-yl)-1,3-benzothiazol-6-yl]-2-methylimidazo[1,2-b]pyridazin-8-yl}acetic acid;

2-methyl-6-{2-[(2,2,6,6-tetramethylpiperidin-4-yl)amino][1,3]thiazolo[4,5-c]pyridin-6-yl}imidazo[1,2-a]pyridine-8-carbonitrile;

6-{2-[(3-exo)-8-azabicyclo[3.2.1]oct-3-yloxy][1,3]thiazolo[4,5-c]pyridin-6-yl}-2-methylimidazo[1,2-a]pyridine-8-carbonitrile;

6-[4-fluoro-2-(piperidin-4-yl)-1,3-benzothiazol-6-yl]-2-methylimidazo[1,2-b]pyridazine-8-carboxamide;

6-(1,3-dimethylpyrrolo[1,2-a]pyrazin-7-yl)-4-fluoro-N-methyl-N-(piperidin-4-yl)-1,3-benzothiazol-2-amine;

6-{4-fluoro-2-[methyl(piperidin-4-yl)amino]-1,3-benzothiazol-6-yl}-2-methylimidazo[1,2-a]pyridine-8-carbonitrile;

N-[(8-anti)-3-azabicyclo[3.2.1]oct-8-yl]-5-(8-fluoro-2-methylimidazo[1,2-a]pyridin-6-yl)-N-methyl[1,3]thiazolo[5,4-d]pyrimidin-2-amine;

6-{2-[(8-anti)-3-azabicyclo[3.2.1]oct-8-yl(methyl)amino][1,3]thiazolo[5,4-d]pyrimidin-5-yl}-2-methylimidazo[1,2-a]pyridine-8-carbonitrile;

2-[4-fluoro-2-(piperidin-4-yl)-1,3-benzothiazol-6-yl]-6,8-dimethylimidazo[1,2-a]pyrazine;

6-[4-fluoro-2-(piperidin-4-yl)-1,3-benzothiazol-6-yl]-2-methylimidazo[1,2-b]pyridazine-8-carbonitrile;

6-{4-fluoro-2-[methyl(piperidin-4-yl)amino]-1,3-benzothiazol-6-yl}-2-methylimidazo[1,2-b]pyridazine-8-carbonitrile;

6-(7-fluoro-2-methyl-2H-indazol-5-yl)-N-(2,2,6,6-tetramethylpiperidin-4-yl)[1,3]thiazolo[4,5-c]pyridin-2-amine;

2-methyl-5-{2-[(2,2,6,6-tetramethylpiperidin-4-yl)amino][1,3]thiazolo[4,5-c]pyridin-6-yl}-2H-indazole-7-carbonitrile;

6-(8-fluoro-2-methylimidazo[1,2-a]pyridin-6-yl)-N-(2,2,6,6-tetramethylpiperidin-4-yl)[1,3]thiazolo[4,5-c]pyridin-2-amine;

6-{2-[(3-exo)-8-azabicyclo[3.2.1]oct-3-yl(methyl)amino]-4-fluoro-1,3-benzothiazol-6-yl}-2-methylimidazo[1,2-b]pyridazine-8-carbonitrile;

6-{2-[(3-exo)-8-azabicyclo[3.2.1]oct-3-yl(methyl)amino]-4-fluoro-1,3-benzothiazol-6-yl}-2-methylimidazo[1,2-b]pyridazine-8-carboxamide;

N-[(3-exo)-8-azabicyclo[3.2.1]oct-3-yl]-4-fluoro-N-methyl-6-(2-methyl-2H-pyrazolo[4,3-b]pyridin-5-yl)-1,3-benzothiazol-2-amine;

2-methyl-5-(2-{methyl[(3-exo)-8-methyl-8-azabicyclo[3.2.1]oct-3-yl]amino}[1,3]thiazolo[4,5-c]pyridin-6-yl)-2H-indazole-7-carbonitrile;

6-(8-fluoro-2-methylimidazo[1,2-a]pyridin-6-yl)-N-methyl-N-[(3-exo)-8-methyl-8-azabicyclo[3.2.1]oct-3-yl][1,3]thiazolo[4,5-c]pyridin-2-amine;

2-methyl-6-(2-{methyl[(3-exo)-8-methyl-8-azabicyclo[3.2.1]oct-3-yl]amino}[1,3]thiazolo[4,5-c]pyridin-6-yl)imidazo[1,2-a]pyridine-8-carbonitrile;

6-(7-fluoro-2-methyl-2H-indazol-5-yl)-N-methyl-N-[(3-exo)-8-methyl-8-azabicyclo[3.2.1]oct-3-yl][1,3]thiazolo[4,5-c]pyridin-2-amine;

6-{2-[ethyl(2,2,6,6-tetramethylpiperidin-4-yl)amino][1,3]thiazolo[5,4-d]pyrimidin-5-yl}-2-methylimidazo[1,2-a]pyridine-8-carbonitrile;

N-ethyl-5-(8-fluoro-2-methylimidazo[1,2-a]pyridin-6-yl)-N-(2,2,6,6-tetramethylpiperidin-4-yl)[1,3]thiazolo[5,4-d]pyrimidin-2-amine;

2-methyl-5-(2-{[(3-exo)-8-methyl-8-azabicyclo[3.2.1]oct-3-yl]amino}[1,3]thiazolo[4,5-c]pyridin-6-yl)-2H-indazole-7-carbonitrile;

2-methyl-6-(2-{[(3-exo)-8-methyl-8-azabicyclo[3.2.1]oct-3-yl]amino}[1,3]thiazolo[4,5-c]pyridin-6-yl)imidazo[1,2-a]pyridine-8-carbonitrile;

6-(7-fluoro-2-methyl-2H-indazol-5-yl)-N-[(3-exo)-8-methyl-8-azabicyclo[3.2.1]oct-3-yl][1,3]thiazolo[4,5-c]pyridin-2-amine;

6-(8-fluoro-2-methylimidazo[1,2-a]pyridin-6-yl)-N-[(3-exo)-8-methyl-8-azabicyclo[3.2.1]oct-3-yl][1,3]thiazolo[4,5-c]pyridin-2-amine;

N-(azetidin-3-yl)-6-(2,8-dimethylimidazo[1,2-b]pyridazin-6-yl)-4-fluoro-N-methyl-1,3-benzothiazol-2-amine;

5-[4-fluoro-2-(piperidin-4-yl)-1,3-benzothiazol-6-yl]-2-methylpyrazolo[1,5-a]pyrimidine;

4-fluoro-N-methyl-6-(2-methylpyrazolo[1,5-a]pyrimidin-5-yl)-N-(piperidin-4-yl)-1,3-benzothiazol-2-amine;

6-{2-[9-azabicyclo[3.3.1]non-3-yl(methyl)amino][1,3]thiazolo[4,5-c]pyridin-6-yl}-2-methylimidazo[1,2-a]pyridine-8-carbonitrile;

5-{2-[9-azabicyclo[3.3.1]non-3-yl(methyl)amino][1,3]thiazolo[4,5-c]pyridin-6-yl}-2-methyl-2H-indazole-7-carbonitrile;

N-(9-azabicyclo[3.3.1]non-3-yl)-6-(7-fluoro-2-methyl-2H-indazol-5-yl)-N-methyl[1,3]thiazolo[4,5-c]pyridin-2-amine;

5-{2-[(1,5-dimethyl-8-azabicyclo[3.2.1]oct-3-yl)(methyl)amino][1,3]thiazolo[5,4-d]pyrimidin-5-yl}-2-methyl-2H-indazole-7-carbonitrile;

6-(2-{[(1R)-1,5-dimethyl-8-azabicyclo[3.2.1]oct-3-yl](methyl)amino}[1,3]thiazolo[5,4-d]pyrimidin-5-yl)-2-methylimidazo[1,2-a]pyridine-8-carbonitrile;

6-{2-[(1R,5S)-9-azabicyclo[3.3.1]non-3-yl(methyl)amino][1,3]thiazolo[5,4-d]pyrimidin-5-yl}-2-methylimidazo[1,2-a]pyridine-8-carbonitrile;

N-[(1R,5S)-9-azabicyclo[3.3.1]non-3-yl]-5-(8-fluoro-2-methylimidazo[1,2-a]pyridin-6-yl)-N-methyl[1,3]thiazolo[5,4-d]pyrimidin-2-amine;

4-fluoro-N-methyl-6-(2-methylimidazo[1,2-b]pyridazin-6-yl)-N-[(2S,4S)-2-methylpiperidin-4-yl]-1,3-benzothiazol-2-amine;

4-fluoro-N-methyl-6-(2-methylimidazo[1,2-b]pyridazin-6-yl)-N-[(2S,4R)-2-methylpiperidin-4-yl]-1,3-benzothiazol-2-amine;

N-(9-azabicyclo[3.3.1]non-3-yl)-N-methyl-6-(2-methylimidazo[1,2-a]pyridine-6-yl)[1,3]thiazolo[4,5-c]pyridin-2-amine;

N-(9-azabicyclo[3.3.1]non-3-yl)-6-(2,8-dimethylimidazo[1,2-a]pyridin-6-yl)-N-methyl[1,3]thiazolo[4,5-c]pyridin-2-amine;

N-(9-azabicyclo[3.3.1]non-3-yl)-N-methyl-6-(2-methyl-2H-indazol-5-yl)[1,3]thiazolo[4,5-c]pyridin-2-amine;

N-(9-azabicyclo[3.3.1]non-3-yl)-6-(2,7-dimethyl-2H-indazol-5-yl)-N-methyl[1,3]thiazolo[4,5-c]pyridin-2-amine;

N-(9-azabicyclo[3.3.1]non-3-yl)-6-(7-methoxy-2-methyl-2H-indazol-5-yl)-N-methyl[1,3]thiazolo[4,5-c]pyridin-2-amine;

5-(1,3-dimethylpyrrolo[1,2-a]pyrazin-7-yl)-N-methyl-N-(2,2,6,6-tetramethylpiperidin-4-yl)[1,3]thiazolo[5,4-d]pyrimidin-2-amine;

2-methyl-6-{2-[(1,2,2,6,6-pentamethylpiperidin-4-yl)amino][1,3]thiazolo[4,5-c]pyridin-6-yl}imidazo[1,2-a]pyridine-8-carbonitrile;

6-(8-fluoro-2-methylimidazo[1,2-a]pyridin-6-yl)-N-(1,2,2,6,6-pentamethylpiperidin-4-yl)[1,3]thiazolo[4,5-c]pyridin-2-amine;

2-methyl-5-{2-[(1,2,2,6,6-pentamethylpiperidin-4-yl)amino][1,3]thiazolo[4,5-c]pyridin-6-yl}-2H-indazole-7-carbonitrile;

6-(7-fluoro-2-methyl-2H-indazol-5-yl)-N-(1,2,2,6,6-pentamethylpiperidin-4-yl)[1,3]thiazolo[4,5-c]pyridin-2-amine;

2-methyl-6-{2-[methyl(9-methyl-9-azabicyclo[3.3.1]non-3-yl)amino][1,3]thiazolo[4,5-c]pyridin-6-yl}imidazo[1,2-a]pyridine-8-carbonitrile;

6-(8-fluoro-2-methylimidazo[1,2-a]pyridin-6-yl)-N-methyl-N-(9-methyl-9-azabicyclo[3.3.1]non-3-yl)[1,3]thiazolo[4,5-c]pyridin-2-amine;

2-methyl-5-{2-[methyl(9-methyl-9-azabicyclo[3.3.1]non-3-yl)amino][1,3]thiazolo[4,5-c]pyridin-6-yl}-2H-indazole-7-carbonitrile;

6-(7-fluoro-2-methyl-2H-indazol-5-yl)-N-methyl-N-(9-methyl-9-azabicyclo[3.3.1]non-3-yl)[1,3]thiazolo[4,5-c]pyridin-2-amine;

2-{2-[methyl(piperidin-4-yl)amino][1,3]thiazolo[4,5-b]pyrazin-6-yl}-5-(1H-pyrazol-4-yl)phenol;

2-methyl-6-{2-[methyl(2,2,6,6-tetramethylpiperidin-4-yl)amino][1,3]thiazolo[5,4-d]pyrimidin-5-yl}-1,3-benzoxazole-4-carbonitrile;

6-{2-[(3-exo)-8-azabicyclo[3.2.1]oct-3-yl(methyl)amino][1,3]thiazolo[5,4-b]pyridin-5-yl}-2-methylimidazo[1,2-a]pyridine-8-carbonitrile;

N-[(3-exo)-8-azabicyclo[3.2.1]oct-3-yl]-5-(8-fluoro-2-methylimidazo[1,2-a]pyridin-6-yl)-N-methyl[1,3]thiazolo[5,4-b]pyridin-2-amine;

5-{2-[(3-exo)-8-azabicyclo[3.2.1]oct-3-yl(methyl)amino][1,3]thiazolo[5,4-b]pyridin-5-yl}-2-methyl-2H-indazole-7-carbonitrile 6-{2-[(3-exo)-9-azabicyclo[3.3.1]non-3-yl(methyl)amino][1,3]thiazolo[5,4-b]pyridin-5-yl}-2-methylimidazo[1,2-a]pyridine-8-carbonitrile;

N-[(3-exo)-9-azabicyclo[3.3.1]non-3-yl]-5-(8-fluoro-2-methylimidazo[1,2-a]pyridin-6-yl)-N-methyl[1,3]thiazolo[5,4-b]pyridin-2-amine;

5-{2-[(3-exo)-9-azabicyclo[3.3.1]non-3-yl(methyl)amino][1,3]thiazolo[5,4-b]pyridin-5-yl}-2-methyl-2H-indazole-7-carbonitrile;

2-{6-[methyl(piperidin-4-yl)amino][1,3]thiazolo[4,5-c]pyridazin-3-yl}-5-(1H-pyrazol-4-yl)phenol;

2-{6-[methyl(1-methylpiperidin-4-yl)amino][1,3]thiazolo[4,5-c]pyridazin-3-yl}-5-(1H-pyrazol-4-yl)phenol;

N-[(1R,3s,5S)-1,5-dimethyl-8-azabicyclo[3.2.1]octan-3-yl]-5-(8-fluoro-2-methylimidazo[1,2-a]pyridin-6-yl)-N-methyl[1,3]thiazolo[5,4-d]pyrimidin-2-amine;

6-(2-{[(1R,3s,5S)-1,5-dimethyl-8-azabicyclo[3.2.1]octan-3-yl](methyl)amino}[1,3]thiazolo[4,5-c]pyridin-6-yl)-2-methylimidazo[1,2-a]pyridine-8-carbonitrile;

N-[(1R,3s,5S)-1,5-dimethyl-8-azabicyclo[3.2.1]octan-3-yl]-6-(8-fluoro-2-methylimidazo[1,2-a]pyridin-6-yl)-N-methyl[1,3]thiazolo[4,5-c]pyridin-2-amine;

5-(2-{[(1R,3s,5S)-1,5-dimethyl-8-azabicyclo[3.2.1]octan-3-yl](methyl)amino}[1,3]thiazolo[4,5-c]pyridin-6-yl)-2-methyl-2H-indazole-7-carbonitrile;

6-(2,8-dimethylimidazo[1,2-a]pyridin-6-yl)-N-methyl-N-(piperidin-4-yl)[1,3]thiazolo[4,5-b]pyrazin-2-amine;

N-[(1R)-1,5-dimethyl-8-azabicyclo[3.2.1]octan-3-yl]-5-(7-fluoro-2-methyl-2H-indazol-5-yl)-N-methyl[1,3]thiazolo[5,4-d]pyrimidin-2-amine;

6-(2-{[(1R)-1,5-dimethyl-8-azabicyclo[3.2.1]octan-3-yl](methyl)amino}[1,3]thiazolo[5,4-d]pyrimidin-5-yl)-2-methyl-1,3-benzoxazole-4-carbonitrile;

6-(2-{[(1R,3s,5S)-1,5-dimethyl-8-azabicyclo[3.2.1]octan-3-yl](methyl)amino}[1,3]thiazolo[5,4-b]pyridin-5-yl)-2-methylimidazo[1,2-a]pyridine-8-carbonitrile;

N-[(1R,3s,5S)-1,5-dimethyl-8-azabicyclo[3.2.1]octan-3-yl]-5-(8-fluoro-2-methylimidazo[1,2-a]pyridin-6-yl)-N-methyl[1,3]thiazolo[5,4-b]pyridin-2-amine;

5-(2-{[(1R,3s,5S)-1,5-dimethyl-8-azabicyclo[3.2.1]octan-3-yl](methyl)amino}[1,3]thiazolo[5,4-b]pyridin-5-yl)-2-methyl-2H-indazole-7-carbonitrile;

N-[(1R,3s,5S)-1,5-dimethyl-8-azabicyclo[3.2.1]octan-3-yl]-5-(7-fluoro-2-methyl-2H-indazol-5-yl)-N-methyl[1,3]thiazolo[5,4-b]pyridin-2-amine;

N-(9-azabicyclo[3.3.1]nonan-3-yl)-5-(7-fluoro-2-methyl-2H-indazol-5-yl)-N-methyl[1,3]thiazolo[5,4-b]pyridin-2-amine;

6-(6,8-dimethylimidazo[1,2-a]pyrazin-2-yl)-N-methyl-N-(2,2,6,6-tetramethylpiperidin-4-yl)[1,3]thiazolo[4,5-c]pyridin-2-amine;

6-(1,3-dimethylpyrrolo[1,2-a]pyrazin-7-yl)-N-methyl-N-(2,2,6,6-tetramethylpiperidin-4-yl)[1,3]thiazolo[4,5-c]pyridin-2-amine;

N-[(1R,3s,5S)-1,5-dimethyl-8-azabicyclo[3.2.1]octan-3-yl]-6-(7-fluoro-2-methyl-2H-indazol-5-yl)-N-methyl[1,3]thiazolo[4,5-c]pyridin-2-amine;

N-[(1R,3s,5S)-1,5-dimethyl-8-azabicyclo[3.2.1]octan-3-yl]-6-(2,8-dimethylimidazo[1,2-a]pyridin-6-yl)-N-methyl[1,3]thiazolo[4,5-c]pyridin-2-amine;

N-[(1R,3s,5S)-1,5-dimethyl-8-azabicyclo[3.2.1]octan-3-yl]-N-methyl-6-(2-methylimidazo[1,2-a]pyridin-6-yl)[1,3]thiazolo[4,5-c]pyridin-2-amine;

6-(2-{[(1R,3s,5S)-1,5-dimethyl-8-azabicyclo[3.2.1]octan-3-yl](methyl)amino}[1,3]thiazolo[4,5-c]pyridin-6-yl)-2-methyl-1,3-benzoxazole-4-carbonitrile;

N-methyl-6-(2-methylimidazo[2,1-b][1,3]thiazol-6-yl)-N-(2,2,6,6-tetramethylpiperidin-4-yl)[1,3]thiazolo[4,5-c]pyridin-2-amine;

6-(2-{[(1R,3r,5S)-1,5-diethyl-8-azabicyclo[3.2.1]octan-3-yl](methyl)amino}[1,3]thiazolo[5,4-d]pyrimidin-5-yl)-2-methylimidazo[1,2-a]pyridine-8-carbonitrile;

N-[(1R,3r,5S)-1,5-diethyl-8-azabicyclo[3.2.1]octan-3-yl]-5-(8-fluoro-2-methylimidazo[1,2-a]pyridin-6-yl)-N-methyl[1,3]thiazolo[5,4-d]pyrimidin-2-amine;

N-methyl-6-(3-methylimidazo[2,1-b][1,3]thiazol-6-yl)-N-(2,2,6,6-tetramethylpiperidin-4-yl)[1,3]thiazolo[4,5-c]pyridin-2-amine;

6-{4-fluoro-2-[(piperidin-4-yl)oxy]-1,3-benzothiazol-6-yl}-2,8-dimethylimidazo[1,2-b]pyridazine;

4-fluoro-6-(7-fluoro-2-methyl-2H-indazol-5-yl)-2-[(piperidin-4-yl)oxy]-1,3-benzothiazole;

N-methyl-6-(2-methylimidazo[2,1-b][1,3,4]thiadiazol-6-yl)-N-(2,2,6,6-tetramethylpiperidin-4-yl)[1,3]thiazolo[4,5-c]pyridin-2-amine;

2-methyl-6-{2-[(2,2,6,6-tetramethylpiperidin-4-yl)oxy][1,3]thiazolo[4,5-c]pyridin-6-yl}imidazo[1,2-a]pyridine-8-carbonitrile;

6-(8-fluoro-2-methylimidazo[1,2-a]pyridin-6-yl)-2-[(2,2,6,6-tetramethylpiperidin-4-yl)oxy][1,3]thiazolo[4,5-c]pyridine;

2-methyl-5-{2-[(2,2,6,6-tetramethylpiperidin-4-yl)oxy][1,3]thiazolo[4,5-c]pyridin-6-yl}-2H-indazole-7-carbonitrile;
6-(7-fluoro-2-methyl-2H-indazol-5-yl)-2-[(2,2,6,6-tetramethylpiperidin-4-yl)oxy][1,3]thiazolo[4,5-c]pyridine;
2-methyl-6-{2-[(piperidin-4-yl)oxy][1,3]thiazolo[4,5-c]pyridin-6-yl}imidazo[1,2-a]pyridine-8-carbonitrile;
6-(8-fluoro-2-methylimidazo[1,2-a]pyridin-6-yl)-2-[(piperidin-4-yl)oxy][1,3]thiazolo[4,5-c]pyridine;
2-methyl-5-{2-[(piperidin-4-yl)oxy][1,3]thiazolo[4,5-c]pyridin-6-yl}-2H-indazole-7-carbonitrile;
6-(7-fluoro-2-methyl-2H-indazol-5-yl)-2-[(piperidin-4-yl)oxy][1,3]thiazolo[4,5-c]pyridine;
6-{4-fluoro-2-[(piperidin-4-yl)oxy]-1,3-benzothiazol-6-yl}-2-methylimidazo[1,2-a]pyridine-8-carbonitrile;
5-{4-fluoro-2-[(piperidin-4-yl)oxy]-1,3-benzothiazol-6-yl}-2-methyl-2H-indazole-7-carbonitrile;
6-(2,8-dimethylimidazo[1,2-a]pyridin-6-yl)-4-fluoro-2-[(piperidin-4-yl)oxy]-1,3-benzothiazole;
6-{4-fluoro-2-[(1-methylpiperidin-4-yl)oxy]-1,3-benzothiazol-6-yl}-2,8-dimethylimidazo[1,2-b]pyridazine;
6-{2-[(1-ethylpiperidin-4-yl)oxy]-4-fluoro-1,3-benzothiazol-6-yl}-2,8-dimethylimidazo[1,2-b]pyridazine;
N-[(1R,3s,5S)-1,5-dimethyl-8-azabicyclo[3.2.1]octan-3-yl]-6-(6,8-dimethylimidazo[1,2-a]pyrazin-2-yl)-N-methyl[1,3]thiazolo[4,5-c]pyridin-2-amine;
N-[(1R,3s,5S)-1,5-dimethyl-8-azabicyclo[3.2.1]octan-3-yl]-5-(1,3-dimethylpyrrolo[1,2-a]pyrazin-7-yl)-N-methyl[1,3]thiazolo[5,4-d]pyrimidin-2-amine;
6-(2-{[(3R,4R)-3-fluoro-2,2,6,6-tetramethylpiperidin-4-yl](methyl)amino}[1,3]thiazolo[5,4-d]pyrimidin-5-yl)-2-methylimidazo[1,2-a]pyridine-8-carbonitrile;
6-(2-{[(3R,4R)-3-fluoro-2,2,6,6-tetramethylpiperidin-4-yl](methyl)amino}[1,3]thiazolo[4,5-c]pyridin-6-yl)-2-methylimidazo[1,2-a]pyridine-8-carbonitrile;
N-[(1R,2S,3S,5S)-2-fluoro-1,5-dimethyl-8-azabicyclo[3.2.1]octan-3-yl]-6-(8-fluoro-2-methylimidazo[1,2-a]pyridin-6-yl)-N-methyl[1,3]thiazolo[4,5-c]pyridin-2-amine;
5-(1H-imidazol-1-yl)-2-{6-[methyl(piperidin-4-yl)amino][1,3]thiazolo[4,5-c]pyridazin-3-yl}phenol;
3-[2,5-difluoro-4-(1H-pyrazol-4-yl)phenyl]-N-methyl-N-(piperidin-4-yl)[1,3]thiazolo[4,5-c]pyridazin-6-amine;
5-(3-fluoro-1H-pyrazol-4-yl)-2-{6-[methyl(piperidin-4-yl)amino][1,3]thiazolo[4,5-c]pyridazin-3-yl}phenol;
5-(1H-imidazol-1-yl)-2-{6-[methyl(1-methylpiperidin-4-yl)amino][1,3]thiazolo[4,5-c]pyridazin-3-yl}phenol;
3-[2,5-difluoro-4-(3-fluoro-1H-pyrazol-4-yl)phenyl]-N-methyl-N-(piperidin-4-yl)[1,3]thiazolo[4,5-c]pyridazin-6-amine;
5-(3-fluoro-1H-pyrazol-4-yl)-2-{6-[methyl(1-methylpiperidin-4-yl)amino][1,3]thiazolo[4,5-c]pyridazin-3-yl}phenol;
2-{6-[(3R,5S)-3,5-dimethylpiperazin-1-yl][1,3]thiazolo[4,5-c]pyridazin-3-yl}-5-(1H-pyrazol-4-yl)phenol;
2-[6-(piperazin-1-yl)[1,3]thiazolo[4,5-c]pyridazin-3-yl]-5-(1H-pyrazol-4-yl)phenol;
5-(1H-pyrazol-4-yl)-2-[6-(1,2,3,6-tetrahydropyridin-4-yl)[1,3]thiazolo[4,5-c]pyridin-2-yl]phenol;
2-(6-{[(3R,4S)-4-fluoro-1-methylpyrrolidin-3-yl]amino}[1,3]thiazolo[4,5-c]pyridazin-3-yl)-5-(1H-pyrazol-4-yl)phenol;
5-(1H-pyrazol-4-yl)-2-[6-(2,2,6,6-tetramethyl-1,2,3,6-tetrahydropyridin-4-yl)[1,3]thiazolo[4,5-c]pyridin-2-yl]phenol;
2-[6-(2,6-diazaspiro[3.5]nonan-2-yl)[1,3]thiazolo[4,5-c]pyridazin-3-yl]-5-(1H-pyrazol-4-yl)phenol;
2-[6-(7-methyl-1,7-diazaspiro[3.5]nonan-1-yl)[1,3]thiazolo[4,5-c]pyridazin-3-yl]-5-(1H-pyrazol-4-yl)phenol;
2-[6-(7-methyl-2,7-diazaspiro[4.4]nonan-2-yl)[1,3]thiazolo[4,5-c]pyridazin-3-yl]-5-(1H-pyrazol-4-yl)phenol;
2-[6-(2,7-diazaspiro[3.5]nonan-2-yl)[1,3]thiazolo[4,5-c]pyridazin-3-yl]-5-(3-fluoro-1H-pyrazol-4-yl)phenol;
2-(6-{[(3S,4S)-4-fluoro-1-methylpyrrolidin-3-yl]amino}[1,3]thiazolo[4,5-c]pyridazin-3-yl)-5-(1H-pyrazol-4-yl)phenol;
2-{6-[methyl(1-methylazetidin-3-yl)amino][1,3]thiazolo[4,5-c]pyridazin-3-yl}-5-(1H-pyrazol-4-yl)phenol;
2-{6-[(3aS,7aR)-octahydro-1H-pyrrolo[3,2-c]pyridin-1-yl][1,3]thiazolo[4,5-c]pyridazin-3-yl}-5-(1H-pyrazol-4-yl)phenol;
2-(6-{methyl[(1s,4s)-4-(methylamino)cyclohexyl]amino}[1,3]thiazolo[4,5-c]pyridazin-3-yl)-5-(1H-pyrazol-4-yl)phenol;
2-(6-{[(3R,4S)-4-fluoropyrrolidin-3-yl](methyl)amino}[1,3]thiazolo[4,5-c]pyridazin-3-yl)-5-(1H-pyrazol-4-yl)phenol;
2-{6-[(3aS,7aR)-5-methyloctahydro-1H-pyrrolo[3,2-c]pyridin-1-yl][1,3]thiazolo[4,5-c]pyridazin-3-yl}-5-(1H-pyrazol-4-yl)phenol;
2-(6-{methyl[(3R)-piperidin-3-yl]amino}[1,3]thiazolo[4,5-c]pyridazin-3-yl)-5-(1H-pyrazol-4-yl)phenol;
2-(6-{methyl[(3S)-piperidin-3-yl]amino}[1,3]thiazolo[4,5-c]pyridazin-3-yl)-5-(1H-pyrazol-4-yl)phenol;
2-(6-{methyl[3-(methylamino)cyclobutyl]amino}[1,3]thiazolo[4,5-c]pyridazin-3-yl)-5-(1H-pyrazol-4-yl)phenol;
2-(6-{[(1r,4r)-4-(dimethylamino)cyclohexyl](methyl)amino}[1,3]thiazolo[4,5-c]pyridazin-3-yl)-5-(1H-pyrazol-4-yl)phenol;
2-(6-{methyl[(3S)-1-methylpiperidin-3-yl]amino}[1,3]thiazolo[4,5-c]pyridazin-3-yl)-5-(1H-pyrazol-4-yl)phenol;
2-[6-[(azetidin-3-yl)(methyl)amino][1,3]thiazolo[4,5-c]pyridazin-3-yl]-5-(1H-pyrazol-4-yl)phenol;
2-[6-(1,7-diazaspiro[3.5]nonan-1-yl)[1,3]thiazolo[4,5-c]pyridazin-3-yl]-5-(1H-pyrazol-4-yl)phenol;
2-{6-[(3,3-dimethylpiperidin-4-yl)(methyl)amino][1,3]thiazolo[4,5-c]pyridazin-3-yl}-5-(1H-pyrazol-4-yl)phenol;
2-{6-[(2-azaspiro[3.3]heptan-6-yl)(methyl)amino][1,3]thiazolo[4,5-c]pyridazin-3-yl}-5-(1H-pyrazol-4-yl)phenol;
2-{6-[(piperidin-4-yl)amino][1,3]thiazolo[4,5-c]pyridazin-3-yl}-5-(1H-pyrazol-4-yl)phenol;
2-(6-{[(3R,4S)-3-fluoropiperidin-4-yl](methyl)amino}[1,3]thiazolo[4,5-c]pyridazin-3-yl)-5-(1H-pyrazol-4-yl)phenol;
5-{2-[(2R,4r,6S)-2,6-dimethylpiperidin-4-yl]-4-fluoro-1,3-benzothiazol-6-yl}-2,7-dimethyl[1,3]oxazolo[5,4-b]pyridine;
2-{6-[methyl(1,3,3-trimethylpiperidin-4-yl)amino][1,3]thiazolo[4,5-c]pyridazin-3-yl}-5-(1H-pyrazol-4-yl)phenol;
2-(6-{methyl[(1s,3s)-3-(methylamino)cyclobutyl]amino}[1,3]thiazolo[4,5-c]pyridazin-3-yl)-5-(1H-pyrazol-4-yl)phenol;
2-{6-[(3aR,7aS)-octahydro-1H-pyrrolo[2,3-c]pyridin-1-yl][1,3]thiazolo[4,5-c]pyridazin-3-yl}-5-(1H-pyrazol-4-yl)phenol;

2-[6-(1,6-diazaspiro[3.5]nonan-1-yl)[1,3]thiazolo[4,5-c]pyridazin-3-yl]-5-(1H-pyrazol-4-yl)phenol;
2-(6-{[(1s,3s)-3-(dimethylamino)cyclobutyl](methyl)amino}[1,3]thiazolo[4,5-c]pyridazin-3-yl)-5-(1H-pyrazol-4-yl)phenol;
2-(6-{[(3R,4R)-3-fluoropiperidin-4-yl](methyl)amino}[1,3]thiazolo[4,5-c]pyridazin-3-yl)-5-(1H-pyrazol-4-yl)phenol;
2-{6-[(1-methylpiperidin-4-yl)amino][1,3]thiazolo[4,5-c]pyridazin-3-yl}-5-(1H-pyrazol-4-yl)phenol;
5-(1H-pyrazol-4-yl)-2-{6-[(pyrrolidin-3-yl)amino][1,3]thiazolo[4,5-c]pyridazin-3-yl}phenol;
2-[6-(2,6-diazaspiro[3.3]heptan-2-yl)[1,3]thiazolo[4,5-c]pyridazin-3-yl]-5-(3-fluoro-1H-pyrazol-4-yl)phenol;
2-{6-[(3aR,7aS)-6-methyloctahydro-1H-pyrrolo[2,3-c]pyridin-1-yl][1,3]thiazolo[4,5-c]pyridazin-3-yl}-5-(1H-pyrazol-4-yl)phenol;
2-[6-(6-methyl-1,6-diazaspiro[3.5]nonan-1-yl)[1,3]thiazolo[4,5-c]pyridazin-3-yl]-5-(1H-pyrazol-4-yl)phenol;
2-(6-{[(2S,4S)-2-(hydroxymethyl)piperidin-4-yl](methyl)amino}[1,3]thiazolo[4,5-c]pyridazin-3-yl)-5-(1H-pyrazol-4-yl)phenol;
2-(6-{[(2S,4S)-2-(hydroxymethyl)-1-methylpiperidin-4-yl](methyl)amino}[1,3]thiazolo[4,5-c]pyridazin-3-yl)-5-(1H-pyrazol-4-yl)phenol;
2-{6-[(1-methylpyrrolidin-3-yl)amino][1,3]thiazolo[4,5-c]pyridazin-3-yl}-5-(1H-pyrazol-4-yl)phenol;
2-{6-[methyl(pyrrolidin-3-yl)amino][1,3]thiazolo[4,5-c]pyridazin-3-yl}-5-(1H-pyrazol-4-yl)phenol;
2-{6-[methyl(1-methylpyrrolidin-3-yl)amino][1,3]thiazolo[4,5-c]pyridazin-3-yl}-5-(1H-pyrazol-4-yl)phenol;
2-(6-{methyl[(1r,3r)-3-(methylamino)cyclobutyl]amino}[1,3]thiazolo[4,5-c]pyridazin-3-yl)-5-(1H-pyrazol-4-yl)phenol;
5-{2-[(1,2-dimethylpiperidin-4-yl)(methyl)amino][1,3]thiazolo[4,5-c]pyridin-6-yl}-2-methyl-2H-indazole-7-carbonitrile;
N-(1,2-dimethylpiperidin-4-yl)-6-(7-fluoro-2-methyl-2H-indazol-5-yl)-N-methyl[1,3]thiazolo[4,5-c]pyridin-2-amine;
6-{2-[(1,2-dimethylpiperidin-4-yl)(methyl)amino][1,3]thiazolo[4,5-c]pyridin-6-yl}-2-methylimidazo[1,2-a]pyridine-8-carbonitrile;
N-(1,2-dimethylpiperidin-4-yl)-6-(8-fluoro-2-methylimidazo[1,2-a]pyridin-6-yl)-N-methyl[1,3]thiazolo[4,5-c]pyridin-2-amine;
2-(6-{[(3S,4S)-4-fluoropyrrolidin-3-yl](methyl)amino}[1,3]thiazolo[4,5-c]pyridazin-3-yl)-5-(1H-pyrazol-4-yl)phenol;
2-(6-{[(3S,4S)-4-fluoro-1-methylpyrrolidin-3-yl](methyl)amino}[1,3]thiazolo[4,5-c]pyridazin-3-yl)-5-(1H-pyrazol-4-yl)phenol;
2-{6-[(1-cyclopropylpiperidin-4-yl)(methyl)amino][1,3]thiazolo[4,5-c]pyridazin-3-yl}-5-(1H-pyrazol-4-yl)phenol;
2-(6-{[1-(2-fluoroethyl)piperidin-4-yl](methyl)amino}[1,3]thiazolo[4,5-c]pyridazin-3-yl)-5-(1H-pyrazol-4-yl)phenol;
5-(3-fluoro-1H-pyrazol-4-yl)-2-[6-(6-methyl-2,6-diazaspiro[3.3]heptan-2-yl)[1,3]thiazolo[4,5-c]pyridazin-3-yl]phenol;
2-{6-[(1S,6R)-3,8-diazabicyclo[4.2.0]octan-8-yl][1,3]thiazolo[4,5-c]pyridazin-3-yl}-5-(1H-pyrazol-4-yl)phenol;
5-(3-fluoro-1H-pyrazol-4-yl)-2-{6-[methyl(pyrrolidin-3-yl)amino][1,3]thiazolo[4,5-c]pyridazin-3-yl}phenol;
2-{6-[(1S,6R)-3-methyl-3,8-diazabicyclo[4.2.0]octan-8-yl][1,3]thiazolo[4,5-c]pyridazin-3-yl}-5-(1H-pyrazol-4-yl)phenol;
2-{6-[(1R,6S)-3,8-diazabicyclo[4.2.0]octan-8-yl][1,3]thiazolo[4,5-c]pyridazin-3-yl}-5-(1H-pyrazol-4-yl)phenol;
2-{6-[(1R,6S)-3-methyl-3,8-diazabicyclo[4.2.0]octan-8-yl][1,3]thiazolo[4,5-c]pyridazin-3-yl}-5-(1H-pyrazol-4-yl)phenol;
5-(3-fluoro-1H-pyrazol-4-yl)-2-{6-[methyl(1-methylpyrrolidin-3-yl)amino][1,3]thiazolo[4,5-c]pyridazin-3-yl}phenol;
5-(3-fluoro-1H-pyrazol-4-yl)-2-[6-(7-methyl-2,7-diazaspiro[3.5]nonan-2-yl)[1,3]thiazolo[4,5-c]pyridazin-3-yl]phenol;
2-{6-[methyl(1-propylpiperidin-4-yl)amino][1,3]thiazolo[4,5-c]pyridazin-3-yl}-5-(1H-pyrazol-4-yl)phenol;
2-(6-{methyl[(2S,4S)-2-methylpiperidin-4-yl]amino}[1,3]thiazolo[4,5-c]pyridazin-3-yl)-5-(1H-pyrazol-4-yl)phenol;
2-(6-{[(2S,4S)-1,2-dimethylpiperidin-4-yl](methyl)amino}[1,3]thiazolo[4,5-c]pyridazin-3-yl)-5-(1H-pyrazol-4-yl)phenol;
2-(6-{methyl[(2R,4S)-2-methylpiperidin-4-yl]amino}[1,3]thiazolo[4,5-c]pyridazin-3-yl)-5-(1H-pyrazol-4-yl)phenol;
2-(6-{[(2R,4S)-1,2-dimethylpiperidin-4-yl](methyl)amino}[1,3]thiazolo[4,5-c]pyridazin-3-yl)-5-(1H-pyrazol-4-yl)phenol;
2-{6-[(azepan-4-yl)(methyl)amino][1,3]thiazolo[4,5-c]pyridazin-3-yl}-5-(3-fluoro-1H-pyrazol-4-yl)phenol;
2-(6-{[1-(2-hydroxyethyl)piperidin-4-yl](methyl)amino}[1,3]thiazolo[4,5-c]pyridazin-3-yl)-5-(1H-pyrazol-4-yl)phenol;
6-[4-fluoro-2-(1,2,3,6-tetrahydropyridin-4-yl)-1,3-benzothiazol-6-yl]-2-methylimidazo[1,2-b]pyridazine;
6-[4-fluoro-2-(piperidin-4-yl)-1,3-benzothiazol-6-yl]-2-methylimidazo[1,2-b]pyridazine;
6-[4-fluoro-2-(1,2,3,6-tetrahydropyridin-4-yl)-1,3-benzothiazol-6-yl]-2,8-dimethylimidazo[1,2-b]pyridazine;
6-[4-fluoro-2-(piperidin-4-yl)-1,3-benzothiazol-6-yl]-2,8-dimethylimidazo[1,2-b]pyridazine;
N-methyl-6-[2-methyl-7-(trifluoromethyl)-2H-indazol-5-yl]-N-(2,2,6,6-tetramethylpiperidin-4-yl)-1,3-benzothiazol-2-amine;
6-[4-fluoro-2-(1,2,3,6-tetrahydropyridin-4-yl)-1,3-benzothiazol-6-yl]-2,8-dimethylimidazo[1,2-a]pyrazine;
6-(2-methyl-2H-indazol-5-yl)-2-(2-methyl-1,2,3,6-tetrahydropridin-4-yl)-1,3-benzothiazole;
6-(2,7-dimethyl-2H-indazol-5-yl)-N-methyl-N-(2-methylpiperidin-4 -yl)-1,3-benzothiazol-2-amine;
6-(2-methyl-2H-indazol-5-yl)-2-(6-methyl-1,2,3,6-tetrahydropyridin-4-yl)-1,3-benzothiazole;
6-(2,7-dimethyl-2H-indazol-5-yl)-2-[(2,2,6,6-tetramethylpiperidin-4-yl)oxy]-1,3-benzothiazole;
4fluoro-6-(2-methyl-2H-indazol-5-yl)-2-(1,2,3,6-tetrahydropyridin-4-yl)-1,3-benzothiazole;
N-methyl-6-(2-methyl-2H-indazol-5-yl)-N-(2-methylpiperidin-4-yl)1,3benzothiazol -2-amine;
6-(2,7-dimethyl-2H-indazol-5-yl)-4-methoxy-2-(1,2,3,6-tetrahydropridin-4-yl)-1,3-benzothiazole;
2-methyl-5-[2-(piperidin-4-yl)[1,3]thiazolo[5,4-d]pyrimidin-5-yl]-2H-indazole-7-carbonitrile;
6-[2-(3,5-dimethylpiperazin-1-yl)-4-fluoro-1,3-benzothiazol-6-yl]-2,8-dimethylimidazo[1,2-b]pyridazine;

4-fluoro-6-(8-fluoro-2-methylimidazo[1,2-a]pyridin-6-yl)-2-(piperidin-4-yl)-1,3-benzothiazole;
4-chloro-6-(7-fluoro-2-methyl-2H-indazol-5-yl)-2-(1,2,3,6-tetrahydropyridin-4-yl)-1,3-benzothiazole;
N-(2,2-dimethylpiperidin-4-yl)-N-methyl-6-(2-methyl-2H-indazol-5-yl)-1,3-benzothiazol-2-amine;
6-[4-fluoro-2-(octahydroindolizin-7-yl)-1,3-benzothiazol-6-yl]-2-methylimidazo[1,2-b]pyridazine;
4-fluoro-N-methyl-6-(2-methylpyrazolo[1,5-a]pyrimidin-5-yl)-N-(piperidin-4-yl)-,3-benzothiazol-2-amine; and
N-(9-azabicyclo[3.3.1]non-3-yl)-N-methyl-6-(2-methylimidazo[1,2-a]pyridin-6-yl) [1,3]thiazolo[4,5-c]pyridin-2-amine;
wherein a form of the compound is selected from the group consisting of a salt, hydrate, solvate, racemate, enantiomer, diastereomer, stereoisomer, and tautomer form thereof.

6. The method of claim 5, wherein the compound is a compound salt or a form thereof, selected from the group consisting of:
N-methyl-6-(2-methyl-2H-indazol-5-yl)-N-(piperidin-4-yl)[1,3]thiazolo[4,5-b]pyridin-2-amine hydrochloride;
6-(2,7-dimethyl-2H-indazol-5-yl)-N-methyl-N-(piperidin-4-yl)[1,3]thiazolo[4,5-b]pyridin-2-amine hydrochloride;
6-(2,7-dimethyl-2H-indazol-5-yl)-N-(piperidin-4-yl)[1,3]thiazolo[4,5-b]pyridin-2-amine hydrochloride;
6-(2-methyl-2H-indazol-5-yl)-N-(piperidin-4-yl)[1,3]thiazolo[4,5-b]pyridin-2-amine hydrochloride;
6-(2,7-dimethyl-2H-indazol-5-yl)-2-(1,2,3,6-tetrahydropyridin-4-yl)-1,3-benzothiazole hydrochloride;
6-(2,7-dimethyl-2H-indazol-5-yl)-2-(piperidin-4-yl)-1,3-benzothiazole hydrochloride;
N-methyl-5-(2-methyl-2H-indazol-5-yl)-N-(2,2,6,6-tetramethylpiperidin-4-yl)[1,3]thiazolo[5,4-b]pyridin-2-amine hydrochloride;
N-methyl-5-(2-methyl-2H-indazol-5-yl)-N-(piperidin-4-yl)[1,3]thiazolo[5,4-b]pyridin-2-amine hydrochloride;
N-methyl-6-(2-methyl-2H-indazol-5-yl)-N-(piperidin-4-yl)[1,3]thiazolo[4,5-c]pyridin-2-amine hydrochloride;
N,N-dimethyl-1-[6-(2-methyl-2H-indazol-5-yl)-1,3-benzothiazol-2-yl]piperidin-4-amine hydrochloride;
1-[6-(2-methyl-2H-indazol-5-yl)-1,3-benzothiazol-2-yl]piperidin-4-amine hydrochloride;
6-(2,7-dimethyl-2H-indazol-5-yl)-N-methyl-N-(piperidin-4-yl)[1,3]thiazolo[4,5-c]pyridin-2-amine hydrochloride;
6-(1H-indazol-5-yl)-N-methyl-N-(2,2,6,6-tetramethylpiperidin-4-yl)-1,3-benzothiazol-2-amine hydrochloride;
6-(2-methyl-2H-indazol-5-yl)-N-(piperidin-4-yl)-1,3-benzothiazol-2-amine hydrochloride;
5-(2,7-dimethyl-2H-indazol-5-yl)-N-methyl-N-(piperidin-4-yl)[1,3]thiazolo[5,4-b]pyridin-2-amine hydrochloride;
N-methyl-6-(2-methyl-2H-indazol-5-yl)-N-(pyrrolidin-3-yl)-1,3-benzothiazol-2-amine hydrochloride;
N-methyl-6-(2-methylimidazo[1,2-b]pyridazin-6-yl)-N-(2,2,6,6-tetramethylpiperidin-4-yl)-1,3-benzothiazol-2-amine hydrochloride;
2-(4-fluoropiperidin-4-yl)-6-(2-methyl-2H-indazol-5-yl)-1,3-benzothiazole hydrochloride;
2-(azepan-4-yl)-6-(2-methyl-2H-indazol-5-yl)-1,3-benzothiazole hydrochloride;
6-[4-fluoro-2-(1,2,3,6-tetrahydropyridin-4-yl)-1,3-benzothiazol-6-yl]-2-methylimidazo[1,2-b]pyridazine hydrochloride;
6-[4-fluoro-2-(piperidin-4-yl)-1,3-benzothiazol-6-yl]-2-methylimidazo[1,2-b]pyridazine hydrochloride;
6-[4-fluoro-2-(1,2,3,6-tetrahydropyridin-4-yl)-1,3-benzothiazol-6-yl]-2,8-dimethylimidazo[1,2-b]pyridazine hydrochloride;
6-[4-fluoro-2-(piperidin-4-yl)-1,3-benzothiazol-6-yl]-2,8-dimethylimidazo[1,2-b]pyridazine hydrochloride;
N-methyl-6-[2-methyl-7-(trifluoromethyl)-2H-indazol-5-yl]-N-(2,2,6,6-tetramethylpiperidin-4-yl)-1,3-benzothiazol-2-amine hydrochloride;
6-[4-fluoro-2-(1,2,3,6-tetrahydropyridin-4-yl)-1,3-benzothiazol-6-yl]-2,8-dimethylimidazo[1,2-a]pyrazine hydrochloride;
6-(1,3-dimethylpyrrolo[1,2-a]pyrazin-7-yl)-N-methyl-N-(2,2,6,6-tetramethylpiperidin-4-yl)-1,3-benzothiazol-2-amine hydrochloride;
6-(7-fluoro-2-methyl-2H-indazol-5-yl)-N-methyl-N-(2,2,6,6-tetramethylpiperidin-4-yl)-1,3-benzothiazol-2-amine hydrochloride;
6-(2-methyl-2H-indazol-5-yl)-2-(2-methylpiperidin-4-yl)-1,3-benzothiazole hydrochloride;
6-(2,7-dimethyl-2H-indazol-5-yl)-2-(piperidin-4-yl)[1,3]thiazolo[4,5-c]pyridine hydrochloride;
6-[2-methyl-7-(trifluoromethyl)-2H-indazol-5-yl]-2-(piperidin-4-yl)[1,3]thiazolo[4,5-c]pyridine hydrochloride;
6-(2,8-dimethylimidazo[1,2-b]pyridazin-6-yl)-2-(piperidin-4-yl)[1,3]thiazolo[4,5-b]pyridine hydrochloride;
2-methyl-5-{2-[methyl(2,2,6,6-tetramethylpiperidin-4-yl)amino]-1,3-benzothiazol-6-yl}-2H-indazole-7-carbonitrile hydrochloride;
N-methyl-6-(2-methylimidazo[1,2-a]pyridin-6-yl)-N-(2,2,6,6-tetramethylpiperidin-4-yl)-1,3-benzothiazol-2-amine hydrochloride;
6-(2-methyl-2H-indazol-5-yl)-2-(2-methyl-1,2,3,6-tetrahydropyridin-4-yl)-1,3-benzothiazole hydrochloride;
6-(2,7-dimethyl-2H-indazol-5-yl)-N-methyl-N-(2-methylpiperidin-4-yl)-1,3-benzothiazol-2-amine hydrochloride;
6-(2-methyl-2H-indazol-5-yl)-2-(6-methyl-1,2,3,6-tetrahydropyridin-4-yl)-1,3-benzothiazole hydrochloride;
6-(2,7-dimethyl-2H-indazol-5-yl)-2-[(2,2,6,6-tetramethylpiperidin-4-yl)oxy]-1,3-benzothiazole hydrochloride;
6-[4-fluoro-2-(piperidin-4-yl)-1,3-benzothiazol-6-yl]-2-methyl-1,3-benzoxazole hydrochloride;
6-(2,8-dimethylimidazo[1,2-a]pyridin-6-yl)-4-fluoro-2-(1,2,3,6-tetrahydropyridin-4-yl)-1,3-benzothiazole hydrochloride;
4-fluoro-6-(2-methyl-2H-indazol-5-yl)-2-(1,2,3,6-tetrahydropyridin-4-yl)-1,3-benzothiazole hydrochloride;
4-fluoro-6-(2-methyl-2H-indazol-5-yl)-2-(piperidin-4-yl)-1,3-benzothiazole hydrochloride;
2-methyl-5-[2-(piperidin-4-yl)[1,3]thiazolo[4,5-c]pyridin-6-yl]-2H-indazole-7-carbonitrile hydrochloride;
6-(7-ethyl-2-methyl-2H-indazol-5-yl)-2-(piperidin-4-yl)[1,3]thiazolo[4,5-c]pyridine hydrochloride;
6-(7-fluoro-2-methyl-2H-indazol-5-yl)-2-(piperidin-4-yl)[1,3]thiazolo[4,5-c]pyridine hydrochloride;
6-(2-methylimidazo[1,2-a]pyridin-6-yl)-2-(piperidin-4-yl)[1,3]thiazolo[4,5-c]pyridine hydrochloride;

5-[4-fluoro-2-(piperidin-4-yl)-1,3-benzothiazol-6-yl]-1H-pyrazolo[4,3-b]pyridine hydrochloride;

5-[4-fluoro-2-(piperidin-4-yl)-1,3-benzothiazol-6-yl]-2-methyl-2H-pyrazolo[4,3-b]pyridine hydrochloride;

6-(7-cyclopropyl-2-methyl-2H-indazol-5-yl)-N-methyl-N-(2,2,6,6-tetramethylpiperidin-4-yl)-1,3-benzothiazol-2-amine hydrochloride;

N-methyl-6-(2-methyl-2H-indazol-5-yl)-N-(2-methylpiperidin-4-yl)-1,3-benzothiazol-2-amine hydrochloride;

2-methyl-5-[2-(piperidin-4-yl)-1,3-benzothiazol-6-yl]-2H-indazole-7-carbonitrile hydrochloride;

6-(8-ethyl-2-methylimidazo[1,2-a]pyridin-6-yl)-N-methyl-N-(2,2,6,6-tetramethylpiperidin-4-yl)-1,3-benzothiazol-2-amine hydrochloride;

6-(2,4-dimethyl-1H-benzimidazol-6-yl)-2-(piperidin-4-yl)-1,3-benzothiazole hydrochloride;

6-(2-methyl-1H-benzimidazol-6-yl)-2-(piperidin-4-yl)-1,3-benzothiazole dihydrochloride;

2-methyl-6-[2-(piperidin-4-yl)-1,3-benzothiazol-6-yl]imidazo[1,2-b]pyridazine hydrochloride;

6-(2,7-dimethyl-2H-indazol-5-yl)-4-methoxy-2-(1,2,3,6-tetrahydropyridin-4-yl)-1,3-benzothiazole hydrochloride;

6-(2,7-dimethyl-2H-indazol-5-yl)-4-methoxy-2-(piperidin-4-yl)-1,3-benzothiazole hydrochloride;

6-(2,7-dimethyl-2H-indazol-5-yl)-2-(1,2,3,6-tetrahydropyridin-4-yl)-1,3-benzothiazol-4-ol hydrobromide 5-[4-fluoro-2-(1,2,3,6-tetrahydropyridin-4-yl)-1,3-benzothiazol-6-yl]-2-methyl-2H-indazole-7-carbonitrile hydrochloride;

1-{5-[4-fluoro-2-(piperidin-4-yl)-1,3-benzothiazol-6-yl]-2-methyl-2H-indazol-7-yl}methanamine dihydrochloride;

5-[4-fluoro-2-(piperidin-4-yl)-1,3-benzothiazol-6-yl]-2-methyl-2H-indazole-7-carbonitrile hydrochloride;

2-methyl-5-[2-(piperidin-4-yl)[1,3]thiazolo[5,4-d]pyrimidin-5-yl]-2H-indazole-7-carbonitrile hydrochloride;

5-(2,7-dimethyl-2H-indazol-5-yl)-2-(piperidin-4-yl)[1,3]thiazolo[5,4-d]pyrimidine hydrochloride;

6-(8-fluoro-2-methylimidazo[1,2-a]pyridin-6-yl)-N-methyl-N-(2,2,6,6-tetramethylpiperidin-4-yl)-1,3-benzothiazol-2-amine hydrochloride;

6-(8-fluoro-2-methylimidazo[1,2-a]pyridin-6-yl)-2-(piperidin-4-yl)-1,3-benzothiazole hydrochloride;

6-(2,8-dimethylimidazo[1,2-a]pyridin-6-yl)-2-(piperidin-4-yl)-1,3-benzothiazole hydrochloride;

2-(2,2-dimethylpiperidin-4-yl)-6-(2-methyl-2H-indazol-5-yl)-1,3-benzothiazole hydrochloride;

2-{6-[methyl(2,2,6,6-tetramethylpiperidin-4-yl)amino][1,3]thiazolo[4,5-c]pyridazin-3-yl}-5-(1H-pyrazol-4-yl)phenol hydrochloride;

2-{2-[methyl(2,2,6,6-tetramethylpiperidin-4-yl)amino][1,3]thiazolo[4,5-b]pyrazin-6-yl}-5-(1H-pyrazol-4-yl)phenol hydrochloride;

6-[2-(3,5-dimethylpiperazin-1-yl)-4-fluoro-1,3-benzothiazol-6-yl]-2,8-dimethylimidazo[1,2-b]pyridazine hydrochloride;

6-{4-fluoro-2-[(2,2,6,6-tetramethylpiperidin-4-yl)oxy]-1,3-benzothiazol-6-yl}-2,8-dimethylimidazo[1,2-b]pyridazine hydrochloride;

6-{2-[(2,6-dimethylpiperidin-4-yl)oxy]-4-fluoro-1,3-benzothiazol-6-yl}-2,8-dimethylimidazo[1,2-b]pyridazine hydrochloride;

2-{2-[methyl(2,2,6,6-tetramethylpiperidin-4-yl)amino][1,3]thiazolo[4,5-c]pyridin-6-yl}-5-(1H-pyrazol-4-yl)phenol hydrochloride;

2-methyl-6-{2-[methyl(2,2,6,6-tetramethylpiperidin-4-yl)amino]-1,3-benzothiazol-6-yl}imidazo[1,2-a]pyridine-8-carbonitrile hydrochloride;

2,8-dimethyl-6-[2-(piperidin-4-yl)-1,3-benzothiazol-6-yl]imidazo[1,2-b]pyridazine hydrochloride;

2-{2-[methyl(2,2,6,6-tetramethylpiperidin-4-yl)amino][1,3]thiazolo[5,4-d]pyrimidin-5-yl}-5-(1H-pyrazol-4-yl)phenol hydrochloride;

6-{4-fluoro-2-[(2R)-2-methylpiperidin-4-yl]-1,3-benzothiazol-6-yl}-2-methylimidazo[1,2-b]pyridazine hydrochloride;

6-[4-fluoro-2-(1,2,3,6-tetrahydropyridin-4-yl)-1,3-benzothiazol-6-yl]-8-methoxy-2-methylimidazo[1,2-b]pyridazine hydrochloride;

6-(2,7-dimethyl-2H-indazol-5-yl)-N-(2,2-dimethylpiperidin-4-yl)-N-methyl-1,3-benzothiazol-2-amine hydrochloride;

2-{2-[methyl(2,2,6,6-tetramethylpiperidin-4-yl)amino][1,3]thiazolo[5,4-b]pyridin-5-yl}-5-(1H-pyrazol-4-yl)phenol hydrochloride;

6-[4-fluoro-2-(piperidin-4-yl)-1,3-benzothiazol-6-yl]-8-methoxy-2-methylimidazo[1,2-b]pyridazine hydrochloride;

4-fluoro-6-(8-fluoro-2-methylimidazo[1,2-a]pyridin-6-yl)-2-(piperidin-4-yl)-1,3-benzothiazole hydrochloride;

4-chloro-6-(7-fluoro-2-methyl-2H-indazol-5-yl)-2-(1,2,3,6-tetrahydropyridin-4-yl)-1,3-benzothiazole hydrochloride;

5-[4-chloro-2-(1,2,3,6-tetrahydropyridin-4-yl)-1,3-benzothiazol-6-yl]-2-methyl-2H-indazole-7-carbonitrile hydrochloride;

N-(2,2-dimethylpiperidin-4-yl)-N-methyl-6-(2-methyl-2H-indazol-5-yl)-1,3-benzothiazol-2-amine hydrochloride;

6-[2,3-difluoro-4-(1H-pyrazol-4-yl)phenyl]-N-methyl-N-(2,2,6,6-tetramethylpiperidin-4-yl)[1,3]thiazolo[4,5-b]pyrazin-2-amine hydrochloride;

4-fluoro-N-methyl-6-(2-methylimidazo[1,2-b]pyridazin-6-yl)-N-[(2S)-2-methylpiperidin-4-yl]-1,3-benzothiazol-2-amine hydrochloride;

6-(2,8-dimethylimidazo[1,2-b]pyridazin-6-yl)-4-fluoro-N-methyl-N-[(2S)-2-methylpiperidin-4-yl]-1,3-benzothiazol-2-amine hydrochloride;

6-[4-fluoro-2-(octahydroindolizin-7-yl)-1,3-benzothiazol-6-yl]-2-methylimidazo[1,2-b]pyridazine hydrochloride;

6-[4-fluoro-2-(piperidin-4-yl)-1,3-benzothiazol-6-yl]-N,2-dimethylimidazo[1,2-b]pyridazin-8-amine hydrochloride;

6-[4-fluoro-2-(piperidin-4-yl)-1,3-benzothiazol-6-yl]-N,N,2-trimethylimidazo[1,2-b]pyridazin-8-amine hydrochloride;

6-(7-cyano-2-methyl-2H-indazol-5-yl)-2-(1,2,3,6-tetrahydropyridin-4-yl)-1,3-benzothiazole-4-carbonitrile hydrochloride;

2-methyl-6-[2-(piperazin-1-yl)[1,3]thiazolo[4,5-b]pyrazin-6-yl]imidazo[1,2-a]pyridine-8-carbonitrile hydrochloride;

6-(8-fluoro-2-methylimidazo[1,2-a]pyridin-6-yl)-2-(piperazin-1-yl)[1,3]thiazolo[4,5-b]pyrazine hydrochloride;

6-(2,7-dimethyl-2H-indazol-5-yl)-N-(2,6-dimethylpiperidin-4-yl)-N-methyl-1,3-benzothiazol-2-amine hydrochloride;

N-(2,6-dimethylpiperidin-4-yl)-N-methyl-6-(2-methyl-2H-indazol-5-yl)-1,3-benzothiazol-2-amine hydrochloride;

6-(2-methylimidazo[1,2-b]pyridazin-6-yl)-2-(piperazin-1-yl)[1,3]thiazolo[4,5-b]pyrazine hydrochloride;

4-fluoro-N-methyl-6-(2-methylimidazo[1,2-b]pyridazin-6-yl)-N-(piperidin-4-yl)-1,3-benzothiazol-2-amine hydrochloride;

6-(2,8-dimethylimidazo[1,2-b]pyridazin-6-yl)-4-fluoro-N-methyl-N-(piperidin-4-yl)-1,3-benzothiazol-2-amine hydrochloride;

8-(benzyloxy)-6-[4-fluoro-2-(piperidin-4-yl)-1,3-benzothiazol-6-yl]-2-methylimidazo[1,2-b]pyridazine hydrochloride;

6-[4-fluoro-2-(piperidin-4-yl)-1,3-benzothiazol-6-yl]-2-methylimidazo[1,2-b]pyridazin-8-amine hydrochloride;

6-[4-fluoro-2-(piperidin-4-yl)-1,3-benzothiazol-6-yl]-2-methylimidazo[1,2-b]pyridazin-8-ol hydrochloride;

2-(2,6-dimethylpiperidin-4-yl)-6-(2-methyl-2H-indazol-5-yl)-1,3-benzothiazole hydrochloride;

4-fluoro-6-(4-fluoro-3-methoxyphenyl)-2-(piperidin-4-yl)-1,3-benzothiazole hydrochloride;

N-[(3-exo)-8-azabicyclo[3.2.1]oct-3-yl]-6-(2,8-dimethylimidazo[1,2-b]pyridazin-6-yl)-4-fluoro-N-methyl-1,3-benzothiazol-2-amine hydrochloride;

2-methyl-5-{2-[methyl(piperidin-4-yl)amino][1,3]thiazolo[5,4-d]pyrimidin-5-yl}-2H-indazole-7-carbonitrile hydrochloride;

6-[2-(1-azabicyclo[2.2.2]oct-4-yl)-4-fluoro-1,3-benzothiazol-6-yl]-2,8-dimethylimidazo[1,2-b]pyridazine hydrochloride;

6-[4-fluoro-2-(piperidin-4-yl)-1,3-benzothiazol-6-yl]-2-methyl-8-phenoxyimidazo[1,2-b]pyridazine hydrochloride;

2-methyl-6-{2-[methyl(piperidin-4-yl)amino][1,3]thiazolo[5,4-d]pyrimidin-5-yl}imidazo[1,2-a]pyridine-8-carbonitrile hydrochloride;

2-methyl-6-{2-[methyl(piperidin-4-yl)amino][1,3]thiazolo[4,5-c]pyridin-6-yl}imidazo[1,2-a]pyridine-8-carbonitrile hydrochloride;

6-{2-[(3-exo)-8-azabicyclo[3.2.1]oct-3-ylamino][1,3]thiazolo[4,5-c]pyridin-6-yl}-2-methylimidazo[1,2-a]pyridine-8-carbonitrile hydrochloride;

6-{4-fluoro-2-[methyl(2,2,6,6-tetramethylpiperidin-4-yl)amino]-1,3-benzothiazol-6-yl}-2-methylimidazo[1,2-b]pyridazin-8-amine hydrochloride;

4-fluoro-6-(8-methoxy-2-methylimidazo[1,2-b]pyridazin-6-yl)-N-methyl-N-(piperidin-4-yl)-1,3-benzothiazol-2-amine hydrochloride;

6-{2-[(3-exo)-8-azabicyclo[3.2.1]oct-3-yl(methyl)amino][1,3]thiazolo[4,5-c]pyridin-6-yl}-2-methylimidazo[1,2-a]pyridine-8-carbonitrile hydrochloride;

N-[(3-exo)-8-azabicyclo[3.2.1]oct-3-yl]-6-(8-fluoro-2-methylimidazo[1,2-a]pyridin-6-yl)-N-methyl[1,3]thiazolo[4,5-c]pyridin-2-amine hydrochloride;

N-[(3-exo)-8-azabicyclo[3.2.1]oct-3-yl]-6-(7-fluoro-2-methyl-2H-indazol-5-yl)-N-methyl[1,3]thiazolo[4,5-c]pyridin-2-amine hydrochloride;

5-{2-[(3-exo)-8-azabicyclo[3.2.1]oct-3-yl(methyl)amino][1,3]thiazolo[4,5-c]pyridin-6-yl}-2-methyl-2H-indazole-7-carbonitrile hydrochloride;

6-{2-[(3-exo)-8-azabicyclo[3.2.1]oct-3-yl(methyl)amino][1,3]thiazolo[5,4-d]pyrimidin-5-yl}-2-methylimidazo[1,2-a]pyridine-8-carbonitrile hydrochloride;

5-{2-[(3-exo)-8-azabicyclo[3.2.1]oct-3-yl(methyl)amino][1,3]thiazolo[5,4-d]pyrimidin-5-yl}-2-methyl-2H-indazole-7-carbonitrile hydrochloride;

N-[(3-exo)-8-azabicyclo[3.2.1]oct-3-yl]-4-fluoro-N-methyl-6-(2-methylimidazo[1,2-b]pyridazin-6-yl)-1,3-benzothiazol-2-amine hydrochloride;

6-[4-fluoro-2-(4-methylpiperidin-4-yl)-1,3-benzothiazol-6-yl]-2,8-dimethylimidazo[1,2-b]pyridazine hydrochloride;

N-[(3-exo)-8-azabicyclo[3.2.1]oct-3-yl]-6-(7-fluoro-2-methyl-2H-indazol-5-yl)[1,3]thiazolo[4,5-c]pyridin-2-amine hydrochloride;

N-[(3-exo)-8-azabicyclo[3.2.1]oct-3-yl]-6-(8-fluoro-2-methylimidazo[1,2-a]pyridin-6-yl)[1,3]thiazolo[4,5-c]pyridin-2-amine hydrochloride;

5-{2-[(3-exo)-8-azabicyclo[3.2.1]oct-3-ylamino][1,3]thiazolo[4,5-c]pyridin-6-yl}-2-methyl-2H-indazole-7-carbonitrile hydrochloride;

2-methyl-5-{2-[methyl(piperidin-4-yl)amino][1,3]thiazolo[4,5-c]pyridin-6-yl}-2H-indazole-7-carbonitrile hydrochloride;

6-(8-fluoro-2-methylimidazo[1,2-a]pyridin-6-yl)-N-methyl-N-(piperidin-4-yl)[1,3]thiazolo[4,5-c]pyridin-2-amine hydrochloride;

6-(7-fluoro-2-methyl-2H-indazol-5-yl)-N-methyl-N-(piperidin-4-yl)[1,3]thiazolo[4,5-c]pyridin-2-amine hydrochloride;

N-[(3-exo)-8-azabicyclo[3.2.1]oct-3-yl]-5-(8-fluoro-2-methylimidazo[1,2-a]pyridin-6-yl)-N-methyl[1,3]thiazolo[5,4-d]pyrimidin-2-amine hydrochloride;

N-[(3-exo)-8-azabicyclo[3.2.1]oct-3-yl]-5-(7-fluoro-2-methyl-2H-indazol-5-yl)-N-methyl[1,3]thiazolo[5,4-d]pyrimidin-2-amine hydrochloride;

6-[4-fluoro-2-(piperidin-4-yl)-1,3-benzothiazol-6-yl]-2-methylimidazo[1,2-b]pyridazine-8-carboxylic acid hydrochloride;

methyl {6-[4-fluoro-2-(piperidin-4-yl)-1,3-benzothiazol-6-yl]-2-methylimidazo[1,2-b]pyridazin-8-yl}acetate hydrochloride;

{6-[4-fluoro-2-(piperidin-4-yl)-1,3-benzothiazol-6-yl]-2-methylimidazo[1,2-b]pyridazin-8-yl}acetic acid hydrochloride;

6-{2-[(3-exo)-8-azabicyclo[3.2.1]oct-3-yloxy][1,3]thiazolo[4,5-c]pyridin-6-yl}-2-methylimidazo[1,2-a]pyridine-8-carbonitrile hydrochloride;

6-[4-fluoro-2-(piperidin-4-yl)-1,3-benzothiazol-6-yl]-2-methylimidazo[1,2-b]pyridazine-8-carboxamide trifluoroacetate;

6-{4-fluoro-2-[methyl(piperidin-4-yl)amino]-1,3-benzothiazol-6-yl}-2-methylimidazo[1,2-a]pyridine-8-carbonitrile hydrochloride;

N-[(8-anti)-3-azabicyclo[3.2.1]oct-8-yl]-5-(8-fluoro-2-methylimidazo[1,2-a]pyridin-6-yl)-N-methyl[1,3]thiazolo[5,4-d]pyrimidin-2-amine hydrochloride;

6-{2-[(8-anti)-3-azabicyclo[3.2.1]oct-8-yl(methyl)amino][1,3]thiazolo[5,4-d]pyrimidin-5-yl}-2-methylimidazo[1,2-a]pyridine-8-carbonitrile hydrochloride;

2-[4-fluoro-2-(piperidin-4-yl)-1,3-benzothiazol-6-yl]-6,8-dimethylimidazo[1,2-a]pyrazine hydrochloride;

6-[4-fluoro-2-(piperidin-4-yl)-1,3-benzothiazol-6-yl]-2-methylimidazo[1,2-b]pyridazine-8-carbonitrile hydrochloride;
6-{4-fluoro-2-[methyl(piperidin-4-yl)amino]-1,3-benzothiazol-6-yl}-2-methylimidazo[1,2-b]pyridazine-8-carbonitrile hydrochloride;
6-(7-fluoro-2-methyl-2H-indazol-5-yl)-N-(2,2,6,6-tetramethylpiperidin-4-yl)[1,3]thiazolo[4,5-c]pyridin-2-amine hydrochloride;
6-{2-[(3-exo)-8-azabicyclo[3.2.1]oct-3-yl(methyl)amino]-4-fluoro-1,3-benzothiazol-6-yl}-2-methylimidazo[1,2-b]pyridazine-8-carbonitrile hydrochloride;
6-{2-[(3-exo)-8-azabicyclo[3.2.1]oct-3-yl(methyl)amino]-4-fluoro-1,3-benzothiazol-6-yl}-2-methylimidazo[1,2-b]pyridazine-8-carboxamide hydrochloride;
N-[(3-exo)-8-azabicyclo[3.2.1]oct-3-yl]-4-fluoro-N-methyl-6-(2-methyl-2H-pyrazolo[4,3-b]pyridin-5-yl)-1,3-benzothiazol-2-amine hydrochloride;
N-(azetidin-3-yl)-6-(2,8-dimethylimidazo[1,2-b]pyridazin-6-yl)-4-fluoro-N-methyl-1,3-benzothiazol-2-amine hydrochloride;
5-[4-fluoro-2-(piperidin-4-yl)-1,3-benzothiazol-6-yl]-2-methylpyrazolo[1,5-a]pyrimidine hydrochloride;
4-fluoro-N-methyl-6-(2-methylpyrazolo[1,5-a]pyrimidin-5-yl)-N-(piperidin-4-yl)-,3-benzothiazol-2-amine hydrochloride;
6-{2-[9-azabicyclo[3.3.1]non-3-yl(methyl)amino][1,3]thiazolo[4,5-c]pyridin-6-yl}-2-methylimidazo[1,2-a]pyridine-8-carbonitrile hydrochloride;
5-{2-[9-azabicyclo[3.3.1]non-3-yl(methyl)amino][1,3]thiazolo[4,5-c]pyridin-6-yl}-2-methyl-2H-indazole-7-carbonitrile hydrochloride;
N-(9-azabicyclo[3.3.1]non-3-yl)-6-(7-fluoro-2-methyl-2H-indazol-5-yl)-N-methyl[1,3]thiazolo[4,5-c]pyridin-2-amine hydrochloride;
6-{2-[(1R,5S)-9-azabicyclo[3.3.1]non-3-yl(methyl)amino][1,3]thiazolo[5,4-d]pyrimidin-5-yl}-2-methylimidazo[1,2-a]pyridine-8-carbonitrile hydrochloride;
N-[(1R,5S)-9-azabicyclo[3.3.1]non-3-yl]-5-(8-fluoro-2-methylimidazo[1,2-a]pyridin-6-yl)-N-methyl[1,3]thiazolo[5,4-d]pyrimidin-2-amine hydrochloride;
4-fluoro-N-methyl-6-(2-methylimidazo[1,2-b]pyridazin-6-yl)-N-[(2S,4S)-2-methylpiperidin-4-yl]-1,3-benzothiazol-2-amine hydrochloride;
4-fluoro-N-methyl-6-(2-methylimidazo[1,2-b]pyridazin-6-yl)-N-[(2S,4R)-2-methylpiperidin-4-yl]-1,3-benzothiazol-2-amine hydrochloride;
N-(9-azabicyclo[3.3.1]non-3-yl)-N-methyl-6-(2-methylimidazo[1,2-a]pyridin-6-yl)[1,3]thiazolo[4,5-c]pyridin-2-amine hydrochloride;
N-(9-azabicyclo[3.3.1]non-3-yl)-6-(2,8-dimethylimidazo[1,2-a]pyridin-6-yl)-N-methyl[1,3]thiazolo[4,5-c]pyridin-2-amine hydrochloride;
N-(9-azabicyclo[3.3.1]non-3-yl)-N-methyl-6-(2-methyl-2H-indazol-5-yl)[1,3]thiazolo[4,5-c]pyridin-2-amine hydrochloride;
N-(9-azabicyclo[3.3.1]non-3-yl)-6-(2,7-dimethyl-2H-indazol-5-yl)-N-methyl[1,3]thiazolo[4,5-c]pyridin-2-amine hydrochloride;
N-(9-azabicyclo[3.3.1]non-3-yl)-6-(7-methoxy-2-methyl-2H-indazol-5-yl)-N-methyl[1,3]thiazolo[4,5-c]pyridin-2-amine hydrochloride;
2-methyl-6-{2-[(1,2,2,6,6-pentamethylpiperidin-4-yl)amino][1,3]thiazolo[4,5-c]pyridin-6-yl}imidazo[1,2-a]pyridine-8-carbonitrile hydrochloride;
6-(8-fluoro-2-methylimidazo[1,2-a]pyridin-6-yl)-N-(1,2,2,6,6-pentamethylpiperidin-4-yl)[1,3]thiazolo[4,5-c]pyridin-2-amine hydrochloride;
2-methyl-5-{2-[(1,2,2,6,6-pentamethylpiperidin-4-yl)amino][1,3]thiazolo[4,5-c]pyridin-6-yl}-2H-indazole-7-carbonitrile hydrochloride;
6-(7-fluoro-2-methyl-2H-indazol-5-yl)-N-(1,2,2,6,6-pentamethylpiperidin-4-yl)[1,3]thiazolo[4,5-c]pyridin-2-amine hydrochloride;
2-{2-[methyl(piperidin-4-yl)amino][1,3]thiazolo[4,5-b]pyrazin-6-yl}-5-(1H-pyrazol-4-yl)phenol hydrochloride;
6-{2-[(3-exo)-8-azabicyclo[3.2.1]oct-3-yl(methyl)amino][1,3]thiazolo[5,4-b]pyridin-5-yl}-2-methylimidazo[1,2-a]pyridine-8-carbonitrile hydrochloride;
N-[(3-exo)-8-azabicyclo[3.2.1]oct-3-yl]-5-(8-fluoro-2-methylimidazo[1,2-a]pyridin-6-yl)-N-methyl[1,3]thiazolo[5,4-b]pyridin-2-amine hydrochloride;
5-{2-[(3-exo)-8-azabicyclo[3.2.1]oct-3-yl(methyl)amino][1,3]thiazolo[5,4-b]pyridin-5-yl}-2-methyl-2H-indazole-7-carbonitrile hydrochloride;
6-{2-[(3-exo)-9-azabicyclo[3.3.1]non-3-yl(methyl)amino][1,3]thiazolo[5,4-b]pyridin-5-yl}-2-methylimidazo[1,2-a]pyridine-8-carbonitrile hydrochloride;
N-[(3-exo)-9-azabicyclo[3.3.1]non-3-yl]-5-(8-fluoro-2-methylimidazo[1,2-a]pyridin-6-yl)-N-methyl[1,3]thiazolo[5,4-b]pyridin-2-amine hydrochloride;
5-{2-[(3-exo)-9-azabicyclo[3.3.1]non-3-yl(methyl)amino][1,3]thiazolo[5,4-b]pyridin-5-yl}-2-methyl-2H-indazole-7-carbonitrile hydrochloride;
2-{6-[methyl(piperidin-4-yl)amino][1,3]thiazolo[4,5-c]pyridazin-3-yl}-5-(1H-pyrazol-4-yl)phenol hydrochloride;
2-{6-[methyl(1-methylpiperidin-4-yl)amino][1,3]thiazolo[4,5-c]pyridazin-3-yl}-5-(1H-pyrazol-4-yl)phenol hydrochloride;
N-[(1R,3s,5S)-1,5-dimethyl-8-azabicyclo[3.2.1]octan-3-yl]-6-(8-fluoro-2-methylimidazo[1,2-a]pyridin-6-yl)-N-methyl[1,3]thiazolo[4,5-c]pyridin-2-amine hydrochloride;
6-(2,8-dimethylimidazo[1,2-a]pyridin-6-yl)-N-methyl-N-(piperidin-4-yl)[1,3]thiazolo[4,5-b]pyrazin-2-amine hydrochloride;
N-(9-azabicyclo[3.3.1]nonan-3-yl)-5-(7-fluoro-2-methyl-2H-indazol-5-yl)-N-methyl[1,3]thiazolo[5,4-b]pyridin-2-amine hydrochloride;
6-(6,8-dimethylimidazo[1,2-a]pyrazin-2-yl)-N-methyl-N-(2,2,6,6-tetramethylpiperidin-4-yl)[1,3]thiazolo[4,5-c]pyridin-2-amine hydrochloride;
6-(1,3-dimethylpyrrolo[1,2-a]pyrazin-7-yl)-N-methyl-N-(2,2,6,6-tetramethylpiperidin-4-yl)[1,3]thiazolo[4,5-c]pyridin-2-amine hydrochloride;
6-(2-{[(1R,3s,5S)-1,5-dimethyl-8-azabicyclo[3.2.1]octan-3-yl](methyl)amino}[1,3]thiazolo[4,5-c]pyridin-6-yl)-2-methyl-1,3-benzoxazole-4-carbonitrile trifluoroacetate;
N-methyl-6-(2-methylimidazo[2,1-b][1,3]thiazol-6-yl)-N-(2,2,6,6-tetramethylpiperidin-4-yl)[1,3]thiazolo[4,5-c]pyridin-2-amine hydrochloride;
6-{4-fluoro-2-[(piperidin-4-yl)oxy]-1,3-benzothiazol-6-yl}-2,8-dimethylimidazo[1,2-b]pyridazine hydrochloride;

4-fluoro-6-(7-fluoro-2-methyl-2H-indazol-5-yl)-2-[(piperidin-4-yl)oxy]-1,3-benzothiazole hydrochloride;

N-methyl-6-(2-methylimidazo[2,1-b][1,3,4]thiadiazol-6-yl)-N-(2,2,6,6-tetramethylpiperidin-4-yl)[1,3]thiazolo[4,5-c]pyridin-2-amine hydrochloride;

2-methyl-6-{2-[(piperidin-4-yl)oxy][1,3]thiazolo[4,5-c]pyridin-6-yl}imidazo[1,2-a]pyridine-8-carbonitrile hydrochloride;

6-(8-fluoro-2-methylimidazo[1,2-a]pyridin-6-yl)-2-[(piperidin-4-yl)oxy][1,3]thiazolo[4,5-c]pyridine hydrochloride;

2-methyl-5-{2-[(piperidin-4-yl)oxy][1,3]thiazolo[4,5-c]pyridin-6-yl}-2H-indazole-7-carbonitrile hydrochloride;

6-(7-fluoro-2-methyl-2H-indazol-5-yl)-2-[(piperidin-4-yl)oxy][1,3]thiazolo[4,5-c]pyridine hydrochloride;

6-{4-fluoro-2-[(piperidin-4-yl)oxy]-1,3-benzothiazol-6-yl}-2-methylimidazo[1,2-a]pyridine-8-carbonitrile hydrochloride;

5-{4-fluoro-2-[(piperidin-4-yl)oxy]-1,3-benzothiazol-6-yl}-2-methyl-2H-indazole-7-carbonitrile hydrochloride;

6-(2,8-dimethylimidazo[1,2-a]pyridin-6-yl)-4-fluoro-2-[(piperidin-4-yl)oxy]-1,3-benzothiazole hydrochloride;

6-(2-{[(3R,4R)-3-fluoro-2,2,6,6-tetramethylpiperidin-4-yl](methyl)amino}[1,3]thiazolo[5,4-d]pyrimidin-5-yl)-2-methylimidazo[1,2-a]pyridine-8-carbonitrile dihydrochloride;

6-(2-{[(3R,4R)-3-fluoro-2,2,6,6-tetramethylpiperidin-4-yl](methyl)amino}[1,3]thiazolo[4,5-c]pyridin-6-yl)-2-methylimidazo[1,2-a]pyridine-8-carbonitrile dihydrochloride;

N-[(1R,2S,3S,5S)-2-fluoro-1,5-dimethyl-8-azabicyclo[3.2.1]octan-3-yl]-6-(8-fluoro-2-methylimidazo[1,2-a]pyridin-6-yl)-N-methyl[1,3]thiazolo[4,5-c]pyridin-2-amine dihydrochloride;

5-(1H-imidazol-1-yl)-2-{6-[methyl(piperidin-4-yl)amino][1,3]thiazolo[4,5-c]pyridazin-3-yl}phenol formate;

3-[2,5-difluoro-4-(1H-pyrazol-4-yl)phenyl]-N-methyl-N-(piperidin-4-yl)[1,3]thiazolo[4,5-c]pyridazin-6-amine formate;

3-[2,5-difluoro-4-(3-fluoro-1H-pyrazol-4-yl)phenyl]-N-methyl-N-(piperidin-4-yl)[1,3]thiazolo[4,5-c]pyridazin-6-amine formate;

2-[6-(piperazin-1-yl)[1,3]thiazolo[4,5-c]pyridazin-3-yl]-5-(1H-pyrazol-4-yl)phenol formate;

5-(1H-pyrazol-4-yl)-2-[6-(1,2,3,6-tetrahydropyridin-4-yl)[1,3]thiazolo[4,5-c]pyridin-2-yl]phenol hydrochloride;

2-(6-{[(3R,4S)-4-fluoro-1-methylpyrrolidin-3-yl]amino}[1,3]thiazolo[4,5-c]pyridazin-3-yl)-5-(1H-pyrazol-4-yl)phenol formate;

5-(1H-pyrazol-4-yl)-2-[6-(2,2,6,6-tetramethyl-1,2,3,6-tetrahydropyridin-4-yl)[1,3]thiazolo[4,5-c]pyridin-2-yl]phenol hydrochloride;

2-[6-(2,6-diazaspiro[3.5]nonan-2-yl)[1,3]thiazolo[4,5-c]pyridazin-3-yl]-5-(1H-pyrazol-4-yl)phenol dihydrochloride;

2-[6-(7-methyl-1,7-diazaspiro[3.5]nonan-1-yl)[1,3]thiazolo[4,5-c]pyridazin-3-yl]-5-(1H-pyrazol-4-yl)phenol dihydrochloride;

2-[6-(7-methyl-2,7-diazaspiro[4.4]nonan-2-yl)[1,3]thiazolo[4,5-c]pyridazin-3-yl]-5-(1H-pyrazol-4-yl)phenol dihydrochloride;

2-[6-(2,7-diazaspiro[3.5]nonan-2-yl)[1,3]thiazolo[4,5-c]pyridazin-3-yl]-5-(3-fluoro-1H-pyrazol-4-yl)phenol formate;

2-(6-{[(3S,4S)-4-fluoro-1-methylpyrrolidin-3-yl]amino}[1,3]thiazolo[4,5-c]pyridazin-3-yl)-5-(1H-pyrazol-4-yl)phenol formate;

2-{6-[(3aS,7aR)-octahydro-1H-pyrrolo[3,2-c]pyridin-1-yl][1,3]thiazolo[4,5-c]pyridazin-3-yl}-5-(1H-pyrazol-4-yl)phenol dihydrochloride;

2-(6-{methyl[(1s,4s)-4-(methylamino)cyclohexyl]amino}[1,3]thiazolo[4,5-c]pyridazin-3-yl)-5-(1H-pyrazol-4-yl)phenol dihydrochloride;

2-(6-{[(3R,4S)-4-fluoropyrrolidin-3-yl](methyl)amino}[1,3]thiazolo[4,5-c]pyridazin-3-yl)-5-(1H-pyrazol-4-yl)phenol formate;

2-{6-[(3 aS,7aR)-5-methyloctahydro-1H-pyrrolo[3,2-c]pyridin-1-yl][1,3]thiazolo[4,5-c]pyridazin-3-yl}-5-(1H-pyrazol-4-yl)phenol dihydrochloride;

2-(6-{methyl[(3R)-piperidin-3-yl]amino}[1,3]thiazolo[4,5-c]pyridazin-3-yl)-5-(1H-pyrazol-4-yl)phenol dihydrochloride;

2-(6-{methyl[(3S)-piperidin-3-yl]amino}[1,3]thiazolo[4,5-c]pyridazin-3-yl)-5-(1H-pyrazol-4-yl)phenol dihydrochloride;

2-(6-{methyl[3-(methylamino)cyclobutyl]amino}[1,3]thiazolo[4,5-c]pyridazin-3-yl)-5-(1H-pyrazol-4-yl)phenol ditrifluoroacetate;

2-(6-{[(1r,4r)-4-(dimethylamino)cyclohexyl](methyl)amino}[1,3]thiazolo[4,5-c]pyridazin-3-yl)-5-(1H-pyrazol-4-yl)phenol dihydrochloride;

2-(6-{methyl[(3S)-1-methylpiperidin-3-yl]amino}[1,3]thiazolo[4,5-c]pyridazin-3-yl)-5-(1H-pyrazol-4-yl)phenol dihydrochloride;

2-{6-[(azetidin-3-yl)(methyl)amino][1,3]thiazolo[4,5-c]pyridazin-3-yl}-5-(1H-pyrazol-4-yl)phenol dihydrochloride;

2-[6-(1,7-diazaspiro[3.5]nonan-1-yl)[1,3]thiazolo[4,5-c]pyridazin-3-yl]-5-(1H-pyrazol-4-yl)phenol dihydrochloride;

2-{6-[(3,3-dimethylpiperidin-4-yl)(methyl)amino][1,3]thiazolo[4,5-c]pyridazin-3-yl}-5-(1H-pyrazol-4-yl)phenol dihydrochloride;

2-{6-[(2-azaspiro[3.3]heptan-6-yl)(methyl)amino][1,3]thiazolo[4,5-c]pyridazin-3-yl}-5-(1H-pyrazol-4-yl)phenol dihydrochloride;

5-{2-[(2R,4r,6S)-2,6-dimethylpiperidin-4-yl]-4-fluoro-1,3-benzothiazol-6-yl}-2,7-dimethyl[1,3]oxazolo[5,4-b]pyridine hydrochloride;

2-{6-[methyl(1,3,3-trimethylpiperidin-4-yl)amino][1,3]thiazolo[4,5-c]pyridazin-3-yl}-5-(1H-pyrazol-4-yl)phenol dihydrochloride;

2-(6-{methyl[(1s,3s)-3-(methylamino)cyclobutyl]amino}[1,3]thiazolo[4,5-c]pyridazin-3-yl)-5-(1H-pyrazol-4-yl)phenol dihydrochloride;

2-{6-[(3 aR,7aS)-octahydro-1H-pyrrolo[2,3-c]pyridin-1-yl][1,3]thiazolo[4,5-c]pyridazin-3-yl}-5-(1H-pyrazol-4-yl)phenol dihydrochloride;

2-[6-(1,6-diazaspiro[3.5]nonan-1-yl)[1,3]thiazolo[4,5-c]pyridazin-3-yl]-5-(1H-pyrazol-4-yl)phenol dihydrochloride;

2-(6-{[(1s,3s)-3-(dimethylamino)cyclobutyl](methyl)amino}[1,3]thiazolo[4,5-c]pyridazin-3-yl)-5-(1H-pyrazol-4-yl)phenol dihydrochloride;

2-(6-{[(3R,4R)-3-fluoropiperidin-4-yl](methyl)amino}[1,3]thiazolo[4,5-c]pyridazin-3-yl)-5-(1H-pyrazol-4-yl)phenol formate;

5-(1H-pyrazol-4-yl)-2-{6-[(pyrrolidin-3-yl)amino][1,3]thiazolo[4,5-c]pyridazin-3-yl}phenol formate;

2-[6-(2,6-diazaspiro[3.3]heptan-2-yl)[1,3]thiazolo[4,5-c]pyridazin-3-yl]-5-(3-fluoro-1H-pyrazol-4-yl)phenol formate;

2-{6-[(3 aR,7aS)-6-methyloctahydro-1H-pyrrolo[2,3-c]pyridin-1-yl][1,3]thiazolo[4,5-c]pyridazin-3-yl}-5-(1H-pyrazol-4-yl)phenol dihydrochloride;

2-[6-(6-methyl-1,6-diazaspiro[3.5]nonan-1-yl)[1,3]thiazolo[4,5-c]pyridazin-3-yl]-5-(1H-pyrazol-4-yl)phenol dihydrochloride;

2-(6-{[(2S,4S)-2-(hydroxymethyl)piperidin-4-yl](methyl)amino}[1,3]thiazolo[4,5-c]pyridazin-3-yl)-5-(1H-pyrazol-4-yl)phenol dihydrochloride;

2-(6-{[(2S,4S)-2-(hydroxymethyl)-1-methylpiperidin-4-yl](methyl)amino}[1,3]thiazolo[4,5-c]pyridazin-3-yl)-5-(1H-pyrazol-4-yl)phenol dihydrochloride;

2-(6-{methyl[(1r,3r)-3-(methylamino)cyclobutyl]amino}[1,3]thiazolo[4,5-c]pyridazin-3-yl)-5-(1H-pyrazol-4-yl)phenol dihydrochloride;

N-(1,2-dimethylpiperidin-4-yl)-6-(8-fluoro-2-methylimidazo[1,2-a]pyridin-6-yl)-N-methyl[1,3]thiazolo[4,5-c]pyridin-2-amine trifluoroacetate;

2-{6-[(1S,6R)-3,8-diazabicyclo[4.2.0]octan-8-yl][1,3]thiazolo[4,5-c]pyridazin-3-yl}-5-(1H-pyrazol-4-yl)phenol trifluoroacetate;

2-{6-[(1S,6R)-3-methyl-3,8-diazabicyclo[4.2.0]octan-8-yl][1,3]thiazolo[4,5-c]pyridazin-3-yl}-5-(1H-pyrazol-4-yl)phenol trifluoroacetate;

2-{6-[(1R,6S)-3,8-diazabicyclo[4.2.0]octan-8-yl][1,3]thiazolo[4,5-c]pyridazin-3-yl}-5-(1H-pyrazol-4-yl)phenol trifluoroacetate;

2-{6-[(1R,6S)-3-methyl-3,8-diazabicyclo[4.2.0]octan-8-yl][1,3]thiazolo[4,5-c]pyridazin-3-yl}-5-(1H-pyrazol-4-yl)phenol trifluoroacetate;

2-(6-{methyl[(2S,4S)-2-methylpiperidin-4-yl]amino}[1,3]thiazolo[4,5-c]pyridazin-3-yl)-5-(1H-pyrazol-4-yl)phenol trifluoroacetate;

2-(6-{[(2S,4S)-1,2-dimethylpiperidin-4-yl](methyl)amino}[1,3]thiazolo[4,5-c]pyridazin-3-yl)-5-(1H-pyrazol-4-yl)phenol trifluoroacetate;

2-(6-{methyl[(2R,4S)-2-methylpiperidin-4-yl]amino}[1,3]thiazolo[4,5-c]pyridazin-3-yl)-5-(1H-pyrazol-4-yl)phenol trifluoroacetate, and 2-(6-{[(2R,4S)-1,2-dimethylpiperidin-4-yl](methyl)amino}[1,3]thiazolo[4,5-c]pyridazin-3-yl)-5-(1H-pyrazol-4-yl)phenol trifluoroacetate;

wherein a form of the compound salt is selected from the group consisting of a hydrate, solvate, racemate, enantiomer, diastereomer, stereoisomer, and tautomer form thereof.

7. The method of claim 1, wherein the effective amount of the compound is in a range of from about 0.001 mg/kg/day to about 500 mg/kg/day.

8. The method of claim 1, wherein a pharmaceutical composition comprises the compound or form thereof and at least one pharmaceutically acceptable excipient.

9. The method of claim 5, wherein a pharmaceutical composition comprises the compound or form thereof and at least one pharmaceutically acceptable excipient.

* * * * *